(12) United States Patent
Maynard et al.

(10) Patent No.: US 7,186,734 B2
(45) Date of Patent: Mar. 6, 2007

(54) ARYL IMIDAZOLES AND RELATED COMPOUNDS AS C5A RECEPTOR MODULATORS

(75) Inventors: George D. Maynard, Clinton, CT (US); Andrew Thurkauf, Danbury, CT (US); He Zhao, Branford, CT (US); Bertrand L. Chenard, Waterford, CT (US); Yang Gao, Branford, CT (US)

(73) Assignee: Neurogen Corporation, Branford, CT (US)

( * ) Notice: Subject to any disclaimer, the term of this patent is extended or adjusted under 35 U.S.C. 154(b) by 324 days.

(21) Appl. No.: 10/405,989

(22) Filed: Mar. 28, 2003

(65) Prior Publication Data

US 2004/0116424 A1 Jun. 17, 2004

Related U.S. Application Data

(60) Provisional application No. 60/392,145, filed on Jun. 26, 2002, provisional application No. 60/369,112, filed on Mar. 29, 2002.

(51) Int. Cl.
*A61K 31/4439* (2006.01)
*A61K 31/4164* (2006.01)
*A61K 31/4178* (2006.01)
*C07D 401/04* (2006.01)
*C07D 233/61* (2006.01)
*C07D 233/54* (2006.01)

(52) U.S. Cl. .................. 514/341; 514/397; 514/400; 546/274.1; 548/340.1; 548/311.7

(58) Field of Classification Search .............. 548/340.1, 548/311.7; 514/400, 397, 341; 546/274.1
See application file for complete search history.

(56) References Cited

U.S. PATENT DOCUMENTS

| | | | |
|---|---|---|---|
| 5,159,083 | A | 10/1992 | Thurkauf et al. |
| 5,428,164 | A | 6/1995 | Thurkauf et al. |
| 5,478,934 | A | 12/1995 | Yuan et al. |
| 5,633,376 | A | 5/1997 | Thurkauf et al. |
| 5,633,377 | A | 5/1997 | Thurkauf et al. |
| 5,646,280 | A | 7/1997 | Thurkauf et al. |
| 5,681,956 | A | 10/1997 | Thurkauf et al. |
| 6,723,743 | B1 | 4/2004 | Thurkauf et al. |
| 6,884,815 | B1 | 4/2005 | Thurkauf et al. |

FOREIGN PATENT DOCUMENTS

WO    WO 02/14265    2/2002

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet,URL;http://www.cnn.com/2003/HEALTH/conditions/09/24/alzheimers.drug.ap/index.html>.*
Database CA on STN, (Columbus, OH, USA), No. 128:3703, Thurkauf, et al. 'Preparation of 4-aryl substituted piperazinylmethylphenyl imidazoles as a new class of dopamine receptor subtype specific ligands', abstract, Oct. 28, 1997.
Database CA on STN, (Columbus, OH, USA), No. 123:55767, Thurkauf, et al. '2-Phenyl-4-(aminomethyl)imidazoles as potential antipsychotic agents. Synthesis and dopamine D2 receptor binding, abstract, J. Med. Chem., vol. 38, No. 12, pp. 2251-2255, 1995.
Database CA on STN, (Columbus, OH, USA), No. 117: 2513500350, Thurkauf, etal., 'Preparation of (aminomethyl)phenylimidazoles as dopamine receptor ligands,' abstract, Jul. 23, 1992.
Database CA on STN, (Columbus, OH, USA), No. 105:191381, Shiga, et al., 'Silane derivatives,' abstract, Mar. 24, 1986.
Database CA on STN, (Columbus, OH, USA), No. 131:257737, He, et al., 'Enantioselective total synthesis of aspidophytine,' abstract, J. Am. Chem. Soc., vol. 121, No. 28, pp. 6771-6772, 1999.
Drug Report for "C5a antagonists", Merck & Co., from the Investigational Drugs database, search done Feb. 18, 2002, last update Apr. 17, 2001. Summary, 1 page.
de Laszio et al., "A Nonpeptide Agonist Ligand of the Human C5A Receptor: Synthesis, Binding Affinity Optimization and Functional Characterization," *Bioorganic & Medicinal Chemistry Letters* vol. 7, No. 2 pp. 213-218 and pp. 907-912 (1997).
Shilcrat, et al, "A New Regioselective Synthesis of 1,2,5-Trisubstituted 1H-Imidazoles and its Application to the Development of Eprosartan", J. Org. Chem. 1997, 62, pp. 8449-8454.

(Continued)

*Primary Examiner*—Kamal A. Saeed
*Assistant Examiner*—Rebecca Anderson
(74) *Attorney, Agent, or Firm*—Edwards Angell Palmer & Dodge LLP; Peter F. Corless; John B. Alexander

(57) ABSTRACT

The invention provides Aryl substituted imidazoles, pyrazoles, pyridizines and related compounds of the Formula where the variables are defined herein.

Such compounds are ligands of C5a receptors. Preferred compounds of the invention act bind to C5a receptors with high affinity and exhibit neutral antagonist or inverse agonist activity at C5a receptos. This invention also relates to pharmaceutical compositions comprising such compounds. It further relates to the use of such compounds in treating a variety of inflammatory and immune system disorders.

36 Claims, No Drawings

OTHER PUBLICATIONS

U.S. Appl. No. 10/853,731, filed May 24, 2004, Thurkauf et al.

M. Abe, et al., "Contribution of Anaphylatoxin C5a to Late Airway Responses After Repeated Exposure of Antigen to Allergic Rats", *The American Association of Immunologists*, vol. 167, pp. 4651-4660 (2001).

T. Woodruff, et al., "Antiarthritic Activity of an Orally active C5a Receptor Antagonist Against Antigen-Induced Monarticular Arthritis in the Rat", *Arthritis & Rheumatism*, vol. 46, No. 9, pp. 2476-2485 (Sep. 2002).

F. Niculescu, et al., Complement activation and atherosclerosis, *Molecular Immunology*, vol. 36, pp. 949-955 (1999).

R. Riley, et al., "Recombinant Human Complement C5a Receptor Antagonist Reduces Infarct Size after Surgical Revascularization", *The Journal of Thoracic and Cardiovascular Surgery*, vol. 120, No. 2, pp. 351-358 (2000).

H. Sumichika, "C5a receptor antagonists for the treatment of inflammation", *Current Opinion in Investigational Drugs*, vol. 5, No. 5, pp. 505-510 (2004).

Promics, "Another positive performance for Promics' Anti-Anflammatory Drug PMX53," www.promics.com.au/news/newitem.asp?itemid=50&archive=true (Mar. 10, 2004).

* cited by examiner

ARYL IMIDAZOLES AND RELATED COMPOUNDS AS C5A RECEPTOR MODULATORS

CROSS-REFERENCE TO RELATED APPLICATIONS

This application claims priority to U.S. Provisional Application No. 60/369,112 filed Mar. 29, 2002, and No. 60/392,145, filed Jun. 26, 2002.

FIELD OF THE INVENTION

This invention includes substituted aryl imidazoles and related compounds that modulate a mammalian complement C5a receptor. Certain compounds provided herein act as high affinity C5a receptor ligands and/or act as antagonists (including inverse agonists) of complement C5a receptors, preferably human C5a receptors. This invention also relates to pharmaceutical compositions comprising such compounds, and to the use of such compounds for treating a variety of inflammatory and immune system disorders. Additionally, this invention relates to the use such compounds as probes for the localization of C5a receptors.

BACKGROUND OF THE INVENTION

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Considerable experimental evidence implicates increased levels of C5a in a number of autoimmune diseases and inflammatory and related disorders.

Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions.

SUMMARY OF THE INVENTION

The present invention provides substituted aryl imidazoles and related compounds of Formula I, below. Such compounds are useful as modulators of C5a receptor and preferably inhibit C5a receptor activation and/or C5a receptor-mediated signal transduction.

The invention provides compounds of Formula I:

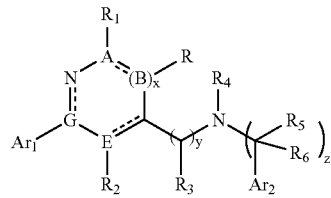

Formula I and the pharmaceutically acceptable salts thereof, wherein the ring system represented by

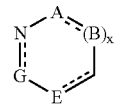

is a 5 membered heteroaryl ring system, in which x is 0, A is chosen from carbon and heteroatoms nitrogen, oxygen, and sulfur, and E and G are independently carbon or nitrogen, provided that the 5 membered heteroaryl ring system does not contain more than 3 heteroatoms or more than 1 oxygen or sulfur atom, or a 6 membered heteroaryl ring system, in which x is 1, and A, B, E, and G are independently chosen from carbon and nitrogen, provided that the 6 membered heteroaryl ring system does not contain more than 3 nitrogen atoms.

R and $R_1$ independently represent:

i) hydrogen, hydroxy, halogen, amino, cyano, nitro, —CHO, —CONH$_2$, $C_1$–$C_6$haloalkyl, or $C_1$–$C_6$haloalkoxy, ii) $C_1$–$C_6$alkyl, $C_1$–$C_6$alkenyl, $C_1$–$C_6$alkynyl, $C_1$–$C_6$alkanoyl, $C_1$–$C_6$alkoxy, $C_3$–$C_7$cycloalkyl, ($C_3$–$C_7$cycloalkyl)$C_1$–$C_4$alkyl, mono- or di-$C_1$–$C_6$alkylamino, mono- or di-$C_1$–$C_6$alkylaminoC$_1$–$C_6$alkyl, mono- or di-$C_1$–$C_6$alkylcarboxamide, $C_1$–$C_6$alkoxycarbonyl, —SO$_n$($C_1$–$C_6$alkyl), —NHSO$_n$$C_1$–$C_6$alkyl, —SO$_n$N($C_1$–$C_6$alkyl)($C_1$–$C_6$alkyl), phenyl-SO$_n$—, each of which is optionally substituted, or iii) naphthyl, phenyl, phenylC$_1$–$C_4$carbhydryl, 5- or 6-membered heteroaryl, or 5- or 6-membered heteroarylC$_1$–$C_4$carbhydryl, each of which is optionally substituted.

When E is Nitrogen, $R_2$, is chosen from $C_1$–$C_7$alkyl, $C_2$–$C_7$alkenyl, $C_2$–$C_7$alkynyl, $C_3$–$C_7$cycloalkyl ($C_1$–$C_4$alkyl), benzyl, and $C_1$–$C_6$haloalkyl, each of which is optionally substituted; and when E is Carbon, $R_2$ is chosen from (i) hydrogen, halogen, hydroxy; $C_1$–$C_6$haloalkyl, and $C_1$–$C_6$haloalkoxy, and (ii) $C_1$–$C_7$ alkyl, $C_2$–$C_7$ alkenyl, $C_2$–$C_7$ alkynyl, $C_1$–$C_7$ alkoxy, $C_1$–$C_7$alkylamino, $C_3$–$C_7$cycloalkyl($C_1$–$C_4$alkyl), and benzyl; each of which is optionally substituted;

$R_3$ is hydrogen, $C_1$–$C_6$alkyl, $C_2$–$C_6$ alkenyl, $C_1$–$C_6$hydroxyalkyl, $C_1$–$C_6$haloalkyl, $C_3$–$C_7$cycloalkyl, ($C_3$–$C_7$cycloalkyl)$C_1$–$C_4$alkyl, or phenyl($C_1$–$C_4$alkyl).

When x is 0, R, and $R_3$ may be joined to form an optionally substituted cycloalkyl ring having from 3 to 7 carbon atoms.

$R_4$ is $C_1$–$C_6$alkyl, $C_2$–$C_6$ alkenyl, $C_2$–$C_6$ alkynyl, $C_3$–$C_7$ cycloalkyl, $C_3$–$C_7$ cycloalkenyl, ($C_3$–$C_7$cycloalkyl)$C_1$–$C_4$alkyl, ($C_3$–$C_7$cycloalkenyl)$C_1$–$C_4$alkyl, or hexahydro-1,3-benzodioxolylmethyl, each of which is optionally substituted; or $R_4$ is (i) optionally substituted aryl$C_1$–$C_4$alkyl having from 1 ring or 2 fused or pendant rings, (ii) an aryl$C_1$–$C_4$alkyl group, wherein the aryl portion is fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy, (iii) optionally substituted heterocycloalkyl($C_0$–$C_4$alkyl), (iv) optionally substituted heteroaryl$C_0$–$C_2$alkyl, having 1 ring or 2 fused or pendant rings, from 5 to 7 members in each ring, and in at least one ring 1 to 3 heteroatoms selected from N, O, and S, or (v) optionally substituted saturated or partially unsaturated heterocyclic($C_0$–$C_4$alkyl) wherein the heterocyclic portion has from 4 to 7 ring members, 1 or 2 of which ring members are N, S or O, with remaining ring members being carbon.

$R_5$ and $R_6$ are independently chosen from hydrogen and $C_1$–$C_6$alkyl, and z is 1, 2, or 3.

$Ar_1$ represents (i) optionally substituted aryl, (ii) optionally substituted phenyl fused to a 5- to 7-membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy, or (iii) optionally substituted heteroaryl, having 1 ring or 2 fused or pendant rings, from 5 to 7 members in each ring, and in at least one ring 1 to 3 heteroatoms selected from N, O, and S.

$Ar_2$ represents:

(i) $C_3$–$C_7$cycloalkyl, $C_3$–$C_7$cycloalkyl($C_1$–$C_4$alkyl), $C_3$–$C_7$cycloalkenyl, $C_3$–$C_7$cycloalkenyl($C_1$–$C_4$alkyl), or hexahydro-1,3-benzodioxolyl, each of which is optionally substituted (ii) an optionally substituted aryl having 1 ring or 2 fused or pendant rings, (iii) an optionally substituted phenyl fused to a 5- to 7-membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy, or (iv) optionally substituted heteroaryl, having 1 ring or 2 fused or pendant rings, from 5 to 7 members in each ring, and in at least one ring 1 to 3 heteroatoms selected from N, O, and S.

In Formula I n is independently chosen from 0, 1, or 2; and y is an integer of from 1 to 6.

DETAILED DESCRIPTION OF THE INVENTION

Chemical Description and Terminology

Compounds of the present invention are generally described using standard nomenclature.

The term "aryl imidazole," as used herein, encompasses all compounds that satisfy one or more of Formulas I, IA, and II–XIV herein, as well as pharmaceutically acceptable salts, prodrugs and hydrates of such compounds.

Certain compounds described herein contain one or more asymmetric elements such as stereogenic centers, stereogenic axes and the like (e.g., asymmetric carbon atoms) so that the compounds can exist in different stereoisomeric forms. These compounds can be, for example, racemates or optically active forms. For compounds with two or more asymmetric elements, these compounds can additionally be mixtures of diastereomers. Unless otherwise specified all optical isomers and mixtures thereof are encompassed for compounds having asymmetric centers. In addition, compounds with carbon-carbon double bonds may occur in Z- and E-forms, with all isomeric forms of the compounds being included in the present invention unless otherwise specified. Where a compound exists in various tautomeric forms, the invention is not limited to any one of the specific tautomers, but rather encompasses all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula, such as Formula I, which includes variables, such as $Ar^1$, $R^1$, and $R^2$. Unless otherwise specified, each variable within such a formula is defined independently of other variables. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

A "substituent," as used herein, refers to a molecular moiety that is covalently bonded to an atom within a molecule of interest. For example, a "ring substituent" may be a moiety such as a halogen, alkyl group, haloalkyl group or other substituent discussed herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e.,=O), then 2 hydrogens on the atom are replaced. When aromatic moieties are substituted by an oxo group, the aromatic ring is replaced by the corresponding partially unsaturated ring. For example a pyridyl group substituted by oxo is a tetrahydropyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Various groups within the compounds and formulae set forth herein are "optionally substituted" including, for example, $R^1$, $R^2$, and $Ar^1$. Optional substitution may also be indicated by the phrase "substituted with from 0 to X substituents," in which X is the maximum number of substituents.

Suitable substituents include, for example, halogen, cyano, amino, hydroxy, nitro, azido, carboxamido, —COOH, $SO_2NH_2$, alkyl (e.g., $C_1$–$C_8$alkyl), alkenyl (e.g., $C_2$–$C_8$alkenyl), alkynyl (e.g., $C_2$–$C_8$alkynyl), alkoxy (e.g., $C_1$–$C_8$alkoxy), alkyl ether (e.g., $C_2$–$C_8$alkyl ether), alkylthio (e.g., $C_1$–$C_8$alkylthio), mono- or di-($C_1$–$C_8$alkyl)amino, haloalkyl (e.g., $C_1$–$C_6$haloalkyl), hydroxyalkyl (e.g., $C_1$–$C_6$hydroxyalkyl), aminoalkyl (e.g., $C_1$–$C_6$aminoalkyl), haloalkoxy (e.g., $C_1$–$C_6$haloalkoxy), alkanoyl (e.g., $C_1$–$C_8$alkanoyl), alkanone (e.g., $C_1$–$C_8$alkanone), alkanoyloxy (e.g., $C_1$–$C_8$alkanoyloxy), alkoxycarbonyl (e.g., $C_1$–$C_8$alkoxycarbonyl), mono- and di-($C_1$–$C_8$alkyl)amino, mono- and di-($C_1$–$C_8$alkyl)amino$C_1$–$C_8$alkyl, mono- and di-($C_1$–$C_8$alkyl)carboxamido, mono- and di-($C_1$–$C_8$alkyl) sulfonamido, alkylsulfinyl (e.g., $C_1$–$C_8$alkylsulfinyl), alkylsulfonyl (e.g., $C_1$–$C_8$alkylsulfonyl), aryl (e.g., phenyl), arylalkyl (e.g., ($C_6$–$C_{18}$aryl)$C_1$–$C_8$alkyl, such as benzyl and phenethyl), aryloxy (e.g., $C_6$–$C_{18}$aryloxy such as phenoxy), arylalkoxy (e.g., ($C_6$–$C_{18}$aryl)$C_1$–$C_8$alkoxy) and/or 3- to 8-membered heterocyclic groups. Certain groups within the formulas provided herein are optionally substituted with from 1 to 3, 1 to 4 or 1 to 5 independently selected substituents.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, and where specified, having the specified number of carbon atoms. Thus, the term $C_1$–$C_6$alkyl, as used herein, indicates an alkyl group having from 1 to 6 carbon atoms. "$C_0$–$C_4$alkyl" refers to a bond or a $C_1$–$C_4$alkyl group. Alkyl groups include groups having from 1 to 8 carbon atoms ($C_1$–$C_8$alkyl), from 1 to 6 carbon atoms ($C_1$–$C_6$alkyl) and from 1 to 4 carbon atoms ($C_1$–$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. "Aminoalkyl" is an alkyl group as defined herein substituted with one or more —$NH_2$ groups. "Hydroxyalkyl" is a hydroxy group as defined herein substituted with one or more —OH groups.

"Alkenyl" refers to a straight or branched hydrocarbon chain comprising one or more unsaturated carbon-carbon bonds, such as ethenyl and propenyl. Alkenyl groups include $C_2$–$C_8$alkenyl, $C_2$–$C_6$alkenyl and $C_2$–$C_4$alkenyl groups (which have from 2 to 8, 2 to 6 or 2 to 4 carbon atoms, respectively), such as ethenyl, allyl or isopropenyl.

"Alkynyl" refers to straight or branched hydrocarbon chains comprising one or more triple carbon-carbon bonds. Alkynyl groups include $C_2$–$C_8$alkynyl, $C_2$–$C_6$alkynyl and $C_2$–$C_4$alkynyl groups, which have from 2 to 8, 2 to 6 or 2 to 4 carbon atoms, respectively. Alkynyl groups include for example groups such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

The term "alkanoyl" refers to an acyl group in a linear or branched arrangement (e.g., —(C=O)-alkyl). Alkanoyl groups include $C_2$–$C_8$alkanoyl, $C_2$–$C_6$alkanoyl and $C_2$–$C_4$alkanoyl groups, which have from 2 to 8, 2 to 6, or 2 to 4 carbon atoms, respectively. "$C_1$alkanoyl" refers to —(=O)—H, which (along with $C_2$–$C_8$alkanoyl) is encompassed by the term "$C_1$–$C_8$alkanoyl."

The term, "alkyl ether" refers to a linear or branched ether substituent linked via a carbon-carbon bond. Alkyl ether groups include $C_2$–$C_8$alkyl ether, $C_2$–$C_6$alkyl ether and $C_2$–$C_6$alkyl ether groups, which have 2 to 8, 2 to 6, or 2 to 4 carbon atoms, respectively. By way of example, a $C_2$alkyl ether group has the structure —$CH_2$—O—$CH_3$.

The term "alkoxycarbonyl" refers to an alkoxy group linked via a carbonyl (i.e., a group having the general structure —C(=O—)—O-alkyl). Alkoxycarbonyl groups include $C_2$–$C_8$, $C_2$–$C_6$, and $C_2$–$C_4$alkoxycarbonyl groups, which have from 2 to 8, 2 to 6, or 2 to 4 carbon atoms, respectively. "$C_1$alkoxycarbonyl" refers to —C(=O)OH, and is encompassed by "$C_1$–$C_8$alkoxycarbonyl."

"Alkanoyloxy," as used herein, refers to an alkanoyl group linked via an oxygen bridge (i.e., a group having the general structure —O—C(=O)-alkyl). Alkanoyloxy groups include $C_2$–$C_8$, $C_2$–$C_6$, and $C_2$–$C_4$alkanoyloxy groups, which have from 2 to 8, 2 to 6, or 2 to 4 carbon atoms, respectively.

As used herein, the term "alkylthio" refers to an alkyl group attached via a thioether linkage. Alkylthio groups include $C_1$–$C_8$alkylthio, $C_1$–$C_6$alkylthio and $C_1$–$C_4$alkylthio, which have from 1 to 8, 1 to 6 or 1 to 4 carbon atoms, respectively.

"Alkylsulfinyl," as used herein, refers to an alkyl group attached via a sulfinyl linkage. Alkylsulfinyl groups include $C_1$–$C_8$alkylsulfinyl, $C_1$–$C_6$alkylsulfinyl, and $C_1$–$C_4$alkylsulfinyl, which have from 1 to 8, 1 to 6, and 1 to 4 carbon atoms, respectively.

By "alkylsulfonyl," as used herein, is meant an alkyl group attached via a sulfonyl linkage. Alkylsulfonyl groups include $C_1$–$C_8$alkylsulfonyl, $C_1$–$C_6$alkylsulfonyl, and $C_1$–$C_4$alkylsulfonyl, which have from 1 to 8, 1 to 6, and 1 to 4 carbon atoms, respectively.

"Alkylamino" refers to a secondary or tertiary amine having the general structure —NH-alkyl or —N(alkyl)(alkyl), wherein each alkyl may be the same or different. Such groups include, for example, mono- and di-($C_1$–$C_8$alkyl)amino groups, in which each alkyl may be the same or different and may contain from 1 to 8 carbon atoms, as well as mono- and di-($C_1$–$C_6$alkyl)amino groups and mono- and di-($C_1$–$C_4$alkyl)amino groups. Alkylaminoalkyl refers to an alkylamino group linked via an alkyl group (i.e., a group having the general structure-alkyl-NH-alkyl or -alkyl-N(alkyl)(alkyl)). Such groups include, for example, mono- and di-($C_1$–$C_8$alkyl)amino$C_1$–$C_8$alkyl, mono- and di-($C_1$–$C_6$alkyl)amino$C_1$–$C_6$alkyl, and mono- and di-($C_1$–$C_4$alkyl)amino$C_1$–$C_4$alkyl, in which each alkyl may be the same or different.

The term "carboxamido" or "amido" refers to an amide group (i.e., —(C=O)$NH_2$). "Alkylcarboxamido" refers to —NHC(=O)alkyl, preferably —NHC(=O)$C_1$–$C_2$alkyl.

"Carbhydryl" is intended to include both branched and straight-chain hydrocarbon groups, which is saturated or unsaturated, having the specified number of carbon atoms.

The term "cycloalkyl" refers to hydrocarbon ring groups, having the specified number of carbon atoms, usually from 3 to about 8 ring carbon atoms, or from. Cycloalkyl groups include $C_3$–$C_8$, and $C_3$–$C_7$ cycloalkyl groups, which have from 3 to 8 and 3 to 7 carbon atoms, respectively. Examples of cycloalkyl groups include cyclopropyl, cyclobutyl, cyclopentyl, and cyclohexyl groups, as well as bridged and caged saturated ring groups such as norbornane or adamantane and the like.

In the term "(cycloalkyl)alkyl," "cycloalkyl" and "alkyl" are as defined above, and the point of attachment is on the alkyl group. This term encompasses, but is not limited to, cyclopropylmethyl, cyclohexylmethyl, and cyclohexylethyl.

The term "halogen" indicates fluorine, chlorine, bromine, or iodine.

"Haloalkyl" refers to both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

As used herein, the term "aryl" indicates aromatic groups containing only carbon in the aromatic ring(s). Such aromatic groups may be further substituted with carbon or non-carbon atoms or groups. Typical aryl groups contain 1 to 3 separate or fused rings, at least one of which is aromatic, and from 6 to about 18 ring atoms, without heteroatoms as ring members. Specifically preferred carbocyclic aryl groups include phenyl and napthyl, including 1-naphthyl and 2-naphthyl. When indicated, carbon atoms present within a carbocyclic ring may be optionally substituted with any of variety of ring substituents, as described above, or with specifically listed substituents.

The term "arylalkyl" refers to an aryl group is linked via an alkyl group. Certain arylalkyl groups are ($C_6$–$C_{18}$aryl)$C_1$–$C_8$alkyl groups (i.e., groups in which a 6- to 18-membered aryl group is linked via a $C_1$–$C_8$alkyl group). Such groups include, for example, groups in which phenyl or naphthyl is linked via a bond or $C_1$–$C_8$alkyl, preferably via $C_1$–$C_4$alkyl, such as benzyl, 1-phenyl-ethyl, 1-phenyl-propyl and 2-phenyl-ethyl.

The term "aryloxy" refers to an aryl group linked via a carbonyl (i.e., a group having the general structure —C(=O)—O-aryl). Phenoxy is a representative aryloxy group.

As used herein, the term "heteroaryl" is intended to indicate a stable 5-to 7-membered monocyclic or bicyclic or 7-to 10-membered bicyclic heterocyclic ring which contains at least 1 aromatic ring that contains from 1 to 4 heteroatoms selected from N, O, and S, with remaining ring atoms being carbon. When the total number of S and O atoms in the heteroaryl group exceeds 1, then these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

The term "heterocyclic group" or "heterocycle" is used to indicate saturated, partially unsaturated, or aromatic groups having 1 or 2 rings, 3 to 8 atoms in each ring and in at least one ring between 1 and 3 heteroatoms selected from N, O, and S. Any nitrogen or sulfur heteroatoms may optionally be oxidized. The heterocyclic group may be attached to its pendant group at any heteroatom or carbon atom that results in a stable structure. The heterocyclic groups described herein may be substituted on a carbon or nitrogen atom if the resulting compound is stable. A nitrogen atom in the heterocycle may optionally be quaternized.

Representative examples of heteroaryl groups and heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"A C5a receptor" is a G-coupled protein receptor that specifically binds C5a protein.

Preferably the C5a receptor is a human C5a receptor such as the protein product of the sequence of the resulting PCR product described by Gerard and Gerard, (1991) *Nature* 349:614–17. The human C5a receptor may also be that described by Boulay (1991) *Biochemistry,* 30(12): 2993–9 (GENBANK Accession No. M62505). Non-primate C5a receptors may be a rat C5a receptor such as a rat C5a receptor, GENBANK Accession Nos. X65862, Y09613, and AB003042, a canine C5a receptor, GENBANK Accession No. X65860, or a guinea pig C5a receptor, GENBANK Accession No. U86103.

A "C5a receptor modulator" is any compound that modulates C5a receptor activation and/or activity (i.e., C5a receptor-mediated signal transduction, as measured using a C5a receptor-mediated chemotaxis, radioligand binding assay, or calcium mobilization assay as provided herein). In certain embodiments, such a modulator may be exhibit an affinity constant or $IC_{50}$ for binding to a C5a receptor of less than 1 micromolar. In other embodiments the a C5a receptor modulator may exhibit an affinity constant or $IC_{50}$ of less than 500 nM, 200 nM, 100 nM, 50 nM, 25 nM, 10 nM or 5 nM in a standard C5a receptor-mediated chemotaxis assay, radioligand binding assay, or calcium mobilization assay. A modulator may be a C5a receptor agonist or antagonist, although, for certain purposes described herein, a modulator preferably inhibits C5a activation resulting from binding of C5a (i.e., the modulator is an antagonist). Preferred antagonists exhibit an antagonist $IC_{50}$ (which is used herein interchangeably with $EC_{50}$) of less than 1 micromolar, preferably less than 100 nanomolar, in an assay of C5a receptor-mediated chemotaxis, radioligand binding, and/or calcium mobilization. In addition, or alternatively, a modulator may act as an inverse agonist of C5a receptor. In certain embodiments, modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for the C5a receptor of that particular species is preferred.

An "inverse agonist" of the C5a receptor is a compound which inhibits the activity of C5a at the C5a receptor, and reduces the activity of the C5a receptor below its basal activity level in the absence of added C5a. Inverse agonists of the C5a receptor may also inhibit binding of C5a to the C5a receptor. The ability of a compound to inhibit the binding of C5a to the C5a receptor may be measured by a binding assay, such as the radioligand binding assay given in Example 51. The basal activity of the C5a receptor may be determined from a GTP binding assay, such as the assay of Example 52. The reduction of C5a activity may also be determined from a GTP binding assay such as the assay of Example 52 or a calcium mobilization assay such as the assay of Example 53.

A "neutral antagonist" of the C5a receptor is a compound which inhibits the activity of C5a at the C5a receptor, but does not significantly change the basal activity of the C5a receptor. Neutral antagonists of the C5a receptor may inhibit the binding of C5a to the C5a receptor.

A "partial agonist" of the C5a receptor elevates the activity of the C5a receptor above the basal activity level of the receptor in the absence of C5a, but does not elevate the activity of the C5a receptor to the level brought about by saturating levels of the natural agonist, C5a. Partial agonist compounds may inhibit the binding of C5a to the C5a receptor. Partial agonists of the C5a receptor usually elevate the active of the C5a receptor from 5% to 90% of the activity level brought about by saturated concentrations of the natural agonist, C5a.

A "C5a receptor modulatory amount" of a compound is an amount that is sufficient to yield a plasma concentration of the compound (or its active metabolite, if a prodrug) high enough to detectably alter (modulate) C5a receptor activity and/or ligand binding, when that concentration is used in an in vitro assay. Suitable in vitro assays include the standard in vitro C5 receptor-mediated chemotaxis assay (described in Example 46 herein); C5a receptor-mediated calcium mobilization assay (described in Example 53 herein); and/or radioligand binding assay such as the assay provided in Example 51.

A "therapeutically effective amount" of a compound is an amount that is sufficient to result in a discernible patient benefit. For example, a therapeutically effective amount may reduce symptom severity or frequency. Alternatively, or in addition, a therapeutically effective amount may improve patient outcome and/or prevent or delay disease or symptom onset.

As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC-(CH_2)_n-COOH$ where n is 0–4 and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited. A wide variety of synthetic procedures is available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water, an organic solvent, or a mixture of the two; generally, nonaqueous media like ether, ethyl acetate, ethanol, isopropanol or acetonitrile are preferred.

A "prodrug" is a compound that may not fully satisfy the structural requirements of the compounds provided herein, but is modified in vivo, following administration to a patient, to produce a compound of Formula I. For example, a prodrug may be an acylated derivative of a compound as provided herein. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol and amine functional groups within the compounds provided herein. Preferred prodrugs include acylated derivatives. Prodrugs may be prepared by modifying functional groups present in the compounds in such a way that the modifications are cleaved to the parent compounds. Those of ordinary skill in the art will recognize various synthetic methods that may be employed to prepare prodrugs of the compounds provided herein.

A "patient" is any individual treated with a C5a modulator as provided herein. Patients include humans, as well as other animals such as companion animals (e.g., dogs and cats) and livestock. Patients may be experiencing one or more symptoms of a condition responsive to C5an receptor modulation, or may be free of such symptom(s) (i.e., treatment may be prophylactic).

C5a Receptor Modulators

As noted above, the present invention provides C5a receptor modulators (i.e., compounds that modulate C5a receptor-mediated signal transduction; preferably compounds that also detectably bind to C5a receptor). C5a receptor modulators may be used to modulate C5a receptor activity in a variety of contexts, including in the treatment of patients suffering from diseases or disorders responsive to C5a receptor modulation, such as autoimmune disorders and inflammatory conditions. C5a receptor modulators may also be used within a variety of in vitro assays (e.g., assays for receptor activity), as probes for detection and localization of C5a receptor and as standards in assays of ligand binding and C5a receptor-mediated signal transduction.

C5a receptor modulators provided herein are aryl imidazoles and related compounds of Formula I (as well as pharmaceutically acceptable salts and prodrugs thereof) that detectably alter, preferably decrease, C5a receptor activation and/or signal transduction activity at submicromolar concentrations. Such an alteration in C5a receptor activity may be measured using a standard in vitro C5a receptor-mediated chemotaxis assay (Example 46), a C5a receptor-mediated calcium mobilization assay (Example 53) and/or a radioligand binding assay (Example 51). The present invention is based, in part, on the discovery that small molecules of Formula I act as antagonists and/or inverse agonists of C5a receptors.

Thus, an embodiment of the invention is directed to compounds and the pharmaceutically acceptables salts of Formula I Formula I

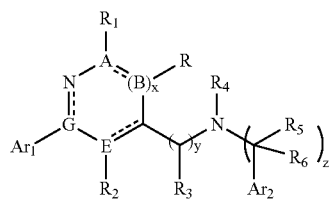

wherein the ring system represented by

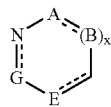

is a 5 membered heteroaryl ring system, in which x is 0, A is chosen from carbon and heteroatoms nitrogen, oxygen, and sulfur, and E and G are independently carbon or nitrogen, provided that the 5 membered heteroaryl ring system does not contain more than 3 heteroatoms or more than 1 oxygen or sulfur atom, or a 6 membered heteroaryl ring system, in which x is 1, and A, B, E, and G are independently chosen from carbon and nitrogen, provided that the 6 membered heteroaryl ring system does not contain more than 3 nitrogen atoms.

R and $R_1$, in this embodiment are independently chosen from:
i) hydrogen, hydroxy, halogen, amino, cyano, nitro, —CHO, —CONH$_2$, $C_1$–$C_6$haloalkyl, $C_1$–$C_6$haloalkoxy,
ii) $C_1$–$C_6$alkyl, $C_1$–$C_6$alkenyl, $C_1$–$C_6$alkynyl, $C_1$–$C_6$alkanoyl, $C_1$–$C_6$alkoxy, $C_3$–$C_7$cycloalkyl, ($C_3$–$C_7$cycloalkyl)$C_1$–$C_4$alkyl, mono- and di-$C_1$–$C_6$alkylamino, mono- and di-$C_1$–$C_6$alkylamino$C_1$–$C_6$alkyl, mono- and di-$C_1$–$C_6$alkylcarboxamide, $C_1$–$C_6$alkoxycarbonyl, —NHSO$_n$$C_1$–$C_6$alkyl, —SO$_n$($C_1$–$C_6$alkyl), —($C_1$–$C_6$alkyl)SO,($C_1$–$C_6$alkyl), —SO$_n$N($C_1$–$C_6$alkyl) ($C_1$–$C_6$alkyl), and phenyl-SO$_n$—, each of which is substituted with from 0 to 3 substituents independently chosen from hydrogen, hydroxy, halogen, amino, cyano, oxo, $C_1$–$C_4$alkyl, $C_1$–$C_4$alkoxy, and $C_1$–$C_2$alkoxycarbonyl, and
iii) naphthyl, phenyl, phenyl$C_1$–$C_4$carbhydryl, pyridyl, thiazolyl, pyrimidinyl, thienyl, pyridyl$C_1$–$C_4$carbhydryl, thiazolyl$C_1$–$C_4$carbhydryl, pyrimidinyl$C_1$–$C_4$carbhydryl, and thienyl$C_1$–$C_4$carbhydryl, each of which is substituted with from 0 to 3 substituents independently chosen from hydroxy, halogen, amino, cyano, nitro, —COOH, —CONH$_2$, —SO$_2$NH$_2$, $C_1$–$C_6$haloalkyl, $C_1$–$C_6$haloalkoxy, $C_1$–$C_6$alkyl, $C_1$–$C_6$alkoxy, 1,3-dioxol-5-yl, $C_1$–$C_6$alkanoyl, $C_1$–$C_6$alkylsulfonyl, $C_1$–$C_6$alkylsulfinyl, $C_1$–$C_6$alkylthio, $C_2$–$C_6$alkanone; $C_1$–$C_6$alkanoyl; $C_2$–$C_6$alkyl ether; $C_1$–$C_6$ alkanoyloxy; $C_1$–$C_6$alkoxycarbonyl, and $C_1$–$C_6$alkylcarboxamide.

$R_2$, when E is Nitrogen, is chosen from $C_1$–$C_7$alkyl, substituted with from 0 to 3 substituents independently chosen from hydroxy, halogen, amino, cyano, oxo, $C_1$–$C_4$alkyl, $C_1$–$C_4$alkoxy, $C_2$–$C_7$ alkenyl, $C_2$–$C_7$ alkynyl, $C_3$–$C_7$cycloalkyl($C_1$–$C_4$alkyl), benzyl, $C_1$–$C_6$haloalkyl, and $C_1$–$C_6$haloalkoxy.

$R_2$, when E is Carbon, is chosen from (i) hydrogen; halogen, and hydroxy; and (ii) $C_1$–$C_7$alkyl substituted with from 0 to 3 substitutents independently chosen from hydroxy, halogen, amino, cyano, oxo, $C_1$–$C_4$alkyl, $C_1$–$C_4$alkoxy, $C_2$–$C_7$alkenyl, $C_2$–$C_7$alkynyl, $C_1$–$C_7$alkoxy; $C_1$–$C_7$alkylamino; $C_3$–$C_7$cycloalkyl($C_1$–$C_4$alkyl), benzyl, $C_1$–$C_6$haloalkyl, and $C_1$–$C_6$haloalkoxy.

When x is 0, $R_1$ and $R_3$ may be joined to form a cycloalkyl ring having from 3 to 7 carbon atoms, which is substituted with from 0 to 4 substituents independently chosen from hydroxy, halogen, cyano, $C_1$–$C_2$alkyl, $C_1$–$C_2$alkoxy, $C_1$–$C_2$haloalkyl, and $C_1$–$C_2$haloalkoxy;

$R_4$ represents $C_1$–$C_6$alkyl, $C_2$–$C_6$ alkenyl, $C_2$–$C_6$ alkynyl, $C_3$–$C_7$ cycloalkyl, $C_3$–$C_7$ cycloalkenyl, ($C_3$–$C_7$cycloalkyl) $C_1$–$C_4$alkyl, ($C_3$–$C_7$cycloalkenyl)$C_1$–$C_4$alkyl, or hexahydro-1,3-benzodioxolylmethyl, each of which is substituted with from 0 to 3 substituents independently chosen from hydrogen, hydroxy, halogen, amino, cyano, $C_1$–$C_2$alkyl, $C_1$–$C_2$alkoxy, and $C_1$–$C_2$alkoxycarbonyl; or $R_4$ represents:
(i) aryl$C_0$–$C_4$alkyl having 1 ring or 2 fused or pendant rings,
(ii) benzyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, $C_1$–$C_4$alkyl, $C_1$–$C_4$alkoxy, $C_1$–$C_2$haloalkyl, and $C_1$–$C_2$haloalkoxy,
(iii) heterocycloalkyl($C_0$–$C_4$alkyl), or
(iv) heteroaryl$C_0$–$C_2$alkyl, having 1 ring to 2 fused or pendant rings, from 5 to 7 members in each ring, and in at least one ring 1 to 3 heteroatoms selected from N, O, and S, wherein each of (i), (ii) (iii) and (iv) are substituted with from 0 to 4 substituents independently chosen from hydroxy, halogen, amino, cyano, nitro, —COOH, —CONH$_2$, —SO$_2$NH$_2$, oxo, $C_1$–$C_6$haloalkyl, $C_1$–$C_6$haloalkoxy, $C_1$–$C_6$alkyl, $C_1$–$C_6$alkoxy, mono- and di-($C_1$–$C_6$)alkylamino, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkyl ether; $C_1$–$C_6$ alkanoyloxy; $C_1$–$C_6$alkoxycarbonyl, and $C_1$–$C_6$alkylcarboxamide.

Ar$_1$ represents phenyl, quinolinyl, isoquinolinyl, phthalizinayl, benzimidazolyl, indanyl, tetralinyl, chromanyl, naphthyl, pyridyl, pyrimidinyl, pyridizinyl, pyrazinyl, pyrazolyl, imidazolyl, thiazolyl, isothiazolyl, pyrrolyl, oxazolyl, furanyl, or thienyl, each of which is substituted with from 0 to 3 substituents independently chosen from hydroxy, halogen, amino, $C_1$–$C_6$alkylamino, $C_1$–$C_6$alkylamino$C_1$–$C_6$alkyl, cyano, nitro, $C_1$–$C_6$haloalkyl, $C_1$–$C_6$ haloalkoxy, $C_1$–$C_6$alkyl, and $C_1$–$C_6$ alkoxy.

Ar$_2$ represents (v) $C_3$–$C_7$cycloalkyl, $C_3$–$C_7$cycloalkyl ($C_1$–$C_4$alkyl), $C_3$–$C_7$cycloalkenyl, $C_3$–$C_7$cycloalkenyl ($C_1$–$C_4$alkyl), or hexahydro-1,3-benzodioxolyl, (vi) aryl having 1 ring or 2 fused or pendant rings, (vii) phenyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, $C_1$–$C_4$alkyl, $C_1$–$C_4$alkoxy, $C_1$–$C_2$haloalkyl, and $C_1$–$C_2$haloalkoxy, or (viii) heteroaryl, having 1 ring or 2 fused or pendant rings, from 5 to 7 members in each ring, and in at least one ring 1 to 3 heteroatoms selected from N, O, and S; wherein each of (v), (vi), (vii) and (viii) are substituted with from 0 to 4 substituents independently chosen from hydroxy, halogen, amino, cyano, nitro, —COOH, —CONH$_2$, —SO$_2$NH$_2$, oxo, $C_1$–$C_6$haloalkyl, $C_1$–$C_6$ haloalkoxy, $C_1$–$C_6$alkyl, $C_1$–$C_6$alkoxy, mono- or di-$C_1$–$C_6$alkylamino, $C_1$–$C_6$alkanoyl, $C_1$–$C_6$alkylsulfonyl, $C_1$–$C_6$alkylsulfinyl, $C_1$–$C_6$alkylthio, $C_2$–$C_6$alkanone, $C_2$–$C_6$alkylether; $C_1$–$C_6$alkanoyloxy $C_1$–$C_6$alkoxycarbonyl, $C_1$–$C_6$alkylcarboxamide, $C_2$–$C_6$cycloalkylamino, and $C_2$–$C_6$cycloalkylamino($C_1$–$C_4$alkyl).

The invention includes compounds and pharmaceutically acceptable salts of Formula I wherein x is 0; A and G are carbon; E is nitrogen; and $R_1$ and $R_3$ are not joined to form a cycloalkyl ring; i.e. compounds of Formula II:

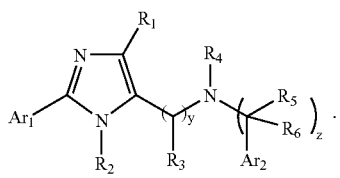

Formula II

The invention also includes compounds and pharmaceutically acceptable salts of Formula I wherein x is 0; A and E are carbon; G is nitrogen; and $R_1$ and $R_3$ are not joined to form a cycloalkyl ring, i.e. compounds of Formula III

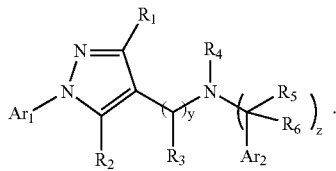

Formula III

The invention further includes compounds and pharmaceutically acceptable salts of Formula I wherein x is 0; E and G are carbon; A is nitrogen; and $R_1$ and $R_3$ are not joined to form a cycloalkyl ring, i.e. compounds of Formula IV

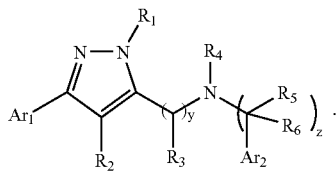

Formula IV

The invention includes compounds and pharmaceutically acceptable salts of Formula I wherein x is 0, G is carbon, A and E are nitrogen, i.e. compounds of Formula V

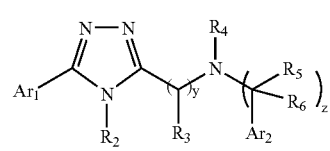

Formula V

In yet another embodiment the invention includes compounds and pharmaceutically acceptable salts of Formula I wherein x is 0, A is sulfur, G and E are carbon; and $R_1$ and $R_3$ are not joined to form a cycloalkyl ring, i.e. compounds of Formula VI

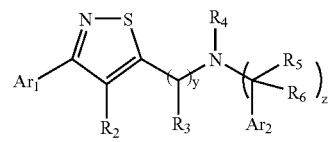

Formula VI

In still another embodiment the invention includes compounds and pharmaceutically acceptable salts of Formula I wherein x is 0, A is oxygen, G and E are carbon; and $R_1$ and $R_3$ are not joined to form a cycloalkyl ring, i.e. compounds of Formula VII

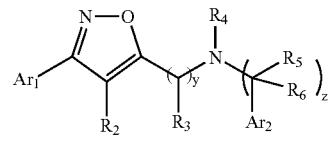

Formula VII

In another embodiment the invention includes compounds and pharmaceutically acceptable salts of Formula I wherein x is 1, and A, E, and G are carbon, and B is nitrogen, i.e. compounds of Formula VIII

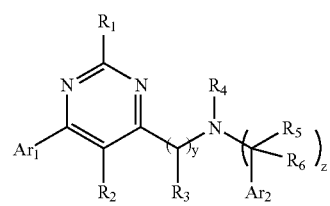

Formula VIII

In another embodiment the invention includes compounds and pharmaceutically acceptable salts of Formula I wherein x is 1, and A, B, E, and G are carbon, i.e. compounds of Formula IX

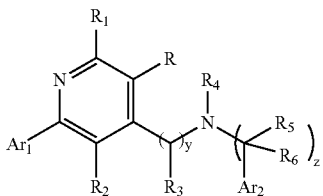

Formula IX

Another embodiment the invention includes compounds and pharmaceutically acceptable salts of Formula I wherein x is 1, and A is nitrogen and B E, and G are carbon, i.e. compounds of Formula X

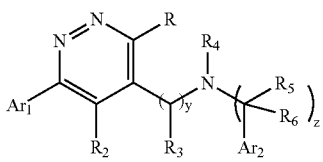

Formula X

Certain embodiments of the invention pertain to compounds and salts of Formula I (or the subformulae thereof) in which z is 1; $R_5$ is hydrogen; and $R_6$ is hydrogen, methyl, or ethyl.

Other embodiments of the invention pertain to compounds and salts of Formula I (or the subformulae thereof) in which z is 1; $R_5$ is hydrogen, $R_6$ is hydrogen, methyl, or ethyl; and $Ar_1$ is phenyl, pyrazolyl, or thienyl, each of which is substituted with 0 to 2 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy.

Still other embodiments of the invention pertain to compounds and salts of Formula I (or the subformulae thereof) in which z is 1, $R_5$ and $R_6$ are hydrogen, and $Ar_1$ is unsubstituted phenyl or unsubstituted thienyl.

The Variable $R_1$:

The invention includes compounds and pharmaceutically acceptable salts of the formulae and embodiments listed herein in which $R_1$ is phenyl substituted with from 0 to 4 substituents independently chosen from hydroxy, halogen, amino, cyano, nitro, —COOH, —CONH$_2$, —SO$_2$NH$_2$, $C_1$–$C_6$ haloalkyl, $C_1$–$C_6$haloalkoxy, $C_1$–$C_6$alkyl, $C_1$–$C_6$alkoxy, 1,3-dioxol-5-yl, $C_1$–$C_6$alkanoyl, $C_1$–$C_6$alkylsulfonyl, $C_1$–$C_6$alkylsulfinyl, $C_1$–$C_6$alkylthio, $C_2$–$C_6$alkanone; $C_1$–$C_6$alkanoyl; $C_2$–$C_6$alkyl ether; $C_1$–$C_6$ alkanoyloxy, $C_1$–$C_6$alkoxycarbonyl, and $C_1$–$C_6$alkylcarboxamide.

In other embodiments the invention pertains to compounds and pharmaceutically acceptable salts of the formulae and embodiments listed herein in $R_1$ is phenyl substituted with from 0 to 2 substituents independently chosen from hydroxy, halogen, amino, cyano, nitro, —COOH, —CONH$_2$, —SO$_2$NH$_2$, $C_1$–$C_2$ haloalkyl, $C_1$–$C_2$ haloalkoxy, $C_1$–$C_2$alkyl, and $C_1$–$C_2$alkoxy.

In other embodiments $R_1$ is unsubstituted phenyl.

The invention pertains to compounds and salts of the formulae described herein in which $R_1$ is thienyl or pyridyl, each of which is substituted with from 0 to 2 substituents independently chosen from hydroxy, halogen, amino, cyano, nitro, —COOH, —CONH$_2$, —SO$_2$NH$_2$, $C_1$–$C_2$ haloalkyl, $C_1$–$C_2$ haloalkoxy, $C_1$–$C_2$alkyl, and $C_1$–$C_2$alkoxy.

In certain embodiments of the formulae described described herein $R_1$ is hydrogen.

In other certain embodiments of the formulae described described herein $R_1$ is halogen, $C_1$–$C_4$alkyl, $C_1$–$C_4$alkoxy, cyano, trifluoromethyl, pentafluoroethyl, $C_1$–$C_2$alkylamino$C_1$–$C_2$alkyl, hydroxymethyl, or hydroxyethyl.

In still other embodiments of the formulae described described herein $R_1$ is halogen.

The invention further includes compounds and salts of the formulae described herein $R_1$ is trifluoromethyl, pentafluoroethyl, difluoromethyl, trifluoromethoxy, or difluoromethoxy.

The Variable $R_2$:

The invention includes compounds and salts Formula I and the subformulae therof in which $R_2$ is propyl, butyl, pentyl, 3-methylbutyl, methoxyethyl.

The Variable $R_3$:

The invention pertains to compounds and salts Formula I and the subformulae therof in which $R_3$ is hydrogen.

The invention further pertains to compounds and salts Formula I and the subformulae therof wherein $R_3$ is $C_1$–$C_5$ alkyl.

The invention includes still other compounds and salts Formula I and the subformulae therof in which $R_4$ represents $C_1$–$C_6$alkyl.

The Variable $R_4$:

The invention pertains to compounds and salts Formula I and the subformulae therof in which $R_4$ represents $C_1$–$C_6$alkyl, $C_2$–$C_6$ alkenyl, $C_2$–$C_6$ alkynyl, $C_3$–$C_7$ cycloalkyl, $C_3$–$C_7$ cycloalkenyl, ($C_3$–$C_7$cycloalkyl)$C_1$–$C_4$alkyl, ($C_3$–$C_7$cycloalkenyl)$C_1$–$C_4$alkyl, or hexahydro-1,3-benzodioxolylmethyl, each of which is substituted with from 0 to 3 substituents independently chosen from hydroxy, halogen, amino, cyano, $C_1$–$C_2$alkyl, $C_1$–$C_2$alkoxy, and $C_1$–$C_2$alkoxycarbonyl.

The includes compounds and salts Formula I and the subformulae therof in which $R_4$ represents $C_1$–$C_6$alkyl, $C_3$–$C_7$ cycloalkenyl, ($C_3$–$C_7$cycloalkyl)$C_1$–$C_4$alkyl, ($C_3$–$C_7$cycloalkenyl) $C_1$–$C_4$alkyl, or hexahydro-1,3-benzodioxolylmethyl.

The invention also pertains to compounds and salts Formula I and the subformulae therof in which $R_4$ represents cyclopentyl, cyclohexyl, cyclohexenyl, cyclohexylmethyl, cyclohexenylmethyl, cyclhexenyl, or hexahydro-1,3-benzodioxolylmethyl.

The invention also includes compounds and salts Formula I and the subformulae therof in which $R_4$ represents cyclohexylmethyl.

Further included in the invention are compounds and salts Formula I and the subformulae therof in which $R_4$ $R_4$ represents (i) aryl or aryl($C_1$–$C_2$)alkyl having 1 ring or 2 fused or pendant rings, (ii) benzyl fused to a 5- to 7-membered saturated or partially unsaturated ring that (a) has 0, 1, or 2 ring atoms independently chosen from N, O and S, with remaining ring atoms being carbon, and (b) is substituted with from 0 to 3 substituents independently chosen from halogen, $C_1$–$C_4$alkyl, $C_1$–$C_4$alkoxy, $C_1$–$C_2$haloalkyl, and $C_1$–$C_2$haloalkoxy;

(iii) saturated or partially unsaturated heterocyclic ($C_0$–$C_4$alkyl) having 1 ring or 2 fused or pendant rings, from 5 to 7 members in each ring, and in at least one ring 1 to 3 heteroatoms selected from N, O, and S; or (iv) heteroaryl or heteroaryl($C_0$–$C_2$alkyl), having 1 ring or 2 fused or pendant rings, from 5 to 7 members in each ring, and in at least one ring 1 to 3 heteroatoms selected from N, O, and S, wherein each of (i), (ii), (iii), and (iv) are substituted with from 0 to 4 substituents independently chosen from hydroxy, halogen, amino, cyano, nitro, —COOH, —CONH$_2$, —SO$_2$NH$_2$, oxo, $C_1$–$C_6$ haloalkyl, $C_1$–$C_6$haloalkoxy, $C_1$–$C_6$alkyl, $C_1$–$C_6$alkoxy, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_1$–$C_6$alkanone, $C_2$–$C_6$alkyl ether, $C_1$–$C_6$ alkanoyloxy, $C_1$–$C_6$alkoxycarbonyl, and $C_1$–$C_6$alkylcarboxamide.

The invention pertains to compounds and salts Formula I and the subformulae therof in which $R_4$ is benzyl substituted with from 0 to 4 substituents independently chosen from hydroxy, halogen, amino, cyano, nitro, —COOH, —CONH$_2$, —SO$_2$NH$_2$, $C_1$–$C_6$ haloalkyl, $C_1$–$C_6$ haloalkoxy, mono- and di-($C_1$–$C_6$)alkylamino, $C_1$–$C_6$ alkyl, $C_1$–$C_6$alkoxy, $C_1$–$C_6$alkanoyl, $C_1$–$C_6$alkylsulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkyl ether, $C_1$–$C_6$ alkanoyloxy, $C_1$–$C_6$alkoxycarbonyl, and $C_1$–$C_6$alkylcarboxamide.

Also included in the invention are compounds and salts Formula I and the subformulae therof in which $R_4$ represents benzyl substituted with from 0 to 3 substituents independently chosen from hydroxy, halogen, amino, cyano, nitro, —COOH, —CONH$_2$, —SO$_2$NH$_2$, —SH, $C_1$–$C_2$haloalkyl, $C_1$–$C_2$ haloalkoxy, mono- and di-($C_1$–$C_2$)alkylamino, $C_1$–$C_4$alkoxy, $C_1$–$C_2$alkanoyl, $C_1$–$C_2$alkylsulfonate, $C_1$–$C_2$alkylsulfonyl, $C_1$–$C_2$alkylsulfinyl, $C_1$–$C_2$alkylthio, $C_2$–$C_3$alkanone, $C_2$–$C_6$alkylether, $C_1$–$C_4$alkanoyloxy, $C_1$–$C_4$alkoxycarbonyl, and $C_1$–$C_2$alkylcarboxamide.

Included in the invention are compounds and salts Formula I and the subformulae therof in which $R_4$ represents benzyl substituted with from 0 to 3 substituents independently chosen from hydroxy, halogen, amino, cyano, nitro, —COOH, —CONH$_2$, —SO$_2$NH$_2$, pentafluoroethyl, tetrafluoromethyl, trifluoromethyl, difluoromethyl, pentafluoroethoxy, tetrafluoroethoxy, trifluoromethoxy, difluoromethoxy, $C_1$–$C_2$ alkyl, $C_1$–$C_4$alkoxy, $C_1$–$C_2$alkanoyl, $C_1$–$C_2$alkylsulfonate, $C_1$–$C_2$alkylsulfonyl, $C_1$–$C_2$alkylsulfinyl, $C_1$–$C_2$alkylthio, $C_2$–$C_3$alkanone; $C_1$–$C_4$alkanoyloxy, ethoxycarbonyl, methoxycarbonyl, and —NH$_2$(C═O)CH$_3$.

The invention also pertains to compounds and salts Formula I and the subformulae therof in which $R_4$ represents pyridylmethyl, pyrimidylmethyl, thienylmethyl, napthylmethyl, indolylmethyl, benzoxadialolylmethyl, benzoxazolylmethyl, quinazolinylmethyl, benzothiazolylmethyl, or benzimidazolylmethyl, optionally substituted with from 0 to 2 substituents independently chosen from hydroxy, halogen, amino, cyano, $C_1$–$C_2$ alkyl, $C_1$–$C_2$alkoxy, $C_1$–$C_2$haloalkyl, $C_1$–$C_2$haloalkoxy, and mono- and di-($C_1$–$C_2$)alkylamino.

In certain embodiments the invention pertains to compounds and salts Formula I and the subformulae therof in which $R_4$ represents benzoxadiazol-5-ylmethyl.

The invention includes compounds and salts Formula I and the subformulae therof in which $R_4$ represents benzyl fused to a 5- to 7-membered saturated or partially unsaturated ring that (a) has 0, 1, or 2 ring atoms independently chosen from N, O and S, with remaining ring atoms being carbon, and (b) is substituted with from 0 to 3 substituents independently chosen from hydroxy, halogen, amino, cyano, nitro, —COOH, —CONH$_2$, —SO$_2$NH$_2$, oxo, $C_1$–$C_6$ haloalkyl, $C_1$–$C_6$ haloalkoxy, $C_1$–$C_6$alkyl, $C_1$–$C_6$alkoxy, mono- and di-($C_1$–$C_6$)alkylamino, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkyl ether; $C_1$–$C_6$ alkanoyloxy; $C_1$–$C_6$alkoxycarbonyl, and $C_1$–$C_6$alkylcarboxamide.

In yet other embodiments the invention includes compounds and salts of Formula I in which $R_4$ represents 1,3-benzodioxol-5-ylmethyl, 2,3-dihydro-1-benzofuran-6-ylmethyl, 2,3-dihydro-1-benzofuran-5-ylmethyl, 2,3-dihydro-1,4-benzodioxin-6-ylmethyl, chroman-6-ylmethyl, chroman-7-ylmethyl, 1,3-benzothiazolylmethyl, 2,3-dihydroindol-5-ylmethyl, each of which is substituted from 0 to 2 substituents independently selected from hydroxy, halogen, amino, cyano, oxo, $C_1$–$C_2$haloalkyl, $C_1$–$C_2$haloalkoxy, $C_1$–$C_2$alkyl, $C_1$–$C_2$alkoxy, mono- and di-($C_1$–$C_2$)alkylamino.

In certain embodiments $R_4$ represents 1,3-benzodioxol-5-ylmethyl.

In still other embodiments $R_4$ is a saturated or partially unsaturated heterocyclic($C_0$–$C_4$alkyl) group having from 4 to 7 ring members, 1 or 2 of which ring members are N, S or O, with remaining ring members being carbon, substituted with from 0 to 4 substituents independently chosen from hydroxy, halogen, amino, cyano, nitro, —COOH, —CONH$_2$, —SO$_2$NH$_2$, oxo, $C_1$–$C_6$ haloalkyl, $C_1$–$C_6$haloalkoxy, $C_1$–$C_6$alkyl, $C_1$–$C_6$alkoxy, mono- and di-($C_1$–$C_6$)alkylamino, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkylether, $C_1$–$C_6$alkanoyloxy, $C_1$–$C_6$alkoxycarbonyl, and $C_1$–$C_6$alkylcarboxamide.

The invention also pertains to compounds and salts of Formula I and the subformulae thereof in which $R_4$ is morpholinyl($C_0$–$C_4$alkyl), azetidinyl($C_0$–$C_4$alkyl), piperazinyl($C_0$–$C_4$alkyl), piperidinyl($C_0$–$C_4$alkyl), pyrrolidinyl ($C_0$–$C_4$alkyl), tetrahydropyranyl($C_0$–$C_4$alkyl), or tetrahydropyridinyl($C_0$–$C_4$alkyl), each of which is substituted by from 0 to 2 substituents independently selected from hydroxy, halogen, amino, cyano, oxo, $C_1$–$C_2$ alkyl, $C_1$–$C_2$alkoxy, $C_1$–$C_2$haloalkyl, $C_1$–$C_2$haloalkoxy, mono- and di-($C_1$–$C_2$)alkylamino.

Also included in the invention are compounds and salts of Formula I and the subformulae thereof in which: $R_4$ is a heteroaryl or heteroaryl($C_1$–$C_2$alkyl) group, having 1 ring or 2 fused or pendant rings, from 5 to 7 members in each ring, and in at least one ring 1 to 3 heteroatoms selected from N, O, and S, substituted with from 0 to 4 substituents independently chosen from hydroxy, halogen, amino, cyano, nitro, —COOH, —CONH$_2$, —SO$_2$NH$_2$, oxo, $C_1$–$C_6$ alkyl, $C_1$–$C_6$alkoxy, $C_1$–$C_6$haloalkyl, $C_1$–$C_6$haloalkoxy, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_1$–$C_6$alkanone, $C_2$–$C_6$alkyl ether, $C_1$–$C_6$ alkanoyloxy, $C_1$–$C_6$alkoxycarbonyl, and $C_1$–$C_6$alkylcarboxamide.

The invention pertains to compounds and salts of Formula I and the subformulae thereof in which $R_4$ is pyridylmethyl, pyrimidinylmethyl, thienylmethyl, naphthylmethyl, indolylmethyl, benzoxadiazolylmethyl, benzoxazolylmethyl, quinazolinylmethyl, or benzimidazolylmethyl, each of which is substituted with from 0 to 2 substituents independently chosen from hydroxy, halogen, amino, cyano, $C_1$–$C_2$haloalkyl, $C_1$–$C_2$haloalkoxy, $C_1$–$C_2$ alkyl, and $C_1$–$C_2$alkoxy.

The Variable Ar₂

In other embodiments the invention pertains to compounds and salts of Formula I and the subformulae thereof in which Ar₂ represents $C_3$–$C_7$cycloalkyl, $C_3$–$C_7$cycloalkenyl, $(C_3$–$C_7$cycloalkyl)$C_1$–$C_4$alkyl, $(C_3$–$C_7$cycloalkenyl)$C_1$–$C_4$alkyl, or hexahydro-1,3-benzodioxolyl, each of which is substituted with from 0 to 3 substituents independently chosen from hydroxy, halogen, amino, cyano, $C_1$–$C_2$alkyl, $C_1$–$C_2$alkoxy, and $C_1$–$C_2$alkoxycarbonyl.

The invention includes compounds and salts of Formula I and the subformulae thereof in which
Ar₂ represents
(i) $C_1$–$C_6$cycloalkyl, $C_3$–$C_7$ cycloalkenyl, or hexahydro-1,3-benzodioxolyl; or
(ii) cyclopentyl, cyclohexyl, cyclohexenyl, or hexahydro-1,3-benzodioxolyl; or
(iii) phenyl substituted with from 0 to 4 substituents independently chosen from hydroxy, halogen, amino, cyano, nitro, —COOH, —CONH₂, —SO₂NH₂, oxo, $C_1$–$C_6$ haloalkyl, $C_1$–$C_6$ haloalkoxy, $C_1$–$C_6$ alkyl, $C_1$–$C_6$alkoxy, mono- and di-$C_1$–$C_6$alkylamino, $C_1$–$C_6$alkanoyl, $C_1$–$C_6$alkylsulfonyl, $C_1$–$C_6$alkylsulfinyl, $C_1$–$C_6$alkylthio, $C_2$–$C_6$alkanone, $C_2$–$C_6$alkylether; $C_1$–$C_6$alkanoyloxy $C_1$–$C_6$alkoxycarbonyl, $C_1$–$C_6$alkylcarboxamide, $C_2$–$C_6$cycloalkylamino, and $C_2$–$C_6$cycloalkylamino ($C_1$–$C_4$alkyl); or
(iv) phenyl substituted with from 0 to 3 substituents independently chosen from hydroxy, halogen, amino, cyano, nitro, —COOH, —CONH₂, —SO₂NH₂, —SH, $C_1$–$C_2$ haloalkyl, $C_1$–$C_2$ haloalkoxy, $C_1$–$C_2$alkyl, $C_1$–$C_4$alkoxy, $C_1$–$C_2$alkanoyl, mono- and di-$C_1$–$C_2$alkylamino, $C_1$–$C_2$alkylsulfonate, $C_1$–$C_2$alkylsulfonyl, $C_1$–$C_2$alkylsulfinyl, $C_1$–$C_2$alkylthio, $C_2$–$C_3$alkanone, $C_2$–$C_6$alkyl ether, $C_1$–$C_4$alkanoyloxy, $C_1$–$C_4$alkoxycarbonyl, $C_1$–$C_2$alkylcarboxamide, and $C_2$–$C_6$cycloalkylamino.

In other embodiments the invention pertains to compounds and salts of Formula I and the subformulae thereof in which Ar₂ represents phenyl substituted with from 0 to 3 substituents independently chosen from hydroxy, halogen, amino, cyano, nitro, —COOH, —CONH₂, —SO₂NH₂, pentafluoroethyl, tetrafluoromethyl, trifluoromethyl, difluoromethyl, pentafluoroethoxy, tetrafluoroethoxy, trifluoromethoxy, difluoromethoxy, $C_1$–$C_2$ alkyl, $C_1$–$C_4$alkoxy, $C_1$–$C_2$alkanoyl, mono- and di-$C_1$–$C_2$alkylamino, $C_1$–$C_2$alkylsulfonate, $C_1$–$C_2$alkylsulfonyl, $C_1$–$C_2$alkylsulfinyl, $C_1$–$C_2$alkylthio, $C_2$–$C_3$alkanone; $C_1$–$C_4$alkanoyloxy, ethoxycarbonyl, methoxycarbonyl, —NH₂(C═O)CH₃, and $C_2$–$C_6$cycloalkylamino.

The invention also includes compounds and salts of Formula I and the subformulae thereof in which Ar₂ represents pyridyl, pyrimidyl, thienyl, naphthyl, indolyl, benzoxadiazolyl, benzoxazolyl, quinazolinyl, or benzimidazolyl substituted with from 0 to 2 substituents independently chosen from hydroxy, halogen, amino, cyano, $C_1$–$C_2$haloalkyl, $C_1$–$C_2$haloalkoxy, $C_1$–$C_2$ alkyl, $C_1$–$C_2$alkoxy, mono- and di-$C_1$–$C_2$alkylamino, and $C_2$–$C_6$cycloalkylamino.

In other embodiments the invention pertains to compounds and salts of Formula I and the subformulae thereof in which Ar₂ represents benzoxadiazol-5-yl.

Further included in the invention are compounds and salts of Formula I and the subformulae thereof in which Ar₂ represents
(i) phenyl fused to a 5- to 7-membered saturated or partially unsaturated ring that (a) has 0, 1, or 2 ring atoms independently chosen from N, O and S, with remaining ring atoms being carbon, and (b) is substituted with from 0 to 3 substituents independently chosen from halogen, $C_1$–$C_4$alkyl, $C_1$–$C_4$alkoxy, $C_1$–$C_2$haloalkyl, and $C_1$–$C_2$haloalkoxy
(ii) a heteroaryl or heteroaryl($C_1$–$C_2$alkyl) group, having 1 ring or 2 fused or pendant rings, from 5 to 7 members in each ring, and in at least one ring 1 to 3 heteroatoms selected from N, O, and S, wherein each of (i) and (ii) are substituted with from 0 to 4 substituents independently chosen from hydroxy, halogen, amino, cyano, nitro, —COOH, —CONH₂, —SO₂NH₂, oxo, $C_1$–$C_6$haloalkyl, $C_1$–$C_6$haloalkoxy, $C_1$–$C_6$alkyl, $C_1$–$C_6$alkoxy, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkyl ether, $C_1$–$C_6$ alkanoyloxy; $C_1$–$C_6$alkoxycarbonyl, and $C_1$–$C_6$alkylcarboxamide.

The invention includes compounds and salts of Formula I and the subformulae thereof in which Ar₂ represents 1,3-benzodioxol-5-yl, 2,3-dihydro-1-benzofuran-6-yl, 2,3-dihydro-1-benzofuran-5-yl, 2,3-dihydro-1,4-benzodioxin-6-yl, chroman-6-yl, chroman-7-yl, 1,3-benzothiazolyl, or 2,3-dihydroindol-5-yl, each of which is substituted with from 0 to 2 substituents independently selected from hydroxy, halogen, amino, cyano, oxo, $C_1$–$C_2$haloalkyl, $C_1$–$C_2$haloalkoxy, $C_1$–$C_2$ alkyl, and $C_1$–$C_2$alkoxy.

In other embodiments the invention pertains compounds and salts of Formula I and the subformulae thereof in which Ar₂ represents Ar₂ represents 1,3-benzodioxol-5-yl.

Additional Embodiments

In another embodiment the invention includes compounds and salts of Formula I in which R₁ and R₃ are joined to form a cycloalkyl ring substituted with from 0 to 4 substituents independently chosen from hydroxy, halogen, cyano, $C_1$–$C_2$alkyl, $C_1$–$C_2$alkoxy, $C_1$–$C_2$haloalkyl, and $C_1$–$C_2$haloalkoxy, e.g. compounds of Formula XI:

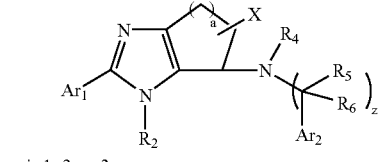

Formula XI a is 1, 2, or 3
X is an optional substituent

The invention includes compounds and salts of Formula XI are those wherein z is 1, R₅ is hydrogen, and R₆ is hydrogen or methyl.

The invention also includes compounds and salts of Formula XI are those wherein a is 1 and XI is represents from 0 to 2 substituents chosen from 1 or 2 groups independently chosen from hydroxy, halogen, $C_1$–$C_2$alkyl, and $C_1$–$C_2$alkoxy.

The invention further includes compounds and salts of Formula XI also include those wherein a is 2 and XI is represents from 0 to 2 optional substituents chosen from 1 or 2 groups independently chosen from hydroxy, halogen, $C_1$–$C_2$alkyl, and $C_1$–$C_2$alkoxy.

The invention pertains to compounds and salts of Formula XI in which R₂ is propyl, butyl, pentyl and 3-methylbutyl; butyl is preferred.

In other embodiments the invention pertains to compounds and salts of Formula XI is phenyl in which Ar₁ is optionally substituted with from 1 to 3 groups independently chosen from hydroxy, halogen, amino, cyano, nitro, $C_1$–$C_2$haloalkyl, and $C_1$–$C_2$haloalkoxy.

Values of $R_4$ for compounds and salts of Formula XI include $C_3$–$C_5$ alkyl.

Other values of $R_4$ for compounds and salts of Formula XI include benzyl optionally substituted with from 1 to 3 groups independently chosen from hydroxy, halogen, amino, cyano, nitro, $C_1$–$C_2$haloalkyl, and $C_1$–$C_2$haloalkoxy.

Values of $Ar_2$ for compounds and salts of Formula XI include phenyl optionally substituted with from 1 to 3 groups independently chosen from hydroxy, halogen, amino, cyano, nitro, $C_1$–$C_2$haloalkyl, $C_1$–$C_2$alkylamino, $C_1$–$C_2$haloalkoxy, and $C_2$–$C_6$cycloalkylamino.

Additional embodiments of the invention include compounds of Formula XII–Formula XXIX as follows:

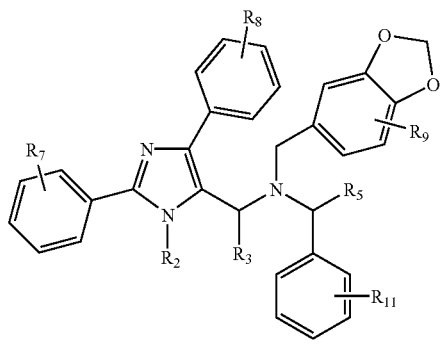

Formula XII

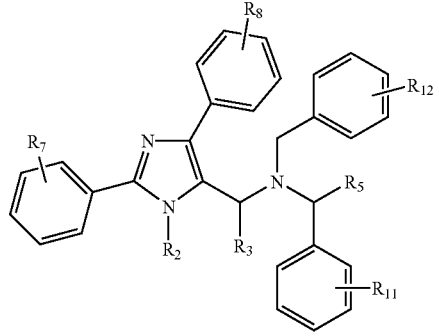

Formula XIII

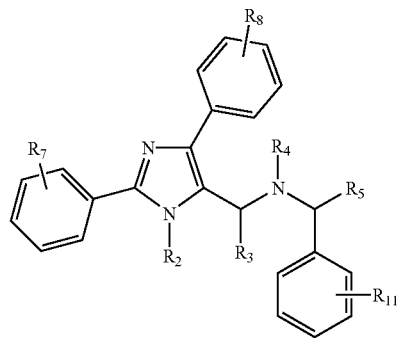

Formula XIV

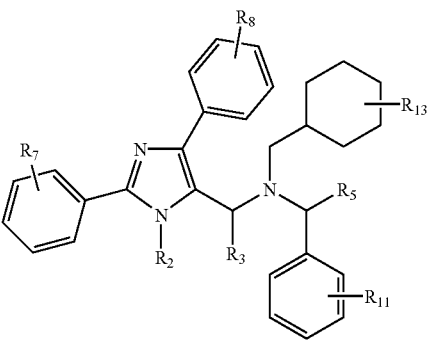

Formula XV

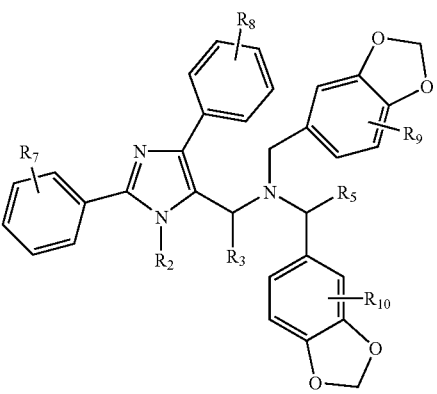

Formula XVI

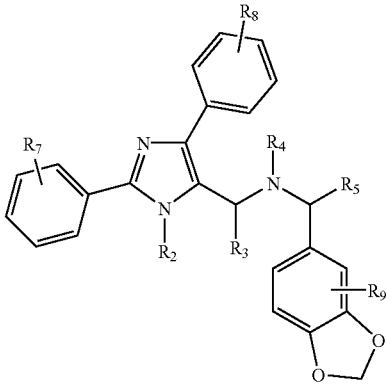

Formula XVII

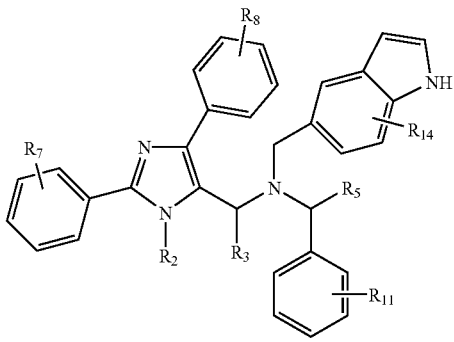

Formula XVIII

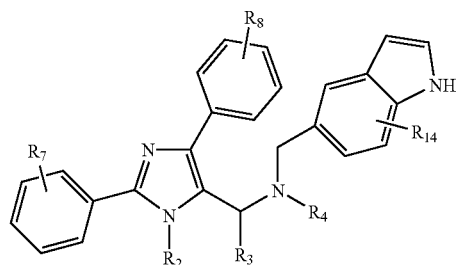
Formula XVIX
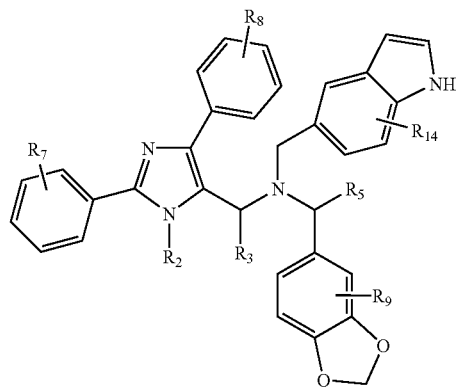
Formula XX
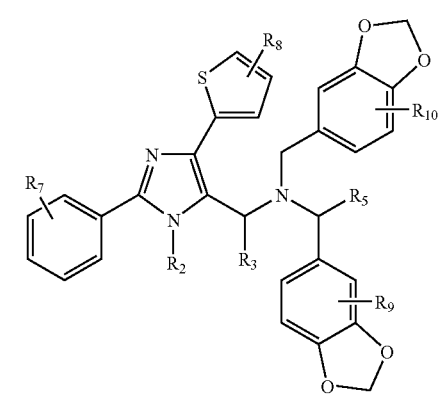
Formula XXI
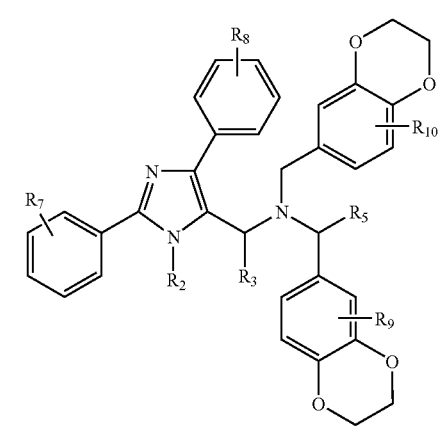
Formula XXII
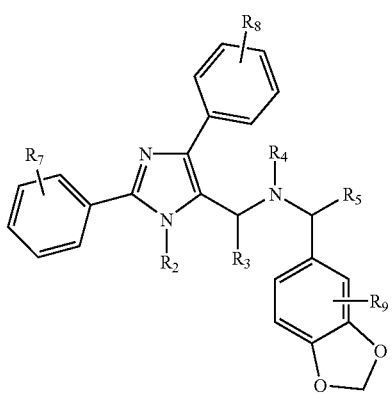
Formula XXIII
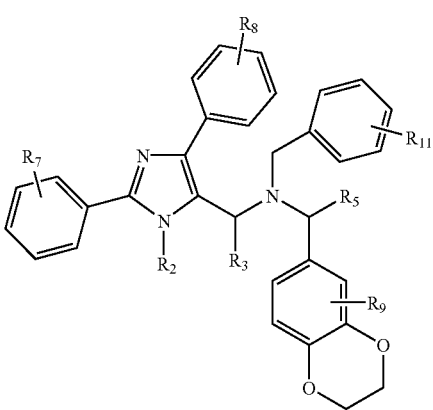
Formula XXIV
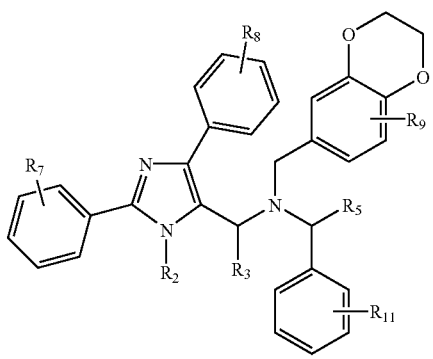
Formula XXV

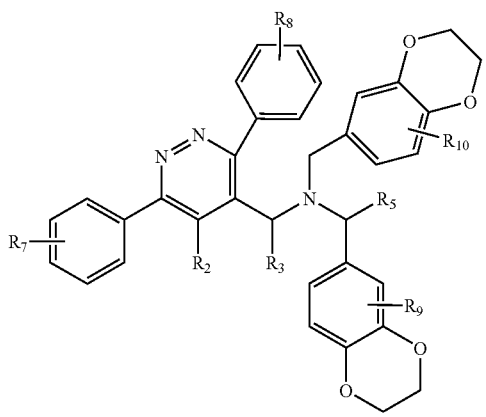

Formula XXVI

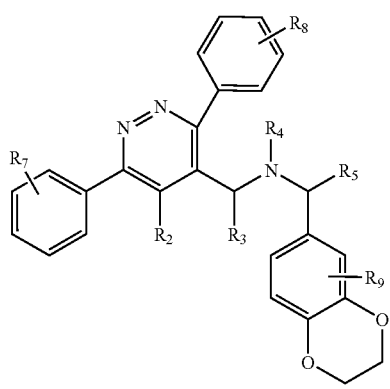

Formula XXVII

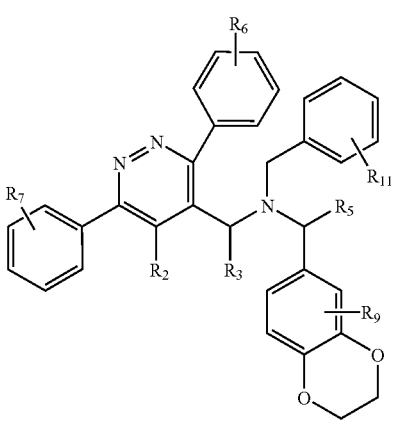

Formula XXVIII

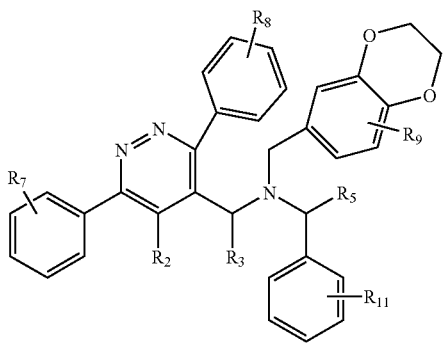

Formula XXIX and the pharmaceutically acceptable salts thereof, wherein:

$R_2$ is $C_3$–$C_5$ alkyl. Preferably $R_2$ is butyl or methoxyethyl $R_3$ is hydrogen or methyl.

$R_4$ in Formula XIV, Formula XVII, and Formula XVIX represents a straight or branched chain $C_3$–$C_6$ alkyl group. Preferably $R_4$ is butyl, isobutyl, neopentyl, or cyclohexylmethyl.

$R_5$ is hydrogen or methyl, preferably hydrogen.

$R_7$ represents 0 to 3 groups independently chosen from hydroxy, cyano, halogen, methyl, ethyl, methoxy, and ethoxy. Preferably $R_7$ is absent or methyl. In certain compounds of the invention the phenyl group shown in Formula XII–XXIX as substituted with $R_7$ (corresponding to $Ar_1$ in Formula I, is instead a thienyl or pyrazolyl group, each of which is optionally substituted by $R_7$). In other compounds of the invention this phenyl group is a 2,6-dimethylphenyl or a 2,6-diethylphenyl.

$R_8$ represents 0 to 3 groups independently chosen from halogen, hydroxy, nitro, methyl, ethyl, methoxy, ethoxy, trifluoromethyl, difluoromethyl, trifluoromethoxy, difluoromethoxy, —CONH$_2$, —OC(=O)CH$_3$, —COOH, methylthio, ethylthio, and —SO$_2$CH$_3$. In certain preferred compounds of the invention the phenyl group shown in Formula XII–XX and Formula XXII–XXIX as substituted with $R_8$ (corresponding to $R_1$ in Formula I for the imidazole compounds and R for the pyridizine compounds, is instead a thienyl group, which is optionally substituted by $R_8$).

$R_9$ and $R_{10}$ may occur at any position on the piperonyl or benzodioxanyl group available for substitution and independently represent 0 to 3 chosen from halogen, methyl, and methoxy. Preferably $R_9$ and $R_{10}$ are absent.

$R_{11}$ and $R_{12}$ independently represent 0 to 3 groups chosen from halogen, hydroxy, nitro, methyl, ethyl, methoxy, ethoxy, trifluoromethyl, difluoromethyl, pentafluoroethyl, —CF$_2$CHF$_2$, trifluoromethoxy, difluoromethoxy, pentafluoroethoxy, —OCF$_2$CHF$_2$, —CONH$_2$, —C(=O)OCH$_3$, —OC(=O)CH$_3$, —COOH, methylthio, ethylthio, —SO$_2$NH$_2$, and —SO$_2$CH$_3$. Compounds in which $R_{11}$ or $R_{12}$ represents a single meta or para substituent are particularly embodied.

$R_{13}$ represents 0 to 3 groups independently chosen from halogen, methyl, and $C_1$–$C_4$ alkoxy. $R_{13}$ is absent in certain embodiments of the invention.

$R_{14}$ may occur at any position on the indole, indazole, or benzisoxazole group available for substitution and represents 0 to 3 groups independently chosen from halogen, methyl, cyano, and amino. $R_{14}$ is absent in certain embodiments of the invention.
Additionally the invention pertains to compounds of Formulae XXX–Formula XXXVIII:
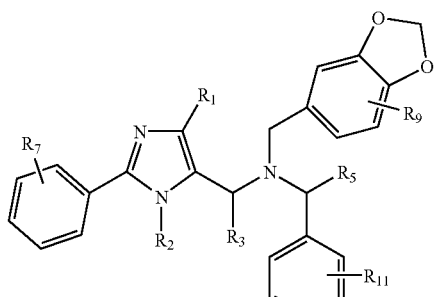
Formula XXX
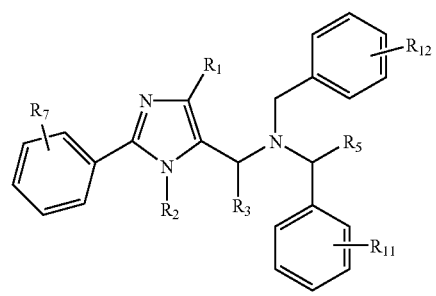
Formula XXXI
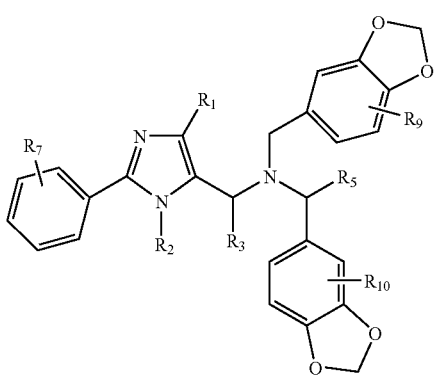
Formula XXII
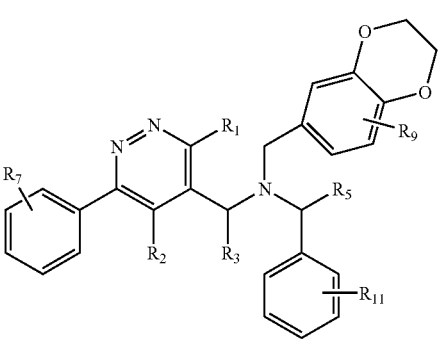
Formula XXXIII
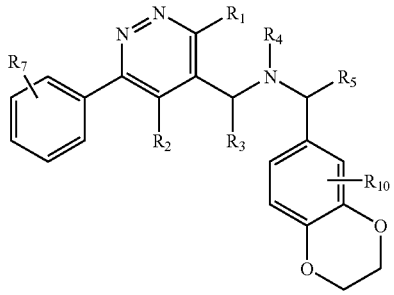
Formula XXXIV
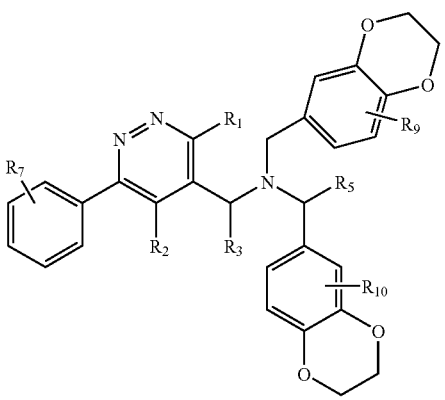
Formula XXXV
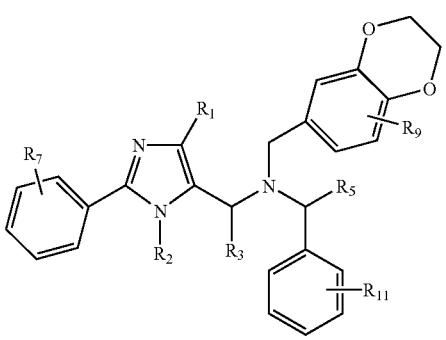
Formula XXXVI
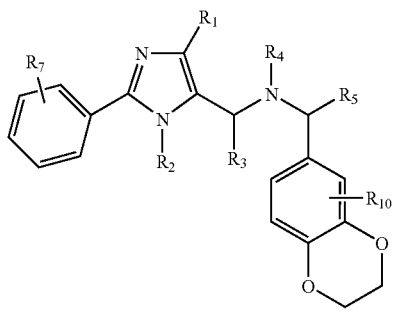
Formula XXXVII

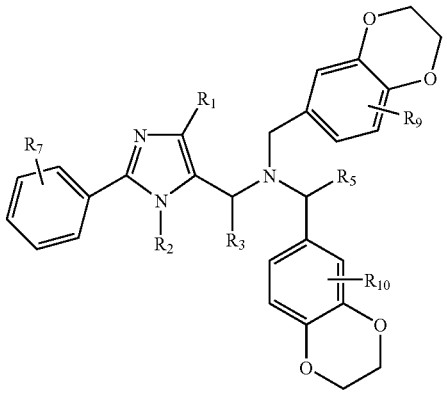

Formula XXXXVIII

As well as compound of Formula XXXVIII-a

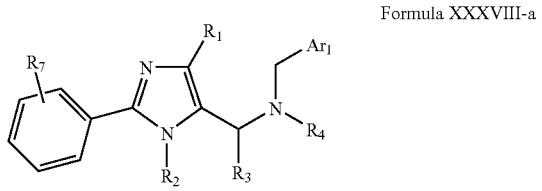

Formula XXXVIII-a in Ar$_2$ is chosen from:

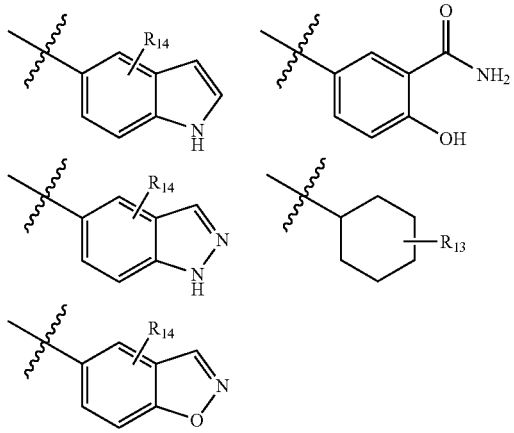

and the pharmaceutically acceptable salts thereof, wherein:

R$_1$ is selected from halogen, cyano, nitro, amino, —CHO, C$_1$–C$_4$alkyl, C$_1$–C$_4$alkoxy, C$_1$–C$_2$haloalyl, C$_1$–C$_2$haloalkoxy, C$_1$–C$_2$alkoxyC$_1$–C$_2$allyl, mono- or di-(C$_1$–C2)alkylaminoC$_1$–C$_2$alkyl, C$_1$–C$_2$alkoxycarbonyl, C$_1$–C$_2$alkylthio, C$_1$–C$_2$alkylsulfinyl, and C$_1$–C$_2$alkylsulfonyl.

Values of R$_1$ include halogen, particularly fluoro, chloro, and bromo. Other preferred values of R$_1$ for compounds and salts of Formula XXX–XXXVIII include cyano, C$_1$–C$_2$haloalkyl, C$_1$–C$_2$haloalkoxy, particularly, trifluoromethyl, difluoromethyl, trifluoromethoxy, and difluoromethoxy.

R$_2$ is C$_3$–C$_5$ alkyl. Preferably R$_2$ is butyl or methoxyethyl

R$_3$ is hydrogen or methyl.

R$_4$ is C$_3$–C$_6$alkyl. In certain embodiments R$_4$ is butyl, isobutyl, neopentyl, and cyclohexylmethyl.

R$_5$ is hydrogen or methyl, preferably hydrogen.

R$_7$ represents 0 to 3 groups independently chosen from hydroxy, cyano, halogen, methyl, ethyl, methoxy, and ethoxy. Preferably R$_7$ is absent or methyl. In certain preferred compounds of the invention the phenyl group shown in Formula XXX–XXXVIII as substituted with R$_7$ (corresponding to Ar$_1$ in Formula I, is instead a thienyl or pyrazolyl group, each of which is optionally substituted by R$_7$). In other embodiments this phenyl group is a 2,6-dimethylphenyl or 2,6-diethylphenyl R$_9$ and R$_{10}$ may occur at any position on the piperonyl or benzodioxanyl group available for substitution and independently represent 0 to 3 chosen from halogen, methyl, and methoxy. Preferably R$_9$ and R$_{10}$ are absent.

R$_{11}$ and R$_{12}$ independently represent 0 to 3 groups chosen from halogen, hydroxy, nitro, methyl, ethyl, methoxy, ethoxy, trifluoromethyl, difluoromethyl, pentafluoroethyl, —CF$_2$CHF$_2$, trifluoromethoxy, difluoromethoxy, pentafluoroethoxy, —OCF$_2$CHF$_2$, —CONH$_2$, —C(=O)OCH$_3$, —OC(=O)CH$_3$, —COOH, methylthio, ethylthio, —SO$_2$NH$_2$, and —SO$_2$CH$_3$. Compounds in which R$_1$, or R$_{12}$ represents a single meta or para substituent are embodied.

The invention is directed to compounds of Formulae XXXIX–Formula XLII

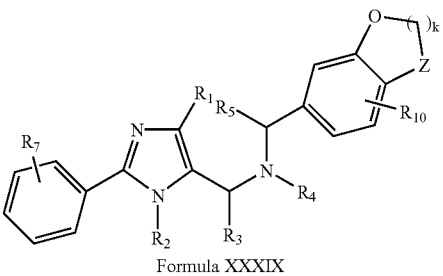

Formula XXXIX

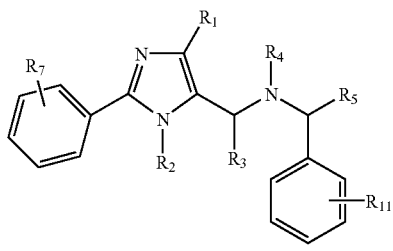

Formula XL

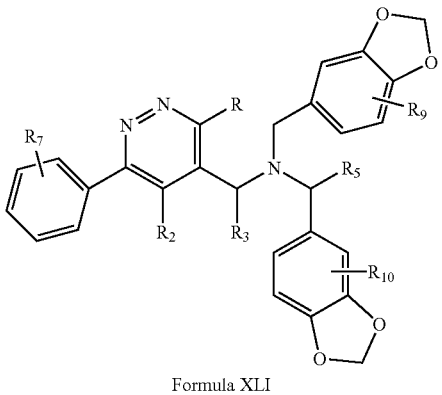

Formula XLI

-continued

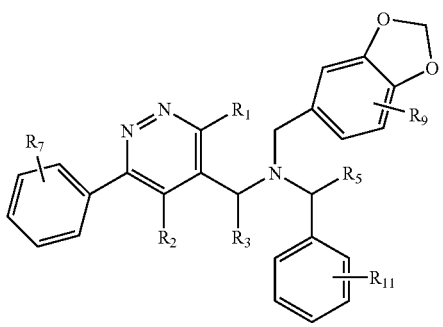

Formula XLII and the pharmaceutically acceptable salts thereof, wherein:

$R_1$ (or R) is selected from halogen, cyano, nitro, amino, —CHO, $C_1$–$C_4$alkyl, $C_1$–$C_4$alkoxy, $C_1$–$C_2$haloalkyl, $C_1$–$C_2$haloalkoxy, $C_1$–$C_2$alkoxy$C_1$–$C_2$alkyl, mono- or di-($C_1$–$C_2$)alkylamino$C_1$–$C_2$alkyl, $C_1$–$C_2$alkoxycarbonyl, $C_1$–$C_2$alkylthio, $C_1$–$C_2$alkylsulfinyl, and $C_1$–$C_2$alkylsulfonyl.

Values of $R_1$ and R include halogen, particularly fluoro, chloro, and bromo. Other preferred values of $R_1$ and R for compounds and salts of Formula XXII–XXIV include cyano, $C_1$–$C_2$haloalkyl, $C_1$–$C_2$haloalkoxy, particularly, trifluoromethyl, difluoromethyl, trifluoromethoxy, and difluoromethoxy.

$R_2$ is $C_3$–$C_5$ alkyl. Preferably $R_2$ is butyl or methoxybutyl $R_3$ is $C_1$–$C_6$ alkyl.

$R_4$ represents $C_1$–$C_6$alkyl, $C_3$–$C_7$ cycloalkenyl, ($C_3$–$C_7$cycloalkyl) $C_1$–$C_4$alkyl, ($C_3$–$C_7$cycloalkenyl) $C_1$–$C_4$alkyl. Preferably $R_4$ is $C_1$–$C_5$ alkyl.

$R_5$ is $C_1$–$C_6$alkyl, preferably methyl.

$R_7$ represents 0 to 3 groups independently chosen from hydroxy, cyano, halogen, methyl, ethyl, methoxy, and ethoxy. Preferably $R_7$ is absent or methyl. In certain preferred compounds of the invention the phenyl group shown in Formula I–XLII as substituted with $R_7$ (corresponding to Ar, in Formula I, is instead a thienyl or pyrazolyl group, each of which is optionally substituted by $R_7$).

$R_9$ and $R_{10}$ may occur at any position on the piperonyl or other heterocyclic group available for substitution and independently represent 0 to 3 chosen from halogen, methyl, and methoxy. Preferably $R_9$ and $R_{10}$ are absent.

$R_{11}$, represents 0 to 3 groups chosen from halogen, hydroxy, nitro, methyl, ethyl, methoxy, ethoxy, trifluoromethyl, difluoromethyl, pentafluoroethyl, —$CF_2CHF_2$, trifluoromethoxy, difluoromethoxy, pentafluoroethoxy, —$OCF_2CHF_2$, —$CONH_2$, —C(=O)$OCH_3$, —OC(=O)$CH_3$, —COOH, methylthio, ethylthio, —$SO_2NH_2$, and —$SO_2CH_3$. Compounds in which $R_1$, or $R_{12}$ represents a single meta or para substituent are particularly preferred.

Representative compounds of Formul I provided herein include, but are not limited to, those specifically described in Examples 141. It will be apparent that the specific compounds recited therein are representative only, and are not intended to limit the scope of the present invention. Further, as noted above, all compounds of the present invention may be present as a hydrate, free base or a pharmaceutically acceptable acid addition salt.

Certain substituted compounds Formulae I (and the subformula thereof) have one or more stereogenic centers. In certain embodiment thereof, such compounds may be enantiomers, and may have an enantiomeric excess of at least 55%. Within further embodiments thereof, such compounds have an enantiomeric excess of at least 60%, 70%, 80%, 85%, 90%, 95%, 98%, or 99%. Certain compounds having one or more stereogenic centers have a enantiomeric excess of at least 99%.

Certain compounds of Formulae I (and the subformulae thereof) have two or more stereogenic centers. In certain embodiments thereof, such compounds have a diastereomeric excess of at least 55%. In other embodiments thereof such compounds have a diastereomeric excess of 60%, 70%, 80%, 85%, 90%, 95%, or 98%. Certain compounds having two or more stereogenic centers have a diastereomeric excess of at least 99%.

Aryl imidazoles and related compounds provided herein detectably alter (modulate) C5a receptor activity and/or ligand binding, as determined using a standard in vitro CS receptor-mediated chemotaxis assay (described in Example 46), radioligand binding (described in Example 51), or C5a receptor-mediated calcium mobilization assay (described in Example 53). Preferred compounds exhibit an $IC_{50}$ of about 500 nM or less in such a standard C5a receptor-mediated chemotaxis, radioligand binding, and/or calcium mobilization assay, more preferably an $IC_{50}$ of about 250 nM or less in such an assay, still more preferably an $IC_{50}$ of about 200, 150, 100, 50, 25, 10, or 5 nM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6–9, columns 19–23, as well as for its discussion of complement and inflammation at columns 1–2. Those of skill in the art will recognize that such assays can be readily adapted to the use of cells or animals of different species as deemed appropriate.

In certain embodiments, preferred compounds have favorable pharmacological properties, including oral bioavailability (such that a sub-lethal or preferably a pharmaceutically acceptable oral dose, preferably less than 2 grams, more preferably of less than or equal to one gram, can provide a detectable in vivo effect such as a reduction of C5a-induced neutropenia), ability to inhibit leukocyte chemotaxis at nanomolar concentrations and preferably at sub-nanomolar concentrations, low toxicity (a preferred compound is non-toxic when a C5a receptor-modulatory amount is administered to a subject), minimal side effects (a preferred compound produces side effects comparable to placebo when a C5a receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1–27. Compound half-life is inversely proportional to the frequency of dosage of a compound required to achieve an effective amount. In vitro half-lives of compounds may be predicted from assays of microsomal half-life as described by Kuhnz and Gieschen (1998) *Drug Metabolism and Disposition* 26:1120–27.

Toxicity and side effects may be assessed using any standard method. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). Toxicity may be also evaluated using the assay detecting an effect on cellular ATP production. Other assays that may be used include bacterial reverse mutation assays, such as an Ames test, as well as standard teratogenicity and tumorogenicity assays. Preferably, administration of compounds provided herein at certain doses (i.e., doses yielding effective in vivo concentrations) does not result in prolongation of heart QT intervals (i.e., as determined by electrocardiography in guinea pigs, minipigs or dogs). When administered daily for five or preferably ten days, such doses also do not cause liver enlargement resulting in an increase of liver to body weight ratio of more than 100%, preferably not more than 75%, and more preferably not more than 50% over matched controls in laboratory rodents (e.g., mice or rats). Such doses also preferably do not cause liver enlargement resulting in an increase of liver to body weight ratio of more than 50%, preferably not more than 25%, and more preferably not more than 10% over matched untreated controls in dogs or other non-rodent mammals.

Certain preferred compounds also do not promote substantial release of liver enzymes (e.g., ALT, LDH or AST) from hepatocytes in vivo. Preferably the above doses do not elevate serum levels of such enzymes by more than 100%, preferably not by more than 75%, and more preferably not by more than 50% over matched untreated controls in vivo in laboratory rodents. Similarly, concentrations (in culture media or other such solutions that are contacted and incubated with cells in vitro) equivalent to two-fold, preferably five-fold, and most preferably ten-fold the minimum in vivo therapeutic concentration do not cause detectable release of any of such liver enzymes from hepatocytes in vitro into culture medium above baseline levels seen in media from untreated cells.

In certain embodiments, preferred compounds exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. The invention also includes highly specific C5a receptor modulatory compounds that exhibit 200-fold greater affinity for the C5a receptor that for other cellular receptors. Such receptors include neurotransmitter receptors such as alpha- or beta-adrenergic receptors, muscarinic receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CRF receptors, thyrotropin releasing hormone receptors or melanin-concentrating hormone receptors). Compounds that act with high specificity generally exhibit fewer undesirable side effects.

Within certain embodiments, modulators provided herein do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,212, which is incorporated herein by reference for its disclosure of a $GABA_A$ receptor binding assays in Examples 14, columns 16–17, in U.S. patent application Ser. No. 10/152,189 which is incorporated herein by reference for its disclosure of an MCH receptor binding assay in Example 2, pages 104–105, in U.S. Pat. No. 6,362,186, which is incorporated herein by reference for its disclosure of CRF1 and NPY receptor binding assays in Examples 19, columns 45–46, in U.S. Pat. No. 6,355,644, which is incorporated herein by reference for its disclosure of a dopamine receptor binding assay at column 10, and in U.S. Pat. No. 6,482,611, which is incorporated herein by reference for its disclosure of VR1 receptor binding assays in Examples 4–5, column 14. It will be apparent that the C5a receptor modulators provided herein may, but need not, bind to one or more other receptors known to mediate inflammatory responses, such as C3a receptors and/or $A_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 52, by measuring small molecule mediated GTP binding in the absence of the natural agonist, C5a. Similarly, in a calcium mobilization assay (e.g., that of Example 53) a small molecule compound can be directly assayed for the ability of the compound to stimulate calcium levels in the absence of the natural agonist, C5a. The preferred extent of C5a agonist activity exhibited by compounds provided herein is less than 10%, 5% or 2% of the response elicited by the natural agonist, C5a.

Additionally, preferred C5a receptor modulators do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity. Preferred C5a receptor modulators also do not exhibit cytotoxicity in vitro or in vivo, are not clastogenic (e.g., as determined using a mouse erythrocyte precursor cell micronucleus assay, an Ames micronucleus assay, a spiral micronucleus assay or the like) and do not induce sister chromatid exchange (e.g., in Chinese hamster ovary cells). Also preferred are C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I (or any other formula specifically recited herein) may have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^{2}H$) can afford certain therapeutic advantages resulting from greater metabolic stability, for example increased in vivo half-life or reduced dosage requirements and, hence, may be preferred in some circumstances.

Methods of Use

C5a modulators provided herein may be used as agonists or (preferably) antagonists of C5a receptors in a variety of contexts, both in vitro and in vivo. Within certain aspects, C5a antagonists may be used to inhibit the binding of C5a receptor ligand (e.g., C5a) to C5a receptor in vitro or in vivo. In general, such methods comprise the step of contacting a C5a receptor with a sufficient amount of one or more substituted compound of Formula I as provided herein, in the presence of C5a receptor ligand in aqueous solution and under conditions otherwise suitable for binding of the ligand to C5a receptor. The C5a receptor may be present in suspension (e.g., in an isolated membrane or cell preparation), or in a cultured or isolated cell. Within certain embodiments, the C5a receptor is expressed by a cell present in a patient, and the aqueous solution is a body fluid. In general, the amount of C5a receptor modulator contacted with the receptor should yield a concentration in the aqueous solution sufficient to inhibit C5a binding to C5a receptor in vitro as measured, for example, using a radioligand binding assay as described in Example 51, a calcium mobilization assay as described in Example 53, or a chemotaxis assay as described in Example 46. Preferably the concentration is sufficient to inhibit chemotaxis of white blood cells in an in vitro chemotaxis assay, so that the levels of chemotaxis observed in a control assay (e.g., one to which a compound provided herein has not been added) are significantly higher (significance here measured as $p \leq 0.05$ using a conventional parametric statistical analysis method such as a student's T-test) than the levels observed in an assay to which a compound as described herein has been added.

Also provided herein are methods for modulating, preferably inhibiting, the signal-transducing activity of a C5a receptor. Such modulation may be achieved by contacting a C5a receptor (either in vitro or in vivo) with an effective amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. In general, an effective amount of C5a modulator(s) is an amount sufficient to yield a concentration (in an aqueous solution that is in contact with the receptor) that is sufficient to modulate C5a receptor signal transducing activity in vitro within a calcium mobilization assay as described in Example 53 or C5a receptor-mediated cellular chemotaxis within an assay as described in Example 46. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to C5a receptor modulation" if modulation of C5a receptor activity results reduction of inappropriate activity of a C5a receptor, regardless of the amount of C5a receptor ligand present locally and/or in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimmune disorders—e.g., rheumatoid arthritis, systemic lupus erythematosus (and associated glomerulonephritis), psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, and hyperacute rejection of transplanted organs.

Inflammatory disorders and related conditions—e.g., neutropenia, sepsis, septic shock, Alzheimer's disease, stroke, inflammation associated with severe burns, lung injury, and ischemia-reperfusion injury, osteoarthritis, as well as acute (adult) respiratory distress syndrome (ARDS), systemic inflammatory response syndrome (SIRS), and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via, a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and/or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Treatment methods provided herein include in general administration to a patient an effective amount of one or more compounds of the invention. Suitable patients include those patients suffering from or susceptible to (i.e., prophylactic treatment) a disorder or disease identified herein. Typical patients for treatment in accordance with the invention include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

As noted above, compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Pharmaceutical Preparations

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an active compound prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

Compositions intended for oral use may be prepared according to any method known to the art for the manufacture of pharmaceutical compositions and may contain one or more agents sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate), and condensation products of partial esters derived from fatty acids and hexitol with ethylene oxide (e.g., polyoxyethylene sorbitan monoleate). An emulsion may also comprise one or more sweetening and/or flavoring agents.

The pharmaceutical composition may be prepared as a sterile injectible aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectible compositions, and adjuvants such as local anesthetics, preservatives and/or buffering agents can be dissolved in the vehicle.

C5a receptor modulators may also be administered in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

C5a receptor modulators provided herein are generally administered in an amount that achieves a concentration in a body fluid (e.g., blood, plasma, serum, CSF, synovial fluid, lymph, cellular interstitial fluid, tears or urine) that is sufficient to detectably inhibit the binding of C5a to C5a receptor when assayed in vitro. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5–20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to C5a receptor modulation (e.g., rheumatoid arthritis, psoriasis, cardiovascular disease, reperfusion injury, bronchial asthma, Alzheimer's disease, stroke, myocardial infarction, atherosclerosis, ischemic heart disease or ischemia-reperfusion injury). Packaged pharmaceutical compositions may include a container holding a effective amount of at least one C5a receptor modulator as described herein and instructions (e.g., labeling) indicating that the contained composition is to be used for treating a condition responsive to C5a receptor modulation in the patient Preparation of Compounds Representative methods for preparing the compounds of the invention are shown in the following Schemes. A number of abbreviations are used in the schemes and accompanying examples and are listed here.

| ABBREVIATIONS USED | |
|---|---|
| DMF | dimethylformamide |
| DMA | dimethylacetamide |
| DME | ethylene glycol dimethyl ether |
| THF | tetrahydrofuran |
| DMSO | dimethyl sulfoxide |
| DCM | dichloromethane |
| DCE | 1,2-dichloroethane |
| MeOH | methanol |
| EtOH | ethanol |
| Et$_2$O | diethyl ether |
| Hex | hexane |
| HOAc | acetic acid |
| AcOH | acetic acid |
| NaOAc | sodium acetate |
| AcONa | sodium acetate |
| TFA | trifluoroacetic acid |
| pTsOH | p-toluenesulfonic acid |
| HCl | hydrochloric acid |
| H$_3$O$^+$ | aqueous acid |
| HCHO | formaldehyde |
| TEA | triethylamine |

| -continued | |
|---|---|
| ABBREVIATIONS USED | |
| MsCl | methanesulfonyl chloride |
| MeLi | methyl lithium |
| n-BuLi | n-butyllithium |
| SAMP | (S)-(−)-1-amino-2-(methoxymethyl)pyrrolidine |
| RAMP | (R)-(+)-1-amino-2-(methoxymethyl)pyrrolidine |
| EtOAc | ethyl acetate |
| NaOEt | sodium ethoxide |
| NaOH | sodium hydroxide |
| KOH | potassium hydroxide |
| NH$_4$OH | ammonium hydroxide |
| NH$_3$—H$_2$O | ammonium hydroxide |
| Na$_2$SO$_4$ | sodium sulfate |
| MgSO$_4$ | magnesium sulfate |
| K$_2$CO$_3$ | potassium carbonate |
| Cs$_2$CO$_3$ | cesium carbonate |
| NaH | sodium hydride |
| MeI | iodomethane |
| BuBr | n-butyl bromide |
| n-BuI | n-butyl iodide |
| NaCl | sodium chloride |
| NaI | sodium iodide |
| CDI | 1,1'-carbonyldiimidazole |
| SOCl$_2$ | thionyl chloride |
| POCl$_3$ | phosphorous oxychloride |
| Me$_2$NH | dimethyl amine |
| RB(OH)$_2$ | alkyl or aryl boronic acid |
| Pd(PPh$_3$)$_4$ | tetrakis(triphenylphosphine)palladium (0) |
| NaBH$_4$ | sodium borohydride |
| BH$_3$ | borane |
| NaBH(OAc)$_3$ | sodium triacetoxyborohydride |
| Br$_2$ | bromine |
| NBS | N-bromosuccinimde |
| NCS | N-chlorosuccinimde |
| CuBr$_2$ | copper (II) bromide |
| DAST | (diethylamino)sulfur trifluoride |
| [O] | oxidation |
| AgNO$_3$ | silver nitrate |
| DDQ | 2,3-dichloro-5,6-dicyano-1,4-benzophenone |
| MnO$_2$ | manganese(II) dioxide |
| SiO$_2$ | silica |
| LC-MS | liquid chromatography/mass spectrometry |
| HPLC | high pressure liquid chromatography |
| TLC | thin layer chromatography |
| $^1$H NMR | proton nuclear magnetic resonance |
| MHz | megahertz |
| Hz | hertz |
| δ | chemical shift |
| CDCl$_3$ | deuterated chloroform |
| MS | mass spectrometry |
| m/z | mass/charge ratio |
| (M + 1) | mass + 1 |
| [α]$_D$ | specific rotation |
| c | concentration |
| eq. | equivalents |

Within Schemes 1–10 the variables e.g., Ar$_1$, Ar$_2$, R$_1$, R$_2$, R$_3$ and R$_4$, are defined as above for Formula I, unless otherwise specified.

Scheme 1.
Synthesis of 1-Alkyl-2-aryl-5-aminomethylimidazoles

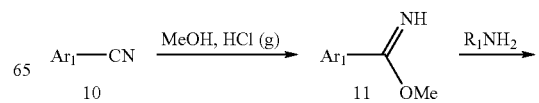

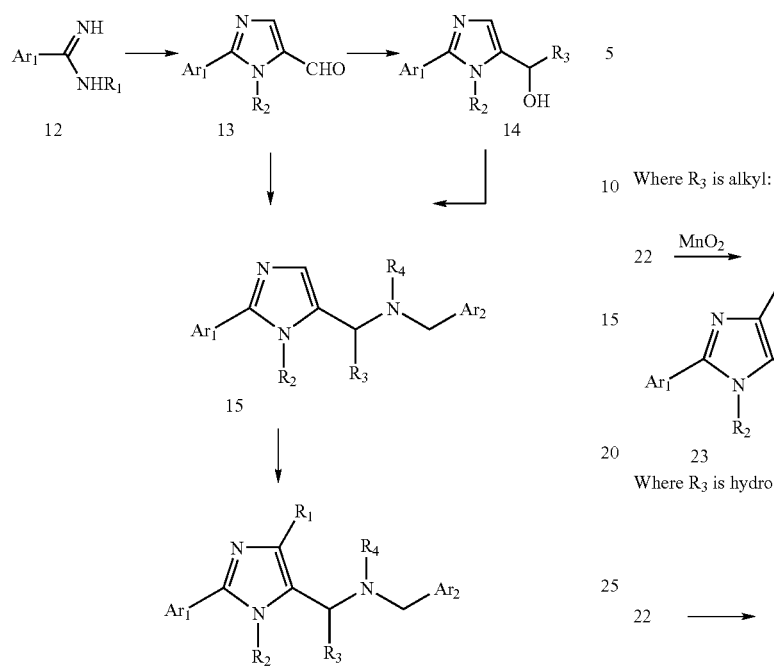

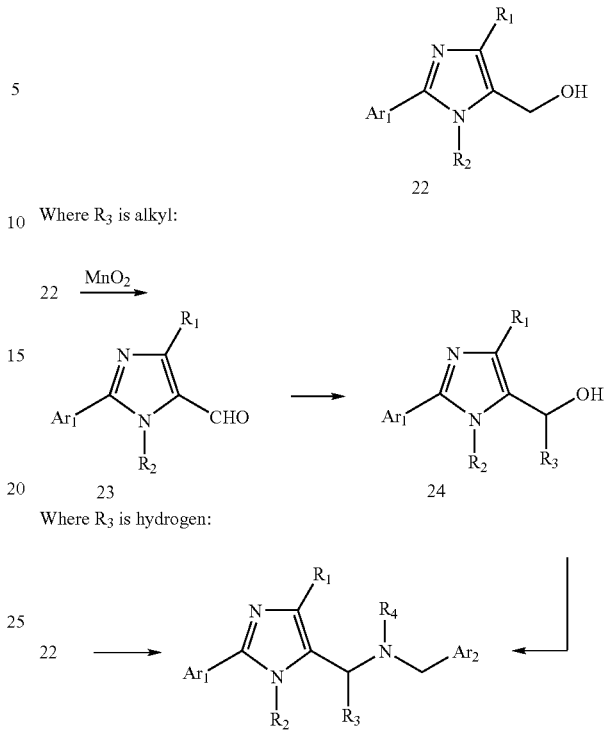

Where R₃ is alkyl:

Where R₃ is hydrogen:

As shown in Scheme 1, an appropriately substituted arylnitrile 10 is converted to the imidate 11 via treatment with hydrogen chloride gas in methanol followed by subsequent treatment with base to release the free base. Amidine 12 is prepared from 11 by treatment with a primary amine. 2-Arylimidazole-4-carboxaldehyde 13 is prepared from 12 by one of several methods described in the chemical literature, for instance, by treatment with 2-bromo-3-isopropoxyacrolein in the presence of base. See, for example, J. Org. Chem., 62: 8449 (Shilcrat et al., 1997).

Aldehyde 13 can then be transformed into hydroxymethylimidazole by treatment with the appropriate organometallic. The hydroxy group of 14 is converted to either a halogen or sulfonate ester leaving group. Treatment of this intermediate with an appropriate secondary amine in the presence of base provides 2-aryl-4-aminomethylimidazole 15. Alternatively, the aminoalkyl functionality of 15 may be elaborated by sequential amination-acylation-reduction steps. In situations where R₁ is a halogen, it may be prepared from 15 (R₁=H) by treatment with the molecular halogen, a halosuccinimide or the like.

As shown in Scheme 2, an appropriately substituted 2-aryl-4-substituted imidazole 20 can be N-alkylated by treatment with base such as sodium hydride, and an alkyl halide, or alkylsulfonate ester to provide the trisubstituted imidazole 21. Hydroxymethylation of 21 under the conditions of the Mannich reaction provides hydroxymethylimidazole 22. In examples where R₃ is alkyl, the hydroxymethyl derivative 24 is prepared from 22 by oxidation to aldehyde 23 and subsequent treatment with an appropriate organometallic reagent such as an alkyl lithium or Grignard reagent. Conversion of 22 or 24 to the desired 2-aryl-5-aminomethylimidazoles is carried out by conversion of the hydroxymethyl to a halogen or sulfonate ester leaving group followed by treatment with a secondary amine. Alternatively, the aminoalkyl functionality of the 2-aryl-5-aminomethylimidazole product may be elaborated by sequential amination-acylation-reduction steps.

The 2-aryl-4-substituted imidazole 20 may be prepared by methods described in the chemical literature, for instance, via condensation of an arylamidine with a halomethyl or hydroxymethyl ketone.

Scheme 2.
Synthesis of 2-Arylimidazoles

Where R₁ is alkyl:

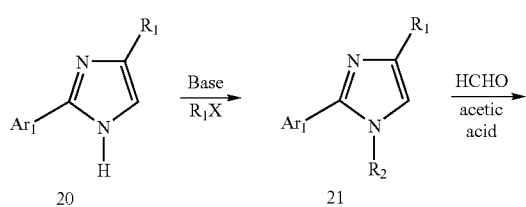

Scheme 3.
Preparation of Cycloalkylimidazoles

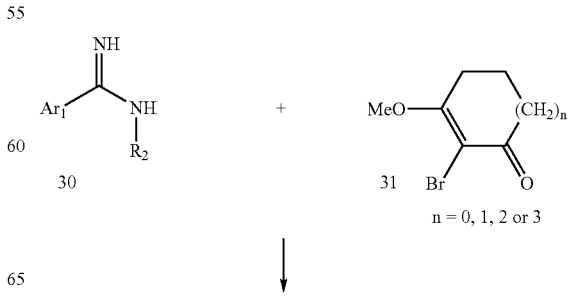

n = 0, 1, 2 or 3

-continued

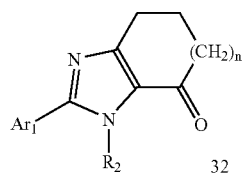
32

↓

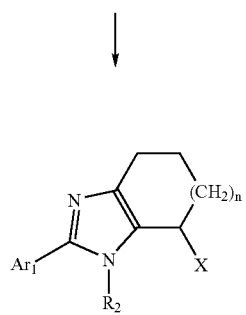

Compound 33 X = OH
Compound 34 X = halogen or sulphonate ester

↓

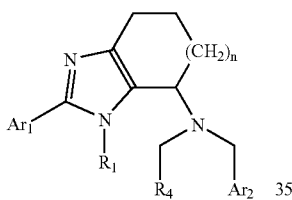
35

An illustration of the preparation of compounds of the Cycloalkylimidazole compounds of the present invention is given in Scheme 3. Within Scheme 3 the variables $Ar_1$, $Ar_2$, $R_2$, $R_3$, and $R_4$ are as defined previously.

As shown in Scheme 3, an appropriately substituted arylamidine 30 is condensed with an appropriately substituted 2-halo-3-alkoxyenone 31 to provide a 2-aryl-4,5-cycloalkylimidazole 32. The ketone functionality of 32 can be reduced to give the cyclic alcohol 33. Compounds of general formula 34 can be prepared from 33 by one of several methods described in the chemical literature, for instance, by treatment with thionyl chloride or by treatment with an alkyl or arylsulphonyl chloride in the presence of base.

Compounds of formula 34 can then be transformed into compounds of general Formula 35 by direct treatment with the appropriate secondary amine. Alternatively, the X functionality of 34 may be transformed into a tertiary amine in a stepwise manner. In this case, 34 would be treated with a primary amine to provide an intermediate secondary amine. This, in turn, could be alkylated to give cycloalkylimidazole compounds of the invention.

Scheme 4.
Preparation of Aryl Pyridines

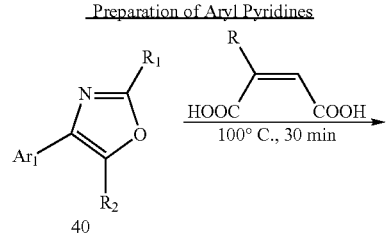
40

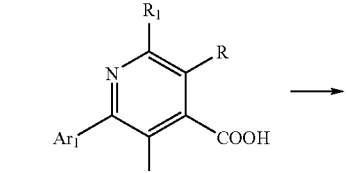
41

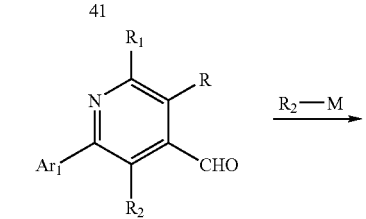
42

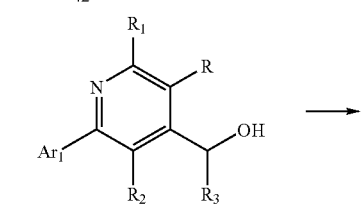
43

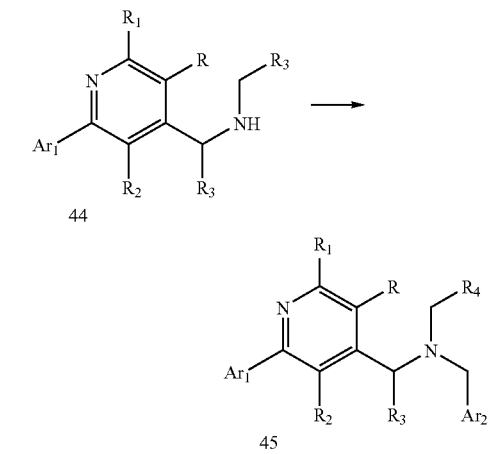
44

45

An illustration of the preparation of pyridine compounds of the present invention is given in Scheme 4. Those having skill in the art will recognize that the starting materials may be varied and additional steps employed to produce compounds encompassed by the present invention. Within Scheme 4 the variables $Ar_1$, $Ar_2$, R, $R_1$, $R_2$, $R_3$, and $R_4$ are defined as previously described.

As shown in Scheme 4, an appropriately substituted 4-phenyloxazole 40 is condensed with an appropriately substituted maleic acid to provide a 2-phenylisonicotinic acid 41. The carboxylic acid functionality of 41 can be reduced directly to the primary alcohol (43, $R_3$=H) or converted by methods known to the art to an intermediate aldehyde 42 and subsequently treated with the appropriate organometallic (for cases where $R_3$ is alkyl) to give a secondary alcohol 43. Compounds of general formula 44 can be prepared from 43 by one of several methods described in the chemical literature, for instance, by initial treatment with thionyl chloride or with an alkyl or arylsulphonyl chloride in the presence of base, followed by subsequent condensation with a primary amine. Compounds of formula 44 can then be transformed into compounds of formula 45 by direct treatment with the appropriate alkylating agent or, alternatively, by reductive alkylation. Alternatively, the tertiary amine functionality of formula 45 may be realized directly from compounds of formula 43 by initial treatment with thionyl chloride or with an alkyl or arylsulphonyl chloride in the presence of base, followed by subsequent condensation with a secondary amine.

An illustration of the preparation of arylpyrazole compounds of the present invention is given in Scheme 5. Within Scheme 5 the variables $Ar_1$, $Ar_2$, $R_1$, $R_2$, $R_3$, and $R_4$ are defined as previously described.

As shown in Scheme 5, an appropriately substituted phenylhydrazine adduct 50 is condensed with an appropriately substituted α-ketoester 51, in the presence of a Lewis acid, preferably $ZnCl_2$, with heating at 50–200° C., preferably at 125° C. to provide a 1-phenylpyrazole ester 52. The carboxylic acid functionality of 52 can be reduced directly to the primary alcohol (53, $R_3$=H) or converted by methods known to the art to an intermediate aldehyde and subsequently treated with the appropriate the appropriate organometallic (for cases where $R_3$ is alkyl) to give a secondary alcohol 53. Compounds of general formula 54, where LG represents a leaving group, can be prepared from 53 by one of several methods described in the chemical literature, for instance, by initial treatment with thionyl chloride or with an alkyl or arylsulphonyl chloride in the presence of base, followed by subsequent condensation with a primary amine. Compounds of formula 54 can then be transformed into compounds of formula 58 by sequential treatment with the appropriate primary amine followed by direct alkylation or reductive alkylation of the intermediate secondary amine. Alternatively, the tertiary amine functionality of formula 58 may be realized directly from compounds of formula 53 by initial treatment with thionyl chloride or with an alkyl or arylsulphonyl chloride in the presence of base, followed by subsequent condensation with a secondary amine.

An alternative route to the preparation of compounds of Formula 58 from the 1-phenylpyrazole ester 52 may be realized by hydrolysis of 52 to a carboxylic acid of general structure 56, followed by amide formation to provide 57 and, finally, reduction of the amide functionality to the tertiary amine of 58 ($R_3$=H).

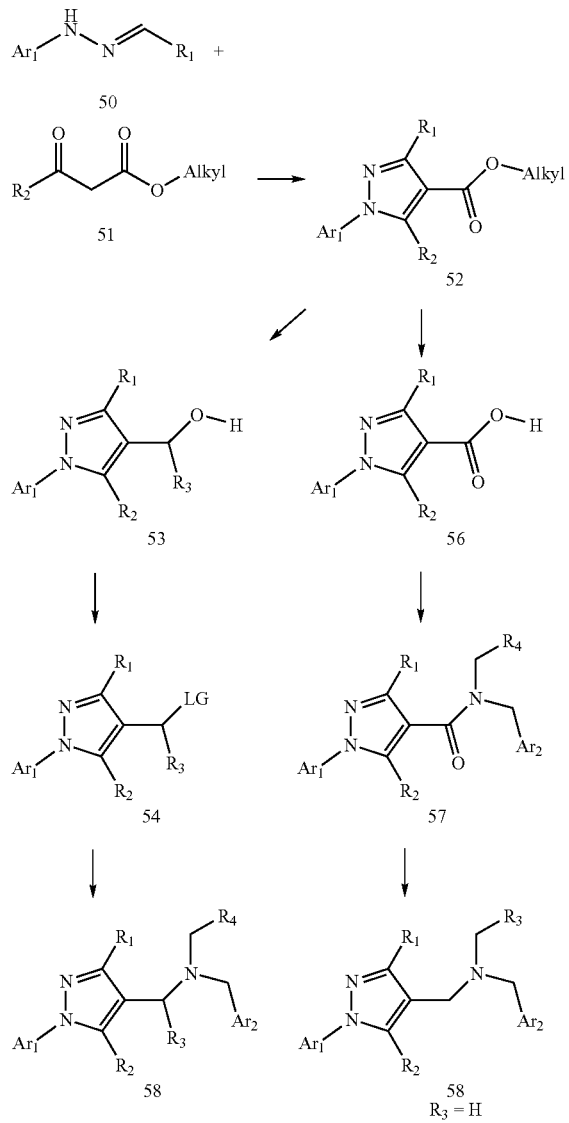

Scheme 5.
Preparation of Arylpyrazoles

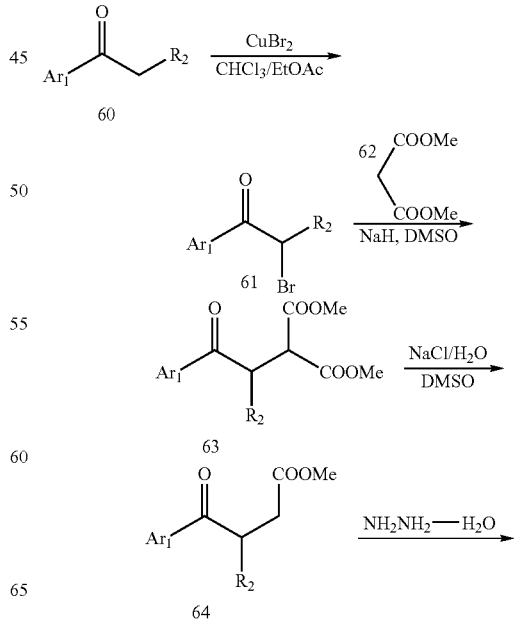

Scheme 6.
Preparation of 6-aryl-pyridazine

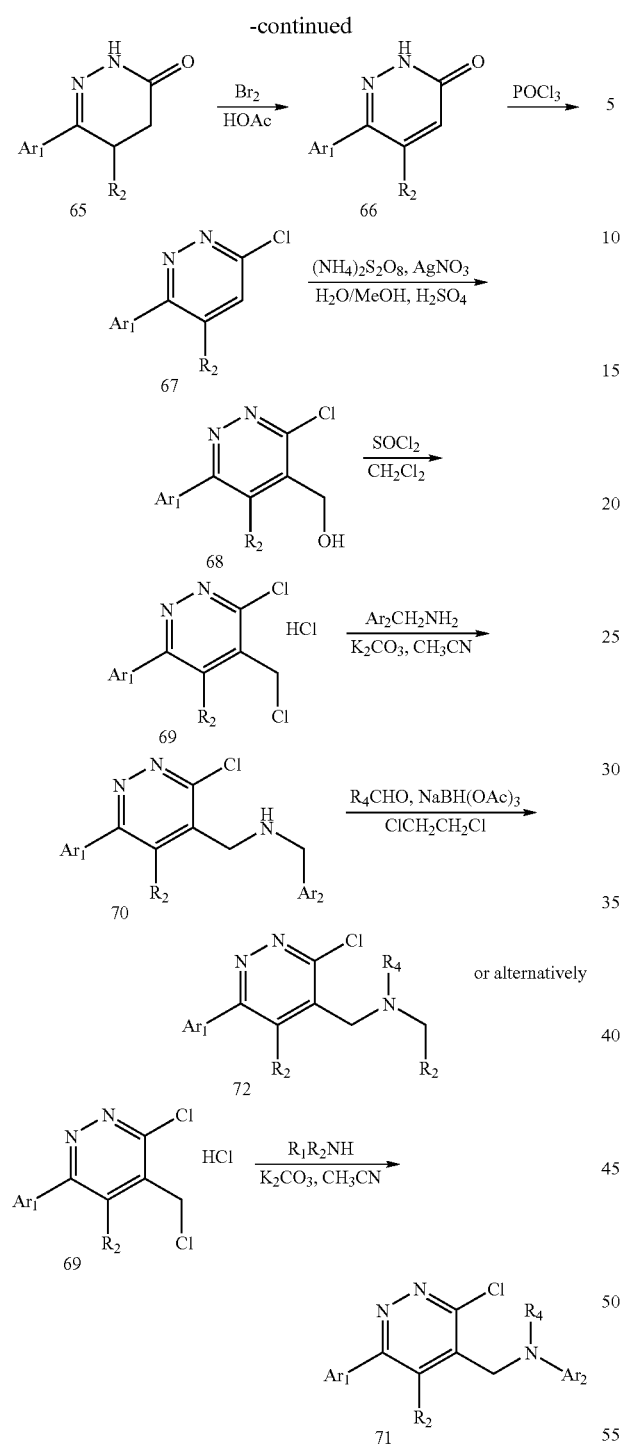

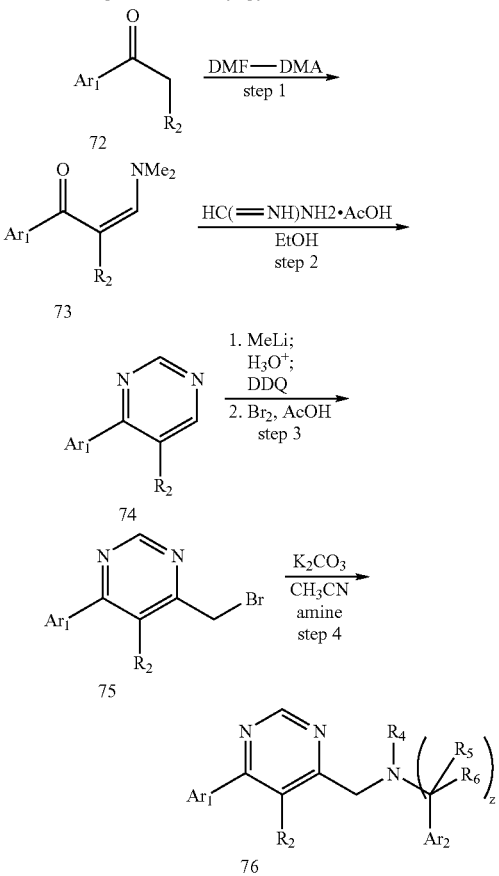

plished by treatment of it with $Br_2$ in HOAc at 80° C. The resulting pyridazinone 66 is then converted into chloropyridazine 8 by heating 66 in $POCl_3$ at 85° C. for 3 hours. Free radical hydroxymethylation of 67 by heating with $(NH_4)_2S_2O_8$ and $H_2SO_4$ with a catalytic amount of $AgNO_3$ in methanol and water provides the desired 5-hydroxymethyl pyridazine 68 in low to moderate yield. Subsequently treatment of 68 with $SOCl_2$ gives the chloromethylpyridazine 69 as a hydrochloric salt. Compound 69 then is converted to secondary amine 70 by reacting with various primary amines in presence of excess $K_2CO_3$ in $CH_3CN$. Finally, reductive amination of 70 with wide range of aldehydes provides the desired 6-aryl-pyridazine compound 71. In some cases, 71 can be prepared directly from 69 by treatment with a secondary amine and $K_2CO_3$ in refluxing $CH_3CN$.

The preparation of 6-aryl-pyridazine is shown in Scheme 6. The bromoketone 61 is prepared by treatment of the corresponding ketone 60 with two equivalents $CuBr_2$ refluxing in $CHCl_3$ and EtOAc. After workup and without further purification, these bromoketones are reacted with NaH and dimethyl malonate 62 to give the adduct ketodiester 63. Decarboxylation of 63 with $NaCl/H_2O$ in DMSO at 155–160° C. provides ketoester 64 cleanly. Condensation of 64 with hydrazine monohydrate refluxing in EtOH furnishes the dihydro-pyridazinone 65. Aromatization of 65 is accom- Scheme 7 illustrates a method for preparing pyrimidines of Formula I where $R_1$ is hydrogen. In step 1, an appropriately substituted arylalkylketone is reacted with dimethylformamide dimethyl acetal to produce the corresponding enaminoketone. The enaminoketone intermediate is heated in a sealed tube with formamidine acetate to obtain the corresponding 4,5-disubstituted pyrimidine in step 2. In step 3, addition of methyllithium to the pyrimidine yields the corresponding 1,6-dihydropyrimidine which is oxidized in situ with DDQ (2,3-dichloro-5,6-dicyano-1,4-benzoquinone) to yield the 4,5,6-trisubstituted pyrimidine which is subsequently brominated to form the 6-(bromomethyl)

pyrimidine. In step 4, reaction with various appropriately substituted secondary amines provides pyrimidines of formula I. Those skilled in the art will realize that minor modifications to this synthetic route can be used to obtain differently substituted pyrimidines of Formula I. For example, use of alkylamidines in step 2 can be used to obtain compounds of Formula I where $R_1$ is alkyl.

ing 2,4-dichloropyrimidine. This material is reacted under Suzuki coupling conditions in step 4 to replace the 4-chloro group with $Ar_1$. Bromination and subsequent reaction with appropriate secondary amines in steps 5 and 6 provides 2-chloropyrimidines of Formula I. Displacement of the 2-chloro substituent in step 7 provides 2-alkoxypyrimidines of Formula I (NaOR' represents an appropriate sodium alkoxide). Those skilled in the art will realize that minor modifications to Scheme 8 can be used to obtain differently substituted pyrimidines of Formula I. For example, displacement of the 2-chloro substituent with amines in step 7 can be used to obtain 2-aminopyrimidines of Formula I.

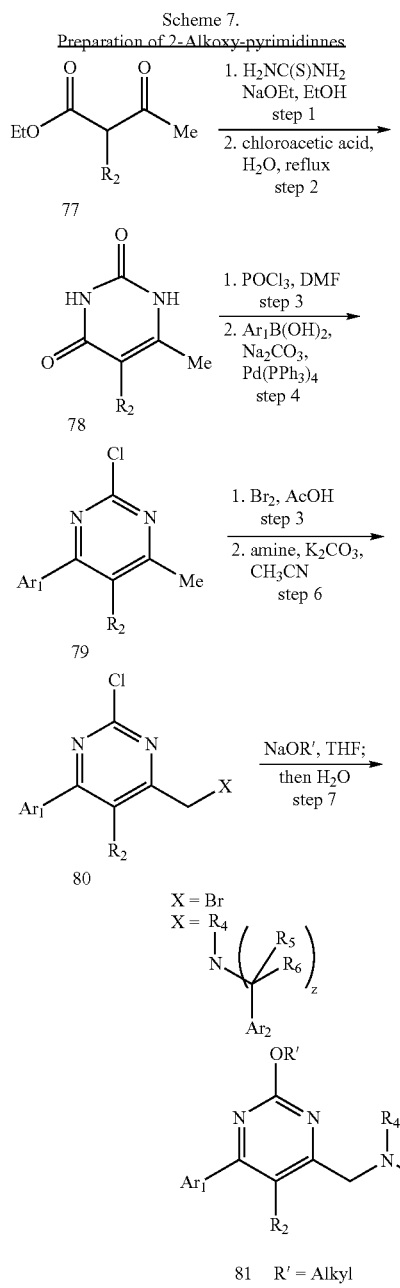

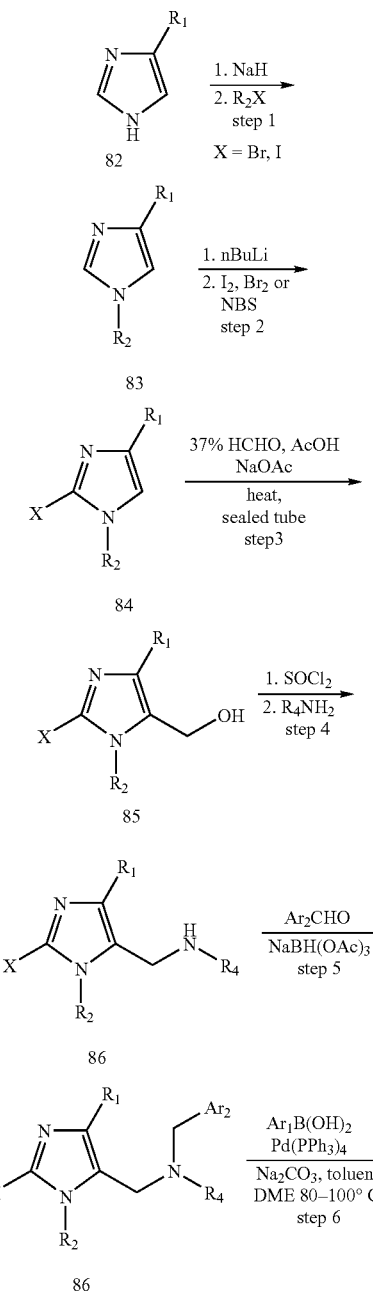

Scheme 8 illustrates a route for preparing pyrimidines of Formula I where $R_1$ is alkoxy. In step 1, an appropriately substituted 1,3-ketoester is reacted with thiourea in the presence of base to obtain the corresponding 2-thioxo-2,3-dihydro-1H-pyrimidin-4-one which is hydrolyzed in step 2 to the corresponding 1H-pyrimidine-2,4-dione. In step 3, the 1H-pyrimidine-2,4-dione is reacted with phosphorous oxychloride and dimethylformamide to obtain the correspond-

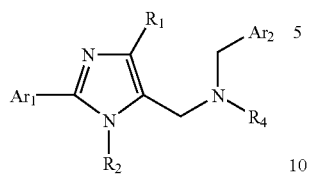

Scheme 9 illustrates a route for preparing imidazoles of Formula I where $R_1$ is aryl or heteroaryl and $Ar_1$ is a variety of aryl and heteraryl groups. In step 1, an aryl imidazole 82 is alkylated to obtain an isomeric mixture. This mixture is separated by chromatography to provide the desired isomer 83. In step 2, imidazole 83 is lithiated at the 2-position and reacted with an electrophilic iodine or bromine source to provide 2-haloimidazole 84. In step 3, imidazole 84 is converted to the corresponding hydroxymethyl derivative by heating under pressure with aqueous formaldehyde in the presence of acetic acid and sodium acetate to yield 85. Hydroxymethylimidazole 85 is converted to the chloride and used to alkylate various amines in step 4 to obtain aminomethylimidazoles 86. Reductive amination of aminomethylimidazole 86 in step 5 provides 2-haloimidazole 87. Step 6 illustrates a particular set of conditions for conversion of 2-haloimidazole 87 to imidazoles of formula I. Those skilled in the art will recognize that the route illustrated in Scheme 8 can be modified by changing the sequence of steps or the reactants to produce a wide variety of imidazoles of Formula I. For example, 2-haloimidazole 87 can be coupled with alternative organometallics ($Ar_1M$, M=Sn, Mg, Zn) to enhance the variety of imidazoles of Formula I accessible by this route.

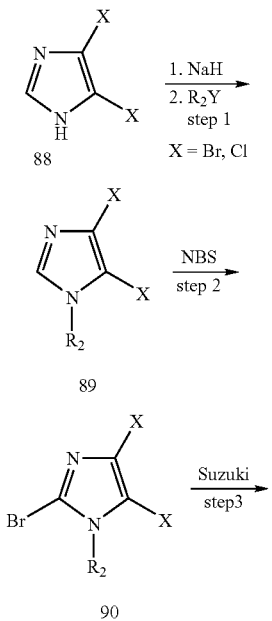

Scheme 10.
Trihalogenated Imidazoles for Preparing Imidazoles of Formula I

Scheme 10 illustrates a route for preparing imidazoles of Formula I utilizing trihaloimidazole 90. In steps 1 and 2, 90 is prepared from dihaloimidazole 88 by alkylation with $R_2Y$ wherein Y is a suitable leaving group such as bromo, iodo or mesylate followed by electrophilic bromination. In step 3, 90 is selective coupled at the 2-position with various aryl boronic acids in the presence of palladium catalyst. In step 4, metal-halogen exchange occurs selectively at the 5-position of 91 to yield, after reaction with DMF, aldehyde 92. In steps 5 and 6, aldehyde 92 is reduced to the corresponding alchohol 93, activated as the chloride and displaced with an appropriately substitued amine to yield imdiazoles compounds of Formula I, where $R_1$ is chloro or bromo (94). Optional subsequent steps may be employed to convert X to a variety of $R_1$ subtituents according to the Formula I. As illustrated in Schemes 1–9 and the accompanying examples, a variety of straight-forward modifications to Scheme 10 can be employed to access a wide variety of compounds of Formula I.

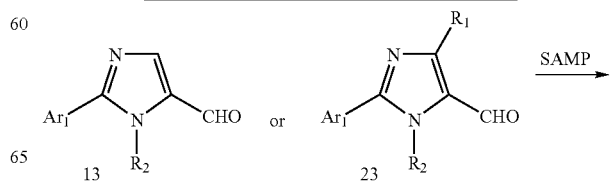

-continued

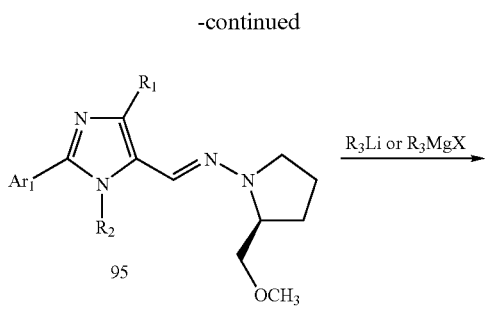
95

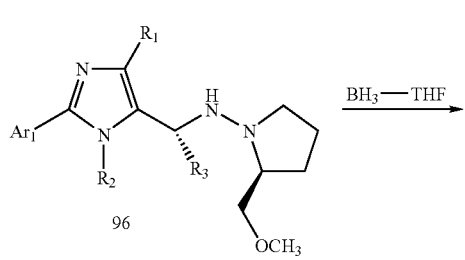
96

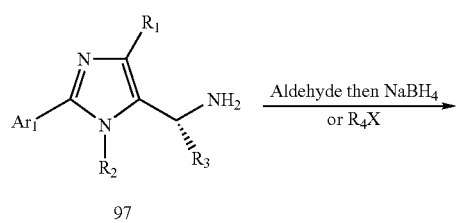
97

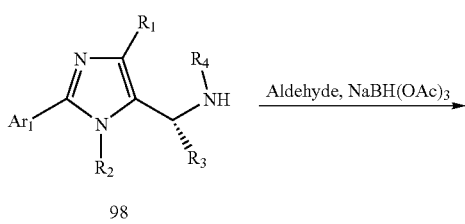
98

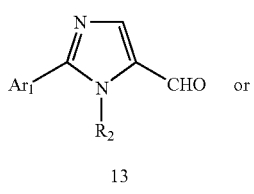
13

-continued

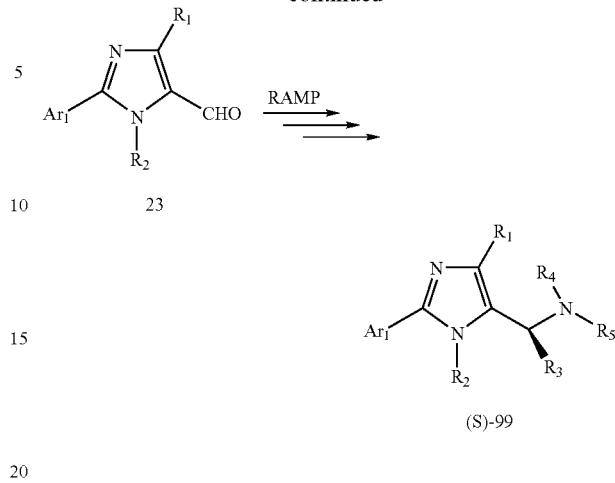

Scheme 11 illustrates a route for preparing imidazoles of Formula I wherein $R_3$ is incorporated in a stereospecific manner in a similar manner to a published procedure (Enders, D.; Thiebes, C. J. *Synthesis* 2000, 510–512).

EXAMPLES

The general methods given in Schemes 1 to 11 above for the preparation of compounds of the present invention are further illustrated by the following examples. Specifically, the methods given in Schemes 1 and 2 for the preparation of aryl imidazoles are illustrated by Examples 1–9, shown below. An example of the method shown in Scheme 3 for the preparation of cycloalkylimidazoles is given in example 10, an example of the method shown in Scheme 4 for the preparation of arylpyridines is given in example 11, and an example of the method shown in Scheme 5 for the preparation of arylpyrazoles is further illustrated in examples 12 and 14. Example 13 provides a method for the synthesis of aryl substituted triazoles. Methods for the synthesis of aryl substituted pyridizines are given in examples 15–18. Methods for the synthesis of compounds in which y is greater than 1 are given in examples 19 and 22. Examples 20–21 provide methods for the synthesis of 4-aryl-pyrimidines. Examples 22 and 24–26 provide supporting chemistry for the synthesis of compounds of Formula I bearing some particular funtionalized $Ar_2$ or $R_4$ substituents. Example 23 further illustrates the route outlined in Scheme 9. Examples 27 and 28 further illustrates the chiral synthesis of $R_3$=alkyl compounds described in Scheme 11. Examples 29–40 are provided to illustrate the synthesis of a variety of intermediates and compounds wherein $R_1$ is substituted alkyl. Example 41 provides for the synthesis of intermediates used in the synthesis of certain compounds prepared according to Scheme 10. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

Example 1

Preparation of an Arylimidazole Compound: 1-(1-butyl)-2-phenyl-5-(N,N-di[3,4-methlenedioxyphenyl Methyl])aminomethylimidazole (Compound 106)

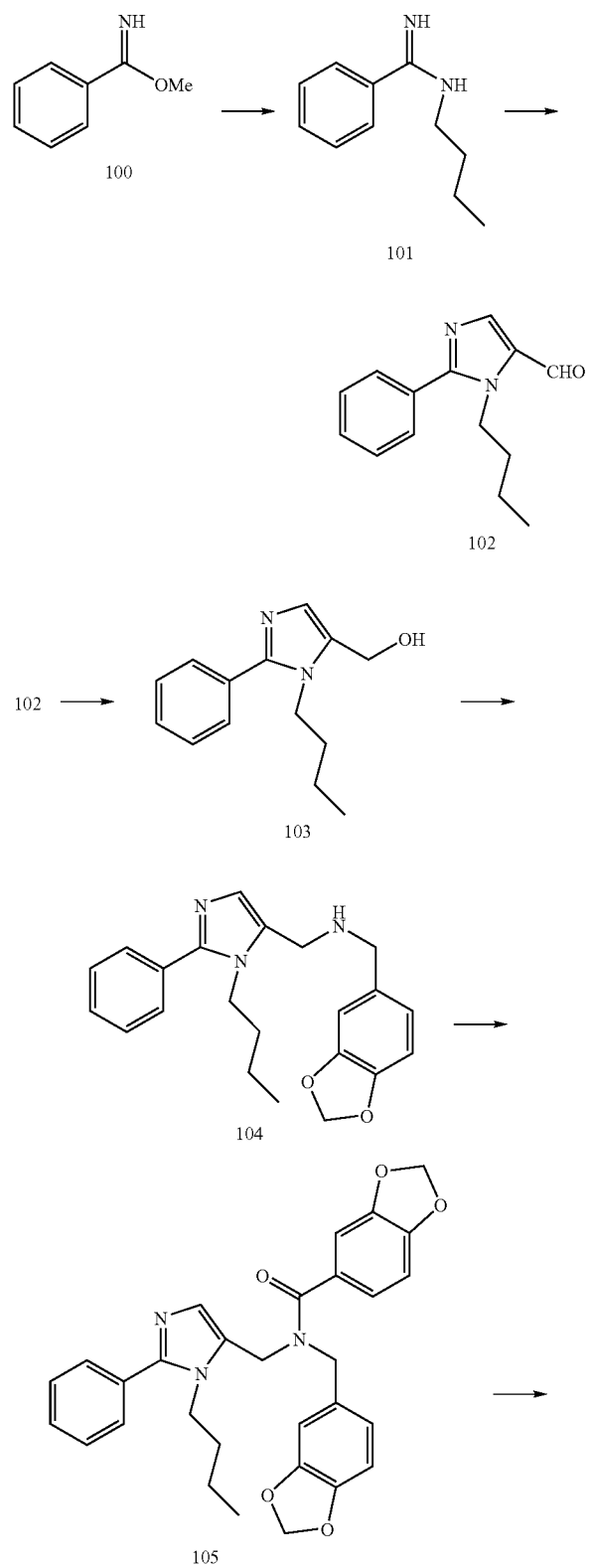

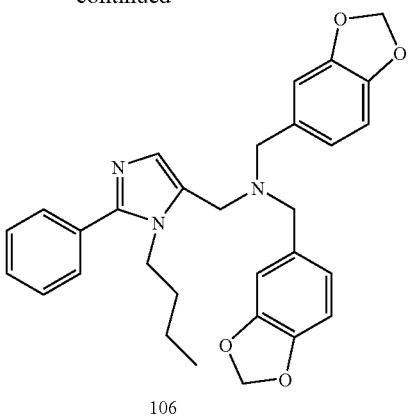

N-(n-butyl)-benzamidine (101). 7 ml of triethylamine is added to a solution of methyl benzimidate hydrochloride (12 g, 0.07 mole) in dimethylformamide (DMF, 20 mL) at 0° C. After 2 h the reaction is filtered to remove triethylamine hydrochloride. 3.68 g of 1-butylamine is added to the filtrate and the mixture is heated to 60° C. for 6 hours. After cooling the mixture is partitioned between ethyl acetate and water. The organic layer is washed with brine, dried over sodium sulfate, and concentrated to provide the amidine as a yellow oil. $^1$H NMR (400 MHz, CDCl$_3$) δ 7.55 (m, 2H), 7.4 (m, 3H), 3.37 (bm, 2H), 1.62 (m, 2H), 1.42 (m, 2H), 0.95 (t, J=7 Hz, 3H).

1-(1-Butyl)-2-phenylimidazole-5-carboxaldehyde (102). Potassium carbonate (15.5 g) and water (19 mL) are added to a solution of 101 (13.28 g) and 2-bromo-3-isopropoxy-acrolein (22 g) in chloroform (150 mL). The mixture is stirred at room temperature overnight. The aqueous layer is discarded and the organic layer is washed with water (3×100 mL), dried (Na$_2$SO$_4$) and concentrated. The residue is purified via flash chromatography (5% MeOH/CHCl$_3$) to provide the desired imidazole carboxaldehyde as a pale yellow oil. $^1$H NMR (400 MHz, CDCl$_3$) δ 9.75 (s, 1H), 7.90 (s, 1H), 7.55 (m, 2H), 7.45 (m, 3H), 4.38 (t, J=8 Hz, 2H), 1.75 (m, 2H), 1.22 (m, 2H), 0.91 (t, J=7 Hz, 3H).

1-(1-Butyl)-2-phenyl-5-hydroxymethylimidazole (103). Aldehyde 102 is dissolved in methanol (150 mL). Sodium borohydride (3 g) is added in portions. After the addition is complete, the reaction is diluted with water and concentrated. The residue is dissolved in ethyl acetate, washed with brine, dried (Na$_2$SO$_4$) and concentrated. The product is purified by flash chromatography on silica gel (5% MeOH/CHCl$_3$) to give 103 as a cream colored solid. $^1$HNMR (400 MHz, CDCl$_3$): δ 0.79 (3H, t, J=7.4 Hz), 1.18 (2H, m, J=7.4 Hz), 1.60 (2H, m, J=7.6 Hz), 4.03 (2H, dd, J=7.6 Hz), 4.56 (2H, s), 6.84 (1H, s), 7.39–7.50 (3H, m),7.50–7.53 (2H, m).

1-(1-Butyl)-2-phenyl-5-(N-[3,4-methylenedioxyphenyl-methyl])aminomethyl imidazole (104). Hydroxymethylimidazole 103 (0.82 g) is dissolved in chloroform (10 mL) and treated with thionyl chloride (1 mL). The solution is heated to 50° C. for 30 min, cooled and evaporated. The residue is washed with benzene and evaporated to give the intermediate chloromethyl hydrochloride as a white powder which is taken up in acetonitrile (30 mL). This is added dropwise to a solution of piperonylamine (5 mL) in acetonitrile (10 mL). The reaction is allowed to stand overnight and then evaporated. The residue is taken up in ethyl acetate and washed with water. The organic layer is dried (Na$_2$SO$_4$) and concentrated. Purification on silica gel (10% MeOH/CHCl$_3$) provides the product as a pale yellow oil. $^1$H NMR (400 MHz, CDCl$_3$): δ 0.79 (3H, t, J=7.4 Hz), 1.18 (2H, m, J=7.4 Hz), 1.56 (2H, m, J=7.4 Hz), 3.75 (4H, s), 4.04 (2H, dd, J=8

Hz), 5.92 (2H, s), 6.76 (2H, m), 6.84 (1H, s), 6.97 (1H, s), 7.38–7.44 (3H, m), 7.53–7.56 (2H, m).

1-(1-Butyl)-2-phenyl-5-(N-[3,4-methylenedioxyphenyl methyl]-N-(3,4-methylenedioxyphenylcarboxy]) aminomethylimidazole (105). Compound 104 (160 mg, 0.44 mmol) is dissolved in chloroform (5 ml, pentene stabilized) and treated sequentially with piperonyl chloride (100 mg) and triethylamine (1 mL). The mixture is stirred at room temperature overnight. The solution is concentrated and the residue taken up in ethyl acetate. The organic is washed with water, dried (Na$_2$SO$_4$) and concentrated. Purification by preparative thin layer chromatography (5% MeOH/CHCl$_3$) provides compound 105 as a pale yellow oil. $^1$H NMR (400 MHz, CDCl$_3$): δ 0.75 (3H, br), 1.16 (2H, br), 1.49 (2H, br), 4.01 (2H, br), 4.54 (2H, br), 4.68 (2H, br), 5.97 (2H, s), 5.99 (2H, s), 6.66 (2H, d, J=7.2 Hz), 6.80 (2H, t, J=8 Hz), 6.98–7.02 (2H, m), 7.40–7.47 (3H, m), 7.56 (2H, d, J=6.8 Hz).

1-(1-Butyl)-2-phenyl-5-(N,N-di[3,4-methylenedioxy phenylmethyl])-aminomethylimidazole (106). Amide 105 (215 mg) in tetrahydrofuran (THF, 3 mL) is added dropwise to a solution of alane (1 M in THF, 2 mL) and the resulting solution is stirred for 2.5 h at room temperature. A solution of sodium hydroxide (15% NaOH, 1 mL) is added and the mixture is extracted with chloroform. The organic extracts are dried (Na$_2$SO$_4$) and concentrated. Purification by preparative thin layer chromatography (10% MeOH/CHCl$_3$) provided compound 106 as a colorless oil. $^1$H NMR (400 MHz, CDCl$_3$): δ 0.70 (3H, t, J=7.6 Hz), 0.98 (2H, m, J=7.6 Hz), 1.30 (2H, m), 3.44 (4H, s), 3.52 (2H, s), 3.98 (2H, dd, J=8 Hz), 5.92 (4H, s), 6.74 (4H, s), 6.69 (2H, s), 7.02 (1H, s), 7.36–7.42 (3H, m), 7.54 (2H, dd, J=1.4, 6.6 Hz). The hydrochloride salt (m.p. 187–190° C.) is prepared in isopropanol.

Example 2

Preparation of 1-(1-butyl)-2-phenyl-5-(1-[N-{3,4-methylenedioxyphenylmethyl}-N-phenylmethyl] amino)ethylimidazole (Compound 108)

1-Butyl-2-phenyl-5-(1-hydroxyethyl)imidazole (107). A solution of aldehyde 102 (230 mg) in diethyl ether (30 mL) is placed in a separatory funnel and treated with a solution of methyl lithium (1.4 M in THF, 1.5 mL). After 10 min, the solution is washed with ammonium chloride solution (1 M, 20 mL), dried (Na$_2$SO$_4$) and concentrated. The resulting dark oil is purified by preparative TLC (10% MeOH/CHCl$_3$) to provide compound 107 as a colorless oil. $^1$H NMR (400 MHz, CDCl$_3$) δ 7.56 (d, J=2 Hz, 2H), 7.4 (m, 3H), 7.01 (s, 1H), 4.86 (q, J=7 Hz, 1H), 4.18 (m, 1H), 4.0 (m, 1H), 1.63 (d, J=6.6 Hz, 3H), 1.63 (m, 2H), 1.23 (m, 2H), 0.81 (t, J=7 Hz, 3H).

1-Butyl-2-phenyl-5-(N-[3,4-methylenedioxyphenyl]-N-phenylmethyl)aminoethylimidazole (108). A solution of compound 107 (80 mg) in chloroform (10 mL) is treated with thionyl chloride (10 mL) and heated to 50° C. for 30 minutes The solution is then concentrated, diluted with chloroform and reconcentrated to provide the intermediate chloromethyl hydrochloride as an oil. This material is taken up in chloroform (5 mL) and treated sequentially with N-benzylpiperonylamine (80 mg) and triethylamine. After stirring overnight, the reaction is washed with saturated potassium carbonate solution, dried (Na$_2$SO$_4$) and concentrated. Purification by preparative thin layer chromatography (10% MeOH/CHCl$_3$) provides compound 108 as a colorless oil. $^1$H NMR (400 MHz, CDCl$_3$) δ 7.46–7.43 (m, 1H), 7.2–7.3 (m, 9H), 6.74–6.86 (m, 4H), 5.94 (s, 2H), 4.82 (q, J=6.8 Hz, 1H), 4.33 (m, 2H), 3.78 (s, 2H), 3.53 (s, 2H), 1.83 (d, J=6.8 Hz, 3H), 1.62–1.68 (m, 2H), 1.21 (q, J=7.8 Hz, 2H), 0.82 (t, J=7.8 Hz, 3H).

Example 3

Preparation of 1-butyl-2-phenyl-4-bromo-5-(N-phenylmethyl-N-[1-butyl])amino-methylimidazole (Compound 110)

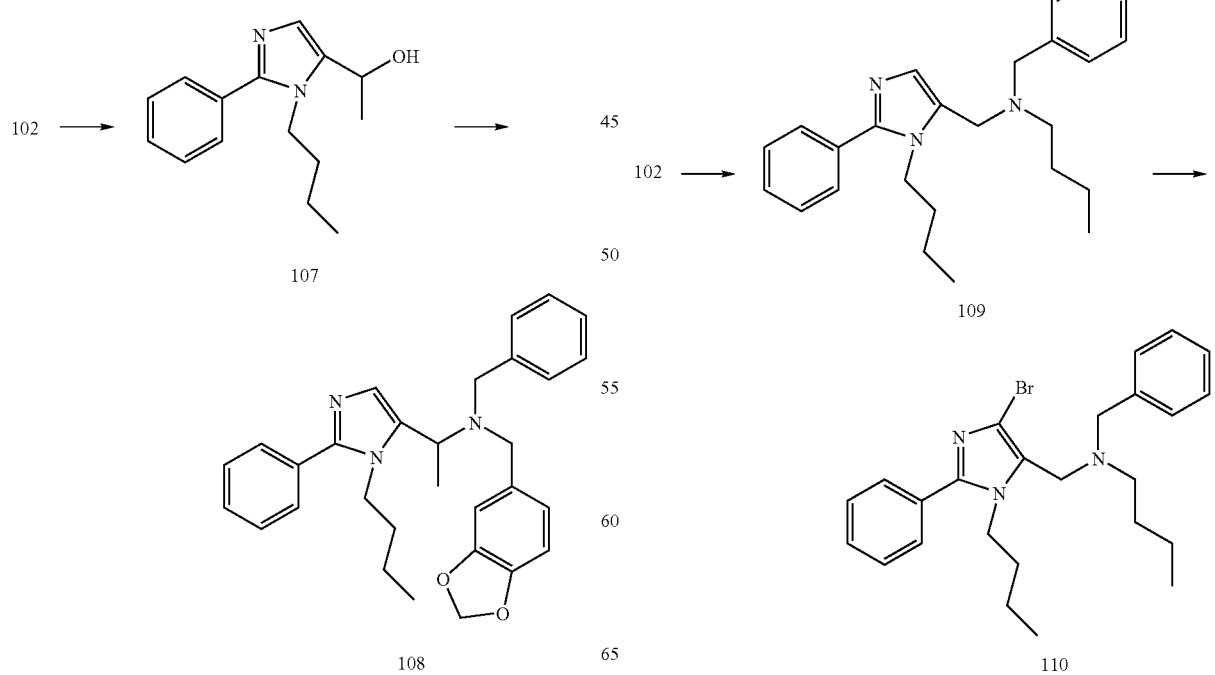

1-Butyl-2-phenyl-5-(N-benzyl-N-butyl)aminomethylimidazole (109). A solution of compound 102 (115 mg) and N-butylbenzylamine (85 mg) in toluene (10 mL) is allowed to stand overnight. Treatment of the reaction with sodium borohydride (100 mg) and ethanol (2 mL) followed by aqueous workup and purification on silica gel (10% MeOH/CHCl$_3$) provides compound 109 as a colorless oil. $^1$H NMR (400 MHz, CDCl$_3$) δ 7.2–7.5 (m, 10H), 6.98 (s, 1H), 4.0 (t, J=8 Hz, 2H), 3.55 (s, 2H), 3.52 (s, 2H), 2.42 (t, J=8 Hz, 2H), 1.2–1.55 (m, 6H), 1.05 (in, 2H), 0.84 (t, J=7 Hz, 3H), 0.72 (t, J=7 Hz, 3H).

1-Butyl-2-phenyl-4-bromo-5-(N-phenylmethyl-N-[1-butyl])aminomethyl imidazole (110). N-bromosuccinimide (16 mg) is added to a solution of 109 (30 mg) in acetonitrile (4 mL). The resulting mixture is heated to 60° C. and the progress of the reaction followed by TLC. The cooled reaction mixture is diluted with ethyl acetate and washed twice with water. Purification by preparative thin layer chromatography (10% MeOH/CHCl$_3$) provides compound 110 as a colorless oil. $^1$H NMR (400 MHz, CDCl$_3$) δ 7.2–7.5 (m, 10H), 3.98 (t, J=8 Hz, 2H), 3.55 (s, 2H), 3.53 (s, 2H), 2.46 (t, J=7 Hz, 2H), 1.52 (m, 2H), 1.3 (m, 4H), 0.98 (q, J=7 Hz, 2H), 0.84 (t, J=7 Hz, 3H), 0.70 (t, J=7 Hz, 3H).

Example 4

Preparation of 1-(1-butyl)-2-phenyl-4-methyl-5-(N-[3,4-methylenedioxyphenyl-methyl]-N-phenylmethyl)aminomethylimidazole. (Compound 114)

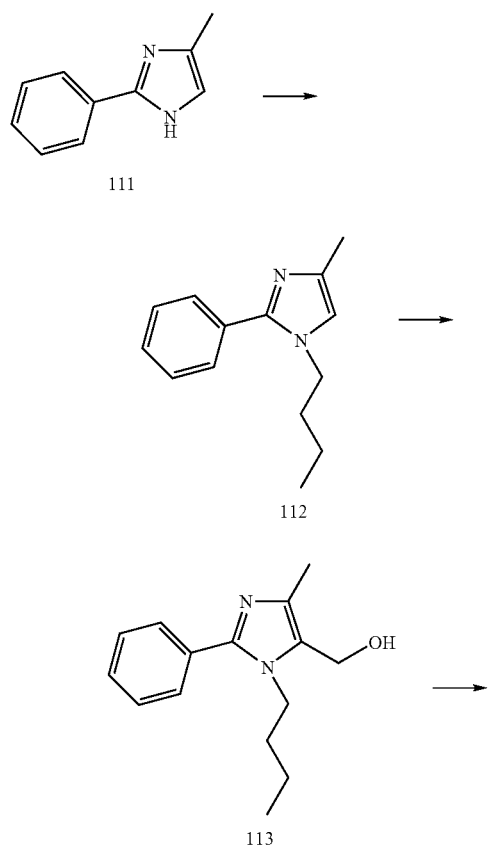

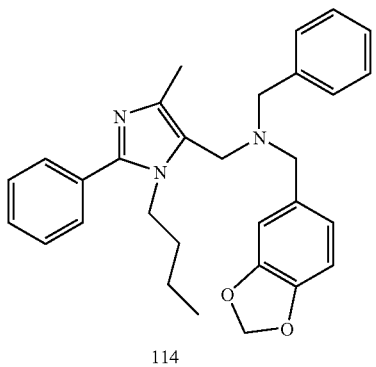

1-Butyl-2-phenyl-4-methylimidazole (112). Sodium hydride (4.4 g, 60% in mineral oil) is added to a solution of 4-methyl-2-phenylimidazole (111, 15.8 g) in dimethylformamide (100 mL) in small portions. After the addition is complete, the mixture is stirred for an additional 20 minutes and treated with 1-iodobutane (18.8 g). The reaction is fitted with a reflux condensor and heated at 100° C. for 12 hours. The cooled reaction mixture is partitioned between water (300 mL) and diethyl ether (300 mL). The organic layer is washed with water (3×200 mL), dried (Na$_2$SO$_4$) and concentrated to provide N-butylimidazoles. Analysis by $^1$H NMR and GC-MS revealed mixture of 1-butyl-2-phenyl-4-methylimidazole (112) and 1-butyl-2-phenyl-5-methylimidazole in a ratio of 11.5/1. The mixture is carried to the next step without purification.

1-Butyl-2-phenyl-4-methyl-5-hydroxymethylimidazole (113). A solution of 112 (1 g) in acetic acid (10 mL) and 40% aqueous formaldehyde (2 mL) is refluxed for 14 hours. The reaction is then concentrated and dried by repeated reconcentration with toluene. The residue is purified by column chromatography (10% MeOH/CHCl$_3$). The fractions are assayed by GC and those fractions uncontaminated by the isomeric hydroxymethylimidazole combined. Concentration of the combined fractions provides compound 113 (320 mg) as a pale yellow oil. $^1$H NMR (400 MHz, CDCl$_3$) δ 7.4–7.6 (m, 6H), 4.61 (s, 2H, CH$_2$OH), 4.02 (t, J=7 Hz, 2H, NCH$_2$), 2.22 (s, 3H, Me), 1.63 (m, 2H, 1.25 (m, 2H), 0.81 (t, J=7 Hz, 3H).

1-Butyl-2-phenyl-4-methyl-5-(N-benzyl-N-butyl)aminomethylimidazole (114). Compound 114 (23 mg) is prepared from 113 (50 mg) in a method similar to that used to obtain compound 108. $^1$H NMR (400 MHz, CDCl$_3$) δ 7.5–7.55 (m,2H), 7.38–7.42 (m, 3H), 7.23–7.30 (m, 5H), 3.95 (t, J=7.5 Hz, 2H), 3.55 (s, 2H), 3.53 (s, 2H), 2.40 (t, J=7 Hz, 2H), 2.22 (s, 3H), 1.25–1.40 (m, 6H), 1.05 (m, 2H), 0.82 (t, J=7 Hz, 3H). 0.70 (t, J=7 Hz, 3H); MS (LCMS) m/e 390 (M$^+$+1)

Example 5

Preparation of 1-butyl-2,4-diphenyl-5-(N-butyl-N-benzyl)aminomethylimidazole (118)

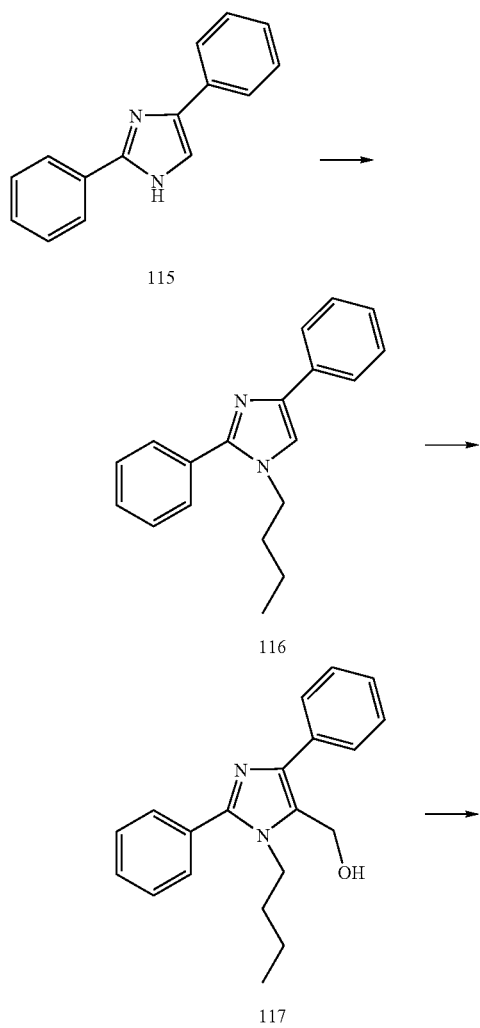

water and ether. The ether layer is dried (Na₂SO₄) and concentrated to provide the desired N-alkyl imidazole as an oil (2.2 g). ¹H NMR (CDCl₃)7.82 (d, J=5 Hz, 2H), 7.63 (d, J=4 Hz, 2H), 7.2–7.5 (m, 7H), 4.0 (t, J=7 Hz, 2H), 1.77 (m, 2H0, 1.3 (m, 2H), 0.88 (t, J=7 Hz, 3H).

1-Butyl-2,4-diphenyl-5-hydroxymethylimidazole (117). 1-Butyl-2,4-diphenylimidazole (3 g) is dissolved in 50 ml of acetic acid with 50 ml of 37% aqueous formalin solution. The mixture is heated at reflux for 48 h, cooled and the solvents evaporated. The residue is triturated with ether and filtered. The filtrate is concentrated and partitioned between ethyl acetate (100 mL) and 5% aqueous acetic acid (100 mL). The aqueous layer is extracted with ethyl acetate (100 mL). The combined organic extracts are washed with 1N NaOH solution, brine, dried over Na₂SO₄, and concentrated. The crude product is triturated with ethyl acetate to give the product as a white solid. ¹H NMR (CDCl₃) 7.73 (d, J=5 Hz, 2H), 7.62 (d, J=4 Hz, 2H), 7.3–7.5 (m, 6H), 4.82 (s, 2H), 4.10 (t, J=7 Hz, 2H), 1.7 (m, 2H), 1.25 (m, 2H), 0.85 (t, J=7 Hz, 3H).

1-Butyl-2,4-diphenyl-5-(N-butyl-N-benzyl)aminomethylimidazole dihydrochloride (118). Thionyl chloride (1 ml) is added to a solution of 1-butyl-2,4-diphenyl-5-hydroxymethylimidazole (0.5 g) in chloroform (10 mL) and the mixture is heated to reflux for 10 minutes The reaction is then concentrated and dried on a vacuum pump. The crude chloride is dissolved in acetonitrile (10 mL) and N-butylbenzylamine (0.27 g, 1 equiv). Potassium carbonate (1 g) is added. The reaction is heated at 60° C. for 8 h, cooled and partitioned between ether and water. The ether layer is dried (Na₂SO₄) and concentrated. The crude product is purified on silica (5% MeOH/CH₂Cl₂) to give the desired product as an oil. ¹H NMR (CDCl₃)7.70 (d, J=5 Hz, 2H), 7.58 (d, J=4 Hz, 2H), 7.2–7.5 (m, 11H), 4.15 (t, J=7 Hz, 2H), 3.77 (s, 2H), 3.52 (s, 2H0, 2.38 (t, J=7 Hz, 2H), 1.6 (m, 4H), 1.2 (m, 2H), 1.05 (m, 2H), 0.8 (t, J=7 Hz, 3H), 0.73 (t, J=7 Hz, 3H). The free base is converted to the hydrochloride salt $C_{31}H_{37}N_3 2HCl \cdot \frac{1}{2} H_2O$.

C, H, N Calc: 69.78; 7.56; 7.86. Found: 69.79; 7.81; 7.46.

Example 6

Preparation of Bis-benzo[1,3]dioxol-5-ylmethyl-(3-butyl-2-phenyl-5-trifluoromethyl-3H-imidazol-4-ylmethyl)-amine (125)

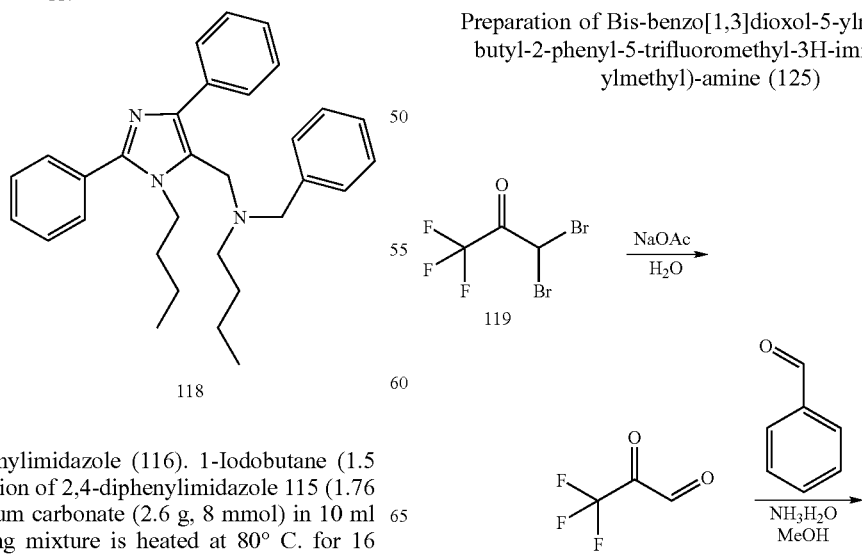

1-Butyl-2,4-diphenylimidazole (116). 1-Iodobutane (1.5 g) is added to a solution of 2,4-diphenylimidazole 115 (1.76 g, 8 mmol) and cesium carbonate (2.6 g, 8 mmol) in 10 ml of DM. The resulting mixture is heated at 80° C. for 16 hours. After cooling, the reaction is partitioned between

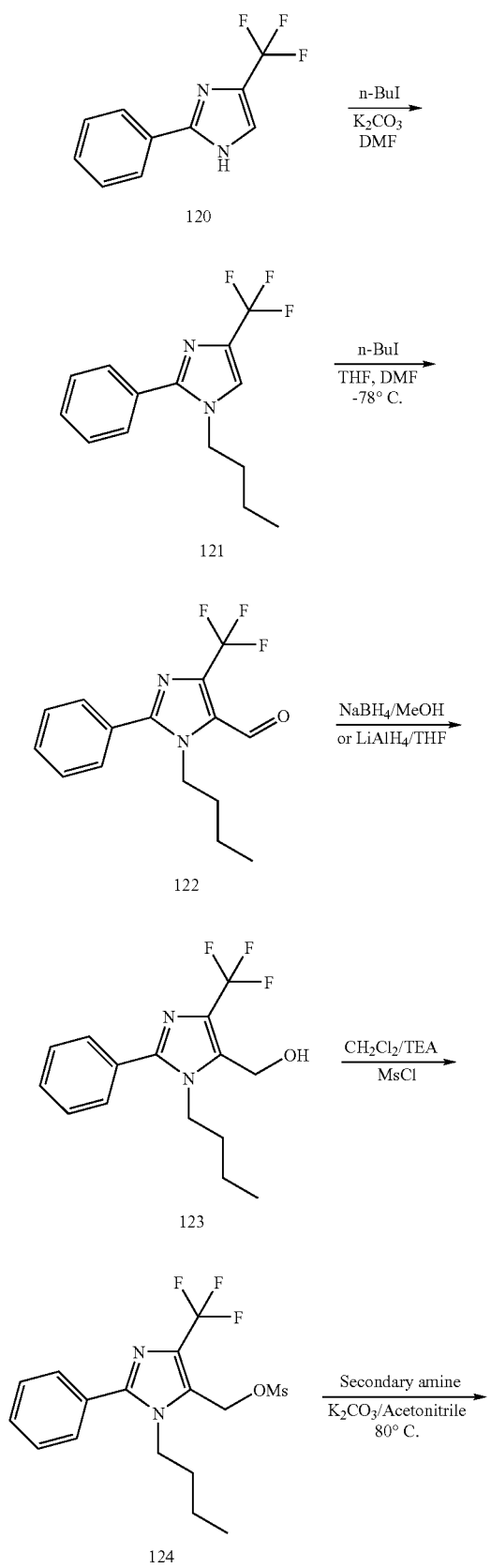

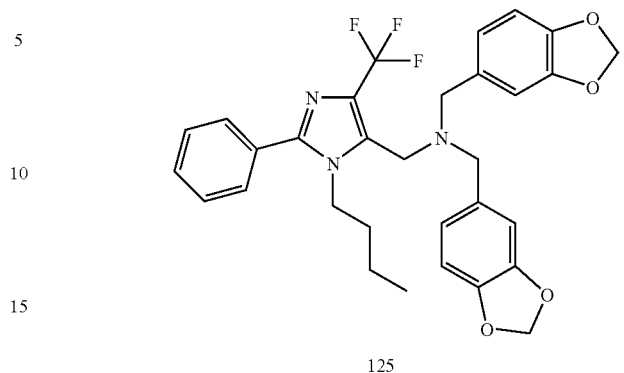

4-Trifluoromethyl 2-phenylimidazole (120). 1,1,1-Trifluoro-3,3-dibromoacetone is added to a solution of NaOAc (11.97 g, 145 mmol) in water (40 mL). The reaction mixture is stirred at 70–80° C. for 30 minutes. After cooling, the solution is added to benzaldehyde (4.25 g, 40 mmol) in methanol (200 mL) and concentrated ammonium hydroxide (50 mL) at room temperature. The mixture is stirred for 4 h. The reaction is monitored by TLC. The reaction mixture is evaporated in vacuo to remove the organic solvent and cooled to room temperature. The solid is collected by filtration gave desired product 120.

NMR (CDCl$_3$, δ ppm): 7.38–7.42 (m, 1H), 7.46 (t, J=7.2 Hz, 2H), 7.85 (d, J=1.3 Hz, 1H), 7.96–7.99 (dd, J=1.5, 7.2 Hz, 2H).

N-Butyl 4-Trifluoromethyl 2-phenylmidazole (121) Powdered KOH (3 mmol) is suspended in DMSO (4 mL). A solution of 120 (2 mmol) and n-BuI (4.5 mmol) in DMSO (4 mL) is added and the solution is stirred overnight. The reaction mixture is diluted with ether (80 mL) and water (80 mL). The aqueous phase is extracted with ether (20 ml×2). Combined organic phase are washed with water (2×100 mL), dried over MgSO$_4$, and concentrated in vacuo to dryness to provide the product 121 as a colorless oil. NMR (CDCl$_3$, δ ppm): 0.88 (t, J=7.5 Hz, 3H), 1.26–1.31(m, 2H), 1.72–1.75 (m, 2H), 4.00 (t, J=7.5 Hz, 2H), 7.35 (s, 1H), 7.45–7.47 (m, 3H), 7.55–7.57 (m, 2H).

n-Butyl 4-Trifluoromethyl 5-formyl 2-phenylmidazole (122) n-BuLi (1.6M in hexane, 30 mL) is added to a solution of 121 (10.8 g, 40.3 mmol) in anhydrous THF (100 mL) at −78° C. under N$_2$ over a 30 minute period The reaction mixture is stirred at −78° C. for 1 h, followed by the followed by the addition of anhydrous DMF (5 mL), and stirred at −78° C. for 3 h. 20 ml of water is added at −50° C. and the reaction-mixture is diluted with EtOAc. Organic layer are separated and washed with H$_2$O and brine, and dried over MgSO$_4$. Concentration in vacuo to dryness provides the desired product 122. $^1$H NMR (CDCl$_3$, δ ppm): 0.83 (t, J=7.5 Hz, 3H), 1.13–1.26 (m, 2H), 1.66–1.70 (m, 2H), 4.34 (t, J=7.5 Hz, 2H), 7.50–7.52 (m, 3H), 7.53–7.59 (m, 2H), 10.0 (s, 1H).

N-Butyl 4-trifluoromethyl 5-hydroxymethyl 2-phenylmidazole (123) NaBH$_4$ is added to a solution of 122 (8.0 g, 27 mmol) in methanol (150 mL) in small portions at 0° C. After the addition is complete, the mixture is stirred at 0° C. for an additional 30 minutes Ice (30 g) is added slowly and the mixture is evaporated in vacuo to remove the organic solvent. Product is collected the solid by filtration, washed with water, dried in vacuo at 35° C. overnight, to give the desired product 123. $^1$H NMR (CDCl$_3$, δ ppm): 0.83 (t, J=8.0 Hz, 3H), 1.21–1.26 (m, 2H), 1.65–1.69 (m, 2H), 4.08 (t, J=8.0 Hz, 2H), 4.79 (s, 2H), 7.45–7.48 (m, 3H), 7.53–7.56 (m, 2H).

Bis-benzo[1,3]dioxol-5-ylmethyl-(3-butyl-2-phenyl-5-trifluoromethyl-3H-imidazol-4-ylmethyl)-amine (125) Mesyl chloride is added to a solution of 123 (393 mg, 1.32 mmol) and TEA (2.6 mmol) in chloroform (10 mL) at 0–5° C. The reaction mixture is stirred at room temperature for 4 h. until the reaction complete and then concentrated in vacuo to dryness. The residue is dissolved in acetonitrile (20 mL) and dipiperonylamine (376 mg, 1.32 mmol) and K$_2$CO$_3$ (728 mg, 5.28 mmol) are added. The reaction mixture is heated under reflux overnight. The solvent is removed in vacuo, the residue is dissolved in ethyl acetate, washed with water, and dried over MgSO$_4$. Concentration in vacuo gives the product 125. $^1$H NMR (CDCl$_3$, δ ppm): 0.67 (t, J=7.7 Hz, 3H), 0.88–0.94 (m, 2H), 1.18–1.22 (m, 2H), 3.44 (s, 4H), 3.68 (s, 2H), 4.04 (t, J=7.1 Hz, 2H), 5.92 (s, 4H), 6.73–6.74 (m, 4H), 6.76 (s, 2H), 7.41–7.44 (m, 3H), 7.48–7.51 (m, 2H).

Example 7

Preparation of 5-[(Bis-benzo[1,3]dioxol-5-ylmethyl-amino)-methyl]-1-butyl-2-phenyl-1h-imidazole-4-carbonitrile (129)

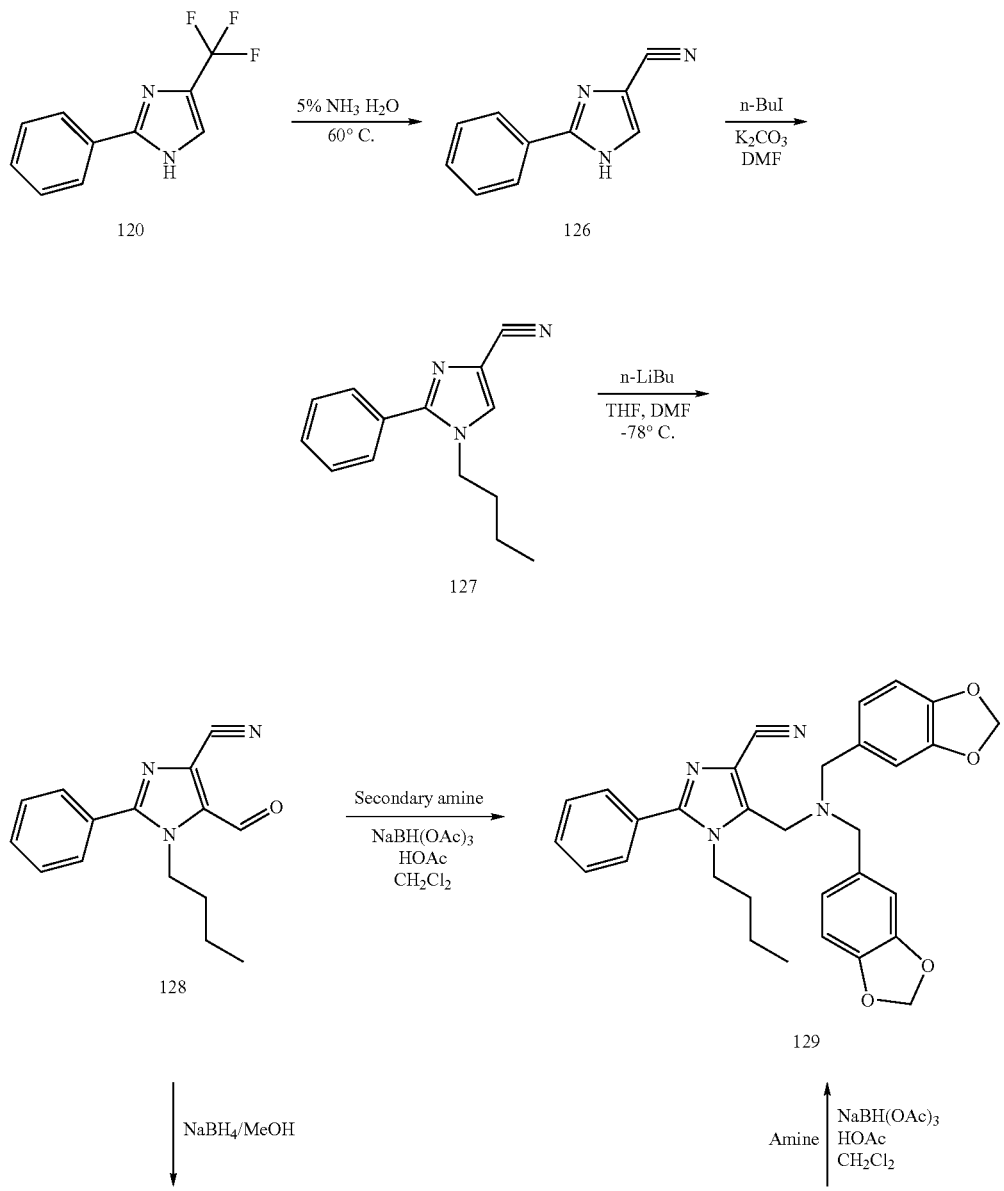

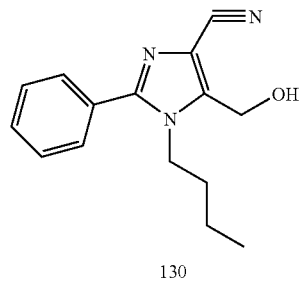

130

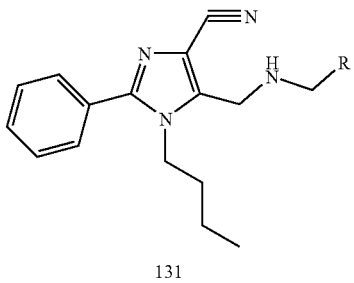

131

4-Cyano2-phenylimidazole (126). 4-Trifluoromethyl 2-phenylimidazole (20 g, 94 mmol) is added to a 5% ammonium hydroxide solution (200 mL). The mixture is then warmed to 60–65° C. and stirred for 2 h, extracted with ethyl acetate (300 ml×3), and dried over MgSO₄. Evaporation to dryness gives the desired product 126 (14 g).

¹H NMR (CDCl₃, δ ppm): 7.40–7.45 (m, 3H), 7.73 (s, 1H), 7.82–7.85 (m, 2H).

N-Butyl 4-Cyano2-phenylimidazole (127). N-Butyl 4-Cyano2-phenylimidazole is synthesized by the procedure given for compound 121. ¹H NMR (CDCl₃, δ ppm): 0.73 (t, J=7.6 Hz, 3H), 1.11–1.16 (m, 2H), 1.57–1.61 (m, 2H), 3.93 (t, J=7.6 Hz, 2H), 7.34–7.37 (m, 3H), 7.42–7.45 (m, 2H). 7.51 (s, 1H).

N-Butyl 4-cyano-5-formyl 2-phenylmidazole (128). N-Butyl 4-cyano-5-formyl 2-phenylmidazole is synthesized by the procedure given for compound 121. ¹H NMR (CDCl₃, δ ppm): 0.82 (t, J=7.5 Hz, 3H), 1.19–1.26 (m, 2H), 1.63–1.68 (m, 2H), 4.34 (t, J=15=7.5 Hz, 2H), 7.49–7.57 (m, 5H), 9.99 (s, 11H).

Bis-benzo[1,3]dioxol-5-ylmethyl-(3-butyl-2-phenyl-5-cyano-3H-imidazol-4-ylmethyl)-amine (129) Bis-benzo[1,3]dioxol-5-ylmethyl-(3-butyl-2-phenyl-5-cyano-3H-imidazol-4-ylmethyl)-amine is synthesized by the procedure given for compound 125. ¹H NMR (CDCl₃, δ ppm): 0.68 (t, J=7.4 Hz, 3H), 0.84–0.96 (m, 2H), 1.18–1.26 (m, 2H), 3.49 (s, 4H), 3.68 (s, 2H), 3.99 (t, J=7 Hz, 2H), 5.90 (s, 4H), 6.73 (s, 4H), 6.77 (s, 2H), 7.44 (brs, 5H).

Example 8

Preparation of Bis-benzo[1,3]dioxol-5-yethyl-[3-butyl-5-(5-methyl-thiophen-2-yl)-2-phenyl-3H-imidazol-4-ylmethyl]-amine

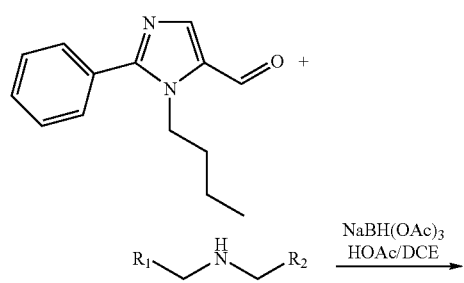

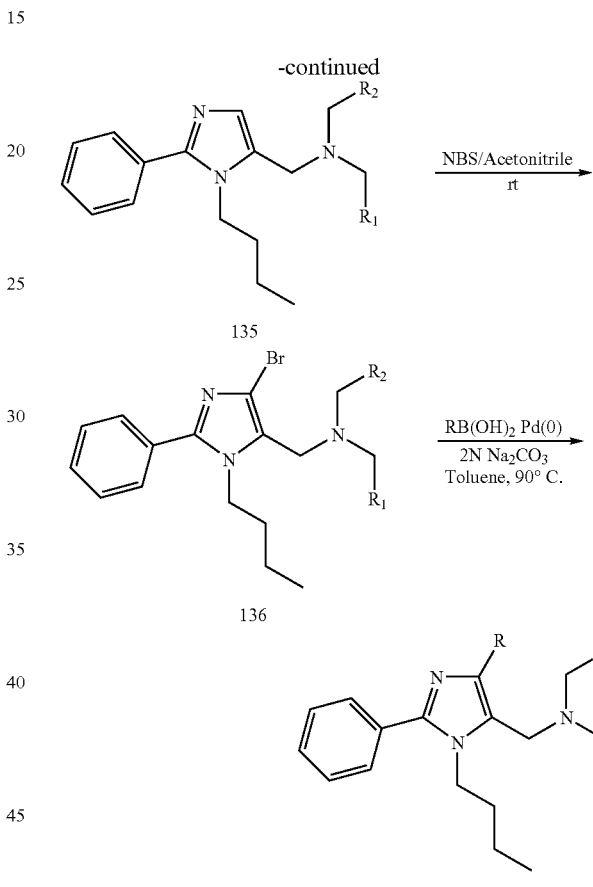

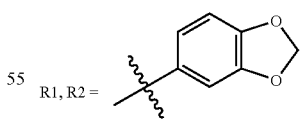

Bis-benzo[1,3]dioxol-5-ylmethyl-(3-butyl-2-phenyl-3H-imidazol-4-ylmethyl)-amine (136) is synthesized via the procedure given for compound 125.

¹H NMR (CDCl₃, δ ppm): 0.69 (t, J=7.4 Hz, 3H), 0.95–1.00 (m, 2H), 1.22–1.31 (m, 2H), 3.44 (s, 4H), 3.54 (s, 2H), 3.98 (t, J=7. Hz, 2H), 5.91 (s, 4H), 6.73 (s, 4H), 6.79 (s, 2H), 7.01 (s, 1H), 7.38–7.42 (m, 3H), 7.51–7.54 (m, 2H).

Bis-benzo[1,3]dioxol-5-ylmethyl-(3-butyl-2-phenyl-5-bromo-3H-imidazol-4-ylmethyl)-amine (137). ¹H NMR (CDCl₃, δ ppm): 0.69 (t, J=7.4 Hz, 3H), 0.89–0.96 (m, 2H), 1.24–1.28 (m, 2H), 3.45 (s, 4H), 3.54 (s, 2H), 4.00 (t, J=7. Hz, 2H), 5.90 (s, 4H), 6.73 (s, 4H), 6.77 (s, 2H), 7.38–7.42 (m, 3H), 7.48–7.51 (m, 2H).

Bis-benzo[1,3]dioxol-5-ylmethyl-(3-butyl-2-phenyl-5-bromo-3H-imidazol-4-ylmethyl)-amine (138). ¹H NMR (CDCl₃, δ ppm): 0.69 (t, J=7.4 Hz, 3H), 0.89–0.96 (m, 2H), 1.24–1.28 (m, 2H), 2.52 (s, 3H), 3.48 (s, 4H), 3.80 (s, 2H), 4.06 (t, J=7. Hz, 2H), 5.91 (s, 4H), 6.73 (m, 5H), 6.77 (s, 2H), 7.17 (d, J=3.3 Hz, 1H), 7.38–7.46 (m, 3H), 7.55–7.58 (m, 2H).

Example 9

Preparation of 4-fluoroimidazole Compounds

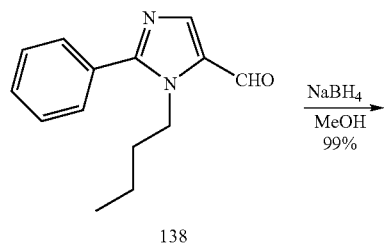

138

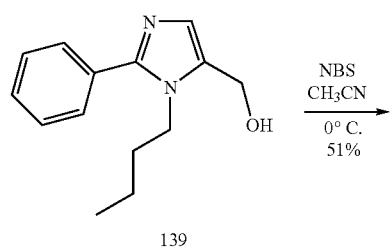

139

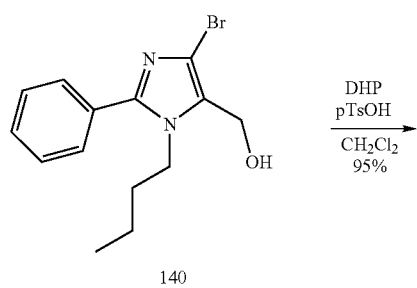

140

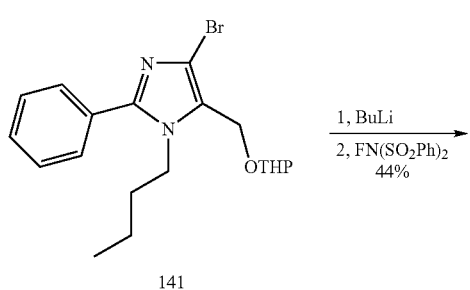

141

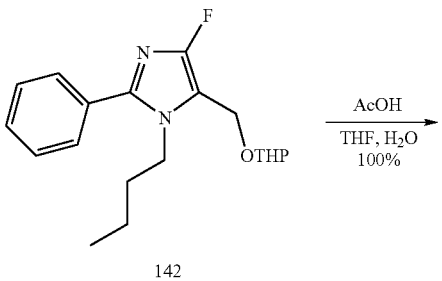

142

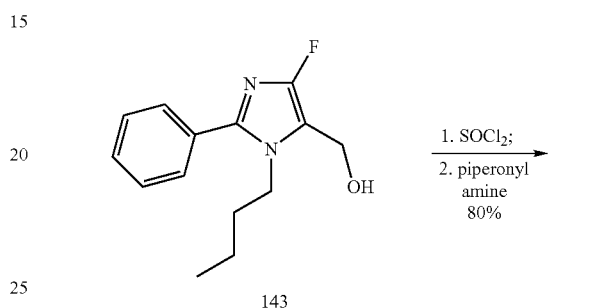

143

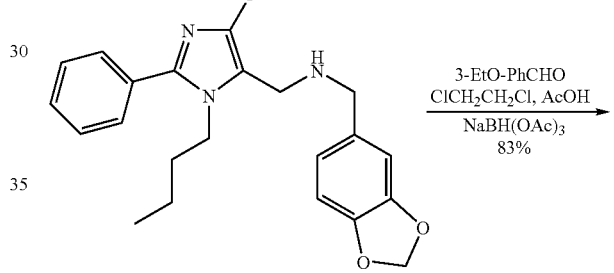

144

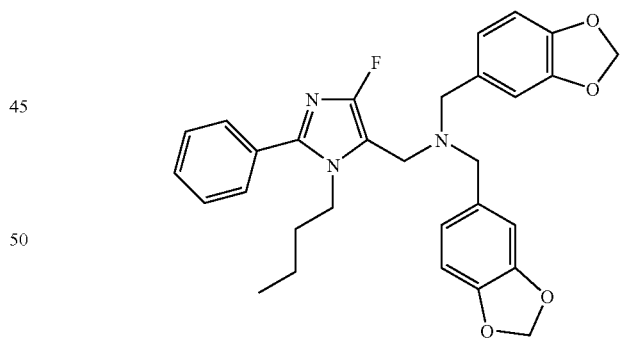

145

1-Butyl-2-phenyl-5-hydroxymethylimidazole (139). Sodium borohydride (1.135 g, 30 mmol) is added to a solution of aldehyde 138 (6.849 g, 30 mmol) in 100 ml of methanol cooled to 0° C. The resulting solution is stirred at 0° C. for 30 min, evaporated and the residue dissolved in 150 ml of ethyl acetate, washed with water and brine, dried over Na₂SO₄, concentrated and taken to dryness under high vacuum to give the product 139 as an oil. MS (+VE) m/z 231 (M+1).

1-Butyl-2-phenyl-4-bromo-5-hydroxymethylimidazole (140). N-bromo succinimide (3.56 g, 20 mmol) is added to a solution of alcohol 139 (4.60 g, 20 mmol) in 100 ml of anhydrous acetonitrile cooled to 0° C., in portions over 15 minutes. The resulting mixture is stirred at 0° C. for 60 min, water is added to quench the reaction, the acetonitrile is evaporated, and the residue dissolved in 100 ml of ethyl acetate, washed with water and brine, and dried over $Na_2SO_4$. The solvent is evaporated and the residue purified by silica gel flash chromatography (hexanes/ethyl acetate, from 6:1 to 3:1) to give 3.15 g of product 140. $^1$H NMR (300 MHz, $CDCl_3$) δ 7.48–7.56 (2H, m), 7.40–7.47 (3H, m), 4.67 (2H, s), 4.07 (2H, t, J=7.60 Hz), 1.65 (2H, m), 1.24 (2H, m), 0.83 (3H, t, J=7.5 Hz). MS (+VE) m/z 309 (M$^+$), 311 (M+2).

Compound (141). 3,4-Dihydro-2H-pyran (1.41 g, 16.8 mmol, 5 eq.) is added to a solution of alcohol 140 (1.04 g, 3.36 mmol) in 20 ml of anhydrous dichloromethane cooled to 0° C., followed by addition of p-toluenesulfonic acid monohydrate (10 mg). The mixture is stirred at room temperature overnight. The solution is diluted with 20 ml of ether and washed with a solution made up of 5 ml of $NaHCO_3$-5 ml brine-10 ml water. The aqueous phase is extracted with ether and the combined organic solutions are dried with $Na_2SO_4$. The solvent is evaporated and the residue purified by silica gel flash chromatography (hexanes/ethyl acetate, from 8:1 to 5:1) to give compound 141 as a sticky oil. $^1$H NMR (300 MHz, $CDCl_3$) δ 7.54–7.58 (2H, m), 7.72–7.47 (3H, m), 4.75 (1H, d, J=13 Hz), 4.73 (1H, m), 4.58 (1H, d, J=13 Hz), 4.06 (2H, m), 3.94 (1H, m), 3.61 (1H, m), 1.45–1.88 (8H, m), 1.23 (2H, m), 0.83 (3H, t, J=7.5 Hz). MS (+VE) m/z 393 (M$^+$), 395 (M+2).

Compound (142). A solution of butyl lithium in hexanes (1.6M, 1.02 ml, 1.64 mmol) is added to a solution of compound 141 (537 mg, 1.37 mmol) in 10 ml of anhydrous THF at −78° C. under nitrogen. The resulting mixture is stirred at −78° C. for 60 min; a solution of N-fluorobenzenesulfonimide (516 mg, 1.64 mmol) in 10 ml of THF is then added dropwise. The resulting solution is stirred at −78° C. for 30 min, warmed to room temperature, and then stirred overnight. 10 ml of saturated $NaHCO_3$ is added to quench the reaction. The mixture is diluted with 50 ml of ethyl acetate, the organic layer is separated, washed with water and brine, and dried over $Na_2SO_4$ Concentration and purification through silica gel chromatography (hexanes/ethyl acetate, from 8:1 to 5:1) affords compound 142. $^1$H NMR (400 MHz, $CDCl_3$) δ 7.52–7.55 (2H, m), 7.37–7.44 (3H, m), 4.70 (1H, d, J=13 Hz), 4.69 (1H, m), 4.51 (1H, d, J=13 Hz), 3.95–4.07 (2H, m), 3.88 (1H, m), 3.56 (1H, m), 1.48–1.82 (8H, m), 1.22 (2H, m), 0.82 (3H, t, J=7.2 Hz). MS (+VE) m/z 333 (M+1).

1-Butyl-4-fluoro-5-hydroxymethyl-2-phenylimidazole (143). 1-Butyl-2-phenyl-4-fluoro-5-hydroxymethylimidazole 142 (100 mg, 0.30 mmol) is dissolved in a solution made up of 1.0 ml acetic acid-1.0 ml THF-1.0 ml water. The solution is heated to 55–60° C. and stirred for 2 h. The acetic acid and THF are evaporated, the residue basified with sodium hydroxide solution, extracted with ethyl acetate, washed with water and brine, and dried over $Na_2SO_4$. The product is concentrated and taken to dryness under high vacuum to give compound 143. MS (+VE) m/z 249 (M+1).

Benzo[1,3]dioxol-5-ylmethyl-(3-butyl-5-fluoro-2-phenyl-3H-imidazol-4-yl methyl)-amine (144). Compound 143 (76 mg, 0.30 mmol) is dissolved in 2 ml dichloromethane and cooled to 0° C. Thionyl chloride (0.05 mL) is added and the resulting solution is stirred at room temperature for 2 h. The solvent and excess thionyl chloride are evaporated. The residue is dissolved in 1.0 ml DMF and added to a solution of piperonyl amine (227 mg, 1.5 mmol) in DMF (2 mL) containing 100 mg potassium carbonate. The resulting mixture is stirred at room temperature for 2 h, then diluted with 20 ml of ethyl acetate, washed with water and brine, dried, and concentrated. The resulting residue is purified with silica gel chromatography (hexanes/ethyl acetate, from 2:1 to 1:1) to provide compound 144. MS (+VE) m/z 382 (M+1).

Benzo[1,3]dioxol-5-ylmethyl-(3-butyl-5-fluoro-2-phenyl-3H-imidazol-4-ylmethyl)-(3-ethoxy-benzyl)-amine (145) Compound 144 (0.079 mmol) is dissolved in 2 ml 1,2-dichloroehane. 3-Ethoxybenzaldehyde (28 mg, 2.0 eq) is added followed by one drop of acetic acid. The solution is stirred at room temperature for 2 hr; sodium triacetoxyborohydride (50 mg, 0.236 mmol, 3.0 eq.) is then added. The resulting mixture is stirred at room temperature overnight. The reaction mixture is diluted with 10 ml of dichloromethane, washed with water and brine, dried, and concentrated. The residue is purified by silica gel flash chromatography (hexanes/ethyl acetate, from 8:1 to 4:1) to afford compound 145 $^1$H NMR (400 MHz, $CDCl_3$) δ 7.47–7.52 (2H, m), 7.38–7.44 (3H, m), 7.21 (1H, t, J=8 Hz), 6.82–6.90 (3H, m), 6.7–6.78 (3H, M), 5.93 (2H, s), 4.01 (2H, q, t=7.2 Hz), 3.92 (2H, t, J=7.6 Hz), 3.52 (2H, s), 3.51 (2H, s), 3.48 (2H, s), 1.41 (3H, t, J=6.8 Hz), 1.34 (2H, m), 0.99 (2H, m), 0.71 (3H, t, J=7.2 Hz). MS (+VE) m/z 516.3 (M+1).

Example 10

Preparation of Cycloalkylimidazole Compounds:
4-{[butyl(1-butyl-2-phenyl(4,5,6-trihydrocyclopenta[3,2-d]imidazol-6-yl)amino]methyl}-3-chlorophenol (156)

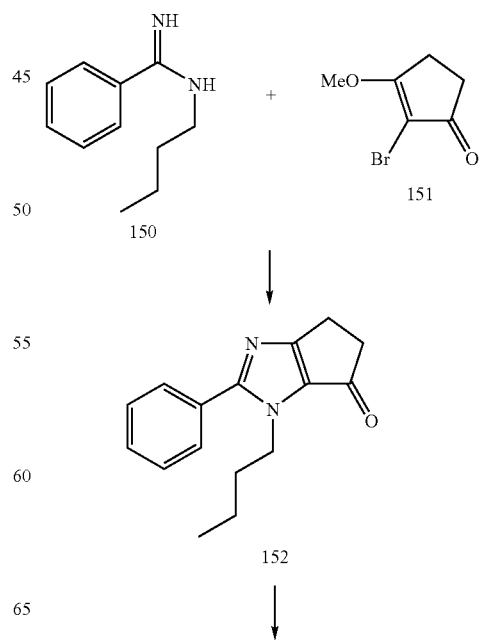

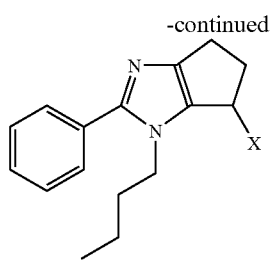

Compound 153 X = OH
Compound 154 X = Cl
Compound 155 X = HNBu

↓

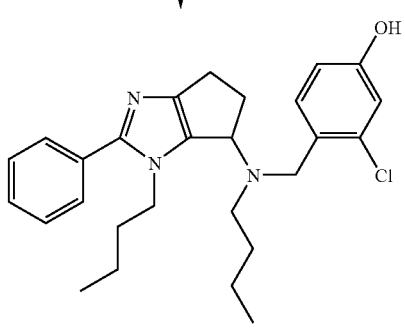

Compound 156

N-(n-butyl)-benzamidine (150). 7 ml of triethylamine is added to a solution of methyl benzimidate hydrochloride (12 g, 0.07 mole) in dimethylformamide (DMF, 20 mL) at 0° C. After 2 h the reaction is filtered to remove triethylamine hydrochloride. 1-Butylamine (3.68 g) is added to the filtrate and the mixture is heated to 60° C. for 6 hours. After cooling the mixture is partitioned between ethyl acetate and water. The organic layer is washed with brine, dried over sodium sulfate and concentrated to provide the amidine as a yellow oil. $^1$H NMR (CDCl$_3$) 7.55 (m, 2H), 7.4 (m, 3H), 3.37 (bm, 2H), 1.62 (m, 2H), 1.42 (m, 2H), 0.95 (t, J=7 Hz, 3H).

2-Bromo-3-methoxycyclopentenone (151) is prepared via the method of Curran et al JACS, vol 112, page 5601. N-Bromosuccinimide (18.2 g) is added to a suspension of 1,3-cyclopentanedione (10 g) in chloroform (700 mL). The mixture is refluxed for 2 h, cooled and concentrated. Methanol (700 mL) and p-toluenesulfonic acid (1 g) are added and the solution is refluxed overnight. The mixture is concentrated to 100 ml, diluted with methylene chloride (500 mL), and poured into water. The aqueous layer is discarded and the organic layer is washed with water (3×100 mL), dried (Na$_2$SO$_4$) and concentrated. The residue is crystallized from ethyl acetate to give 151 as tan crystals (1.67 g).

1-Butyl-2-phenyl-4,5-dihydrocyclopenty[1,2-d]imidazol-6-one (152). Solid potassium carbonate (3.32 g, 24 mmol) is added to a mixture of amidine 150 (3.52 g, 20 mmol) and enone 13 (4.58 g, 24 mmol) in chloroform (40 mL) and water (5 mL). The resulting mixture is refluxed overnight. After cooling, the mixture is washed with water, dried (Na$_2$SO$_4$), and concentrated. Purification on silica gel eluting with 25% ethyl acetate/hexane gives the desired product 152 (3.0 g) LC-MS (M$^+$+1): 255. $^1$H NMR (δ, CDCl$_3$): 0.84 (t, J=7.6 Hz, 3H), 1.23 (dt, J=7.0, 7.6 Hz, 2H), 1.81 (m, 2H), 2.95 (m, 4H), 4.13 (t, J=7.6 Hz, 2H) 7.5–7.45 (m, 3H), 7.76–7.6 (m, 2H) ppm.

1-Butyl-2-phenyl-4,5-dihydrocyclopenty[1,2-d]imidazol-6-ol (153). Sodium borohydride (1.5 equiv) is added to a solution of 152 (2.68 g) in methanol (20 mL) and the mixture is stirred overnight. The mixture is concentrated, diluted with chloroform, and washed with 0.5 N NH$_4$Cl solution. The organic layer is dried (Na$_2$SO$_4$) and concentrated to provide the desired product 153. LC-MS (M+1) 257.

Butyl(1-butyl-2-phenyl-4,5,6-trihydrocyclopentyl[3,2-d]imidazol-6-yl))amine (155). Compound 153 (2 g) is dissolved in chloroform (20 mL) and thionyl chloride (5 mL); the resulting solution is stirred at room temperature overnight. The solvent and excess thionyl chloride are evaporated and the crude chloride 154 dissolved in n-butylamine (10 mL). After 2 h, the excess butylamine is evaporated, the residue dissolved in ethyl acetate and the organic solution washed with 5% NaOH solution and water. The organic layer is dried and concentrated. The organic residue is purified by column chromatography on silaica gel eluting with 10% CH$_3$OH in CHCl$_3$ to provide the desired secondary amine 155. LC-MS (M+1) 312 $^1$H NMR (chemical shift, CDCl$_3$): 0.83 (t, J=7.2 Hz, 3H), 0.9 (t, J=7.2 Hz, 3H), 1.23 (q, J=7.2 Hz, 2H), 1.35 (q, J=7.2 Hz, 2H), 1.46 (m, 2H), 1.70 (m, 2H), 2.24 (m, 1H), 2.55–2.66 (m, 4H), 2.73–2.80 (m, 2H), 3.97–4.04 (m, 2H), 4.30 (d, J=5.6 Hz, 1H), 7.37–7.44 (m, 3H), 7.55–7.57 (m, 2H).

4-{[Butyl(1-butyl-2-phenyl(4,5,6-trihydrocyclopenta[3,2-d]imidazol-6-yl))amino]methyl}-3-chlorophenol (156). Sodium triacetoxyborohydride (100 mg) is added to a solution of 155 (50 mg) in 1,2-dichloroethane (2 mL) and 2-chloro-4-hydroxybenzaldehyde (30 mg) is added The resulting mixture is allowed to stir overnight. After washing with 0.5 ammonium chloride solution, the organic layer is dried (Na$_2$SO$_4$) and concentrated. Purification using preparative thin layer chromatography eluting with 5% CH$_3$OH/CHCl$_3$ provides the desired product 156 as an oil (21 mg). LC-MS (M+1) 452, (M−1) 450. $^1$H NMR (chemical shift, CDCl$_3$): 0.74 (t, J=7.2 Hz, 3H), 0.83 (t, J=7.2 Hz, 3H), 1.11 (q, J=7.2 Hz, 2H), 1.21–1.33 (m, 2H), 1.41–1.51 (m, 4H), 2.34–2.44 (m, 3H), 2.51–2.57 (m, 1H), 2.60–2.67 (m, 1H), 2.69–2.75 (m, 1H), 3.38 (d, J=7.6 Hz, 1H), 3.47 (d, J=13.6 Hz, 1H), 3.65 (d, J=13.6 Hz, 1H), 3.78–3.96 (m, 1H), 6.62 (dd, J=8, 2 Hz, 1H), 6.78 (d, J=2 Hz, 1H), 7.07 (d, J=8 Hz, 1H), 7.35–7.41 (m, 3H), 7.45–7.48 (m, 2H).

Example 11

Preparation of 2-phenyl-4-(N,N-di{2H-benzo[3,4-D]-1,3-dioxolan-5-ylmethyl})aminomethyl-3-butylpyridine (161)

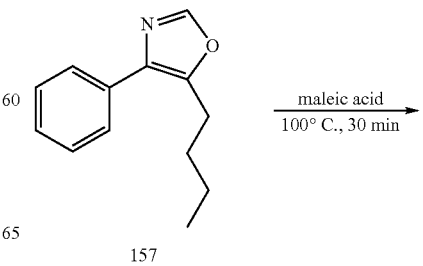

157

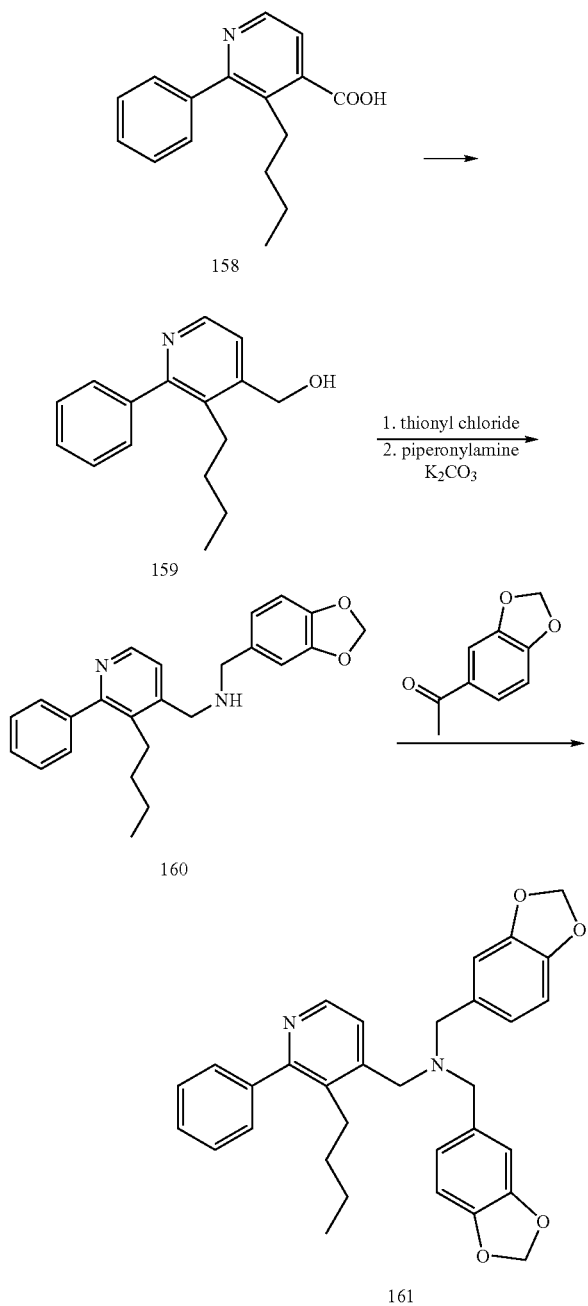

2-Phenyl-3-butylisonicotinic acid (158). A mixture of 4-phenyl-5-butyloxazole (12, 5 g, 25 mmol) and maleic acid (3.5 g, 30 mmol) is heated at 100° C. for 30 minutes After cooling, the semisolid mass is triturated with ether and the solid collected by filtration. $^{1}$H NMR (δ, CDCl$_3$, 400 MHz) 11.68 (brs, 1H), 8.72 (d, J=6.0 Hz, 1H), 7.73 (d, J=5.6 Hz, 1H), 7.48–7.51 (m, 2H), 7.42–7.44 (m, 2H), 6.25 (s, 1H), 2.86 (d, J=7.6 Hz, 2H), 1.36 (m, 2H), 1.11 (dt, J=7.6, 7.2 Hz, 2H), 0.68 (t, J=7.6 Hz, 3H). MS (M+1): 256, (M−1) 254.

2-Phenyl-4-hydroxymethyl-3-butylpyridine (159). Lithium aluminum hydride (4 ml of 1M in tetrahydrofuran) is added to a solution of 2-phenyl-3-butylisonicotinic acid (510 mg, 2 mmol) in tetrahydrofuran (20 mL). The reaction is stirred overnight and then quenched with 5 ml of 15% aqueous NaOH. The resulting mixture is extracted with ether, dried (Na$_2$SO$_4$), and concentrated to provide the desired hydroxymethylpyridine as an oil. LC-MS (M+1): 242; $^{1}$H NMR (δ, CDCL$_3$) 8.35 (1H, d, J=5.2 Hz), 7.30–7.39 (6H, m), 4.59 (2H, s), 2.43 (2H, t, J=8.0 Hz), 1.23 (2H, m), 1.13 (2H, m), 0.70 (3H, t, J=7.2 Hz).

2-Phenyl-4-(N-{2H-benzo[3,4-d]-1,3-dioxolan-5-ylmethyl})aminomethyl-3-butylpyridine (160). Thionyl chloride (200 mg, 1.67 mmol) is added to a solution of 2-phenyl-4-hydroxymethyl-3-butylpyridine (400 mg, 1.66 mmol) in pentene stabilized chloroform (8 mL) and the mixture is heated to 50° C. for 2 hours. The resulting mixture is cooled, washed with saturated sodium bicarbonate solution, dried (Na$_2$SO$_4$) and concentrated. The resulting crude chloride is taken up in dimethylformamide (10 mL) and added dropwise to a refluxing solution of piperonylamine (1.0 g, 4 equiv) in dimethylformamide (30 mL) containing 3 g of powdered potassium carbonate. After the addition is complete, the resulting mixture is refluxed for an additional 3 h, cooled and partitioned between water (200 mL) and ether (100 mL). The ether layer is washed 2 times with water, dried (Na$_2$SO$_4$), and concentrated. The resulting material is purified by chromatography on silica eluting with 10% CH$_3$OH/CHCl$_3$ to give the desired secondary amine 160. LC-MS (M+1): 375.3; $^{1}$H NMR (δ, CDCl$_3$): 0.73 (3H, t, J=7.2 Hz), 1.15 (2H, m J=7.2 Hz), 1.30 (2H, m), 2.58 (2H, t, J=8.0 Hz), 3.79 (2H, s), 3.83 (2H, s), 5.93 (2H, s), 6.75–6.82 (2H, m), 6.89 (1H, d, J=1.2 Hz), 7.36–7.42 (6H, m), 8.45 (1H, d, J=4.8 Hz) ppm.

2-Phenyl-4-(N,N-di {2H-benzo[3,4-d]-1,3-dioxolan-5-ylmethyl})aminomethyl-3-butylpyridine (161). Piperonal (30 mg) is added to a solution of 160 (38 mg) in dichloroethane (5 mL). The resulting mixture is stirred for 3 h after which time sodium triacetoxyborohydride (150 mg) is added in one portion and the resulting mixture is stirred overnight. The reaction mixture is quenched with 10% ammonium hydroxide solution (5 mL). The organic layer is washed with water and extracted with 1N HCl solution. The acidic extract is made basic with 1N NaOH solution and extracted with chloroform. The organic extract is dried (Na$_2$SO$_4$) and concentrated. The resulting oil is purified on preparative thin layer chromatography eluting with 10% CH$_3$OH/CHCl$_3$ to give the desired tertiary amine 161 as an oil. LC-MS (M+1): 509.4; $^{1}$H NMR (δ, CDCl$_3$): 0.71 (3H, t, J=7.2 Hz), 1.10 (2H, m, J=7.2 Hz), 2.60 (2H, t, J=8.0 Hz), 3.48 (4H, s), 3.58 (2H, s), 5.94 (4H, s), 6.75 (1H, d, J=8.0 Hz),6.80 (1H, dd, J=0.8, 8.0 Hz), 6.91 (1H, d, J=0.8 Hz), 7.36–7.43 (5H, m), 7.56 (1H, d, J=5.2 Hz), 8.47 (1H, d, J=5.2 Hz) ppm.

4-Phenyl-5-butyloxazole (157). A mixture of α-bromohexanophenone (25.5 g, 0.1 mole), ammonium formate (22 g, 0.35 mole) and formic acid (110 mL) is refluxed with stirring for 3 hours. The reaction mixture is poured onto ice, made basic with 10 N NaOH, and extracted with ether. The organic layer is washed with water, dried over sodium sulfate, and concentrated. The crude product is purified by flash chromatography on silica gel eluting with 20% ethyl acetate in hexane to provide the desired compound as an oil. $^{1}$H NMR (δ, CDCl$_3$, 400 MHz) 7.55 (m, 2H), 7.40 (s, 1H), 7.34 (dd, J=7, 7 Hz, 2H), 7.22 (dd, J=7, 7 Hz, 1H), 2.74 (m, 2H), 1.6 (m, 2H), 1.30 (m, 2H), 0.84 (t, J=7 Hz, 3H) ppm.

Example 12

Preparation of Arylpyrazole: 1,3-diphenyl-4-(N-{2H-benzo[3,4-D]-1,3-dioxolan-5-ylmethyl}-N-butylamino)methyl-5-propylpyrazole (167)

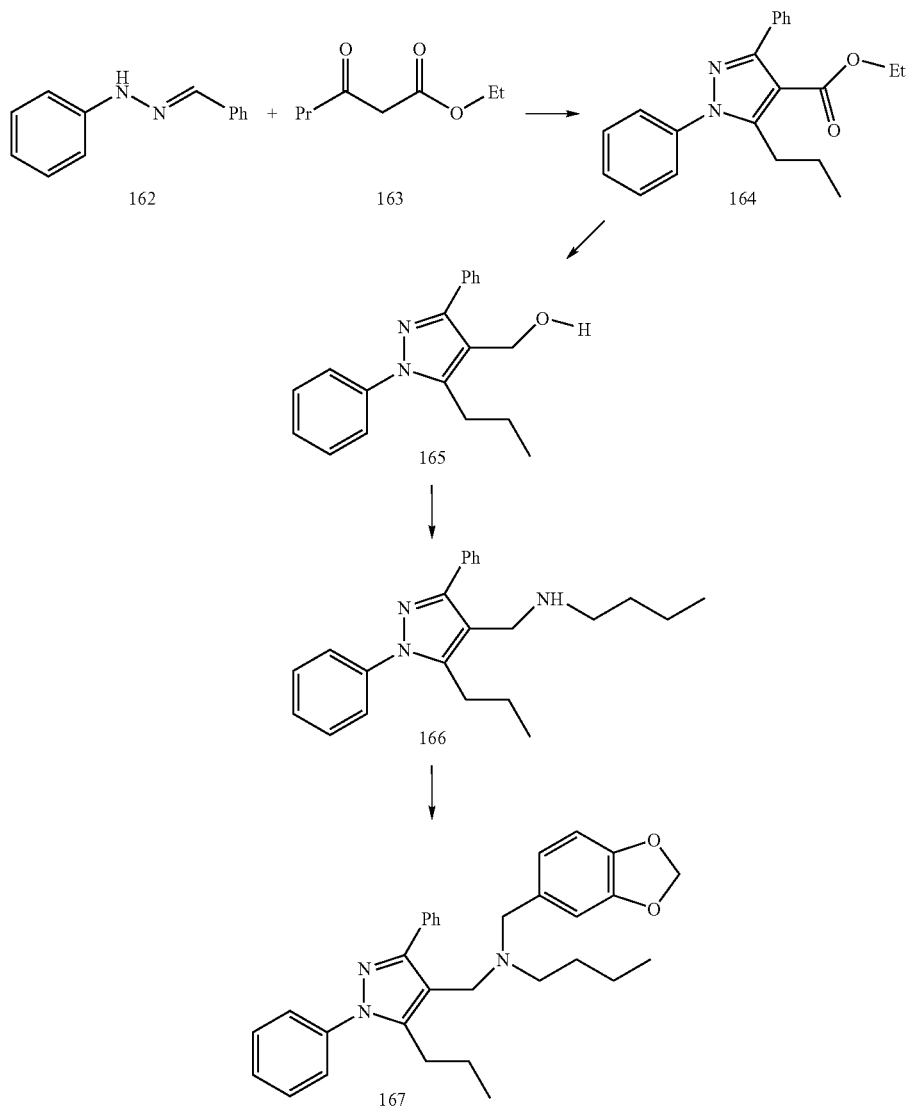

N'-Phenyl-N-phenylhydrazone (162). Benzaldehyde (9.81 g, 9.25 mmol) is added at 0–5° C. to a solution of phenyl hydrazine (10 g, 9.25 mmol) in ethanol (100 mL). A cream colored solid forms and the reaction mixture is allowed to stand for 2 hours. The solid is collected by filtration, washed with ice-cold ethanol and dried under vacuum to provide the desired compound, 162; LC-MS m/z 197.2.

Ethyl 1,3-diphenyl-5-propylpyrazole-4-carboxylate (164). A mixture of 162 (5 g, 25.5 mmol) and ethyl butyrylacetate (20.2 g, 128 mmol) and a catalytic amount of zinc chloride is heated at 125° C. under an air atmosphere for 3 hours. The reaction vessel is fitted with a short path distillation head and excess ethyl butyrylacetate is distilled away under vacuum. The resulting material is purified by column chromatography on silica eluting with 10% ethyl acetate in hexanes to provide the desired ester 164 as a yellow oil which crystallizes upon standing. Recrystallization from diisopropyl ether provides a white solid. MS (M+1): 335.2.

1,3-Diphenyl-4-hydroxymethyl-5-propylpyrazole (165). 4 ml of a 1M solution of lithium aluminum hydride in tetrahydrofuran is added to a solution of ester 164 (670 mg, 2 mmol) in tetrahydrofuran (20 mL). The reaction is stirred overnight and then quenched with 5 ml of 15% aqueous NaOH. The resulting mixture is extracted with ether, dried ($Na_2SO_4$), and concentrated to provide the desired hydroxymethylpyrazole as an oil. LC-MS (M+1): 293.3; $^1$H NMR ($\delta$, $CDCL_3$) 7.86 (dd, J=8.4 Hz, 2H), 7.34–7.52 (m, 8H), 4.65 (s, 2H), 2.72 (t, J=8.0 Hz, 2H), 1.52 (m, 2H), 0.87 (t, J=7.6 Hz, 3H).

[(1,3-Diphenyl-5-propylpyrazol-4-yl)methyl]butylamine (166). Thionyl chloride (1 mL) is added to a solution of 165 (289 mg) in pentene stabilized chloroform (8 mL) and the mixture heated to 60° C. for 2 hours. The resulting mixture is cooled, washed with saturated sodium bicarbonate solution, dried (Na$_2$SO$_4$), and concentrated. The resulting crude chloride is taken up in dimethylformamide (3 mL) and added dropwise to a solution of butylamine (1.0 g) in dimethylformamide (10 mL) containing 2 g of powdered potassium carbonate. After the addition is complete, the resulting mixture is stirred for an additional 3 h and partitioned between water (20 mL) and ether (10 mL). The ether layer is washed 2 times with water, dried (Na$_2$SO$_4$), and concentrated. The resulting material is purified by chromatography on silica eluting with 10% CH$_3$OH/CHCl$_3$ to give the desired secondary amine 166. LC-MS (M+1): 348.3; $^1$H NMR (δ, CDCl$_3$): 7.87 (dd, J=8.0, 1.6 Hz, 2H), 7.32–7.48 (m, 8H), 3.77 (s, 2H), 2.70 (m, 4H), 1.48 (m, 4H), 1.34 (m, 2H), 0.91 (t, J=7.6 Hz, 3H), 0.87 (t, J=7.6 Hz, 3H) ppm.

1,3-Diphenyl-4-(N-{2H-benzo[3,4-d]-1,3-dioxolan-5-yl-methyl}-N-butylamino)methyl-5-propylpyrazole (167). Piperonal (30 mg) is added to a solution of 166 (35 mg) in dichloroethane (5 mL). The resulting mixture is stirred for 3 h after which time sodium triacetoxyborohydride (150 mg) is added in one portion and the resulting mixture is stirred overnight. The reaction mixture is quenched with 10% ammonium hydroxide solution (5 mL). The organic layer is washed with water and extracted with 1N HCl solution. The acidic extract is made basic with 1N NaOH solution and extracted with chloroform. The organic extract is dried (Na$_2$SO$_4$) and concentrated. The resulting oil is purified on preparative thin layer chromatography eluting with 10% CH$_3$OH/CHCl$_3$ to give the desired tertiary amine (167) as an oil. LC-MS (M+1): 482.5; $^1$H NMR (δ, CDCl$_3$): 7.87 (d, J=7.2 Hz, 2H), 7.47 (d, J=4.4 Hz, 4H), 7.33–7.43 (m, 4H), 6.77 (s, 1H), 6.70 (s, 2H), 5.92 (s, 2H), 3.56 (s, 2H), 3.42 (s, 2H), 2.74 (t, J=8.0 Hz, 2H), 2.37 (t, J=7.2 Hz, 2H), 1.42 (m, 4H), 1.21 (m, 2H), 0.83 (t, J=7.6 Hz, 3H), 0.81 (t, J=7.2 Hz, 3H) ppm.

Example 13

Preparation of an Aryltriazole: Benzo[1,3]dioxol-5-ylmethyl-butyl-(4-butyl-5-phenyl-4H-[1,2,4]triazol-3-ylmethyl)-amine (171)

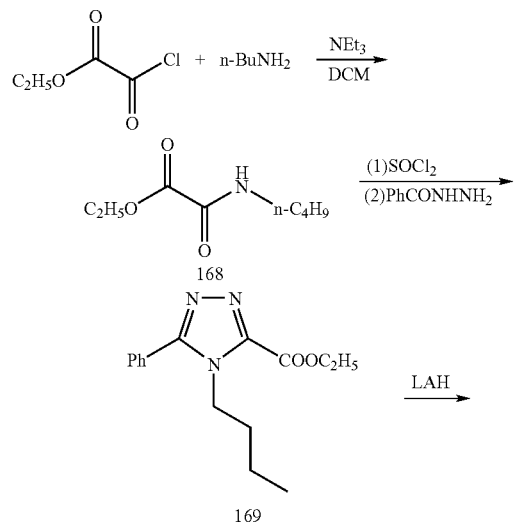

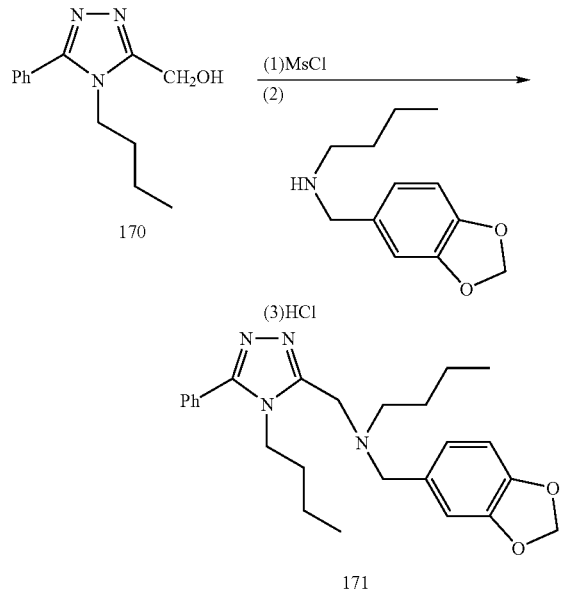

N-Butyl-oxalamic acid ethyl ester (168). Ethyl oxalyl chloride (1.1 eq.) is added slowly to a mixture of n-butylamine (7.31 g, 0.1 mol) and triethylamine (1.2 eq.) in DCM (60 mL) at 0° C., stirred at 0° C. for 2 hours. The reaction mixture is quenched with water, washed with 2N NaOH, 2N HCl and brine, dried with anhydrous Na$_2$SO$_4$, and concentrated. The residue is taken up in ether and the solid removed. The filtrate is concentrated and the residue is taken up in ether, and filtered to remove a slight amount of solid. The filtrate is concentrated to give the product (168). $^1$HNMR(CDCl$_3$): δ=4.32(2H, q, —OCH$_2$—), 3.32(2H, q, —NHCH$_2$—), 1.30–1.60(7H, m), 0.92(3H, t, —OCH$_2$CH$_3$)

4-Butyl-5-phenyl-4H-[1,2,4]triazole-3-carboxylic acid butyl ester (169). Starting material (168) is taken up in 35 ml thionyl chloride, refluxed for 2.5 hours, cooled to room temperature, and the excess thionyl chloride removed. The residue is taken up in 50 ml toluene, benzoic hydrazide (1.0 eq.) is added, the mixture is stirred at room temperature overnight and then refluxed for 2.5 hours. The reaction mixture is cooled to room temperature, mixed with water, and washed with water and brine. Purification by column chromatography with hexane/ethyl acetate gives the product (169). $^1$HNMR(CDCl$_3$): δ=7.52–7.60(5H, m, phenyl-H), 4.50(2H, q, J=7.2 Hz, —OCH$_2$CH$_3$), 4.34(2H, t, J=7.5 Hz, N—CH$_2$-n-C$_3$H$_7$), 1.60–1.80 (2H, m, —CH$_2$—), 1.47(3H, t, J=7.2 Hz, —CH$_3$), 1.18–1.38(2H, m, —CH$_2$—), 0.83(3H, t, J=7.5 Hz, —CH$_3$)

(4-Butyl-5-phenyl-4H-[1,2,4]triazol-3-yl)-methanol (170). 4-Butyl-5-phenyl-4H-[1,2,4]triazole-3-carboxylic acid butyl ester (169) (1.38 g, 5 mmol) is taken up in 50 ml anhydrous THF. LAH is added (3 eq.). The reaction is refluxed for 12 hours and then quenched carefully with water. Purification by column with 2.5% MeOH/DCM gives the desired product (170). $^1$HNMR(CDCl$_3$): δ=7.40–7.60 (5H, m, phenyl-H), 4.88(2H, s, —CH$_2$OH), 4.26(1H, br, —OH), 4.10(2H, t, J=7.8 Hz, —CH$_2$—), 1.58–1.70(2H, m, —CH$_2$—), 1.08–1.30(2H, m, —CH$_2$—), 0.82(3H, t, J=7.5 Hz, —CH$_3$)

Benzo[1,3]dioxol-5-ylmethyl-butyl-(4-butyl-5-phenyl-4H-[1,2,4]triazol-3-ylmethyl)-amine (171) (4-Butyl-5-phenyl-4H-[1,2,4]triazol-3-yl)-methanol (170) (174 mg, 0.75 mmol) is taken up in 5 ml anhydrous DCM, triethylamine (1.2 eq.) is added, MsCl (1.1 eq.) is added at 0° C., and the reaction is then stirred at room temperature for 2 hours, concentrated, and the residue dried on high vacuum for 2 hours. The residue is mixed with amine (1.0 eq.) and K₂CO₃(2.0 eq.) in 5 ml anhydrous CH₃CN and refluxed for 15 hours. The reaction mixture is filtered and washed with ethyl acetate. Purification by column chromatography with hexane/ethyl acetate yields the desired product (171). Treatment with 1.0M HCl in ether gives a white solid HCl salt. ¹HNMR(For free amine, CDCl₃): δ=7.40–7.60(5H, m, phenyl-H), 6.79(1H, s, phenyl-H), 6.74(1H, s, phenyl-H), 6.73 (1H, s, phenyl-H), 5.90(2H, s, —OCH₂O—), 3.98(2H, t, J=7.6 Hz, triazole-N—CH₂—), 3.75(2H, s, triazole-CH₂—N—), 3.50(s, 2H, phenyl-CH₂N—), 2.49(2H, t, J=7.2 Hz, —CH₂-nC₃H₇), 1.40–1.58(2H, m, —CH₂—), 1.20–1.40(4H, m, —CH₂—), 0.84(3H, t, J=7.2 Hz, —CH₃), 0.72(3H, t, J=7.2 Hz, —CH₃) LC-MS: RT=2.76 min, M+1: 421.21

Example 14

Preparation of a Mixture of 5-arylpyrazoles: Benzo[1,3]dioxol-5-ylmethyl-butyl-(4-butyl-1-methyl-5-phenyl-1H-pyrazol-3-ylmethyl)-amine and benzo[1,3]dioxol-5-ylmethyl-butyl-(4-butyl-2-methyl-5-phenyl-11H-pyrazol-3-ylmethyl)-amine (179)

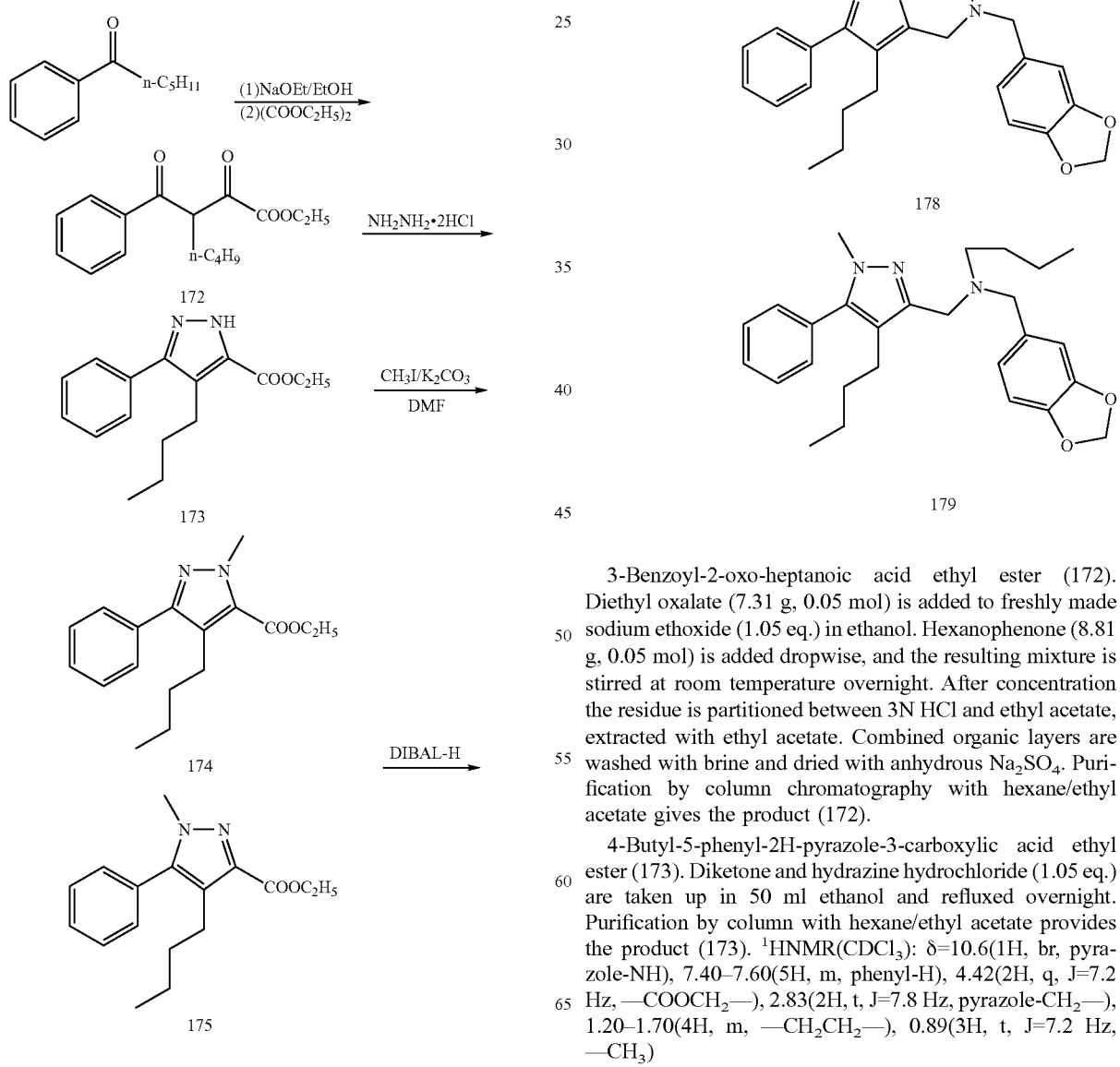

3-Benzoyl-2-oxo-heptanoic acid ethyl ester (172). Diethyl oxalate (7.31 g, 0.05 mol) is added to freshly made sodium ethoxide (1.05 eq.) in ethanol. Hexanophenone (8.81 g, 0.05 mol) is added dropwise, and the resulting mixture is stirred at room temperature overnight. After concentration the residue is partitioned between 3N HCl and ethyl acetate, extracted with ethyl acetate. Combined organic layers are washed with brine and dried with anhydrous Na₂SO₄. Purification by column chromatography with hexane/ethyl acetate gives the product (172).

4-Butyl-5-phenyl-2H-pyrazole-3-carboxylic acid ethyl ester (173). Diketone and hydrazine hydrochloride (1.05 eq.) are taken up in 50 ml ethanol and refluxed overnight. Purification by column with hexane/ethyl acetate provides the product (173). ¹HNMR(CDCl₃): δ=10.6(1H, br, pyrazole-NH), 7.40–7.60(5H, m, phenyl-H), 4.42(2H, q, J=7.2 Hz, —COOCH₂—), 2.83(2H, t, J=7.8 Hz, pyrazole-CH₂—), 1.20–1.70(4H, m, —CH₂CH₂—), 0.89(3H, t, J=7.2 Hz, —CH₃)

4-Butyl-1-methyl-5-phenyl-1H-pyrazole-3-carboxylic acid ethyl ester (175) and 4-Butyl-2-methyl-5-phenyl-1H-pyrazole-3-carboxylic acid ethyl ester (174). Starting material (173) (795 mg, 2.92 mmol) is dissolved in 30 ml anhydrous DMF. Potassium carbonate (3 eq.) is added followed by the addition of iodomethane (5 eq.). The resulting mixture is stirred at room temperature for 15 hours, until TLC shows the reaction is complete. The reaction is diluted with water and extracted with ethyl acetate. The combined organic layers are washed with brine and dried with anhydrous $Na_2SO_4$. Purification by column chromatography with hexane/ethyl acetate gives the 1-methyl substituted (175) and 2-methyl substituted products (174).

1-methyl Substituted pyrazole:

$^1$H NMR(CDCl$_3$): δ=7.50–7.60(2H, m, phenyl-H), 7.30–7.50(3H, m, phenyl-H), 4.40(2H, q, J=7.2 Hz, —COOCH$_2$—), 4.18(3H, s, —NCH$_3$), 2.77(2H, t, J=7.8 Hz, pyrazole-CH$_2$—), 1.30–1.60(7H, m, —CH$_2$CH$_2$CH$_3$), 0.89 (3H, t, J=7.2 Hz, —CH$_3$)

2-methyl Substituted Pyrazole:

$^1$H NMR(CDCl$_3$): δ=7.40–7.60(3H, m, phenyl-H), 7.20–7.30(2H, m, phenyl-H), 4.43(2H, q, J=7.2 Hz, —COOCH$_2$—), 3.78(3H, s, —NCH$_3$), 2.59(2H, t, J=7.8 Hz, pyrazole-CH$_2$—), 1.38–1.50(5H, m, —CH$_2$ and —CH$_3$), 1.18–1.30(2H, m, —CH$_2$—), 0.79(3H, t, J=7.2 Hz, —CH$_3$)

(4-Butyl-1-methyl-5-phenyl-1H-pyrazol-3-yl)-methanol (177). 1-methyl substituted pyrazole compound (175) (380 mg) is dissolved in 30 ml anhydrous THF.1.0 M DIBAL-H (13 ml, ~10 eq.) is added dropwise at −78° C. The resulting mixture is warmed naturally to room temperature and stirred overnight. The reaction is quenched with saturated $Na_2SO_4$. The resulting mixture is filtered and dried with anhydrous $Na_2SO_4$. Concentration provides the crude product (177). $^1$H NMR(CDCl$_3$): δ=7.50–7.60(2H, m, phenyl-H), 7.30–7.50 (3H, m, phenyl-H), 4.63(2H, d, —CH$_2$OH), 3.95(3H, s, —NCH$_3$), 2.58(2H, t, pyrazole-CH$_2$—), 1.30–1.60(4H, m, —CH$_2$CH$_2$—), 0.90(3H, t, —CH$_3$) LC-MS: RT=2.57 min, M+1: 245.23

Benzo[1,3]dioxol-5-ylmethyl-butyl-(4-butyl-2-methyl-5-phenyl-1H-pyrazol-3-ylmethyl)-amine (179). 1-methyl substituted pyrazole alcohol (177) (110 mg) is dissolved in anhydrous DCM (4 mL) and triethylamine (1.2 eq.) is added. MsCl is added at 0° C. and the mixture is stirred at room temperature for 2 hours, concentrated, and dried on high vacuum for 30 minutes The residue is dissolved in 5 ml anhydrous CH$_3$CN followed by the addition of amine (1.2 eq.) and potassium carbonate (5 eq.). The resulting mixture is refluxed for 12 hours. The reaction solution is filtered and washed with ethyl acetate. Purification by column chromatography with hexane/ethyl acetate provides product (179). Treated with 2M HCl in ether to give a white solid. $^1$H NMR(For free amine, CDCl$_3$): δ=7.58–7.60(2H, m, phenyl-H), 7.26–7.40(3H, m, phenyl-H), 6.81(1H, s, phenyl-H), 6.74(2H, s, phenyl-H), 5.94(2H, s, —OCH$_2$O—), 3.87(3H, s, —NCH$_3$), 3.48(2H, s, pyrazole-CH$_2$—), 3.42(2H, s, —CH$_2$Ph), 2.55(2H, t, J=8.0 Hz, —NCH$_2$—C$_3$H$_7$), 2.37 (2H, t, J=7.2 Hz, pyrazole-CH$_2$—), 1.20–1.60(8H, m, 4× (—CH$_2$—)), 0.78–0.90(6H, m, 2×(—CH$_3$))

LC-MS: RT=2.89 minutes, M+1: 434.28

Example 15

Preparation of Benzo[1,3]dioxol-5-ylmethyl-butyl-(5-butyl-3-chloro-6-phenyl-pyridazin-4-ylmethyl)-amine (180)

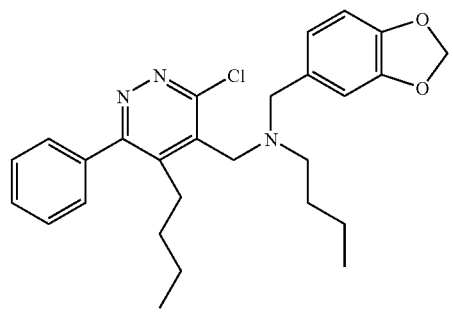

2-Bromo-1-phenyl-hexan-1-one. CuBr$_2$ (26.6 g, 119.2 mmol) is added in small portions to a solution of 1-phenyl-hexan-1-one (10.5 g, 59.6 mmol) in CHCl$_3$ (80 mL) and EtOAc (80 mL) of over a period of 1 h while the temperature maintained at 75–80° C. Heating is continued for 6 h until the green color disappears. The solid is filtered and washed with EtOAc (80 mL). The combined filtrate is evaporated and the residue is dissolved in EtOAc (200 mL), washed with water (200 mL) and brine (200 mL), and dried over Na$_2$SO$_4$. Evaporation of the solvent in vacuo provides a light yellow oil. LC-MS (M+1) 255. $^1$H NMR (δ, CDCl$_3$) 7.92–8.07 (m, 2H), 7.40–7.61 (m, 3H), 5.13 (t, J=7.2 Hz, 1H), 2.02–2.23 (m, 2H), 1.33–1.57 (m, 4H), 0.92 (t, J=7.4 Hz, 3H).

2-(1-Benzoyl-pentyl)-malonic acid dimethyl ester. Small portions of NaH (60%, 7.92 g, 198 mmol) are added to a solution of dimethyl malonate (22.6 ml, 198 mmol) in DMSO (100 mL) at 0° C. The ice bath is removed and the mixture stirred at room temperature for 2 hours. The solution is rechilled to 0° C. and a solution of 2-bromo-1-phenyl-hexan-1-one (2–1) (16.8 g, 66 mmol) in DMSO (50 mL) is added slowly. The ice bath is removed and the mixture stirred overnight. Water (500 mL) is added and the mixture is extracted with EtOAc (4×150 mL). The combined extracts are washed with brine (300 mL), dried (Na$_2$SO$_4$), and evaporated, to provide the product as a light yellow oil. LC-MS (M+1) 307. $^1$H NMR (δ, CDCl$_3$) 7.98–8.02 (m, 2H), 7.46–7.60 (m, 3H), 4.18–4.28 (m, 1H), 4.03–4.12 (m, 1H), 3.80 (s, 3H), 3.6.1 (s, 3H), 1.55–1.63 (m, 2H), 1.02–1.20 (m, 4H), 0.76 (t, J=0.72 Hz, 3H).

3-Benzoyl-heptanoic acid methyl ester. Water (3 ml, 166 mmol) and NaCl (5.3 g, 90.2 mmol) are added to a solution of 2-(1-benzoyl-pentyl)-malonic acid dimethyl ester (25.0 g, 81.7 mmol) in DMSO (150 mL). The mixture is heated at 150° C. for 6 hours. Water (450 mL) is added and the mixture is extracted with EtOAc (4×150 mL). The combined extracts are washed with brine (300 mL), dried (Na$_2$SO$_4$), and evaporated, to provides 3-Benzoyl-heptanoic acid methyl ester as a light yellow oil. LC-MS (M+1) 249. This compound without further purification is used directly to the next step.

5-Butyl-6-phenyl-4,5-dihydro-2H-pyridazin-3-one. A solution of 3-benzoyl-heptanoic acid methyl ester (4.72 g, 19 mmol) and hydrazine monohydrate (4.6 ml, 95 mmol) in ethanol (50 mL) is reflux for 12 hours. The solvent and excess hydrazine monohydrate is removed in vacuo and the residue is partitioned with EtOAc (80 mL) and water (80 mL). The layers are separated and the organic phase is washed with brine (60 mL), dried ($Na_2SO_4$) and evaporated in vacuo. Flash column chromatography of the residue (silica gel, 2:1 hexane, EtOAc) provides a creamy solid. LC-MS (M+1) 231. $^1$H NMR ($\delta$, $CDCl_3$) 8.84 (s, 1H), 7.72–7.79 (m, 2H), 7.37–7.43 (m, 3H), 3.19–3.30 (m, 1H), 2.62 (d, J=6.8 Hz, 2H), 1.52–1.62 (m, 2H). 1.21–1.43 (m, 4H), 0.87 (t, J=7.8 Hz, 3H).

5-Butyl-6-phenyl-2H-pyridazin-3-one. A solution of bromine (0.94 ml, 18.2 mmol) in HOAc (10 mL) is added dropwise to a solution of 5-butyl-6-phenyl-4,5-dihydro-2H-pyridazin-3-one (3.8 g, 16.5 mmol) in HOAc (40 mL) at 80° C. After the addition is complete, the heating is continued for 30 minutes and the solvent is evaporated in vacuo. The residue is partitioned between saturated aqueous $NaHCO_3$ solution (50 mL) and EtOAc (50 mL) and the organic layer washed with water (35 mL), brine (35 mL), and then dried ($Na_2SO_4$). Evaporation of the solvent in vacuo provides the desired product as a yellow solid. LC-MS (M+1) 229. $^1$H NMR ($\delta$, $CDCl_3$) 12.39 (s, 1H), 7.39–7.48 (m, 5H), 6.83 (s, 1H), 2.41 (t, J=7.2 Hz, 2H), 1.20–1.43 (m, 4H), 0.77 (t, J=7.7 Hz, 3H).

5-Butyl-3-chloro-6-phenyl-pyridazine. 5-butyl-6-phenyl-2H-pyridazin-3-one (3.6 g, 15.8 mmol)) is dissolved in $POCl_3$ (40 mL) and the solution is heated at 85° C. for 3 hours. The excess $POCl_3$ is evaporated in vacuo and the residue is partitioned between saturated aqueous $NaHCO_3$ solution (50 mL) and EtOAc (50 mL). The organic layer is washed with water (35 mL), brine (35 mL), and then dried ($Na_2SO_4$). Evaporation of the solvent in vacuo provides a yellow oil. Flash column chromatograph (silica gel, 4:1 hexane, EtOAc) provides a light yellow oil. LC-MS (M+1) 247. $^1$H NMR ($\delta$, $CDCl_3$) 7.47 (s, 5H), 7.42 (s, 1H), 2.62 (t, J=7.2 Hz, 2H), 1.43–1.53(m, 2H), 1.18–1.31 (m, 2H), 0.81 (t, J=7.5 Hz, 3H).

5-Butyl-3-chloro-4-hydroxymethyl-6-phenyl-pyridazine. Concentrated $H_2SO_4$ (0.17 ml, 3.2 mmol), $(NH_4)_2S_2O_8$ (0.575 g, 2.52 mmol) and $AgNO_3$ (4 mg) are added to a solution of 4-butyl-6-chloro-3-phenyl-pyridazine (0.526 g, 2.1 mmol) in MeOH (12 mL) and water (6 mL). The mixture is heated at 75° C. for 3 h and the solvent is then evaporated in vacuo. The residue is partitioned between saturated aqueous $NaHCO_3$ solution (30 mL) and EtOAc (30 mL) and the organic layer is washed with water (25 mL), brine (25 mL), and then dried ($Na_2SO_4$). Evaporation of the solvent in vacuo provides a yellow oil. Flash column chromatography (silica gel, 2:1 hexane, EtOAc) provides the product as a light yellow solid. LC-MS (M+1) 277. $^1$H NMR ($\delta$, $CDCl_3$) 7.42–7.50 (m, 5H), 4.87 (s, 2H), 2.75 (t, J=8.1 Hz, 2H), 2.40 (s, 1H), 1.34–1.43 (m, 2H), 1.17–1.25 (m, 2H), 0.74 (t, J=7.5 Hz, 3H).

5-Butyl-3-chloro-4-chloromethyl-6-phenyl-pyridazine hydrochloride. To a solution of 4-butyl-6-chloro-5-hydroxymethyl-3-phenyl-pyridazine (0.32 g, 1.16 mmol) in $CH_2Cl_2$ (5 mL) is added $SOCl_2$ (2 mL). The resulting clear solution is stirred at room temperature for 3 hours. The solvent is removed in vacuo and the residue is dissolved in toluene (5 mL) and evaporated to remove the remaining $SOCl_2$. The resulting semi-solid is used directly for the next step. LC-MS (M+1) 295.

Benzo[1,3]dioxol-5-ylmethyl-(5-butyl-3-chloro-6-phenyl-pyridazin-4-ylmethyl)-amine. Piperonylamine (0.37 ml, 3 mmol) and $K_2CO_3$ (0.69 g, 3 mmol) are added to a solution of 5-butyl-3-chloro-4-chloromethyl-6-phenyl-pyridazine hydrochloride (0.176 g, 0.6 mmol) in $CH_3CN$ (12 mL). The mixture is stirred at room temperature overnight. The solvent is removed in vacuo and the residue is partitioned between water (20 mL) and EtOAc (20 mL). The organic layer is washed with water (15 mL), brine (15 mL), and then dried ($Na_2SO_4$). Evaporation of the solvent in vacuo provides a yellow oil. Flash column chromatography (silica gel, 10:0.5:0.05 $CH_2Cl_2$, MeOH, $NH_4OH$) of the residue provides a light yellow oil. LC-MS (M+1) 410. $^1$H NMR ($\delta$, $CDCl_3$) 7.41–7.49 (m, 5H), 6.87 (s, 1H), 6.74–6.82 (m, 2H), 5.94 (s, 2H), 3.87 (s, 2H), 3.81 (s, 2H), 2.59 (t, J=7.8 Hz, 2H), 1.81 (s, 1H), 1.25–1.35 (m, 2H), 1.07–1.17 (m, 2H), 0.70 (t, J=7.2 Hz, 3H).

Benzo[1,3]dioxol-5-ylmethyl-butyl-(5-butyl-3-chloro-6-phenyl-pyridazin-4-ylmethyl)-amine. PrCHO (0.036 ml, 0.4 mmol) is added to a solution of benzo[1,3]dioxol-5-ylmethyl-(5-butyl-3-chloro-6-phenyl-pyridazin-4-ylmethyl)-amine (0.04 g, 0.1 mmol) in $CH_2ClCH_2Cl$ (5 mL) and HOAc (0.5 mL). The mixture is stirred at room temperature for 45 min, $NaBH(OAc)_3$ (0.127 g, 0.6 mmol) is then added and the mixture is stirred overnight. The solvent is removed in vacuo, the residue is partitioned between saturated aqueous $NaHCO_3$ solution (20 mL) and EtOAc (20 mL), the organic layer is washed with water (15 mL), brine (15 mL), and then dried ($Na_2SO_4$). Evaporation of the solvent in vacuo provides a yellow oil. Preparative TLC (10:0.5:0.05 $CH_2Cl_2$, MeOH, $NH_4OH$) provides the purified product as a light yellow oil. LC-MS (M+1) 466. $^1$H NMR ($\delta$, $CDCl_3$) 7.39–7.47 (m, 5H), 6.77 (s, 1H), 6.70 (s, 2H), 5.90 (s, 2H), 3.76 (s, 2H), 3.49 (s, 2H), 2.75 (t, J=7.2 Hz, 2H), 2.45 (t, J=7.2 Hz, 2H), 1.45–1.54 (m, 2H), 0.92–1.32 (m, 6H), 0.82 (t, J=7.2 Hz, 3H), 0.63 (t, J=7.2 Hz, 3H).

Example 16

Preparation of Bis-benzo[1,3]dioxol-5-ylmethyl-(5-butyl-3-chloro-6-phenyl-pyridazin-4-ylmethyl)-amine (181)

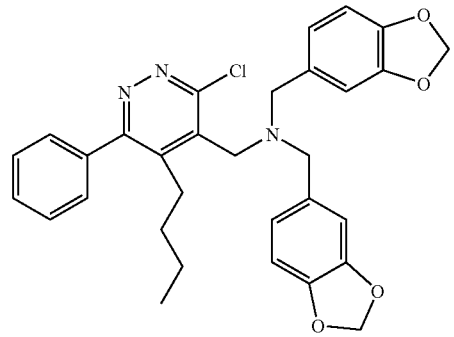

Piperonyl (0.06 g, 0.4 mmol) is added to a solution of benzo[1,3]dioxol-5-ylmethyl-(5-butyl-3-chloro-6-phenyl-pyridazin-4-ylmethyl)-amine (0.042 g, 0.1 mmol) in $CH_2ClCH_2Cl$ (5 mL) and HOAc (0.5 mL). The mixture is stirred at room temperature for 45 minutes, $NaBH(OAc)_3$ (0.127 g, 0.6 mmol) is then added and the mixture is stirred overnight. The solvent is removed in vacuo, the residue is partitioned between saturated aqueous $NaHCO_3$ solution (20 mL) and EtOAc (20 mL), and the organic layer is washed with water (15 mL), brine (15 mL), and then dried ($Na_2SO_4$). Evaporation of the solvent in vacuo provides the compound shown above as a yellow oil. Preparative TLC (3:1 Hexane, EtOAc) of the residue provides a light yellow oil. LC-MS (M+1) 544. $^1$H NMR ($\delta$, $CDCl_3$) 7.37–7.48 (m, 5H), 6.77 (s, 2H), 6.72 (s, 4H), 5.91 (s, 4H), 3.78 (s, 2H), 3.49 (s, 4H), 2.69 (t, J=7.2 Hz, 2H), 0.85–1.02 (m, 4H), 0.59 (t, J=7.0 Hz, 3H).

Example 17

Preparation of Benzo[1,3]dioxol-5-ylmethyl-(5-butyl-3-chloro-6-phenyl-pyridazin-4-ylmethyl)-(3-ethoxy-benzyl)-amine (182)

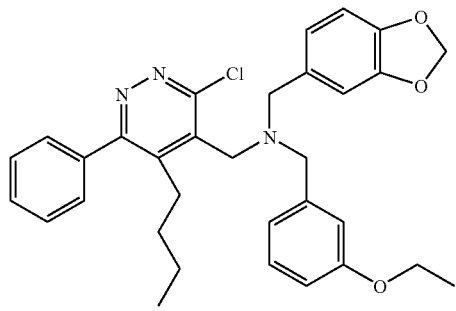

3-Ethoxybenzaldehyde (0.062 ml, 0.44 mmol) is added to a solution of benzo[1,3]dioxol-5-ylmethyl-(5-butyl-3-chloro-6-phenyl-pyridazin-4-ylmethyl)-amine) (0.045 g, 0.1 mmol) in $CH_2ClCH_2Cl$ (5 mL) and HOAc (0.5 mL). The mixture is stirred at room temperature for 45 minutes, $NaBH(OAc)_3$ (0.140 g, 0.66 mmol) is then added and the mixture is stirred over night. The solvent is removed in vacuo, the residue is partitioned between saturated aqueous $NaHCO_3$ solution (20 mL) and EtOAc (20 mL), the organic layer is washed with water (15 mL), brine (15 mL), and then dried ($Na_2SO_4$). Evaporation of the solvent in vacuo provides the product shown above as a yellow oil. Preparative TLC (3:1 Hexane, EtOAc) of the residue provides purified product as a light yellow oil. LC-MS (M+1) 544. $^1$H NMR ($\delta$, $CDCl_3$) 7.36–7.48 (m, 5H), 7.18 (t, J=7.2 Hz, 1H), 6.70–6.87 (m, 6H), 5.91 (s, 2H), 4.00 (q, J=7.0 Hz, 2H), 3.80 (s, 2H), 3.56 (s, 2H), 3.52 (s, 2H), 2.70 (t, J=7.5 Hz, 2H), 1.41 (t, J=7.2 Hz, 2H), 0.84–1.02 (m, 4H), 0.58 (t, J=7.2 Hz, 3H).

Example 18

Preparation of (5-butyl-3-chloro-6-phenyl-pyridazin-4-ylmethyl)-(2,3-dihydro-benzo[1,4]dioxin-6-ylmethyl)-(3-ethoxy-benzyl)-amine (183)

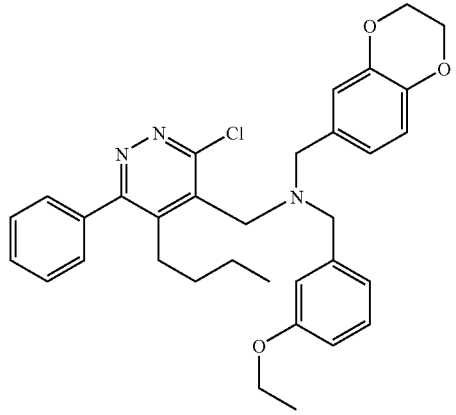

(2,3-Dihydro-benzo[1,4]dioxin-6-ylmethyl)-(3-ethoxybenzyl)-amine (0.211 g, 0.7 mmol) and $K_2CO_3$ (0.69 g, 3 mmol) is added to a solution of 5-butyl-3-chloro-4-chloromethyl-6-phenyl-pyridazine hydrochloride (0.175 g, 0.6 mmol) in $CH_3CN$ (15 mL). The mixture is stirred at 80° C. overnight. The solvent is removed in vacuo and the residue is partitioned between water (20 mL) and EtOAc (20 mL). The organic layer is washed with water (15 mL), brine (15 mL), then dried ($Na_2SO_4$). Evaporation of the solvent in vacuo provides a yellow oil. Preparative TLC (3:1 Hexane, EtOAc) of the residue provides a light yellow oil. LC-MS (M+1) 558 $^1$H NMR ($\delta$, $CDCl_3$) 7.36–7.48 (m, 5H), 7.18 (t, J=7.2 Hz, 1H), 6.72–6.89 (m, 6H), 4.21 (s, 4H), 4.01 (q, J=7.2 Hz, 2H), 3.80 (s, 2H), 3.56 (s, 2H), 3.50 (s, 2H), 2.70 (t, J=7.2 Hz, 2H), 1.41 (t, J=6.9 Hz, 3H), 0.84–1.02 (m, 4H), 0.58 (t, J=7.2 Hz, 3H).

Example 19

Preparation of Bis-benzo[1,3]dioxol-5-ylmethyl-[2-(3-butyl-2,5-diphenyl-3H-imidazol-4-yl)-ethyl]-amine (191)

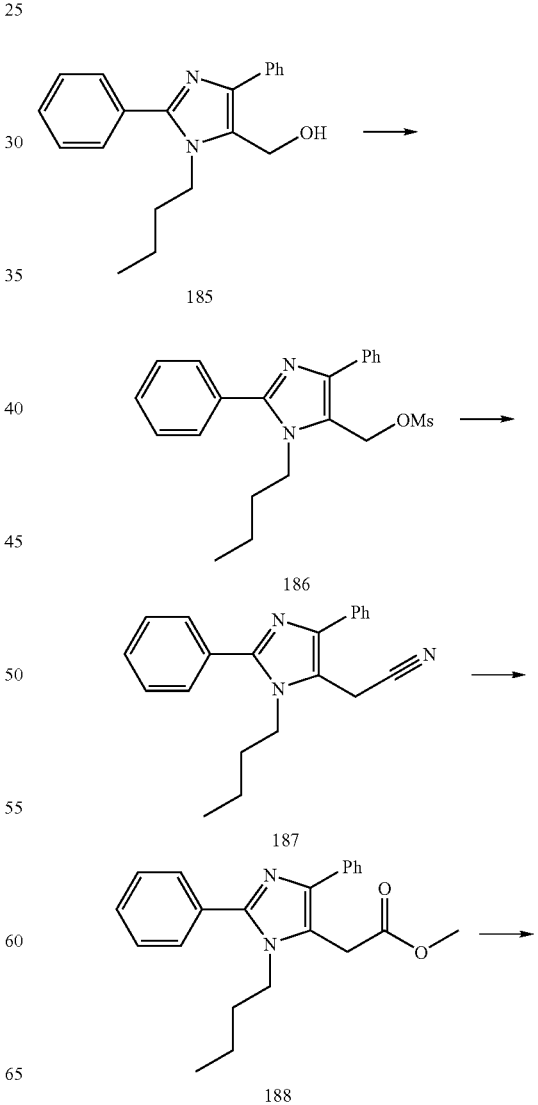

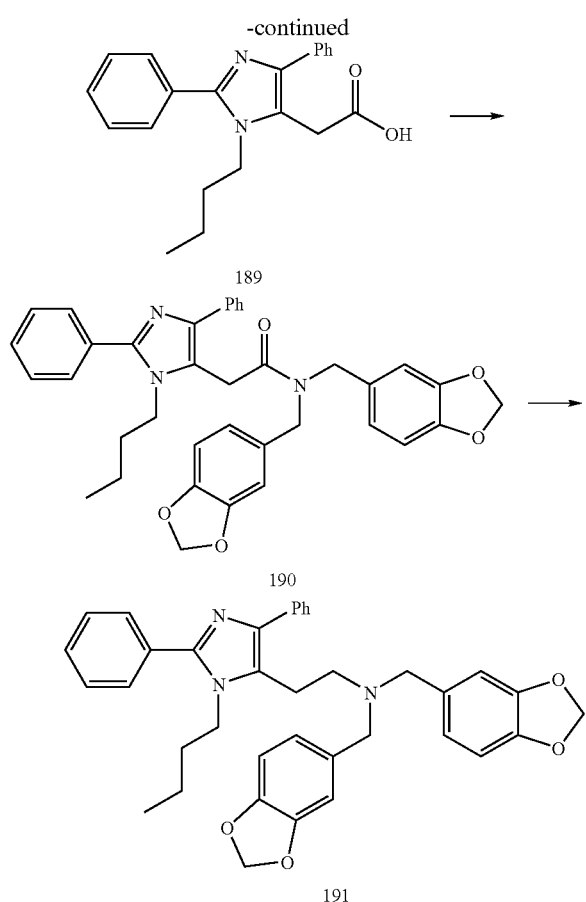

(3-butyl-2,5-diphenyl-3H-imidazol-4-yl)-acetonitrile (187). Triethylamine (1.0 ml, 7.18 mmol) and methanesulfonyl chloride (0.37 ml, 4.89 mmol) are added to a stirred solution of (3-butyl-2,5-diphenyl-3H-imidazol-4-yl)-methanol (1.0 g, 3.26 mmol)(185) in anhydrous acetonitrile (30 mL) at 0° C. After proceeding for 1 hour the reaction is concentrated at 60° C. to remove all solvent and excess MsCl. Cold acetonitrile is added to precipitate triethylammonium chloride, which is then removed by filtration. The remaining solution of mesylate product is reduced to a 30 ml volume; tetraethylammonium cyanide (1.53 g, 9.79 mmol) is added to the solution, and the reaction is heated at 60° C. overnight. Solvent is removed in vacuo and the crude product dissolved in ethyl acetate (100 mL). The organic layer is washed with saturated sodium bicarbonate (2×100 mL), brine (1×100 mL) and dried over magnesium sulfate. The sample is filtered, concentrated and purified by flash chromatography on $SiO_2$ using an eluent of 2:3 acetate:hexane to afford (3-butyl-2,5-diphenyl-3H-imidazol-4-yl)-acetonitrile (187) as a light orange oil.

(3-butyl-2,5-diphenyl-3H-imidazol-4-yl)-acetic acid methyl ester (188). Hydrogen chloride gas is bubbled into solution of (3-butyl-2,5-diphenyl-3H-imidazol-4-yl)-acetonitrile (187) (640 mg, 2.03 mmol) in methanol (30 mL) at 0° C. for 10 minutes, followed by stirring for 30 minutes. Water (0.0365 ml, 2.03 mmol) is then added and the reaction refluxed at 80° C. for 2 hours. The methanol is then removed in vacuo, the reaction crude is dissolved in ethyl acetate (100 mL) and the organic layer is washed with saturated sodium bicarbonate (1×100 mL), brine (1×100 mL), and dried over magnesium sulfate. The sample is filtered, concentrated and purified by flash chromatography on $SiO_2$ using an eluent of 2:3 ethyl acetate:hexane to afford (3-butyl-2,5-diphenyl-3H-imidazol-4-yl)-acetic acid methyl ester (188) as a colorless oil.

(3-butyl-2,5-diphenyl-3H-imidazol-4-yl)-acetic acid (189) 5N sodium hydroxide (100 mL) is added to a solution of (3-butyl-2,5-diphenyl-3H-imidazol-4-yl)-acetic acid methyl ester (188) (460 mg, 1.32 mmol) in ethanol (100 mL). The mixture is stirred at 85° C. for 4 hours. All ethanol is removed in vacuo and the crude extracted with ethyl ether (2×50 mL). The aqueous fraction is then acidified to pH 2 using 1M HCl and the product extracted into ethyl acetate (100 mL). The organic fraction is washed with water (1×100 mL), brine (1×100 mL), and dried over magnesium sulfate. Concentration in vacuo affords (3-butyl-2,5-diphenyl-3H-imidazol-4-yl)-acetic acid (189) as a white foam.

N,N-bis-benzo[1,3]dioxol-5-ylmethyl-2-(3-butyl-2,5-diphenyl-3H-imidazol-4-yl)-acetamide (190). Triethylamine (0.23 ml, 1.64 mmol) and benzotriazol-1-yl-oxy-tris(dimethylamino)phosphonium hexafluorophosphate (330 mg, 0.748 mmol) are added to a solution of (3-butyl-2,5-diphenyl-3H-imidazol-4-yl)-acetic acid (250 mg, 0.748 mmol) (189) in N,N-dimethylformamide (15 mL) and the reaction mixture is allowed to stir overnight at room temperature. The reaction is diluted with ethyl ether (100 mL) and the organic layer washed with saturated sodium bicarbonate (3×100 mL), brine (1×100 mL), and is dried over magnesium sulfate. The crude is filtered, concentrated in vacuo, and flash chromatographed on $SiO_2$ using an eluent of 1:1 ethyl ether:hexane to afford N,N-bis-benzo[1,3]dioxol-5-ylmethyl-2-(3-butyl-2,5-diphenyl-3H-imidazol-4-yl)-acetamide (190) as a colorless waxy solid.

Bis-benzo[1,3]dioxol-5-ylmethyl-[2-(3-butyl-2,5-diphenyl-3H-imidazol-4-yl)-ethyl]-amine (191). A solution of N,N-bis-benzo[1,3]dioxol-5-ylmethyl-2-(3-butyl-2,5-diphenyl-3H-imidazol-4-yl)-acetamide (150 mg, 0.249 mmol) in tetrahydrofuran (25 mL) is cooled to 0° C. under a nitrogen atmosphere. Lithium aluminum hydride (95%, 30 mg, 0.747 mmol) is added in one portion and the reaction allowed to stir overnight warming to room temperature. Water (0.03 mL), sodium hydroxide (15% solution, 0.03 mL), and water (0.09 mL) are added and the reaction mixture is allowed to stir at 0° C. for 15 minutes. Magnesium sulfate is then added and the crude solution is filtered through a bed of Celite washing with 2% methanol in dichloromethane (100 mL). The crude sample is concentrated in vacuo and flash chromatographed on $SiO_2$ using an eluent of dichloromethane:methanol 95:5 to afford bis-benzo[1,3]dioxol-5-ylmethyl-[2-(3-butyl-2,5-diphenyl-3H-imidazol-4-yl)-ethyl]-amine as a colorless syrup.

Example 20

Preparation of (5-butyl-6-phenyl-pyrimidin-4-ylmethyl)-(2,3-dihydro-benzo[1,4]dioxin-6-ylmethyl)-(3-ethoxy-benzyl)-amine

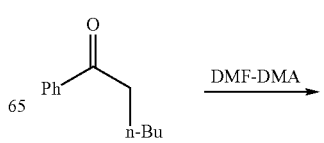

-continued

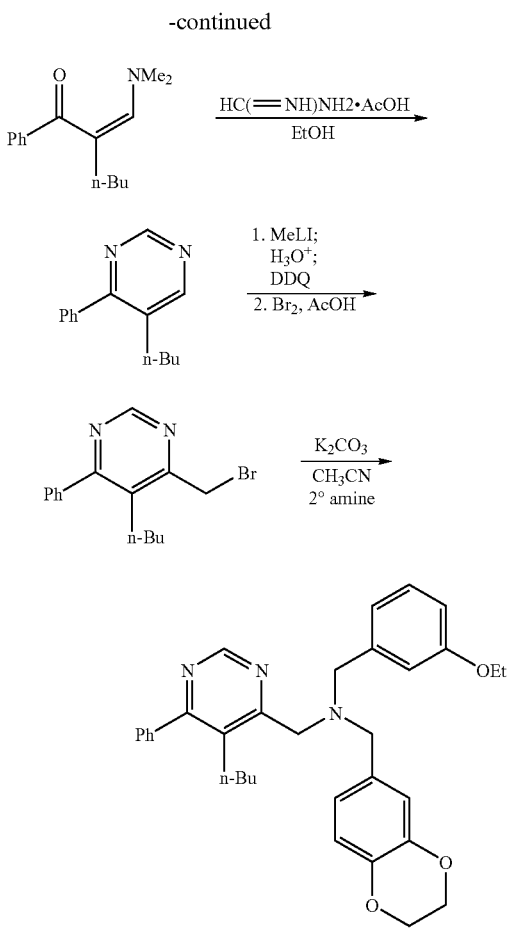

Step 1. Preparation of 2-Butyl-3-dimethylamino-1-phenyl-propenone

A solution of hexanophenone (1.76 g, 10.0 mmol) in dimethylformamide dimethyl acetal (DMF-DMA) (7.07 ml, 50.0 mmol) is stirred at 150° C. in a sealed tube for 16 hours. After cooling, the solution is concentrated in vacuo. EtOH is added and then removed in vacuo in order to aid in the removal of DMF and DMF-DMA. 2-Butyl-3-dimethylamino-1-phenyl-propenone is obtained as an orange oil and is used directly in the next reaction. $^1$H NMR (CDCl$_3$, 300 MHz) δ 7.42–7.39 (m, 2H), 7.36–7.32 (m, 3H), 6.80 (s, 1H), 3.01 (s, 6H), 2.61–2.56 (m, 2H), 1.48–1.36 (m, 4H), 0.93 (t, J=7.2 Hz, 3H) ppm.

Step 2. Preparation of 5-butyl-4-phenyl-pyrimidine

Crude 2-butyl-3-dimethylamino-1-phenyl-propenone is dissolved in EtOH (~5–6 mL) and treated with formamidine acetate (3.12 g, 30.0 mmol). The reaction mixture is then stirred at 120° C. in a sealed tube for 6 hours. After cooling, the reaction mixture is partitioned between EtOAc and H$_2$O (50 mL). The layers are separated, and the organic layer is washed with additional H$_2$O (50 mL) and brine (50 mL). The aqueous washes are reextracted once with EtOAc, and the combined extracts are dried over Na$_2$SO$_4$ and concentrated. The residue is purified by flash chromatography on silica gel. Elution with 3:1 EtOAc-hexanes affords pure 5-butyl-4-phenyl-pyrimidine as a light yellow oil. $^1$H NMR (CDCl$_3$, 300 MHz) δ 9.11 (s, 1H), 8.64 (s, 1H), 7.55–7.46 (m, 5H), 2.73–2.68 (m, 2H), 1.56–1.45 (m, 2H), 1.27 (sext, J=7.2 Hz, 2H), 0.83 (t, J=7.2 Hz, 3H) ppm. MS: m/z 213 [M+1].

Step 3. Preparation of 5-butyl-4-methyl-6-phenyl-pyrimidine 1.4 M MeLi in Et$_2$O (1.54 ml, 2.16 mmol) is slowly added to a solution of 5-butyl-4-phenyl-pyrimidine (436 mg, 2.05 mmol) in Et$_2$O (6 mL) at –30° C. under N$_2$. The reaction mixture is stirred at –30° C. for 30 minutes and then at 0° C. for 45 minutes. Next, a solution of AcOH (0.12 mL) and H$_2$O (0.02 mL) in THF (2 mL) is added, followed by a solution of 2,3-dichloro-5,6-dicyano-1,4-benzophenone (DDQ) (466 mg, 2.05 mmol) in THF (5 mL). The resulting mixture is stirred at room temperature for 5 minutes, recooled to 0° C., and then treated with 3.0 M aqueous NaOH. The mixture is stirred at 0° C. for 5 minutes, diluted with H$_2$O, and extracted twice with Et$_2$O. The combined extracts are dried over Na$_2$SO$_4$ and concentrated. The dark residue is purified by flash chromatography on silica gel. Elution with 2:1 Hex-EtOAc followed by 1:1 hexanes-EtOAc affords 5-butyl-4-methyl-6-phenyl-pyrimidine as a light yellow oil. $^1$H NMR (CDCl$_3$, 300 MHz) δ 8.95 (s, 1H), 7.45 (m, 5H), 2.67–2.62 (m, 2H), 2.61 (s, 3H), 1.48–1.40 (m, 2H), 1.25 (sext, J=7.2 Hz), 0.82 (t, J=7.2 Hz, 3H) ppm. MS: m/z 227 [M+1].

Step 4. Preparation of 4-bromomethyl-5-butyl-6-phenyl-pyrimidine

A solution of 5-butyl-4-methyl-6-phenyl-pyrimidine (320 mg, 1.14 mmol) and Br$_2$ (0.08 ml, 1.48 mmol) in AcOH (2 mL) is stirred at 80° C. for 2 hours. After cooling, the solution is concentrated. The residue is then partitioned between Et$_2$O and half saturated aqueous NaHCO$_3$. The layers are separated, and the aqueous layer is reextracted once with Et$_2$O. The combined extracts are dried over Na$_2$SO$_4$ and concentrated. The residue is purified by flash chromatography on silica gel. Elution with 3:1 hexanes-EtOAc affords 4-bromomethyl-5-butyl-6-phenyl-pyrimidine and a small amount of an unidentified impurity. $^1$H NMR (CDCl$_3$, 300 MHz) δ 9.08 (s, 1H), 7.47 (s, 5H), 4.57 (s, 2H), 2.79–2.74 (m, 2H), 1.52–1.42 (m, 2H), 1.38–1.20 (m, 2H), 0.80 (t, J=7.4 Hz, 3H) ppm.

Step 5. Preparation of (5-butyl-6-phenyl-pyrimidin-4-ylmethyl)-(2,3-dihydro-benzo[1,4]dioxin-6-ylmethyl)-(3-ethoxy-benzyl)-amine A mixture of 4-bromomethyl-5-butyl-6-phenyl-pyrimidine (86 mg), (2,3-dihydro-benzo[1,4]dioxin-6-ylmethyl)-(3-ethoxy-benzyl)-amine (93 mg, 0.310 mmol), and K$_2$CO$_3$ (195 mg, 1.4 mmol) in CH$_3$CN (2.0 mL) is stirred at reflux for 1 h and at room temperature for 16 hours. The reaction mixture is then diluted with CH$_2$Cl$_2$ and filtered. The filtrate is concentrated, and the residue purified by preparative TLC, developing with 2:1 hexanes-EtOAc (+0.5% Et$_3$N). The band containing product affords pure (5-butyl-6-phenyl-pyrimidin-4-ylmethyl)-(2,3-dihydro-benzo[1,4]dioxin-6-ylmethyl)-(3-ethoxy-benzyl)-amine. $^1$H NMR (CDCl$_3$, 300 MHz) δ 8.98 (s, 1H), 7.42 (m, 5H), 7.19 (t, J=8.0 Hz, 1H), 6.92–6.73 (m, 6H), 4.22 (s, 4H), 4.01 (q, J=6.9 Hz, 2H), 3.76 (s, 2H), 3.60 (s, 2H), 3.54 (s, 2H), 2.70–2.64 (m, 2H), 1.41 (t, J=6.9 Hz, 3H), 1.09–0.99 (m, 2H), 0.91 (sext, J=7.2 Hz, 2H), 0.61 (t, J=7.2 Hz, 3H) ppm. MS: m/z 524 [M+1].

Example 21

Preparation of 4-{[(5-butyl-2-isobutoxy-6-phenyl-pyrimidin-4-ylmethyl)-(2,3-dihydro-benzo[1,4]dioxin-6-ylmethyl)-amino]-methyl}-benzoic Acid

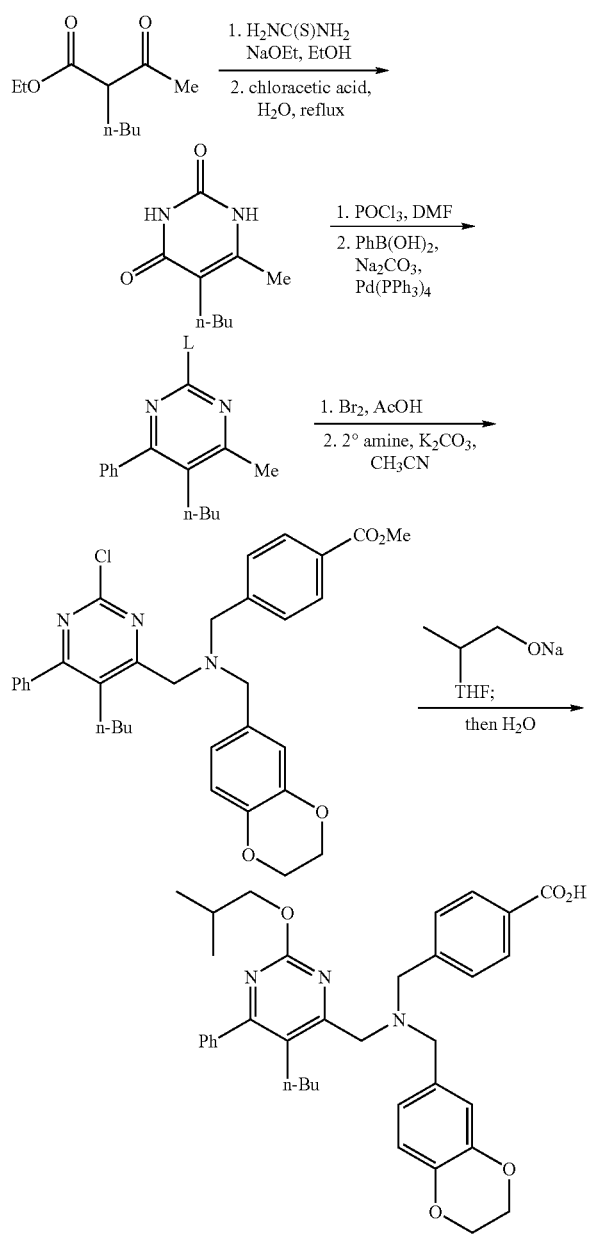

Step 1. Preparation of 5-butyl-6-methyl-2-thioxo-2,3-dihydro-1H-pyrimidin-4-one Sodium metal (1.85 g, 80.5 mmol) is dissolved in EtOH (50 mL). Next, thiourea (5.11 g, 67.1 mmol) is added to the NaOEt solution, followed by ethyl 2-n-butylacetoacetate (2.5 g, 13.4 mmol). The reaction mixture is stirred at reflux for 3 hours and then allowed to cool to room temperature overnight. The EtOH is removed in vacuo. The residue is then suspended in H$_2$O (50 mL) and the resulting mixture carefully treated with concentrated HCl (~7.5 mL) just until pH 4 is reached. After stirring for 15 minutes, the suspension is filtered, and the solid thoroughly washed with H$_2$O.

Drying affords pure 5-butyl-6-methyl-2-thioxo-2,3-dihydro-1H-pyrimidin-4-one as a slightly off-white solid. $^1$H NMR (DMSO-d$_6$, 300 MHz) δ 12.28 (br s, 1H), 12.05 (br s, 1H), 2.21 (m, 2H), 2.18 (s, 3H), 1.30–1.21 (m, 4H), 0.85 (t, J=6.9 Hz, 3H) ppm. MS: m/z 199 [M+1].

Step 2. Preparation of 5-butyl-6-methyl-1H-pyrimidine-2,4-dione

A suspension of 5-butyl-6-methyl-2-thioxo-2,3-dihydro-1H-pyrimidin-4-one in 10% aqueous chloroacetic acid (100 mL) is stirred at reflux for 3 hours and then allowed to cool to room temperature. The suspension is cooled in an ice bath for a few minutes and then filtered. The solid is thoroughly washed with H$_2$O and dried, yielding pure 5-butyl-6-methyl-1H-pyrimidine-2,4-dione as a white solid. $^1$H NMR (DMSO-d$_6$, 300 MHz) δ 10.86 (br s, 1H), 10.57 (br s, 1H), 2.17 (m, 2H), 2.01 (s, 3H), 1.25 (m, 4H), 0.85 (t, J=6.9 Hz, 3H) ppm. MS: m/z 183 [M+1].

Step 3. Preparation of 5-Butyl-2,4-dichloro-6-methyl-pyrimidine

A mixture of 5-butyl-6-methyl-1H-pyrimidine-2,4-dione (1.76 g, 9.66 mmol) in POCl$_3$ (15 mL), containing DMF (0.065 mL) is stirred at reflux for 4 hours. After cooling, the yellow solution is concentrated in vacuo. The flask is placed in an ice bath, and crushed ice (~50–100 g) is added to the residue. The mixture is stirred vigorously until the ice melts. The mixture is then extracted with EtOAc. The extract is washed with H$_2$O (50 mL) and brine (50 mL), dried over Na$_2$SO$_4$, and concentrated to provide pure 5-butyl-2,4-dichloro-6-methyl-pyrimidine as a yellow oil. $^1$H NMR (CDCl$_3$, 300 MHz) δ 2.74–2.57 (m, 2H), 2.56 (s, 3H), 1.55–1.40 (m, 4H), 0.97 (t, J=7.1 Hz, 3H) ppm. MS: m/z 219 [M+1].

Step 4. Preparation of 5-Butyl-2-chloro-4-methyl-6-phenyl-pyrimidine

A mixture of 5-butyl-2,4-dichloro-6-methyl-pyrimidine (711 mg, 3.24 mmol), phenylboronic acid (475 mg, 3.89 mmol), Na$_2$CO$_3$ (1.03 g, 9.73 mmol), and Pd(PPh$_3$)$_4$ (187 mg, 0.162 mmol) in toluene-EtOH—H$_2$O (4 ml-0.5 ml-2 mL) is stirred at relux for 6 hours. After cooling, the reaction mixture is diluted with H$_2$O and extracted with EtOAc. The extract is then washed with brine, dried over Na$_2$SO$_4$, and concentrated. The residue is purified by flash chromatography on silica gel. Elution with 8:1 hexanes-EtOAc followed by 7:1 hexanes-EtOAc affords 5-butyl-2-chloro-4-methyl-6-phenyl-pyrimidine as a colorless oil. $^1$H NMR (CDCl$_3$, 300 MHz) δ 7.45 (m, 5H), 2.65–2.62 (m, 2H), 2.60 (s, 3H), 1.46–1.36 (m, 2H), 1.25 (sext, J=7.2 Hz, 2H), 0.81 (t, J=7.2 Hz, 3H) ppm.

Step 5. Preparation of 4-Bromomethyl-5-butyl-2-chloro-6-phenyl-pyrimidine

A solution of the 5-butyl-2-chloro-4-methyl-6-phenyl-pyrimidine (215 mg, 0.825 mmol) and Br$_2$ (0.042 ml, 0.825 mmol) in AcOH (2 mL) is stirred at 80° C. for 2 hours. After cooling, the solution is concentrated. The residue is partitioned between Et$_2$O and half saturated aqueous NaHCO$_3$. The layers are separated, and the aqueous layer is reextracted once with Et$_2$O. The combined extracts are dried over Na$_2$SO$_4$ and concentrated to 305 mg of crude 4-bromomethyl-5-butyl-2-chloro-6-phenyl-pyrimidine, which also contains small amounts of SM and dibromo material. This material is used without further purification.

Step 6. Preparation of 4-{[(5-butyl-2-chloro-6-phenyl-pyrimidin-4-ylmethyl)-(2,3-dihydro-benzo[1,4]dioxin-6-ylmethyl)-amino]-methyl}-benzoic Acid Methyl Ester A solution of impure 4-bromomethyl-5-butyl-2-chloro-6-phenyl-pyrimidine (288 mg) and 4-{[(2,3-dihydro-benzo[1, 4]dioxin-6-ylmethyl)-amino]-methyl}-benzoic acid methyl ester (190 mg, 0.606 mmol) in CH$_3$CN containing K$_2$CO$_3$ (300 mg) is stirred at room temperature. The reaction is monitored by TLC until complete consumption of 4-bromomethyl-5-butyl-2-chloro-6-phenyl-pyrimidine (24 hours). The mixture is then diluted with CH$_2$Cl$_2$ and filtered. The filtrate is concentrated, and the resulting residue is purified by flash chromatography on silica gel. Elution with 5:1 hexanes-EtOAc followed by 4:1 hexanes-EtOAc affords 215 mg of pure 4-{[(5-butyl-2-chloro-6-phenyl-pyrimidin-4-ylmethyl)-(2,3-dihydro-benzo[1,4]dioxin-6-ylmethyl)-amino]-methyl}-benzoic acid methyl ester. $^1$H NMR (CDCl$_3$, 300 MHz) δ 7.97 (d, J=8.1 Hz, 2H), 7.44–7.33 (m, 7H), 6.84 (s, 1H), 6.79 (s, 2H), 4.22 (s, 4H), 3.90 (s, 3H), 3.74 (s, 2H), 3.72 (s, 2H), 3.55 (s, 2H), 2.64–2.56 (m, 2H), 1.01 (m, 2H), 0.90 (sext, J=7.2 Hz, 2H), 0.61 (t, J=7.2 Hz, 3H) ppm. MS: m/z 572 [M+1].

Step 7. Preparation of 4-{[(5-butyl-2-isobutoxy-6-phenyl-pyrimidin-4-ylmethyl)-(2,3-dihydro-benzo [1,4]dioxin-6-ylmethyl)-amino]-methyl}-benzoic Acid NaH (60% dispersion in mineral oil) (40 mg) is added to a solution of 4-{[(5-butyl-2-chloro-6-phenyl-pyrimidin-4-ylmethyl)-(2,3-dihydro-benzo[1,4]dioxin-6-ylmethyl)-amino]-methyl}-benzoic acid methyl ester (46 mg, 0.0804 mmol) in THF (3 mL) containing isobutyl alcohol (0.5 mL) at room temperature. The mixture is stirred at room temperature for 5 minutes and then at reflux for 2 hours. Next, H$_2$O (0.5 mL) is added and heating is continued for an additional 30 minutes. After cooling to room temperature, the reaction mixture is treated with a few drops of AcOH until pH 4–5. The mixture is then diluted with H$_2$O and extracted twice with CH$_2$Cl$_2$. The combined extracts are dried over Na$_2$SO$_4$ and concentrated. The residue is purified by preparative TLC, eluting with 20:1 CHCl$_3$-MeOH. The band containing the product affords 28.4 mg 4-{[(5-butyl-2-isobutoxy-6-phenyl-pyrimidin-4-ylmethyl)-(2,3-dihydro-benzo[1,4]dioxin-6-ylmethyl)-amino]-methyl}-benzoic acid as a colorless gum. $^1$H NMR (CDCl$_3$, 300 MHz) δ 8.02 (br, 2H), 7.39 (br, 7H), 6.87 (br s, 1H), 6.78 (br s, 2H), 4.21 (br s, 4H), 4.12 (br d, J=6.3 Hz, 2H), 3.70 (br, 4H), 3.54 (br s, 2H), 2.54 (br m, 2H), 2.13 (br, 1H), 1.02 (d, J=6.3 Hz, 6H), 0.94 (br 4H), 0.60 (br, 3H) ppm. MS: m/z 596 [M+1].

Example 22

Preparation of 5-{3-[(3-butyl-5-chloro-2-phenyl-3H-imidazol-4-ylmethyl)-(2,3-dihydro-benzo[1,4]dioxin-6-ylmethyl)-amino]-propyl}-isoxazol-3-ol and 5-{3-[(3-butyl-5-chloro-2-phenyl-3H-imidazol-4-ylmethyl)-(2,3-dihydro-benzo [1,4]dioxin-6-ylmethyl)-amino]-pentyl}-isoxazol-3-ol

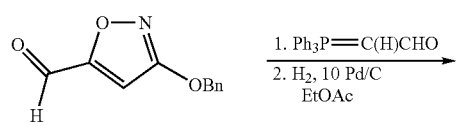

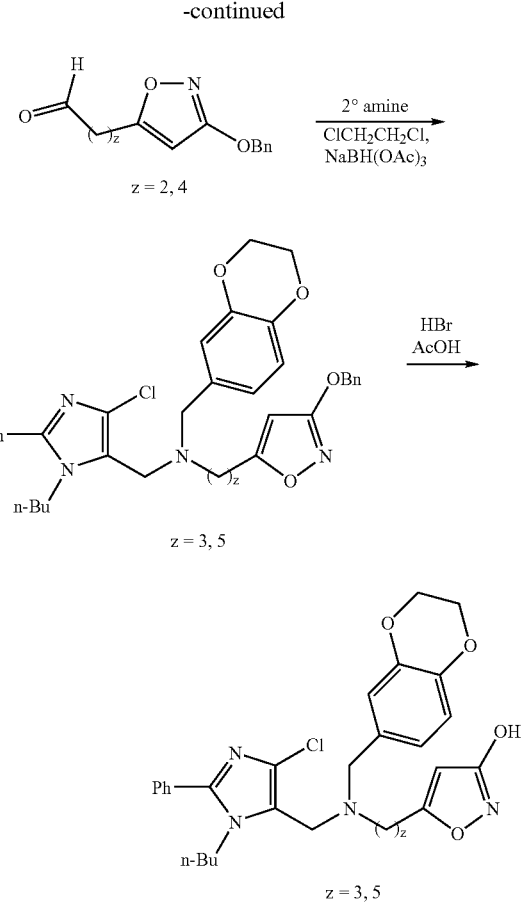

Step 1. Preparation of 5-(3-benzyloxy-isoxazol-5-yl)-propenal (Major) and 5-(3-benzyloxy-isoxazol-5-yl)-penta-2,4-dienal (Triphenylphosphoranylidene)acetaldehyde (785 mg, 2.58 mmol) is added in one portion to a solution of 3-benzyloxy-isoxazole-5-carbaldehyde (403 mg, 1.98 mmol) (prepared according to *Eur. J. Org. Chem.* 1998, 473–479) in 5:1 toluene-CH$_3$CN (12 mL) at room temperature. The reaction mixture is stirred at room temperature overnight. The dark solution is then concentrated in vacuo, and the residue purified by flash chromatography on silica gel. Elution with 4:1 hexanes-EtOAc affords an approximately 2:1 mixture of 3-(3-benzyloxy-isoxazol-5-yl)-propenal (major) and 5-(3-benzyloxy-isoxazol-5-yl)-penta-2,4-dienal (minor). Diagnostic $^1$H NMR signals: Major: $^1$H NMR (CDCl$_3$, 300 MHz) δ 9.72 (d, J=7.8 Hz, 1H), 6.24 (s, 1H), 5.31 (s, 2H) ppm. Minor: $^1$H NMR (CDCl$_3$, 300 MHz) δ 9.66 (d, J=7.8 Hz, 1H), 6.04 (s, 1H), 5.30 (s, 2H) ppm.

A solution of the enal mixture in 10 ml of EtOAc containing a catalytic amount of 10% Pd/C is stirred under an atmosphere of H$_2$ (double-stuffed balloon) for 6 hours. The reaction mixture is then filtered through a pad of Celite. The filtrate is concentrated to a colorless oil, which is used without further purification.

Step 2. Preparation of of [3-(3-benzyloxy-isoxazol-5-yl)-propyl]-(3-butyl-5-chloro-2-phenyl-3H-imidazol-4-ylmethyl)-(2,3-dihydro-benzo[1,4]dioxin-6-ylmethyl)-amine (Major) and [5-(3-benzyloxy-isoxazol-5-yl)-pentyl]-(3-butyl-5-chloro-2-phenyl-3H-imidazol-4-ylmethyl)-(2,3-dihydro-benzo[1,4]dioxin-6-ylmethyl)-amine (Minor)

5 drops of AcOH is added to a solution of (3-butyl-5-chloro-2-phenyl-3H-imidazol-4-ylmethyl)-(2,3-dihydro-benzo[1,4]dioxin-6-ylmethyl)-amine (134 mg, 0.325 mmol) and the crude aldehyde mixture from the previous reaction (75 mg) in 1,2-dichloroethane (5 mL). The mixture is stirred at rt for 15 min., and then NaBH(OAc)$_3$ (103 mg, 0.488 mmol) is added in one portion. The reaction mixture is stirred at room temperature for 60 hours. Next, half saturated NaHCO$_3$ is added. The resulting mixture is stirred for 15 minutes, and then extracted two times with CH$_2$Cl$_2$. The combined extracts are dried over Na$_2$SO$_4$ and concentrated. The residue is purified by preparative TLC, to afford an inseparable mixture of [3-(3-benzyloxy-isoxazol-5-yl)-propyl]-(3-butyl-5-chloro-2-phenyl-3H-imidazol-4-ylmethyl)-(2,3-dihydro-benzo[1,4]dioxin-6-ylmethyl)-amine (major) and [5-(3-benzyloxy-isoxazol-5-yl)-pentyl]-(3-butyl-5-chloro-2-phenyl-3H-imidazol-4-ylmethyl)-(2,3-dihydro-benzo[1,4]dioxin-6-ylmethyl)-amine (minor). Diagnostic $^1$H NMR signals: Major: $^1$H NMR (CDCl$_3$, 300 MHz) δ 5.52 (s, 1H), 5.21 (s, 2H) ppm. Minor: $^1$H NMR (CDCl$_3$, 300 MHz) δ 5.61 (s, 1H), 5.23 (s, 2H) ppm. MS: m/z 627 [M+1] (major) and 655 [M+1] (minor).

Step 3. Preparation of 5-{3-[(3-Butyl-5-chloro-2-phenyl-3H-imidazol-4-ylmethyl)-(2,3-dihydro-benzo[1,4]dioxin-6-ylmethyl)-amino]-propyl}-isoxazol-3-ol and 5-{3-[(3-Butyl-5-chloro-2-phenyl-3H-imidazol-4-ylmethyl)-(2,3-dihydro-benzo[1,4]dioxin-6-ylmethyl)-amino]-pentyl}-isoxazol-3-ol A solution of the amine mixture from the previous reaction in 30% HBr in AcOH (5 mL) is stirred at room temperature overnight. The solution is concentrated in vacuo, and the residue is purified by reversed phase HPLC in order to separate the two amines. The pure fractions are concentrated to approximately 10% of their original volume. The remaining mixtures are treated with a few drops of AcOH in order to adjust the pH to approximately 4. The mixtures are then extracted three times with CH$_2$Cl$_2$. The combined extracts are dried over Na$_2$SO$_4$ and concentrated to the pure amines as colorless gums.

5-{3-[(3-Butyl-5-chloro-2-phenyl-3H-imidazol-4-ylmethyl)-(2,3-dihydro-benzo[1,4]dioxin-6-ylmethyl)-amino]-propyl}-isoxazol-3-ol: $^1$H NMR (CDCl$_3$, 300 MHz) δ 7.52–7.49 (m, 2H), 7.44–7.40 (m, 3H), 6.81–6.73 (m, 3H), 5.50 (s, 1H), 4.22 (s, 4H), 3.95 (m, 2H), 3.52 (s, 2H), 3.46 (s, 2H), 2.58 (t, J=7.7 Hz, 2H), 2.51 (t, J=6.8 Hz, 2H), 1.83 (pent, J=7.2 Hz, 2H), 1.40–1.28 (m, 2H), 1.99 (sext, J=7.2 Hz, 2H), 0.71 (t, J=7.2 Hz, 3H) ppm. MS: m/z 537 [M+1].

5-{5-[(3-Butyl-5-chloro-2-phenyl-3H-imidazol-4-ylmethyl)-(2,3-dihydro-benzo[1,4]dioxin-6-ylmethyl)-amino]-pentyl}-isoxazol-3-ol: $^1$H NMR (CDCl$_3$, 300 MHz) δ 7.52–7.49 (m, 2H), 7.44–7.39 (m, 3H), 6.81–6.72 (m, 3H), 5.60 (s, 1H), 4.21 (s, 4H), 3.97 (m, 2H), 3.51 (s, 2H), 3.44 (s, 2H), 2.57 (t, J=7.4 Hz, 2H), 2.44 (t, J=7.2 Hz, 2H), 1.61–1.25 (m, 8H), 1.02 (sext, J=7.2 Hz, 2H), 0.73 (t, J=7.2 Hz, 3H) ppm. MS: m/z $^{565}$ [M+1].

Example 23

Preparation of Bis-benzo[1,3]dioxol-5-ylmethyl-(3-butyl-5-phenyl-2-o-tolyl-3H-imidazol-4-ylmethyl)-amine

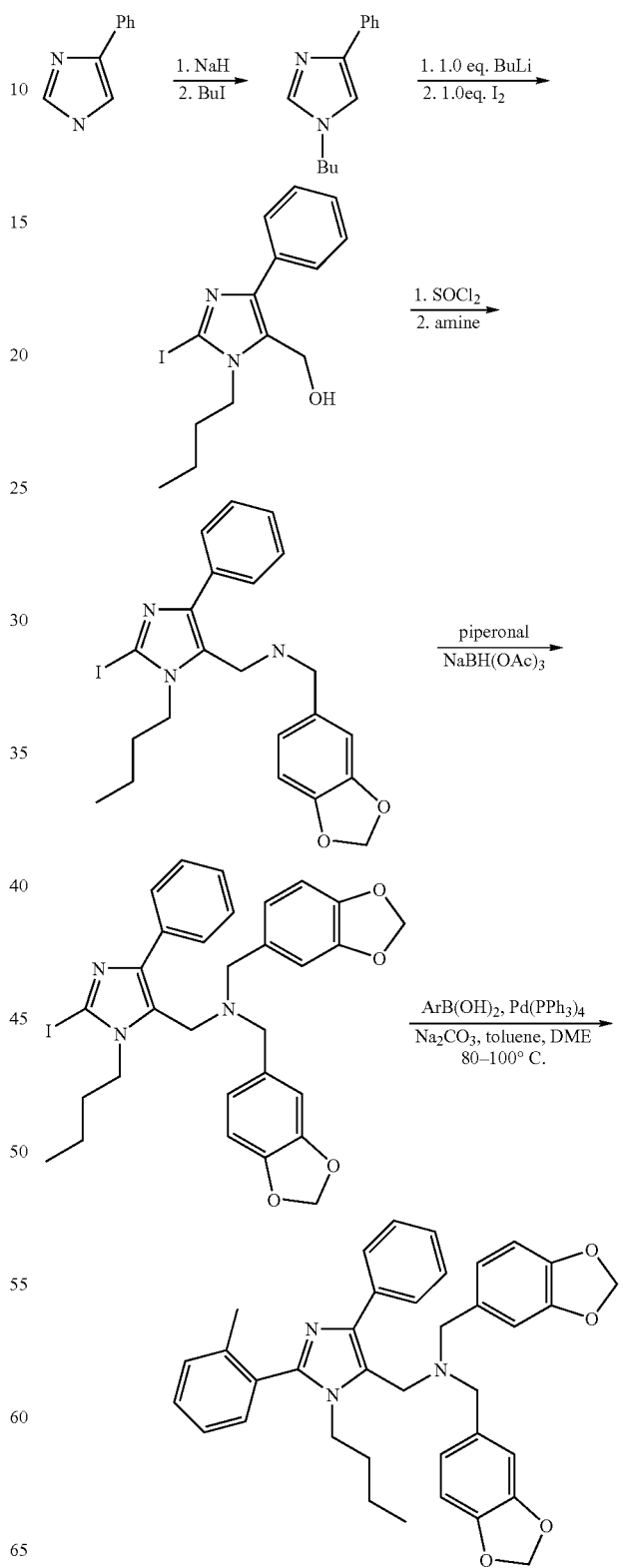

To the suspension of sodium hydride (2.40 g, 60% mineral oil suspension, 60 mmol) in 30 ml of anhydrous DMF is added a solution of 4-phenylimidazole (7.21 g, 50 mmol) in 30 ml of DMF at room temperature, the resulting mixture is stirred at 70° C. 1 h, and then cooled to room temperature followed by the dropwise addition of iodobutane (9.66 g, 52.5 mmol, 1.05 eq.). The mixture is stirred at room temperature for 1 h, heated to 70° C. and stirred for an additional 8 h. The reaction mixture is cooled to room temperature, poured into 200 ml of ice-water, extracted with ethyl acetate (100 ml×3). The combined organics are washed with water, brine, dried over anhydrous sodium sulfate, filtered, evaporated at reduced pressure and purified by flash chromatography on silica gel to obtain 9.08 g of 1-butyl-4-phenylimidazole. $^1$H NMR (400 MHz, CDCl$_3$) δ 7.77 (2H, d, J=7.6 Hz), 7.49 (1H, s), 7.36 (2H, t, J=7.6 Hz), 7.23(1H, m), 7.20 (1H, s), 3.95 (2H, t, J=7.2 Hz), 1.80 (2H, m), 1.36 (2H, m), 0.96 (3H, t, J=7.2 Hz); MS (+VE) m/z 201 (M+1).

To a solution of 1-butyl-4-phenylimidazole (4.0 g, 20 mmol) in 60 ml of anhydrous THF at −78° C. under nitrogen is added a solution of n-butyllithium in hexane (1.6M, 13.13 ml, 21 mmol, 1.05 eq.) dropwise. The resulting mixture is stirred at −78° C. for 1 h followed by dropwise addition of a solution of iodine (5.33 g, 21 mmol, 1.05 eq.) in 40 ml of THF. The resulting solution is stirred at −78° C. for 30 min. and then warmed to room temperature. Saturated ammonium chloride (30 mL) is added to quench the reaction. The resulting mixture is evaporated a reduced pressure to remove THF, extracted with ethyl acetate, washed with water and brine, dried over Na$_2$SO$_4$, filtered and evaporated. Purification by silica gel chromatography (hexanes/ethyl acetate, from 8:1 to 5:1) affords 5.73 g of 1-butyl-2-iodo-4-phenylimidazole. $^1$H NMR (400 MHz, CDCl$_3$) δ 7.73 (2H, dd, J=1.2, 8.4 Hz), 7.36 (2H, m), 7.30 (1H, s), 7.24 (1H, m), 3.92 (2H, t, J=7.2 Hz), 1.79 (2H, m), 1.41 (2H, m), 0.98 (3H, t, J=7.2 Hz); MS (+VE) m/z 327 (M+1).

To a 60 ml sealed flask is added 1-butyl-2-iodo-4-phenylimidazole (3.26 g, 10 mmol) followed by the addition of 5.5 ml of acetic acid, 16 ml of 37% formaldehyde and 7 g of sodium acetate. The resulting mixture is stirred at 115° C. for 10 h, cooled to room temperature and diluted 50 ml of water. The reaction mixture is adjusted to pH=9, extracted with ethyl acetate, washed with water and brine, dried over Na$_2$SO$_4$, filtered and evaporated. Purification by silica gel chromatography (hexanes/ethyl acetate, from 8:1 to 2:1) affords 3.24 of 1-butyl-5-hydroxymethyl-2-iodo-4-phenylimidazole. $^1$H NMR (400 MHz, CDCl$_3$) δ 7.59 (2H, dd, J=1.6, 6.8 Hz), 7.39 (2H, m), 7.31 (1H, m), 4.78 (2H, s), 4.00 (2H, t, J=8.0 Hz), 1.78 (2H, m), 1.46 (2H, m), 1.00 (3H, t, J=7.2 Hz); MS (+VE) m/z 357(M+1).

1-Butyl-5-hydroxymethyl-2-iodo-4-phenylimidazole (1.96 g, 6.1 mmol) is dissolved in 20 ml dichloromethane and cooled to 0° C. To the solution is added 5 equivalents of thionyl chloride and the resulting solution is stirred at room temperature for 2 h. The reaction mixture is evaporated at reduced pressure and 20 ml of toluene is added to the residue and evaporated to remove any residual thionyl chloride. The crude product is dissolved in 20 ml of anhydrous acetonitrile and added to an ice-cooled solution of piperonyl amine (2.0 eq.) in acetonitrile (10 mL) containing potassium carbonate (2 eq.). The resulting mixture is stirred at room temperature for 4 h, diluted with 100 ml of ethyl acetate, washed with water and brine, dried over sodium sulfate and concentrated at reduced pressure. The residue is purified by silica gel chromatography (hexanes/ethyl acetate, from 2:1 to 1:1) to give 2.28 g of 1-butyl-5-chloromethyl-2-iodo-4-phenylimidazole. MS (+VE) m/z 490 (M+1).

To a solution of 1-butyl-5-chloromethyl-2-iodo-4-phenylimidazole (1.22 g, 2.5 mmol) in 1,2-dichloroehane (10 mL) is added piperonal (750 mg, 5.0 mmol, 2.0 eq) followed by 10 drops of acetic acid. The solution is stirred at room temperature for 2 h, sodium triacetoxyborohydride (1.1 g, 5.0 mmol, 2.0 eq.) is added and the resulting mixture is stirred at room temperature overnight. The reaction mixture is diluted with 50 ml of dichloromethane, washed with water and brine, dried and concentrated. The residue is purified by silica gel flash chromatography (hexanes/ethyl acetate, from 8:1 to 4:1) to afford bis-benzo[1,3]dioxol-5-ylmethyl-(3-butyl-2-iodo-5-phenyl-3H-imidazol-4-ylmethyl)-amine. $^1$H NMR (400 MHz, CDCl$_3$) δ 7.57 (2H, m), 7.39 (2H, m), 7.31 (1H, m), 6.70–6.73 (4H, m), 6.64 (2H, d, J=8.0 Hz), 5.94 (4H, s), 4.01 (2H, t, J=6.8 Hz), 3.71 (2H, s), 3.32 (4H, s), 1.41 (2H, m), 1.15 (2H, m), 0.88 (3H, t, J=7.6 Hz); MS (+VE) m/z 624 (M+1).

To a solution of bis-benzo[1,3]dioxol-5-ylmethyl-(3-butyl-2-iodo-5-phenyl-3H-imidazol-4-ylmethyl)-amine (62 mg, 0.1 mmol) and Pd(PPh$_3$)$_4$ (6 mg) in 1 ml of toluene is added aqueous sodium carbonate (0.4 ml of 2.0 N) and 2-methylphenyl boronic acid (18 mg, 0.13 mmol, 1.3 eq.) in 0.3 ml of ethanol under nitrogen, the resulting mixture is stirred at 100° C. for 8 h. After being cooled to room temperature, the reaction mixture is diluted with 10 ml of ethyl acetate, washed with water and brine and dried over sodium sulfate. Concentration and purification by flash chromatography affords 43 mg of bis-benzo[1,3]dioxol-5-ylmethyl-(3-butyl-5-phenyl-2-o-tolyl-3H-imidazol-4-ylmethyl)-amine $^1$H NMR (400 MHz, CDCl$_3$) δ 7.70 (2H, d, J=7.2 Hz), 7.43~7.24 (7H, m), 6.77~6.67 (6H, m), 5.94 (4H, s), 3.87 (2H, t, J=7.6 Hz), 3.78(2H, s), 3.37 (4H, s), 2.20 (3H,s), 1.17 (2H, m), 0.88 (2H, m), 0.63 (3H, t, J=7.2 Hz); MS (+VE) m/z 588 (M+1).

Example 24

Preparation of 4-({[3-butyl-5-(4-methoxy-phenyl)-2-phenyl-3H-imidazol-4-ylmethyl]-cyclohexylmethyl-amino}-methyl)-2-hydroxy-benzamide

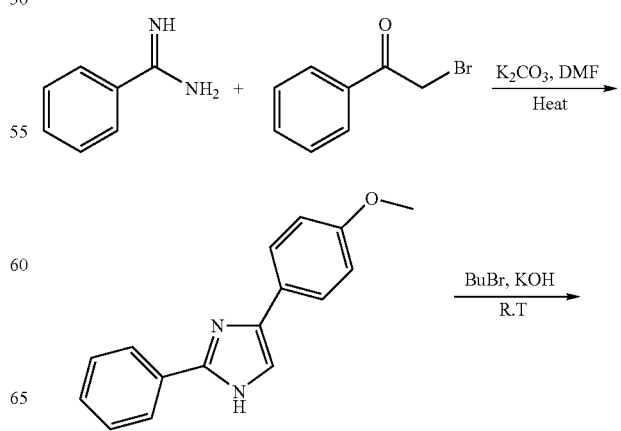

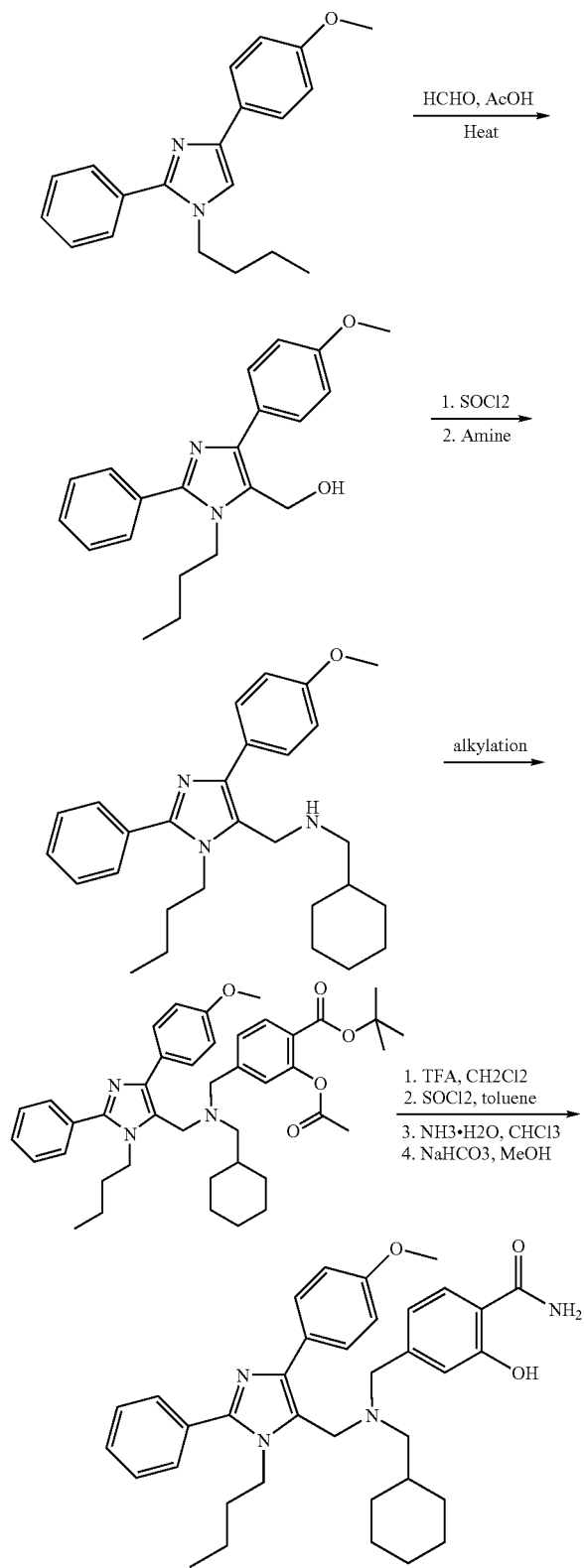

To a solution of benzamidine hydrochloride (31.22 g, 0.2 mmol, 1.17 eq.) in 250 ml of DMF is added potassium carbonate (69 g, 0.5 mol). 2-bromo-4'-methoxyacetophnone is dissolved in 200 ml of DMF and added to the reaction flask dropwise at 55° C. After the addition, the reaction mixture is stirred at 60° C. for 3 h, then cooled to room temperature and poured into 1000 ml of ice-water, the mixture is extracted with ethyl acetate (150 ml×4), washed with water and brine, dried over sodium sulfate, purified through flash chromatography to give 30 g of 2-phenyl-4-(4-methoxyphenyl)imidazole. $^1$H NMR (400 MHz, CDCl$_3$) δ 7.86 (2H, d, J=6.8 Hz), 7.43~7.25 (5H, m), 6.93(2H, d, J=8.8 Hz), 3.83 (3H, s); MS (+VE) m/z 251 (M+1).

Potassium hydroxide (4.36, 76 mmol, 1.3 eq.) is suspended in 40 ml of anhydrous DMSO, to the suspension is added a solution 2-phenyl-4-(4-methoxyphenyl)imidazole (15.02, 60 mmol) and bromobutane (8.63 g, 63 mmol, 1.05 eq.) in 80 ml of DMSO at room temperature over 2 h, the resulting mixture is stirred over 24 h, and then poured into 400 ml of ice-water, extracted with ethyl acetate (100 ml×4), washed with water and brine, dried over anhydrous sodium sulfate. The solvent is evaporated and the product is purified through flash chromatography to give 16.73 g of 4-({[3-Butyl-5-(4-methoxy-phenyl)-2-phenyl-3H-imidazole. MS (+VE) m/z 307 (M+1).

To a 150 ml sealed flask is added 4-({[3-Butyl-5-(4-methoxy-phenyl)-2-phenyl-3H-imidazole (10.72, 35 mmol) followed by the addition of 24 ml of acetic acid and 24 ml of 37% formaldehyde, the resulting mixture is stirred at 70° C. for 8 h, then cooled to room temperature. The organic solvents is evaporated, the residue is diluted 100 ml of water and basified with sodium hydroxide solution, the mixture is extracted with ethyl acetate (100 ml×4), washed with water and brine, dried over Na$_2$SO$_4$ Concentration and purification through silica gel chromatography (hexanes/ethyl acetate, from 8:1 to 1:1) affords 10.0 of 4-({[3-Butyl-5-(4-methoxy-phenyl)-2-phenyl-3H-imidazol-4-ylmethanol as white solid. $^1$H NMR (400 MHz, CDCl$_3$) δ 7.58 (2H, dd, J=8.7 Hz), 7.354~7.51(2H, m), 7.44~7.38 (3H, m), 6.87 (2H, d, J=8.7 Hz), 4.59 (2H, s), 3.95 (2H, t, J=7.5 Hz), 3.784 (3H, s), 1.60 (2H, m), 1.16 (2H, m), 0.77 (3H, t, J=7.2 Hz); MS (+VE) m/z 337(M+1).

4-({[3-Butyl-5-(4-methoxy-phenyl)-2-phenyl-3H-imidazol-4-ylmethanol (6.72 g, 20 mmol) is dissolved in 30 ml dichloromethane and cooled to 0° C., to the solution is added 5 equivalent of thionyl chloride. The resulting solution is stirred at room temperature for 2 h, the solvent and excess of thionyl chloride is evaporated. 20 ml of toluene is added to the residue and evaporated again to remove the remained thionyl chloride. The residual crude product is dissolved in 30 ml of anhydrous acetonitrile and added to an ice-cooled solution of cyclohexanemethyl amine (2.0 eq.) in 20 ml of acetonitrile containing 2 equivalent of potassium carbonate. The resulting mixture is stirred at room temperature for 4 h, then diluted with 200 ml of ethyl acetate, washed with water and brine, dried and concentrated, the residue is purified through silica gel chromatography (hexanes/ethyl acetate, from 2:1 to 1:1) to give 11.26 g of 4-({[3-Butyl-5-(4-methoxy-phenyl)-2-phenyl-3H-imidazol-4-ylmethyl-cyclohexylmethyl-amine. $^1$H NMR (400 MHz, CDCl$_3$) δ 7.64~7.60 (4H, m), 7.47~7.40 (3H, m), 6.94 (2H, d, J=8.8 Hz), 4.11 (2H, m), 3.87 (2H, s), 3.84 (3H,s), 2.52 (2H, d, J=6.4 Hz), 0.91~1.77 (15H, m), 0.84 (3H, t, J=7.2 Hz); MS (+VE) m/z 432 (M+1).

To a solution of 4-({[3-Butyl-5-(4-methoxy-phenyl)-2-phenyl-3H-imidazol-4-ylmethyl]-cyclohexylmethyl-amine (4.0 g, 9.31 mmol) and 3-acetoxy]-4-tert-butoxycarbonyl-benzyl bromide (3.37 g, 10.24 mmol, 1.1 eq.) in 50 ml anhydrous acetonitrile is added anhydrous potassium carbonate (2.82 g, 20.5 mmol, 2.2 eq.), the resulting mixture is stirred at room temperature for 1 h, then raised to 50° C., stirred overnight. The solid precipitate is filtered off, washed with ethyl acetate, the combined organics is concentrated to dryness, purified through silica gel flash chromatography to give 3.99 g of 4-({[3-Butyl-5-(4-methoxy-phenyl)-2-phenyl-3H-imidazol-4-ylmethyl]-cyclohexylmethyl-amino}-methyl)-2-acetoxy-benzoic acid tert-butyl ester MS (+VE) m/z 680 (M+1).

4-({[3-Butyl-5-(4-methoxy-phenyl)-2-phenyl-3H-imidazol-4-ylmethyl]-cyclohexylmethyl-amino}-methyl)-2-acetoxy-benzoic acid tert-butyl ester (3.99 g, 5.87 mmol) is dissolved in 50 ml of dichloromethane, to the solution is added 10 ml of Trifluoroacetic acid at 0° C., after stirring at room temperature for 8 h, the solvent is evaporated under house vacuum and the residue is dissolved in 30 ml of toluene (containing 5 ml of THF), to the solution is added 6 equivalent of thionyl chloride at 0° C., and then the reaction mixture is heated to 60° C., stirred overnight. The solvent and the remained thionyl chloride is evaporated, the residue is dissolved in 50 ml of chloroform and added to concentrated aqueous ammonium hydroxide solution with vigorous stirring slowly, stirred for 4 h. The chloroform layer is collected, and the aqueous phase is extracted with chloroform (50 ml×2), the combined organics is evaporated to dryness, and the residue is dissolved in 60 ml of methanol followed with addition of 30 ml of saturated aqueous sodium bicarbonate solution and 30 ml of water, the mixture is stirred at 40–45° C. overnight. The methanol is evaporated, and the residue is extracted with dichloromethane (50 ml×3), dried over sodium sulfate. Concentration and purification through silica gel flash chromatography affords 2.74 g of 4-({[3-butyl-5-(4-methoxy-phenyl)-2-phenyl-3H-imidazol-4-ylmethyl]-cyclohexylmethyl-amino}-methyl)-2-hydroxy-benzamide. $^1$H NMR (400 MHz, CDCl$_3$) δ 7.57 (2H, d, J=8.7 Hz), 7.39~7.51 (5H, m), 7.27 (H, d, J=8.1 Hz), 6.95 (2H, d, J=9.0 Hz), 6.88 (1H,d, J=1.5Ha), 6.57 (1H, dd, J=1.5, 8.4 Hz), 4.15 (2H, m), 3.84 (3H, s), 3.71 (2H, s), 3.36 (2H, s), 2.19 (2H, d, J=6.9 Hz), 0.77~1.80 (15H, m), 0.70 (3H, t, J=6.9 Hz); MS (+VE) m/z 581 (M+1).

Example 25

Preparation of (3-butyl-5-chloro-2-o-tolyl-3H-imidazol-4-ylmethyl)-(3-chloro-1h-indol-5-ylmethyl)-(3-methyl-butyl)-amine

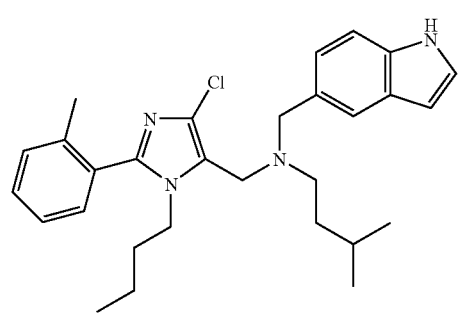

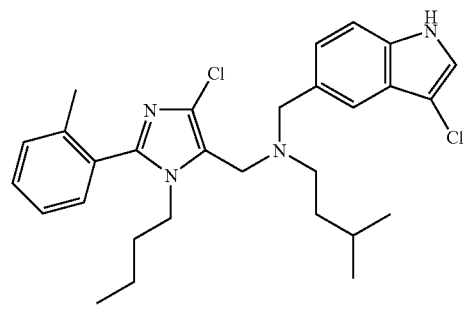

To a solution of (3-Butyl-5-chloro-2-o-tolyl-3H-imidazol-4-ylmethyl)-(1H-indol-5-ylmethyl)-(3-methyl-butyl)-amine (150 mg, 0.31 mmol) in 5 ml of anhydrous acetonitrile cooled to 0° C. is added NCS (44 mg, 0.33 mmol, 1.05 eq.), the resulting mixture is stirred at 40° C. overnight. The solvent is evaporated; the residue is purified through flash chromatography to give 112 mg of (3-butyl-5-chloro-2-o-tolyl-3H-imidazol-4-ylmethyl)-(3-chloro-1H-indol-5-ylmethyl)-(3-methyl-butyl)-amine as a white solid. $^1$H NMR (400 MHz, CDCl$_3$) δ 9.39 (1H, s), 7.52 (1H, S), 7.11~7.36 (6H, m), 6.98 (1H, d, J=2.4 Hz), 3.67 (2H, m), 3.65 (2H, s), 3.54 (2H, s), 2.52 (2H, t, J=7.2 Hz), 2.11 (3H, s), 1.62 (1H, m), 1.45 (2H, q, J=6.9 Hz), 1.10 (2H, m), 0.84 (6H, d, J=6.6 Hz), 0.73 (2H, m), 0.47 (3H, t, J=6.9 Hz); MS (+VE) m/z 511 (M+1).

Example 26

Preparation of 5-{[(3-butyl-5-chloro-2-o-tolyl-3H-imidazol-4-ylmethyl)-(3-methyl-butyl)-amino]-methyl}-1h-indole-3-carbonitrile

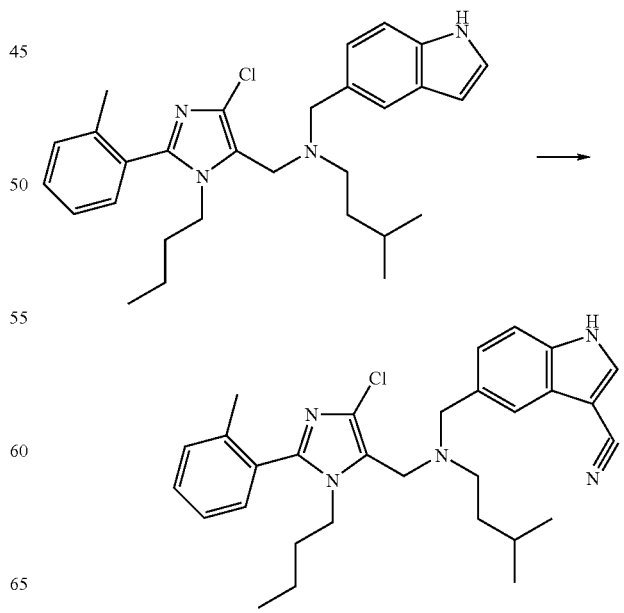

To an ice-cooled solution of 5-{[(3-butyl-5-chloro-2-o-tolyl-3H-imidazol-4-ylmethyl)-(3-methyl-butyl)-amino]-methyl}-1H-indole (173 mg, 0.363 mmol) in 5 ml of anhydrous acetonitrile under nitrogen is added a solution of chlorosulfonyl isocyanate (69.5 mg, 0.491 mmol, 1.35 eq.) in 1 ml of acetonitrile, after stirring for 20 min, a solution of DMF (30.1 mg) in 2 ml of acetonitrile is added dropwise, stirred for additional 1 h. The reaction mixture is poured into ice water and basified with diluted ammonium hydroxide solution; the mixture is extracted with dichloromethane, dried over sodium sulfate. The solvent is evaporated; the residue is purified through flash chromatography to give 11 mg of 5-{[(3-butyl-5-chloro-2-o-tolyl-3H-imidazol-4-ylmethyl)-(3-methyl-butyl)-amino]-methyl}-1H-indole-3-carbonitrile as white solid. $^1$H NMR (400 MHz, CDCl$_3$) δ 7.63 (1H, s), 7.38 (1H, d, J=3 Hz), 7.15~7.36 (4H, m), 7.07 (1H, dd, J=1.2, 8.4 Hz), 6.89~6.93 (2H, m), 3.73 (2H, t, J=7.5 Hz), 3.65 (2H, s), 3.57 (2H, s), 2.55 (2H, d, J=6.9 Hz), 2.02 (3H, s), 1.62 (1H, m), 1.46 (2H, q, J=6.6 Hz), 1.14 (2H,m), 0.85 (6H, d, J=6.6 Hz), 0.75 (2H, m), 0.51 (3H, t, J=7.2 Hz); MS (+VE) m/z 502 (M+1).

Example 27

Preparation of (R)-[1-(3-butyl-2-phenyl-3H-imidazole-4-yl)-pentyl]-cyclohexylmethyl-(4-methoxybenzyl)-amine

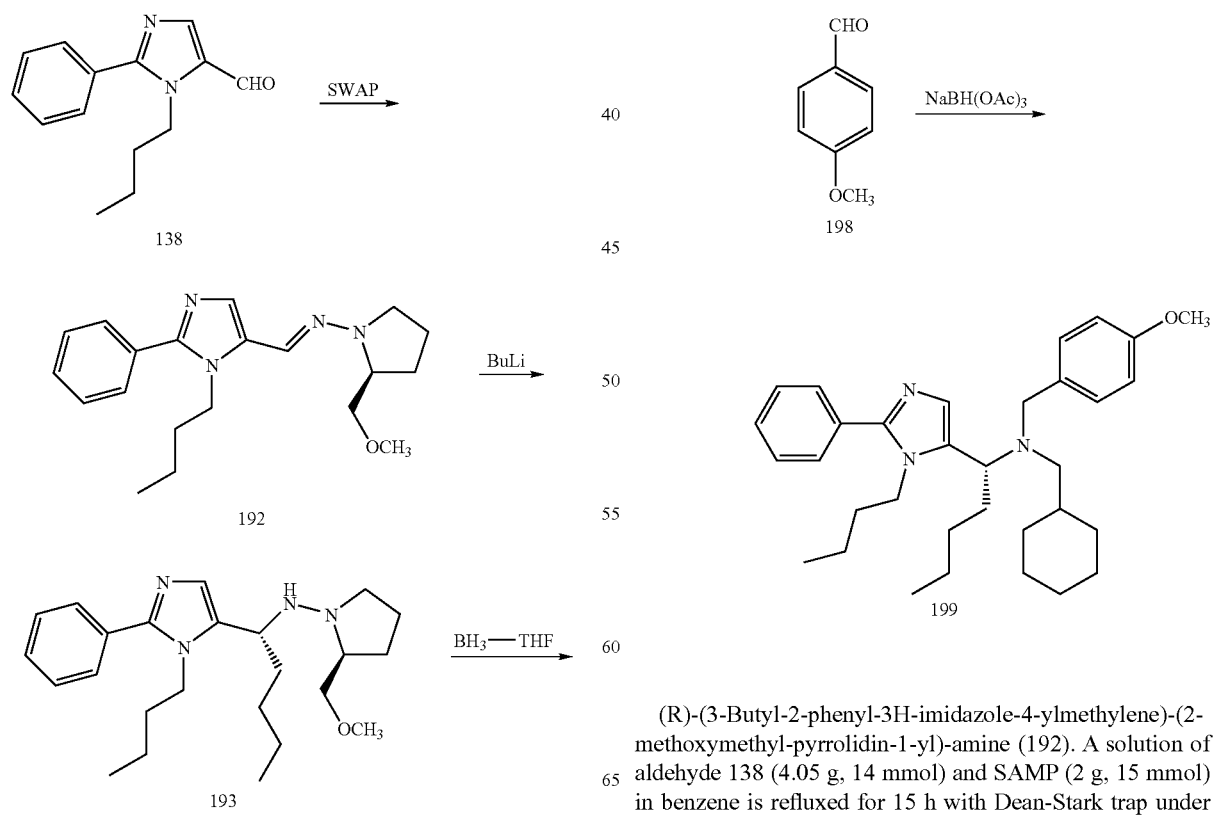

(R)-(3-Butyl-2-phenyl-3H-imidazole-4-ylmethylene)-(2-methoxymethyl-pyrrolidin-1-yl)-amine (192). A solution of aldehyde 138 (4.05 g, 14 mmol) and SAMP (2 g, 15 mmol) in benzene is refluxed for 15 h with Dean-Stark trap under argon. The solvent is then removed and the residue is used for the next step without further purification. LC-MS (MH+): 341.

(R,S)-[1-(3-Butyl-2-phenyl-3H-imidazole-4-yl)-pentyl]-(2-methoxymethyl-pyrrolidin-1-yl)-amine (193). To a solution of BuLi (2.5 M in hexane, 12.5 ml, 31 mmol) under argon in anhydrous THF (15 mL) at −78° C. is slowly added a solution of crude 192 (14 mmol) in THF (15 mL). The mixture is allowed to warm to room temperature over a period of 15 h and quenched with saturated sodium bicarbonate. The aqueous phase is extracted with ethyl acetate and the combined organic phases were washed with water and dried over sodium sulfate. Removal of solvents under reduced pressure and purification of the residue by column chromatograpy affords the desired product as a colorless syrup. Yield: 5.1 g; $[\alpha]_D$ −72 (c=1.2, $CHCl_3$); LC-MS (MH+): 399.

(R)-1-(3-Butyl-2-phenyl-3H-imidazol-4-yl)-pentylamine (194). To a solution of 193 (1.43 g, 3.6 mmol) under argon in anhydrous THF (25 mL) at room temperature is slowly added borane-THF complex (1 M in THF, 54 ml, 54 mmol). The mixture is then refluxed under argon for 16 h. After cooling to room temperature, 10% HCl (20 mL) is added very slowly and the mixture is stirred for 2 h at room temperature. The organic solvent is removed under reduced pressure and the residue is extracted with ether. The aqueous phase is saturated with solid potassium carbonate and extracted with sthyl acetate. The residue obtained after removal of the solvent is purified by column chromatography to afford the desired product as a colorless oil. Yield: 0.6 g; LC-MS (MH+): 286.

(R)-[1-(3-Butyl-2-phenyl-3H-imidazol-4-yl)-pentyl]-cyclohexylmethylene-amine (196) and [1-(3-butyl-2-phenyl-3H-imidazol-4-yl)-pentyl]-cyclohexylmethyl-amine (197). A solution of amine 194 (440 mg, 1.54 mmol) and cyclohexylmethylaldehyde (173 mg, 1.6 mmol) in benzene is refluxed for 16 h with Dean-Stark trap under argon. The solvent is then removed and the residue 196 is used for the next step without further purification. LC-MS (MH+): 380. The crude 196 is dissolved in anhydrous methanol (10 mL) and cooled to 0° C. To this solution, sodium borohydride (80 mg) is added slowly and the mixture is stirred at room temperature for 4 h. The reaction is quenched with water (10 mL) and most methanol is removed under reduced pressure. The residue is extracted with ethyl acetate, and the organic phase is washed with saturated sodium bicarbonate and brine. Evaporation of the solvent and purification of the residue affords a colorless oil. Yield: 560 mg; $[\alpha]_D$ −5.8 (c=1, $CHCl_3$); LC-MS (MH+): 382.

(R)-[1-(3-Butyl-2-phenyl-3H-imidazole-4-yl)-pentyl]-cyclohexylmethyl-(4-methoxy-benzyl)-amine (199). This compound is prepared from amine 197 and aldehyde 198 in the manner as described in Example 9 for preparation of compound 145. The enantiomer excess value of 199 is greater than 97.5% indentifed by chiral column. $[\alpha]_D$ −14.4 (c=1, $CHCl_3$); LC-MS (MH+): 502; $^1H$ NMR (400 MHz, $CDCl_3$) δ 7.46–7.37 (m, 3H), 7.28 (d, J=8.4 Hz, 2H), 7.19 (d, J=8.4 Hz, 2H), 6.99 (s, 1H), 6.89–6.84 (m, 2H), 3.80 (s, 2H), 3.78 (s, 2H), 3.76–3.61 (m, 5H), 2.38–2.32 (m, 1H), 2.17–2.12 (m, 1H), 1.98–1.94 (m, 2H), 1.70–1.52 (m, 5H), 1.46–1.34 (m, 4H), 1.26–0.99 (m, 6H), 0.95 (t, J=7.2 Hz, 3H), 0.82–0.71 (m, 2H), 0.58 (t, J=7.2 Hz, 3H).

Example 28

Preparation of (S)-[1-(3-butyl-2-phenyl-3H-imidazole-4-yl)-pentyl]-cyclohexylmethyl-(4-methoxy-benzyl)-amine

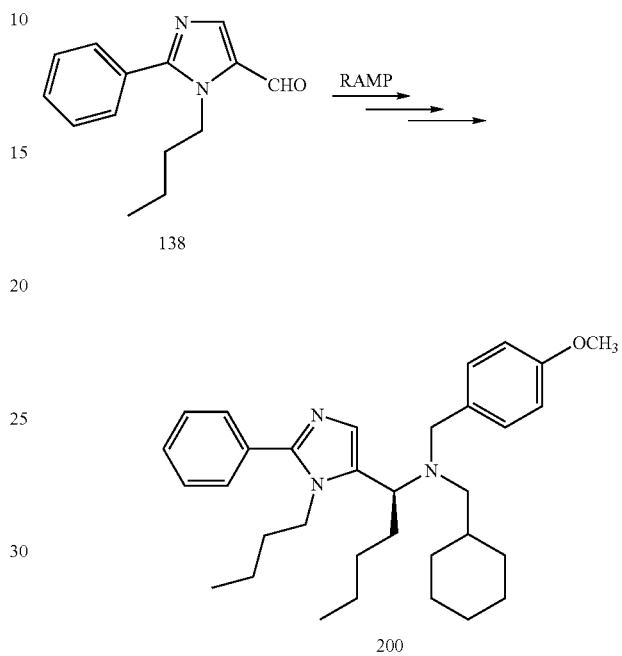

The title compound 200 is prepared in the same manner as in Example 20 using RAMP. The analytical data is intentical to that of compound 199 except for the optical rotation.

Example 29

Preparation of (R)-4-({butyl-[1-(3-butyl-2,5-diphenyl-3H-imidazol-4-yl)-ethyl]-amino}-methyl)-benzamide

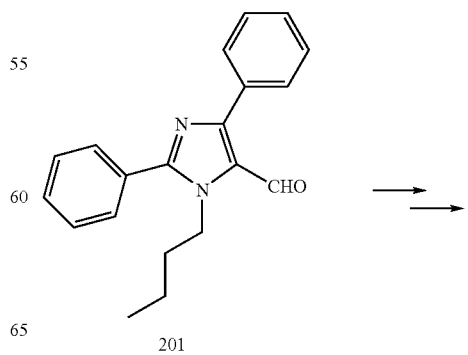

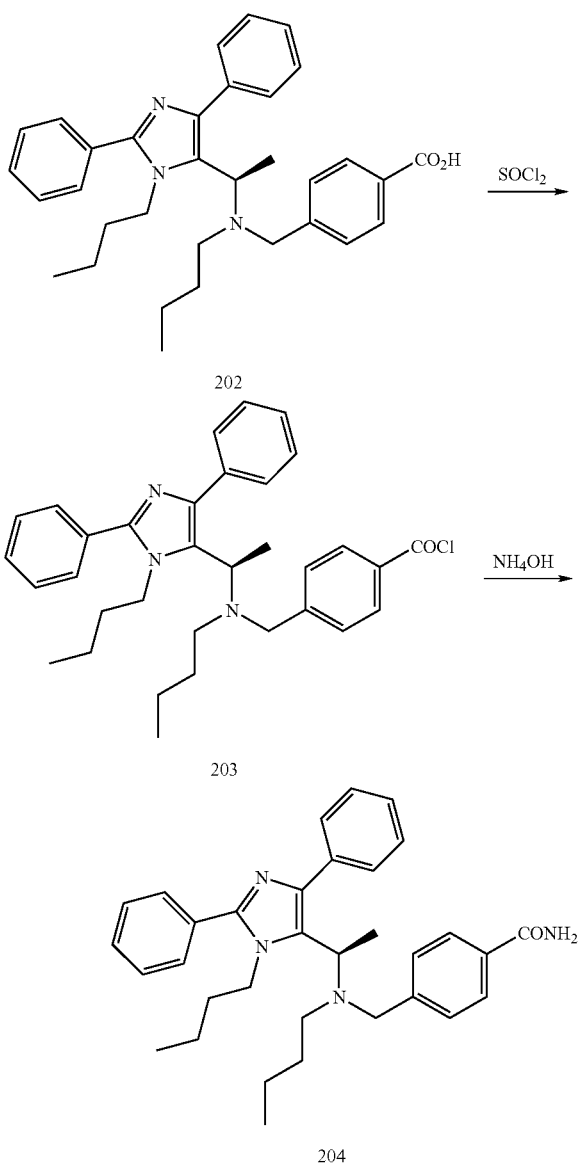

(R)-4({Butyl-[1-(3-butyl-2,5-diphenyl-3H-imidazol-4-yl)-ethyl]-amino}-methyl)-benzoic acid (202). This compound is prepared in the same manner as in Example 20 using aldehyde 201 as the starting material. 4-formylbenzoic acid is employed for the reductive amination step. LC-MS (MH+): 510.

(R)-4({Butyl-[1-(3-butyl-2,5-diphenyl-3H-imidazol-4-yl)-ethyl]-amino}-methyl)-benzamide (204). A solution of compound 202 (110 mg, 0.2 mmol) in anhydrous chloroform is treated with thionyl chloride (0.2 mL) under reflux for 2 h. The solvent and excess of thonyl chloride were evaporated under reduced pressure and the residue is dried in vacuo to yield acid chloride 203 which is used for the next step without further purification. To a vigorously stirred solution of ammonium hydroxide (30% in water, 2 mL) and chloroform (4 mL) is added a solution of 203 in chloroform (2 mL) in one portion at room temperature. The mixture is continued stirring at room temperature overnight. The organic phase is separated and the aqueous phase is extracted with dichloromethane. The combined organic phase is washed with water, saturated sodium bicarbonate and brine. Removal of the solvent and purification of the residue by column chromatography yields the desired product 204. Yield: 98 mg. LC-MS (MH+): 509; $^1$H NMR (300 MHz, CDCl$_3$) δ 7.71 (d, J=7.8 Hz, 2H), 7.60 (d, J=7.8 Hz, 2H), 7.50–7.48 (m, 2H), 7.40–7.38 (m, 4H), 7.32 (d, J=7.5 Hz, 1H), 7.26 (d, J=7.8 Hz, 2H), 6.12 (br s, 1H), 5.75 (br s, 1H), 4.55–4.45 (m, 1H), 4.27 (q, J=6.9 Hz, 1H), 4.14–4.03 (m, 1H), 3.71 (d, J=14.7 Hz, 1H), 3.52 (d, J=14.7 Hz, 1H), 2.53 (d, J=7.4 Hz, 2H), 2.05–1.96 (m, 2H), 1.49 (d, J=6.9 Hz, 3H), 1.44–1.13 (m, 4H), 0.88–0.75 (m, 6H).

Examples 29–40

Preparation of Various 4-substituted Imidazole Derivatives

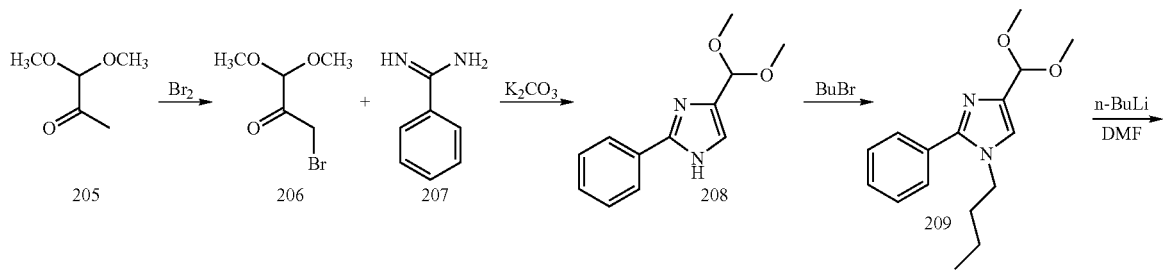

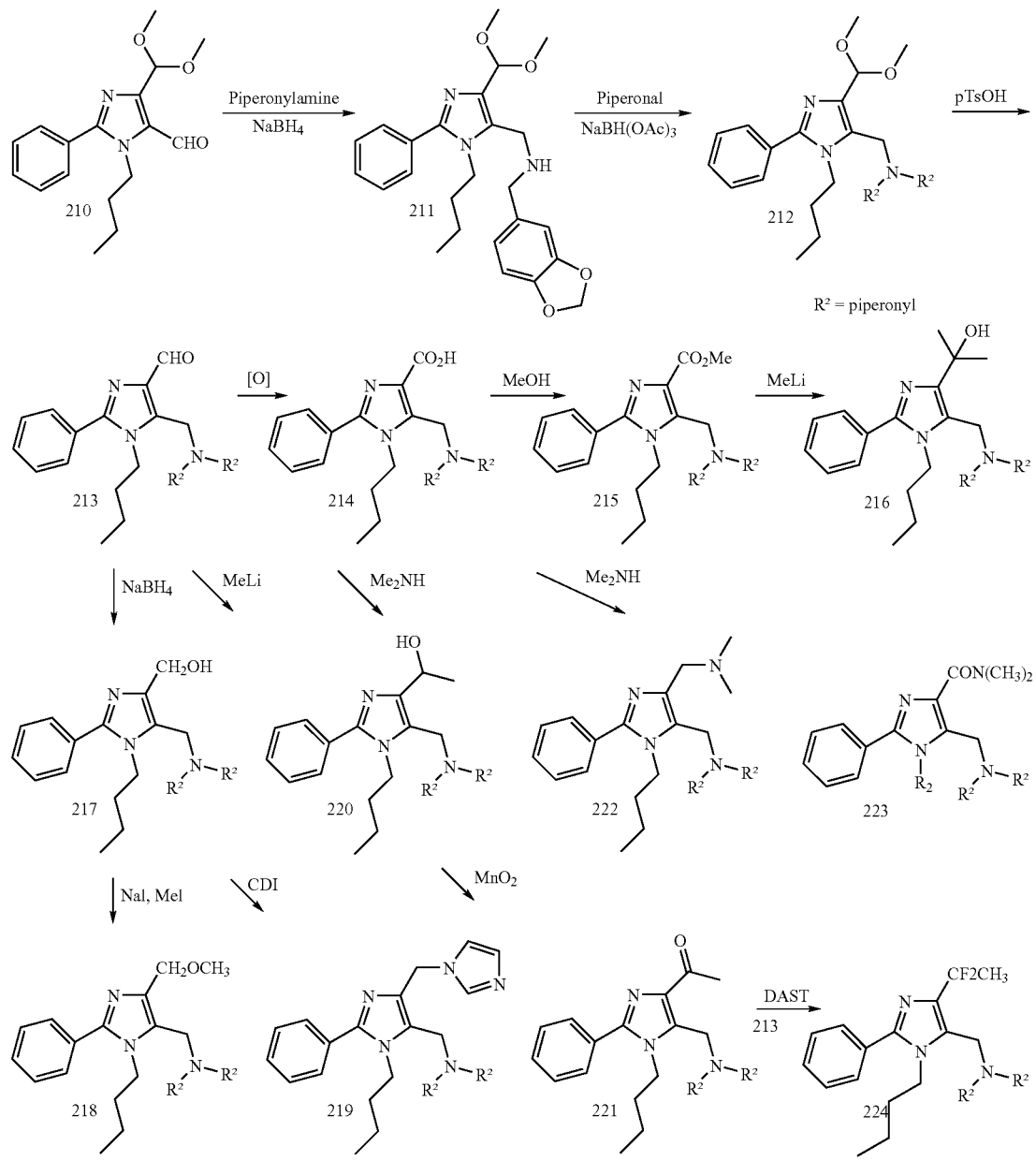

Example 29

Preparation of Bis-benzo[1,3]dioxol-5-ylmethyl-(3-butyl-5-dimethoxymethyl-2-phenyl-3H-imidazol-4-ylmethyl)amine (212)

3-Bromo-1,1-dimethoxy-propan-2-one (206). Bromine (80 g, 0.5 mol) is added dropwise to a solution of 1,1-dimethoxy-propan-2-one 205 (59 g, 0.5 mol) in anhydrous methanol (400 mL) at 0° C. and the solution is continued stirring at room temperature for 48 h. The solvent is removed under reduced pressure and the residue is dried in vacuo and used without further purification.

4-Dimethoxymethyl-2-phenyl-1H-imidazole (208). To a solution of benzamidine 207 (1.44 g, 12 mmol) and potassium carbonate (4.1 g, 30 mmol) in anhydrous DMF (25 mL) is slowly added a solution of 3-bromo-1,1-dimethoxy-propan-2-one 206 (1.97 g, 10 mmol) in anhydrous DMF (10 mL) over 30 min. The mixture is then heated at 50–60° C. for 2 h. After cooling to room temperature, ethyl acetate (100 mL) and water (100 mL) were added. The organic phase is separated and the aqueous phase is extracted with ethyl acetate twice and the combined organic phase is washed with water (3×20 mL) and brine. Removal of solvents under reduced pressure and purification of the residue by column chromatography affords the desired product as a white solid. Yield: 2.08 g; LC-MS (MH+): 219. $^1$H NMR (300 MHz, CDCl$_3$) δ 7.88–7.85 (m, 2H), 7.37–7.46 (m, 4H), 5.49 (s, 1H), 3.36 (s, 6H).

1-Butyl-4-dimethoxymethyl-2-phenyl-1H-imidazole (209). A solution of 4-dimethoxymethyl-2-phenyl-1H-imidazole 208 (2.18 g, 10 mmol) and n-butyl bromide (2.74 g, 20 mmol) in anhydrous DMSO (15 mL) is added to a suspension of powdered potassium hydroxide (0.96 mg, 15 mmol) in DMSO (20 mL) at room temperature over 3 h. The mixture is then stirred at rt for 16 h. The mixture is diluted with ether and washed with water (three times), brine, and dried over anhydrous sodium sulfate. Removal of the solvent and purification of the residue affords the desired product. Yield: 2.5 g; LC-MS (MH+): 275.

3-Butyl-5-dimethoxymethyl-2-phenyl-3H-imidazole-4-carbaldehyde (210). To a solution of 1-butyl-4-dimethoxymethyl-2-phenyl-1H-imidazole 209 (2.74 g, 10 mmol) in anhydrous THF under nitrogen at −78° C., n-BuLi (1.6 M in hexane, 7.5 ml, 12 mmol) is added dropwise and the mixture is continued stirring at this temperature for 30 min. After anhydrous DMF (4 mL) is added, the mixture is stirred at room temperature for 16 h. Saturated ammonium chloride and ethyl acetate were added at 0° C. and the the organic phase is separated. The aqueous phase is extracted with ethyl acetate and the combined organic phase is washed with brine, dried over anhydrous sodium sulfate and concentrated under reduced pressure. The residue is purified by column chromatography to yield the desired product as a white solid. Yield: 1.94 g; LC-MS (MH+): 303. $^1$H NMR (300 MHz, CDCl$_3$) δ 10.18 (s, 1H), 7.60–7.56 (m, 2H), 7.51–7.46 (m, 3H), 5.63 (s, 1H), 4.32 (t, J=6.3 Hz, 2H), 3.47 (s, 6H), 1.73–1.63 (m, 2H), 1.28–1.16 (m, 2H), 0.82 (t, J=7.2 Hz, 3H).

Benzo[1,3]dioxol-5-ylmethyl-(3-butyl-5-dimethoxymethyl-2-phenyl-3H-imidazol-4-ylmethyl)-amine (211). A solution of 3-butyl-5-dimethoxymethyl-2-phenyl-3H-imidazole-4-carbaldehyde (2.1 g, 7 mmol) and piperalamine (7 mmol) in anhydrous methanol (35 mL) is stirred at room temperature overnight. After cooling to 0° C., sodium borohydride (7 mmol) is added slowly in 30 min. The reaction is quenched by addition of water (20 mL) and most methanol is removed under reduced pressure. The residue is extracted with ethyl acetate and washed with water and brine, dried over anhydrous sodium sulfate and concentrated under reduced pressure. The residue is purified by column chromatography to yield the desired product as a colorless syrup. Yield: 2.62 g; LC-MS (MH+): 438.

Bis-benzo[1,3]dioxol-5-ylmethyl-(3-butyl-5-dimethoxymethyl-2-phenyl-3H-imidazol-4-ylmethyl)amine (212). This compound is prepared according to the procedure as preparation of 129 in Example 7. LC-MS (MH+): 572.

Example 30

Preparation of 5-[(Bis-benzo[1,3]dioxol-5-ylmethyl-amino]-1-butyl-2-phenyl-1H-imidazol-4-carbaldehyde (213)

Bis-benzo[1,3]dioxol-5-ylmethyl-(3-butyl-5-dimethoxymethyl-2-phenyl-3H-imidazol-4-ylmethyl)amine 212 (571 mg, 1 mmol) in THF (5 mL) is treated with p-toluenesulfonic acid monohydrate (380 mg, 2 mmol) at room temperature overnight. The solvent is removed and the residue is diluted with ethyl acetate and washed with saturated sodium bicarbonate and brine. The solvent is removed under reduced pressure and the residue is purified by column chromatography to yield the desired product. Yield: 510 mg; LC-MS (MH$^+$): 526.

Example 31

5-[(Bis-benzo[1,3]dioxol-5-ylmethyl-amino]-1-butyl-2-phenyl-1H-imidazol-4-carboxylic Acid (214)

To a solution of 5-[(bis-benzo[1,3]dioxol-5-ylmethyl-amino]-1-butyl-2-phenyl-1H-imidazol-4-carbaldehyde 213 (263 mg, 0.5 mmol) in actone (10 mL) and water (5 mL) is added sulfamic acid (107 mg, 1.11 mmol) at room temperature and the mixture is stirred for 30 min. Sodium chlorite (63 mg, 0.7 mmol) is added and the mixture is stirred for additional 30 min at room temperature. Evaporation of most actone and the residue is extracted with chloroform. The organic phase is washed with water, brine and dried over sodium sulfate. The solvent is removed and the product is dried in vacuo. Yield: 281 mg; LC-MS (MH+): 542.

Example 32

5-[(Bis-benzo[1,3]dioxol-5-ylmethyl-amino]-1-butyl-2-phenyl-1H-imidazol-4-carboxylic Acid Methy Easter (215)

To a solution of 5-[(bis-benzo[1,3]dioxol-5-ylmethyl-amino]-1-butyl-2-phenyl-1H-imidazol-4-carboxylic acid 214 (54 mg, 0.1 mmol) in methanol (5 mL) at 0° C. is added freshly prepared diazomethane ether solution. The mixture is stirred for 1 h and concentrated to provide the desired methyl ester. LC-MS (MH+): 556.

Example 33

2-{5-[(Bis-benzo[1,3]dioxol-5-ylmethyl-amino]-1-butyl-2-phenyl-1H-imidazol-4-yl}-propan-2-ol (216)

To a solution of 5-[(Bis-benzo[1,3]dioxol-5-ylmethyl-amino]-1-butyl-2-phenyl-1H-imidazol-4-carboxylic acid methy easter 215 (40 mg, 0.08 mmol) in anhydrous THF (2 mL) at −78° C. under argon is added methyl lithium (1M solution in ether, 0.2 ml, 0.2 mmol). The mixture is then stirred at room temperature for 1 h and the reaction is quenched with saturated ammonium chloride. The residue is extracted with ethyl acetate, washed with brine, dried over sodium sulfate, concentrated and purified by column chromatography to yield the desired product. Yield: 35 mg; LC-MS (MH+): 556.

Example 34

{5-[(Bis-benzo[1,3]dioxol-5-ylmethyl-amino]-1-butyl-2-phenyl-1H-imidazol-4-yl}-methanol (217)

To a solution of 5-[(bis-benzo[1,3]dioxol-5-ylmethyl-amino]-1-butyl-2-phenyl-1H-imidazol-4-carbaldehyde 213 (52 mg, 0.1 mmol) in anhydrous methanol (5 mL) at room temperature is added sodium borohydride (10 mg) and the mixture is stirred for 30 min. Water is added to quench the reaction and the residue is extracted with ethyl acetate. The organic phase is washed with water, brine and dried over sodium sulfate. The solvent is removed and the residue is purified by column chromatogaraphy to yield the desired product. Yield: 51 mg; LC-MS (MH+): 528.

Example 35

Bis-benzo[1,3]dioxol-5-ylmethyl-(3-butyl-5-methoxymethyl-2-phenyl-1H-imidazol-4-ylmethyl)-amine (218)

To a solution of {5-[(bis-benzo[1,3]dioxol-5-ylmethyl-amino]-1-butyl-2-phenyl-1H-imidazol-4-yl}-methanol 217 (52 mg, 0.1 mmol) and NaH (5 mg) in anhydrous THF (5 mL) at 0° C. under argon is added iodomethane (0.05 mL) and the mixture is stirred for 1 h. Evaporation of the solvent and excess of MeI and the residue is purified by column chromatogaraphy to yield the desired product. Yield: 41 mg; LC-MS (MH+): 542.

Example 36

Bis-benzo[1,3]dioxol-5-ylmethyl-(1'-butyl-2'-phenyl-1'H-[1,4']biimidazolyl-5'-ylmethyl)-amine (219)

To a solution of {5-[(bis-benzo[1,3]dioxol-5-ylmethyl-amino]-1-butyl-2-phenyl-1H-imidazol-4-yl}-methanol 217 (52 mg, 0.1 mmol) in anhydrous acetonitrile (5 mL) at room temperature is added CDI (21 mg, 0.13 mmol) and the mixture is stirred for 1 h. Evaporation of the solvent and excess of MeI and the residue is purified by column chromatogaraphy to yield the desired product. Yield: 561 mg; LC-MS (MH$^+$): 578.

Example 37

1-{5-[(Bis-benzo[1,3]dioxol-5-ylmethyl-amino)-methyl]-1-butyl-2-phenyl-1H-imidazol-4-yl}-ethanol (220)

This compound is prepared in the manner as described for the preparation of 216 to yield the desired product; LC-MS (MH+): 542.

Example 38

1-{5-[(Bis-benzo [1,3]dioxol-5-ylmethyl-amino)-methyl]-1-butyl-2-phenyl-1H-imidazol-4-yl}ethnone (221)

A solution of 1-{5-[(Bis-benzo[1,3]dioxol-5-ylmethyl-amino)-methyl]-1-butyl-2-phenyl-1H-imidazol-4-yl}-ethanol 220 (54 mg, 0.1 mmol) in anhydrous THF (5 mL) is oxidized with MnO$_2$ (100 mg) under reflux for 5 h. After cooling to room temperature, the residue is filtered though celite and concentrated. The residue is purified by column chromatogaraphy to yield the desired product. Yield: 38 mg; LC-MS (MH$^+$): 540.

Example 39

Bis-benzo[1,3]dioxol-5-ylmethyl-(3-butyl-5-dimethylaminomethyl-2-phenyl-3H-imidazol-4-yl}-amine (222)

This compound is prepared in the manner as described for the preparation of 212 to yield the desired product; LC-MS (MH+): 542.

Example 39

5-[(Bis-benzo[1,3]dioxol-5-ylmethyl-amino)-methyl]-1-butyl-2-phenyl-1H-imidazole-4-carboxylic Acid Dimethylamide (223)

To a solution of 5-[(Bis-benzo[1,3]dioxol-5-ylmethyl-amino]-1-butyl-2-phenyl-1H-imidazol-4-carboxylic acid 214. (50 mg, 0.1 mmol) in anhydrous dichloromethane (3 mL) is added dimethylamine (1M solution in THF, 0.4 ml, 0.4 mmol) and DCC (0.2 mmol) and the mixture is stirred for 48 h. Evaporation the solvent and the residue is purified by column chromatography to yield the desired product. Yield: 25 mg; LC-MS (MH+): 569.

Example 40

Bis-benzo[1,3]dioxol-5-ylmethyl-(3-butyl-5-difluoromethyl-2-phenyl-1H-imidazol-4-ylmethyl)-amine (224)

To a solution of 5-[(Bis-benzo[1,3]dioxol-5-ylmethyl-amino]-1-butyl-2-phenyl-1H-imidazol-4-carbaldehyde 213 (42 mg, 0.8 mmol) in anhydrous dichloromethane (2 mL) at −78° C. under argon is added DAST (0.11 ml, 8.1 mmol). The mixture is stirred at room temperature for 16 h and concentrated. The residue is purified by column chromatogaraphy to yield the desired product. Yield: 33 mg; LC-MS (MH+): 548.

Example 41

Preparation of 2-(2,6-diethylphenyl)-4-chloroimidazole-5-carboxyaldehyde

Synthesis of 2,6-diethylphenylboronic Acid

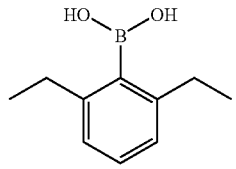

2,6-Diethyl bromobenzene (38.2 g, 180.2 mmol) is added dropwise through an additional funnel over a 1 hour period to a solution of n-BuLi (2.0 M in cyclohexane, 99.1 ml, 198.2 mmol) in THF (380 mL) at −75° C. After addition, the reaction mixture is stirred at −75° C. for 30 minutes; trimethyl borate (28.1 g, 270.3 mmol) is added slowly over a 40 minute period. The reaction mixture is warmed to room temperature overnight. 2N HCl (250 mL) is added slowly and the resulting mixture is stirred for 1 hour. The organic layer is separated and the aqueous layer is extracted with ether (2×200 mL). The combined organic layers are dried over anhydrous Na$_2$SO$_4$ and the solvents are removed in vacuo. Hexane (400 mL) is added to the residue and a white precipitate is formed. Filtration and drying in vacuo gives 19.0 g of 2,6-diethylphenyl boronic acid as a white solid. $^1$H NMR: (CDCl$_3$) 7.22 (t, 1H), 7.04 (s, 2H), 4.65 (s, 2H), 2.64 (q, 4H), 1.22 (t, 6H).

Synthesis of 1-methoxyethyl-3,4-dichloroimidazole

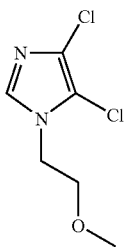

A solution of 1 mmol of 3,4-dichloroimidazole in anhydrous DMF (5 mL) is treated with sodium hydride (1.05 mmol) at 0° C. under nitrogen with magnetic stirring. After 30 min., 2-chloroethyl methyl ether (1 mmol) is added and the reaction mixture is warmed to 60° C. for 2 h. The reaction mixture is cooled, portioned between water and ethyl acetate. The organic layer is separated, washed with water, brine and dried over sodium sulfate. The reaction mixture is filtered, evaporated and purified by chromatography on silica gel to obtain 1-methoxyethyl-3,4-dichloroimidazole.

Synthesis of 2-bromo-1-methoxyethyl-3,4-dichloroimidazole

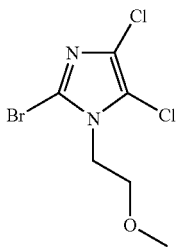

To a solution of 1-methoxyethyl-3,4-dichloroimidazole (1.95 g, 10 mmol) in acetonitrile (50 mL) is added NBS (1.86 g, 1.05 mmol) at room temperature in portions. The reaction mixture is stirred at rt for 30 min. Ethyl acetate (100 mL) is added and washed with water, brine, dried over MgSO$_4$, filtered and evaporated in vacuo to dryness. The crude product is purified by flash chromatography (hexane/ethyl acetate 100/5) to obtain 2-bromo-1-methoxyethyl-3,4-dichloroimidazole.

Synthesis of 2-(2,6-diethylphenyl)-1-methoxyethyl-3,4-dichloroimidazole

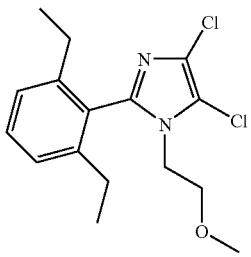

A solution containing 2-bromo-1-methoxyethyl-3,4-dichloroimidazole (2.74 g, 10 mmol), 2,6-diethylphenylboronic acid (2.14 g, 12 mmol.) and Pd(PPh$_3$)$_4$ (0.23 mg, 0.2 mmol) in toluene/2M Na$_2$CO$_3$ (30 ml/15 mL) in a sealed tube is degassed, then allowed to heat to 110° C. overnight. The organic layer is separated and concentrated in vacuo to dryness. The residue is purified by column chromatography on silica gel (hexane/ethyl acetate 100/5) to obtain the 2-(2,6-diethylphenyl)-1-methoxyethyl-3,4-dichloroimidazole.

Synthesis of 2-(2,6-diethylphenyl)-1-methoxyethyl-4-chloro-imidazole-3-carboxaldehyde

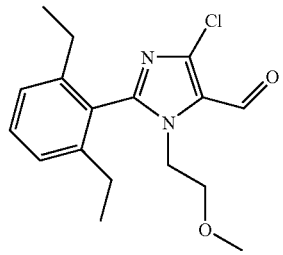

To a solution of N-methoxyethyl 2-(2,6-diethylphenyl)-1-methoxyethyl-3,4-dichloroimidazole (3.27 g, 10 mmol.) in anhydrous THF is added n-BuLi (1.6M in hexane) (9.4 ml, 15 mmol) dropwise at −78° C. After the reaction mixture is stirred at −78° C. for 2 h, anhydrous DMF (3 equiv.) is added in one portion. The mixture is stirred at −78° C. for 30 min, then allowed to warm to room temperature slowly. The reaction mixture is quenched with water and extracted with ethyl acetate, dried over MgSO$_4$, filtered, concentrated in vacuo and purified by chromatography on silica gel to give 2-(2,6-diethylphenyl)-1-methoxyethyl-4-chloro-imidazole-3-carboxaldehyde. This material is used to make various compounds of Formula I as depicted in Scheme 10 and further illustrated in Examples 4–9 and related examples.

Example 42

Pharmaceutical Preparations of Oral and Intravenous Administration

A. Tablets containing a C5a antagonist and an anti-arthritic agent which is not a C5a receptor antagonist can be prepared as illustrated below:

| Ingredient | Amount |
| --- | --- |
| C5a receptor antagonist | 5 mg–500 mg |
| C5a receptor-inactive therapeutic agent | 1 mg–500 mg |
| diluent, binder, distigrant, lubricant excipients | q.s. 200–400 mg. |

B. Tablets containing a C5a receptor antagonist as the only active ingredient can be prepared as illustrated below:

| Ingredient | mg | mg |
| --- | --- | --- |
| C5a receptor antagonist | 10 | 50 |
| Microcrystalline Cellulose | 70.4 | 352 |
| Granular Mannitol | 15.1 | 75.5 |

-continued

| Ingredient | mg | mg |
|---|---|---|
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | mg |
|---|---|---|
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium sterate | 1.25 | 0.5 |

D. Intravaneous formulations containing a C5a receptor antagonist and a C5a receptor inactive agent may be prepared as follows:

| Ingredient | Amount |
|---|---|
| C5a receptor antagonist | 0.5–10 mg |
| C5a receptor inactive therapeutic agent | 0.5–10 mg |
| Sodium Citrate | 5–50 mg |
| Citic Acid | 1–15 mg |
| Sodium Chloride | 1–8 mg |
| Water for Injection | to 1.0 liter |

E. Oral suspensions containing a C5a receptor antagonist and a C5a receptor inactive agent may be prepared as follows:

| Ingredient | Amount per 5 ml dose |
|---|---|
| C5a receptor antagonist | 5–100 mg |
| C5a receptor inactive therapeutic agent | 5–100 mg |
| Polyvinylpyrrolidone | 150 mg |
| Poly oxyethylene sorbitan monolaurate | 25 mg |
| Benzoic Acid | 10 mg to 5 mL with sorbitol solution (70%) |

Example 43

Additional Compounds of the invention, shown in Tables I–IV are prepared via the methods provided in Scheme 1–11 and further illustrated in Examples 1–41. Compounds which have an asterisk in the column labeled $Ca^{2+}$ Mobilization Assay Ki<1 µM, were tested in the standard assay of C5a receptor mediated calcium mobilization given in Example 53 and found to exhibit a Ki of less than 1 µM.

The LC/MS data presented in Tables I–IV were obtained using the following instrumentation and methods. MS spectroscopy data is Electrospray MS, obtained in positive ion mode, with a 15V Cone voltage, using a WATERS ZMD 2000 Mass Spec Detector, equipped with a WATERS 600 pump, WATERS 2487 Dual Wavelength Detector, GILSON 215 Autosampler, and a GILSON 841 Microinjector. MassLynx version 3.4 software was used for data collection and analysis.

Sample, 2–20 uL, was injected onto a 33×4.6 mm YMC ProPack C18;5u column, and eluted using a 2-phase linear gradient at a 4 mL/minute flow rate. Sample was detected at 220 and 254 nm. The elution conditions were as follows: Mobile Phase A-95/5/0.1 Water/Methanol/TFA, Mobile Phase B-5/95/0.1 Water/Methanol/TFA.

| Gradient- | time(min) | % B |
|---|---|---|
| | 0 | 10 |
| | 0.01 | 10 |
| | 2.0 | 100 |
| | 3.5 | 100 |
| | 3.51 | 10 |
| | 3.52 | |

The total run time for the gradient was 4.0 minutes.

TABLE I

| CMP # | STRUCTURE | $Ca^{2+}$ Mob. | IUPAC Name | MASS | Ret. Time |
|---|---|---|---|---|---|
| 225 | 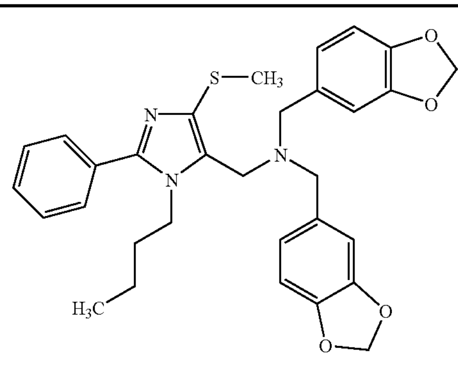 | * | 1-(1,3-benzodioxol-5-yl)-N-(1,3-benzodioxol-5-ylmethyl)-N-{[1-butyl-4-(methylthio)-2-phenyl-1H-imidazol-5-yl]methyl}methanamine | 543.22 | 1.22 |

TABLE I-continued

| CMP # | STRUCTURE | Ca²⁺ Mob. | IUPAC Name | MASS | Ret. Time |
|---|---|---|---|---|---|
| 226 | 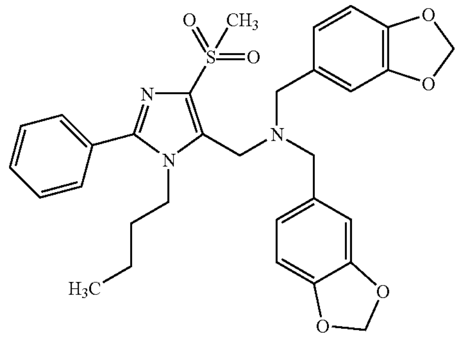 | * | 1-(1,3-benzodioxol-5-yl)-N-(1,3-benzodioxol-5-ylmethyl)-N-{[1-butyl-4-(methylsulfonyl)-2-phenyl-1H-imidazol-5-yl]methyl}methanamine | 575.21 | 1.27 |
| 227 | 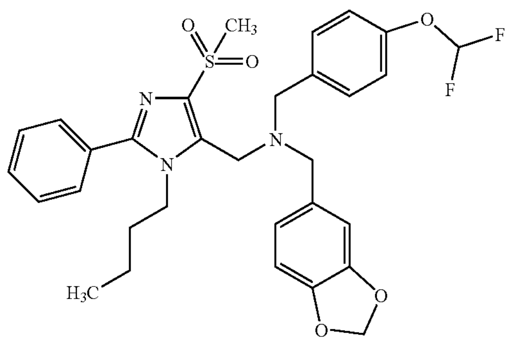 | * | 1-(1,3-benzodioxol-5-yl)-N-{[1-butyl-4-(methylsulfonyl)-2-phenyl-1H-imidazol-5-yl]methyl}-N-[4-(difluoromethoxy)benzyl]methanamine | 597.21 | 1.27 |
| 228 | 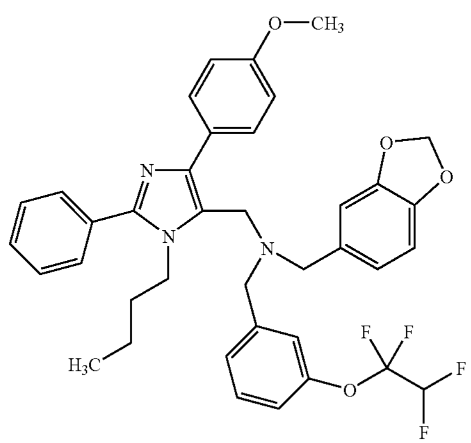 | * | 1-(1,3-benzodioxol-5-yl)-N-{[1-butyl-4-(4-methoxyphenyl)-2-phenyl-1H-imidazol-5-yl]methyl}-N-[3-(1,1,2,2-tetrafluoroethoxy)benzyl]methanamine | 675.27 | 1.23 |
| 229 | 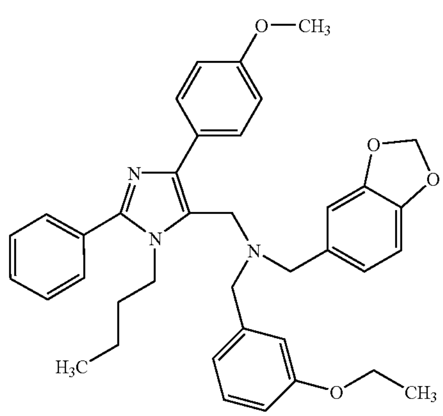 | * | 1-(1,3-benzodioxol-5-yl)-N-{[1-butyl-4-(4-methoxyphenyl)-2-phenyl-1H-imidazol-5-yl]methyl}-N-(3-ethoxybenzyl)methanamine | 603.31 | 1.24 |

TABLE I-continued

| CMP # | STRUCTURE | Ca²⁺ Mob. | IUPAC Name | MASS | Ret. Time |
|---|---|---|---|---|---|
| 230 | 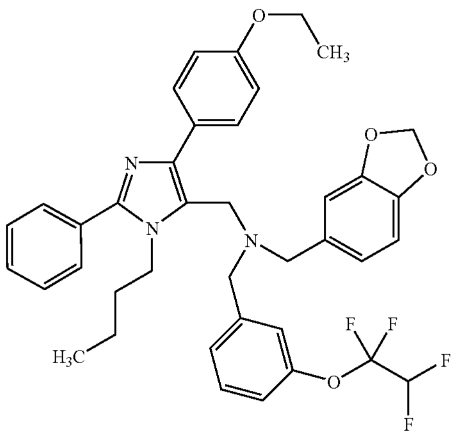 | * | 1-(1,3-benzodioxol-5-yl)-N-{[1-butyl-4-(4-ethoxyphenyl)-2-phenyl-1H-imidazol-5-yl]methyl}-N-[3-(1,1,2,2-tetrafluoroethoxy)benzyl]methanamine | 689.29 | 1.24 |
| 231 | 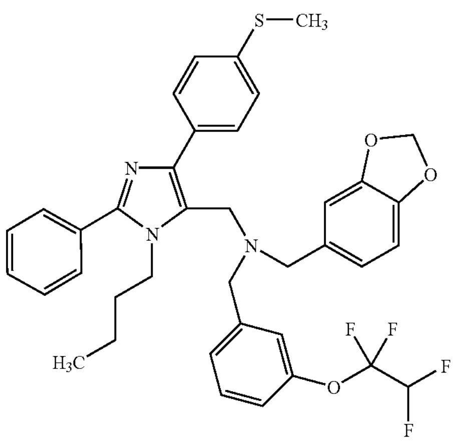 | * | 1-(1,3-benzodioxol-5-yl)-N-({1-butyl-4-[4-(methylthio)phenyl]-2-phenyl-1H-imidazol-5-yl}methyl)-N-[3-(1,1,2,2-tetrafluoroethoxy)benzyl]methanamine | 691.25 | 1.24 |
| 232 | 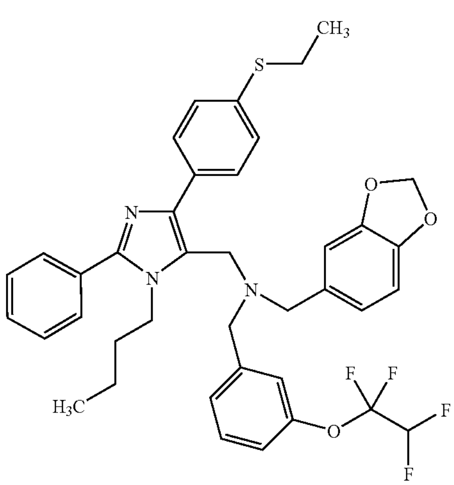 | * | 1-(1,3-benzodioxol-5-yl)-N-({1-butyl-4-[4-(ethylthio)phenyl]-2-phenyl-1H-imidazol-5-yl}methyl)-N-[3-(1,1,2,2-tetrafluoroethoxy)benzyl]methanamine | | |

TABLE I-continued

| CMP # | STRUCTURE | Ca²⁺ Mob. | IUPAC Name | MASS | Ret. Time |
|---|---|---|---|---|---|
| 233 | 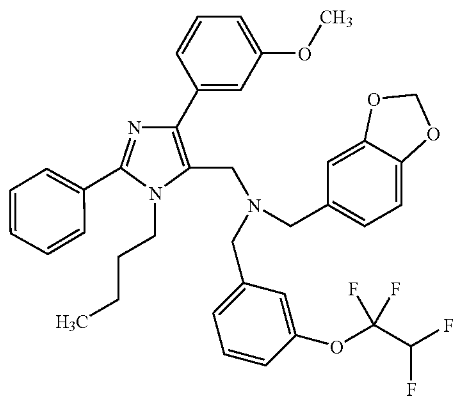 | * | 1-(1,3-benzodioxol-5-yl)-N-{[1-butyl-4-(3-methoxyphenyl)-2-phenyl-1H-imidazol-5-yl]methyl}-N-[3-(1,1,2,2-tetrafluoroethoxy)benzyl]methanamine | 675.27 | 1.23 |
| 234 | 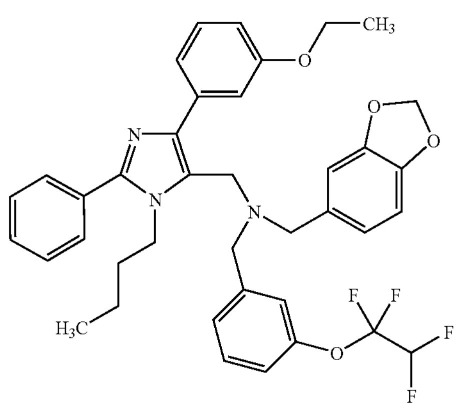 | * | 1-(1,3-benzodioxol-5-yl)-N-{[1-butyl-4-(3-ethoxyphenyl)-2-phenyl-1H-imidazol-5-yl]methyl}-N-[3-(1,1,2,2-tetrafluoroethoxy)benzyl]methanamine | 689.29 | 1.24 |
| 235 | 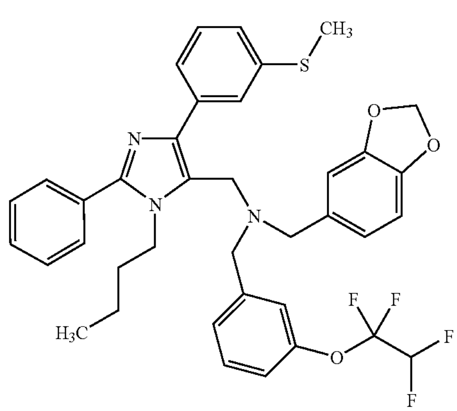 | * | 1-(1,3-benzodioxol-5-yl)-N-({1-butyl-4-[3-(methylthio)phenyl]-2-phenyl-1H-imidazol-5-yl}methyl)-N-[3-(1,1,2,2-tetrafluoroethoxy)benzyl]methanamine | 691.25 | 1.24 |

TABLE I-continued

| CMP # | STRUCTURE | Ca²⁺ Mob. | IUPAC Name | MASS | Ret. Time |
|---|---|---|---|---|---|
| 236 | 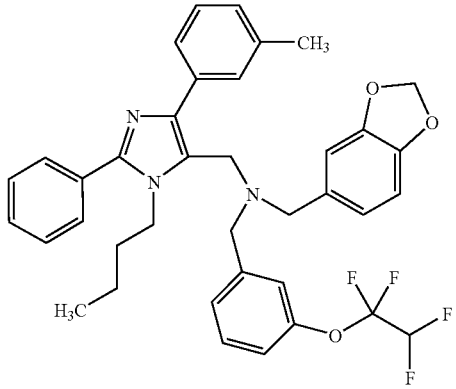 | * | 1-(1,3-benzodioxol-5-yl)-N-{[1-butyl-4-(3-methylphenyl)-2-phenyl-1H-imidazol-5-yl]methyl}-N-[3-(1,1,2,2-tetrafluoroethoxy)benzyl]methanamine | 659.28 | 1.24 |
| 237 | 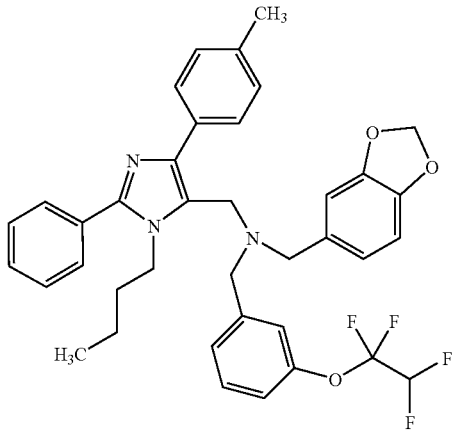 | * | 1-(1,3-benzodioxol-5-yl)-N-{[1-butyl-4-(4-methylphenyl)-2-phenyl-1H-imidazol-5-yl]methyl}-N-[3-(1,1,2,2-tetrafluoroethoxy)benzyl]methanamine | 659.28 | 1.22 |
| 238 | 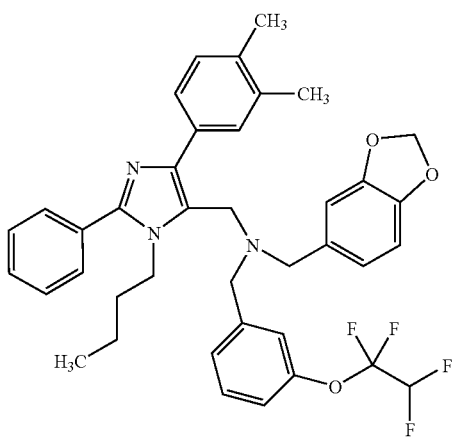 | * | 1-(1,3-benzodioxol-5-yl)-N-{[1-butyl-4-(3,4-dimethylphenyl)-2-phenyl-1H-imidazol-5-yl]methyl)-N-[3-(1,1,2,2-tetrafluoroethoxy)benzyl]methanamine | 673.29 | 1.25 |

TABLE I-continued

| CMP # | STRUCTURE | Ca²⁺ Mob. | IUPAC Name | MASS | Ret. Time |
|---|---|---|---|---|---|
| 239 | 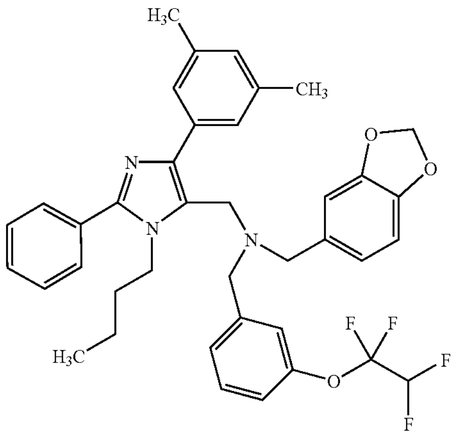 | * | 1-(1,3-benzodioxol-5-yl)-N-{[1-butyl-4-(3,5-dimethylphenyl)-2-phenyl-1H-imidazol-5-yl]methyl]-N-[3-(1,1,2,2-tetrafluoroethoxy)benzyl]methanamine | 673.29 | 1.27 |
| 240 | 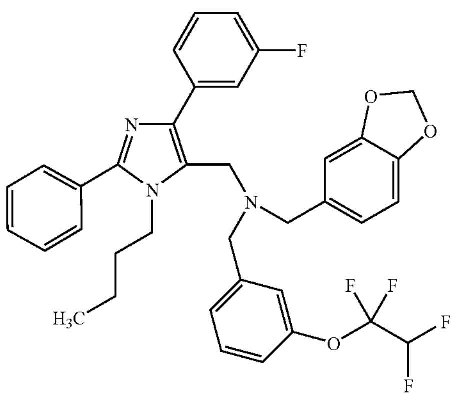 | * | 1-(1,3-benzodioxol-5-yl)-N-{[1-butyl-4-(3-fluorophenyl)-2-phenyl-1H-imidazol-5-yl]methoyl}-N-[3-(1,1,2,2-tetrafluoroethoxy)benzyl]methanamine | 663.25 | 1.23 |
| 241 | 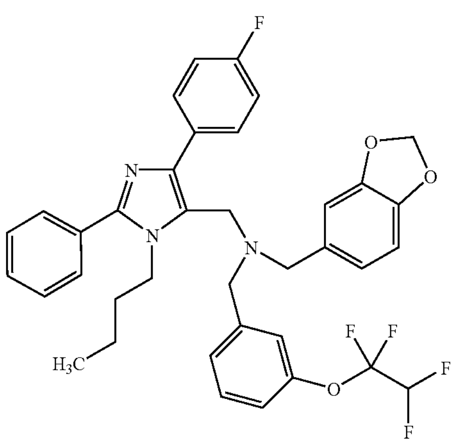 | * | 1-(1,3-benzodioxol-5-yl)-N-{(1-butyl-4-(4-fluorophenyl)-2-phenyl-1H-imidazol-5-yl]methyl}-N-[3-(1,1,2,2-tetrafluoroethoxy)benzyl]methanamine | 663.25 | 1.22 |

TABLE I-continued

| CMP # | STRUCTURE | Ca²⁺ Mob. | IUPAC Name | MASS | Ret. Time |
|---|---|---|---|---|---|
| 242 | 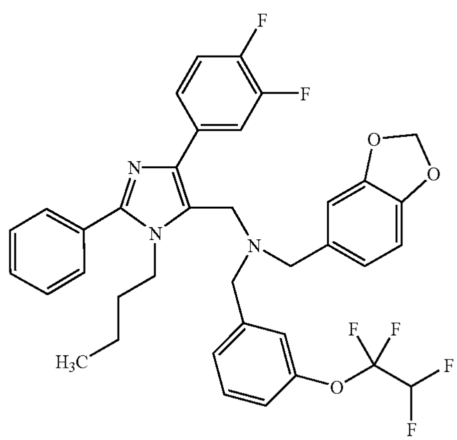 | * | 1-(1,3-benzodioxol-5-yl)-N-{[1-butyl-4-(3,4-difluorophenyl)-2-phenyl-1H-imidazol-5-yl]methyl}-N-[3-(1,1,2,2-tetrafluoroethoxy)benzyl]methanamine | 681.24 | 1.24 |
| 243 | 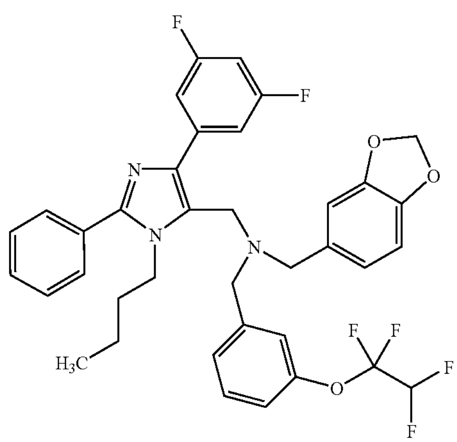 | * | 1-(1,3-benzodioxol-5-yl)-N-{(1-butyl-4-(3,5-difluorophenyl)-2-phenyl-1H-imidazol-5-yl]methyl}-N-[3-(1,1,2,2-tetrafluoroethoxy)benzyl]methanamine | 681.24 | 1.26 |
| 244 | 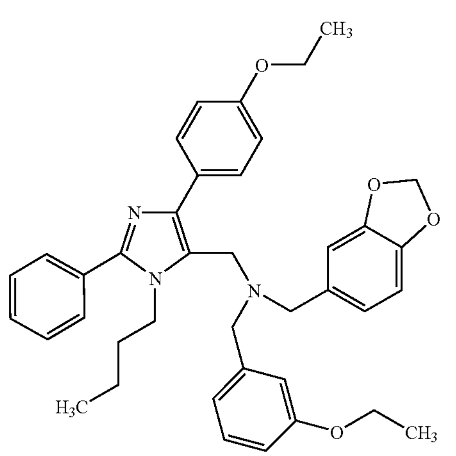 | * | 1-(1,3-benzodioxol-5-yl)-N-{(1-butyl-4-(4-ethoxyphenyl)-2-phenyl-1H-imidazol-5-yl]methyl}-N-(3-ethoxybenzyl)methanamine | 617.33 | 1.26 |

TABLE I-continued

| CMP # | STRUCTURE | Ca²⁺ Mob. | IUPAC Name | MASS | Ret. Time |
|---|---|---|---|---|---|
| 245 | 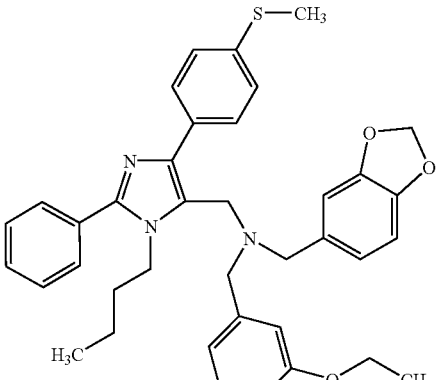 | * | 1-(1,3-benzodioxol-5-yl)-N-({1-butyl-4-[4-(methylthio)phenyl]-2-phenyl-1H-imidazol-5-yl}methyl)-N-(3-ethoxybenzyl)methanamine | 619.29 | 1.26 |
| 246 | 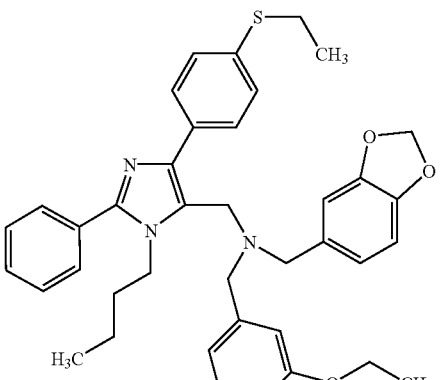 | * | 1-(1,3-benzodioxol-5-yl)-N-({1-butyl-4-[4-(ethylthio)phenyl]-2-phenyl-1H-imidazol-5-yl}methyl)-N-(3-ethoxybenzyl)methanamine | 633.3 | 1.26 |
| 247 | 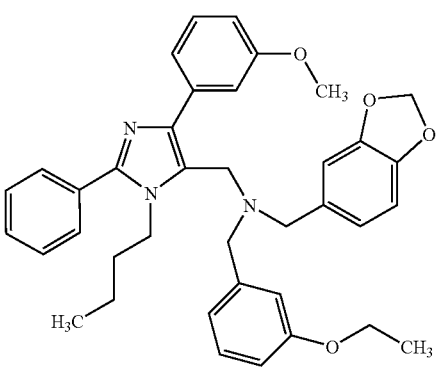 | * | 1-(1,3-benzodioxol-5-yl)-N-{[1-butyl-4-(3-methoxyphenyl)-2-phenyl-1H-imidazol-5-yl]methyl}-N-(3-ethoxybenzyl)methanamine | 603.31 | 1.23 |
| 248 | 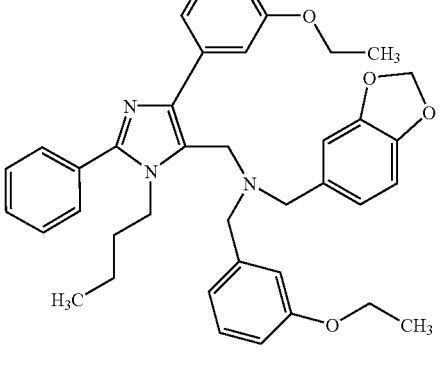 | * | 1-(1,3-benzodioxol-5-yl)-N-{[1-butyl-4-(3-ethoxyphenyl)-2-phenyl-1H-imidazol-5-yl]methyl}-N-(3-ethoxybenzyl)methanamine | 617.33 | 1.26 |

TABLE I-continued

| CMP # | STRUCTURE | Ca²⁺ Mob. | IUPAC Name | MASS | Ret. Time |
|---|---|---|---|---|---|
| 249 | 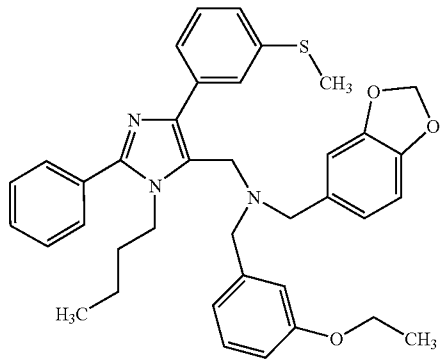 | * | 1-(1,3-benzodioxol-5-yl)-N-({1-butyl-4-[3-(methylthio)phenyl]-2-phenyl-1H-imidazol-5-yl}methyl)-N-(3-ethoxybenzyl)methanamine | 619.29 | 1.25 |
| 250 | 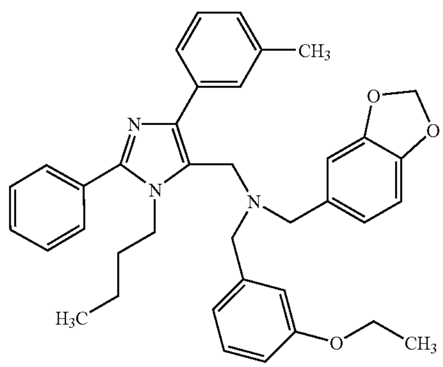 | * | 1-(1,3-benzodioxol-5-yl)-N-{[1-butyl-4-(3-methylphenyl)-2-phenyl-1H-imidazol-5-yl]methyl}-N-(3-ethoxybenzyl)methanamine | 587.31 | 1.25 |
| 251 | 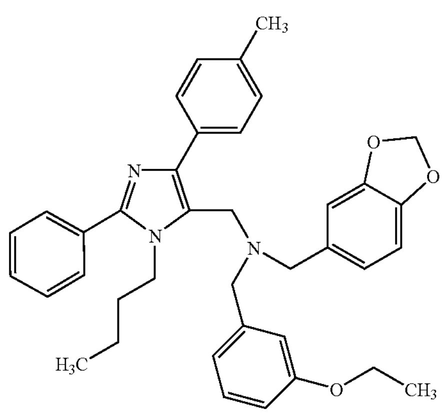 | * | 1-(1,3-benzodioxol-5-yl)-N-{[1-butyl-4-(4-methylphenyl)-2-phenyl-1H-imidazol-5-yl]methyl}-N-(3-ethoxybenzyl)methanamine | 587.31 | 1.25 |
| 252 | 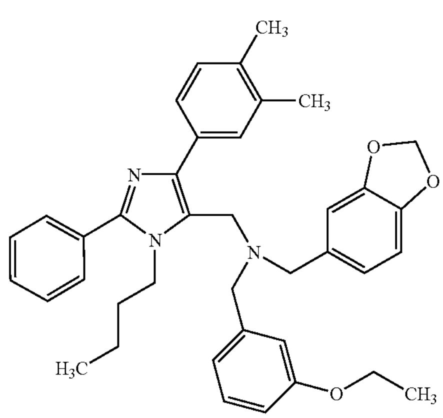 | * | 1-(1,3-benzodioxol-5-yl)-N-{[1-butyl-4-(3,4-dimethylphenyl)-2-phenyl-1H-imidazol-5-yl]methyl}-N-(3-ethoxybenzyl)methanamine | 601.33 | 1.29 |

TABLE I-continued

| CMP # | STRUCTURE | Ca²⁺ Mob. | IUPAC Name | MASS | Ret. Time |
|---|---|---|---|---|---|
| 253 | 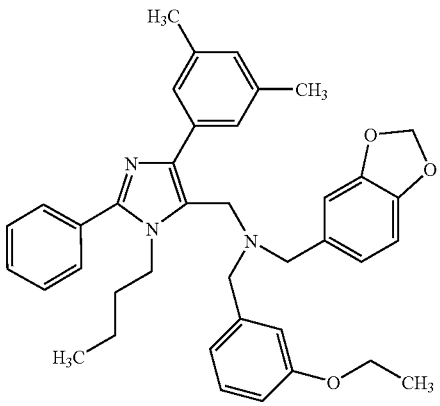 | * | 1-(1,3-benzodioxol-5-yl)-N-{[1-butyl-4-(3,5-dimethylphenyl)-2-phenyl-1H-imidazol-5-yl]methyl}-N-(3-ethoxybenzyl)methanamine | 601.33 | 1.28 |
| 254 | 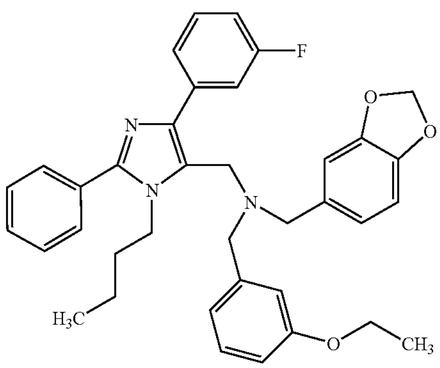 | * | 1-(1,3-benzodioxol-5-yl)-N-{[1-butyl-4-(3-fluorophenyl)-2-phenyl-1H-imidazol-5-yl]methyl}-N-(3-ethoxybenzyl)methanamine | 591.29 | 1.24 |
| 255 | 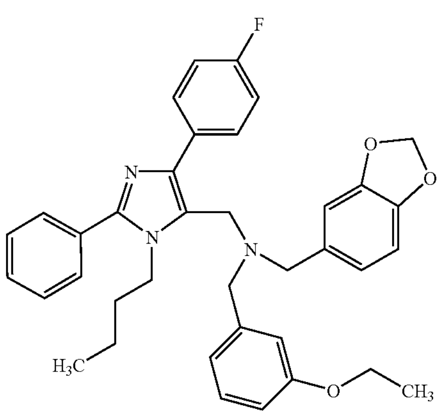 | * | 1-(1,3-benzodioxol-5-yl)-N-{[1-butyl-4-(4-fluorophenyl)-2-phenyl-1H-imidazol-5-yl]methyl}-N-(3-ethoxybenzyl)methanamine | 591.29 | 1.24 |

TABLE I-continued

| CMP # | STRUCTURE | Ca²⁺ Mob. | IUPAC Name | MASS | Ret. Time |
|---|---|---|---|---|---|
| 256 | 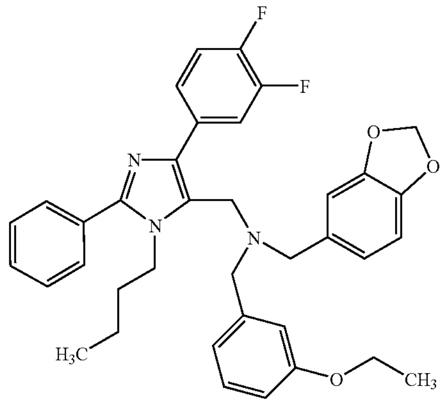 | * | 1-(1,3-benzodioxol-5-yl)-N-{[1-butyl-4-(3,4-difluorophenyl)-2-phenyl-1H-imidazol-5-yl]methyl}-N-(3-ethoxybenzyl)methanamine | 609.28 | 1.26 |
| 257 | 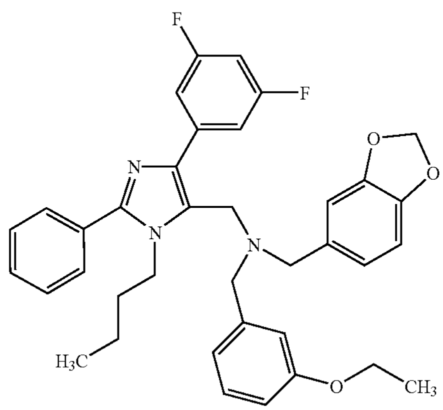 | * | 1-(1,3-benzodioxol-5-yl)-N-{[1-butyl-4-(3,5-difluorophenyl)-2-phenyl-1H-imidazol-5-yl]methyl}-N-(3-ethoxybenzyl)methanamine | 609.28 | 1.28 |
| 258 | 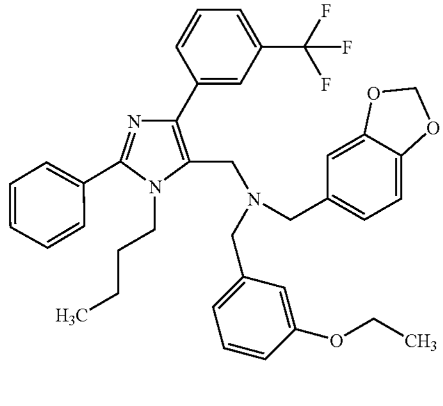 | * | 1-(1,3-benzodioxol-5-yl)-N-({1-butyl-2-phenyl-4-[3-(trifluoromethyl)phenyl]-1H-imidazol-5-yl}methyl)-N-(3-ethoxybenzyl)methanamine | 641.29 | 1.27 |

TABLE I-continued

| CMP # | STRUCTURE | Ca²⁺ Mob. | IUPAC Name | MASS | Ret. Time |
|---|---|---|---|---|---|
| 259 | 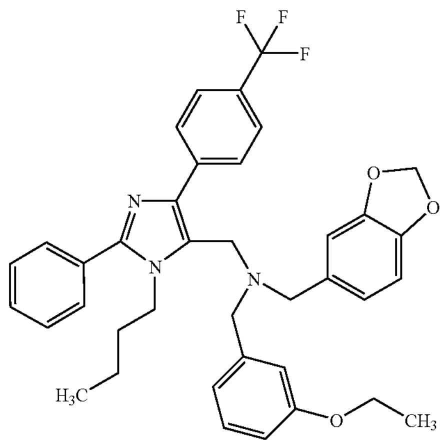 | * | 1-(1,3-benzodioxol-5-yl)-N-({1-butyl-2-phenyl-4-[4-(trifluoromethyl)phenyl]-1H-imidazol-5-yl}methyl)-N-(3-ethoxybenzyl)methanamine | 641.29 | 1.27 |
| 260 | 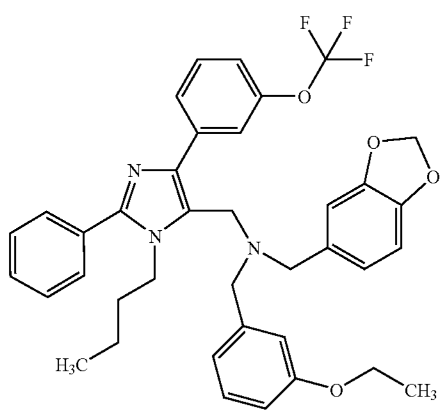 | * | 1-(1,3-benzodioxol-5-yl)-N-({1-butyl-2-phenyl-4-[3-(trifluoromethoxy)phenyl]-1H-imidazol-5-yl}methyl)-N-(3-ethoxybenzyl)methanamine | 657.28 | 1.27 |
| 261 | 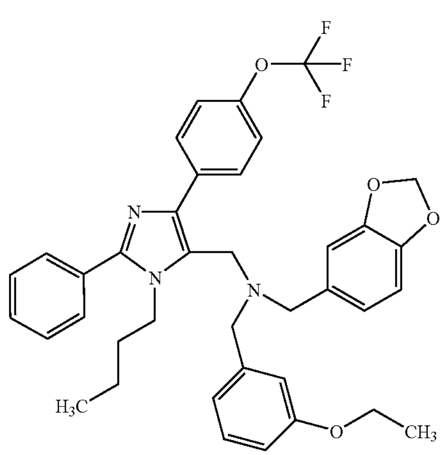 | * | 1-(1,3-benzodioxol-5-yl)-N-({1-butyl-2-phenyl-4-[4-(trifluoromethoxy)phenyl]-1H-imidazol-5-yl}methyl)-N-(3-ethoxybenzyl)methanamine | 657.28 | 1.29 |

TABLE I-continued

| CMP # | STRUCTURE | Ca²⁺ Mob. | IUPAC Name | MASS | Ret. Time |
|---|---|---|---|---|---|
| 262 | 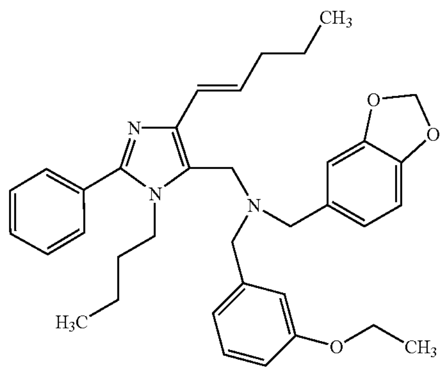 | * | 1-(1,3-benzodioxol-5-yl)-N-({1-butyl-4-[(1E)-pent-1-enyl]-2-phenyl-1H-imidazol-5-yl}methyl)-N-(3-ethoxybenzyl)methanamine | 565.33 | 1.27 |
| 263 | 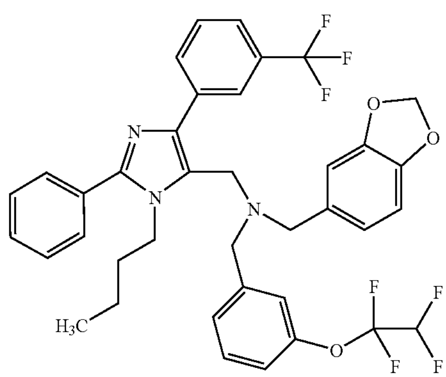 | * | 1-(1,3-benzodioxol-5-yl)-N-({1-butyl-2-phenyl-4-[3-(trifluoromethyl)phenyl]-1H-imidazol-5-yl}methyl)-N-[3-(1,1,2,2-tetrafluoroethoxy)benzyl]methanamine | | |
| 264 | 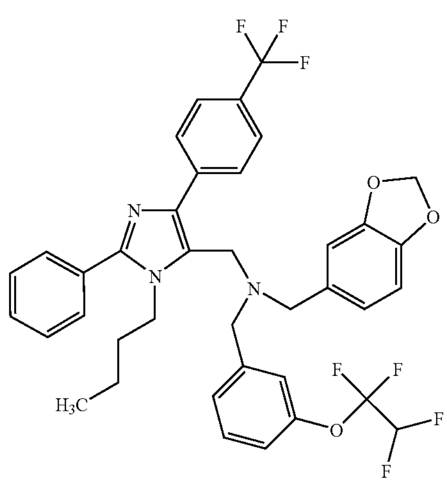 | * | 1-(1,3-benzodioxol-5-yl)-N-({1-butyl-2-phenyl-4-[4-(trifluoromethyl)phenyl]-1H-imidazol-5-yl}methyl)-N-[3-(1,1,2,2-tetrafluoroethoxy)benzyl]methanamine | | |

TABLE I-continued

| CMP # | STRUCTURE | Ca²⁺ Mob. | IUPAC Name | MASS | Ret. Time |
|---|---|---|---|---|---|
| 265 | 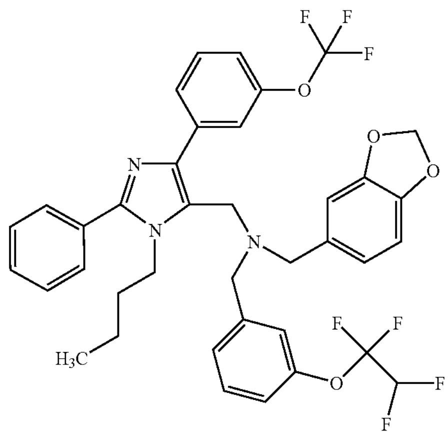 | * | 1-(1,3-benzodioxol-5-yl)-N-({1-butyl-2-phenyl-4-[3-(trifluoromethoxy)phenyl]-1H-imidazol-5-yl}methyl)-N-[3-(1,1,2,2-tetrafluoroethoxy)benzyl]methanamine | | |
| 266 | 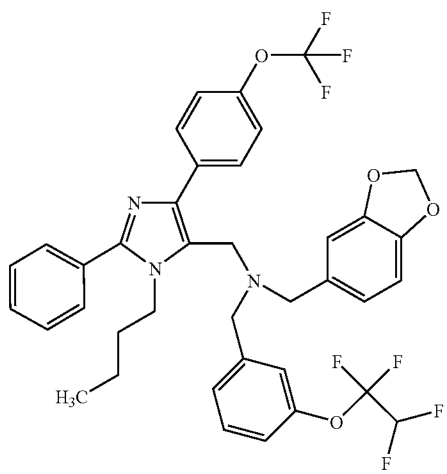 | * | 1-(1,3-benzodioxol-5-yl)-N-({1-butyl-2-phenyl-4-[4-(trifluoromethoxy)phenyl]-1H-imidazol-5-yl}methyl)-N-[3-(1,1,2,2-tetrafluoroethoxy)benzyl]methanamine | | |
| 267 | 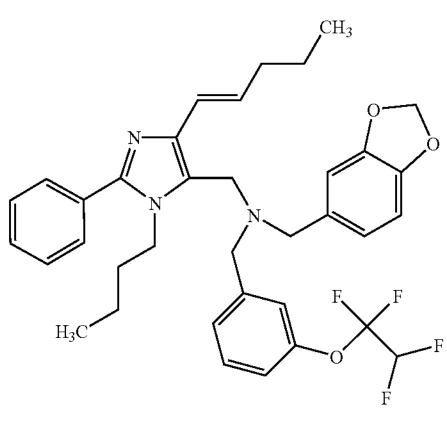 | * | 1-(1,3-benzodioxol-5-yl)-N-({1-butyl-4-[(1E)-pent-1-enyl]-2-phenyl-1H-imidazol-5-yl}methyl)-N-[3-(1,1,2,2-tetrafluoroethoxy)benzyl]methanamine | 637.29 | 1.25 |

TABLE I-continued

| CMP # | STRUCTURE | Ca²⁺ Mob. | IUPAC Name | MASS | Ret. Time |
|---|---|---|---|---|---|
| 268 | 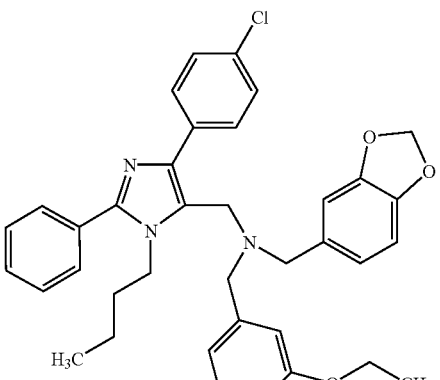 | * | 1-(1,3-benzodioxol-5-yl)-N-{[1-butyl-4-(4-chlorophenyl)-2-phenyl-1H-imidazol-5-yl]methyl}-N-(3-ethoxybenzyl)methanamine | 607.26 | 1.27 |
| 269 | 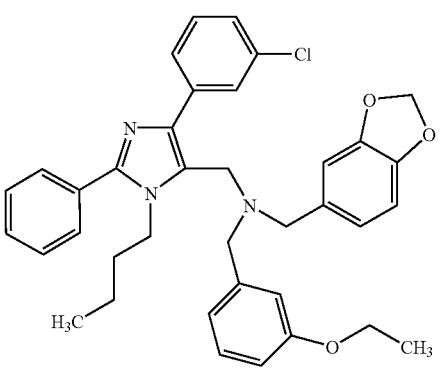 | * | 1-(1,3-benzodioxol-5-yl)-N-{[1-butyl-4-(3-chlorophenyl)-2-phenyl-1H-imidazol-5-yl]methyl}-N-(3-ethoxybenzyl)methanamine | 607.26 | 1.27 |
| 270 | 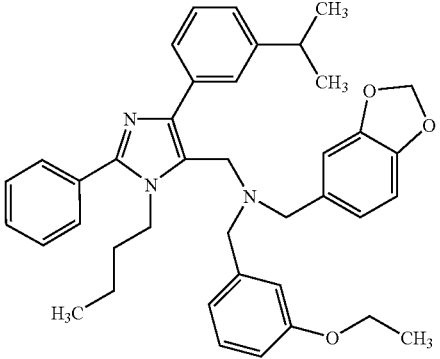 | * | 1-(1,3-benzodioxol-5-yl)-N-{[1-butyl-4-(3-isopropylphenyl)-2-phenyl-1H-imidazol-5-yl]methyl}-N-(3-ethoxybenzyl)methanamine | 615.35 | 1.29 |
| 271 | 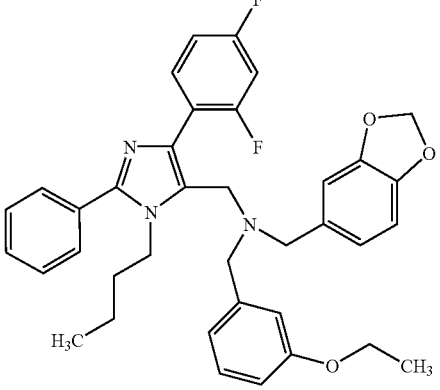 | * | 1-(1,3-benzodioxol-5-yl)-N-{[1-butyl-4-(2,4-difluorophenyl)-2-phenyl-1H-imidazol-5-yl]methyl}-N-(3-ethoxybenzyl)methanamine | 609.28 | 1.25 |

| CMP # | STRUCTURE | Ca²⁺ Mob. | IUPAC Name | MASS | Ret. Time |
|---|---|---|---|---|---|
| 272 | 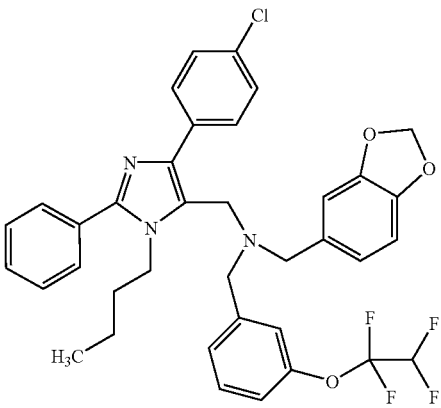 | * | 1-(1,3-benzodioxol-5-yl)-N-{[1-butyl-4-(4-chlorophenyl)-2-phenyl-1H-imidazol-5-yl]methyl}-N-[3-(1,1,2,2-tetrafluoroethoxy)benzyl]methanamine | 679.22 | 1.25 |
| 273 | 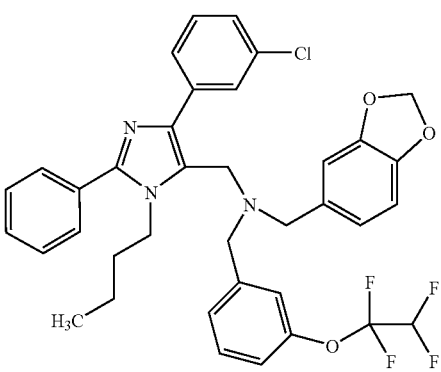 | * | 1-(1,3-benzodioxol-5-yl)-N-{[1-butyl-4-(3-chlorophenyl)-2-phenyl-1H-imidazol-5-yl]methyl}-N-[3-(1,1,2,2-tetrafluoroethoxy)benzyl]methanamine | 679.22 | 1.26 |
| 274 | 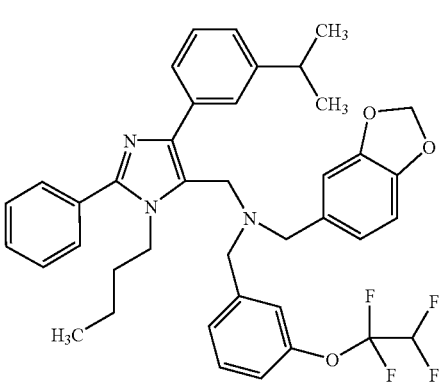 | * | 1-(1,3-benzodioxol-5-yl)-N-{[1-butyl-4-(3-isopropylphenyl)-2-phenyl-1H-imidazol-5-yl]methyl}-N-[3-(1,1,2,2-tetrafluoroethoxy)benzyl]methanamine | 687.31 | 1.26 |

TABLE I-continued

| CMP # | STRUCTURE | Ca²⁺ Mob. | IUPAC Name | MASS | Ret. Time |
|---|---|---|---|---|---|
| 275 | 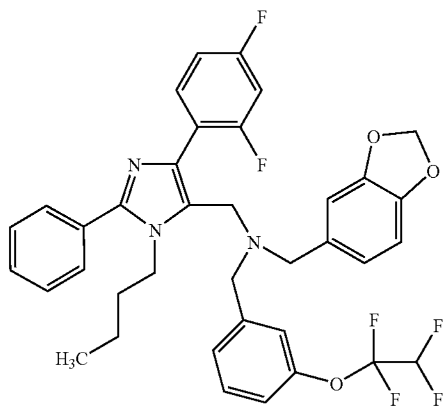 | * | 1-(1,3-benzodioxol-5-yl)-N-{[1-butyl-4-(2,4-difluorophenyl)-2-phenyl-1H-imidazol-5-yl]methyl}-N-[3-(1,1,2,2-tetrafluoroethoxy)benzyl]methanamine | 681.24 | 1.25 |
| 276 | 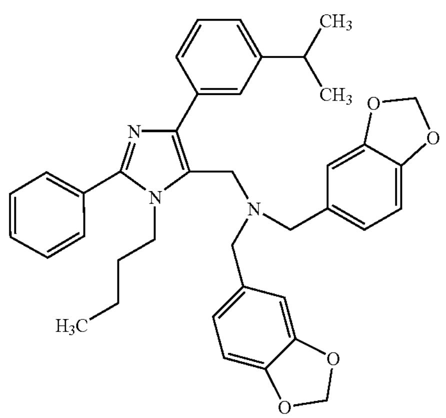 | * | 1-(1,3-benzodioxol-5-yl)-N-(1,3-benzodioxol-5-ylmethyl)-N-{[1-butyl-4-(3-isopropylphenyl)-2-phenyl-1H-imidazol-5-yl]methyl}methanamine | 615.31 | 1.27 |
| 277 | 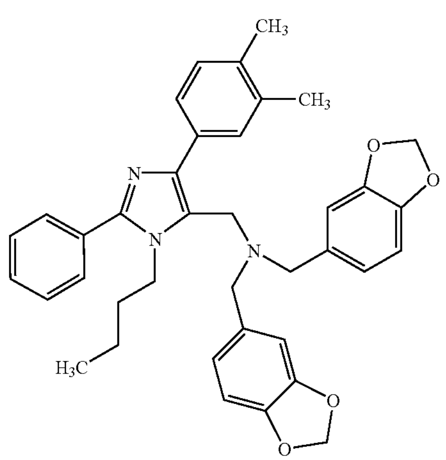 | * | 1-(1,3-benzodioxol-5-yl)-N-(1,3-benzodioxol-5-ylmethyl)-N-{[1-butyl-4-(3,4-dimethylphenyl)-2-phenyl-1H-imidazol-5-yl]methyl}methanamine | | |

TABLE I-continued

| CMP # | STRUCTURE | Ca²⁺ Mob. | IUPAC Name | MASS | Ret. Time |
|---|---|---|---|---|---|
| 278 | 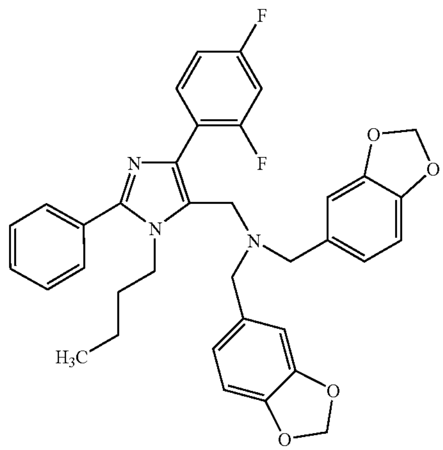 | * | 1-(1,3-benzodioxol-5-yl)-N-(1,3-benzodioxol-5-ylmethyl)-N-{[1-butyl-4-(2,4-difluorophenyl)-2-phenyl-1H-imidazol-5-yl]methyl}methanamine | 609.24 | 1.23 |
| 279 | 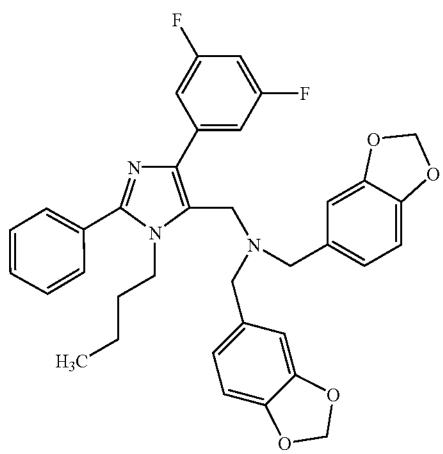 | * | 1-(1,3-benzodioxol-5-yl)-N-(1,3-benzodioxol-5-ylmethyl)-N-{[1-butyl-4-(3,5-difluorophenyl)-2-phenyl-1H-imidazol-5-yl]methyl}methanamine | 609.24 | 1.26 |
| 280 | 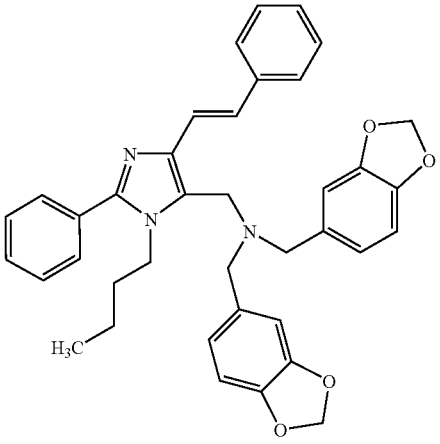 | * | 1-(1,3-benzodioxol-5-yl)-N-(1,3-benzodioxol-5-ylmethyl)-N-({1-butyl-2-phenyl-4-[(E)-2-phenylethenyl]-1H-imidazol-5-yl}methyl)methanamine | 599.28 | 1.23 |

TABLE I-continued

| CMP # | STRUCTURE | Ca²⁺ Mob. | IUPAC Name | MASS | Ret. Time |
|---|---|---|---|---|---|
| 281 | 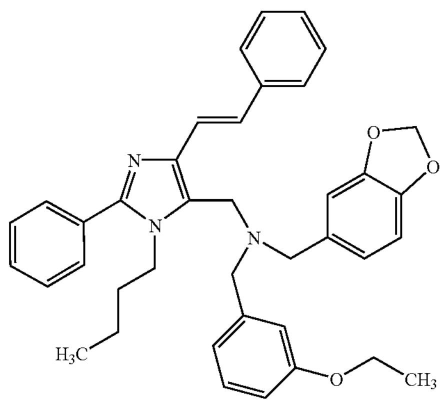 | * | 1-(1,3-benzodioxol-5-yl)-N-({1-butyl-2-phenyl-4-[(E)-2-phenylethenyl]-1H-imidazol-5-yl}methyl)-N-(3-ethoxybenzyl)methanamine | 599.31 | 1.27 |
| 282 | 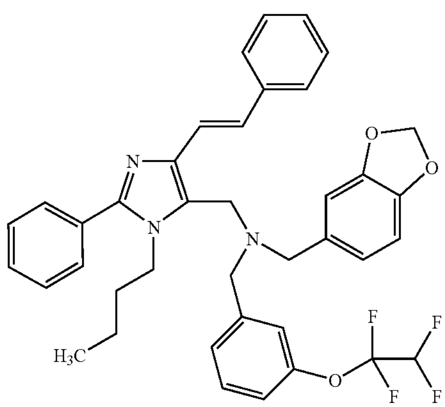 | * | 1-(1,3-benzodioxol-5-yl)-N-({1-butyl-2-phenyl-4-[(E)-2-phenylethenyl]-1H-imidazol-5-yl}methyl)-N-[3-(1,1,2,2-tetrafluoroethoxy)benzyl]methanamine | | |
| 283 | 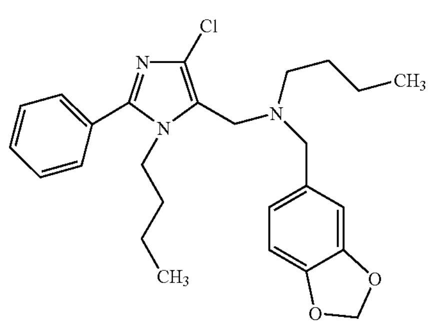 | * | N-(1,3-benzodioxol-5-ylmethyl)-N-[(1-butyl-4-chloro-2-phenyl-1H-imidazol-5-yl)methyl]butan-1-amine | 453.22 | 1.15 |
| 284 | 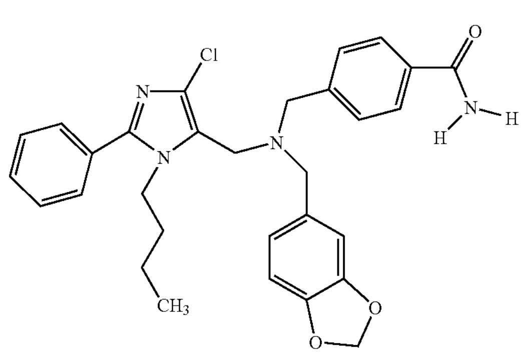 | * | 4-({(1,3-benzodioxol-5-ylmethyl)[(1-butyl-4-chloro-2-phenyl-1H-imidazol-5-yl)methyl]amino}methyl)benzamide | 530.21 | 1.26 |

TABLE I-continued

| CMP # | STRUCTURE | Ca²⁺ Mob. | IUPAC Name | MASS | Ret. Time |
|---|---|---|---|---|---|
| 285 | 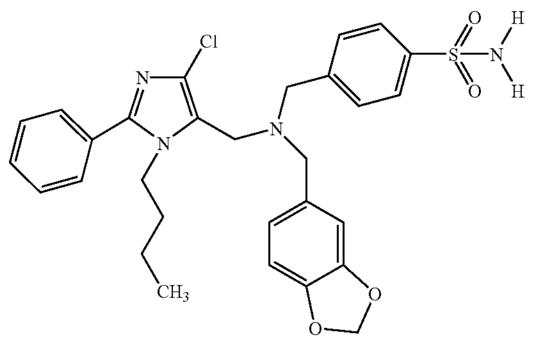 | * | 4-({(1,3-benzodioxol-5-ylmethyl)[(1-butyl-4-chloro-2-phenyl-1H-imidazol-5-yl)methyl]amino}methyl)benzenesulfonamide | 566.18 | 1.24 |
| 286 | 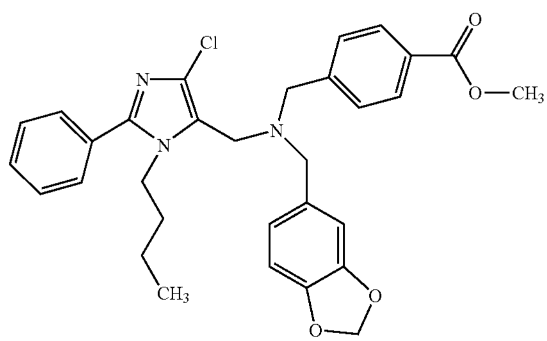 | * | methyl 4-({(1,3-benzodioxol-5-ylmethyl)[(1-butyl-4-chloro-2-phenyl-1H-imidazol-5-yl)methyl]amino}methyl)benzoate | 545.21 | 1.37 |
| 287 | 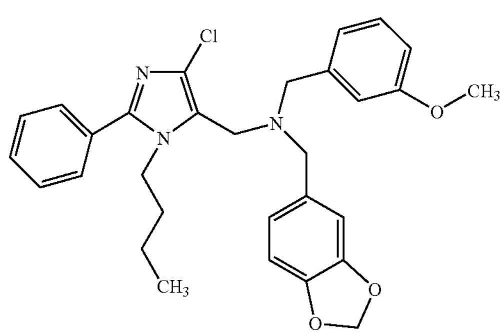 | * | 1-(1,3-benzodioxol-5-yl)-N-[(1-butyl-4-chloro-2-phenyl-1H-imidazol-5-yl)methyl]-N-(3-methoxybenzyl)methanamine | 517.21 | 1.35 |
| 288 | 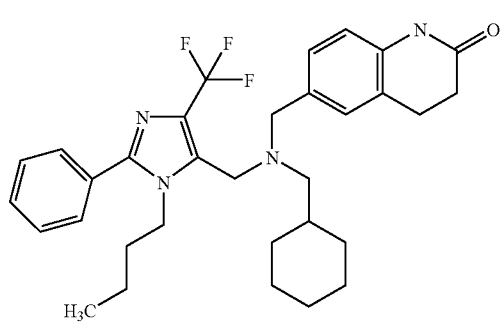 | * | 6-{[{[1-butyl-2-phenyl-4-(trifluoromethyl)-1H-imidazol-5-yl]methyl}(cyclohexylmethyl)amino]methyl}-3,4-dihydroquinolin-2(1H)-one | 552.31 | 1.37 |

TABLE I-continued

| CMP # | STRUCTURE | Ca²⁺ Mob. | IUPAC Name | MASS | Ret. Time |
|---|---|---|---|---|---|
| 289 | 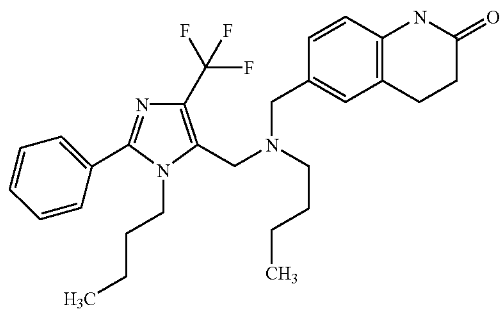 | * | 6-[(butyl{[1-butyl-2-phenyl-4-(trifluoromethyl)-1H-imidazol-5-yl]methyl}amino)methyl]-3,4-dihydroquinolin-2(1H)-one | 512.28 | 1.19 |
| 290 | 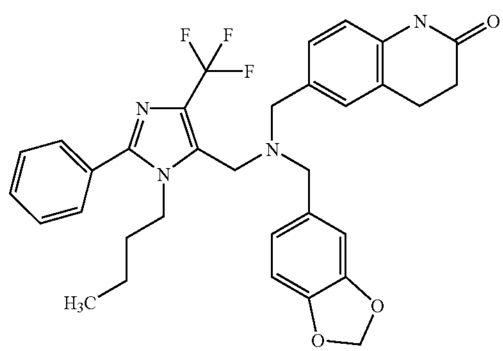 | * | 6-[((1,3-benzodioxol-5-ylmethyl){[1-butyl-2-phenyl-4-(trifluoromethyl)-1H-imidazol-5-yl]methyl}amino)methyl]-3,4-dihydroquinolin-2(1H)-one | 590.25 | 1.3 |
| 291 | 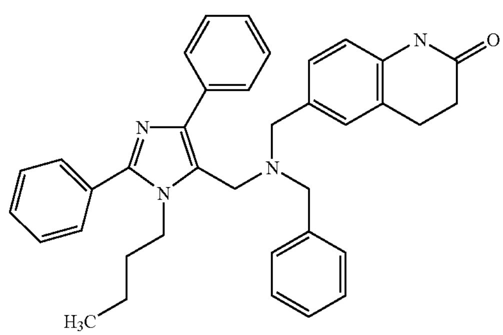 | * | 6-({benzyl[(1-butyl-2,4-diphenyl-1H-imidazol-5-yl)methyl]amino}methyl)-3,4-dihydroquinolin-2(1H)-one | 554.3 | 1.18 |
| 292 | 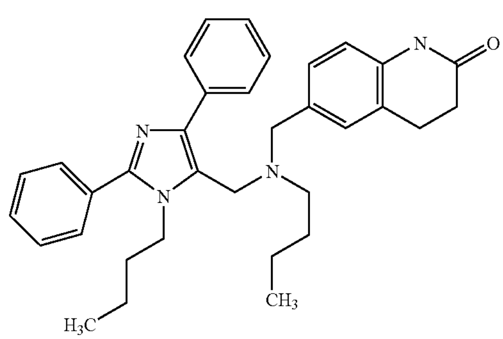 | * | 6-({butyl[(1-butyl-2,4-diphenyl-1H-imidazol-5-yl)methyl]amino}methyl)-3,4-dihydroquinolin-2(1H)-one | 520.32 | 1.13 |

TABLE I-continued

| CMP # | STRUCTURE | Ca²⁺ Mob. | IUPAC Name | MASS | Ret. Time |
|---|---|---|---|---|---|
| 293 | 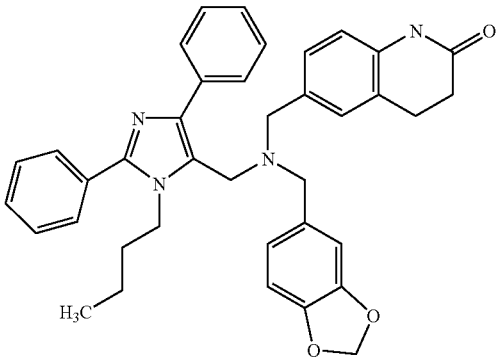 | * | 6-({(1,3-benzodioxol-5-ylmethyl)[(1-butyl-2,4-diphenyl-1H-imidazol-5-yl)methyl]amino}methyl)-3,4-dihydroquinolin-2(1H)-one | 598.29 | 1.17 |
| 294 | 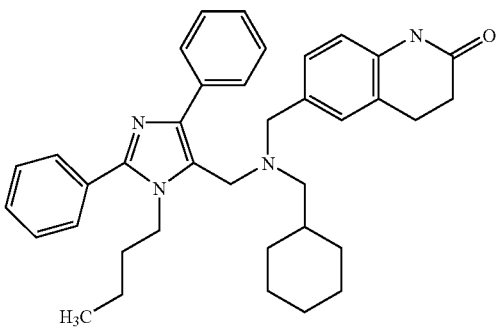 | * | 6-{[[(1-butyl-2,4-diphenyl-1H-imidazol-5-yl)methyl](cyctohexylmethyl)amino]methyl}-3,4-dihydroquinolin-2(1H)-one | 560.35 | 1.23 |
| 295 | 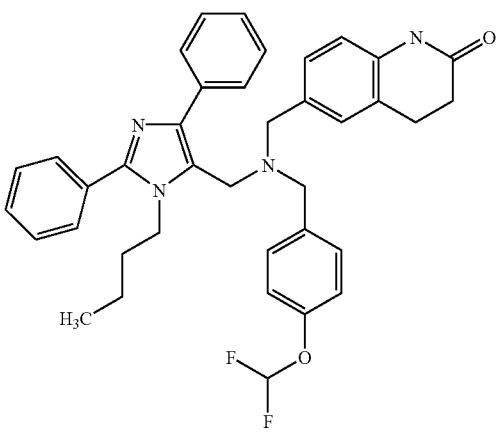 | * | 6-({[(1-butyl-2,4-diphenyl-1H-imidazol-5-yl)methyl][4-(difluoromethoxy)benzyl]amino)methyl)-3,4-dihydroquinolin-2(1H)-one | 620.3 | 1.16 |
| 296 | 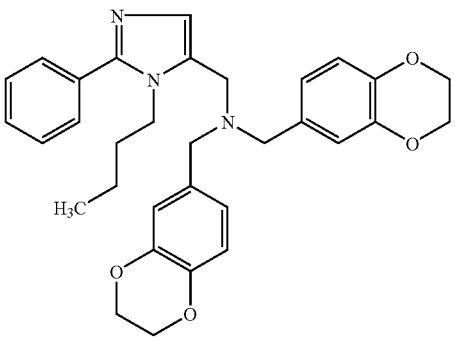 | * | 1-(1-butyl-2-phenyl-1H-imidazol-5-yl)-N,N-bis(2,3-dihydro-1,4-benzodioxin-6-ylmethyl)methanamine | 525.26 | 1.18 |

TABLE I-continued

| CMP # | STRUCTURE | Ca²⁺ Mob. | IUPAC Name | MASS | Ret. Time |
|---|---|---|---|---|---|
| 297 | 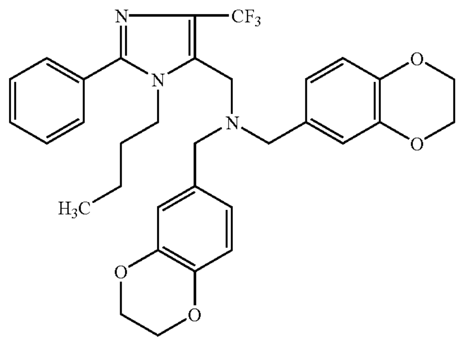 | * | 1-[1-butyl-2-phenyl-4-(trifluoromethyl)-1H-imidazol-5-yl]-N,N-bis(2,3-dihydro-1,4-benzodioxin-6-ylmethyl)methanamine | | |
| 298 | 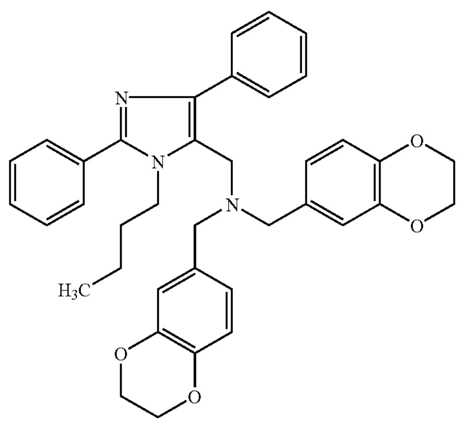 | * | 1-(1-butyl-2,4-diphenyl-1H-imidazol-5-yl)-N,N-bis(2,3-dihydro-1,4-benzodioxin-6-ylmethyl)methanamine | 601.29 | 1.21 |
| 299 | 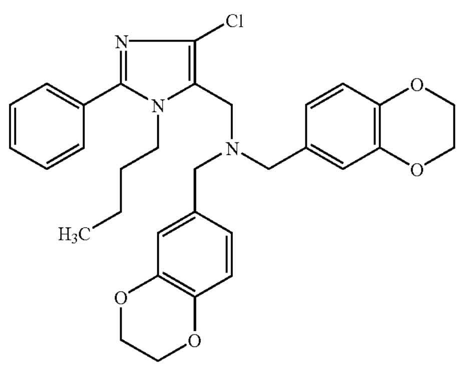 | * | 1-(1,3-benzodioxol-5-yl)-N-[(1-butyl-4-chloro-2-phenyl-1H-imidazol-5-yl)methyl]-N-(2,3-dihydro-1,4-benzodioxin-6-ylmethyl)methanamine | | |
| 300 | 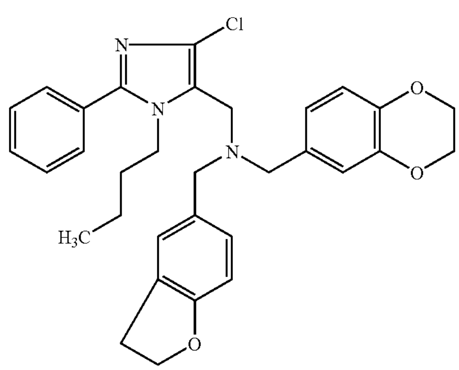 | * | 1-(1,3-benzodioxol-5-yl)-N-[(1-butyl-4-chloro-2-phenyl-1H-imidazol-5-yl)methyl]-N-(2,3-dihydro-1-benzofuran-5-ylmethyl)methanamine | 529.21 | 1.28 |

TABLE I-continued

| CMP # | STRUCTURE | Ca²⁺ Mob. | IUPAC Name | MASS | Ret. Time |
|---|---|---|---|---|---|
| 301 | 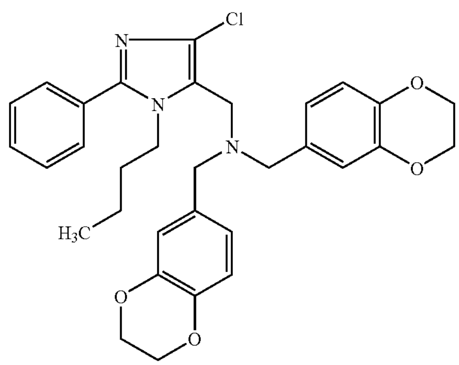 | * | N-[(1-butyl-4-chloro-2-phenyl-1H-imidazol-5-yl)methyl]-N,N-bis(2,3-dihydro-1,4-benzodioxin-6-ylmethyl)amine | 559.22 | 1.28 |
| 302 | 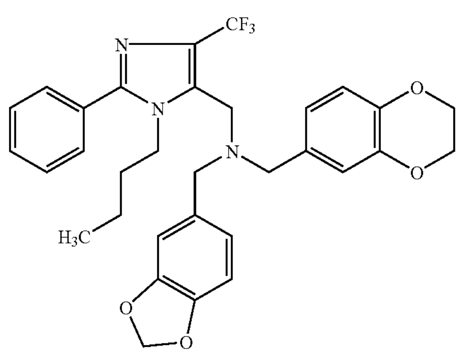 | * | 1-(1,3-benzodioxol-5-yl)-N-{[1-butyl-2-phenyl-4-(trifluoromethyl)-1H-imidazol-5-yl]methyl}-N-(2,3-dihydro-1,4-benzodioxin-6-ylmethyl)methanamine | 579.23 | 1.37 |
| 303 | 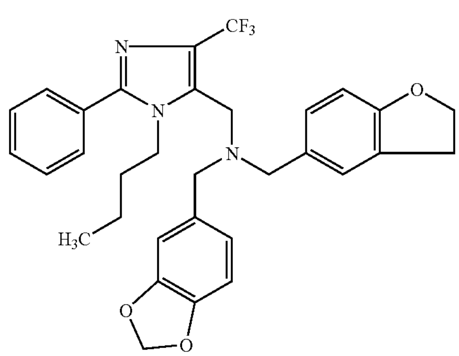 | * | 1-(1,3-benzodioxol-5-yl)-N-{[1-butyl-2-phenyl-4-(trifluoromethyl)-1H-imidazol-5-yl]methyl}-N-(2,3-dihydro-1-benzofuran-5-ylmethyl)methanamine | 563.24 | 1.35 |
| 304 | 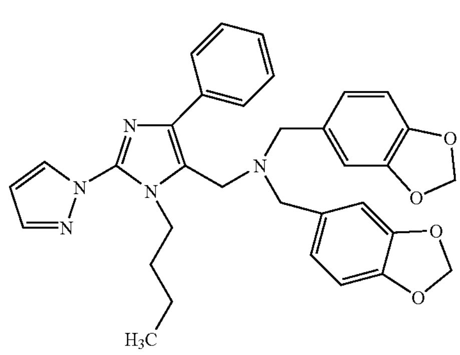 | * | 1-(1,3-benzodioxol-5-yl)-N-(1,3-benzodioxol-5-ylmethyl)-N-{[1-butyl-4-phenyl-2-(1H-pyrazol-1-yl)-1H-imidazol-5-yl]methyl}methanamine | | |

TABLE I-continued

| CMP # | STRUCTURE | Ca²⁺ Mob. | IUPAC Name | MASS | Ret. Time |
|---|---|---|---|---|---|
| 305 | 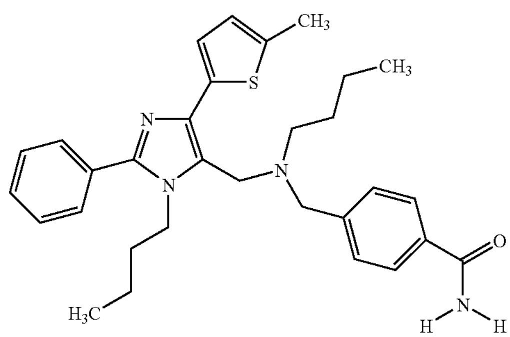 | * | 4-[(butyl{[1-butyl-4-(5-methylthien-2-yl)-2-phenyl-1H-imidazol-5-yl]methyl}amino)methyl]benzamide | 514.28 | 1.17 |
| 306 | 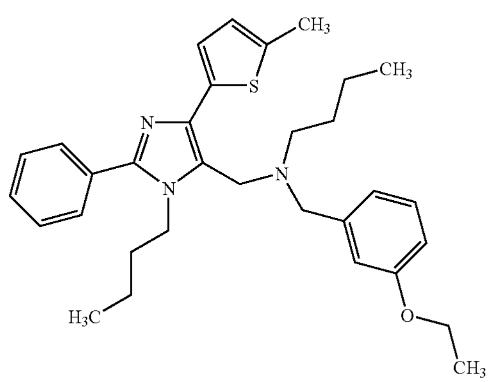 | * | N-{[1-butyl-4-(5-methylthien-2-yl)-2-phenyl-1H-imidazol-5-yl]methyl}-N-(3-ethoxybenzyl)butan-1-amine | 515.3 | 1.25 |
| 307 | 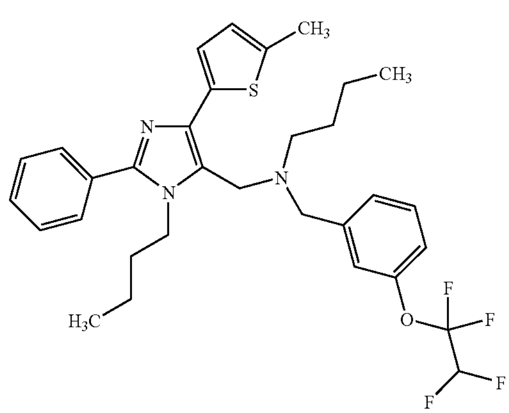 | * | N-{[1-butyl-4-(5-methylthien-2-yl)-2-phenyl-1H-imidazol-5-yl]methyl}-N-[3-(1,1,2,2-tetrafluoroethoxy)benzyl]butan-1-amine | 587.26 | 1.26 |
| 308 | 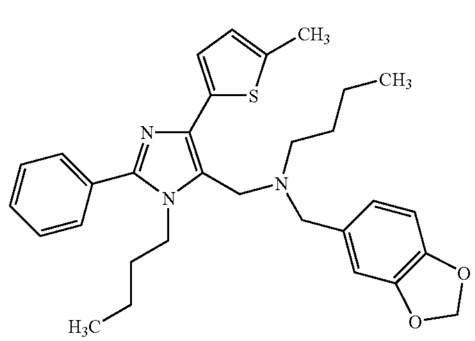 | * | N-(1,3-benzodioxol-5-ylmethyl)-N-{[1-butyl-4-(5-methylthien-2-yl)-2-phenyl-1H-imidazol-5-yl]methyl}butan-1-amine | 515.26 | 1.2 |

TABLE I-continued

| CMP # | STRUCTURE | Ca²⁺ Mob. | IUPAC Name | MASS | Ret. Time |
|---|---|---|---|---|---|
| 309 | 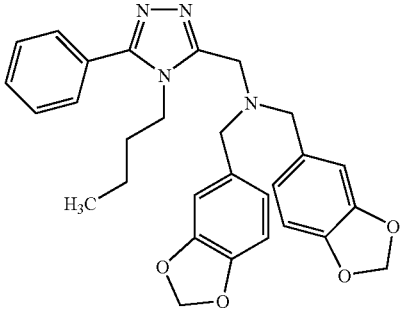 | * | 1-(1,3-benzodioxol-5-yl)-N-(1,3-benzodioxol-5-ylmethyl)-N-[(4-butyl-5-phenyl-4H-1,2,4-triazol-3-yl)methyl]methanamine | 498.23 | 1.23 |
| 310 | 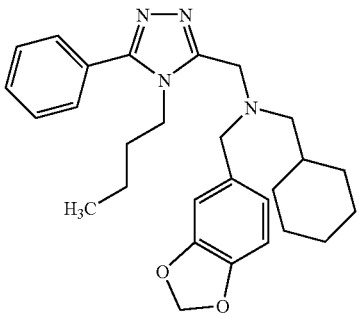 | * | 1-(1,3-benzodioxol-5-yl)-N-[(4-butyl-5-phenyl-4H-1,2,4-triazol-3-yl)methyl]-N-(cyclohexylmethyl)methanamine | 460.28 | 1.28 |
| 311 | 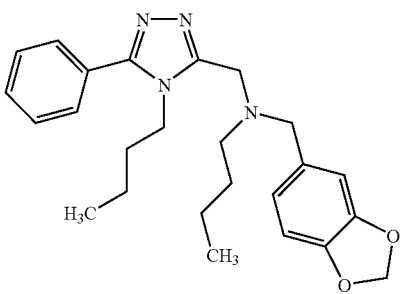 | * | N-(1,3-benzodioxol-5-ylmethyl)-N-[(4-butyl-5-phenyl-4H-1,2,4-triazol-3-yl)methyl]butan-1-amine | 420.25 | 1.14 |
| 312 | 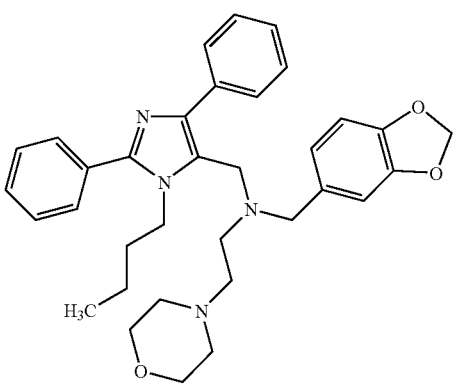 | * | N-(1,3-benzodioxol-5-ylmethyl)-N-[(1-butyl-2,4-diphenyl-1H-imidazol-5-yl)methyl]-2-morpholin-4-ylethanamine | | |

TABLE I-continued

| CMP # | STRUCTURE | Ca²⁺ Mob. | IUPAC Name | MASS | Ret. Time |
|---|---|---|---|---|---|
| 313 | 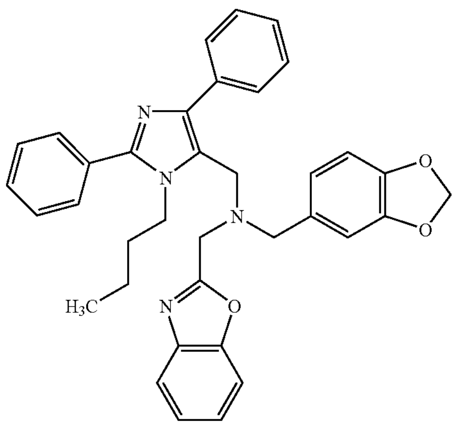 | * | 1-(1,3-benzodioxol-5-yl)-N-(1,3-benzoxazol-2-ylmethyl)-N-[(1-butyl-2,4-diphenyl-1H-imidazol-5-yl)methyl]methanamine | 570.26 | 1.19 |
| 314 | 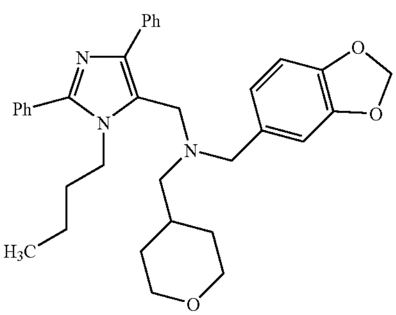 | * | 1-(1,3-benzodioxol-5-yl)-N-[(1-butyl-2,4-diphenyl-1H-imidazol-5-yl)methyl]-N-(tetrahydro-2H-pyran-4-ylmethyl)methanamine | 537.3 | 1.17 |
| 315 | 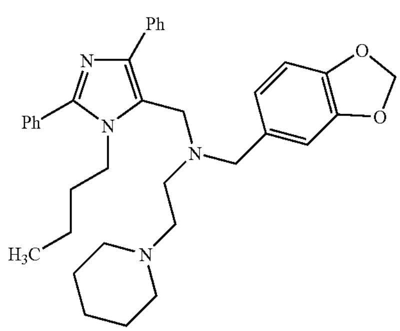 | | N-(1,3-benzodioxol-5-ylmethyl)-N-[(1-butyl-2,4-diphenyl-1H-imidazol-5-yl)methyl]-2-piperidin-1-ylethanamine | 550.33 | 1.06 |
| 316 | 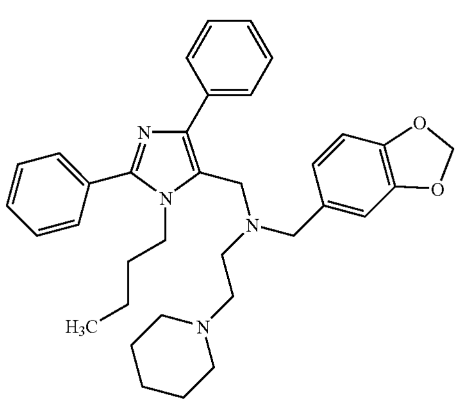 | | N~1~-(1,3-benzodioxol-5-ylmethyl)-N~1~-[(1-butyl-2,4-diphenyl-1H-imidazol-5-yl)methyl]-N~2~,N~2~-diethylethane-1,2-diamine | 538.33 | 1.06 |

TABLE I-continued

| CMP # | STRUCTURE | Ca²⁺ Mob. | IUPAC Name | MASS | Ret. Time |
|---|---|---|---|---|---|
| 317 | 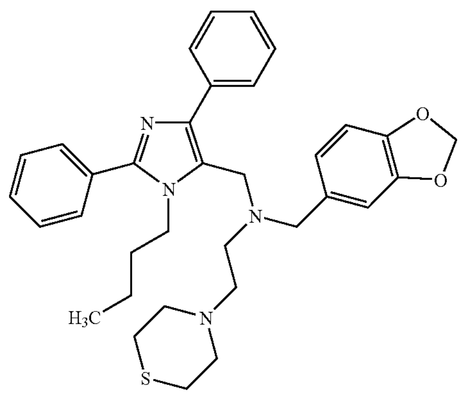 | | N-(1,3-benzodioxol-5-ylmethyl)-N-[(1-butyl-2,4-diphenyl-1H-imidazol-5-yl)methyl]-2-thiomorpholin-4-ylethanamine | | |
| 318 | 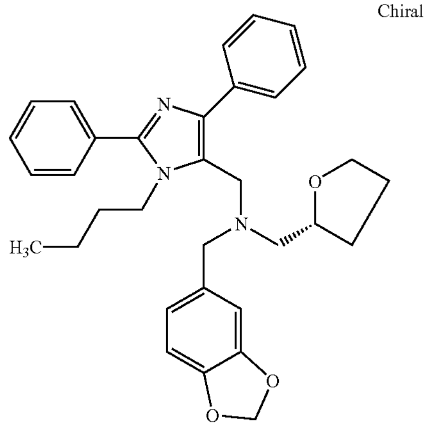 | Chiral | 1-(1,3-benzodioxol-5-yl)-N-[(1-butyl-2,4-diphenyl-1H-imidazol-5-yl)methyl]-N-[(2S)-tetrahydrofuran-2-ylmethyl]methanamine | 523.28 | 1.18 |
| 319 | 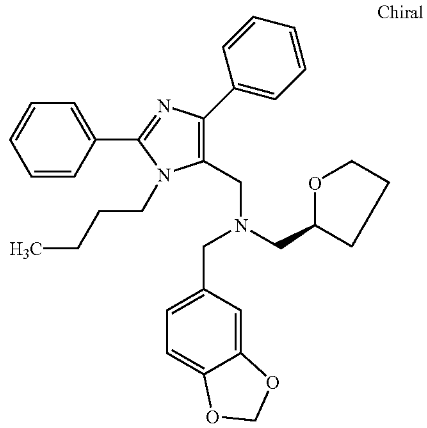 | Chiral | * | 523.28 | 1.18 |

TABLE I-continued

| CMP # | STRUCTURE | Ca²⁺ Mob. | IUPAC Name | MASS | Ret. Time |
|---|---|---|---|---|---|
| 320 | 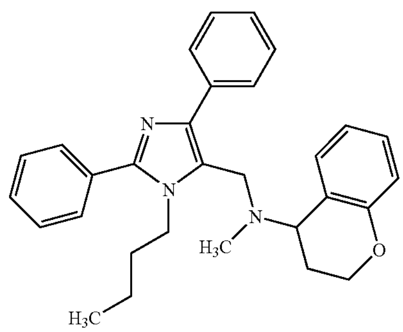 | * | N-[(1-butyl-2,4-diphenyl-1H-imidazol-5-yl)methyl]-N-methylchroman-4-amine | 451.26 | 1.19 |
| 321 | 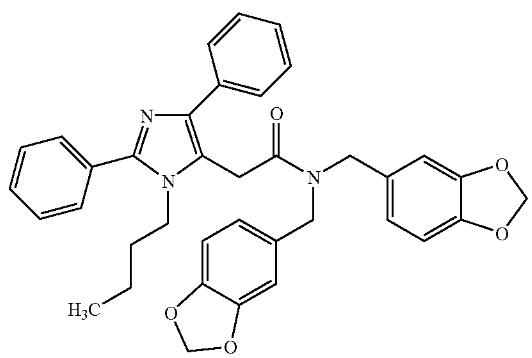 | * | N,N-bis(1,3-benzodioxol-5-ylmethyl)-2-(1-butyl-2,4-diphenyl-1H-imidazol-5-yl)acetamide | 601.26 | 1.17 |
| 322 | 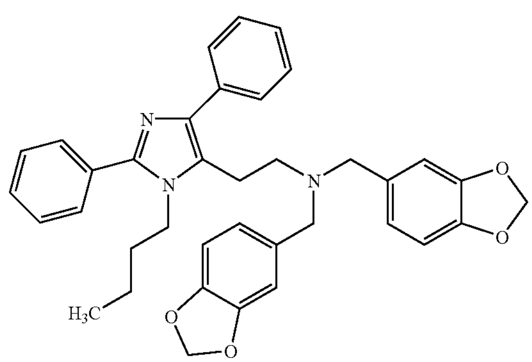 | * | N,N-bis(1,3-benzodioxol-5-ylmethyl)-2-(1-butyl-2,4-diphenyl-1H-imidazol-5-yl)ethanamine | 587.28 | 1.1 |
| 323 | 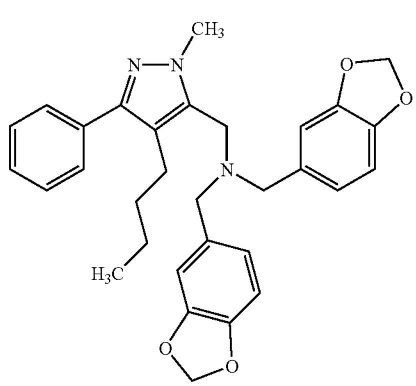 | | 1-(1,3-benzodioxol-5-yl)-N-(1,3-benzodioxol-5-ylmethyl)-N-[(4-butyl-1-methyl-3-phenyl-1H-pyrazol-5-yl)methyl]methanamine | 511.25 | 1.34 |

TABLE I-continued

| CMP # | STRUCTURE | Ca²⁺ Mob. | IUPAC Name | MASS | Ret. Time |
|---|---|---|---|---|---|
| 324 | 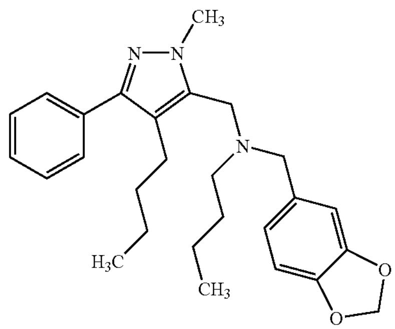 | | N-(1,3-benzodioxol-5-ylmethyl)-N-[(4-butyl-1-methyl-3-phenyl-1H-pyrazol-5-yl)methyl]butan-1-amine | 511.25 | 1.34 |
| 325 | 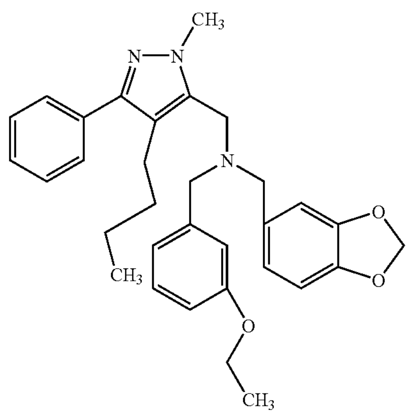 | | 1-(1,3-benzodioxol-5-yl)-N-[(4-butyl-1-methyl-3-phenyl-1H-pyrazol-5-yl)metbyl]-N-(3-ethoxybenzyl)methanamine | 433.27 | 1.18 |
| 326 | 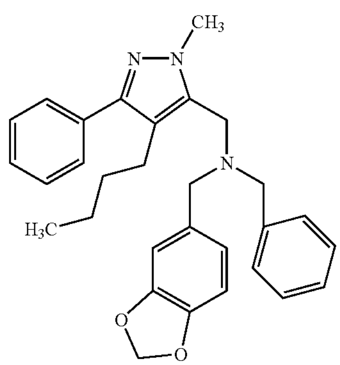 | | 1-(1,3-benzodioxol-5-yl)-N-benzyl-N-[(4-butyl-1-methyl-3-phenyl-1H-pyrazol-5-yl)methyl]methanamine | 511.28 | 1.34 |
| 327 | 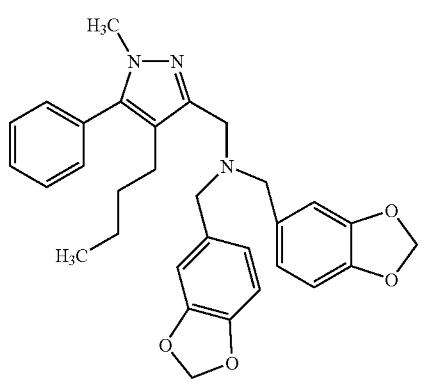 | | 1-(1,3-benzodioxol-5-yl)-N-(1,3-benzodioxol-5-ylmethyl)-N-[(4-butyl-1-methyl-5-phenyl-1H-pyrazol-3-yl)methyl]methanamine | 467.26 | 1.38 |

US 7,186,734 B2
TABLE I-continued
| CMP # | STRUCTURE | Ca²⁺ Mob. | IUPAC Name | MASS | Ret. Time |
|---|---|---|---|---|---|
| 328 | 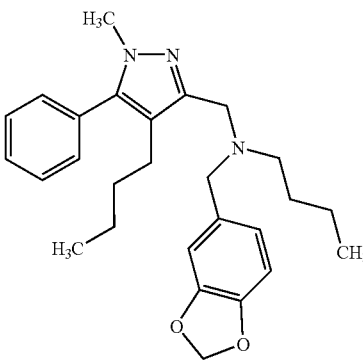 | | N-(1,3-benzodioxol-5-ylmethyl)-N-[(4-butyl-1-methyl-5-phenyl-1H-pyrazol-3-yl)methyl]butan-1-amine | 433.27 | 1.16 |
| 329 | 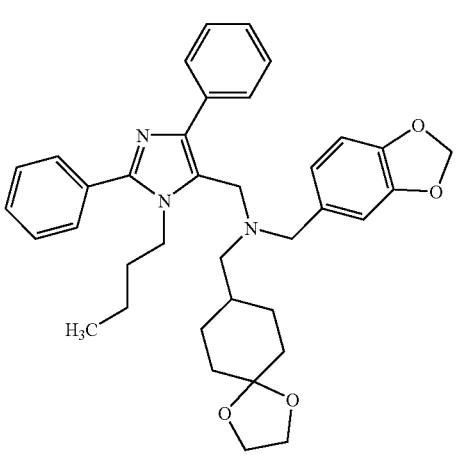 | * | 1-(1,3-benzodioxol-5-yl)-N-[(1-butyl-2,4-diphenyl-1H-imidazol-5-yl)methyl]-N-(1,4-dioxaspiro[4.5]dec-8-ylmethyl)methanamine | | |
| 330 | 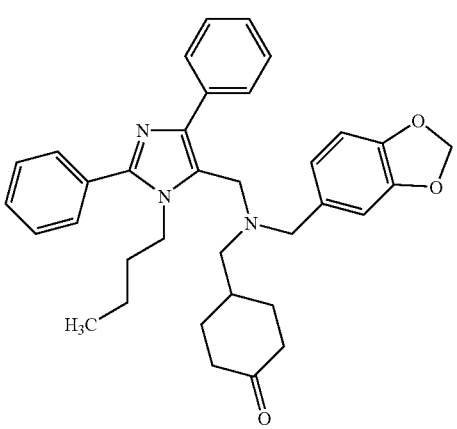 | * | 4-({(1,3-benzodioxol-5-ylmethyl)[(1-butyl-2,4-diphenyl-1H-imidazol-5-yl)methyl]amino}methyl)cyclohexanone | | |

TABLE I-continued

| CMP # | STRUCTURE | Ca²⁺ Mob. | IUPAC Name | MASS | Ret. Time |
|---|---|---|---|---|---|
| 331 | 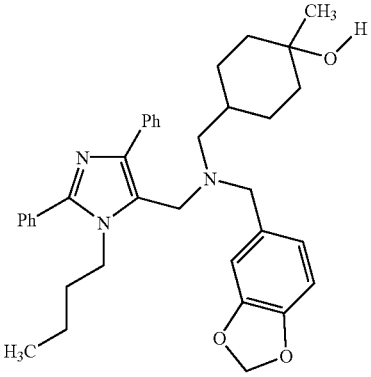 | * | 4-({(1,3-benzodioxol-5-ylmethyl)[(1-butyl-2,4-diphenyl-1H-imidazol-5-yl)methyl]amino}methyl)-1-methylcyclohexanol | | |
| 332 | 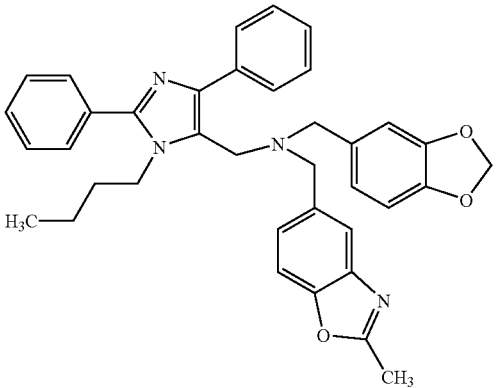 | * | 1-(1,3-benzodioxol-5-yl)-N-[(1-butyl-2,4-diphenyl-1H-imidazol-5-yl)methyl]-N-[(2-methyl-1,3-benzoxazol-5-yl)methyl]methanamine | | |
| 333 | 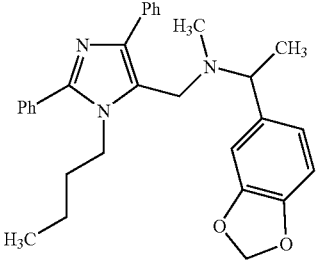 | * | 1-(1,3-benzodioxol-5-yl)-N-[(1-butyl-2,4-diphenyl-1H-imidazol-5-yl)methyl]-N-methylethanamine | | |
| 334 | 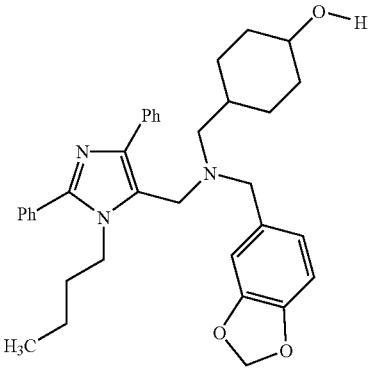 | * | 4-({(1,3-benzodioxol-5-ylmethyl)[(1-butyl-2,4-diphenyl-1H-imidazol-5-yl)methyl]amino}methyl)cyclohexanol | | |

TABLE I-continued

| CMP # | STRUCTURE | Ca²⁺ Mob. | IUPAC Name | MASS | Ret. Time |
|---|---|---|---|---|---|
| 335 | 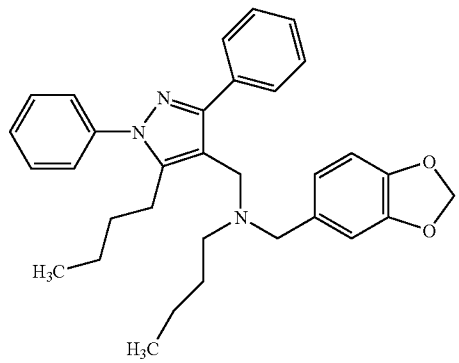 | * | N-(1,3-benzodioxol-5-ylmethyl)-N-[(5-butyl-1,3-diphenyl-1H-pyrazol-4-yl)methyl]butan-1-amine | 495.29 | 1.15 |
| 336 | 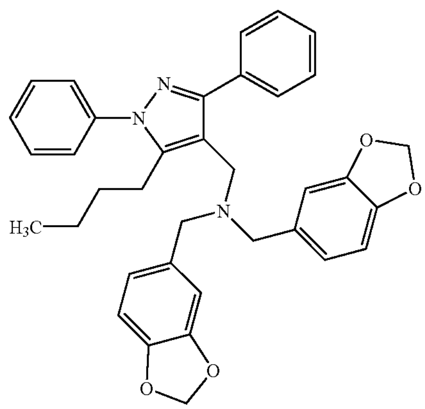 | * | 1-(1,3-benzodioxol-5-yl)-N-(1,3-benzodioxol-5-ylmethyl)-N-[(5-butyl-1,3-diphenyl-1H-pyrazol-4-yl)methyl]methanamine | 573.26 | 1.19 |
| 337 | 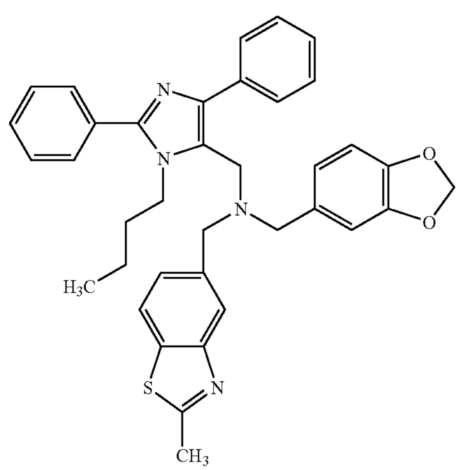 | * | 1-(1,3-benzodioxol-5-yl)-N-[(1-butyl-2,4-diphenyl-1H-imidazol-5-yl)methyl]-N-[(2-methyl-1,3-benzothiazol-5-yl)methyl]methanamine | 600.26 | 1.22 |

TABLE I-continued

| CMP # | STRUCTURE | Ca²⁺ Mob. | IUPAC Name | MASS | Ret. Time |
|---|---|---|---|---|---|
| 338 | 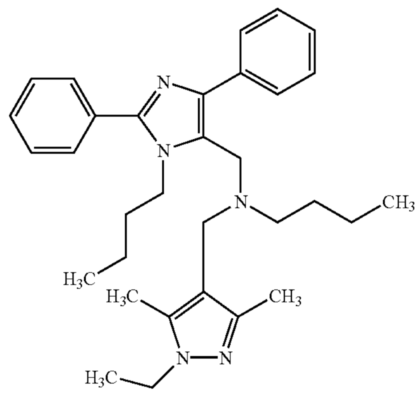 | * | N-[(1-butyl-2,4-diphenyl-1H-imidazol-5-yl)methyl]-N-[(1-ethyl-3,5-dimethyl-1H-pyrazol-4-yl)methyl]butan-1-amine | | |
| 339 | 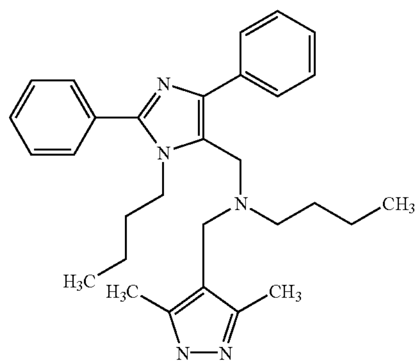 | * | N-[(1-butyl-2,4-diphenyl-1H-imidazol-5-yl)methyl]-N-[(3,5-dimethyl-1H-pyrazol-4-yl)methyl]butan-1-amine | | |
| 340 | 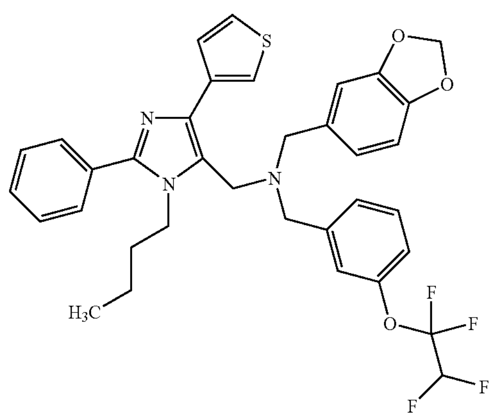 | * | 1-(1,3-benzodioxol-5-yl)-N-[(1-butyl-2-phenyl-4-thien-3-yl-1H-imidazol-5-yl)methyl]-N-[3-(1,1,2,2-tetrafluoroethoxy)benzyl]methanamine | 651.22 | 1.22 |
| 341 | 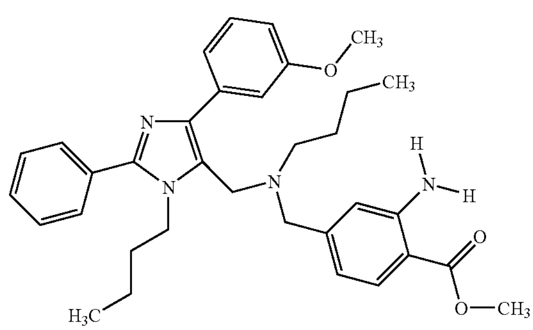 | * | methyl 2-amino-4-[(butyl{[1-butyl-4-(3-methoxyphenyl)-2-phenyl-1H-imidazol-5-yl]methyl}amino)methyl]benzoate | 554.33 | 1.2 |

TABLE I-continued

| CMP # | STRUCTURE | Ca²⁺ Mob. | IUPAC Name | MASS | Ret. Time |
|---|---|---|---|---|---|
| 342 | 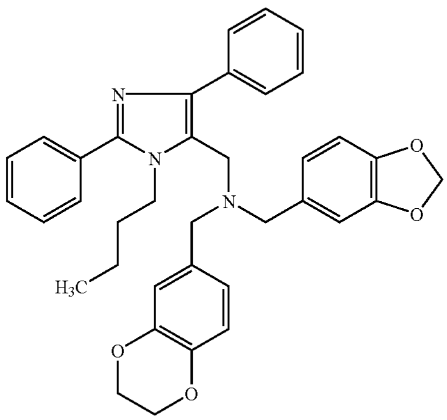 | * | 1-(1,3-benzodioxol-5-yl)-N-[(1-butyl-2,4-diphenyl-1H-imidazol-5-yl)methyl]-N-(2,3-dihydro-1,4-benzodioxin-6-ylmethyl)methanamine | 587.28 | 1.21 |
| 343 | 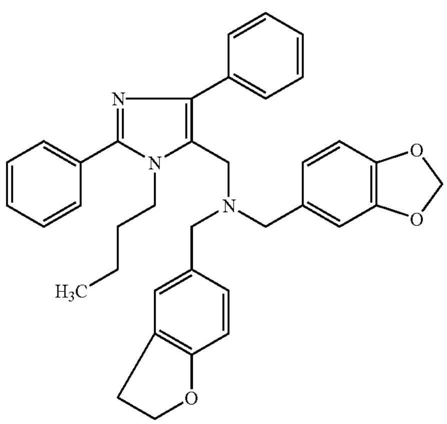 | * | 1-(1,3-benzodioxol-5-yl)-N-[(1-butyl-2,4-diphenyl-1H-imidazol-5-yl)methyl]-N-(2,3-dihydro-1-benzofuran-5-ylmethyl)methanamine | 571.28 | 1.22 |
| 344 | 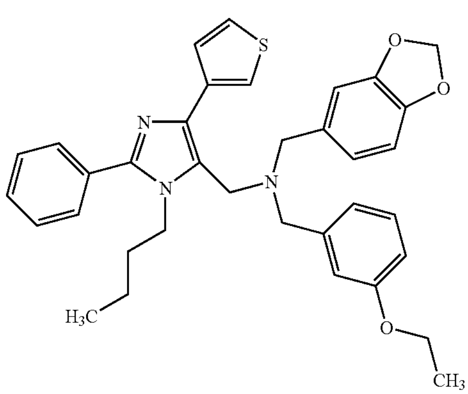 | * | 1-(1,3-benzodioxol-5-yl)-N-[(1-butyl-2-phenyl-4-thien-3-yl-1H-imidazol-5-yl)methyl]-N-(3-ethoxybenzyl)methanamine | 579.26 | 1.23 |

TABLE I-continued

| CMP # | STRUCTURE | Ca²⁺ Mob. | IUPAC Name | MASS | Ret. Time |
|---|---|---|---|---|---|
| 345 | 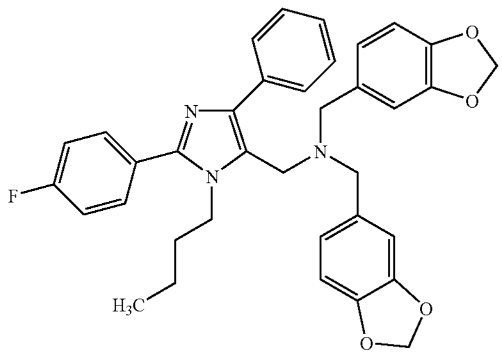 | * | 1-(1,3-benzodioxol-5-yl)-N-(1,3-benzodioxol-5-ylmethyl)-N-{[1-butyl-2-(4-fluorophenyl)-4-phenyl-1H-imidazol-5-yl]methyl}methanamine | | |
| 346 | 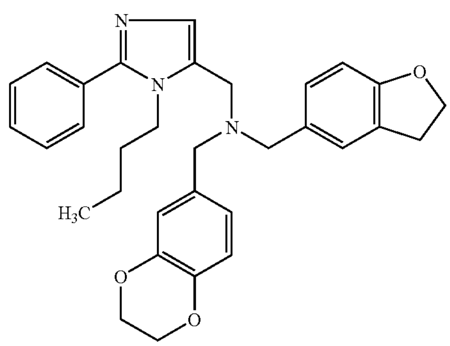 | * | 1-(1-butyl-2-phenyl-1H-imidazol-5-yl)-N-(2,3-dihydro-1,4-benzodioxin-6-ylmethyl)-N-(2,3-dihydro-1-benzofuran-5-ylmethyl)methanamine | 509.27 | 1.16 |
| 347 | 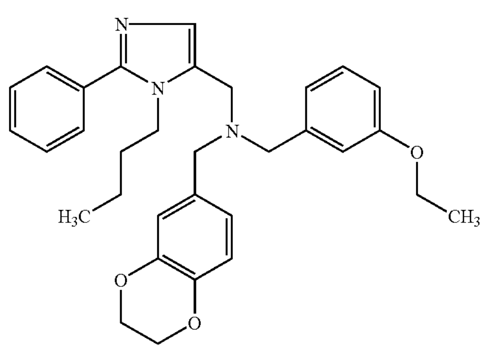 | * | 1-(1-butyl-2-phenyl-1H-imidazol-5-yl)-N-(2,3-dihydro-1,4-benzodioxin-6-ylmethyl)-N-(3-ethoxybenzyl)methanamine | 511.28 | 1.2 |
| 348 | 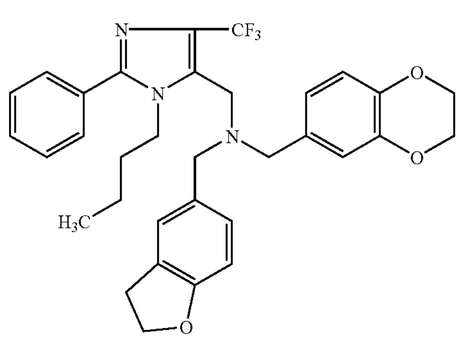 | * | 1-[1-butyl-2-phenyl-4-(trifluoromethyl)-1H-imidazol-5-yl]-N-(2,3-dihydro-1,4-benzodioxin-6-ylmethyl)-N-(2,3-dihydro-1-benzofuran-5-ylmethyl)methanamine | 577.26 | 1.36 |

TABLE I-continued

| CMP # | STRUCTURE | Ca²⁺ Mob. | IUPAC Name | MASS | Ret. Time |
|---|---|---|---|---|---|
| 349 | 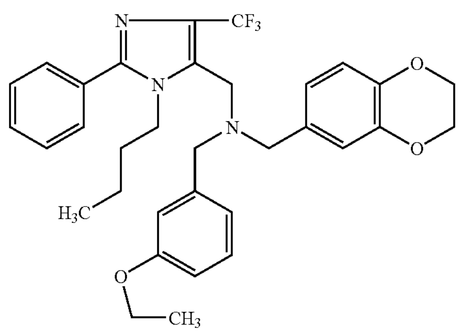 | * | 1-[1-butyl-2-phenyl-4-(trifluoromethyl)-1H-imidazol-5-yl]-N-(2,3-dihydro-1,4-benzodioxin-6-ylmethyl)-N-(3-ethoxybenzyl)methanamine | 579.27 | 1.4 |
| 350 | 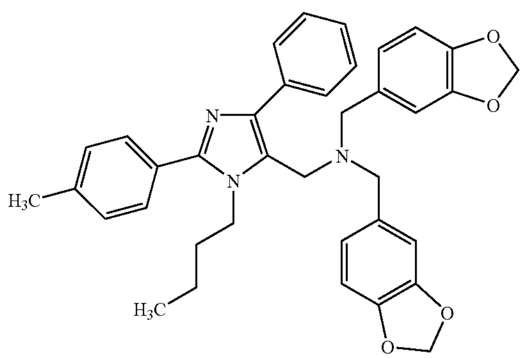 | * | 1-(1,3-benzodioxol-5-yl)-N-(1,3-benzodioxol-5-ylmethyl)-N-{[1-butyl-2-(4-methylphenyl)-4-phenyl-1H-imidazol-5-yl]methyl}methanamine | 587.28 | 1.24 |
| 351 | 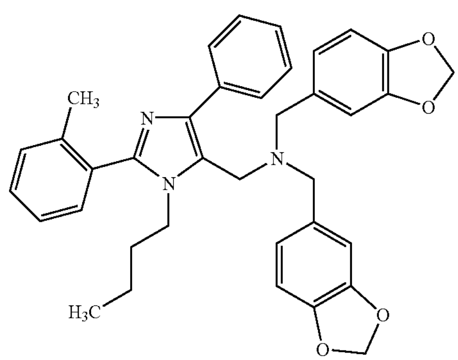 | * | 1-(1,3-benzodioxol-5-yl)-N-(1,3-benzodioxol-5-ylmethyl)-N-{[1-butyl-2-(2-methylphenyl)-4-phenyl-1H-imidazol-5-yl]methyl}methanamine | 587.28 | 1.23 |
| 352 | 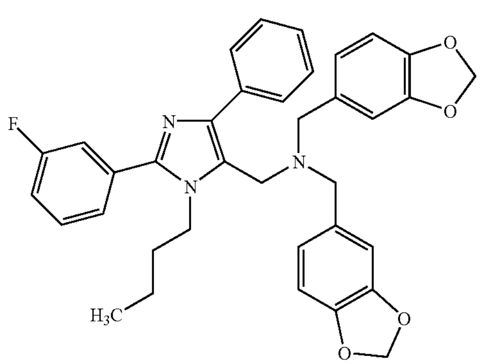 | * | 1-(1,3-benzodioxol-5-yl)-N-(1,3-benzodioxol-5-ylmethyl)-N-{[1-butyl-2-(3-fluorophenyl)-4-phenyl-1H-imidazol-5-yl]methyl}methanamine | 591.25 | 1.22 |

TABLE I-continued

| CMP # | STRUCTURE | Ca²⁺ Mob. | IUPAC Name | MASS | Ret. Time |
|---|---|---|---|---|---|
| 353 | 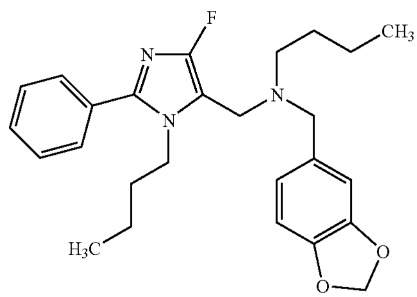 | * | N-(1,3-benzodioxol-5-ylmethyl)-N-[(1-butyl-4-fluoro-2-phenyl-1H-imidazol-5-yl)methyl]butan-1-amine | | |
| 354 | 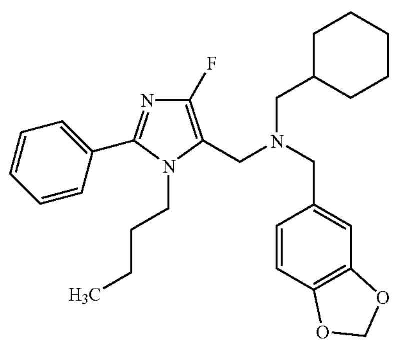 | * | 1-(1,3-benzodioxol-5-yl)-N-[(1-butyl-4-fluoro-2-phenyl-1H-imidazol-5-yl)methyl]-N-(cyclohexylmethyl)methanamine | | |
| 355 | 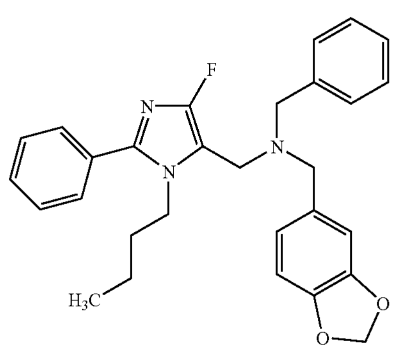 | * | 1-(1,3-benzodioxol-5-yl)-N-benzyl-N-[(1-butyl-4-fluoro-2-phenyl-1H-imidazol-5-yl)methyl]methanamine | | |
| 356 | 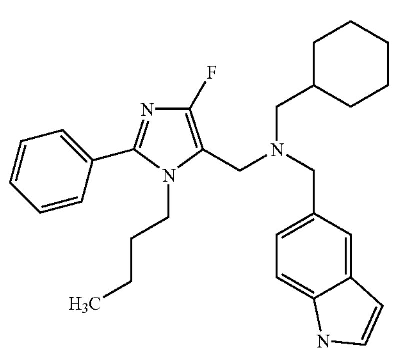 | * | N-[(1-butyl-4-fluoro-2-phenyl-1H-imidazol-5-yl)methyl]-N-(cyclohexylmethyl)-N-(1H-indol-5-ylmethyl)amine | 472.3 | 1.16 |

TABLE I-continued

| CMP # | STRUCTURE | Ca²⁺ Mob. | IUPAC Name | MASS | Ret. Time |
|---|---|---|---|---|---|
| 357 | 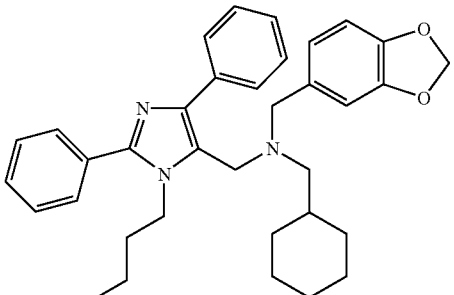 | * | 1-(1,3-benzodioxol-5-yl)-N-[(1-butyl-2,4-diphenyl-1H-imidazol-5-yl)methyl]-N-(cyclohexylmethyl)methanamine | 535.32 | 1.26 |
| 358 | 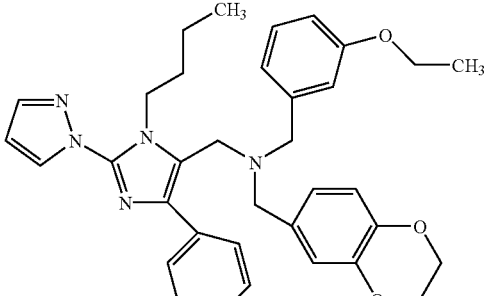 | * | N-{(1-butyl-4-phenyl-2-(1H-pyrazol-1-yl)-1H-imidazol-5-yl]methyl}-N-(2,3-dihydro-1,4-benzodioxin-6-ylmethyl)-N-(3-ethoxybenzyl)amine | | |
| 359 | 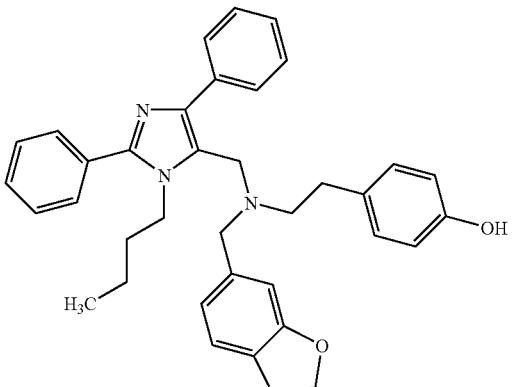 | * | 4-(2-{(1,3-benzodioxol-5-ylmethyl)[(1-butyl-2,4-diphenyl-1H-imidazol-5-yl)methyl]amino}ethyl)phenol | 559.28 | 1.18 |
| 360 | 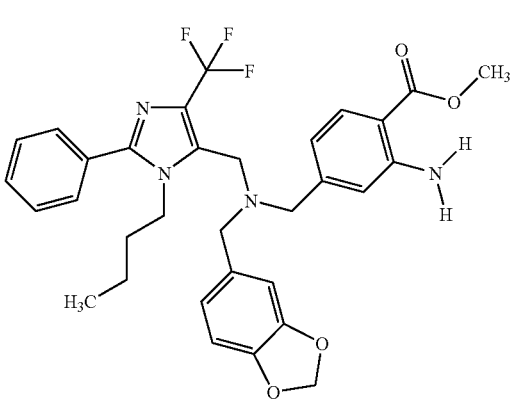 | * | methyl 2-amino-4-[((1,3-benzodioxol-5-ylmethyl){[1-butyl-2-phenyl-4-(trifluoromethyl)-1H-imidazol-5-yl]methyl}amino)methyl]benzoate | 594.25 | 1.34 |

TABLE I-continued

| CMP # | STRUCTURE | Ca²⁺ Mob. | IUPAC Name | MASS | Ret. Time |
|---|---|---|---|---|---|
| 361 | 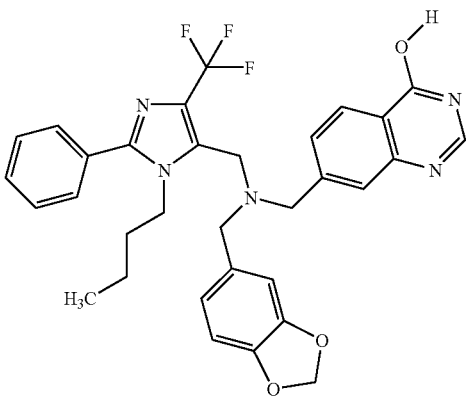 | * | 7-[((1,3-benzodioxol-5-ylmethyl){[1-butyl-2-phenyl-4-(trifluoromethyl)-1H-imidazol-5-yl]methyl}amino)methyl]quinazolin-4-ol | 589.23 | 1.27 |
| 362 | 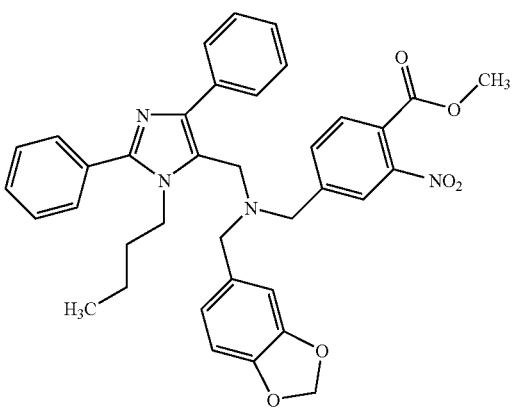 | * | methyl 4-({(1,3-benzodioxol-5-ylmethyl)[(1-butyl-2,4-diphenyl-1H-imidazol-5-yl)methyl]amino}methyl)-2-nitrobenzoate | 632.26 | 1.18 |
| 363 | 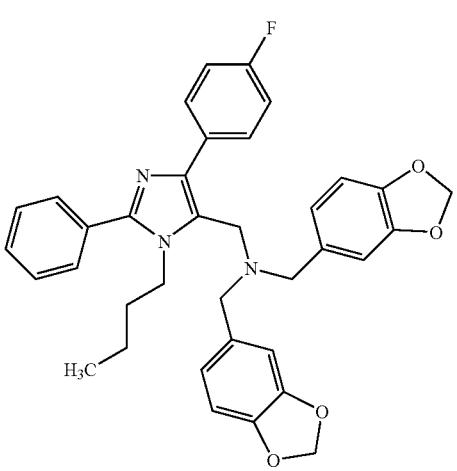 | * | 1-(1,3-benzodioxol-5-yl)-N-(1,3-benzodioxol-5-ylmethyl)-N-{[1-butyl-4-(4-fluorophenyl)-2-phenyl-1H-imidazol-5-yl]methyl}methanamine | 591.25 | 1.22 |

TABLE I-continued
| CMP # | STRUCTURE | Ca²⁺ Mob. | IUPAC Name | MASS | Ret. Time |
|---|---|---|---|---|---|
| 364 | 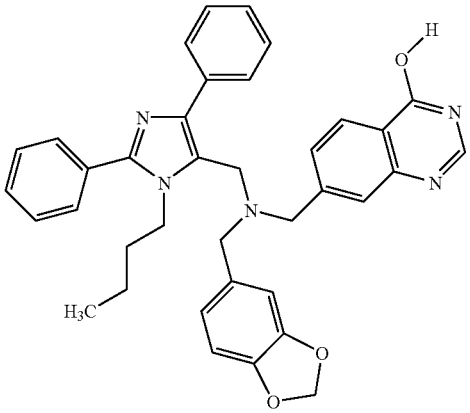 | * | 7-({(1,3-benzodioxol-5-ylmethyl)[(1-butyl-2,4-diphenyl-1H-imidazol-5-yl)methyl]amino}methyl)quinazolin-4-ol | 597.27 | 1.15 |
| 365 | 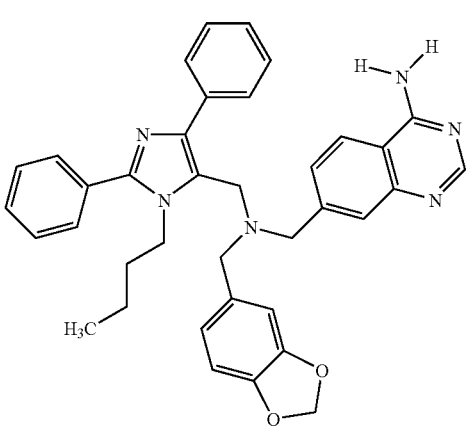 | * | 7-({(1,3-benzodioxol-5-ylmethyl)[(1-butyl-2,4-diphenyl-1H-imidazol-5-yl)methyl]amino}methyl)quinazolin-4-amine | 596.29 | 1.08 |
| 366 | 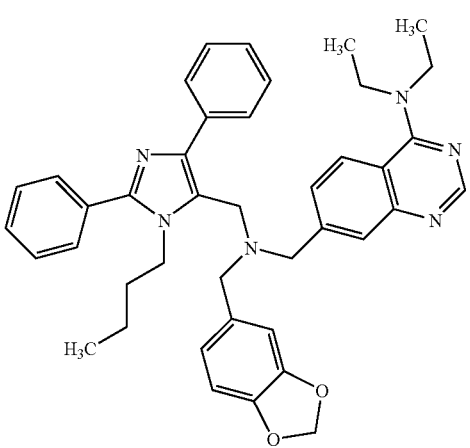 | * | 7-({(1,3-benzodioxol-5-ylmethyl)[(1-butyl-2,4-diphenyl-1H-imidazol-5-yl)methyl]amino}methyl)-N,N-diethylquinazolin-4-amine | | |

TABLE I-continued

| CMP # | STRUCTURE | Ca²⁺ Mob. | IUPAC Name | MASS | Ret. Time |
|---|---|---|---|---|---|
| 367 | 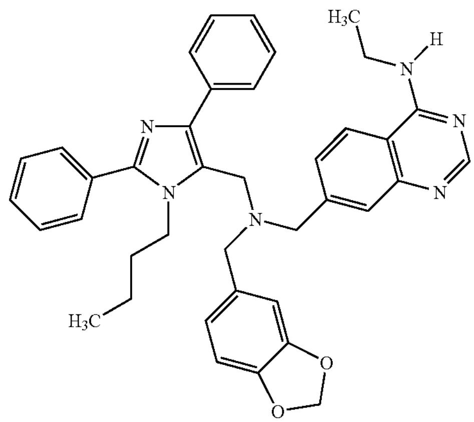 | * | 7-({(1,3-benzodioxol-5-ylmethyl)[(1-butyl-2,4-diphenyl-1H-imidazol-5-yl)methyl]amino}methyl)-N-ethylquinazolin-4-amine | 624.32 | 1.1 |
| 368 | 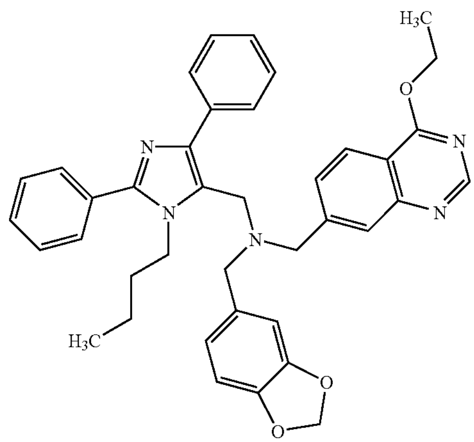 | * | 1-(1,3-benzodioxol-5-yl)-N-[(1-butyl-2,4-diphenyl-1H-imidazol-5-yl)methyl]-N-[(4-ethoxyquinazolin-7-yl)methyl]methanamine | 625.31 | 1.22 |
| 369 | 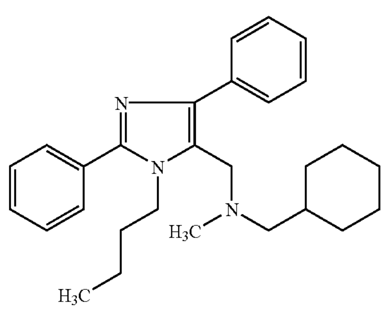 | * | 1-(1-butyl-2,4-diphenyl-1H-imidazol-5-yl)-N-(cyclohexylmethyl)-N-methylmethanamine | | |
| 370 | 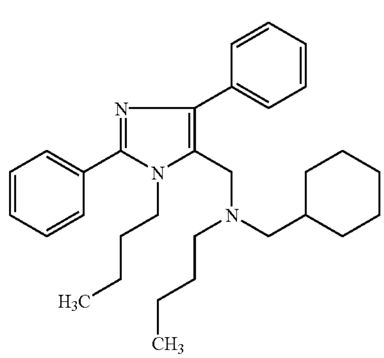 | * | N-[(1-butyl-2,4-diphenyl-1H-imidazol-5-yl)methyl]-N-(cyclohexylmethyl)butan-1-amine | | |

TABLE I-continued

| CMP # | STRUCTURE | Ca²⁺ Mob. | IUPAC Name | MASS | Ret. Time |
|---|---|---|---|---|---|
| 371 | 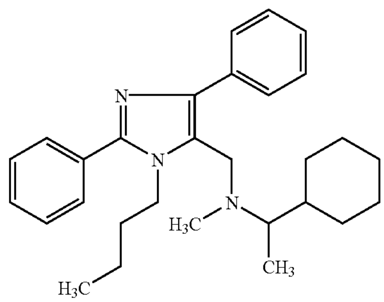 | * | N-[(1-butyl-2,4-diphenyl-1H-imidazol-5-yl)methyl]-1-cyclohexyl-N-methylethanamine | | |
| 372 | 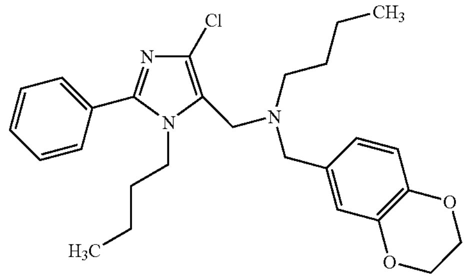 | * | N-[(1-butyl-4-chloro-2-phenyl-1H-imidazol-5-yl)methyl]-N-(2,3-dihydro-1,4-benzodioxin-6-ylmethyl)butan-1-amine | | |
| 373 | 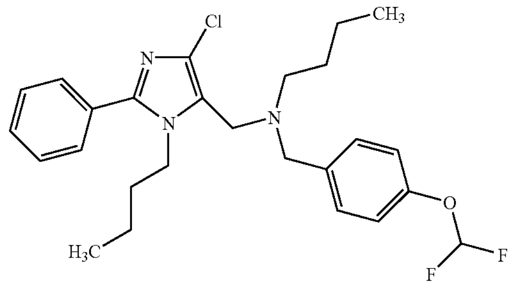 | * | N-[(1-butyl-4-chloro-2-phenyl-1H-imidazol-5-yl)methyl]-N-[4-(difluoromethoxy)benzyl]butan-1-amine | | |
| 374 | 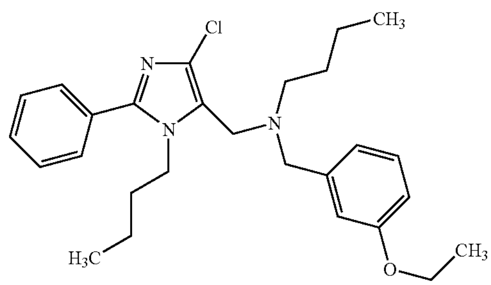 | * | N-[(1-butyl-4-chloro-2-phenyl-1H-imidazol-5-yl)methyl]-N-(3-ethoxybenzyl)butan-1-amine | | |
| 375 | 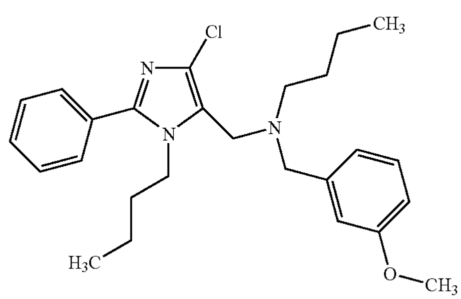 | * | N-[(1-butyl-4-chloro-2-phenyl-1H-imidazol-5-yl)methyl]-N-(3-methoxybenzyl)butan-1-amine | | |

TABLE I-continued

| CMP # | STRUCTURE | Ca²⁺ Mob. | IUPAC Name | MASS | Ret. Time |
|---|---|---|---|---|---|
| 376 | 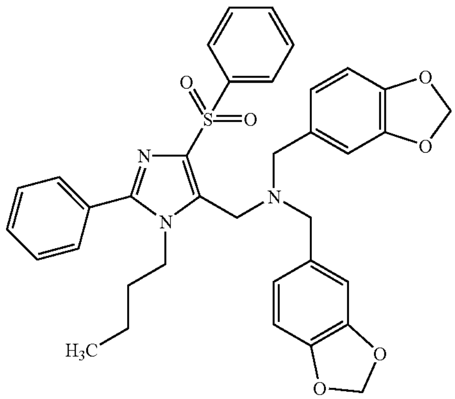 | * | 1-(1,3-benzodioxol-5-yl)-N-(1,3-benzodioxol-5-ylmethyl)-N-{[1-butyl-2-phenyl-4-(phenylsulfonyl)-1H-imidazol-5-yl]methyl}methanamine | 637.22 | 1.31 |
| 377 | 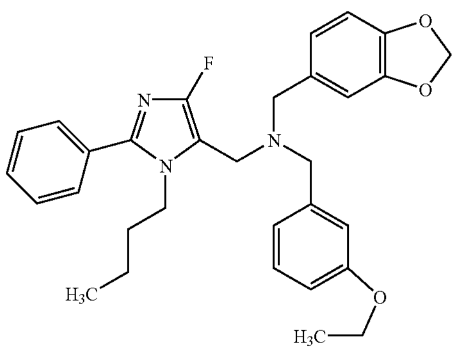 | * | 1-(1,3-benzodioxol-5-yl)-N-[(1-butyl-4-fluoro-2-phenyl-1H-imidazol-5-yl)methyl]-N-(3-ethoxybenzyl)methanamine | 515.26 | 1.29 |
| 378 | 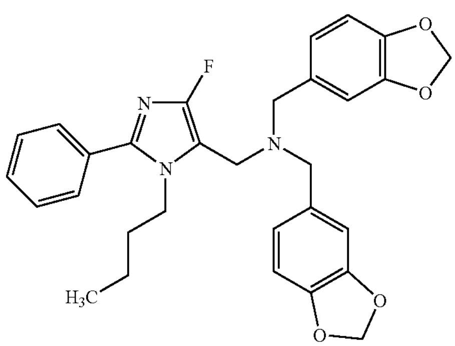 | * | 1-(1,3-benzodioxol-5-yl)-N-(1,3-benzodioxol-5-ylmethyl)-N-[(1-butyl-4-fluoro-2-phenyl-1H-imidazol-5-yl)methyl]methanamine | 515.22 | 1.23 |
| 379 | 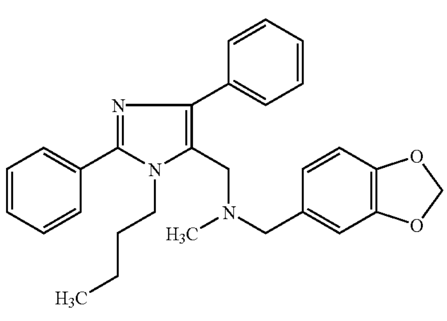 | * | 1-(1,3-benzodioxol-5-yl)-N-[(1-butyl-2,4-diphenyl-1H-imidazol-5-yl)methyl]-N-methylmethanamine | 453.24 | 1.11 |

TABLE I-continued

| CMP # | STRUCTURE | Ca²⁺ Mob. | IUPAC Name | MASS | Ret. Time |
|---|---|---|---|---|---|
| 380 | 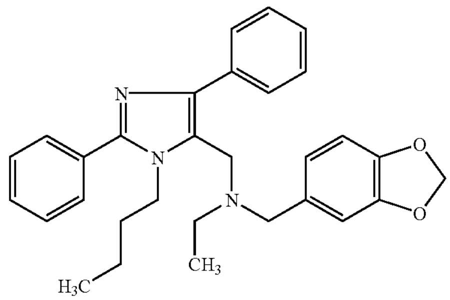 | * | N-(1,3-benzodioxol-5-ylmethyl)-N-[(1-butyl-2,4-diphenyl-1H-imidazol-5-yl)methyl]ethanamine | 467.26 | 1.12 |
| 381 | 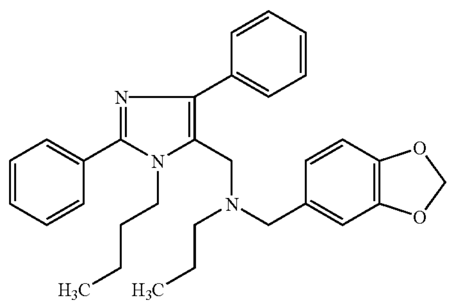 | * | N-(1,3-benzodioxol-5-ylmethyl)-N-[(1-butyl-2,4-diphenyl-1H-imidazol-5-yl)methyl]propan-1-amine | 481.27 | 1.16 |
| 382 | 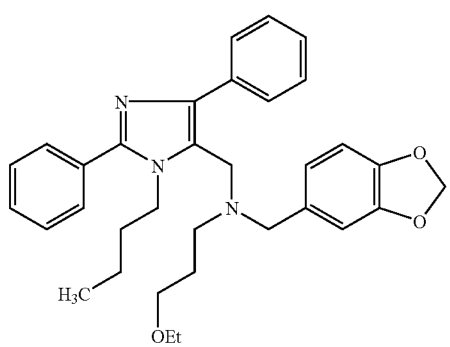 | * | N-(1,3-benzodioxol-5-ylmethyl)-N-[(1-butyl-2,4-diphenyl-1H-imidazol-5-yl)methyl]-3-ethoxypropan-1-amine | 525.3 | 1.17 |
| 383 | 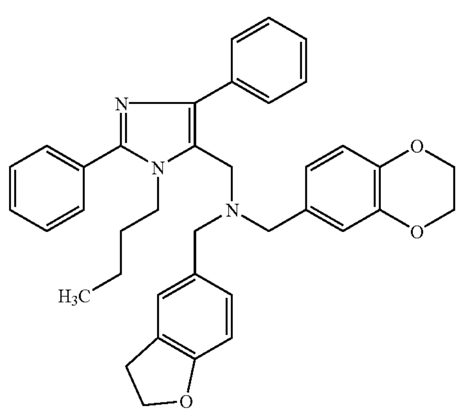 | * | 1-(1-butyl-2,4-diphenyl-1H-imidazol-5-yl)-N-(2,3-dihydro-1,4-benzodioxin-6-ylmethyl)-N-(2,3-dihydro-1-benzofuran-5-ylmethyl)methanamine | 585.3 | 1.22 |

TABLE I-continued

| CMP # | STRUCTURE | Ca²⁺ Mob. | IUPAC Name | MASS | Ret. Time |
|---|---|---|---|---|---|
| 384 | 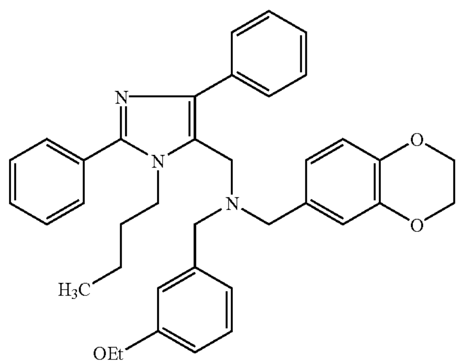 | * | 1-(1-butyl-2,4-diphenyl-1H-imidazol-5-yl)-N-(2,3-dihydro-1,4-benzodioxin-6-ylmethyl)-N-(3-ethoxybenzyl)methanamine | 587.31 | 1.25 |
| 385 | 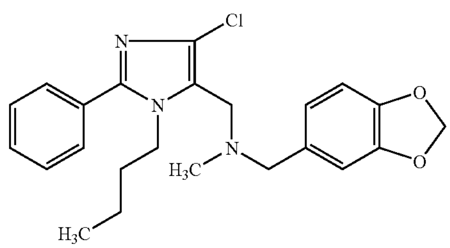 | * | 1-(1,3-benzodioxol-5-yl)-N-[(1-butyl-4-chloro-2-phenyl-1H-imidazol-5-yl)methyl]-N-methylmethanamine | 411.17 | 1.09 |
| 386 | 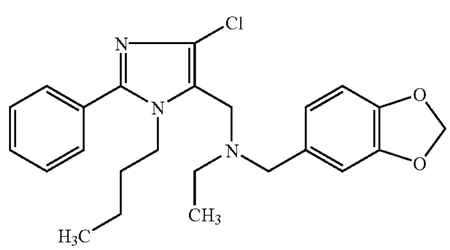 | * | N-(1,3-benzodioxol-5-ylmethyl)-N-[(1-butyl-4-chloro-2-phenyl-1H-imidazol-5-yl)methyl]ethanamine | 425.19 | 1.09 |
| 387 | 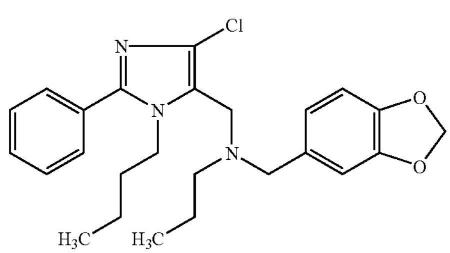 | * | N-(1,3-benzodioxol-5-ylmethyl)-N-[(1-butyl-4-chloro-2-phenyl-1H-imidazol-5-yl)methyl]propan-1-amine | 439.2 | 1.12 |
| 388 | 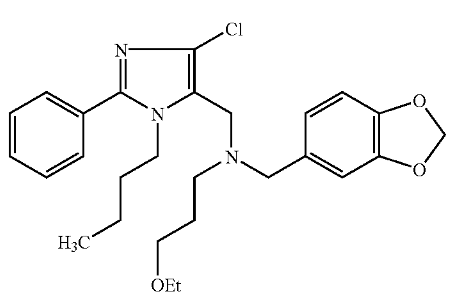 | * | N-(1,3-benzodioxol-5-ylmethyl)-N-[(1-butyl-4-chloro-2-phenyl-1H-imidazol-5-yl)methyl]-3-ethoxypropan-1-amine | | |

TABLE I-continued

| CMP # | STRUCTURE | Ca²⁺ Mob. | IUPAC Name | MASS | Ret. Time |
|---|---|---|---|---|---|
| 389 | 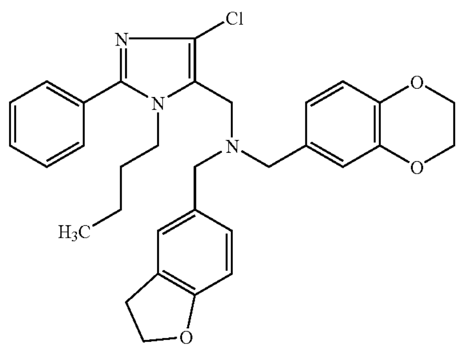 | * | N-[(1-butyl-4-chloro-2-phenyl-1H-imidazol-5-yl)methyl]-N-(2,3-dihydro-1,4-benzodioxin-6-ylmethyl)-N-(2,3-dihydro-1-benzofuran-5-ylmethyl)amine | | |
| 390 | 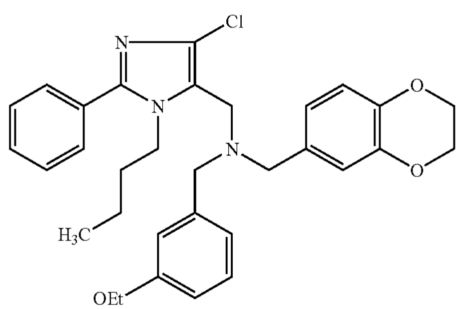 | * | N-[(1-butyl-4-chloro-2-phenyl-1H-imidazol-5-yl)methyl]-N-(2,3-dihydro-1,4-benzodioxin-6-ylmethyl)-N-(3-ethoxybenzyl)amine | | |
| 391 | 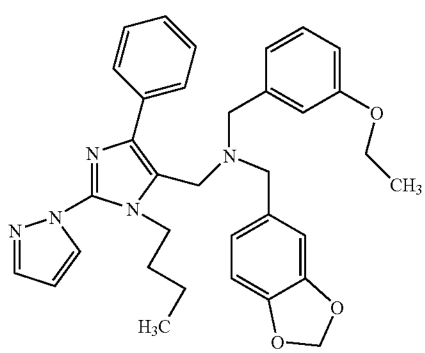 | * | 1-(1,3-benzodioxol-5-yl)-N-{[1-butyl-4-phenyl-2-(1H-pyrazol-1-yl)-1H-imidazol-5-yl]methyl}-N-(3-ethoxybenzyl)methanamine | | |
| 392 | 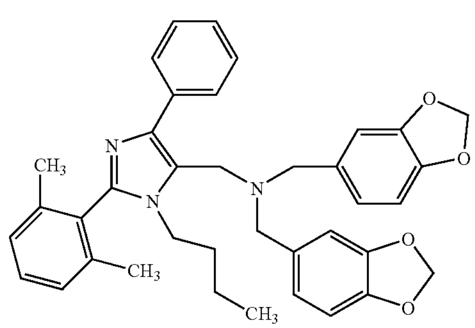 | * | 1-(1,3-benzodioxol-5-yl)-N-(1,3-benzodioxol-5-ylmethyl)-N-{[1-butyl-2-(2,6-dimethylphenyl)-4-phenyl-1H-imidazol-5-yl]methyl}methanamine | | |

TABLE I-continued

| CMP # | STRUCTURE | Ca²⁺ Mob. | IUPAC Name | MASS | Ret. Time |
|---|---|---|---|---|---|
| 393 | 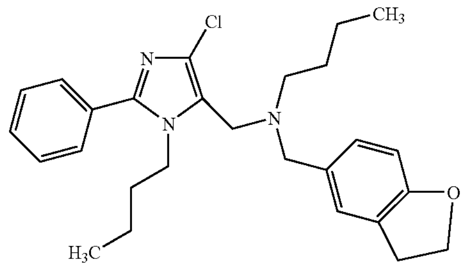 | * | N-[(1-butyl4-chloro-2-phenyl-1H-imidazol-5-yl)methyl]-N-(2,3-dihydro-1-benzofuran-5-ylmethyl)butan-1-amine | | |
| 394 | 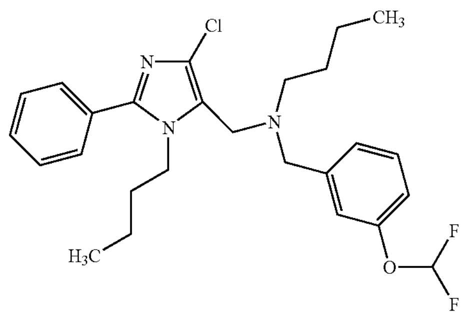 | * | N-[(1-butyl-4-chloro-2-phenyl-1H-imidazol-5-yl)methyl]-N-[3-(difluoromethoxy)benzyl]butan-1-amine | | |
| 395 | 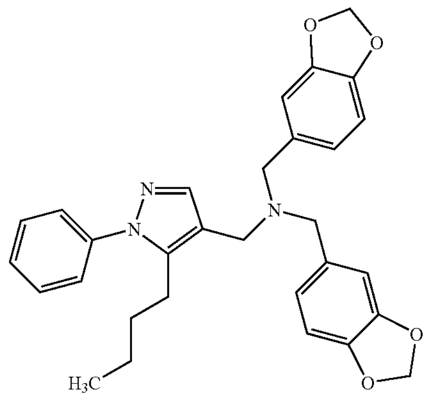 | * | 1-(1,3-benzodioxol-5-yl)-N-(1,3-benzodioxol-5-ylmethyl)-N-[(5-butyl-1-phenyl-1H-pyrazol-4-yl)methyl]methanamine | | |
| 396 | 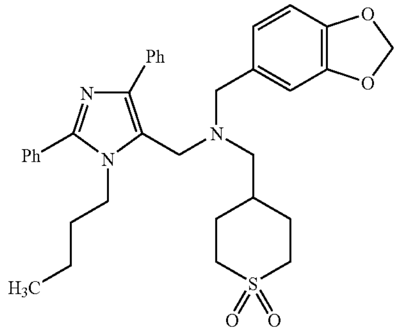 | * | 1-(1,3-benzodioxol-5-yl)-N-[(1-butyl-2,4-diphenyl-1H-imidazol-5-yl)methyl]-N-[(1,1-dioxidotetrahydro-2H-thiopyran-4-yl)methyl]methanamine | | |

TABLE I-continued

| CMP # | STRUCTURE | Ca²⁺ Mob. | IUPAC Name | MASS | Ret. Time |
|---|---|---|---|---|---|
| 397 | 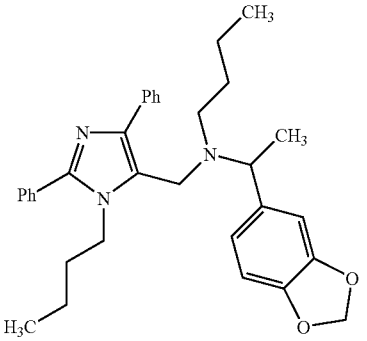 | * | N-[1-(1,3-benzodioxol-5-yl)ethyl]-N-[(1-butyl-2,4-diphenyl-1H-imidazol-5-yl)methyl]butan-1-amine | | |
| 398 | 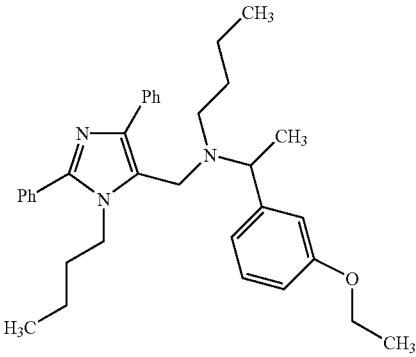 | * | N-[(1-butyl-2,4-diphenyl-1H-imidazol-5-yl)methyl]-N-[1-(3-ethoxyphenyl)ethyl]butan-1-amine | | |
| 399 | 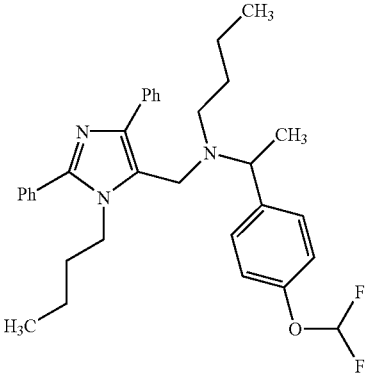 | * | N-[(1-butyl-2,4-diphenyl-1H-imidazol-5-yl)methyl]-N-{1-[4-(difluoromethoxy)phenyl]ethyl}butan-1-amine | | |
| 400 | 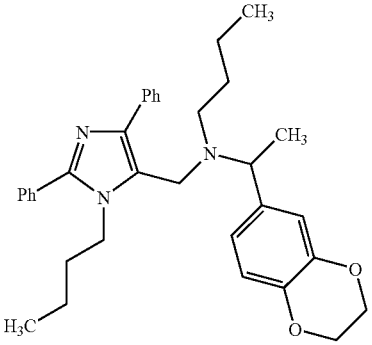 | * | N-[(1-butyl-2,4-diphenyl-1H-imidazol-5-yl)methyl]-N-[1-(2,3-dihydro-1,4-benzodioxin-6-yl)ethyl]butan-1-amine | | |

TABLE I-continued

| CMP # | STRUCTURE | Ca²⁺ Mob. | IUPAC Name | MASS | Ret. Time |
|---|---|---|---|---|---|
| 401 | 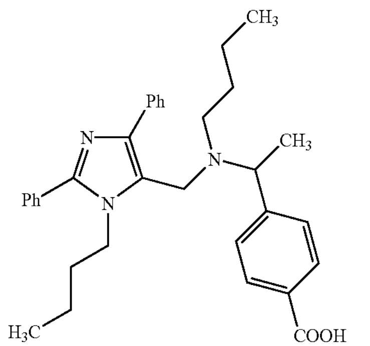 | * | 4-(1-{butyl[(1-butyl-2,4-diphenyl-1H-imidazol-5-yl)methyl]amino}ethyl)benzoic acid | | |
| 402 | 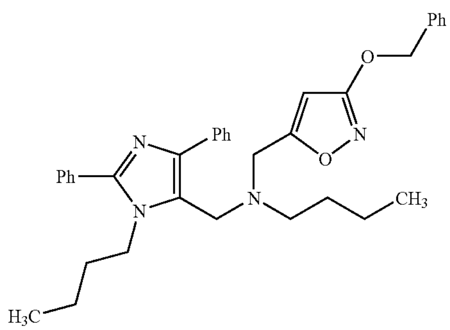 | * | N-{[3-(benzyloxy)isoxazol-5-yl]methyl}-N-[(1-butyl-2,4-diphenyl-1H-imidazol-5-yl)methyl]butan-1-amine | | |
| 403 | 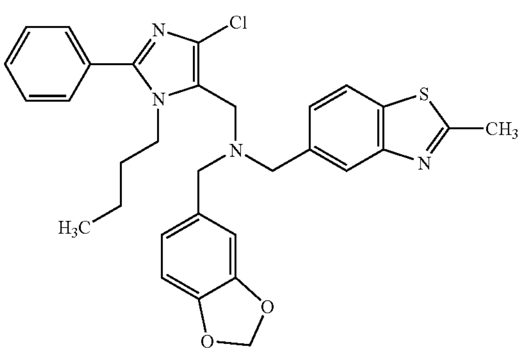 | * | 1-(1,3-benzodioxol-5-yl)-N-[(1-butyl-4-chloro-2-phenyl-1H-imidazol-5-yl)methyl]-N-[(2-methyl-1,3-benzothiazol-5-yl)methyl]methanamine | | |
| 404 | 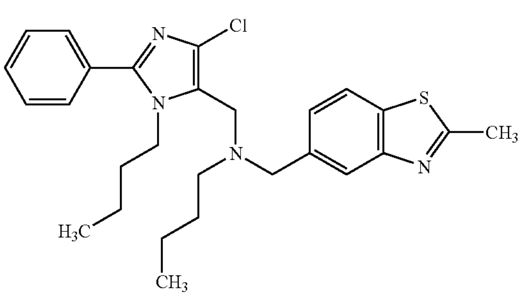 | * | N-[(1-butyl-4-chloro-2-phenyl-1H-imidazol-5-yl)methyl]-N-[(2-methyl-1,3-benzothiazol-5-yl)methyl]butan-1-amine | | |

TABLE I-continued

| CMP # | STRUCTURE | Ca²⁺ Mob. | IUPAC Name | MASS | Ret. Time |
|---|---|---|---|---|---|
| 405 | 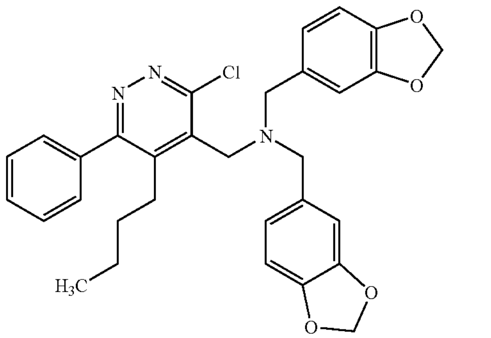 | * | 1-(1,3-benzodioxol-5-yl)-N-(1,3-benzodioxol-5-ylmethyl)-N-[(5-butyl-3-chloro-6-phenylpyridazin-4-yl)methyl]methanamine | | |
| 406 | 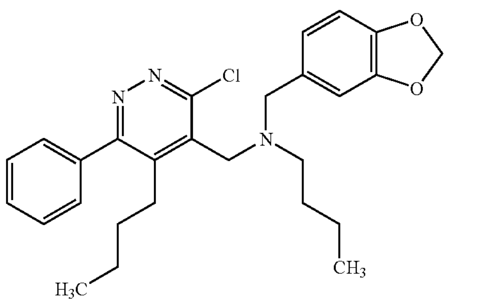 | * | N-(1,3-benzodioxol-5-ylmethyl)-N-[(5-butyl-3-chloro-6-phenylpyridazin-4-yl)methyl]butan-1-amine | | |
| 407 | 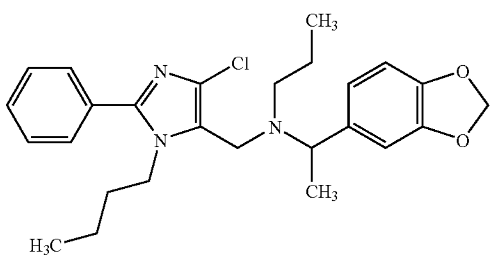 | * | N-[1-(1,3-benzodioxol-5-yl)ethyl]-N-[(1-butyl-4-chloro-2-phenyl-1H-imidazol-5-yl)methyl]propan-1-amine | | |
| 408 | 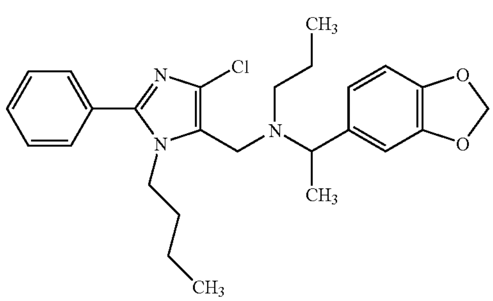 | * | N-[(1-butyl-4-chloro-2-phenyl-1H-imidazol-5-yl)methyl]-N-[1-(2,3-dihydro-1,4-benzodiodn-6-yl)ethyl]propan-1-amine | | |
| 409 | 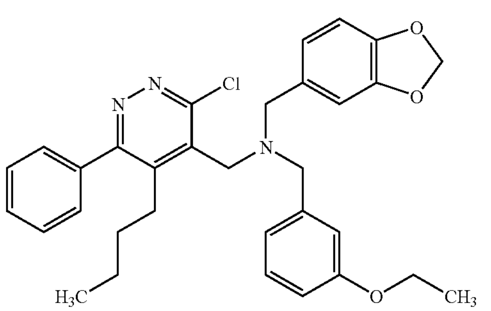 | * | 1-(1,3-benzodioxol-5-yl)-N-[(5-butyl-3-chloro-6-phenylpyridazin-4-yl)methyl]-N-(3-ethoxybenzyl)methanamine | | |

TABLE II

| CMP # | STRUCTURE | Ca²⁺ Mob. | IUPAC Name | MASS | RT (min.) |
|---|---|---|---|---|---|
| 410 | 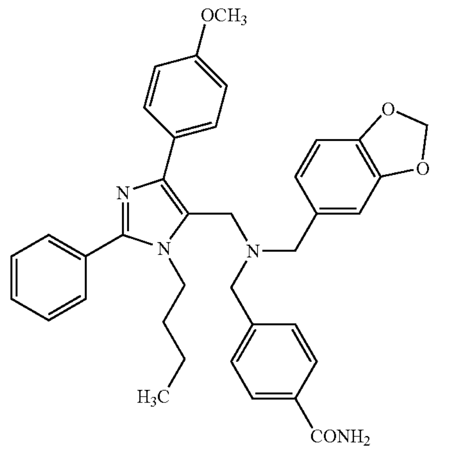 | | 4-[((1,3-benzodioxol-5-ylmethyl){[1-butyl-4-(4-methoxyphenol)-2-phenyl-1H-imidazol-5-yl]methyl}amino)methyl]benzamide | | |
| 411 | 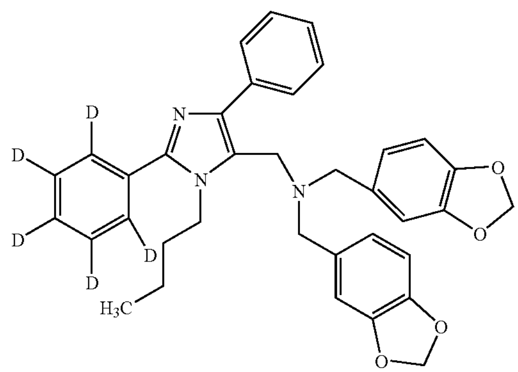 | | 1-(1,3-benzodioxol-5-yl)-N-(1,3-benzodioxol-5-ylmethyl)-N-[(1-butyl-2,4-diphenyl-1H-imidazol-5-yl)methyl]methanamine | | |
| 412 | 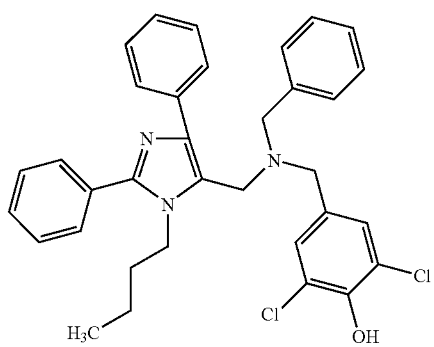 | * | 4-({benzyl[(1-butyl-2,4-diphenyl-1H-imidazol-5-yl)methyl]amino}methyl)-2,6-dichlorophenol | 570.25 | 1.21 |
| 413 | 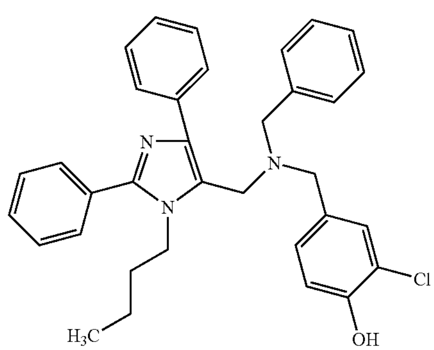 | * | 4-({benzyl[(1-butyl-2,4-diphenyl-1H-imidazol-5-yl)methyl]amino}methyl)-2-chlorophenol | 536.30 | 1.18 |

TABLE II-continued

| CMP # | STRUCTURE | Ca²⁺ Mob. | IUPAC Name | MASS | RT (min.) |
|---|---|---|---|---|---|
| 414 | 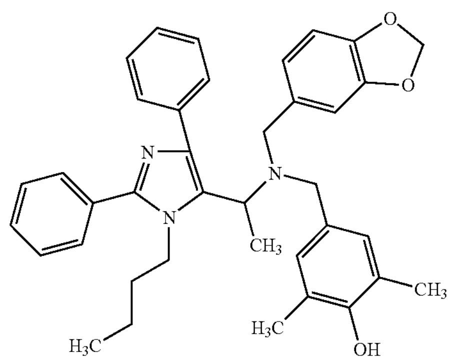 | * | 4-({(1,3-benzodioxol-5-ylmethyl)[1-(1-butyl-2,4-diphenyl-1H-imidazol-5-yl)ethyl]amino}methyl)-2,6-dimethylphenol | 588.42 | 1.21 |
| 415 | 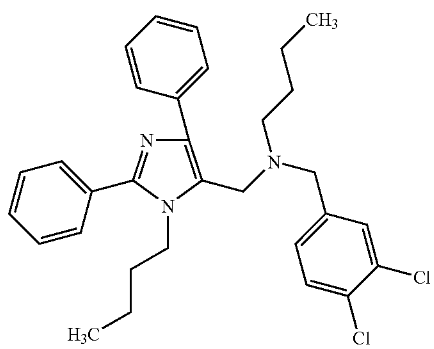 | * | N-[(1-butyl-2,4-diphenyl-1H-imidazol-5-yl)methyl]-N-(3,4-dichlorobenzyl)butan-1-amine | 520.31 | 1.26 |
| 416 | 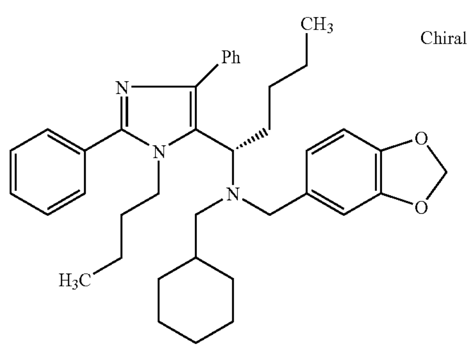 | * | (1R)-N-(1,3-benzodioxol-5-ylmethyl)-1-(1-butyl-2,4-diphenyl-1H-imidazol-5-yl)-N-(cyclohexylmethyl)pentan-1-amine | | |
| 417 | 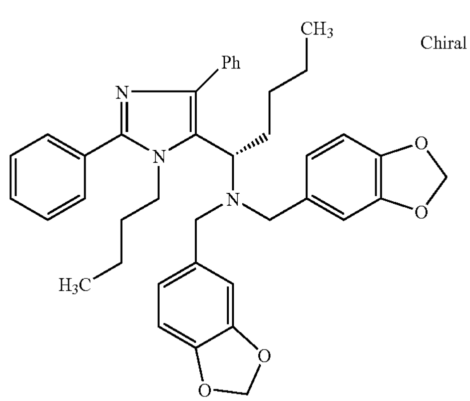 | | (1R)-N,N-bis(1,3-benzodioxol-5-ylmethyl)-1-(1-butyl-2,4-diphenyl-1H-imidazol-5-yl)pentan-1-amine | | |

TABLE II-continued
| CMP # | STRUCTURE | Ca²⁺ Mob. | IUPAC Name | MASS | RT (min.) |
|---|---|---|---|---|---|
| 418 | 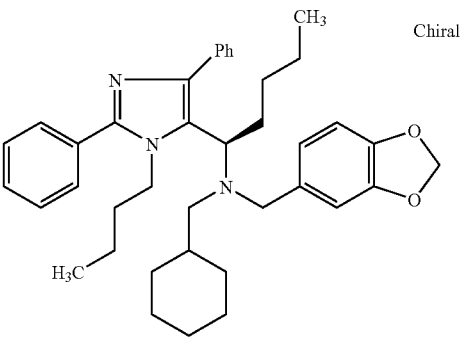 | * | | | |
| 419 | 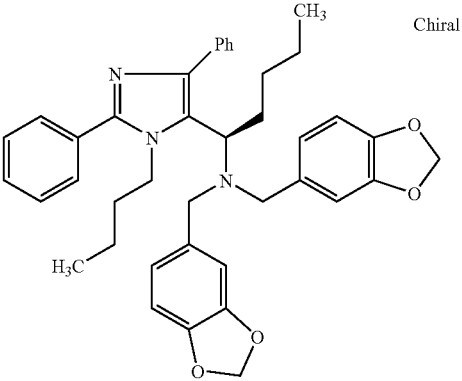 | * | | | |
| 420 | 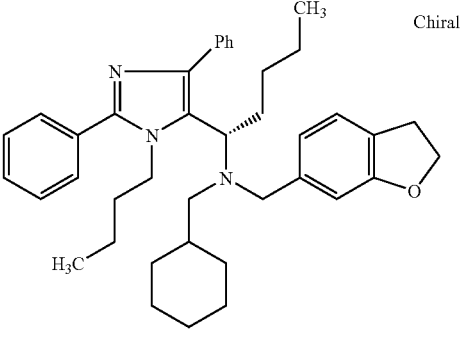 | * | (1R)-1-(1-butyl-2,4-diphenyl-1H-imidazol-5-yl)-N-(cyclohexylmethyl)-N-(2,3-dihydro-1-benzofuran-6-ylmethyl)pentan-1-amine | | |
| 421 | 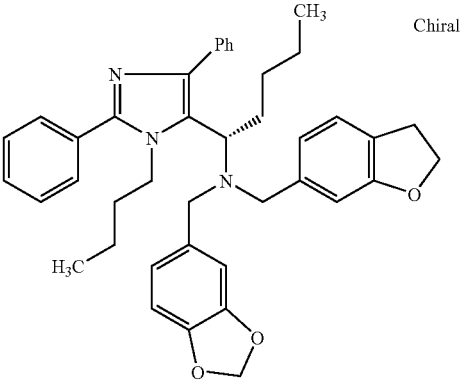 | * | (1R)-N-(1,3-benzodioxol-5-ylmethyl)-1-(1-butyl-2,4-diphenyl-1H-imidazol-5-yl)-N-(2,3-dihydro-1-benzofuran-6-ylmethyl)pentan-1-amine | 628.48 | 1.27 |

TABLE II-continued
| CMP # | STRUCTURE | Ca²⁺ Mob. | IUPAC Name | MASS | RT (min.) |
|---|---|---|---|---|---|
| 422 | 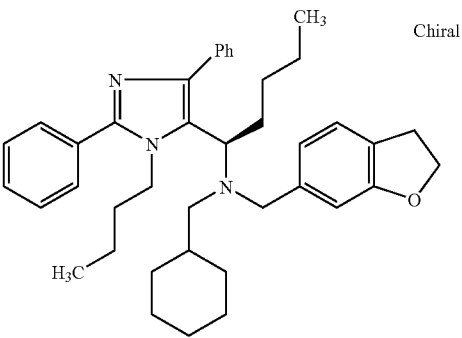 | * | | | |
| 423 | 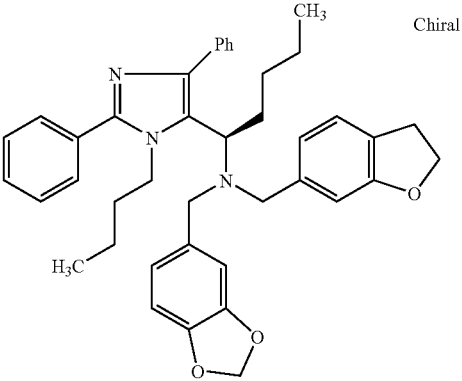 | * | | 628.48 | 1.27 |
| 424 | 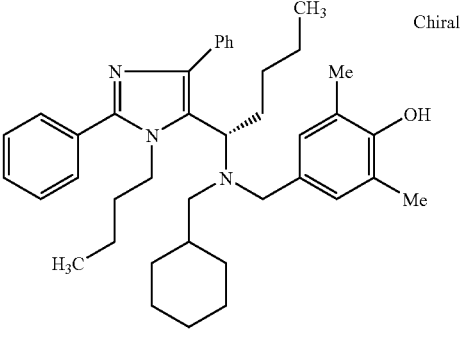 | * | 4-{[[(1R)-1-(1-butyl-2,4-diphenyl-1H-imidazol-5-yl)pentyl](cyclohexylmethyl)amino]methyl}-2,6-dimethylphenol | | |
| 425 | 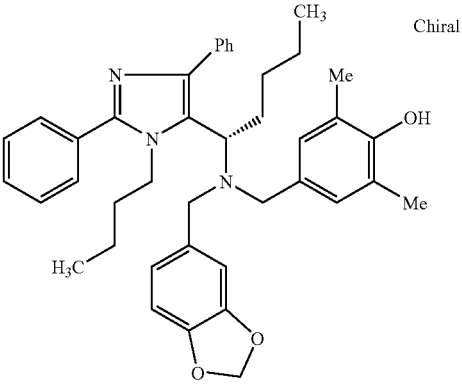 | * | 4-({(1,3-benzodioxol-5-ylmethyl)[(1R)-1-(1-butyl-2,4-diphenyl-1H-imidazol-5-yl)pentyl]amino}methyl)-2,6-dimethylphenol | 630.50 | 1.26 |

TABLE II-continued

| CMP # | STRUCTURE | Ca²⁺ Mob. | IUPAC Name | MASS | RT (min.) |
|---|---|---|---|---|---|
| 426 | 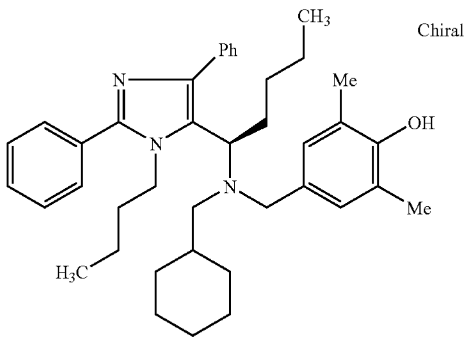 | * | | | |
| 427 | 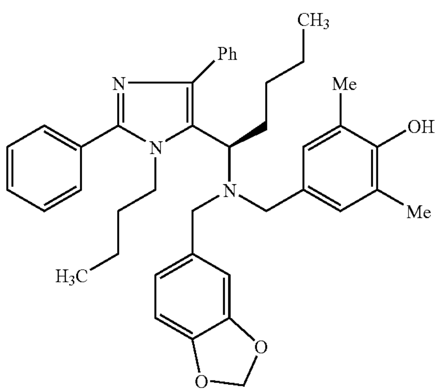 | * | | 630.50 | 1.26 |
| 428 | 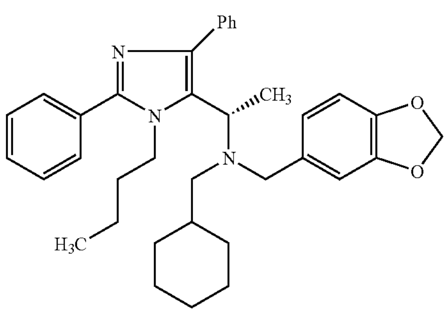 | | (1R)-N-(1,3-benzodioxol-5-ylmethyl)-1-(1-butyl-2,4-diphenyl-1H-imidazol-5-yl)-N-(cyclohexylmethyl)ethanamine | | |
| 429 | 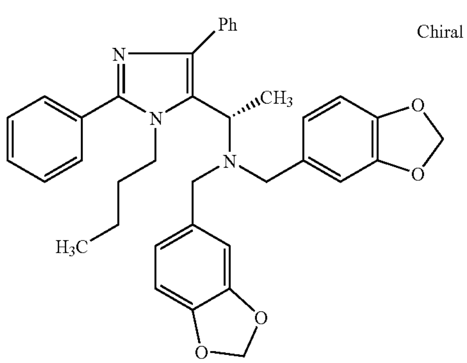 | Chiral | (1R)-N,N-bis(1,3-benzodioxol-5-ylmethyl)-1-(1-butyl-2,4-diphenyl-1H-imidazol-5-yl)ethanamine | | |

TABLE II-continued

| CMP # | STRUCTURE | Ca²⁺ Mob. | IUPAC Name | MASS | RT (min.) |
|---|---|---|---|---|---|
| 430 | 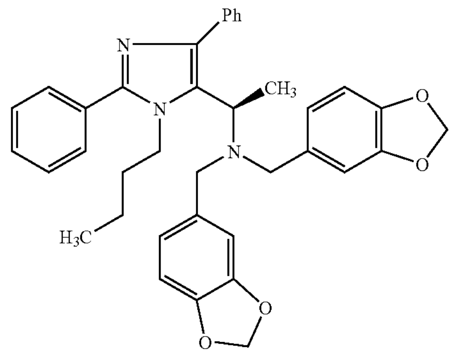 | * | (1S)-N,N-bis(1,3-benzodioxol-5-ylmethyl)-1-(1-butyl-2,4-diphenyl-1H-imidazol-5-yl)ethanamine | | |
| 431 | Chiral | * | (1R)-1-(1-butyl-2,4-diphenyl-1H-imidazol-5-yl)-N-(cyclohexylmethyl)-N-(2,3-dihydro-1-benzofuran-6-ylmethyl)ethanamine | | |
| 432 | Chiral | | (1R)-N-(1,3-benzodioxol-5-ylmethyl)-1-(1-butyl-2,4-diphenyl-1H-imidazol-5-yl)-N-(2,3-dihydro-1-benzofuran-6-ylmethyl)ethanamine | | |
| 433 | Chiral | * | (1S)-1-(1-butyl-2,4-diphenyl-1H-imidazol-5-yl)-N-(cyclohexylmethyl)-N-(2,3-dihydro-1-benzofuran-6-ylmethyl)ethanamine | | |

TABLE II-continued

| CMP # | STRUCTURE | Ca²⁺ Mob. | IUPAC Name | MASS | RT (min.) |
|---|---|---|---|---|---|
| 434 | 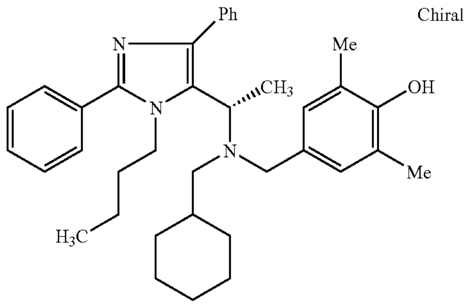 | Chiral | * 4-{[[(1R)-1-(1-butyl-2,4-diphenyl-1H-imidazol-5-yl)ethyl](cyclohexylmethyl)amino]methyl}-2,6-dimethylphenol | | |
| 435 | 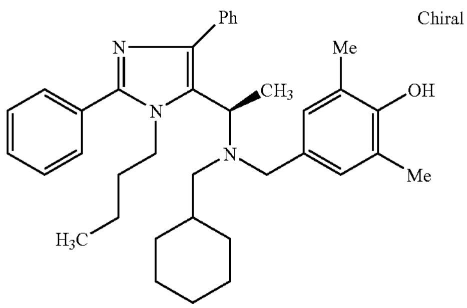 | Chiral | * 4-{[[(1S)-1-(1-butyl-2,4-diphenyl-1H-imidazol-5-yl)ethyl](cyclohexylmethyl)amino]methyl}-2,6-dimethylphenol | | |
| 436 | 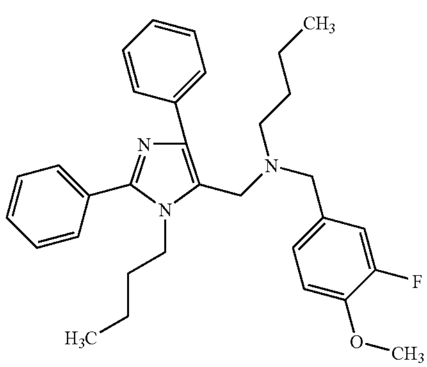 | | * N-[(1-butyl-2,4-diphenyl-1H-imidazol-5-yl)methyl]-N-(3-fluoro-4-methoxybenzyl)butan-1-amine | 500.31 | 1.19 |
| 437 | 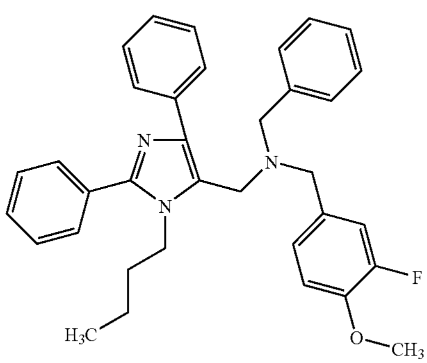 | | * N-benzyl-1-(1-butyl-2,4-diphenyl-1H-imidazol-5-yl)-N-(3-fluoro-4-methoxybenzyl)methanamine | 534.30 | 1.21 |

TABLE II-continued

| CMP # | STRUCTURE | Ca²⁺ Mob. | IUPAC Name | MASS | RT (min.) |
|---|---|---|---|---|---|
| 438 | 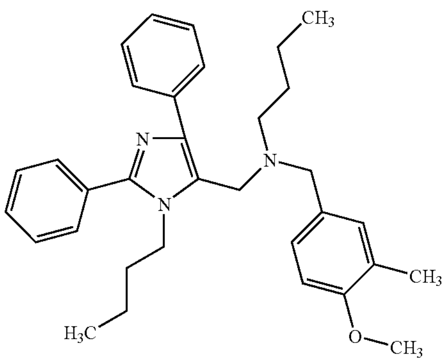 | * | N-[(1-butyl-2,4-diphenyl-1H-imidazol-5-yl)methyl]-N-(4-methoxy-3-methylbenzyl)butan-1-amine | 496.34 | 1.18 |
| 439 | 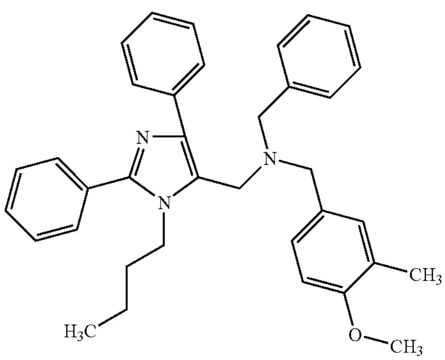 | * | N-benzyl-1-(1-butyl-2,4-diphenyl-1H-imidazol-5-yl)-N-(4-methoxy-3-methylbenzyl)methanamine | 530.32 | 1.24 |
| 440 | 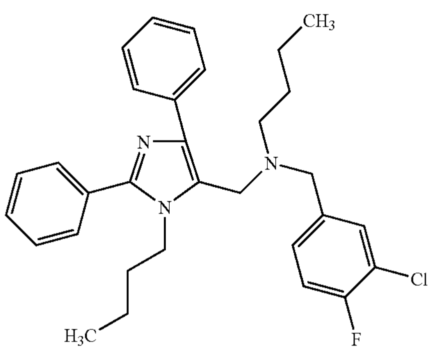 | | N-[(1-butyl-2,4-diphenyl-1H-imidazol-5-yl)methyl]-N-(3-chloro-4-fluorobenzyl)butan-1-amine | 540.27 | 1.24 |
| 441 | 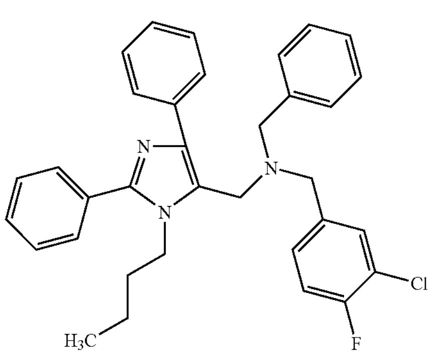 | | N-benzyl-1-(1-butyl-2,4-diphenyl-1H-imidazol-5-yl)-N-(3-chloro-4-fluorobenzyl)methanamine | 538.26 | 1.25 |

TABLE II-continued

| CMP # | STRUCTURE | Ca²⁺ Mob. | IUPAC Name | MASS | RT (min.) |
|---|---|---|---|---|---|
| 442 | 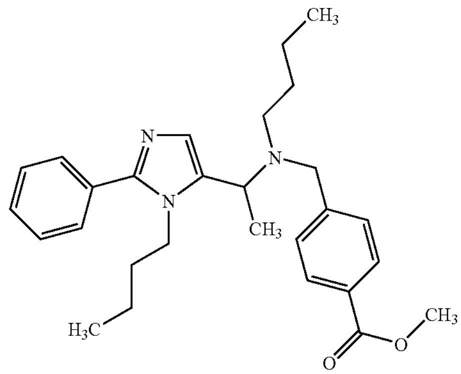 | | methyl 4-({butyl[1-(1-butyl-2-phenyl-1H-imidazol-5-yl)ethyl]amino}methyl)benzoate | 448.31 | 1.19 |
| 443 | 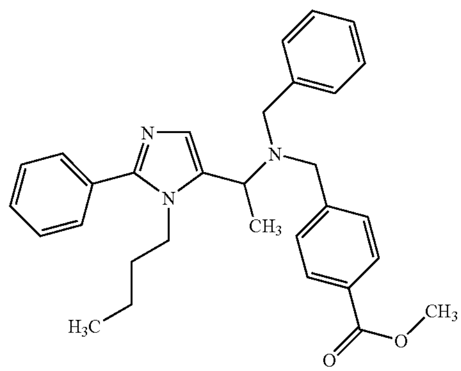 | | methyl 4-({benzyl[1-(1-butyl-2-phenyl-1H-imidazol-5-yl)ethyl]amino}methyl)benzoate | 482.29 | 1.19 |
| 444 | 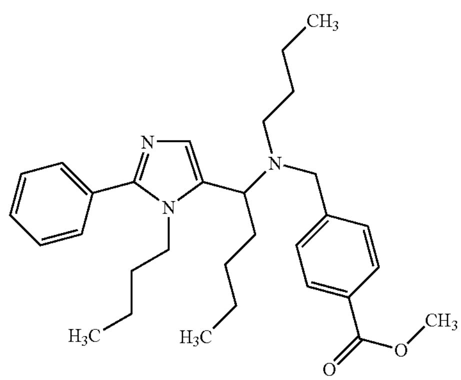 | | methyl 4-({butyl[1-(1-butyl-2-phenyl-1H-imidazol-5-yl)pentyl]amino}methyl)benzoate | 490.35 | 1.23 |
| 445 | 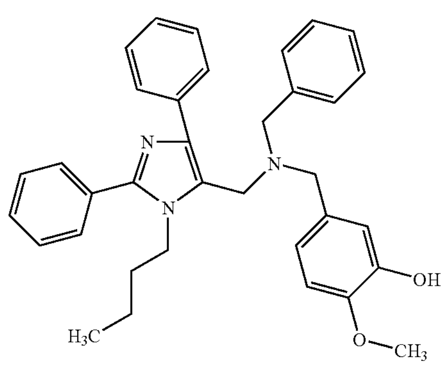 | * | 5-({benzyl[(1-butyl-2,4-diphenyl-1H-imidazol-5-yl)methyl]amino}methyl)-2-methoxyphenol | 532.36 | 1.18 |

TABLE II-continued

| CMP # | STRUCTURE | Ca²⁺ Mob. | IUPAC Name | MASS | RT (min.) |
|---|---|---|---|---|---|
| 446 | 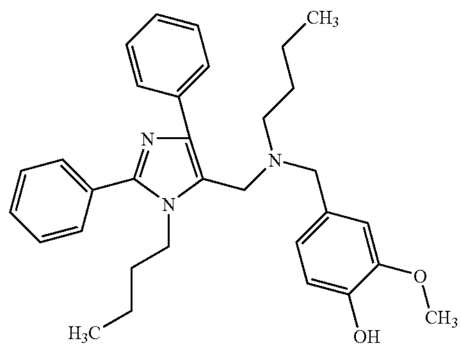 | * | 4-({butyl[(1-butyl-2,4-diphenyl-1H-imidazol-5-yl)methyl]amino}methyl)-2-methoxyphenol | 498.38 | 1.1 |
| 447 | 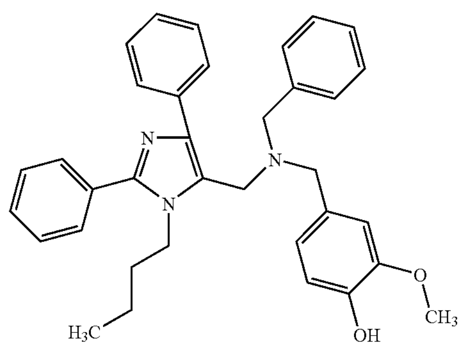 | * | 4-({benzyl[(1-butyl-2,4-diphenyl-1H-imidazol-5-yl)methyl]amino}methyl)-2-methoxyphenol | 532.37 | 1.17 |
| 448 | 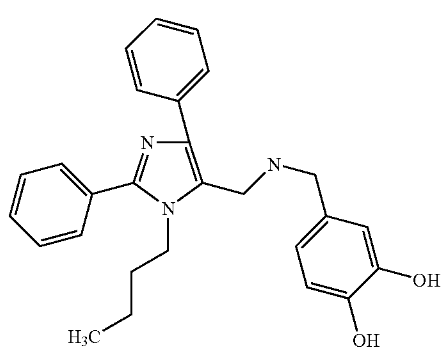 | * | 4-({[(1-butyl-2,4-diphenyl-1H-imidazol-5-yl)methyl]amino}methyl)benzene-1,2-diol | 428.32 | 1 |
| 449 | 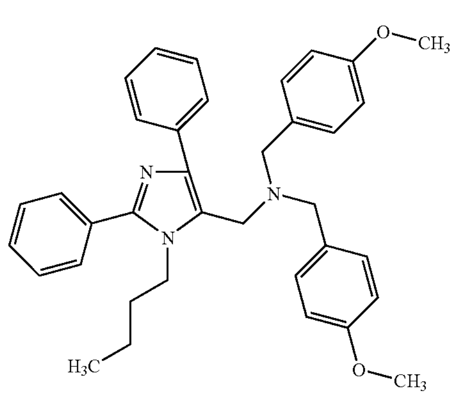 | * | 1-(1-butyl-2,4-diphenyl-1H-imidazol-5-yl)-N,N-bis(4-methoxybenzyl)methanamine | 546.39 | 1.21 |

TABLE II-continued

| CMP # | STRUCTURE | Ca²⁺ Mob. | IUPAC Name | MASS | RT (min.) |
|---|---|---|---|---|---|
| 450 | 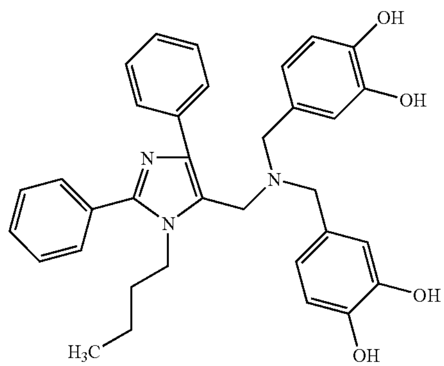 | | 1-(1-butyl-2,4-diphenyl-1H-imidazol-5-yl)-N,N-bis(3,4-dihydroxybenzyl)methanamine | | |
| 451 | 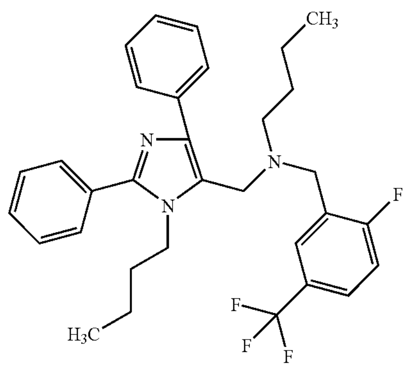 | | N-[(1-butyl-2,4-diphenyl-1H-imidazol-5-yl)methyl]-N-[2-fluoro-5-(trifluoromethyl)benzyl]butan-1-amine | 538.31 | 1.24 |
| 452 | 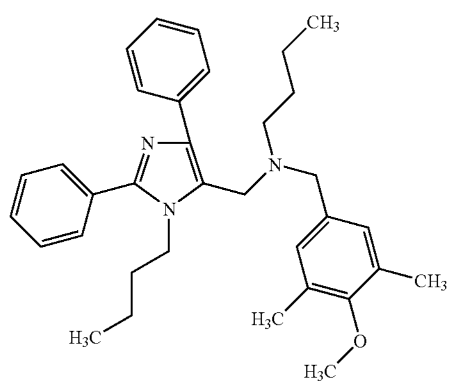 | * | N-[(1-butyl-2,4-diphenyl-1H-imidazol-5-yl)methyl]-N-(4-methoxy-3,5-dimethylbenzyl)butan-1-amine | 510.37 | 1.2 |
| 453 | 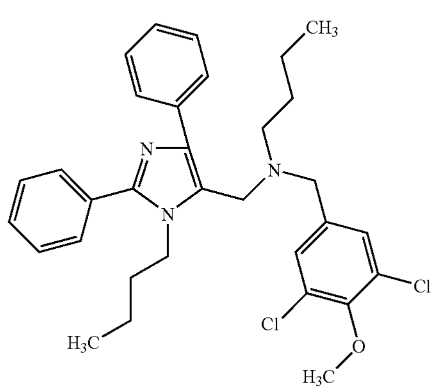 | * | N-[(1-butyl-2,4-diphenyl-1H-imidazol-5-yl)methyl]-N-(3,5-dichloro-4-methoxybenzyl)butan-1-amine | 550.28 | 1.26 |

TABLE II-continued

| CMP # | STRUCTURE | Ca²⁺ Mob. | IUPAC Name | MASS | RT (min.) |
|---|---|---|---|---|---|
| 454 | 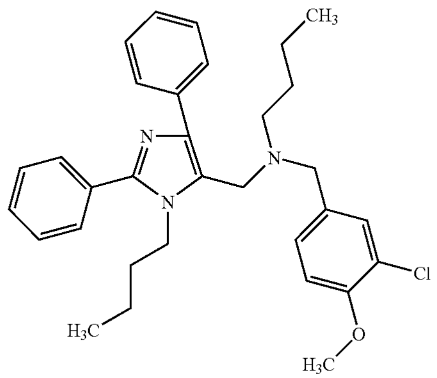 | * | N-[(1-butyl-2,4-diphenyl-1H-imidazol-5-yl)methyl]-N-(3-chloro-4-methoxybenzyl)butan-1-amine | 516.31 | 1.21 |
| 455 | 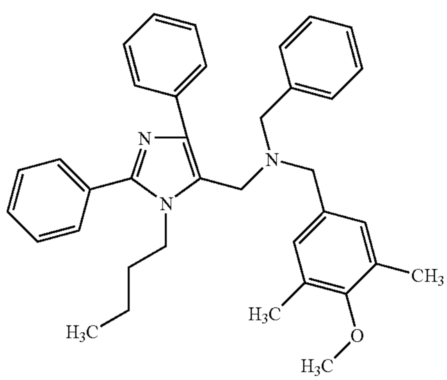 | * | N-benzyl-1-(1-butyl-2,4-diphenyl-1H-imidazol-5-yl)-N-(4-methoxy-3,5-dimethylbenzyl)methanamine | 544.36 | 1.25 |
| 456 | 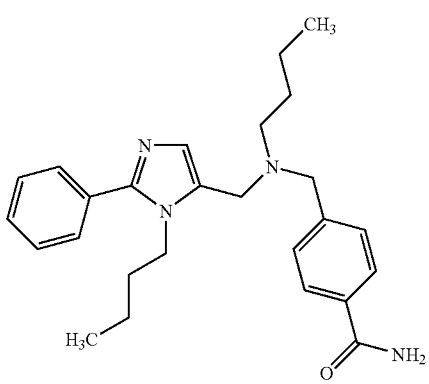 | * | 4-({butyl[(1-butyl-2-phenyl-1H-imidazol-5-yl)methyl]amino}methyl)benzamide | 419.31 | 1.08 |
| 457 | 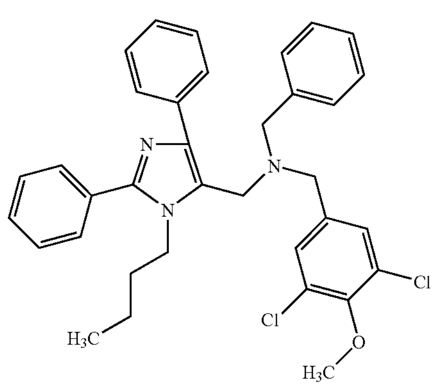 | * | N-benzyl-1-(1-butyl-2,4-diphenyl-1H-imidazol-5-yl)-N-(3,5-dichloro-4-methoxybenzyl)methanamine | 584.26 | 1.25 |

TABLE II-continued

| CMP # | STRUCTURE | Ca²⁺ Mob. | IUPAC Name | MASS | RT (min.) |
|---|---|---|---|---|---|
| 458 | 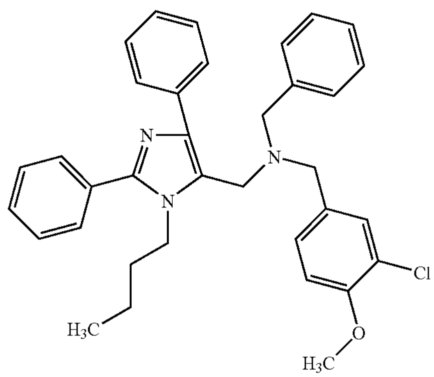 | * | N-benzyl-1-(1-butyl-2,4-diphenyl-1H-imidazol-5-yl)-N-(3-chloro-4-methoxybenzyl)methanamine | 550.30 | 1.23 |
| 459 | 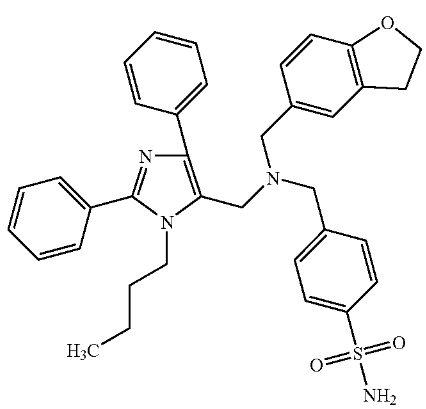 | | 4-{[[(1-butyl-2,4-diphenyl-1H-imidazol-5-yl)methyl](2,3-dihydro-1-benzofuran-5-ylmethyl)amino]methyl}benzenesulfonamide | 607.39 | 1.12 |
| 460 | 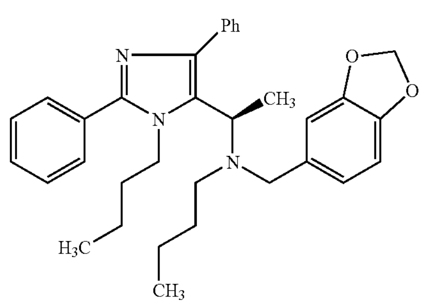 | | N-(1,3-benzodioxol-5-ylmethyl)-N-[(1S)-1-(1-butyl-2,4-diphenyl-1H-imidazol-5-yl)ethyl]butan-1-amine | 510.39 | 1.21 |
| 461 | 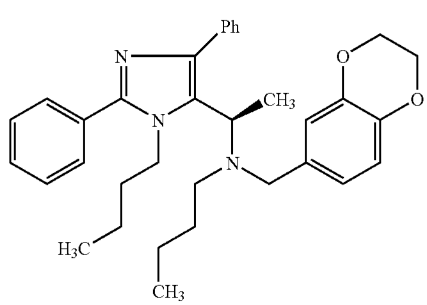 | | N-[(1S)-1-(1-butyl-2,4-diphenyl-1H-imidazol-5-yl)ethyl]-N-(2,3-dihydro-1,4-benzodioxin-6-ylmethyl)butan-1-amine | 524.41 | 1.2 |

TABLE II-continued

| CMP # | STRUCTURE | Ca²⁺ Mob. | IUPAC Name | MASS | RT (min.) |
|---|---|---|---|---|---|
| 462 | 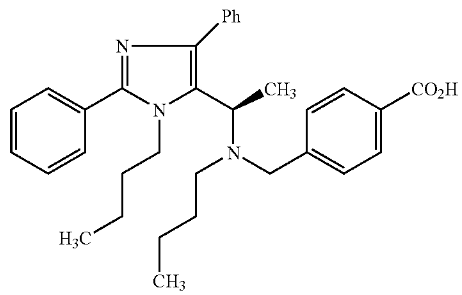 | * | 4-({butyl[(1S)-1-(1-butyl-2,4-diphenyl-1H-imidazol-5-yl)ethyl]amino}methyl)benzoic acid | 510.39 | 1.19 |
| 463 | 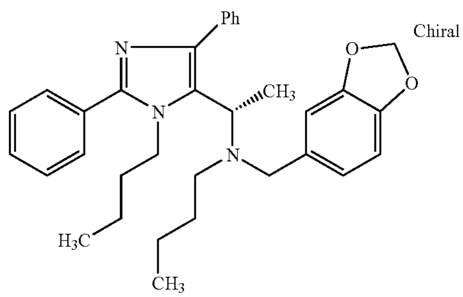 | Chiral | N-(1,3-benzodioxol-5-ylmethyl)-N-[(1R)-1-(1-butyl-2,4-diphenyl-1H-imidazol-5-yl)ethyl]butan-1-amine | 510.40 | 1.21 |
| 464 | 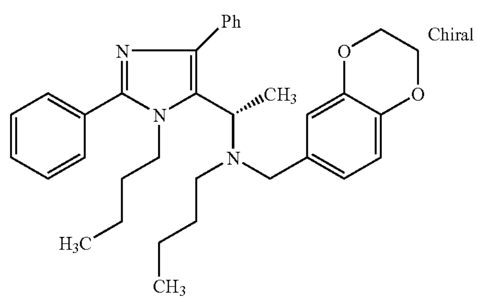 | Chiral | N-[(1R)-1-(1-butyl-2,4-diphenyl-1H-imidazol-5-yl)ethyl]-N-(2,3-dihydro-1,4-benzodioxin-6-ylmethyl)butan-1-amine | 524.41 | 1.21 |
| 465 | 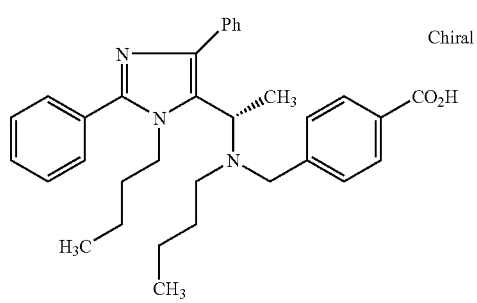 | Chiral | 4-({butyl[(1R)-1-(1-butyl-2,4-diphenyl-1H-imidazol-5-yl)ethyl]amino}methyl)benzoic acid | 510.40 | 1.18 |
| 466 | 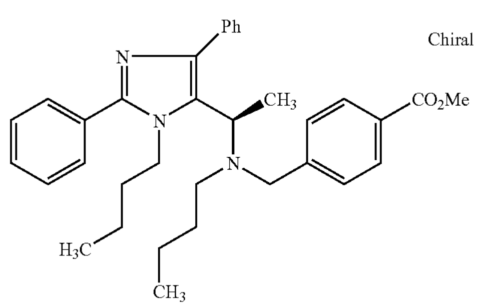 | Chiral | methyl 4-({butyl[(1S)-1-(1-butyl-2,4-diphenyl-1H-imidazol-5-yl)ethyl]amino}methyl)benzoate | 524.41 | 1.22 |

TABLE II-continued

| CMP # | STRUCTURE | Ca²⁺ Mob. | IUPAC Name | MASS | RT (min.) |
|---|---|---|---|---|---|
| 467 | 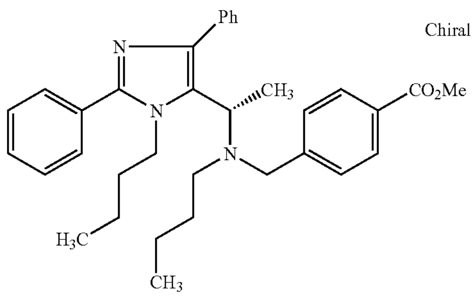 | Chiral | methyl 4-({butyl[(1R)-1-(1-butyl-2,4-diphenyl-1H-imidazol-5-yl)ethyl]amino}methyl)benzoate | 524.41 | 1.22 |
| 468 | 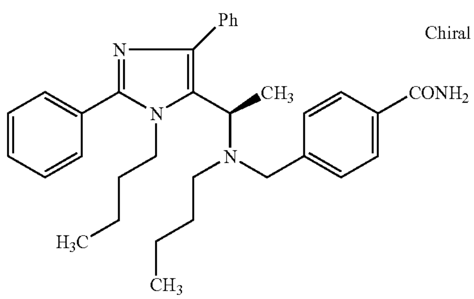 | Chiral * | 4-({butyl[(1S)-1-(1-butyl-2,4-diphenyl-1H-imidazol-5-yl)ethyl]amino}methyl)benzamide | 509.42 | 1.15 |
| 469 | 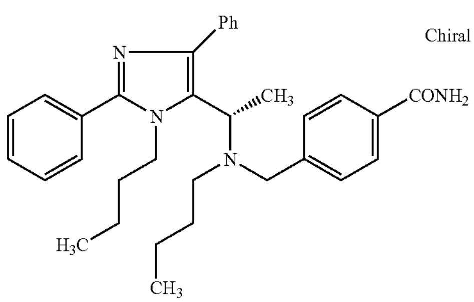 | Chiral | 4-({butyl[(1R)-1-(1-butyl-2,4-diphenyl-1H-imidazol-5-yl)ethyl]amino}methyl)benzamide | 509.43 | 1.15 |
| 470 | 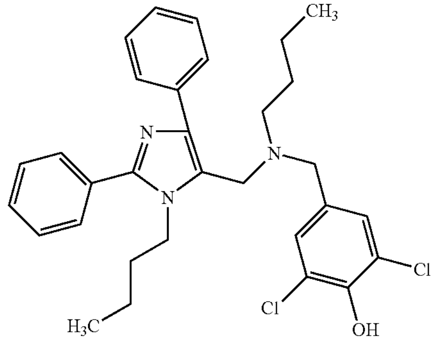 | | 4-({butyl[(1-butyl-2,4-diphenyl-1H-imidazol-5-yl)methyl]amino}methyl)-2,6-dichlorophenol | 536.27 | 1.22 |

TABLE II-continued

| CMP # | STRUCTURE | Ca²⁺ Mob. | IUPAC Name | MASS | RT (min.) |
|---|---|---|---|---|---|
| 471 | 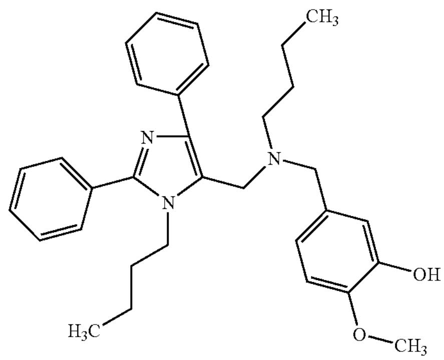 | * | 5-({butyl[(1-butyl-2,4-diphenyl-1H-imidazol-5-yl)methyl]amino}methyl)-2-methoxyphenol | 498.38 | 1.11 |
| 472 | 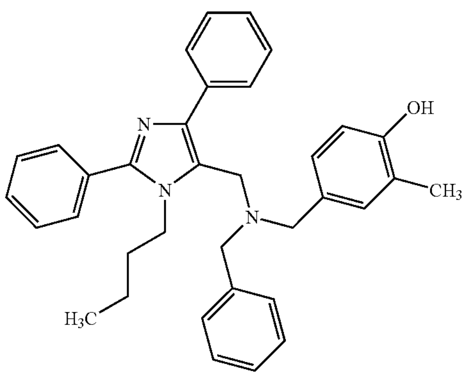 | * | 4-({benzyl[(1-butyl-2,4-diphenyl-1H-imidazol-5-yl)methyl]amino}methyl)-2-methylphenol | 516.37 | 1.21 |
| 473 | 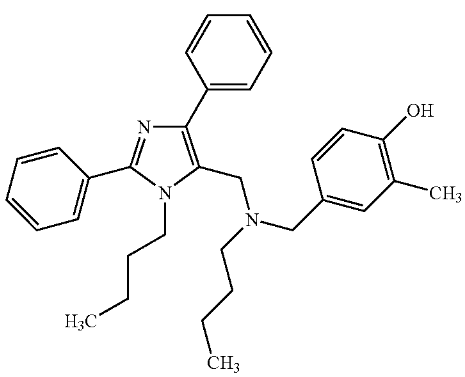 | * | 4-({butyl[(1-butyl-2,4-diphenyl-1H-imidazol-5-yl)methyl]amino}methyl)-2-methylphenol | 482.38 | 1.12 |
| 474 | 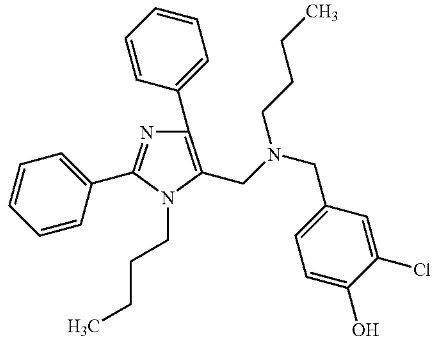 | * | 4-({butyl[(1-butyl-2,4-diphenyl-1H-imidazol-5-yl)methyl]amino}methyl)-2-chlorophenol | 502.33 | 1.16 |

TABLE II-continued

| CMP # | STRUCTURE | Ca²⁺ Mob. | IUPAC Name | MASS | RT (min.) |
|---|---|---|---|---|---|
| 475 | 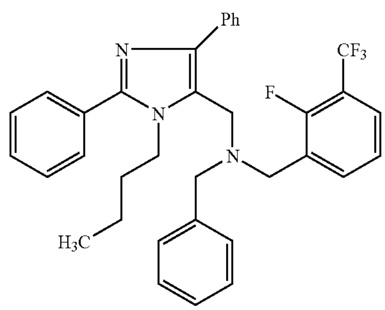 | | N-benzyl-1-(1-butyl-2,4-diphenyl-1H-imidazol-5-yl)-N-[2-fluoro-3-(trifluoromethyl)benzyl]methanamine | 572.32 | 1.24 |
| 476 | 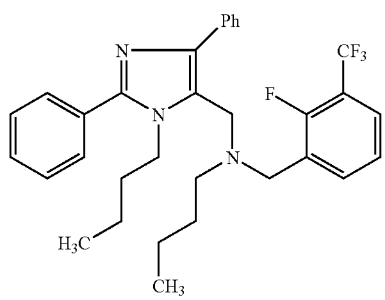 | | N-[(1-butyl-2,4-diphenyl-1H-imidazol-5-yl)methyl]-N-[2-fluoro-3-(trifluoromethyl)benzyl]butan-1-amine | 539.36 | 1.25 |
| 477 | 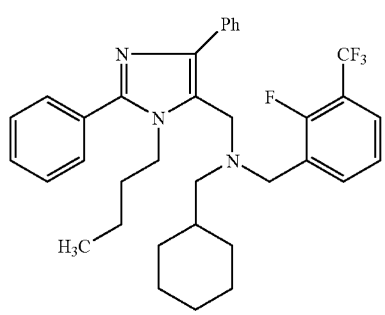 | | 1-(1-butyl-2,4-diphenyl-1H-imidazol-5-yl)-N-(cyclohexylmethyl)-N-[2-fluoro-3-(trifluoromethyl)benzyl]methanamine | 578.38 | 1.29 |
| 478 | 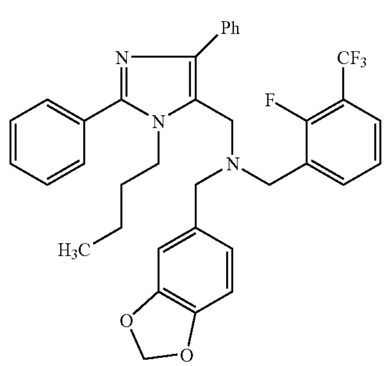 | * | 1-(1,3-benzodioxol-5-yl)-N-[(1-butyl-2,4-diphenyl-1H-imidazol-5-yl)methyl]-N-[2-fluoro-3-(trifluoromethyl)benzyl]methanamine | 616.32 | 1.22 |

TABLE II-continued

| CMP # | STRUCTURE | Ca²⁺ Mob. | IUPAC Name | MASS | RT (min.) |
|---|---|---|---|---|---|
| 479 | 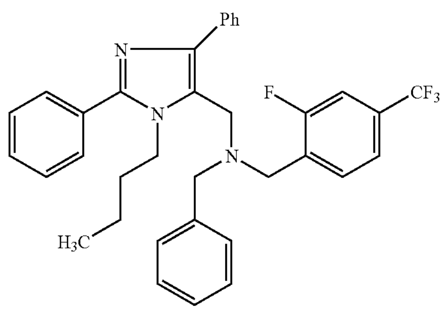 | | N-benzyl-1-(1-butyl-2,4-diphenyl-1H-imidazol-5-yl)-N-[2-fluoro-4-(trifluoromethyl)benzyl]methanamine | 573.35 | 1.25 |
| 480 | 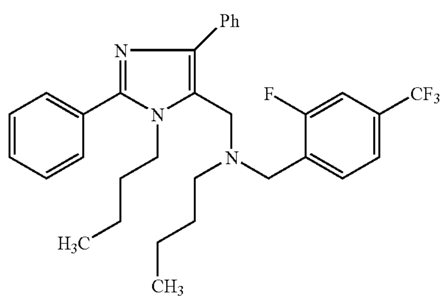 | | N-[(1-butyl-2,4-diphenyl-1H-imidazol-5-yl)methyl]-N-[2-fluoro-4-(trifluoromethyl)benzyl]butan-1-amine | 538.33 | 1.25 |
| 481 | 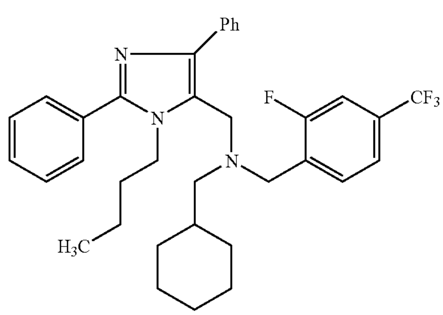 | | 1-(1-butyl-2,4-diphenyl-1H-imidazol-5-yl)-N-(cyclohexylmethyl)-N-[2-fluoro-4-(trifluoromethyl)benzyl]methanamine | 579.40 | 1.29 |
| 482 | 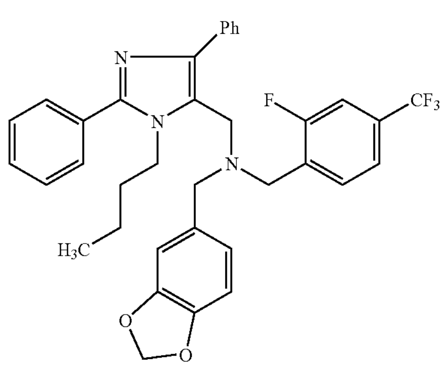 | * | 1-(1,3-benzodioxol-5-yl)-N-[(1-butyl-2,4-diphenyl-1H-imidazol-5-yl)methyl]-N-[2-fluoro-4-(trifluoromethy)benzyl]methanamine | 616.32 | 1.24 |

TABLE II-continued

| CMP # | STRUCTURE | Ca²⁺ Mob. | IUPAC Name | MASS | RT (min.) |
|---|---|---|---|---|---|
| 483 | 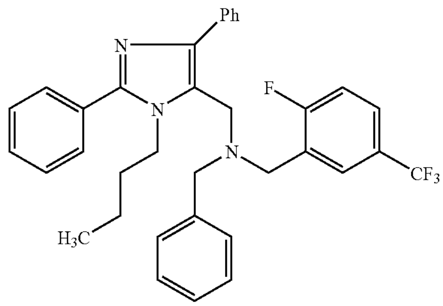 | | N-benzyl-1-(1-butyl-2,4-diphenyl-1H-imidazol-5-yl)-N-[2-fluoro-5-(trifluoromethyl)benzyl]methanamine | 573.35 | 1.24 |
| 484 | 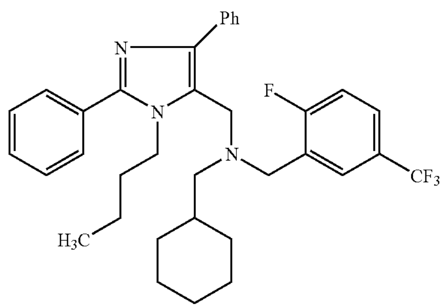 | * | 1-(1-butyl-2,4-diphenyl-1H-imidazo-5-yl)-N-(cyclohexylmethyl)-N-[2-fluoro-5-(trifluoromethyl)benzyl]methanamine | 579.40 | 1.28 |
| 485 | 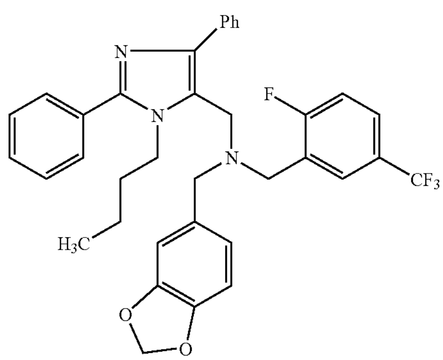 | * | 1-(1,3-benzodioxol-5-yl)-N-[(1-butyl-2,4-diphenyl-1H-imidazol-5-yl)methyl]-N-[2-fluoro-5-(trifluoromethyl)benzyl]methanamine | 617.35 | 1.23 |
| 486 | 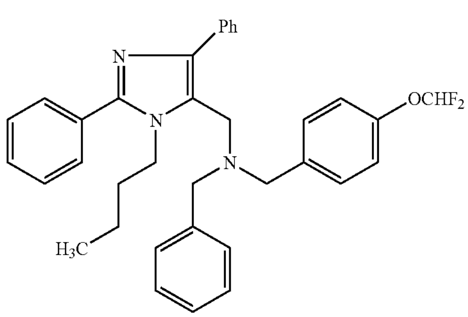 | * | N-benzyl-1-(1-butyl-2,4-diphenyl-1H-imidazol-5-yl)-N-[4-(difluoromethoxy)benzyl]methanamine | 553.36 | 1.22 |

TABLE II-continued

| CMP # | STRUCTURE | Ca²⁺ Mob. | IUPAC Name | MASS | RT (min.) |
|---|---|---|---|---|---|
| 487 | 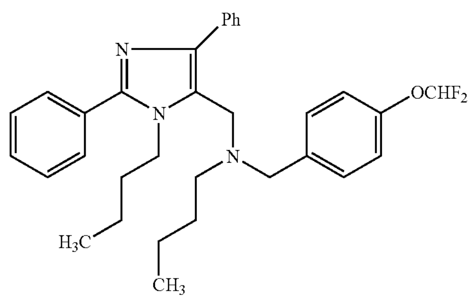 | * | N-[(1-butyl-2,4-diphenyl-1H-imidazol-5-yl)methyl]-N-[4-(difluoromethoxy)benzyl]butan-1-amine | 518.35 | 1.2 |
| 488 | 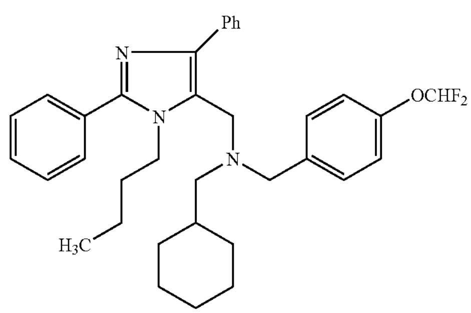 | * | 1-(1-butyl-2,4-diphenyl-1H-imidazol-5-yl)-N-(cyclohexylmethyl)-N-[4-(difluoromethoxy)benzyl]methanamine | 559.41 | 1.26 |
| 489 | 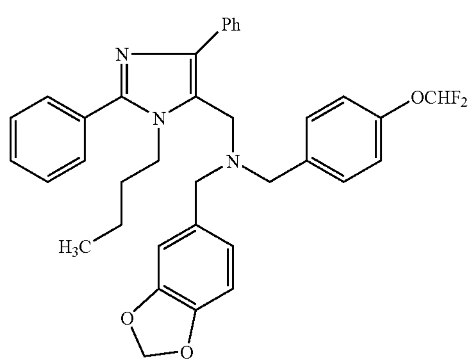 | * | 1-(1,3-benzodioxol-5-yl)-N-[(1-butyl-2,4-diphenyl-1H-imidazol-5-yl)methyl]-N-[4-(difluoromethoxy)benzyl]methanamine | 596.34 | 1.21 |
| 490 | 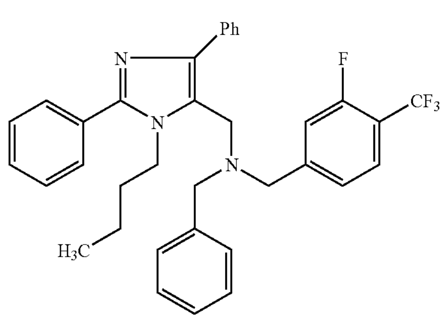 | | N-benzyl-1-(1-butyl-2,4-diphenyl-1H-imidazol-5-yl)-N-[3-fluoro-4-(trifluoromethyl)benzyl]methanamine | 572.32 | 1.24 |

TABLE II-continued

| CMP # | STRUCTURE | Ca²⁺ Mob. | IUPAC Name | MASS | RT (min.) |
|---|---|---|---|---|---|
| 491 | 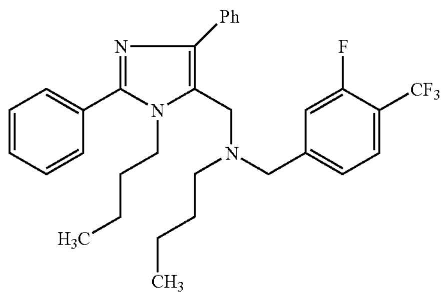 | * | N-[(1-butyl-2,4-diphenyl-1H-imidazol-5-yl)methyl]-N-[3-fluoro-4-(trifluoromethyl)benzyl]butan-1-amine | 538.33 | 1.25 |
| 492 | 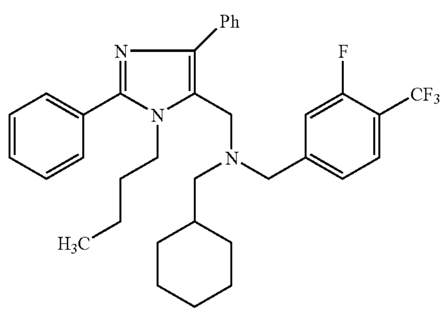 | | 1-(1-butyl-2,4-diphenyl-1H-imidazol-5-yl)-N-(cyclohexylmethyl)-N-[3-fluoro-4-(trifluoromethyl)benzyl]methanamine | 579.40 | 1.28 |
| 493 | 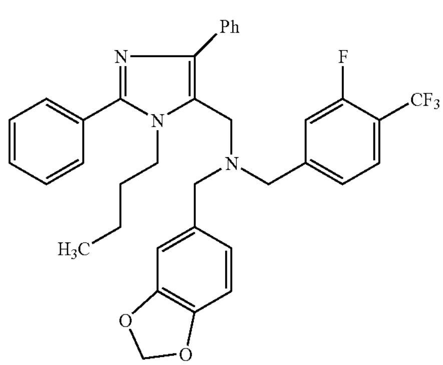 | * | 1-(1,3-benzodioxol-5-yl)-N-[(1-butyl-2,4-diphenyl-1H-imidazol-5-yl)methyl]-N-[3-fluoro-4-(trifluoromethyl)benzyl]methanamine | 616.32 | 1.23 |
| 494 | 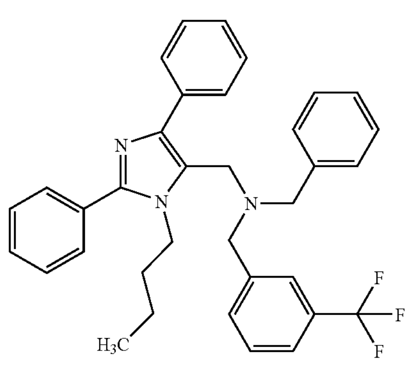 | * | N-benzyl-1-(1-butyl-2,4-diphenyl-1H-imidazol-5-yl)-N-[3-(trifluoromethyl)benzyl]methanamine | 552.29 | 1.22 |

TABLE II-continued

| CMP # | STRUCTURE | Ca²⁺ Mob. | IUPAC Name | MASS | RT (min.) |
|---|---|---|---|---|---|
| 495 | 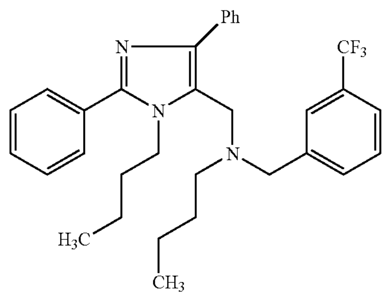 | * | N-[(1-butyl-2,4-diphenyl-1H-imidazol-5-yl)methyl]-N-[3-(trifluoromethyl)benzyl]butan-1-amine | 518.30 | 1.2 |
| 496 | 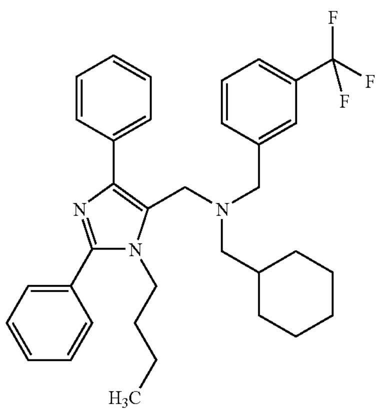 | * | 1-(1-butyl-2,4-diphenyl-1H-imidazol-5-yl)-N-(cyclohexylmethyl)-N-[3-(trifluoromethyl)benzyl]methanamine | 558.33 | 1.26 |
| 497 | 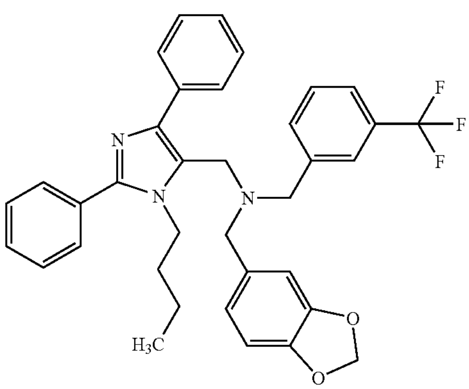 | * | 1-(1,3-benzodioxol-5-yl)-N-[(1-butyl-2,4-diphenyl-1H-imidazol-5-yl)methyl]-N-[3-(trifluoromethyl)benzyl]methanamine | 596.28 | 1.21 |
| 498 | 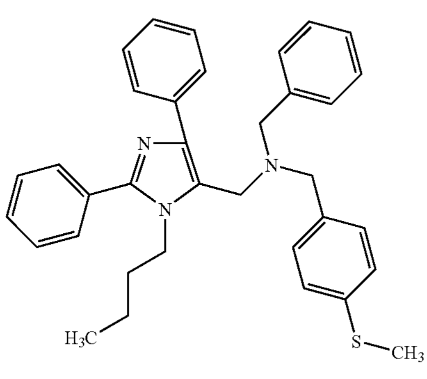 | * | N-benzyl-1-(1-butyl-2,4-diphenyl-1H-imidazol-5-yl)-N-[4-(methylthio)benzyl]methanamine | 532.31 | 1.24 |

TABLE II-continued

| CMP # | STRUCTURE | Ca²⁺ Mob. | IUPAC Name | MASS | RT (min.) |
|---|---|---|---|---|---|
| 499 | 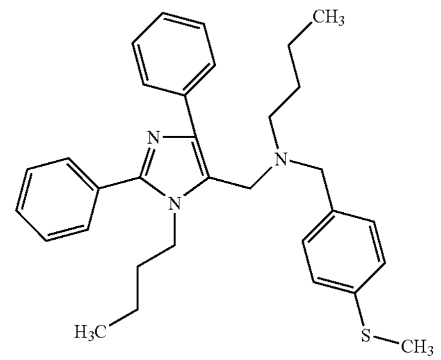 | * | N-[(1-butyl-2,4-diphenyl-1H-imidazol-5-yl)methyl]-N-[4-(methylthio)benzyl]butan-1-amine | 498.33 | 1.2 |
| 500 | 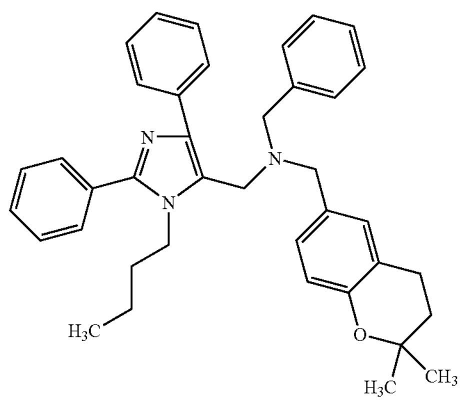 | * | N-benzyl-1-(1-butyl-2,4-diphenyl-1H-imidazol-5-yl)-N-[(2,2-dimethyl-3,4-dihydro-2H-chromen-6-yl)methyl]methanamine | 570.39 | 1.27 |
| 501 | 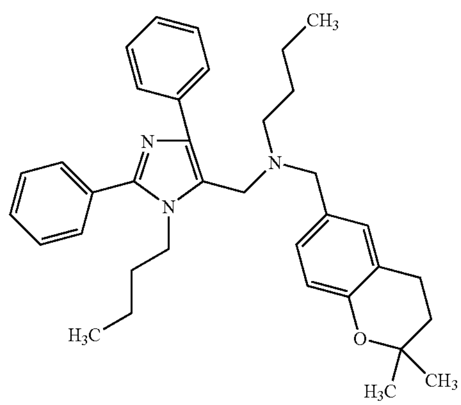 | * | N-[(1-butyl-2,4-diphenyl-1H-imidazol-5-yl)methyl]-N-[(2,2-dimethyl-3,4-dihydro-2H-chromen-6-yl)methyl]butan-1-amine | 536.42 | 1.21 |
| 502 | 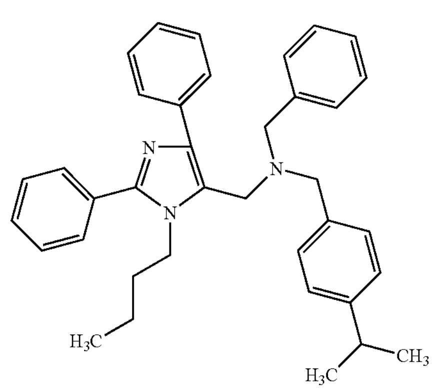 | * | N-benzyl-1-(1-butyl-2,4-diphenyl-1H-imidazol-5-yl)-N-(4-isopropylbenzyl)methanamine | 528.37 | 1.28 |

TABLE II-continued

| CMP # | STRUCTURE | Ca²⁺ Mob. | IUPAC Name | MASS | RT (min.) |
|---|---|---|---|---|---|
| 503 | 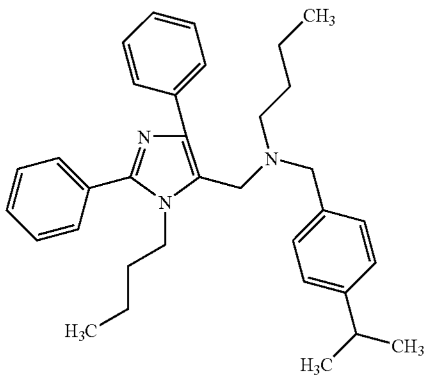 | * | N-[(1-butyl-2,4-diphenyl-1H-imidazol-5-yl)methyl]-N-(4-isopropylbenzyl)butan-1-amine | 494.38 | 1.24 |
| 504 | 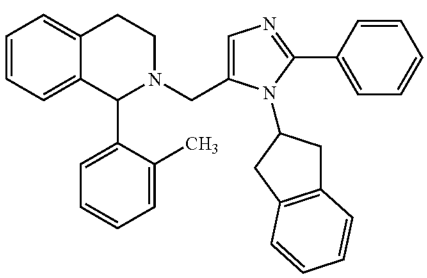 | * | 2-{[1-(2,3-dihydro-1H-inden-2-yl)-2-phenyl-1H-imidazol-5-yl]methyl)-1-(2-methylphenyl)-1,2,3,4-tetrahydroisoquinoline | 496.30 | 1.24 |
| 505 | 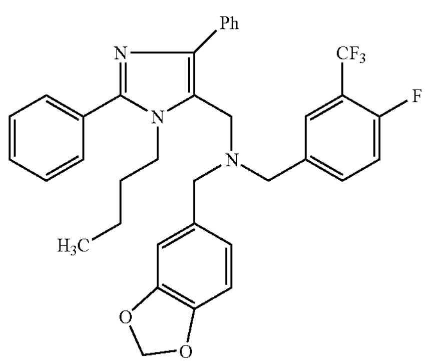 | * | 1-(1,3-benzodioxol-5-yl)-N-[(1-butyl-2,4-diphenyl-1H-imidazol-5-yl)methyl]-N-[4-fluoro-3-(trifluoromethyl)benzyl]methanamine | 616.30 | 1.23 |
| 506 | 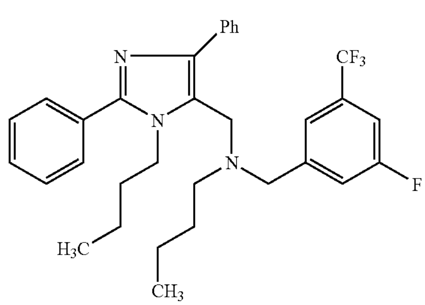 | | N-[(1-butyl-2,4-diphenyl-1H-imidazol-5-yl)methyl]-N-[3-fluoro-5-(trifluoromethyl)benzyl]butan-1-amine | 538.30 | 1.26 |

TABLE II-continued

| CMP # | STRUCTURE | Ca²⁺ Mob. | IUPAC Name | MASS | RT (min.) |
|---|---|---|---|---|---|
| 507 | 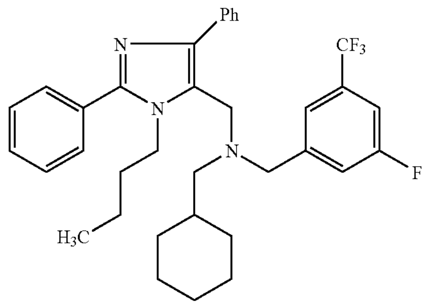 | | 1-(1-butyl-2,4-diphenyl-1H-imidazol-5-yl)-N-(cyclohexylmethyl)-N-[3-fluoro-5-(trifluoromethyl)benzyl]methanamine | 578.34 | 1.28 |
| 508 | 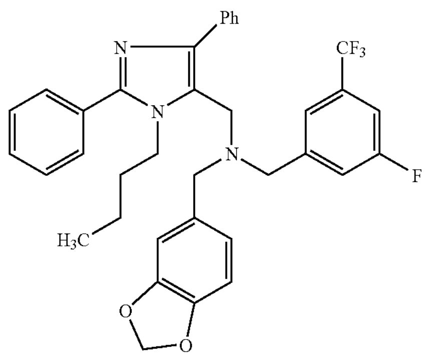 | * | 1-(1,3-benzodioxol-5-yl)-N-[(1-butyl-2,4-diphenyl-1H-imidazol-5-yl)methyl]-N-[3-fluoro-5-(trifluoromethyl)benzyl]methanamine | 616.29 | 1.24 |
| 509 | 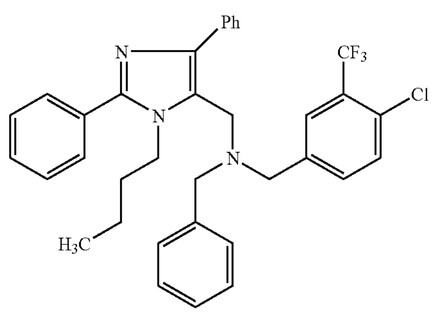 | | N-benzyl-1-(1-butyl-2,4-diphenyl-1H-imidazol-5-yl)-N-[4-chloro-3-(trifluoromethyl)benzyl]methanamine | 588.28 | 1.26 |
| 510 | 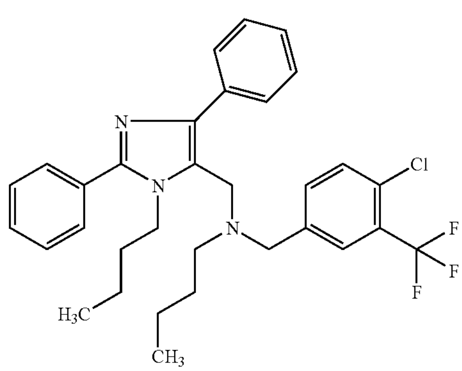 | | N-[(1-butyl-2,4-diphenyl-1H-imidazol-5-yl)methyl]-N-[4-chloro-3-(trifluoromethyl)benzyl]butan-1-amine | 554.30 | 1.25 |

TABLE II-continued

| CMP # | STRUCTURE | Ca²⁺ Mob. | IUPAC Name | MASS | RT (min.) |
|---|---|---|---|---|---|
| 511 | 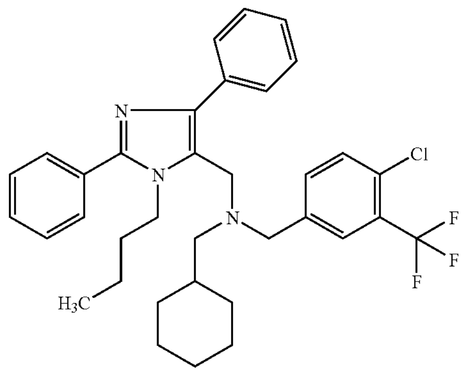 | | 1-(1-butyl-2,4-diphenyl-1H-imidazol-5-yl)-N-[4-chloro-3-(trifluoromethyl)benzyl]-N-(cyclohexylmethyl)methanamine | 594.33 | 1.3 |
| 512 | 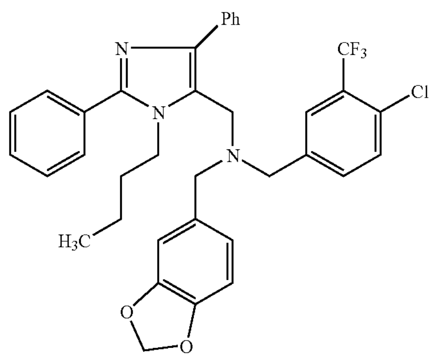 | | 1-(1,3-benzodioxol-5-yl)-N-[(1-butyl-2,4-diphenyl-1H-imidazol-5-yl)methyl]-N-[4-chloro-3-(trifluoromethyl)benzyl]methanamine | 632.28 | 1.24 |
| 513 | 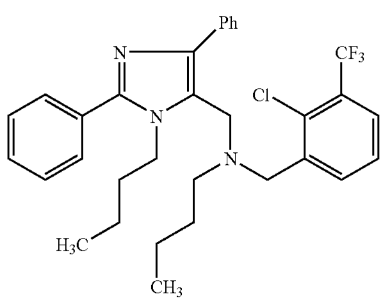 | | N-[(1-butyl-2,4-diphenyl-1H-imidazol-5-yl)methyl]-N-[2-chloro-3-(trifluoromethyl)benzyl]butan-1-amine | 554.28 | 1.26 |
| 514 | 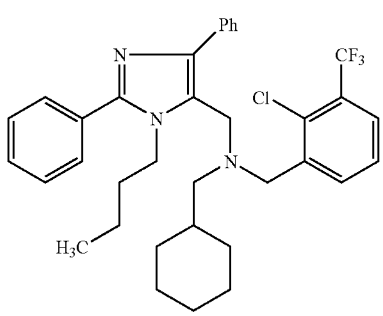 | | 1-(1-butyl-2,4-diphenyl-1H-imidazol-5-yl)-N-[2-chloro-3-(trifluoromethyl)benzyl]-N-(cyclohexylmethyl)methanamine | 594.32 | 1.3 |

TABLE II-continued

| CMP # | STRUCTURE | Ca²⁺ Mob. | IUPAC Name | MASS | RT (min.) |
|---|---|---|---|---|---|
| 515 | 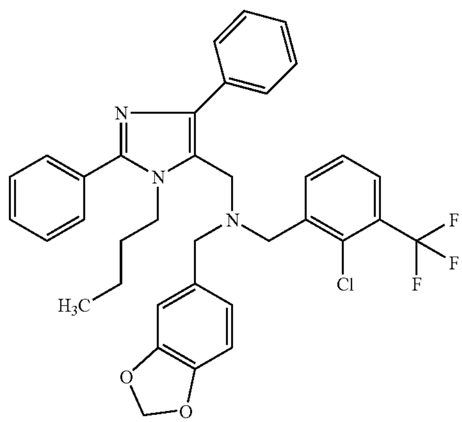 | * | 1-(1,3-benzodioxol-5-yl)-N-[(1-butyl-2,4-diphenyl-1H-imidazol-5-yl)methyl]-N-[2-chloro-3-(trifluoromethyl)benzyl]methanamine | 632.27 | 1.24 |
| 516 | 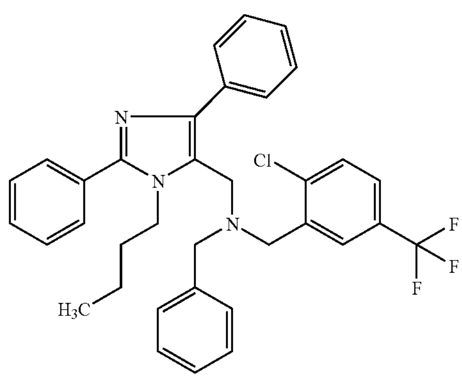 | | N-benzyl-1-(1-butyl-2,4-diphenyl-1H-imidazol-5-yl)-N-[2-chloro-5-(trifluoromethyl)benzyl]methanamine | 588.28 | 1.25 |
| 517 | 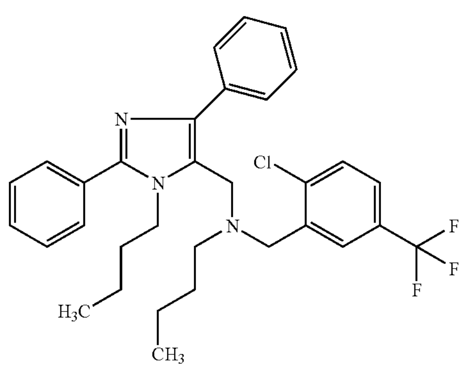 | | N-[(1-butyl-2,4-diphenyl-1H-imidazol-5-yl)methyl]-N-[2-chloro-5-(trifluoromethyl)benzyl]butan-1-amine | 554.28 | 1.26 |
| 518 | 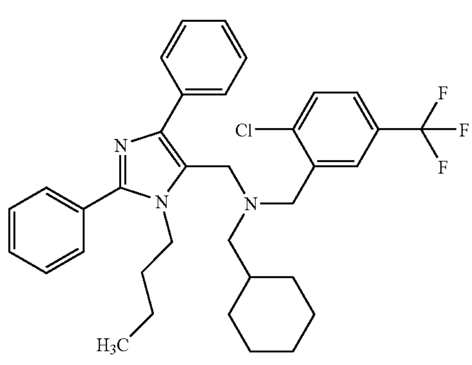 | | 1-(1-butyl-2,4-diphenyl-1H-imidazol-5-yl)-N-[2-chloro-5-(trifluoromethyl)benzyl]-N-(cyclohexylmethyl)methanamine | 594.34 | 1.29 |

TABLE II-continued

| CMP # | STRUCTURE | Ca²⁺ Mob. | IUPAC Name | MASS | RT (min.) |
|---|---|---|---|---|---|
| 519 | 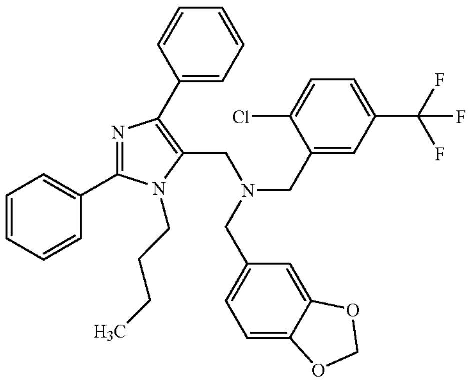 | | 1-(1,3-benzodioxol-5-yl)-N-[(1-butyl-2,4-diphenyl-1H-imidazol-5-yl)methyl]-N-[2-chloro-5-(trifluoromethyl)benzyl]methanamine | 632.27 | 1.25 |
| 520 | 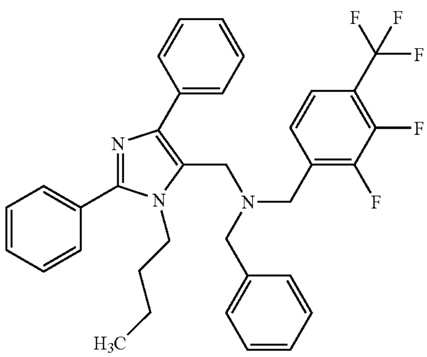 | | N-benzyl-1-(1-butyl-2,4-diphenyl-1H-imidazol-5-yl)-N-[2,3-difluoro-4-(trifluoromethyl)benzyl]methanamine | 590.28 | 1.24 |
| 521 | 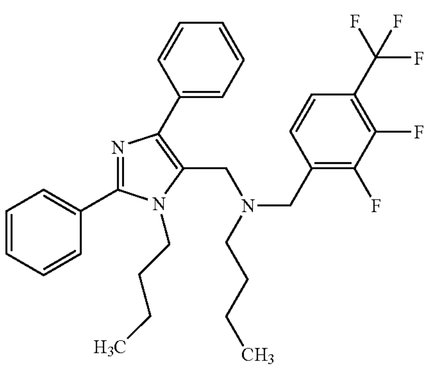 | | N-[(1-butyl-2,4-diphenyl-1H-imidazol-5-yl)methyl]-N-[2,3-difluoro-4-(trifluoromethyl)benzyl]butan-1-amine | 557.33 | 1.26 |
| 522 | 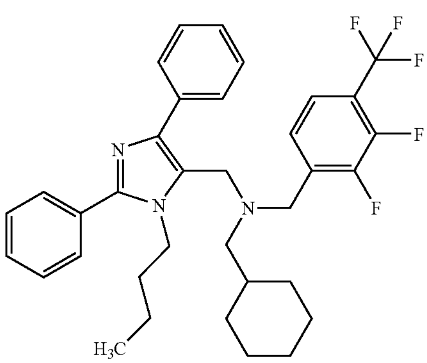 | | 1-(1-butyl-2,4-diphenyl-1H-imidazol-5-yl)-N-(cyclohexylmethyl)-N-[2,3-difluoro-4-(trifluoromethyl)benzyl]methanamine | 596.34 | 1.29 |

TABLE II-continued

| CMP # | STRUCTURE | Ca²⁺ Mob. | IUPAC Name | MASS | RT (min.) |
|---|---|---|---|---|---|
| 523 | 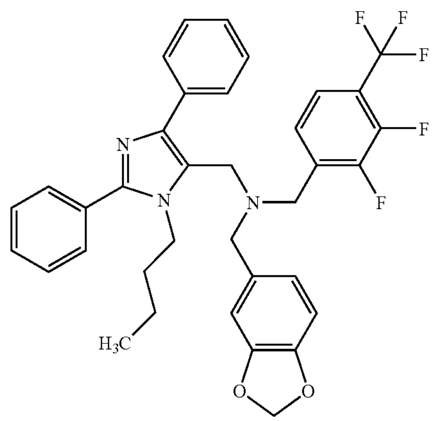 | * | 1-(1,3-benzodioxol-5-yl)-N-[(1-butyl-2,4-diphenyl-1H-imidazol-5-yl)methyl]-N-[2,3-difluoro-4-(trifluoromethyl)benzyl]methanamine | 634.28 | 1.23 |
| 524 | 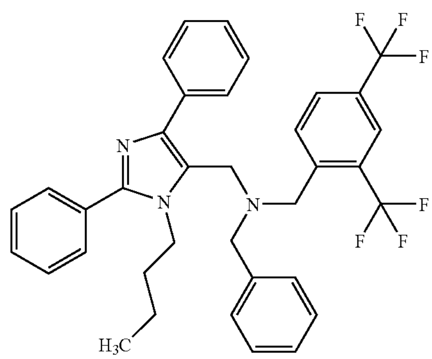 | | N-benzyl-1-[2,4-bis(trifluoromethyl)phenyl]-N-[(1-butyl-2,4-diphenyl-1H-imidazol-5-yl)methyl]methanamine | 622.30 | 1.27 |
| 525 | 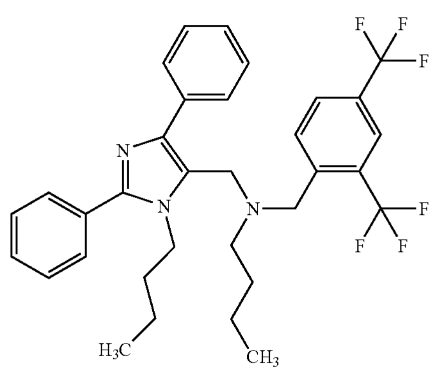 | | N-[2,4-bis(trifluoromethyl)benzyl]-N-[(1-butyl-2,4-diphenyl-1H-imidazol-5-yl)methyl]butan-1-amine | 589.34 | 1.28 |
| 526 | 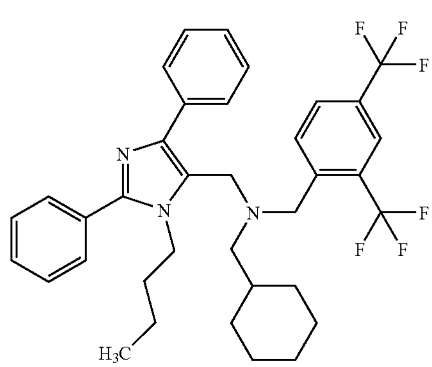 | | 1-[2,4-bis(trifluoromethyl)phenyl]-N-[(1-butyl-2,4-diphenyl-1H-imidazol-5-yl)methyl]-N-(cyclohexylmethyl)methanamine | 628.34 | 1.31 |

TABLE II-continued

| CMP # | STRUCTURE | Ca²⁺ Mob. | IUPAC Name | MASS | RT (min.) |
|---|---|---|---|---|---|
| 527 | 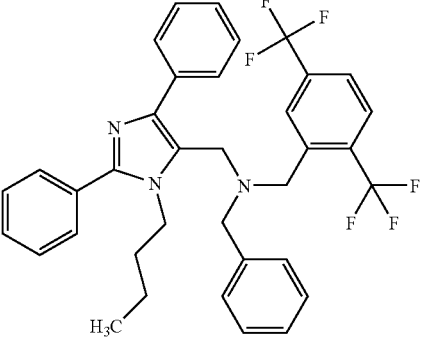 | | N-benzyl-1-[2,5-bis(trifluoromethyl)phenyl]-N-[(1-butyl-2,4-diphenyl-1H-imidazol-5-yl)methyl]methanamine | 622.32 | 1.26 |
| 528 | 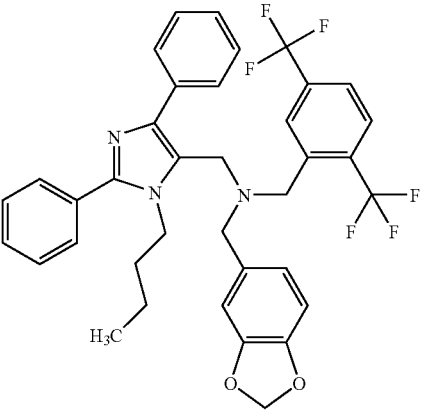 | * | 1-(1,3-benzodioxol-5-yl)-N-[2,5-bis(trifluoromethyl)benzyl]-N-[(1-butyl-2,4-diphenyl-1H-imidazol-5-yl)methyl]methanamine | 666.31 | 1.25 |
| 529 | 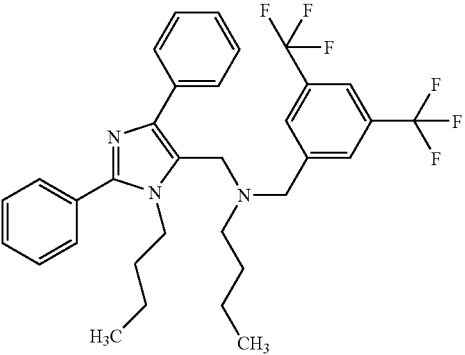 | | N-[3,5-bis(trifluoromethyl)benzyl]-N-[(1-butyl-2,4-diphenyl-1H-imidazol-5-yl)methyl]butan-1-amine | 588.32 | 1.27 |
| 530 | 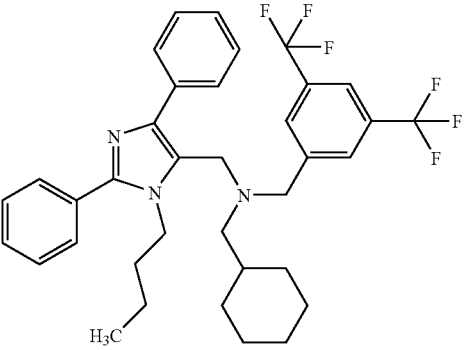 | | 1-[3,5-bis(trifluoromethyl)phenyl]-N-[(1-butyl-2,4-diphenyl-1H-imidazol-5-yl)methyl]-N-(cyclohexylmethyl)methanamine | 628.39 | 1.32 |

TABLE II-continued
| CMP # | STRUCTURE | Ca²⁺ Mob. | IUPAC Name | MASS | RT (min.) |
|---|---|---|---|---|---|
| 531 | 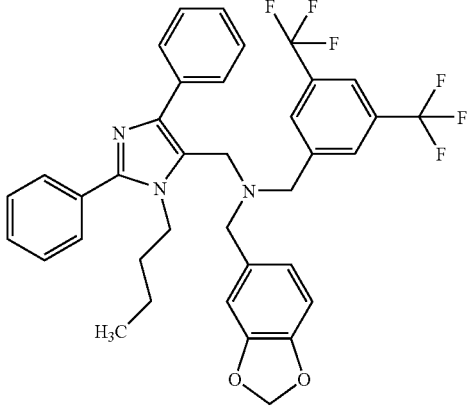 | * | 1-(1,3-benzodioxol-5-yl)-N-[3,5-bis(trifluoromethyl)benzyl]-N-[(1-butyl-2,4-diphenyl-1H-imidazol-5-yl)methyl]methanamine | 667.33 | 1.25 |
| 532 | 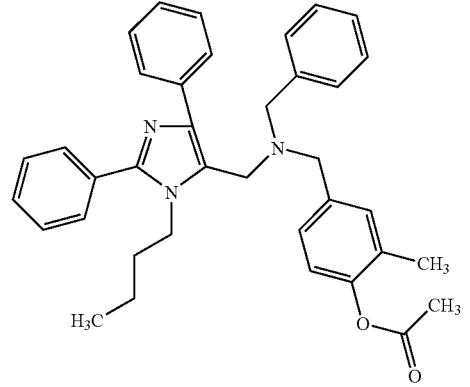 | * | 4-({benzyl[(1-butyl-2,4-diphenyl-1H-imidazol-5-yl)methyl]amino}methyl)-2-methylphenyl acetate | 558.35 | 1.22 |
| 533 | 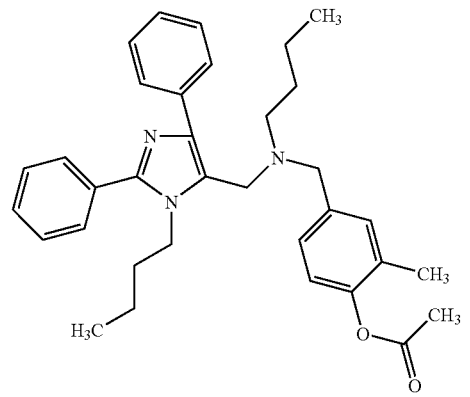 | * | 4-({butyl[(1-butyl-2,4-diphenyl-1H-imidazol-5-yl)methyl]amino}methyl)-2-methylphenyl acetate | 524.37 | 1.19 |

TABLE II-continued

| CMP # | STRUCTURE | Ca²⁺ Mob. | IUPAC Name | MASS | RT (min.) |
|---|---|---|---|---|---|
| 534 | 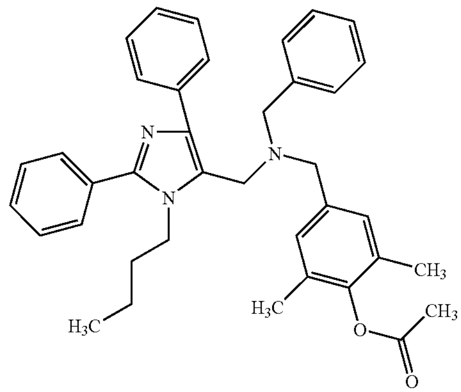 | * | 4-({benzyl[(1-butyl-2,4-diphenyl-1H-imidazol-5-yl)methyl]amino}methyl)-2,6-dimethylphenyl acetate | 572.37 | 1.23 |
| 535 | 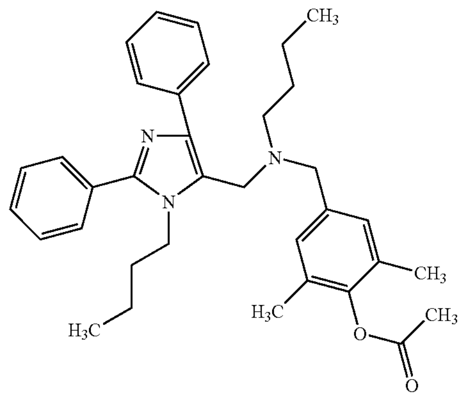 | * | 4-({butyl[(1-butyl-2,4-diphenyl-1H-imidazol-5-yl)methyl]amino}methyl)-2,6-dimethylphenyl acetate | 538.38 | 1.2 |
| 536 | 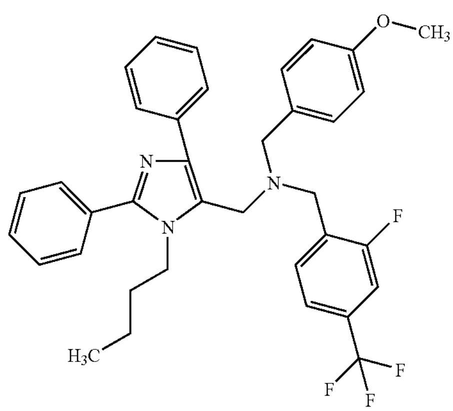 | | 1-(1-butyl-2,4-diphenyl-1H-imidazol-5-yl)-N-[2-fluoro-4-(trifluoromethyl)benzyl]-N-(4-methoxybenzyl)methanamine | 602.35 | 1.25 |
| 537 | 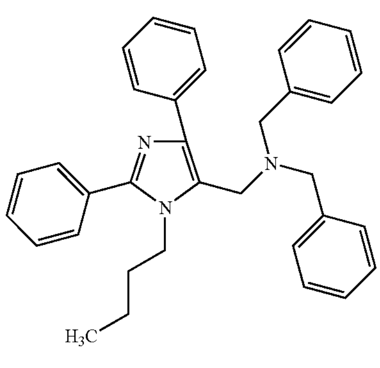 | * | N,N-dibenzyl-1-(1-butyl-2,4-diphenyl-1H-imidazol-5-yl)methanamine | 486.35 | 1.23 |

TABLE II-continued

| CMP # | STRUCTURE | Ca²⁺ Mob. | IUPAC Name | MASS | RT (min.) |
|---|---|---|---|---|---|
| 538 | 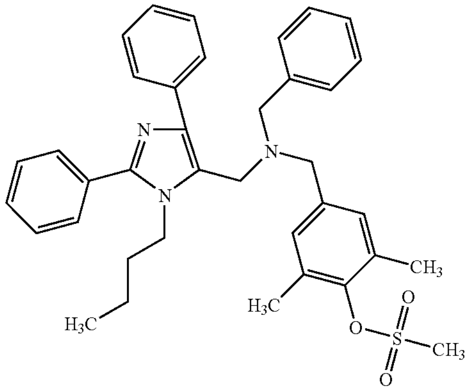 | | 4-({benzyl[(1-butyl-2,4-diphenyl-1H-imidazol-5-yl)methyl]amino}methyl)-2,6-dimethylphenyl methanesulfonate | 608.37 | 1.21 |
| 539 | 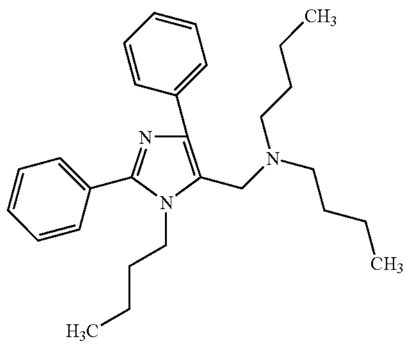 | * | N-butyl-N-[(1-butyl-2,4-diphenyl-1H-imidazol-5-yl)methyl]butan-1-amine | 418.37 | 1.12 |
| 540 | 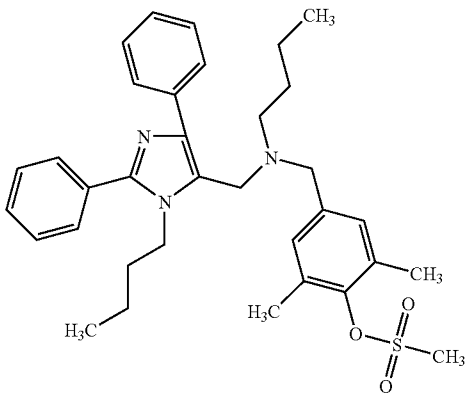 | | 4-({butyl[(1-butyl-2,4-diphenyl-1H-imidazol-5-yl)methyl]amino}methyl)-2,6-dimethylphenyl methanesulfonate | 574.38 | 1.21 |
| 541 | 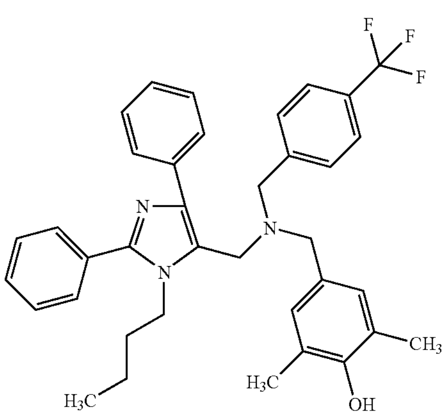 | * | 4-({[(1-butyl-2,4-diphenyl-1H-imidazol-5-yl)methyl][4-(trifluoromethyl)benzyl]amino}methyl)-2,6-dimethylphenol | 598.37 | 1.25 |

TABLE II-continued

| CMP # | STRUCTURE | Ca²⁺ Mob. | IUPAC Name | MASS | RT (min.) |
|---|---|---|---|---|---|
| 542 | 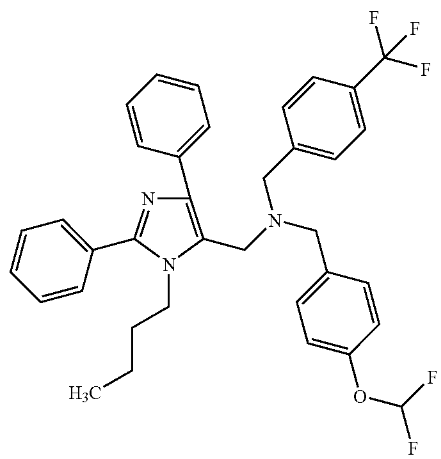 | * | 1-(1-butyl-2,4-diphenyl-1H-imidazol-5-yl)-N-[4-(difluoromethoxy)benzyl]-N-[4-(trifluoromethyl)benzyl]methanamine | 620.34 | 1.23 |
| 543 | 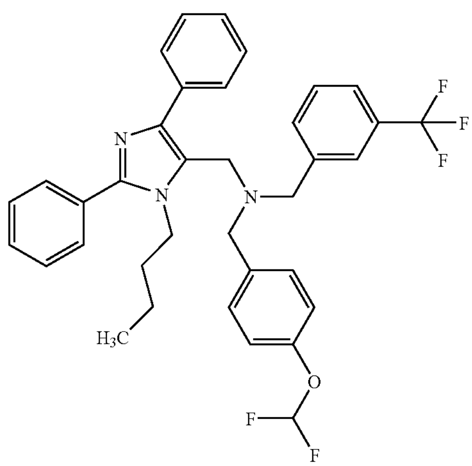 | | 1-(1-butyl-2,4-diphenyl-1H-imidazol-5-yl)-N-[4-(difluoromethoxy)benzyl]-N-[3-(trifluoromethyl)benzyl]methanamine | 620.28 | 1.22 |
| 544 | 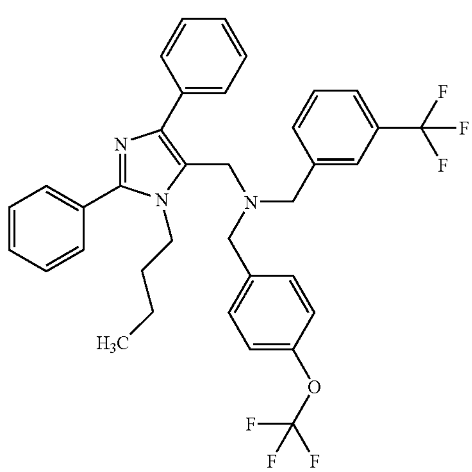 | | 1-(1-butyl-2,4-diphenyl-1H-imidazol-5-yl)-N-[4-(trifluoromethoxy)benzyl]-N-[3-(trifluoromethyl)benzyl]methanamine | 639.30 | 1.26 |

TABLE II-continued

| CMP # | STRUCTURE | Ca²⁺ Mob. | IUPAC Name | MASS | RT (min.) |
|---|---|---|---|---|---|
| 545 | 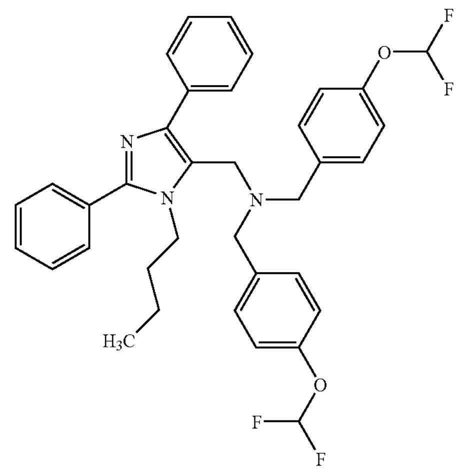 | * | 1-(1-butyl-2,4-diphenyl-1H-imidazol-5-yl)-N,N-bis[4-(difluoromethoxy)benzyl]methanamine | 618.28 | 1.2 |
| 546 | 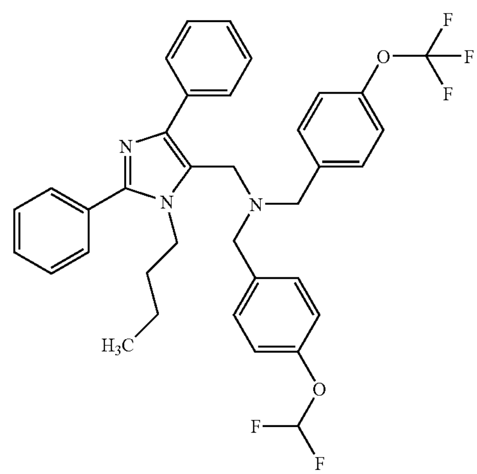 | | 1-(1-butyl-2,4-diphenyl-1H-imidazol-5-yl)-N-[4-(difluoromethoxy)benzyl]-N-[4-(trifluoromethoxy)benzyl]methanamine | | |
| 547 | 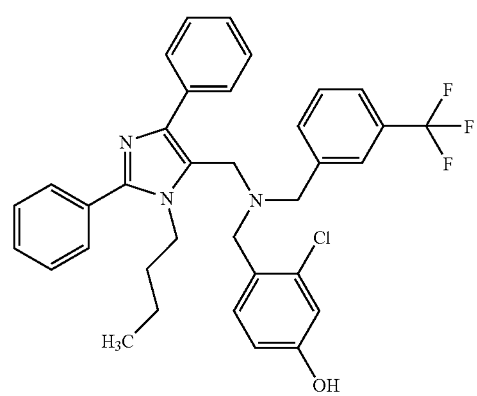 | | 4-({[(1-butyl-2,4-diphenyl-1H-imidazol-5-yl)methyl][3-(trifluoromethyl)benzyl]amino}methyl)-3-chlorophenol | 604.25 | 1.22 |

TABLE II-continued

| CMP # | STRUCTURE | Ca²⁺ Mob. | IUPAC Name | MASS | RT (min.) |
|---|---|---|---|---|---|
| 548 | 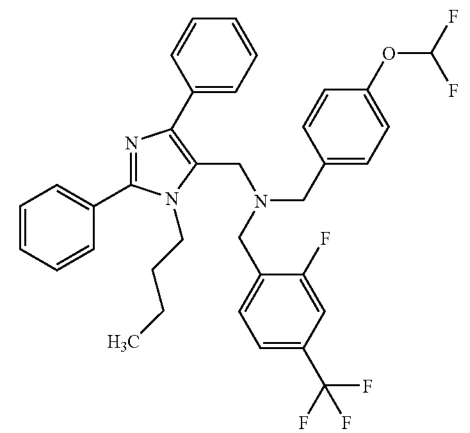 | | 1-(1-butyl-2,4-diphenyl-1H-imidazol-5-yl)-N-[4-(difluoromethoxy)benzyl]-N-[2-fluoro-4-(trifluoromethyl)benzyl]methanamine | 638.26 | 1.23 |
| 549 | 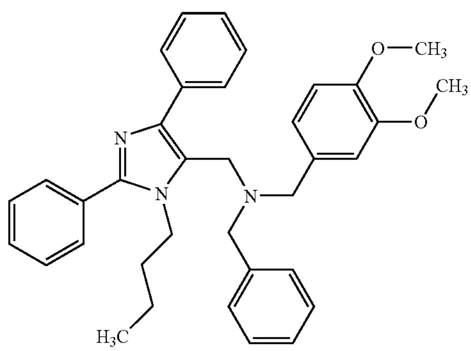 | | N-benzyl-1-(1-butyl-2,4-diphenyl-1H-imidazol-5-yl)-N-(3,4-dimethoxybenzyl)methanamine | 546.32 | 1.19 |
| 550 | 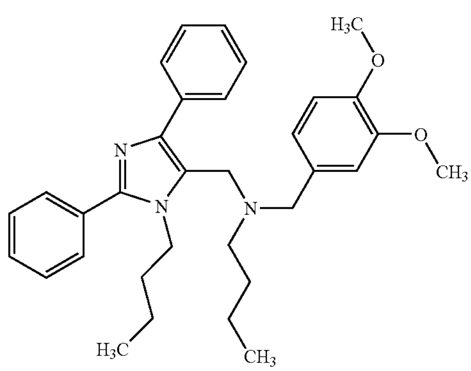 | * | N-[(1-butyl-2,4-diphenyl-1H-imidazol-5-yl)methyl]-N-(3,4-dimethoxybenzyl)butan-1-amine | 512.33 | 1.13 |
| 551 | 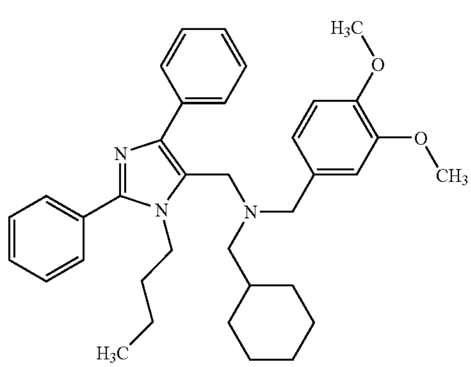 | * | 1-(1-butyl-2,4-diphenyl-1H-imidazol-5-yl)-N-(cyclohexylmethyl)-N-(3,4-dimethoxybenzyl)methanamine | 552.37 | 1.24 |

TABLE II-continued

| CMP # | STRUCTURE | Ca²⁺ Mob. | IUPAC Name | MASS | RT (min.) |
|---|---|---|---|---|---|
| 552 | 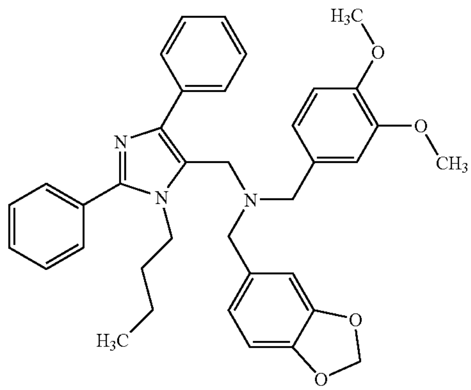 | | 1-(1,3-benzodioxol-5-yl)-N-[(1-butyl-2,4-diphenyl-1H-imidazol-5-yl)methyl]-N-(3,4-dimethoxybenzyl)methanamine | 590.31 | 1.18 |
| 553 | 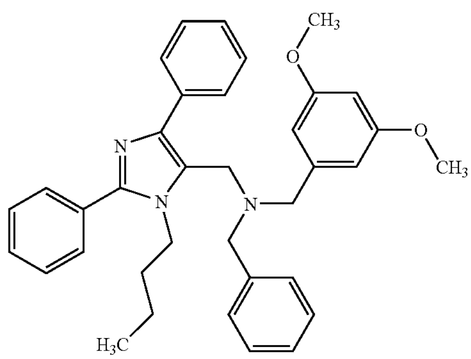 | * | N-benzyl-1-(1-butyl-2,4-diphenyl-1H-imidazol-5-yl)-N-(3,5-dimethoxybenzyl)methanamine | 546.32 | 1.23 |
| 554 | 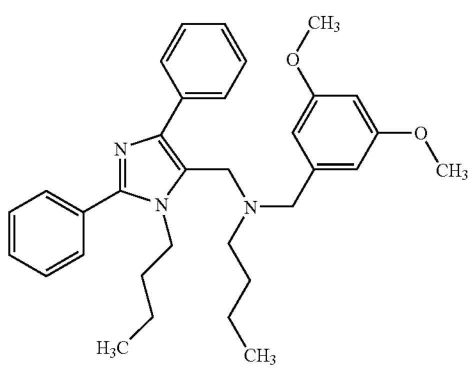 | | N-[(1-butyl-2,4-diphenyl-1H-imidazol-5-yl)methyl]-N-(3,5-dimethoxybenzyl)butan-1-amine | 512.32 | 1.2 |
| 555 | 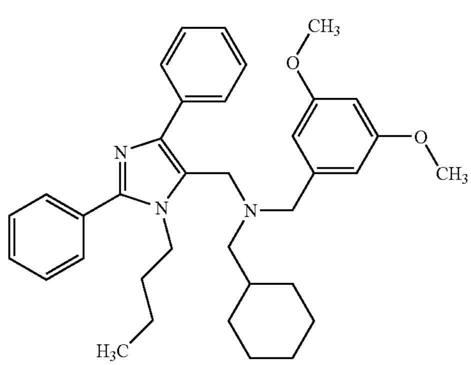 | * | 1-(1-butyl-2,4-diphenyl-1H-imidazol-5-yl)-N-(cyclohexylmethyl)-N-(3,5-dimethoxybenzyl)methanamine | 552.36 | 1.27 |

TABLE II-continued

| CMP # | STRUCTURE | Ca²⁺ Mob. | IUPAC Name | MASS | RT (min.) |
|---|---|---|---|---|---|
| 556 | 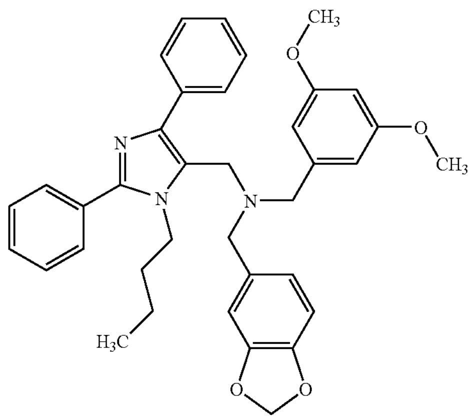 | * | 1-(1,3-benzodioxol-5-yl)-N-[(1-butyl-2,4-diphenyl-1H-imidazol-5-yl)methyl]-N-(3,5-dimethoxybenzyl)methanamine | 590.31 | 1.21 |
| 557 | 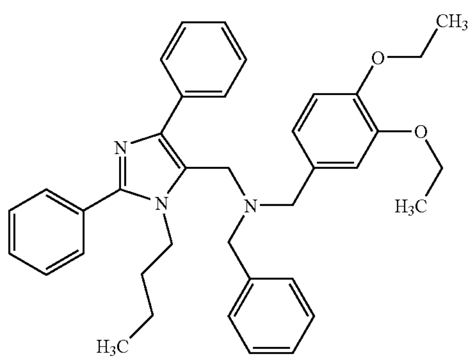 | | N-benzyl-1-(1-butyl-2,4-diphenyl-1H-imidazol-5-yl)-N-(3,4-diethoxybenzyl)methanamine | 574.35 | 1.23 |
| 558 | 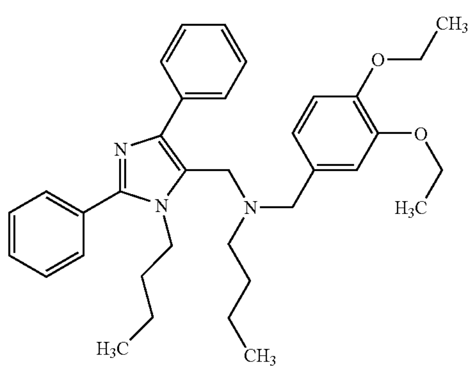 | * | N-[(1-butyl-2,4-diphenyl-1H-imidazol-5-yl)methyl]-N-(3,4-diethoxybenzyl)butan-1-amine | 540.36 | 1.17 |
| 559 | 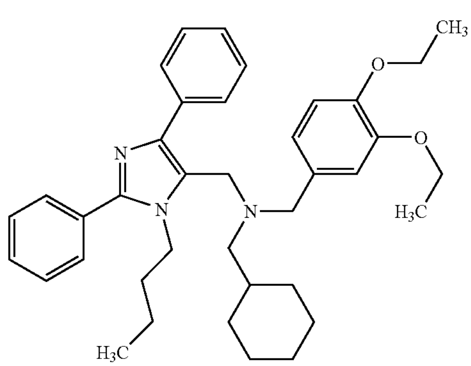 | * | 1-(1-butyl-2,4-diphenyl-1H-imidazol-5-yl)-N-(cyclohexylmethyl)-N-(3,4-diethoxybenzyl)methanamine | 581.42 | 1.28 |

TABLE II-continued

| CMP # | STRUCTURE | Ca²⁺ Mob. | IUPAC Name | MASS | RT (min.) |
|---|---|---|---|---|---|
| 560 | 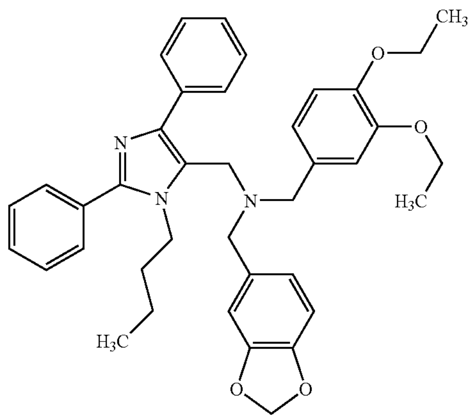 | * | 1-(1,3-benzodioxol-5-yl)-N-[(1-butyl-2,4-diphenyl-1H-imidazol-5-yl)methyl]-N-(3,4-diethoxybenzyl)methanamine | | |
| 561 | 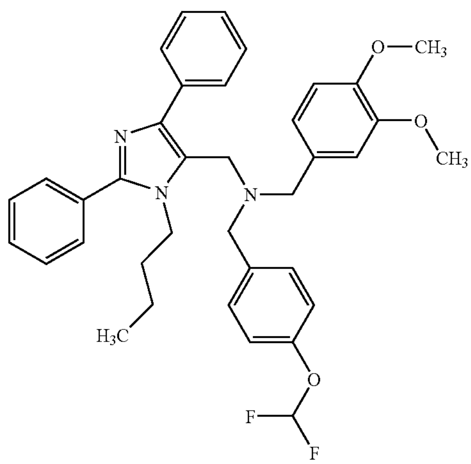 | * | 1-(1-butyl-2,4-diphenyl-1H-imidazol-5-yl)-N-[4-(difluoromethoxy)benzyl]-N-(3,4-dimethoxybenzyl)methanamine | 612.32 | 1.19 |
| 562 | 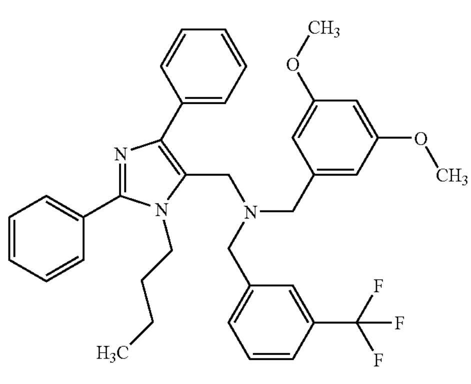 | * | 1-(1-butyl-2,4-diphenyl-1H-imidazol-5-yl)-N-(3,5-dimethoxybenzyl)-N-[3-(trifluoromethyl)benzyl]methanamine | 614.30 | 1.23 |

TABLE II-continued

| CMP # | STRUCTURE | Ca²⁺ Mob. | IUPAC Name | MASS | RT (min.) |
|---|---|---|---|---|---|
| 563 | 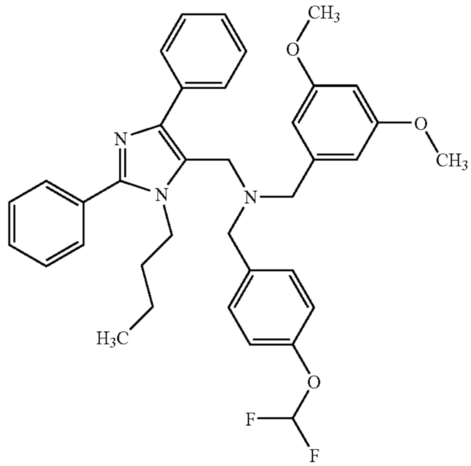 | * | 1-(1-butyl-2,4-diphenyl-1H-imidazol-5-yl)-N-[4-(difluoromethoxy)benzyl]-N-(3,5-dimethoxybenzyl)methanamine | 612.31 | 1.21 |
| 564 | 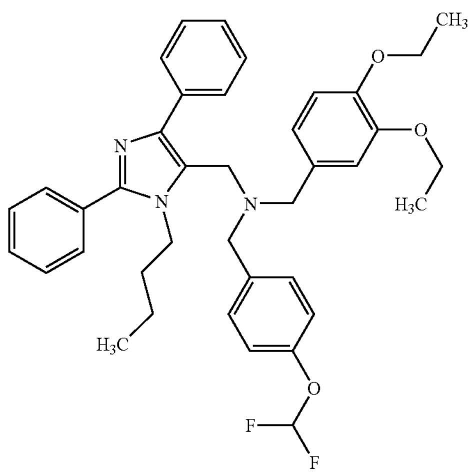 | * | 1-(1-butyl-2,4-diphenyl-1H-imidazol-5-yl)-N-(3,4-diethoxybenzyl)-N-[4-(difluoromethoxy)benzyl]methanamine | 640.34 | 1.22 |
| 565 | 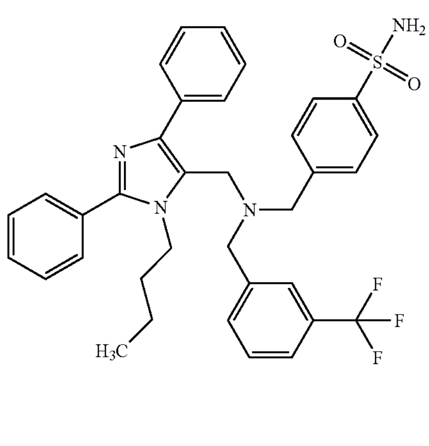 | * | 4-({[(1-butyl-2,4-diphenyl-1H-imidazol-5-yl)methyl][3-(trifluoromethyl)benzyl]amino}methyl)benzenesulfonamide | 633.27 | 1.15 |

TABLE II-continued

| CMP # | STRUCTURE | Ca²⁺ Mob. | IUPAC Name | MASS | RT (min.) |
|---|---|---|---|---|---|
| 566 | 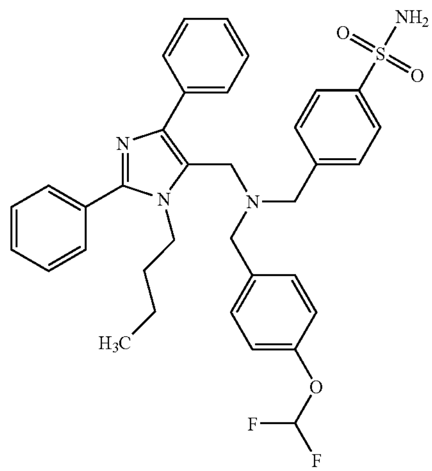 | * | 4-({[(1-butyl-2,4-diphenyl-1H-imidazol-5-yl)methyl][4-(difluoromethoxy)benzyl]amino}methyl)benzenesulfonamide | | |
| 567 | 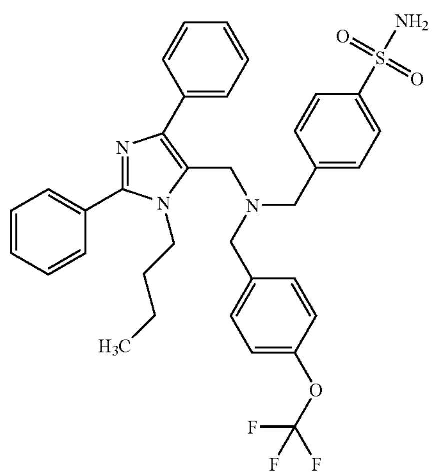 | * | 4-({[(1-butyl-2,4-diphenyl-1H-imidazol-5-yl)methyl][4-(trifluoromethoxy)benzyl]amino}methyl)benzenesulfonamide | 649.27 | 1.16 |
| 568 | 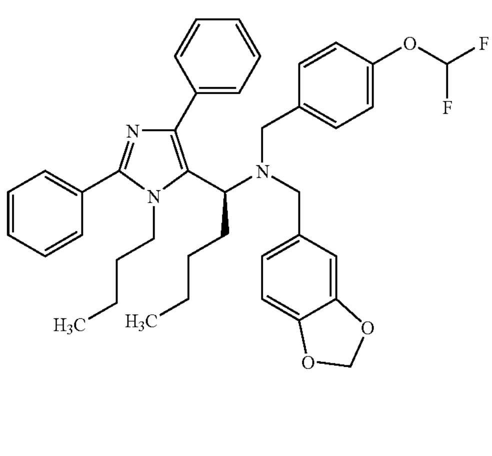 | * | (1R)-N-(1,3-benzodioxol-5-ylmethyl)-1-(1-butyl-2,4-diphenyl-1H-imidazol-5-yl)-N-[4-(difluoromethoxy)benzyl]pentan-1-amine | 652.43 | 1.26 |

TABLE II-continued

| CMP # | STRUCTURE | Ca²⁺ Mob. | IUPAC Name | MASS | RT (min.) |
|---|---|---|---|---|---|
| 569 | 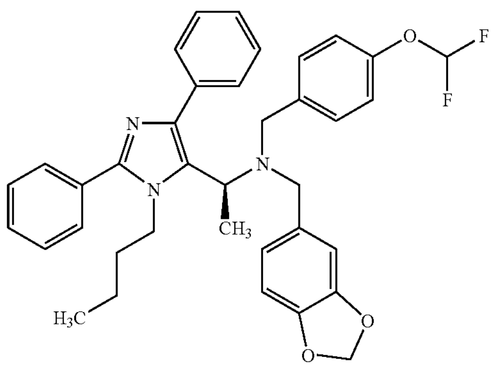 | * | (1R)-N-(1,3-benzodioxol-5-ylmethyl)-1-(1-butyl-2,4-diphenyl-1H-imidazol-5-yl)-N-[4-(difluoromethoxy)benzyl]ethanamine | 611.40 | 1.21 |
| 570 | 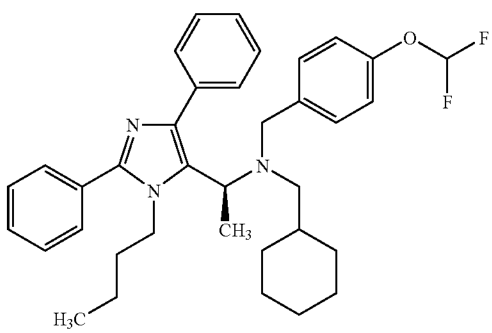 | | (1R)-1-(1-butyl-2,4-diphenyl-1H-imidazol-5-yl)-N-(cyclohexylmethyl)-N-[4-(difluoromethoxy)benzyl]ethanamine | 572.41 | 1.26 |
| 571 | 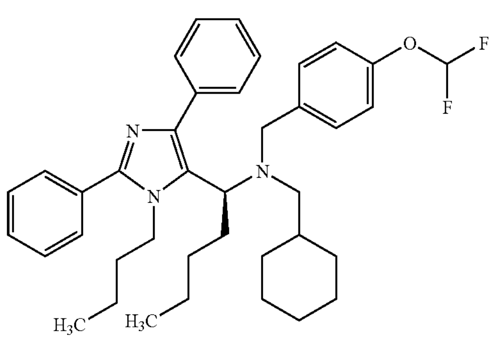 | * | (1S)-1-(1-butyl-2,4-diphenyl-1H-imidazol-5-yl)-N-(cyclohexylmethyl)-N-[4-(difluoromethoxy)benzyl]pentan-1-amine | 615.50 | 1.3 |
| 572 | Chiral | * | (1S)-1-(1-butyl-2,4-diphenyl-1H-imidazol-5-yl)-N-(cyclohexylmethyl)-N-[4-(difluoromethoxy)benzyl]ethanamine | 572.41 | 1.26 |

TABLE II-continued
| CMP # | STRUCTURE | Ca²⁺ Mob. | IUPAC Name | MASS | RT (min.) |
|---|---|---|---|---|---|
| 573 | 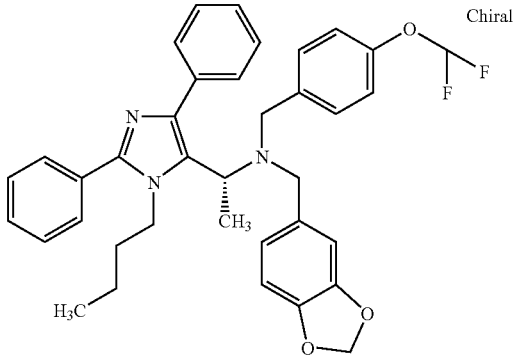 | * | | 610.37 | 1.22 |
| 574 | 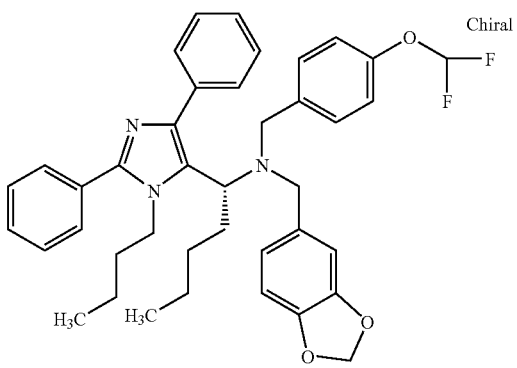 | * | | 652.42 | 1.26 |
| 575 | 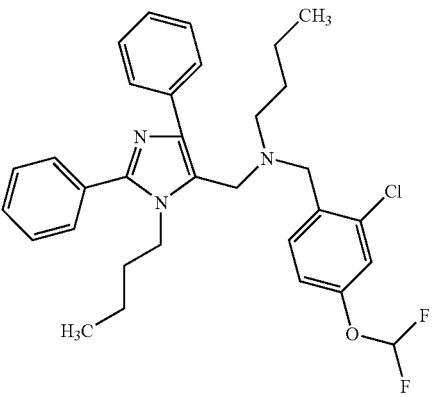 | * | N-[(1-butyl-2,4-diphenyl-1H-imidazol-5-yl)methyl]-N-[2-chloro-4-(difluoromethoxy)benzyl]butan-1-amine | 552.27 | 1.25 |
| 576 | 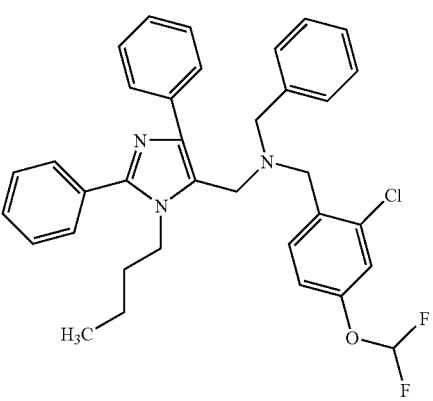 | * | N-benzyl-1-(1-butyl-2,4-diphenyl-1H-imidazol-5-yl)-N-[2-chloro-4-(difluoromethoxy)benzyl]methanamine | 586.26 | 1.24 |

TABLE II-continued

| CMP # | STRUCTURE | Ca²⁺ Mob. | IUPAC Name | MASS | RT (min.) |
|---|---|---|---|---|---|
| 577 | 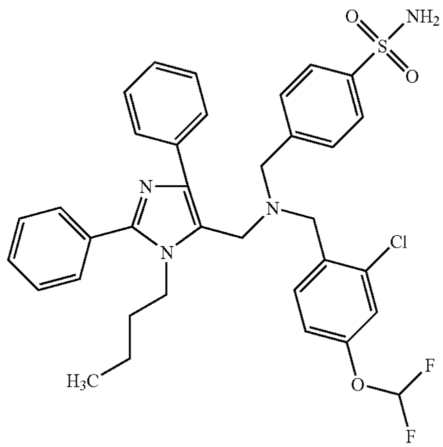 | * | 4-({[(1-butyl-2,4-diphenyl-1H-imidazol-5-yl)methyl][2-chloro-4-(difluoromethoxy)benzyl]amino}methyl)benzenesulfonamide | 665.25 | 1.15 |
| 578 | 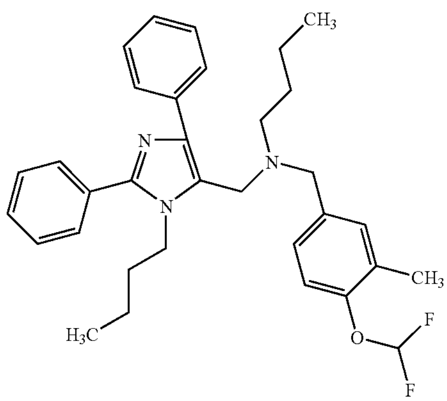 | * | N-[(1-butyl-2,4-diphenyl-1H-imidazol-5-yl)methyl]-N-[4-(difluoromethoxy)-3-methylbenzyl]butan-1-amine | 533.35 | 1.21 |
| 579 | 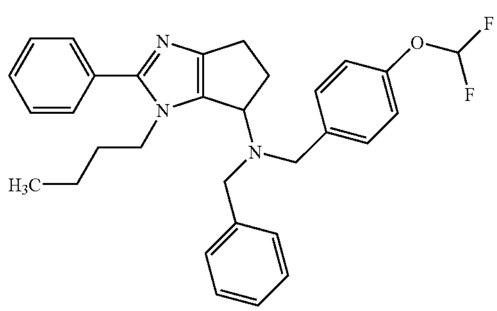 | * | N-benzyl-3-butyl-N-[4-(difluoromethoxy)benzyl]-2-phenyl-3,4,5,6-tetrahydrocyclopenta[d]imidazol-4-amine | 502.28 | 1.19 |
| 580 | 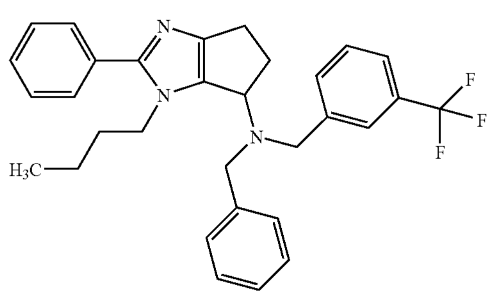 | | N-benzyl-3-butyl-2-phenyl-N-[3-(trifluoromethyl)benzyl]-3,4,5,6-tetrahydrocyclopenta[d]imidazol-4-amine | 504.27 | 1.22 |

TABLE II-continued

| CMP # | STRUCTURE | Ca$^{2+}$ Mob. | IUPAC Name | MASS | RT (min.) |
|---|---|---|---|---|---|
| 581 | 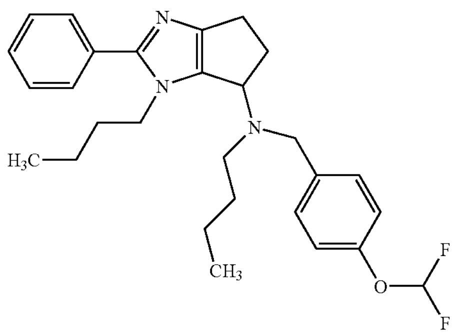 | * | N,3-dibutyl-N-[4-(difluoromethoxy)benzyl]-2-phenyl-3,4,5,6-tetrahydrocyclopenta[d]imidazol-4-amine | 468.33 | 1.2 |
| 582 | 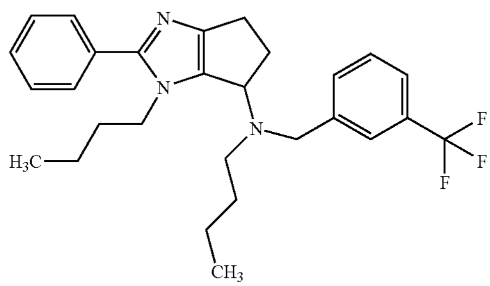 | * | N,3-dibutyl-2-phenyl-N-[3-(trifluoromethyl)benzyl]-3,4,5,6-tetrahydrocyclopenta[d]imidazol-4-amine | 470.30 | 1.23 |
| 583 | 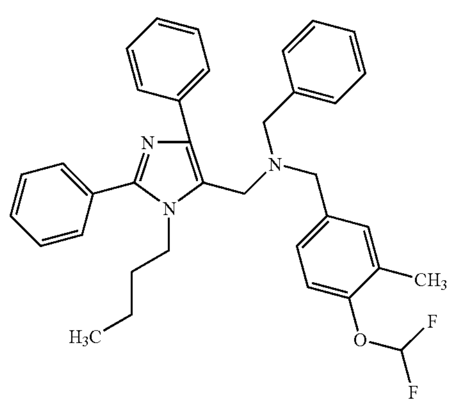 | * | N-benzyl-1-(1-butyl-2,4-diphenyl-1H-imidazol-5-yl)-N-[4-(difluoromethoxy)-3-methylbenzyl]methanamine | 566.31 | 1.24 |
| 584 | 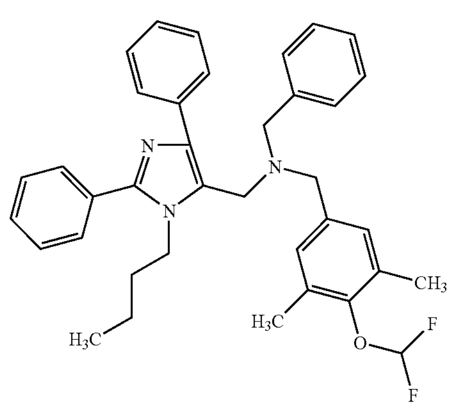 | * | N-benzyl-1-(1-butyl-2,4-diphenyl-1H-imidazol-5-yl)-N-[4-(difluoromethoxy)-3,5-dimethylbenzyl]methanamine | 580.37 | 1.25 |

TABLE II-continued

| CMP # | STRUCTURE | Ca²⁺ Mob. | IUPAC Name | MASS | RT (min.) |
|---|---|---|---|---|---|
| 585 | 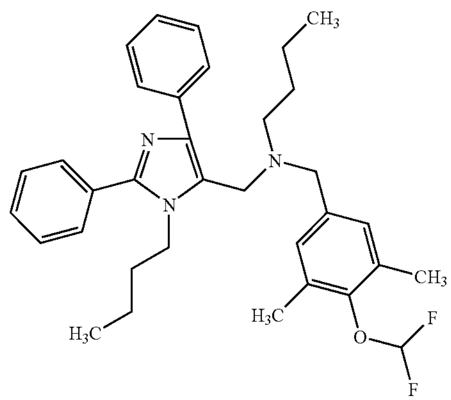 | * | N-[(1-butyl-2,4-diphenyl-1H-imidazol-5-yl)methyl]-N-[4-(difluoromethoxy)-3,5-dimethylbenzyl]butan-1-amine | 546.38 | 1.24 |
| 586 | 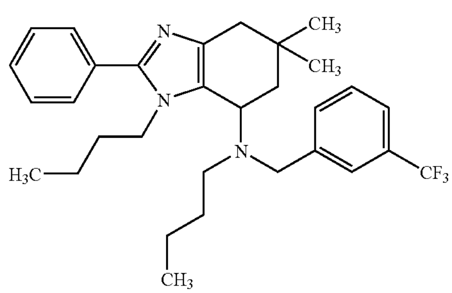 | * | N,1-dibutyl-5,5-dimethyl-2-phenyl-N-[3-(trifluoromethyl)benzyl]-4,5,6,7-tetrahydro-1H-benzimidazol-7-amine | 281.21 | 1.23 |
| 587 | 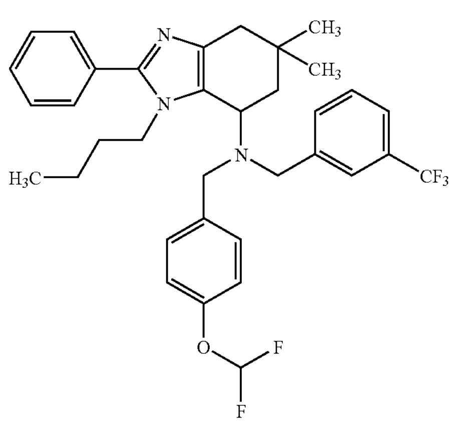 | * | 1-butyl-N-[4-(difluoromethoxy)benzyl]-5,5-dimethyl-2-phenyl-N-[3-(trifluoromethyl)benzyl]-4,5,6,7-tetrahydro-1H-benzimidazol-7-amine | 281.21 | 1.23 |
| 588 | 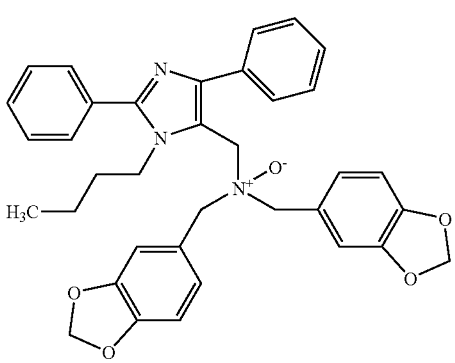 | * | bis(1,3-benzodioxol-5-ylmethyl)(1-butyl-2,4-diphenyl-1H-imidazol-5-yl)methylamine oxide | 590.29 | 1.22 |

TABLE II-continued

| CMP # | STRUCTURE | Ca²⁺ Mob. | IUPAC Name | MASS | RT (min.) |
|---|---|---|---|---|---|
| 589 | 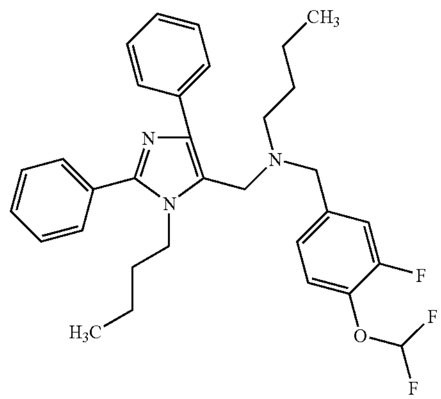 | * | N-[(1-butyl-2,4-diphenyl-1H-imidazol-5-yl)methyl]-N-[4-(difluoromethoxy)-3-fluorobenzyl]butan-1-amine | 590.29 | 1.23 |
| 590 | 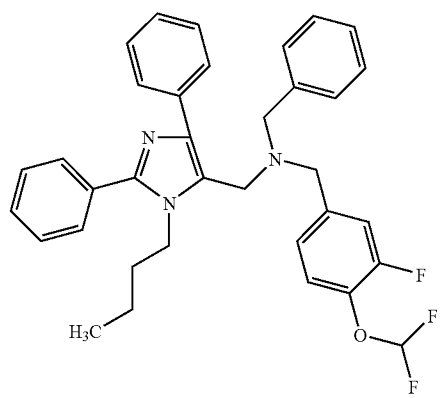 | * | N-benzyl-1-(1-butyl-2,4-diphenyl-1H-imidazol-5-yl)-N-[4-(difluoromethoxy)-3-fluorobenzyl]methanamine | 537.36 | 1.22 |
| 591 | 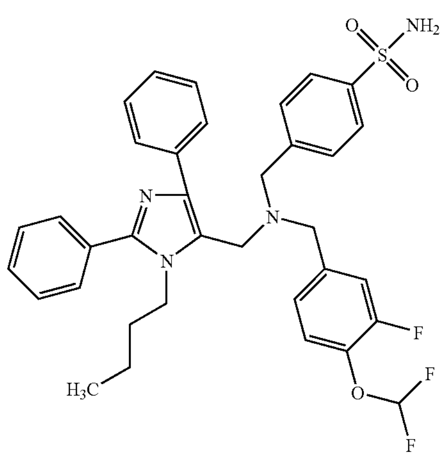 | * | 4-({[(1-butyl-2,4-diphenyl-1H-imidazol-5-yl)methyl][4-(difluoromethoxy)-3-fluorobenzyl]amino}methyl)benzenesulfonamide | 570.33 | 1.22 |

TABLE II-continued

| CMP # | STRUCTURE | Ca²⁺ Mob. | IUPAC Name | MASS | RT (min.) |
|---|---|---|---|---|---|
| 592 | 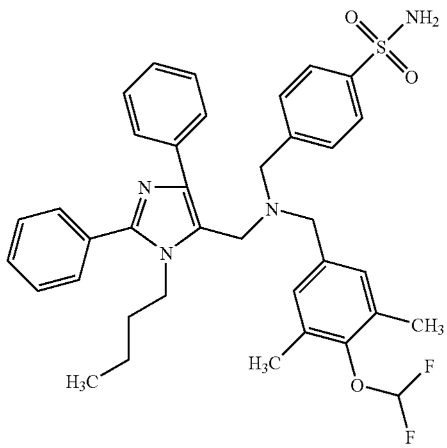 | * | 4-({[(1-butyl-2,4-diphenyl-1H-imidazol-5-yl)methyl][4-(difluoromethoxy)-3,5-dimethyl benzyl]amino}methyl)benzenesulfonamide | 649.33 | 1.13 |
| 593 | Chiral | * | (1S)-1-(1-butyl-2,4-diphenyl-1H-imidazol-5-yl)-N-(cyclohexylmethyl)-N-[3-(trifluoromethyl)benzyl]pentan-1-amine | 659.36 | 1.17 |
| 594 | Chiral | * | (1R)-N-(1,3-benzodioxol-5-ylmethyl)-1-(1-butyl-2,4-diphenyl-1H-imidazol-5-yl)-N-[3-(trifluoromethyl)benzyl]pentan-1-amine | 616.43 | 1.33 |
| 595 | Chiral | * | (1R)-N-(1,3-benzodioxol-5-ylmethyl)-1-(1-butyl-2,4-diphenyl-1H-imidazol-5-yl)-N-[3-(trifluoromethyl)benzyl]ethanamine | 654.38 | 1.28 |

TABLE II-continued

| CMP # | STRUCTURE | Ca²⁺ Mob. | IUPAC Name | MASS | RT (min.) |
|---|---|---|---|---|---|
| 596 | 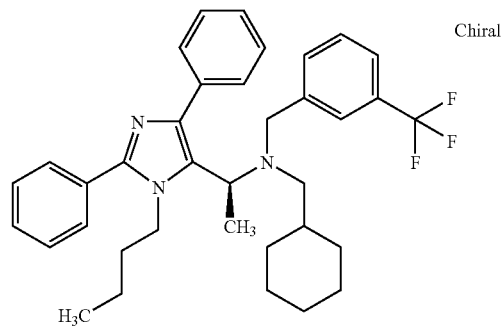 Chiral | * | (1R)-1-(1-butyl-2,4-diphenyl-1H-imidazol-5-yl)-N-(cyclohexylmethyl)-N-[3-(trifluoromethyl)benzyl]ethanamine | 612.33 | 1.23 |
| 597 | 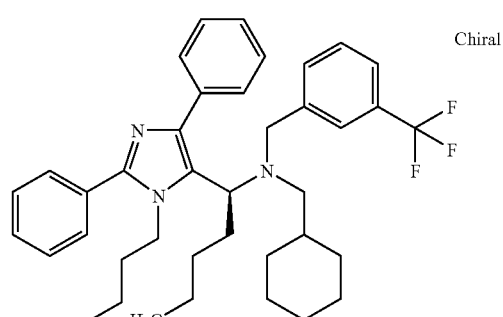 Chiral | * | (1R)-1-(1-butyl-2,4-diphenyl-1H-imidazol-5-yl)-N-(cyclohexylmethyl)-N-[3-(trifluoromethyl)benzyl]pentan-1-amine | 574.37 | 1.28 |
| 598 | 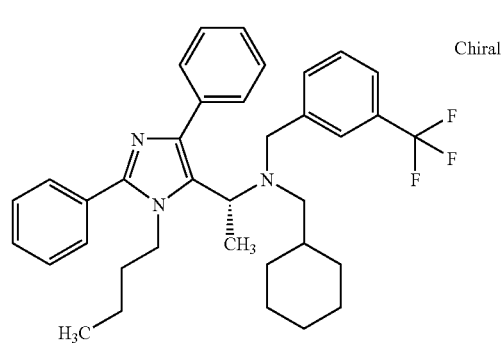 Chiral | * | (1S)-1-(1-butyl-2,4-diphenyl-1H-imidazol-5-yl)-N-(cyclohexylmethyl)-N-[3-(trifluoromethyl)benzyl]ethanamine | 616.42 | 1.32 |
| 599 | 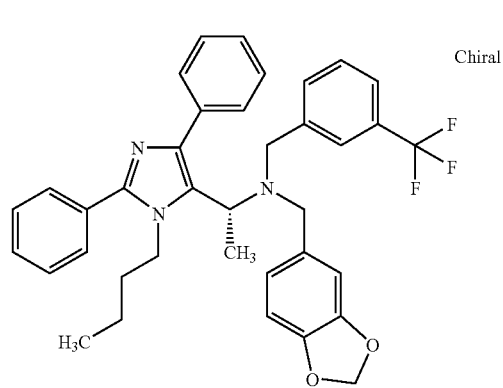 Chiral | * | (1S)-N-(1,3-benzodioxol-5-ylmethyl)-1-(1-butyl-2,4-diphenyl-1H-imidazol-5-yl)-N-[3-(trifluoromethyl)benzyl]ethanamine | 574.37 | 1.29 |

TABLE II-continued

| CMP # | STRUCTURE | Ca²⁺ Mob. | IUPAC Name | MASS | RT (min.) |
|---|---|---|---|---|---|
| 600 | 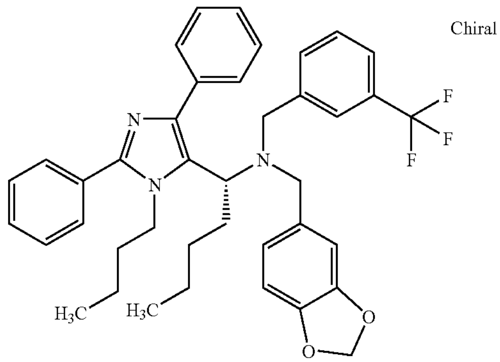 | * | (1S)-N-(1,3-benzodioxol-5-ylmethyl)-1-(1-butyl-2,4-diphenyl-1H-imidazol-5-yl)-N-[3-(trifluoromethyl)benzyl]pentan-1-amine | 612.33 | 1.24 |
| 601 | 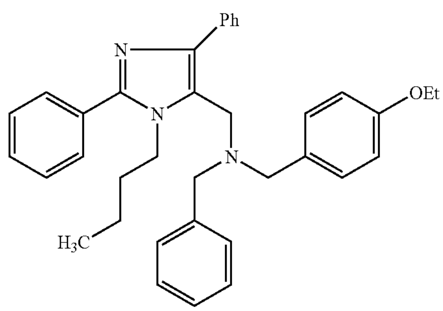 | * | N-benzyl-1-(1-butyl-2,4-diphenyl-1H-imidazol-5-yl)-N-(4-ethoxybenzyl)methanamine | 654.37 | 1.27 |
| 602 | 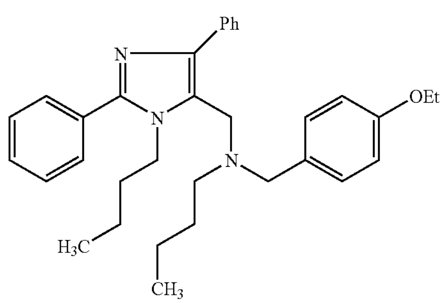 | * | N-[(1-butyl-2,4-diphenyl-1H-imidazol-5-yl)methyl]-N-(4-ethoxybenzyl)butan-1-amine | 530.32 | 1.25 |
| 603 | 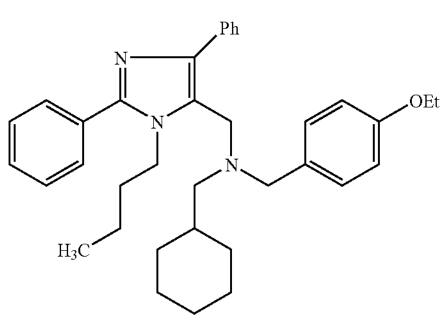 | * | 1-(1-butyl-2,4-diphenyl-1H-imidazol-5-yl)-N-(cyclohexylmethyl)-N-(4-ethoxybenzyl)methanamine | 496.33 | 1.18 |

TABLE II-continued

| CMP # | STRUCTURE | Ca²⁺ Mob. | IUPAC Name | MASS | RT (min.) |
|---|---|---|---|---|---|
| 604 | 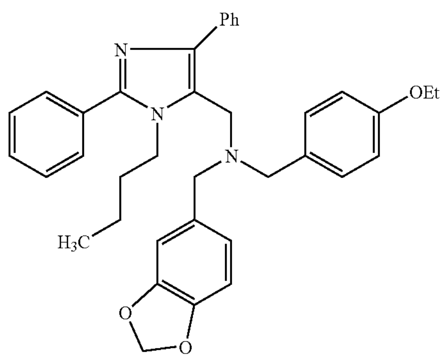 | * | 1-(1,3-benzodioxol-5-yl)-N-[(1-butyl-2,4-diphenyl-1H-imidazol-5-yl)methyl]-N-(4-ethoxybenzyl)methanamine | 536.37 | 1.29 |
| 605 | 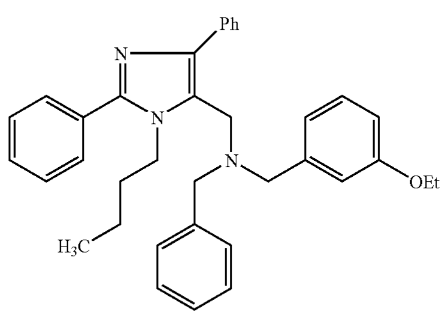 | * | N-benzyl-1-(1-butyl-2,4-diphenyl-1H-imidazol-5-yl)-N-(3-ethoxybenzyl)methanamine | 574.32 | 1.23 |
| 606 | 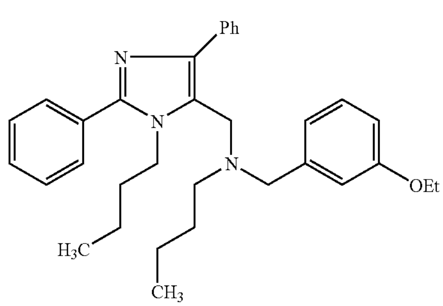 | * | N-[(1-butyl-2,4-diphenyl-1H-imidazol-5-yl)methyl]-N-(3-ethoxybenzyl)butan-1-amine | 530.32 | 1.25 |
| 607 | 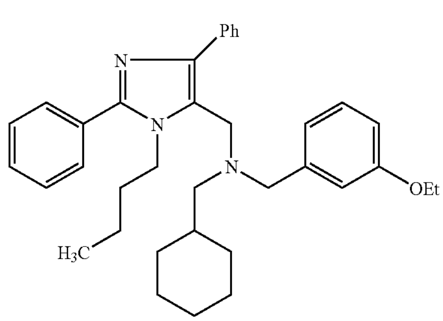 | * | 1-(1-butyl-2,4-diphenyl-1H-imidazol-5-yl)-N-(cyclohexylmethyl)-N-(3-ethoxybenzyl)methanamine | 496.33 | 1.21 |

TABLE II-continued

| CMP # | STRUCTURE | Ca²⁺ Mob. | IUPAC Name | MASS | RT (min.) |
|---|---|---|---|---|---|
| 608 | 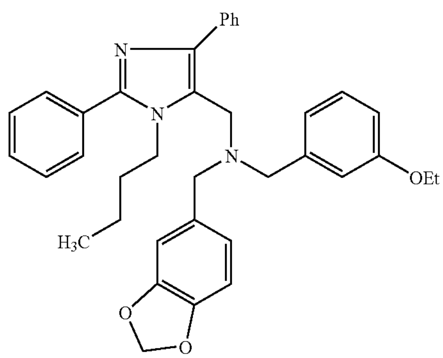 | * | 1-(1,3-benzodioxol-5-yl)-N-[(1-butyl-2,4-diphenyl-1H-imidazol-5-yl)methyl]-N-(3-ethoxybenzyl)methanamine | 536.36 | 1.29 |
| 609 | 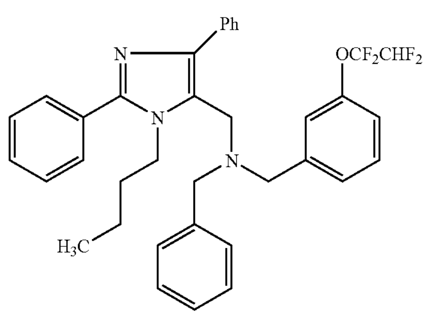 | * | N-benzyl-1-(1-butyl-2,4-diphenyl-1H-imidazol-5-yl)-N-[3-(1,1,2,2-tetrafluoroethoxy)benzyl]methanamine | 574.32 | 1.23 |
| 610 | 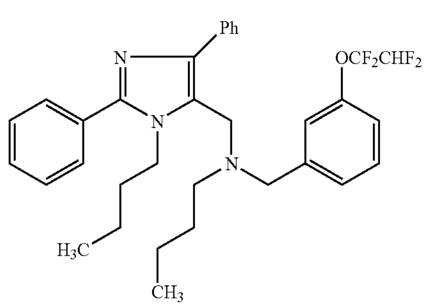 | * | N-[(1-butyl-2,4-diphenyl-1H-imidazol-5-yl)methyl]-N-[3-(1,1,2,2-tetrafluoroethoxy)benzyl]butan-1-amine | 602.29 | 1.22 |
| 611 | 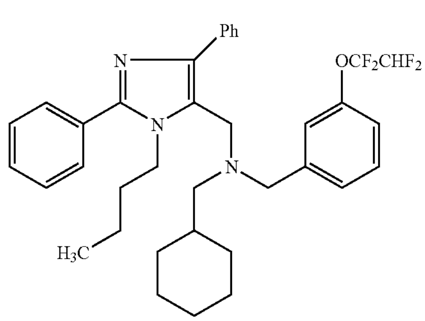 | * | 1-(1-butyl-2,4-diphenyl-1H-imidazol-5-yl)-N-(cyclohexylmethyl)-N-[3-(1,1,2,2-tetrafluoroethoxy)benzyl]methanamine | 568.30 | 1.23 |

TABLE II-continued

| CMP # | STRUCTURE | Ca²⁺ Mob. | IUPAC Name | MASS | RT (min.) |
|---|---|---|---|---|---|
| 612 | 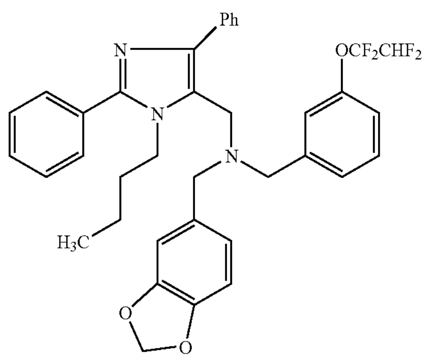 | * | 1-(1,3-benzodioxol-5-yl)-N-[(1-butyl-2,4-diphenyl-1H-imidazol-5-yl)methyl]-N-[3-(1,1,2,2-tetrafluoroethoxy)benzyl]methanamine | 608.33 | 1.27 |
| 613 | 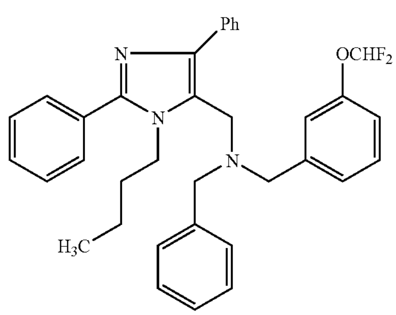 | * | N-benzyl-1-(1-butyl-2,4-diphenyl-1H-imidazol-5-yl)-N-[3-(difluoromethoxy)benzyl]methanamine | 646.28 | 1.22 |
| 614 | 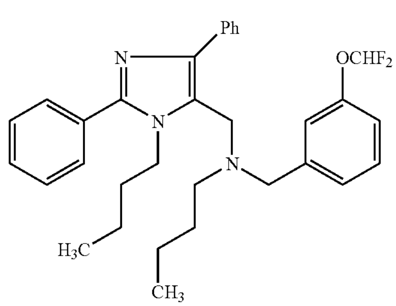 | * | N-[(1-butyl-2,4-diphenyl-1H-imidazol-5-yl)methyl]-N-[3-(difluoromethoxy)benzyl]butan-1-amine | 518.30 | 1.21 |
| 615 | 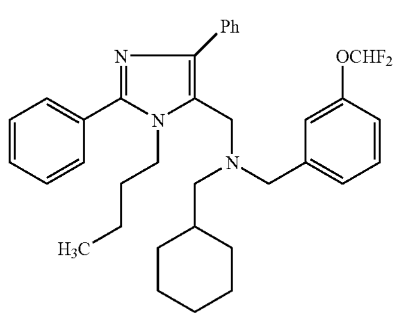 | * | 1-(1-butyl-2,4-diphenyl-1H-imidazol-5-yl)-N-(cyclohexylmethyl)-N-[3-(difluoromethoxy)benzyl]methanamine | 559.36 | 1.26 |

TABLE II-continued

| CMP # | STRUCTURE | Ca²⁺ Mob. | IUPAC Name | MASS | RT (min.) |
|---|---|---|---|---|---|
| 616 | 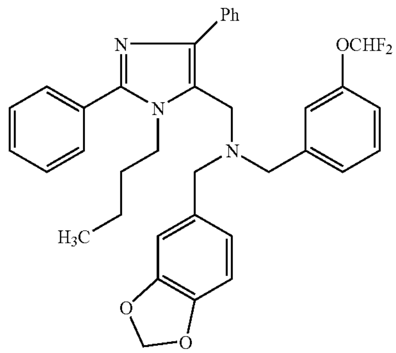 | * | 1-(1,3-benzodioxol-5-yl)-N-[(1-butyl-2,4-diphenyl-1H-imidazol-5-yl)methyl]-N-[3-(difluoromethoxy)benzyl]methanamine | 596.29 | 1.21 |
| 617 | 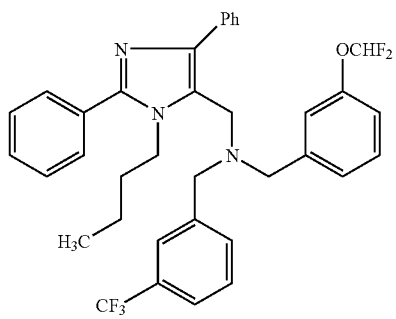 | * | 1-(1-butyl-2,4-diphenyl-1H-imidazol-5-yl)-N-[3-(difluoromethoxy)benzyl]-N-[3-(trifluoromethyl)benzyl]methanamine | 620.27 | 1.23 |
| 618 | 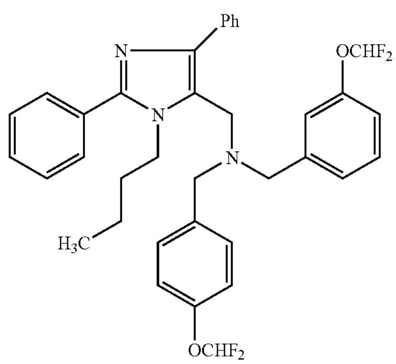 | * | 1-(1-butyl-2,4-diphenyl-1H-imidazol-5-yl)-N-[3-(difluoromethoxy)benzyl]-N-[4-(difluoromethoxy)benzyl]methanamine | 618.28 | 1.21 |
| 619 | 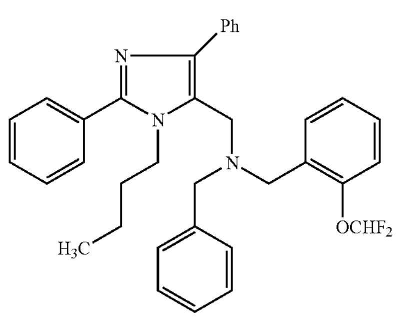 | * | N-benzyl-1-(1-butyl-2,4-diphenyl-1H-imidazol-5-yl)-N-[2-(difluoromethoxy)benzyl]methanamine | 552.29 | 1.22 |

TABLE II-continued

| CMP # | STRUCTURE | Ca²⁺ Mob. | IUPAC Name | MASS | RT (min.) |
|---|---|---|---|---|---|
| 620 | 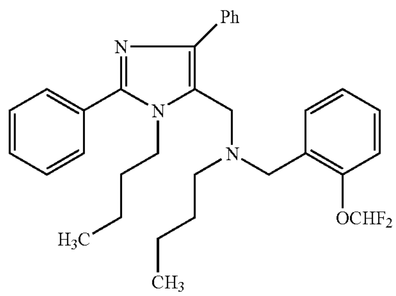 | * | N-[(1-butyl-2,4-diphenyl-1H-imidazol-5-yl)methyl]-N-[2-(difluoromethoxy)benzyl]butan-1-amine | 519.33 | 1.21 |
| 621 | 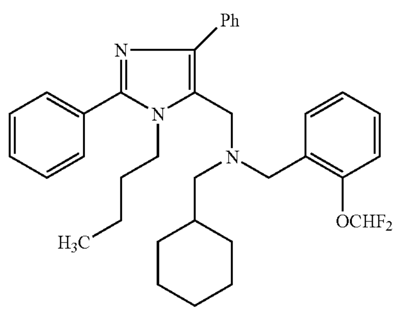 | * | 1-(1-butyl-2,4-diphenyl-1H-imidazol-5-yl)-N-(cyclohexylmethyl)-N-[2-(difluoromethoxy)benzyl]methanamine | 559.37 | 1.26 |
| 622 | 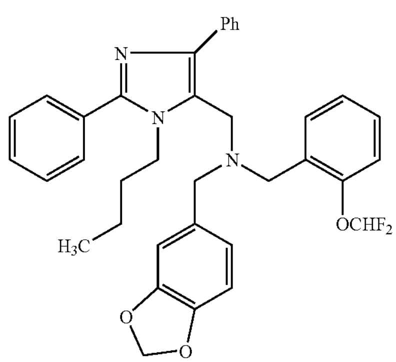 | * | 1-(1,3-benzodioxol-5-yl)-N-[(1-butyl-2,4-diphenyl-1H-imidazol-5-yl)methyl]-N-[2-(difluoromethoxy)benzyl]methanamine | 596.28 | 1.21 |
| 623 | 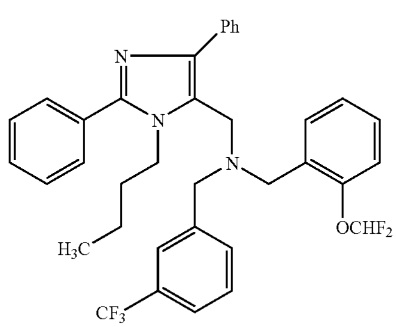 | * | 1-(1-butyl-2,4-diphenyl-1H-imidazol-5-yl)-N-[2-(difluoromethoxy)benzyl]-N-[3-(trifluoromethyl)benzyl]methanamine | 620.28 | 1.23 |

TABLE II-continued

| CMP # | STRUCTURE | Ca²⁺ Mob. | IUPAC Name | MASS | RT (min.) |
|---|---|---|---|---|---|
| 624 | 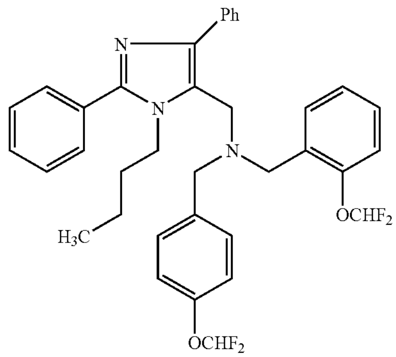 | * | 1-(1-butyl-2,4-diphenyl-1H-imidazol-5-yl)-N-[2-(difluoromethoxy)benzyl]-N-[4-(difluoromethoxy)benzyl]methanamine | 619.32 | 1.2 |
| 625 | 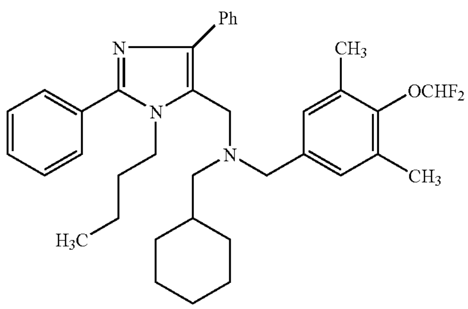 | * | 1-(1-butyl-2,4-diphenyl-1H-imidazol-5-yl)-N-(cyclohexylmethyl)-N-[4-(difluoromethoxy)-3,5-dimethylbenzyl]methanamine | 586.37 | 1.3 |
| 626 | 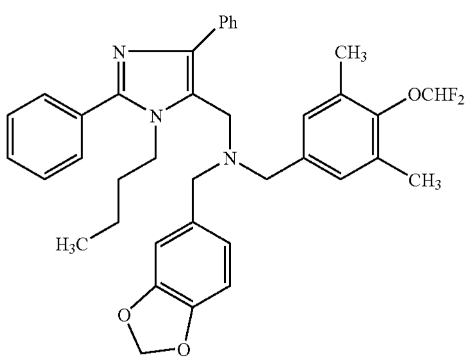 | * | 1-(1,3-benzodioxol-5-yl)-N-[(1-butyl-2,4-diphenyl-1H-imidazol-5-yl)methyl]-N-[4-(difluoromethoxy)-3,5-dimethylbenzyl]methanamine | 625.35 | 1.25 |
| 627 | 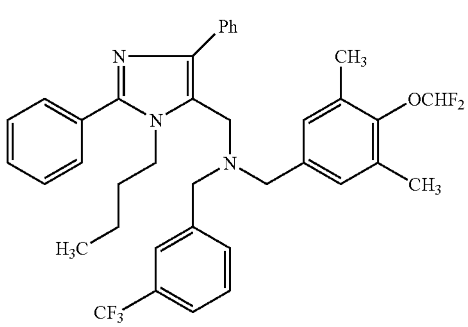 | | 1-(1-butyl-2,4-diphenyl-1H-imidazol-5-yl)-N-[4-(difluoromethoxy)-3,5-dimethylbenzyl]-N-[3-(trifluoromethyl)benzyl]methanamine | 649.35 | 1.27 |

TABLE II-continued

| CMP # | STRUCTURE | Ca²⁺ Mob. | IUPAC Name | MASS | RT (min.) |
|---|---|---|---|---|---|
| 628 | 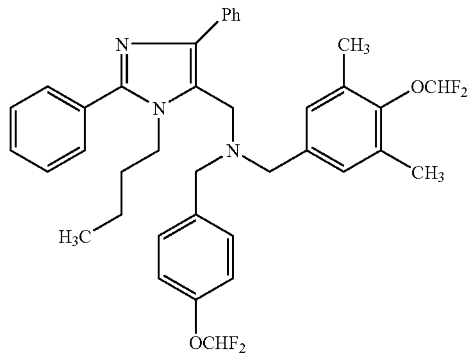 | * | 1-(1-butyl-2,4-diphenyl-1H-imidazol-5-yl)-N-[4-(difluoromethoxy)benzyl]-N-[4-(difluoromethoxy)-3,5-dimethylbenzyl]methanamine | 647.35 | 1.24 |
| 629 | 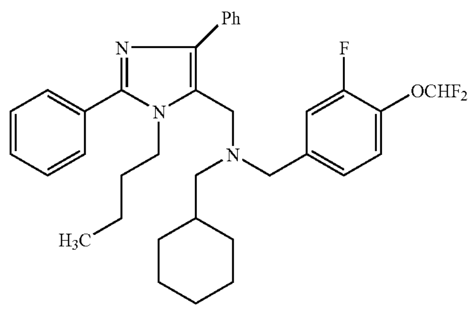 | * | 1-(1-butyl-2,4-diphenyl-1H-imidazol-5-yl)-N-(cyclohexylmethyl)-N-[4-(difluoromethoxy)-3-fluorobenzyl]methanamine | 577.36 | 1.26 |
| 630 | 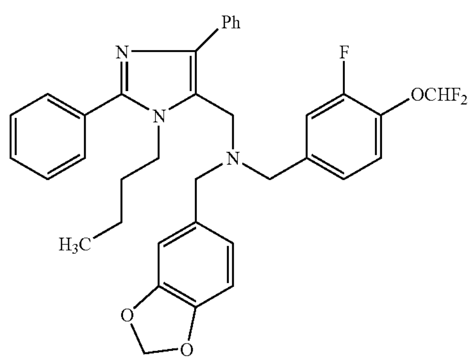 | * | 1-(1,3-benzodioxol-5-yl)-N-[(1-butyl-2,4-diphenyl-1H-imidazol-5-yl)methyl]-N-[4-(difluoromethoxy)-3-fluorobenzyl]methanamine | 614.28 | 1.21 |
| 631 | 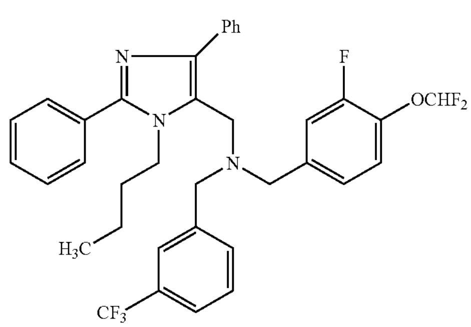 | * | 1-(1-butyl-2,4-diphenyl-1H-imidazol-5-yl)-N-[4-(difluoromethoxy)-3-fluorobenzyl]-N-[3-(trifluoromethyl)benzyl]methanamine | 638.27 | 1.23 |

TABLE II-continued

| CMP # | STRUCTURE | Ca²⁺ Mob. | IUPAC Name | MASS | RT (min.) |
|---|---|---|---|---|---|
| 632 | 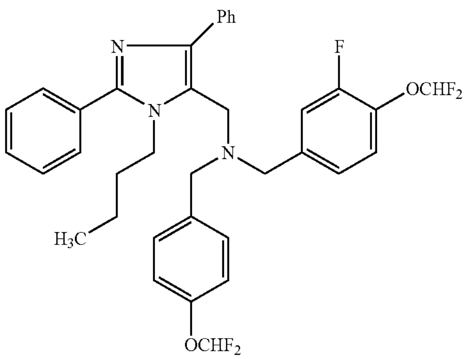 | * | 1-(1-butyl-2,4-diphenyl-1H-imidazol-5-yl)-N-[4-(difluoromethoxy)benzyl]-N-[4-(difluoromethoxy)-3-fluorobenzyl]methanamine | 636.28 | 1.21 |
| 633 | 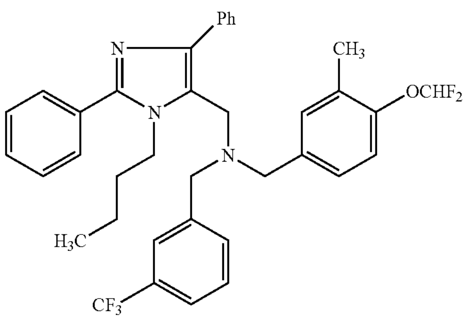 | * | 1-(1-butyl-2,4-diphenyl-1H-imidazol-5-yl)-N-[4-(difluoromethoxy)-3-methylbenzyl]-N-[3-(trifluoromethyl)benzyl]methanamine | 634.29 | 1.25 |
| 634 | 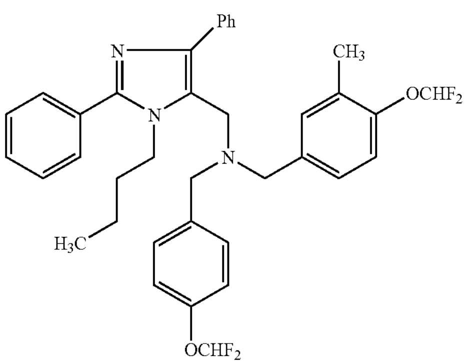 | * | 1-(1-butyl-2,4-diphenyl-1H-imidazol-5-yl)-N-[4-(difluoromethoxy)benzyl]-N-[4-(difluoromethoxy)-3-methylbenzyl]methanamine | 632.31 | 1.23 |
| 635 | 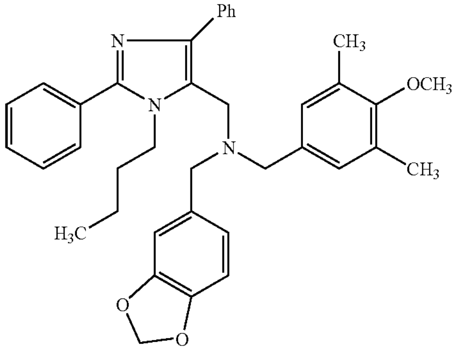 | * | 1-(1,3-benzodioxol-5-yl)-N-[(1-butyl-2,4-diphenyl-1H-imidazol-5-yl)methyl]-N-(4-methoxy-3,5-dimethylbenzyl)methanamine | 588.33 | 1.24 |

TABLE II-continued

| CMP # | STRUCTURE | Ca²⁺ Mob. | IUPAC Name | MASS | RT (min.) |
|---|---|---|---|---|---|
| 636 | 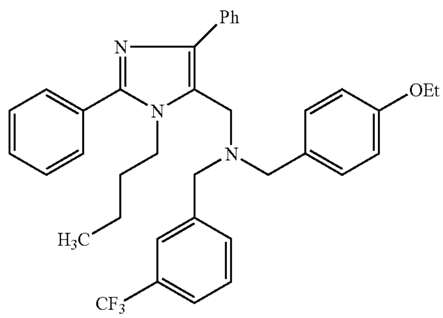 | * | 1-(1-butyl-2,4-diphenyl-1H-imidazol-5-yl)-N-(4-ethoxybenzyl)-N-[3-(trifluoromethyl)benzyl]methanamine | 598.32 | 1.26 |
| 637 | 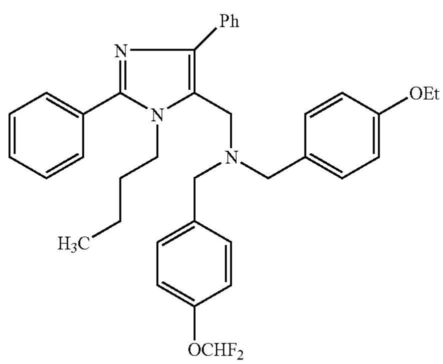 | * | 1-(1-butyl-2,4-diphenyl-1H-imidazol-5-yl)-N-[4-(difluoromethoxy)benzyl]-N-(4-ethoxybenzyl)methanamine | 596.32 | 1.23 |
| 638 | 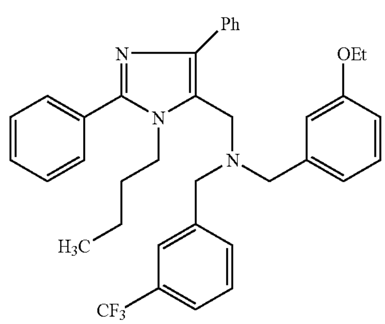 | * | 1-(1-butyl-2,4-diphenyl-1H-imidazol-5-yl)-N-(3-ethoxybenzyl)-N-[3-(trifluoromethyl)benzyl]methanamine | 599.34 | 1.26 |
| 639 | 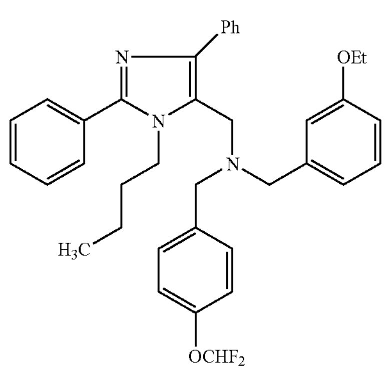 | * | 1-(1-butyl-2,4-diphenyl-1H-imidazol-5-yl)-N-[4-(difluoromethoxy)benzyl]-N-(3-ethoxybenzyl)methanamine | 596.31 | 1.23 |

TABLE II-continued

| CMP # | STRUCTURE | Ca²⁺ Mob. | IUPAC Name | MASS | RT (min.) |
|---|---|---|---|---|---|
| 640 | 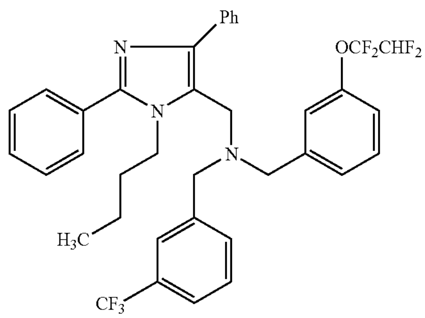 | * | 1-(1-butyl-2,4-diphenyl-1H-imidazol-5-yl)-N-[3-(1,1,2,2-tetrafluoroethoxy)benzyl]-N-[3-(trifluoromethyl)benzyl]methanamine | 670.27 | 1.24 |
| 641 | 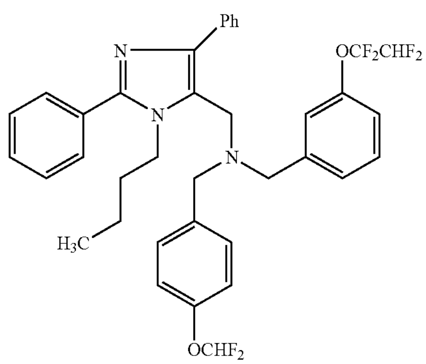 | * | 1-(1-butyl-2,4-diphenyl-1H-imidazol-5-yl)-N-[4-(difluoromethoxy)benzyl]-N-[3-(1,1,2,2-tetrafluoroethoxy)benzyl]methanamine | 668.28 | 1.22 |
| 642 | 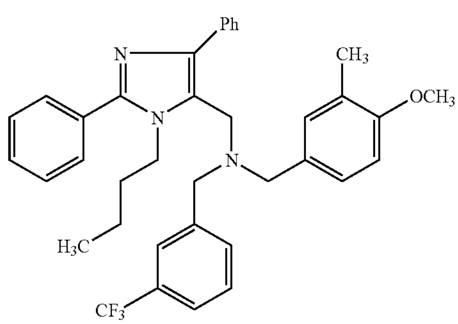 | * | 1-(1-butyl-2,4-diphenyl-1H-imidazol-5-yl)-N-(4-methoxy-3-methylbenzyl)-N-[3-(trifluoromethyl)benzyl]methanamine | 598.31 | 1.27 |
| 643 | 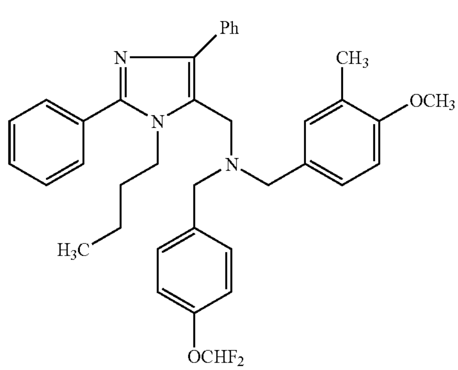 | * | 1-(1-butyl-2,4-diphenyl-1H-imidazol-5-yl)-N-[4-(difluoromethoxy)benzyl]-N-(4-methoxy-3-methylbenzyl)methanamine | 596.32 | 1.24 |

TABLE II-continued

| CMP # | STRUCTURE | Ca²⁺ Mob. | IUPAC Name | MASS | RT (min.) |
|---|---|---|---|---|---|
| 644 | 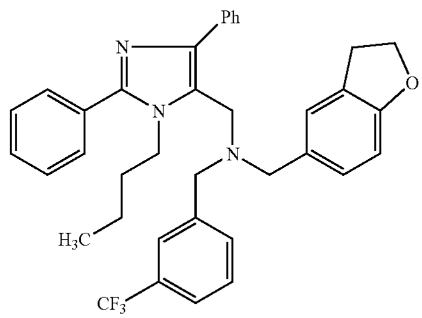 | * | 1-(1-butyl-2,4-diphenyl-1H-imidazol-5-yl)-N-(2,3-dihydro-1-benzofuran-5-ylmethyl)-N-[3-(trifluoromethyl)benzyl]methanamine | 596.30 | 1.24 |
| 645 | 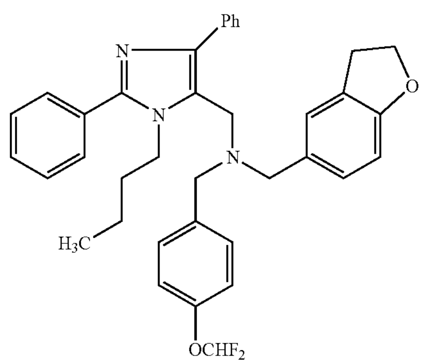 | * | 1-(1-butyl-2,4-diphenyl-1H-imidazol-5-yl)-N-[4-(difluoromethoxy)benzyl]-N-(2,3-dihydro-1-benzofuran-5-ylmethyl)methanamine | 594.31 | 1.22 |
| 646 | 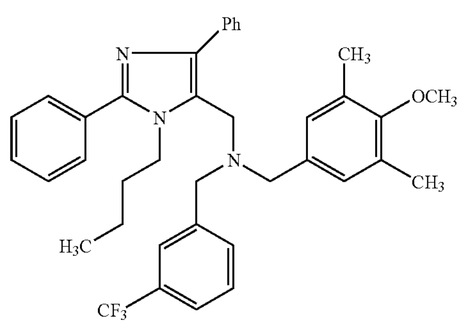 | * | 1-(1-butyl-2,4-diphenyl-1H-imidazol-5-yl)-N-(4-methoxy-3,5-dimethylbenzyl)-N-[3-(trifluoromethyl)benzyl]methanamine | 613.36 | 1.27 |
| 647 | 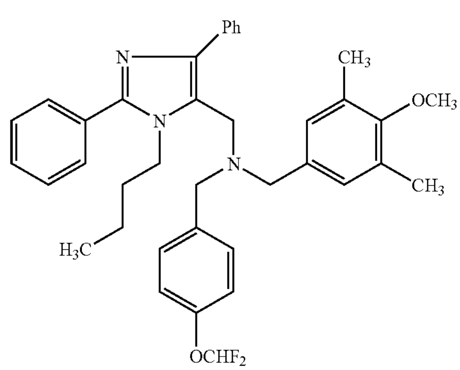 | * | 1-(1-butyl-2,4-diphenyl-1H-imidazol-5-yl)-N-[4-(difluoromethoxy)benzyl]-N-(4-methoxy-3,5-dimethylbenzyl)methanamine | 611.37 | 1.24 |

TABLE II-continued

| CMP # | STRUCTURE | Ca²⁺ Mob. | IUPAC Name | MASS | RT (min.) |
|---|---|---|---|---|---|
| 648 | 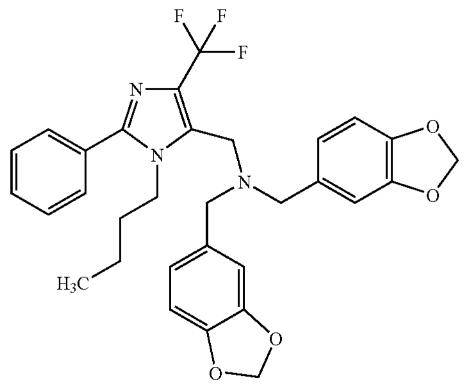 | * | 1-(1,3-benzodioxol-5-yl)-N-(1,3-benzodioxol-5-ylmethyl)-N-{[1-butyl-2-phenyl-4-(trifluoromethyl)-1H-imidazol-5-yl]methyl}methanamine | 566.28 | 1.36 |
| 649 | 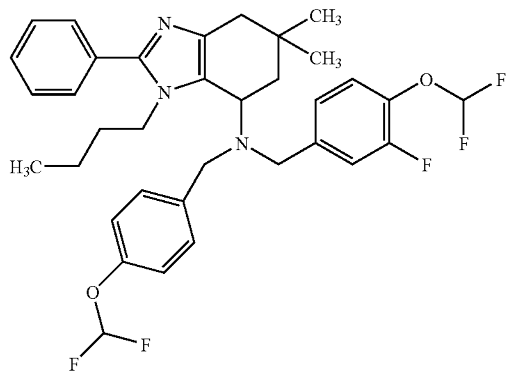 | * | 1-butyl-N-[4-(difluoromethoxy)benzyl]-N-[4-(difluoromethoxy)-3-fluorobenzyl]-5,5-dimethyl-2-phenyl-4,5,6,7-tetrahydro-1H-benzimidazol-7-amine | 281.23 | 1.21 |
| 650 | 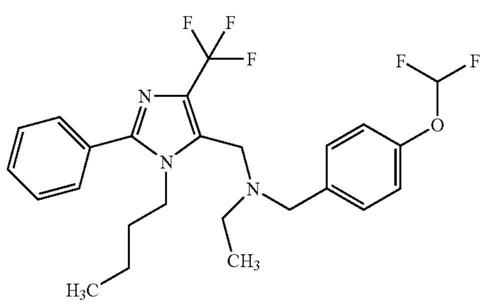 | * | N-{[1-butyl-2-phenyl-4-(trifluoromethyl)-1H-imidazol-5-yl]methyl}-N-[4-(difluoromethoxy)benzyl]ethanamine | 482.23 | 1.2 |
| 651 | 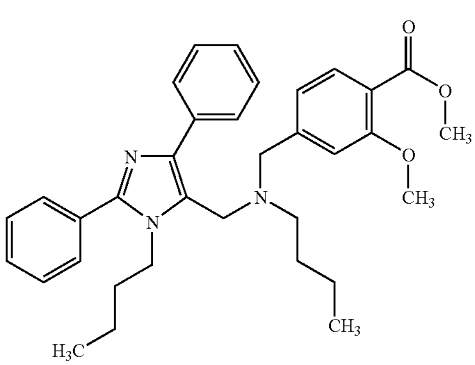 | * | methyl 4-({butyl[(1-butyl-2,4-diphenyl-1H-imidazol-5-yl)methyl]amino}methyl)-2-methoxybenzoate | 540.36 | 1.18 |

TABLE II-continued

| CMP # | STRUCTURE | Ca²⁺ Mob. | IUPAC Name | MASS | RT (min.) |
|---|---|---|---|---|---|
| 652 | 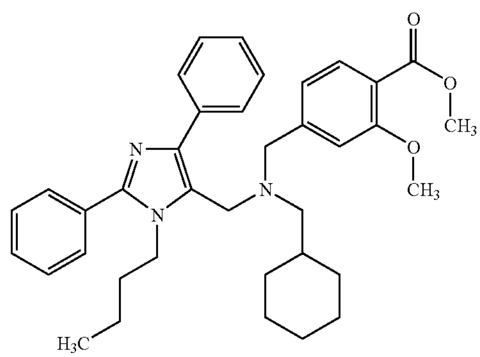 | * | methyl 4-{[[(1-butyl-2,4-diphenyl-1H-imidazol-5-yl)methyl](cyclohexylmethyl)amino]methyl}-2-methoxybenzoate | 580.39 | 1.25 |
| 653 | 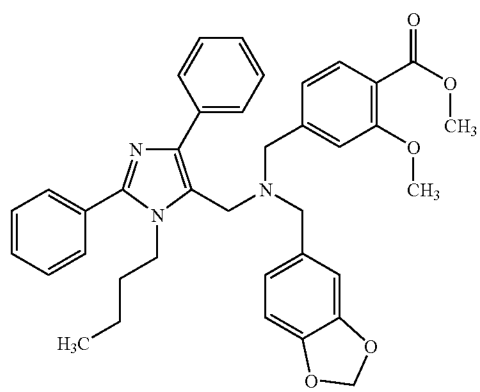 | * | methyl 4-({(1,3-benzodioxol-5-ylmethyl)[(1-butyl-2,4-diphenyl-1H-imidazol-5-yl)methyl]amino}methyl)-2-methoxybenzoate | 619.37 | 1.18 |
| 654 | 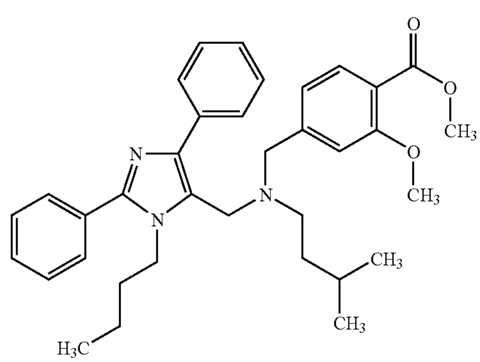 | * | methyl 4-{[[(1-butyl-2,4-diphenyl-1H-imidazol-5-yl)methyl](isopentyl)amino]methyl}-2-methoxybenzoate | 554.37 | 1.21 |
| 655 | 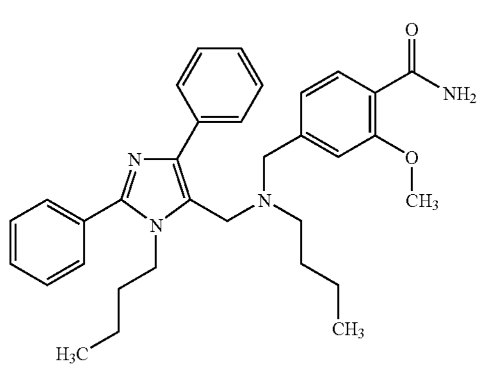 | * | 4-({butyl[(1-butyl-2,4-diphenyl-1H-imidazol-5-yl)methyl]amino}methyl)-2-methoxybenzamide | 525.36 | 1.14 |

TABLE II-continued

| CMP # | STRUCTURE | Ca²⁺ Mob. | IUPAC Name | MASS | RT (min.) |
|---|---|---|---|---|---|
| 656 | 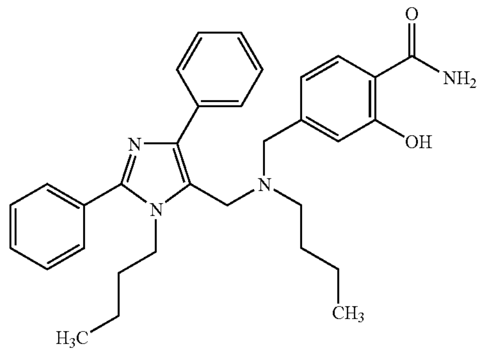 | * | 4-({butyl[(1-butyl-2,4-diphenyl-1H-imidazol-5-yl)methyl]amino}methyl)-2-hydroxybenzamide | 511.34 | 1.16 |
| 657 | 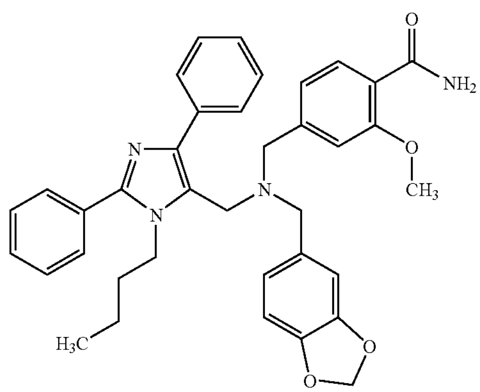 | * | 4-({(1,3-benzodioxol-5-ylmethyl)[(1-butyl-2,4-diphenyl-1H-imidazol-5-yl)methyl]amino}methyl)-2-methoxybenzamide | 604.37 | 1.15 |
| 658 | 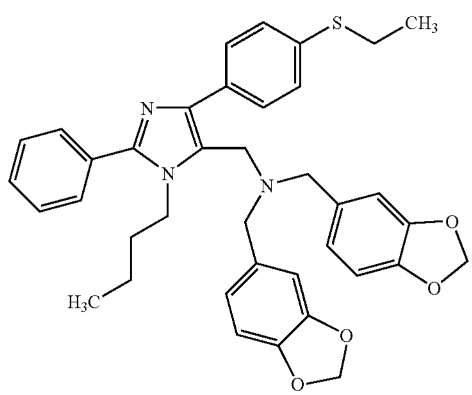 | * | 1-(1,3-benzodioxol-5-yl)-N-(1,3-benzodioxol-5-ylmethyl)-N-({1-butyl-4-[4-(ethylthio)phenyl]-2-phenyl-1H-imidazol-5-yl}methyl)methanamine | 634.40 | 1.25 |
| 659 | 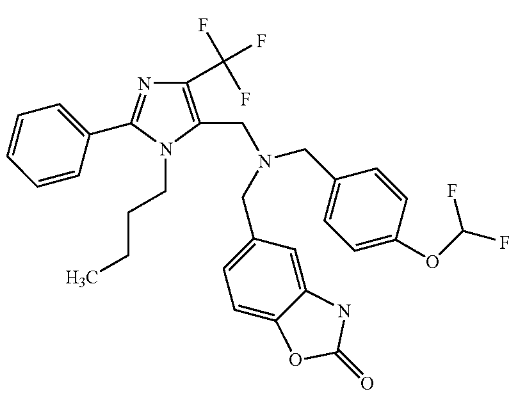 | * | 5-({{[1-butyl-2-phenyl-4-(trifluoromethyl)-1H-imidazol-5-yl]methyl}[4-(difluoromethoxy)benzyl]amino}methyl)-1,3-benzoxazol-2(3H)-one | 601.35 | 1.28 |

TABLE II-continued

| CMP # | STRUCTURE | Ca²⁺ Mob. | IUPAC Name | MASS | RT (min.) |
|---|---|---|---|---|---|
| 660 | 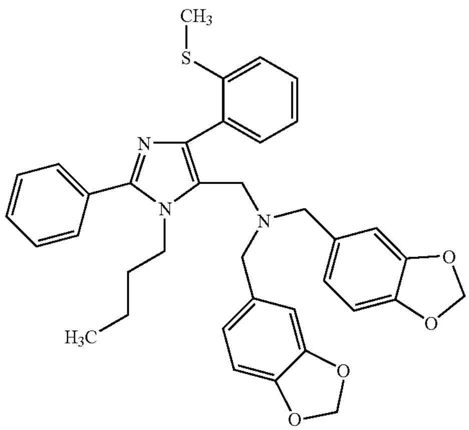 | * | 1-(1,3-benzodioxol-5-yl)-N-(1-3-benzodioxol-5-ylmethyl)-N-({1-butyl-4-[2-(methylthio)phenyl]-2-phenyl-1H-imidazol-5-yl}methyl)methanamine | 620.39 | 1.22 |
| 661 | 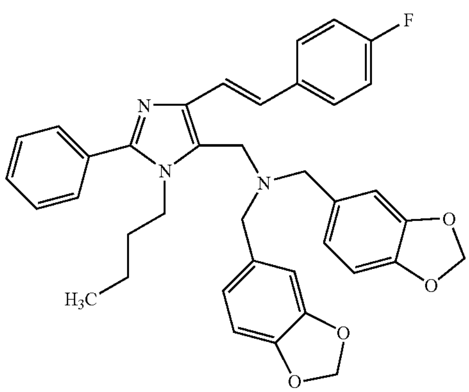 | * | 1-(1,3-benzodioxol-5-yl)-N-(1,3-benzodioxol-5-ylmethyl)-N-({1-butyl-4-[(E)-2-(4-fluorophenyl)ethenyl]-2-phenyl-1H-imidazol-5-yl}methyl)methanamine | 618.41 | 1.23 |
| 662 | 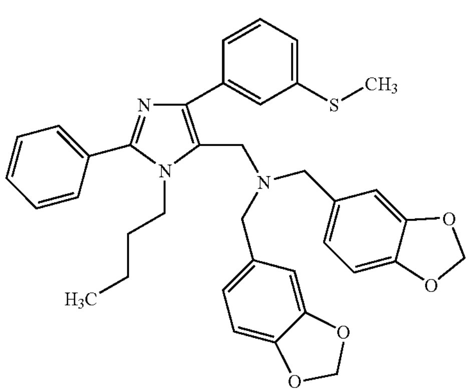 | * | 1-(1,3-benzodioxol-5-yl)-N-(1,3-benzodioxol-5-ylmethyl)-N-({1-butyl-4-[3-(methylthio)phenyl]-2-phenyl-1H-imidazol-5-yl}methyl)methanamine | 621.41 | 1.23 |

TABLE II-continued

| CMP # | STRUCTURE | Ca²⁺ Mob. | IUPAC Name | MASS | RT (min.) |
|---|---|---|---|---|---|
| 663 | 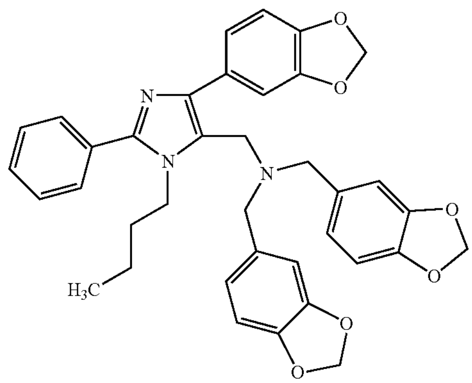 | * | 1-(1,3-benzodioxol-5-yl)-N-{[4-(1,3-benzodioxol-5-yl)-1-butyl-2-phenyl-1H-imidazol-5-yl]methyl}-N-(1,3-benzodioxol-5-ylmethyl)methanamine | 619.42 | 1.21 |
| 664 | 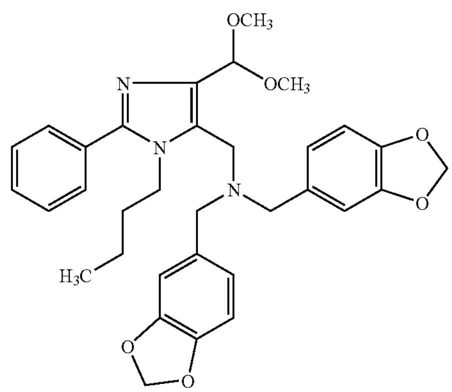 | * | 1-(1,3-benzodioxol-5-yl)-N-(1,3-benzodioxol-5-ylmethyl)-N-{[1-butyl-4-(dimethoxymethyl)-2-phenyl-1H-imidazol-5-yl]methyl}methanamine | 572.41 | 1.19 |
| 665 | 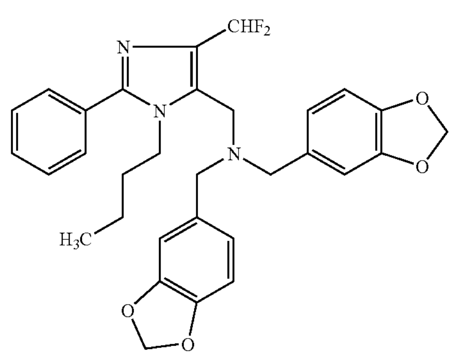 | * | 1-(1,3-benzodioxol-5-yl)-N-(1,3-benzodioxol-5-ylmethyl)-N-{[1-butyl-4-(difluoromethyl)-2-phenyl-1H-imidazol-5-yl]methyl}methanamine | 548.34 | 1.28 |
| 666 | 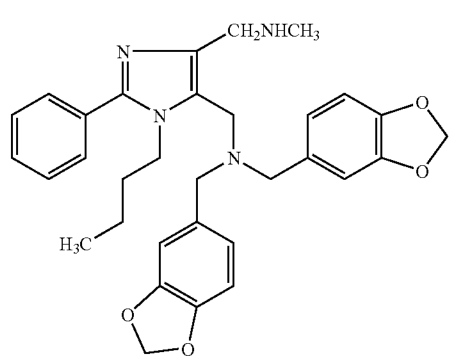 | * | N,N-bis(1,3-benzodioxol-5-ylmethyl)-N-({1-butyl-4-[(methylamino)methyl]-2-phenyl-1H-imidazol-5-yl}methyl)amine | 541.40 | 1.18 |

TABLE II-continued
| CMP # | STRUCTURE | Ca²⁺ Mob. | IUPAC Name | MASS | RT (min.) |
|---|---|---|---|---|---|
| 667 | 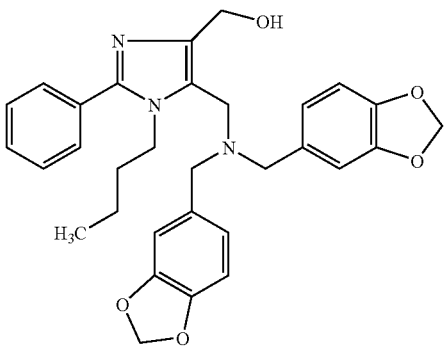 | * | (5-{[bis(1,3-benzodioxol-5-ylmethyl)amino]methyl}-1-butyl-2-phenyl-1H-imidazol-4-yl)methanol | 528.36 | 1.17 |
| 668 | 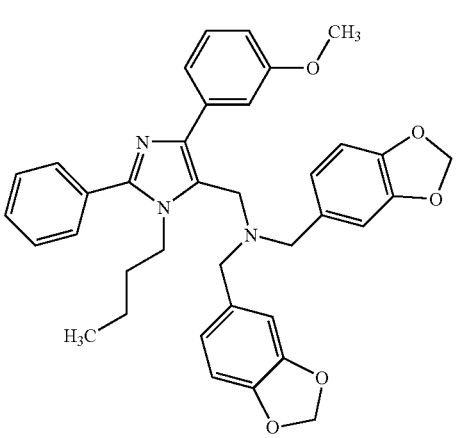 | * | 1-(1,3-benzodioxol-5-yl)-N-(1,3-benzodioxol-5-ylmethyl)-N-{[1-butyl-4-(3-methoxyphenyl)-2-phenyl-1H-imidazol-5-yl]methyl}methanamine | 605.36 | 1.22 |
| 669 | 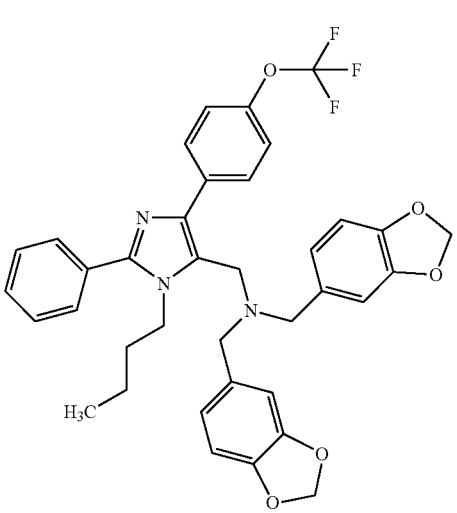 | * | 1-(1,3-benzodioxol-5-yl)-N-(1,3-benzodioxol-5-ylmethyl)-N-({1-butyl-2-phenyl-4-[4-(trifluoromethoxy)phenyl]-1H-imidazol-5-yl}methyl)methanamine | 658.31 | 1.24 |

TABLE II-continued

| CMP # | STRUCTURE | Ca²⁺ Mob. | IUPAC Name | MASS | RT (min.) |
|---|---|---|---|---|---|
| 670 | 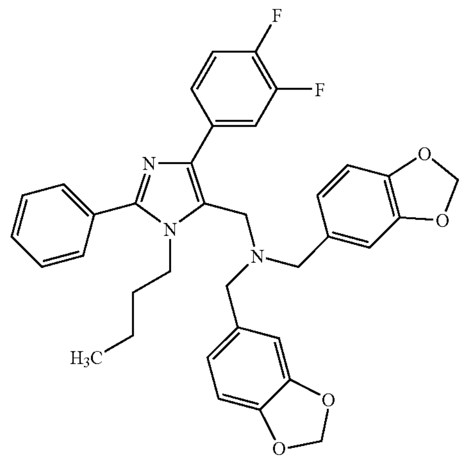 | * | 1-(1,3-benzodioxol-5-yl)-N-(1,3-benzodioxol-5-ylmethyl)-N-{[1-butyl-4-(3,4-difluorophenyl)-2-phenyl-1H-imidazol-5-yl]methyl}methanamine | 611.34 | 1.23 |
| 671 | 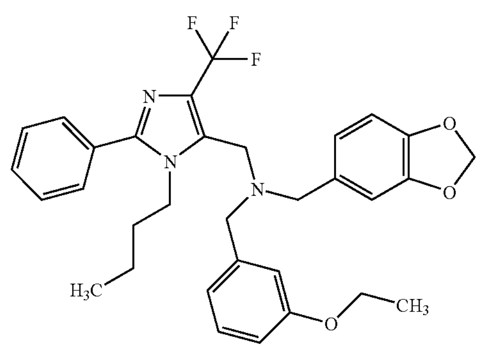 | * | 1-(1,3-benzodioxol-5-yl)-N-{[1-butyl-2-phenyl-4-(trifluoromethyl)-1H-imidazol-5-yl]methyl}-N-(3-ethoxybenzyl)methanamine | 566.31 | 1.4 |
| 672 | 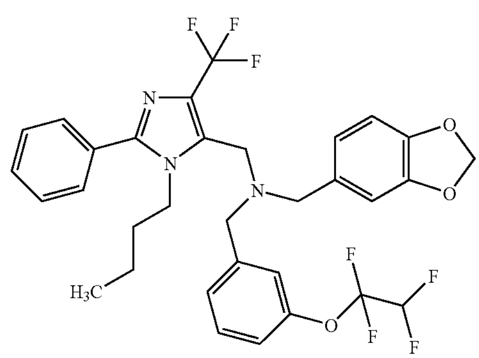 | * | 1-(1,3-benzodioxol-5-yl)-N-{[1-butyl-2-phenyl-4-(trifluoromethyl)-1H-imidazol-5-yl]methyl}-N-[3-(1,1,2,2-tetrafluoroethoxy)benzyl]methanamine | 639.31 | 1.36 |
| 673 | 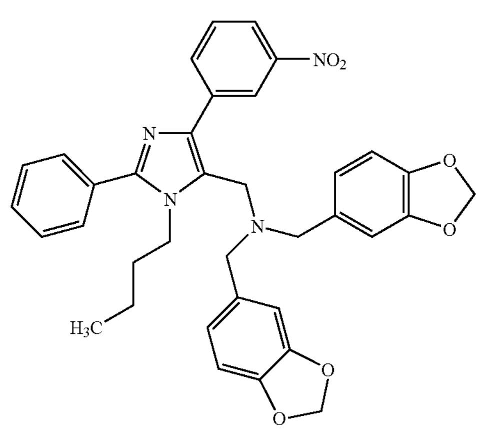 | * | 1-(1,3-benzodioxol-5-yl)-N-(1,3-benzodioxol-5-ylmethyl)-N-{[1-butyl-4-(3-nitrophenyl)-2-phenyl-1H-imidazol-5-yl]methyl}methanamine | 619.32 | 1.23 |

TABLE II-continued

| CMP # | STRUCTURE | Ca²⁺ Mob. | IUPAC Name | MASS | RT (min.) |
|---|---|---|---|---|---|
| 674 | 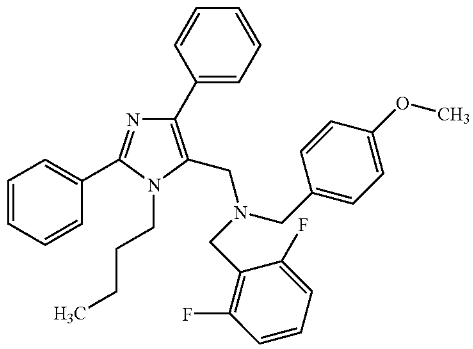 | * | 1-(1-butyl-2,4-diphenyl-1H-imidazol-5-yl)-N-(2,6-difluorobenzyl)-N-(4-methoxybenzyl)methanamine | 552.33 | 1.23 |
| 675 | 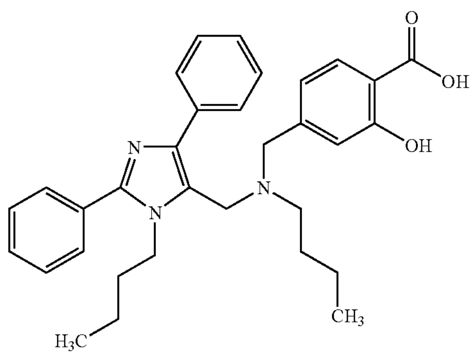 | * | 4-({butyl[(1-butyl-2,4-diphenyl-1H-imidazol-5-yl)methyl]amino}methyl)-2-hydroxybenzoic acid | 512.34 | 1.21 |
| 676 | 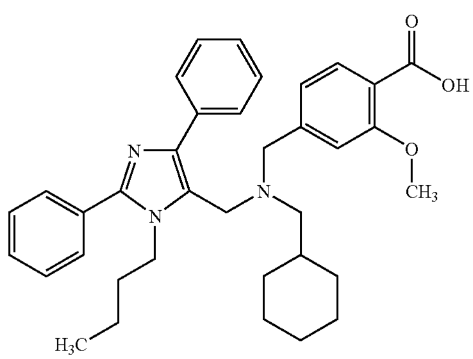 | * | 4-{[[(1-butyl-2,4-diphenyl-1H-imidazol-5-yl)methyl](cyclohexylmethyl)amino]methyl}-2-methoxybenzoic acid | 566.39 | 1.21 |
| 677 | 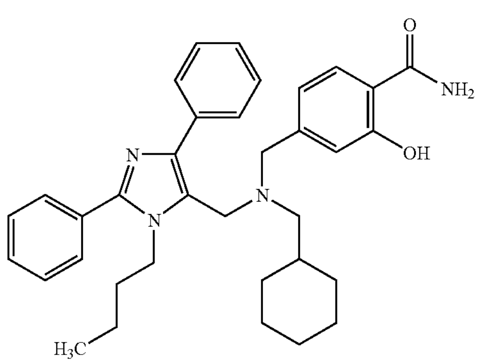 | * | 4-{[[(1-butyl-2,4-diphenyl-1H-imidazol-5-yl)methyl](cyclohexylmethyl)amino]methyl}-2-hydroxybenzamide | 551.39 | 1.22 |

TABLE II-continued

| CMP # | STRUCTURE | Ca²⁺ Mob. | IUPAC Name | MASS | RT (min.) |
|---|---|---|---|---|---|
| 678 | 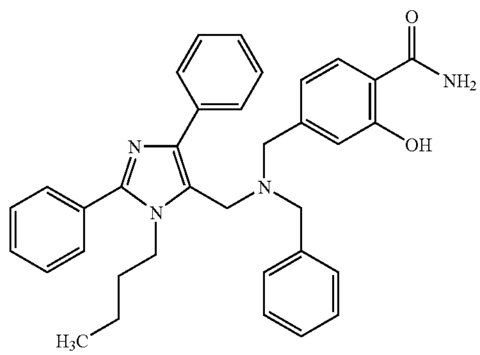 | * | 4-({benzyl[(1-butyl-2,4-diphenyl-1H-imidazol-5-yl)methyl]amino}methyl)-2-hydroxybenzamide | 545.34 | 1.17 |
| 679 | 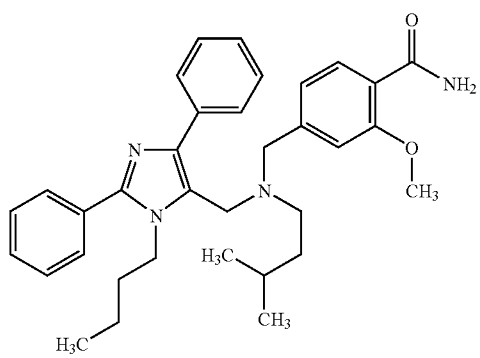 | * | 4-{[[(1-butyl-2,4-diphenyl-1H-imidazol-5-yl)methyl](isopentyl)amino]methyl}-2-methoxybenzamide | 539.39 | 1.16 |
| 680 | 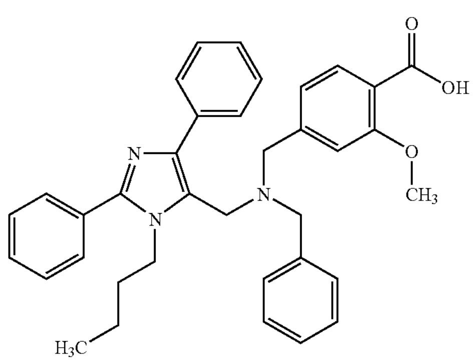 | * | 4-({benzyl[(1-butyl-2,4-diphenyl-1H-imidazol-5-yl)methyl]amino}methyl)-2-methoxybenzoic acid | 560.34 | 1.17 |
| 681 | 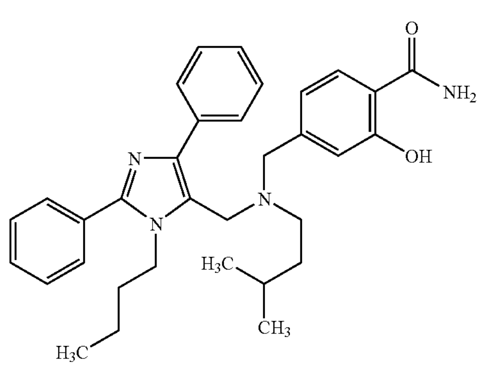 | * | 4-{[[(1-butyl-2,4-diphenyl-1H-imidazol-5-yl)methyl](isopentyl)amino]methyl}-2-hydroxybenzamide | 525.37 | 1.19 |

TABLE II-continued

| CMP # | STRUCTURE | Ca²⁺ Mob. | IUPAC Name | MASS | RT (min.) |
|---|---|---|---|---|---|
| 682 | 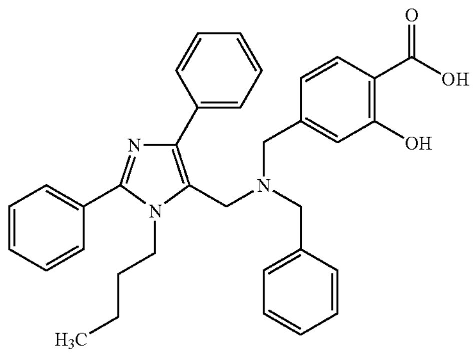 | * | 4-({benzyl[(1-butyl-2,4-diphenyl-1H-imidazol-5-yl)methyl]amino}methyl)-2-hydroxybenzoic acid | 546.33 | 1.21 |
| 683 | 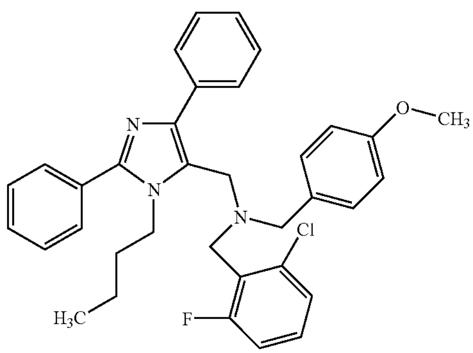 | * | 1-(1-butyl-2,4-diphenyl-1H-imidazol-5-yl)-N-(2-chloro-6-fluorobenzyl)-N-(4-methoxybenzyl)methanamine | 568.31 | 1.24 |
| 684 | 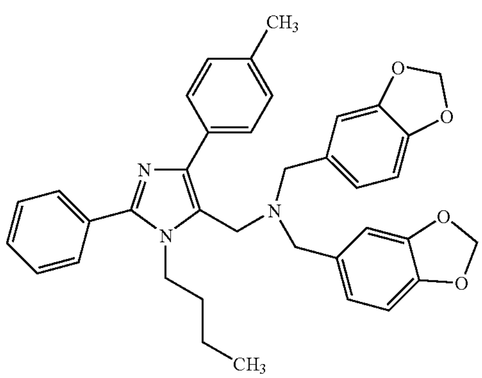 | * | 1-(1,3-benzodioxol-5-yl)-N-(1,3-benzodioxol-5-ylmethyl)-N-{[1-butyl-4-(4-methylphenyl)-2-phenyl-1H-imidazol-5-yl]methyl}methanamine | 588.34 | 1.23 |
| 685 | 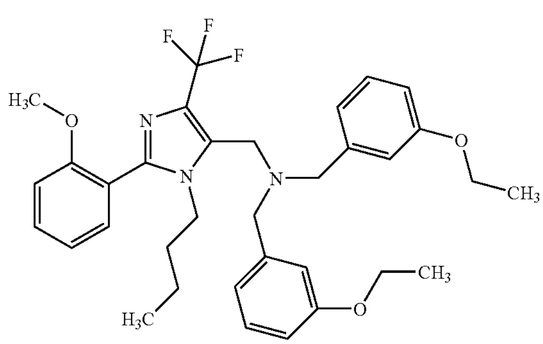 | * | 1-[1-butyl-2-(2-methoxyphenyl)-4-(trifluoromethyl)-1H-imidazol-5-yl]-N,N-bis(3-ethoxybenzyl)methanamine | 596.34 | 1.42 |

TABLE II-continued

| CMP # | STRUCTURE | Ca²⁺ Mob. | IUPAC Name | MASS | RT (min.) |
|---|---|---|---|---|---|
| 686 | 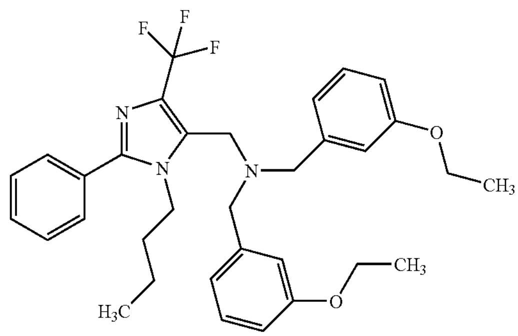 | * | 1-[1-butyl-2-phenyl-4-(trifluoromethyl)-1H-imidazol-5-yl]-N,N-bis(3-ethoxybenzyl)methanamine | 567.36 | 1.43 |
| 687 | 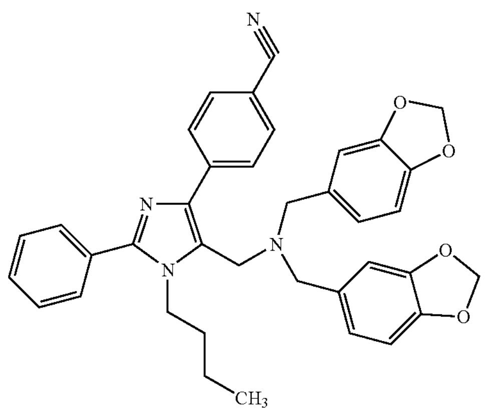 | * | 4-(5-{[bis(1,3-benzodioxol-5-ylmethyl)amino]methyl}-1-butyl-2-phenyl-1H-imidazol-4-yl)benzonitrile | 599.32 | 1.2 |
| 688 | 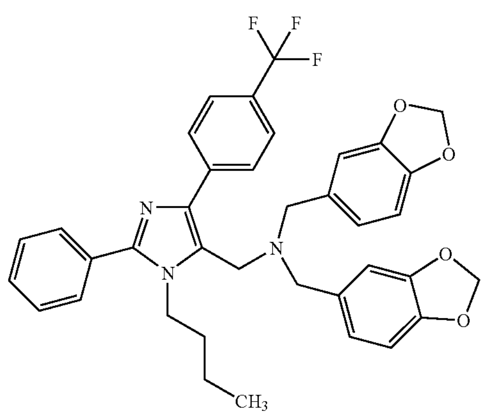 | * | 1-(1,3-benzodioxol-5-yl)-N-(1,3-benzodioxol-5-ylmethyl)-N-({1-butyl-2-phenyl-4-[4-(trifluoromethyl)phenyl]-1H-imidazol-5-yl}methyl)methanamine | 642.30 | 1.24 |
| 689 | 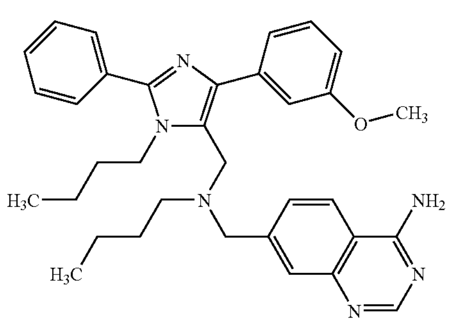 | | 7-[(butyl{[1-butyl-4-(3-methoxyphenyl)-2-phenyl-1H-imidazol-5-yl]methyl}amino)methyl]quinazolin-4-amine | | |

TABLE II-continued

| CMP # | STRUCTURE | Ca²⁺ Mob. | IUPAC Name | MASS | RT (min.) |
|---|---|---|---|---|---|
| 690 | 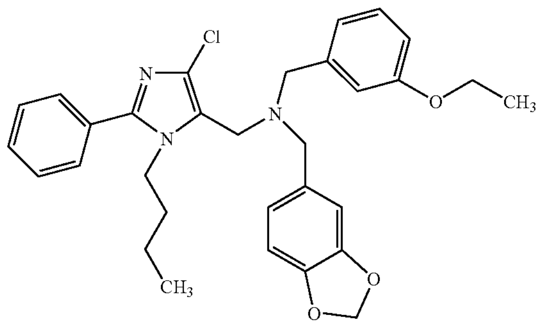 | | 1-(1,3-benzodioxol-5-yl)-N-[(1-butyl-4-chloro-2-phenyl-1H-imidazol-5-yl)methyl]-N-(3-ethoxybenzyl)methanamine | | |
| 691 | 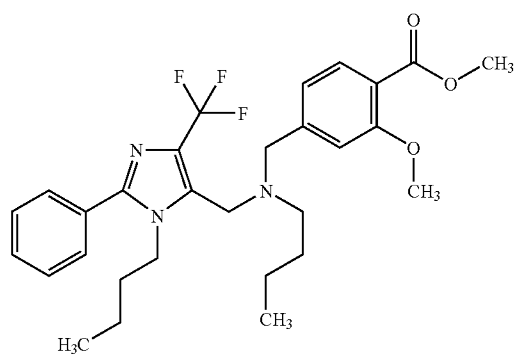 | * | methyl 4-[(butyl{[1-butyl-2-phenyl-4-(trifluoromethyl)-1H-imidazol-5-yl]methyl}amino)methyl]-2-methoxybenzoate | 532.31 | 1.3 |
| 692 | 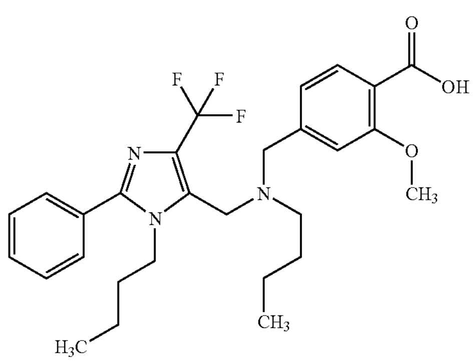 | * | 4-[(butyl{[1-butyl-2-phenyl-4-(trifluoromethyl)-1H-imidazol-5-yl]methyl}amino)methyl]-2-methoxybenzoic acid | 518.30 | 1.26 |
| 693 | 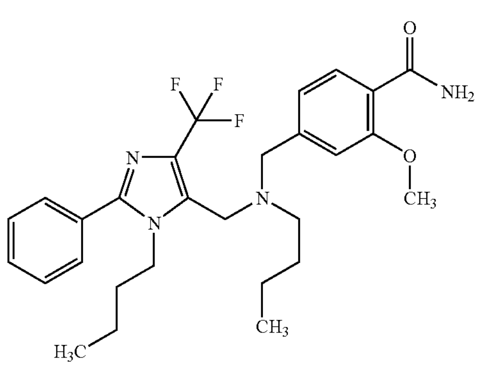 | * | 4-[(butyl{[1-butyl-2-phenyl-4-(trifluoromethyl)-1H-imidazol-5-yl]methyl}amino)methyl]-2-methoxybenzamide | 517.32 | 1.25 |

TABLE II-continued

| CMP # | STRUCTURE | Ca²⁺ Mob. | IUPAC Name | MASS | RT (min.) |
|---|---|---|---|---|---|
| 694 | 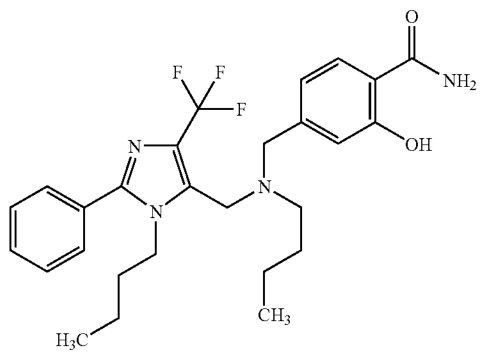 | * | 4-[(butyl{[1-butyl-2-phenyl-4-(trifluoromethyl)-1H-imidazol-5-yl]methyl}amino)methyl]-2-hydroxybenzamide | 503.30 | 1.25 |
| 695 | 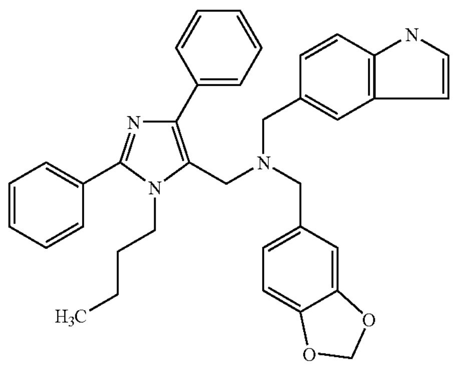 | * | 1-(1,3-benzodioxol-5-yl)-N-[(1-butyl-2,4-diphenyl-1H-imidazol-5-yl)methyl]-N-(1H-indol-5-ylmethyl)methanamine | 569.36 | 1.2 |
| 696 | 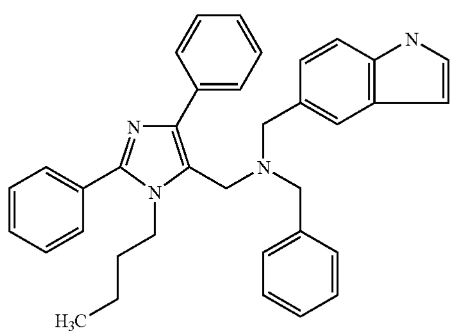 | * | N-benzyl-1-(1-butyl-2,4-diphenyl-1H-imidazol-5-yl)-N-(1H-indol-5-ylmethyl)methanamine | 525.36 | 1.21 |
| 697 | 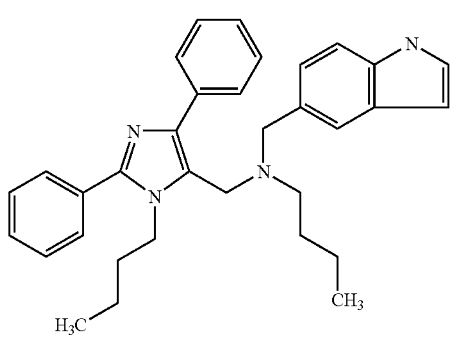 | * | N-[(1-butyl-2,4-diphenyl-1H-imidazol-5-yl)methyl]-N-(1H-indol-5-ylmethyl)butan-1-amine | 491.38 | 1.12 |

TABLE II-continued

| CMP # | STRUCTURE | Ca²⁺ Mob. | IUPAC Name | MASS | RT (min.) |
|---|---|---|---|---|---|
| 698 | 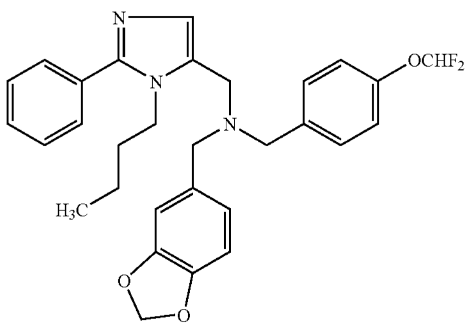 | * | 1-(1,3-benzodioxol-5-yl)-N-[(1-butyl-2-phenyl-1H-imidazol-5-yl)methyl]-N-[4-(difluoromethoxy)benzyl]methanamine | 520.26 | 1.18 |
| 699 | 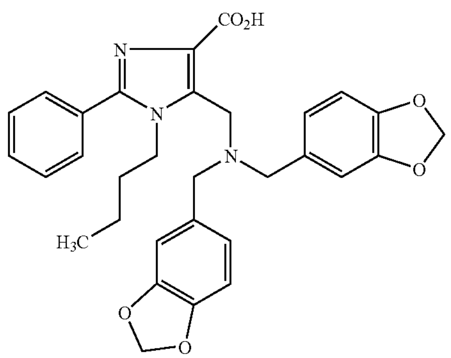 | * | 5-{[bis(1,3-benzodioxol-5-ylmethyl)amino]methyl}-1-butyl-2-phenyl-1H-imidazole-4-carboxylic acid | 542.27 | 1.09 |
| 700 | 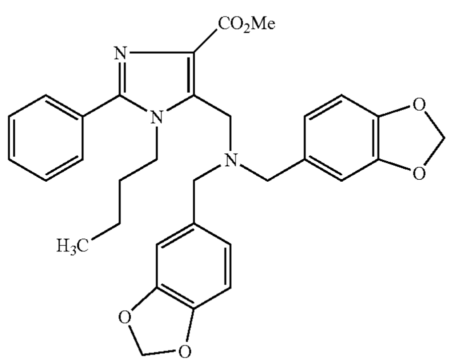 | * | methyl 5-{[bis(1,3-benzodioxol-5-ylmethyl)amino]methyl}-1-butyl-2-phenyl-1H-imidazole-4-carboxylate | 556.27 | 1.21 |
| 701 | 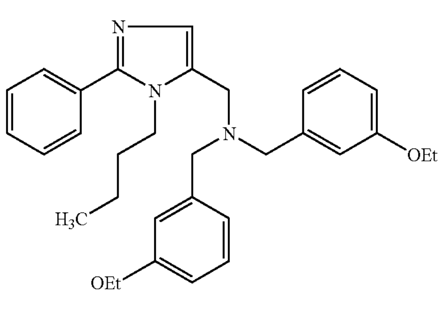 | * | 1-(1-butyl-2-phenyl-1H-imidazol-5-yl)-N,N-bis(3-ethoxybenzyl)methanamine | 498.32 | 1.23 |

TABLE II-continued

| CMP # | STRUCTURE | Ca²⁺ Mob. | IUPAC Name | MASS | RT (min.) |
|---|---|---|---|---|---|
| 702 | 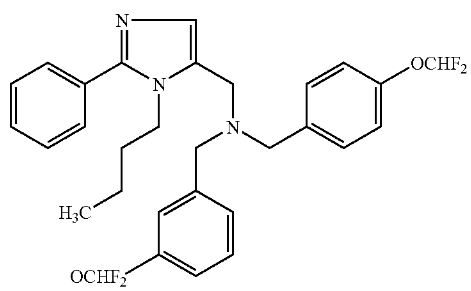 | * | 1-(1-butyl-2-phenyl-1H-imidazol-5-yl)-N-[3-(difluoromethoxy)benzyl]-N-[4-(difluoromethoxy)benzyl]methanamine | 542.26 | 1.18 |
| 703 | 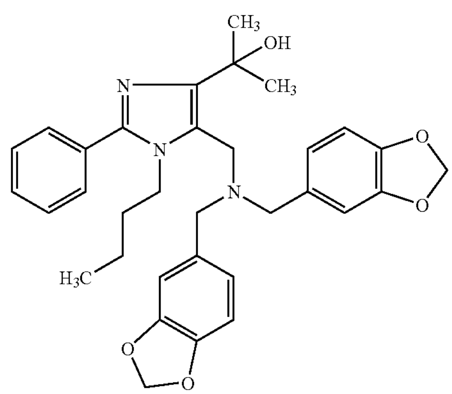 | * | 2-(5-{[bis(1,3-benzodioxol-5-ylmethyl)amino]methyl}-1-butyl-2-phenyl-1H-imidazol-4-yl)propan-2-ol | 556.32 | 1.15 |
| 704 | 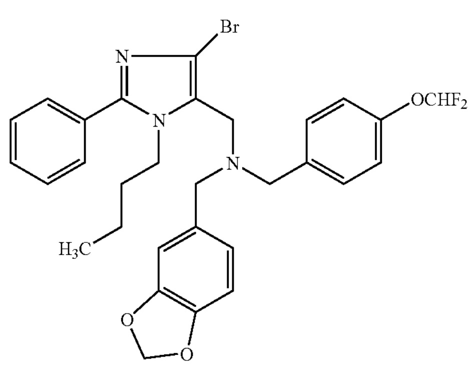 | * | 1-(1,3-benzodioxol-5-yl)-N-[(4-bromo-1-butyl-2-phenyl-1H-imidazol-5-yl)methyl]-N-[4-(difluoromethoxy)benzyl]methanamine | 598.19 | 1.32 |
| 705 | 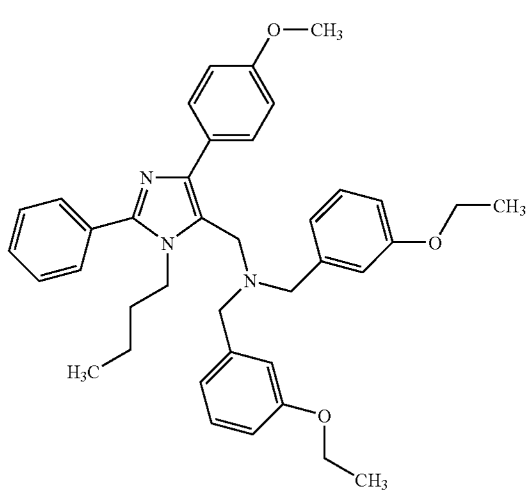 | * | 1-[1-butyl-4-(4-methoxyphenyl)-2-phenyl-1H-imidazol-5-yl]-N,N-bis(3-ethoxybenzyl)methanamine | 605.39 | 1.25 |

TABLE II-continued

| CMP # | STRUCTURE | Ca²⁺ Mob. | IUPAC Name | MASS | RT (min.) |
|---|---|---|---|---|---|
| 706 | 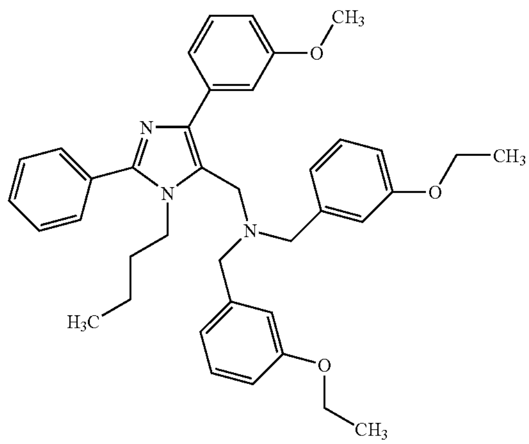 | | 1-[1-butyl-4-(3-methoxyphenyl)-2-phenyl-1H-imidazol-5-yl]-N,N-bis(3-ethoxybenzyl)methanamine | | |
| 707 | 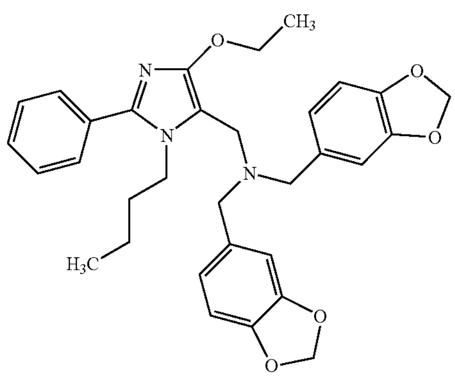 | * | 1-(1,3-benzodioxol-5-yl)-N-(1,3-benzodioxol-5-ylmethyl)-N-[(1-butyl-4-ethoxy-2-phenyl-1H-imidazol-5-yl)methyl]methanamine | 257.18 | 1.18 |
| 708 | 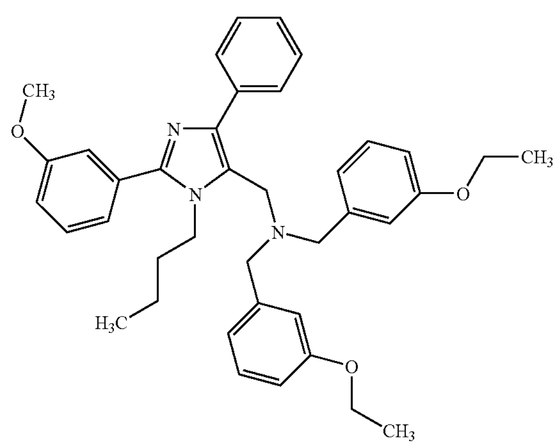 | * | 1-[1-butyl-2-(3-methoxyphenyl)-4-phenyl-1H-imidazol-5-yl]-N,N-bis(3-ethoxybenzyl)methanamine | 604.36 | 1.26 |
| 709 | 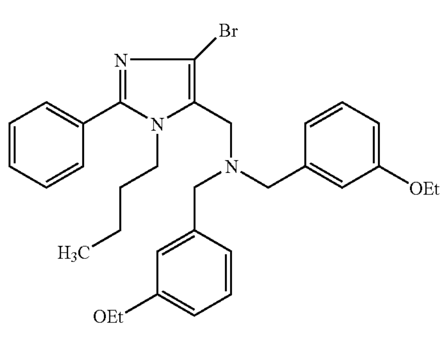 | * | N-[(4-bromo-1-butyl-2-phenyl-1H-imidazol-5-yl)methyl]-N,N-bis(3-ethoxybenzyl)amine | 576.24 | 1.4 |

TABLE II-continued

| CMP # | STRUCTURE | Ca²⁺ Mob. | IUPAC Name | MASS | RT (min.) |
|---|---|---|---|---|---|
| 710 | 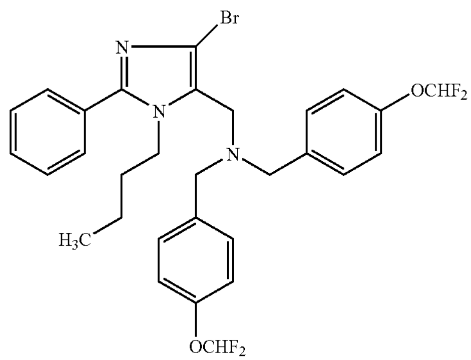 | * | N-[(4-bromo-1-butyl-2-phenyl-1H-imidazol-5-yl)methyl]-N,N-bis[4-(difluoromethoxy)benzyl]amine | 620.18 | 1.31 |
| 711 | 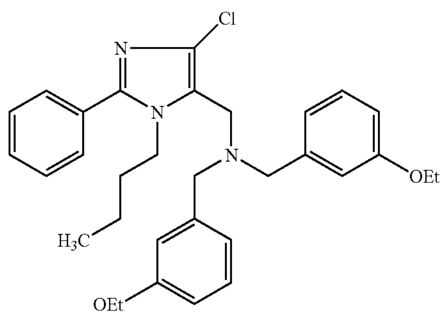 | * | N-[(1-butyl-4-chloro-2-phenyl-1H-imidazol-5-yl)methyl]-N,N-bis(3-ethoxybenzyl)amine | 532.29 | 1.4 |
| 712 | 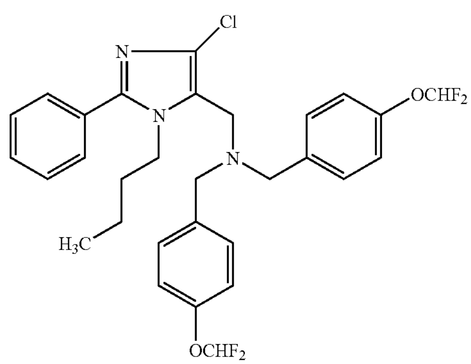 | * | N-[(1-butyl-4-chloro-2-phenyl-1H-imidazol-5-yl)methyl]-N,N-bis[4-(difluoromethoxy)benzyl]amine | 576.22 | 1.33 |
| 713 | 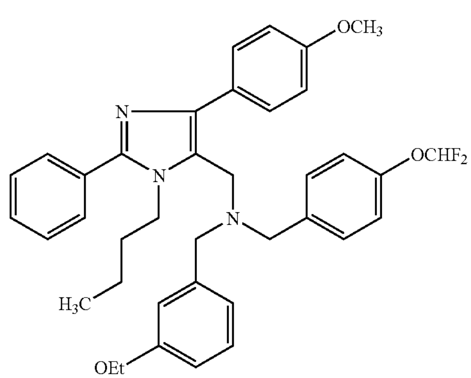 | * | 1-[1-butyl-4-(4-methoxyphenyl)-2-phenyl-1H-imidazol-5-yl]-N-[4-(difluoromethoxy)benzyl]-N-(3-ethoxybenzyl)methanamine | 626.32 | 1.23 |

TABLE II-continued

| CMP # | STRUCTURE | Ca²⁺ Mob. | IUPAC Name | MASS | RT (min.) |
|---|---|---|---|---|---|
| 714 | 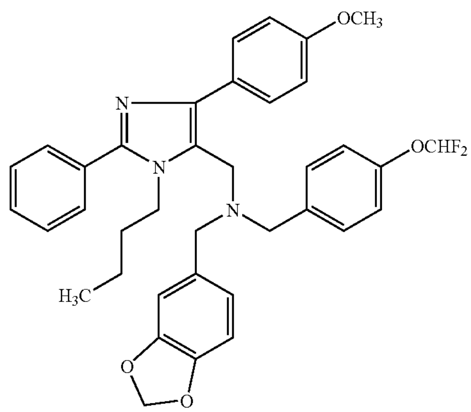 | * | 1-(1,3-benzodioxol-5-yl)-N-{[1-butyl-4-(4-methoxyphenyl)-2-phenyl-1H-imidazol-5-yl]methyl}-N-[4-(difluoromethoxy)benzyl]methanamine | 626.30 | 1.21 |
| 715 | 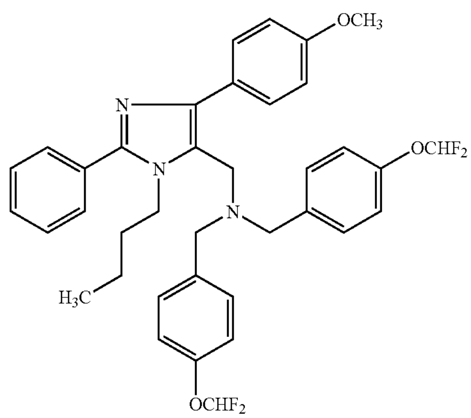 | * | 1-[1-butyl-4-(4-methoxyphenyl)-2-phenyl-1H-imidazol-5-yl]-N,N-bis[4-(difluoromethoxy)benzyl]methanamine | 648.30 | 1.2 |
| 716 | 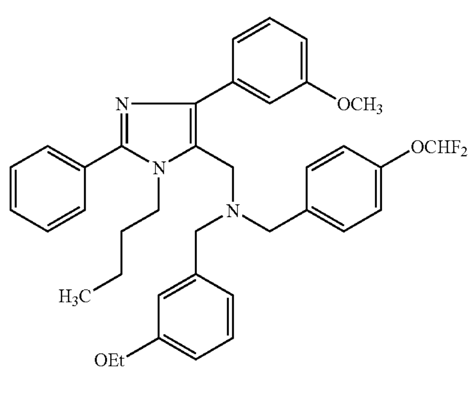 | * | 1-[1-butyl-4-(3-methoxyphenyl)-2-phenyl-1H-imidazol-5-yl]-N-[4-(difluoromethoxy)benzyl]-N-(3-ethoxybenzyl)methanamine | 626.33 | 1.24 |

TABLE II-continued

| CMP # | STRUCTURE | Ca²⁺ Mob. | IUPAC Name | MASS | RT (min.) |
|---|---|---|---|---|---|
| 717 | 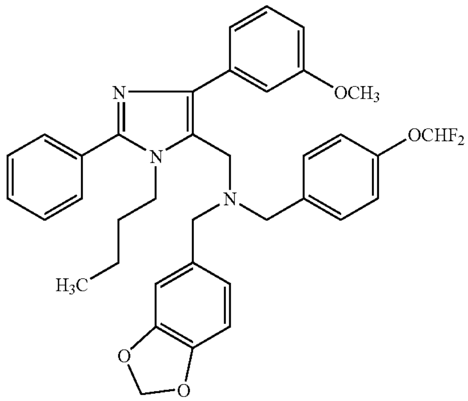 | * | 1-(1,3-benzodioxol-5-yl)-N-{[1-butyl-4-(3-methoxyphenyl)-2-phenyl-1H-imidazol-5-yl]methyl}-N-[4-(difluoromethoxy)benzyl]methanamine | 626.30 | 1.21 |
| 718 | 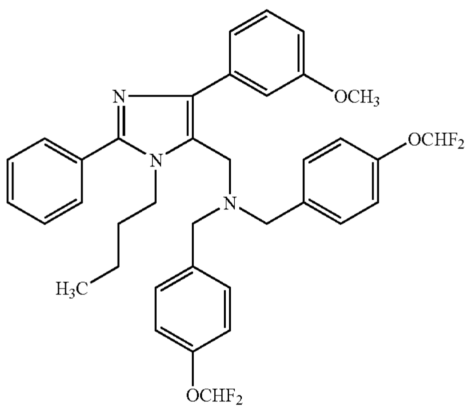 | * | 1-[1-butyl-4-(3-methoxyphenyl)-2-phenyl-1H-imidazol-5-yl]-N,N-bis[4-(difluoromethoxy)benzyl]methanamine | 648.30 | 1.21 |
| 719 | 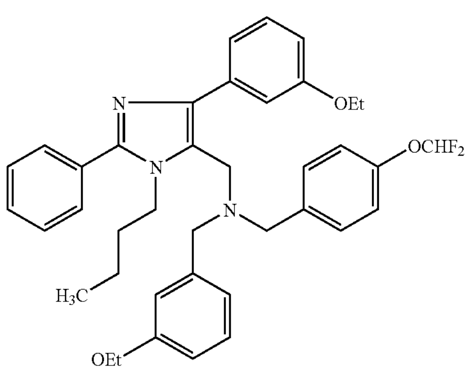 | * | N-{[1-butyl-4-(3-ethoxyphenyl)-2-phenyl-1H-imidazol-5-yl]methyl}-N-[4-(difluoromethoxy)benzyl]-N-(3-ethoxybenzyl)amine | 640.34 | 1.26 |

TABLE II-continued

| CMP # | STRUCTURE | Ca²⁺ Mob. | IUPAC Name | MASS | RT (min.) |
|---|---|---|---|---|---|
| 720 | 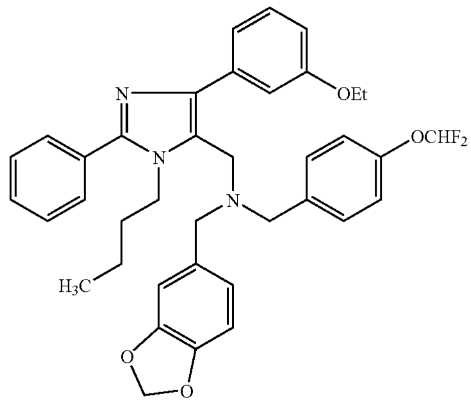 | * | 1-(1,3-benzodioxol-5-yl)-N-{[1-butyl-4-(3-ethoxyphenyl)-2-phenyl-1H-imidazol-5-yl]methyl}-N-[4-(difluoromethoxy)benzyl]methanamine | 640.31 | 1.23 |
| 721 | 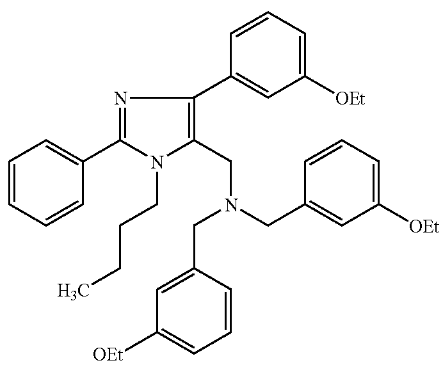 | * | N-{[1-butyl-4-(3-ethoxyphenyl)-2-phenyl-1H-imidazol-5-yl]methyl}-N,N-bis(3-ethoxybenzyl)amine | 619.40 | 1.28 |
| 722 | 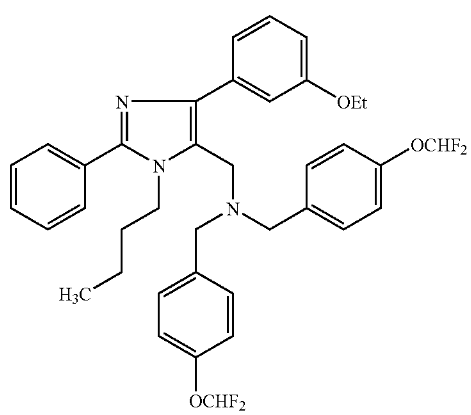 | * | N-{[1-butyl-4-(3-ethoxyphenyl)-2-phenyl-1H-imidazol-5-yl]methyl}-N,N-bis[4-(difluoromethoxy)benzyl]amine | 662.31 | 1.23 |
| 723 | 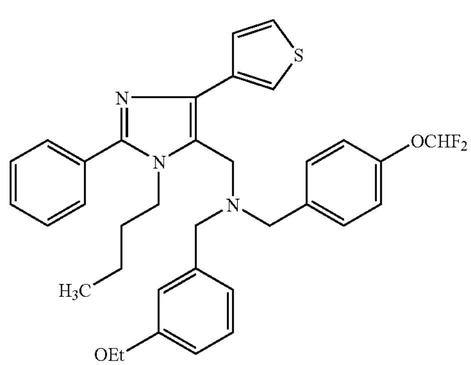 | * | 1-(1-butyl-2-phenyl-4-thien-3-yl-1H-imidazol-5-yl)-N-[4-(difluoromethoxy)benzyl]-N-(3-ethoxybenzyl)methanamine | 602.28 | 1.22 |

TABLE II-continued

| CMP # | STRUCTURE | Ca²⁺ Mob. | IUPAC Name | MASS | RT (min.) |
|---|---|---|---|---|---|
| 724 | 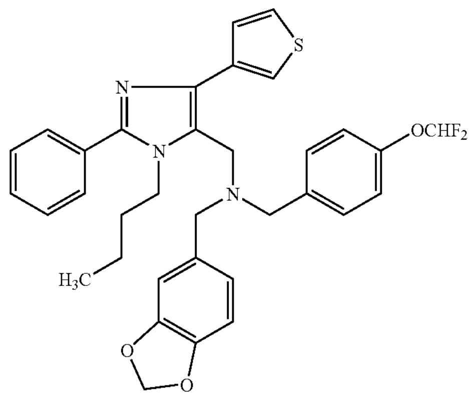 | * | 1-(1,3-benzodioxol-5-yl)-N-[(1-butyl-2-phenyl-4-thien-3-yl-1H-imidazol-5-yl)methyl]-N-[4-(difluoromethoxy)benzyl]methanamine | 598.19 | 1.31 |
| 725 | 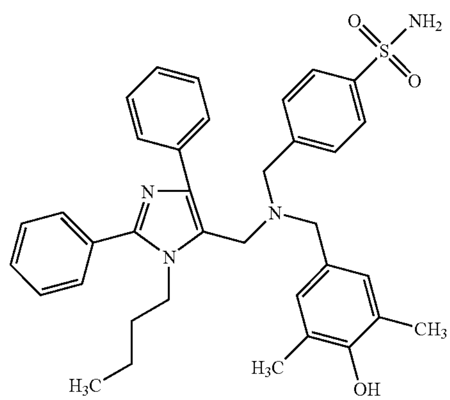 | * | 4-{[[(1-butyl-2,4-diphenyl-1H-imidazol-5-yl)methyl](4-hydroxy-3,5-dimethylbenzyl)amino]methyl}benzenesulfonamide | 609.35 | 1.12 |
| 726 | 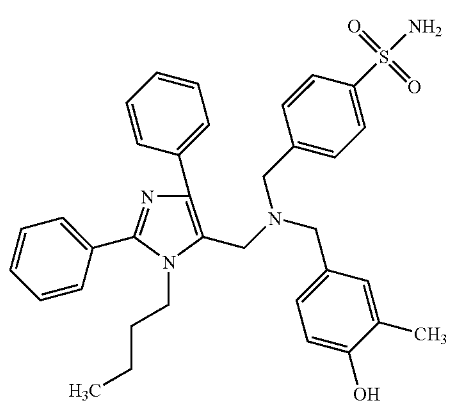 | * | 4-{[[(1-butyl-2,4-diphenyl-1H-imidazol-5-yl)methyl](4-hydroxy-3-methylbenzyl)amino]methyl}benzenesulfonamide | 595.32 | 1.1 |

TABLE II-continued

| CMP # | STRUCTURE | Ca²⁺ Mob. | IUPAC Name | MASS | RT (min.) |
|---|---|---|---|---|---|
| 727 | 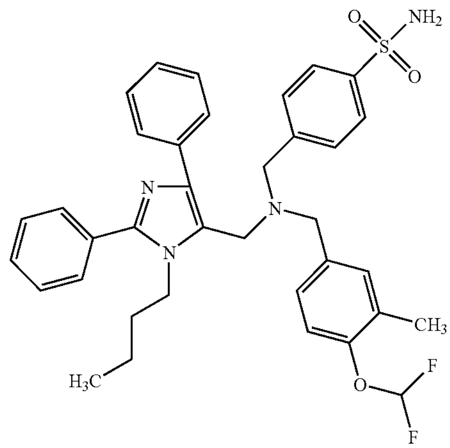 | * | 4-({[(1-butyl-2,4-diphenyl-1H-imidazol-5-yl)methyl][4-(difluoromethoxy)-3-methylbenzyl]amino}methyl)benzenesulfonamide | 645.29 | 1.15 |
| 728 | 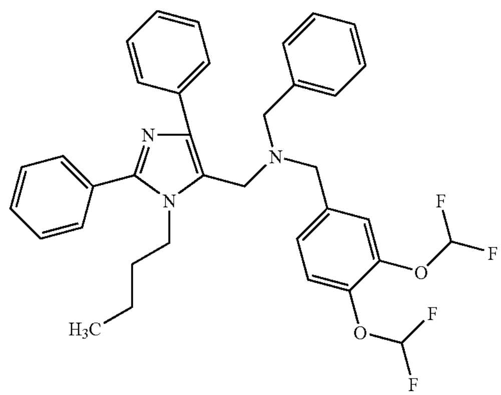 | * | N-benzyl-1-[3,4-bis(difluoromethoxy)phenyl]-N-[(1-butyl-2,4-diphenyl-1H-imidazol-5-yl)methyl]methanamine | 618.28 | 1.21 |
| 729 | 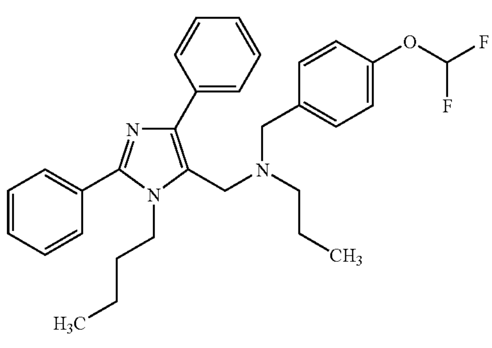 | * | N-[(1-butyl-2,4-diphenyl-1H-imidazol-5-yl)methyl]-N-[4-(difluoromethoxy)benzyl]propan-1-amine | 504.30 | 1.18 |
| 730 | 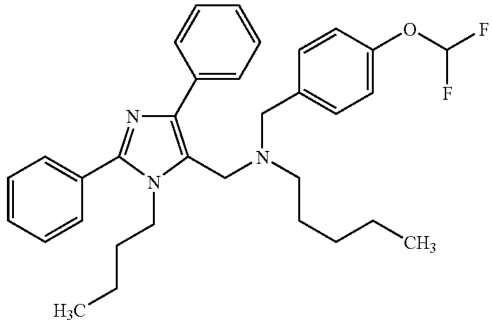 | * | N-[(1-butyl-2,4-diphenyl-1H-imidazol-5-yl)methyl]-N-[4-(difluoromethoxy)benzyl]pentan-1-amine | 532.33 | 1.22 |

TABLE II-continued

| CMP # | STRUCTURE | Ca$^{2+}$ Mob. | IUPAC Name | MASS | RT (min.) |
|---|---|---|---|---|---|
| 731 | 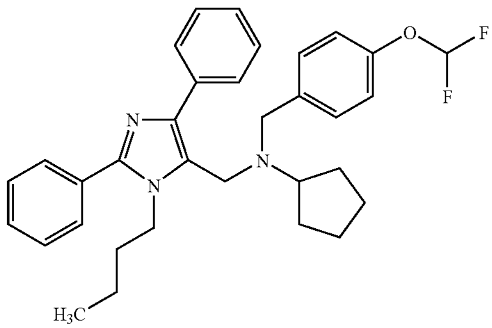 | * | N-[(1-butyl-2,4-diphenyl-1H-imidazol-5-yl)methyl]-N-[4-(difluoromethoxy)benzyl]cyclopentan-amine | 530.32 | 1.21 |
| 732 | 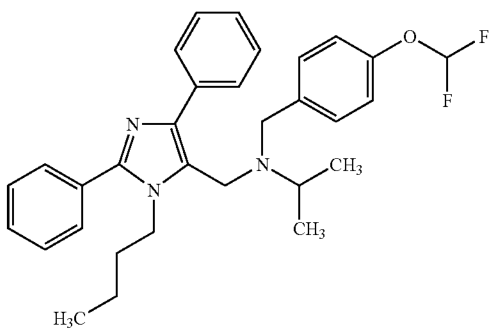 | * | N-[(1-butyl-2,4-diphenyl-1H-imidazol-5-yl)methyl]-N-[4-(difluoromethoxy)benzyl]propan-2-amine | 504.29 | 1.18 |
| 733 | 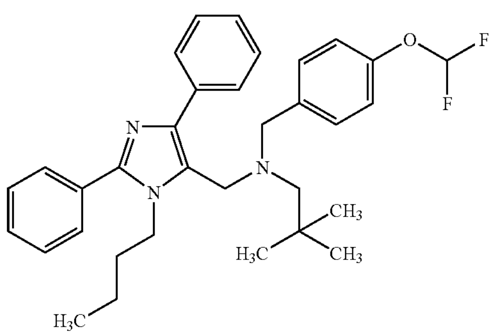 | * | N-[(1-butyl-2,4-diphenyl-1H-imidazol-5-yl)methyl]-N-[4-(difluoromethoxy)benzyl]-2,2-dimethylpropan-1-amine | 533.35 | 1.24 |
| 734 | 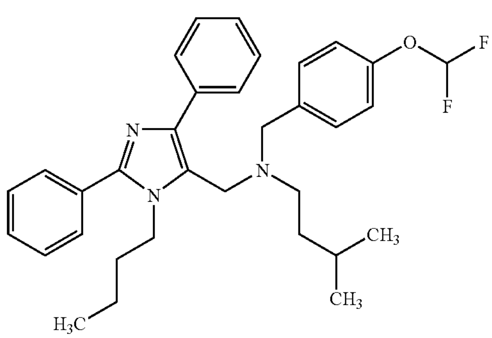 | * | N-[(1-butyl-2,4-diphenyl-1H-imidazol-5-yl)methyl]-N-[4-(difluoromethoxy)benzyl]-3-methylbutan-1-amine | 533.35 | 1.22 |

TABLE II-continued

| CMP # | STRUCTURE | Ca²⁺ Mob. | IUPAC Name | MASS | RT (min.) |
|---|---|---|---|---|---|
| 735 | 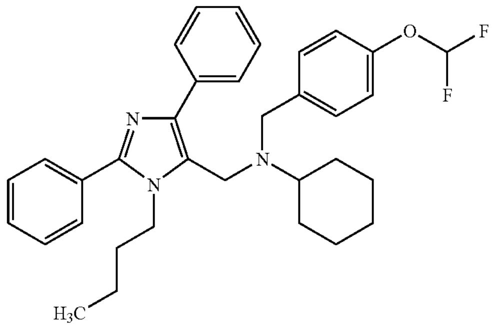 | * | N-[(1-butyl-2,4-diphenyl-1H-imidazol-5-yl)methyl]-N-[4-(difluoromethoxy)benzyl]cyclohex-anamine | 544.33 | 1.23 |
| 736 | 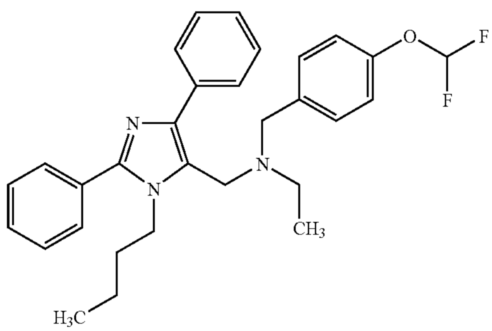 | * | N-[(1-butyl-2,4-diphenyl-1H-imidazal-5-yl)methyl]-N-[4-(difluoromethoxy)benzyl]ethanamine | 490.28 | 1.16 |
| 737 | 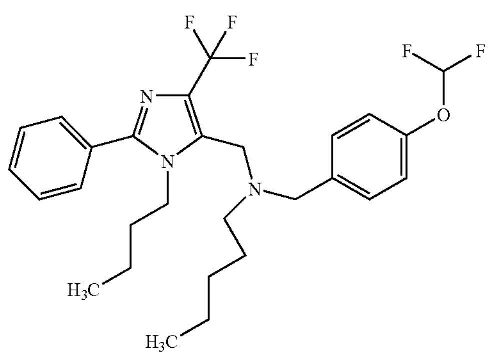 | * | N-{[1-butyl-2-phenyl-4-(trifluoromethyl)-1H-imidazol-5-yl]methyl}-N-[4-(difluoromethoxy)benzyl]pentan-1-amine | 524.28 | 1.32 |
| 738 | 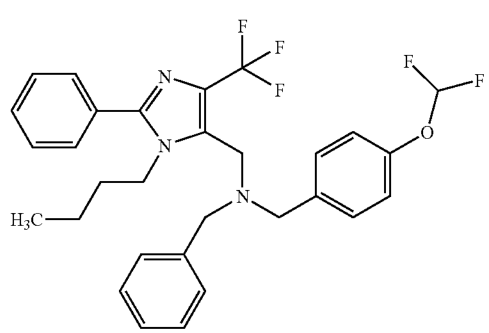 | * | N-benzyl-1-[1-butyl-2-phenyl-4-(trifluoromethyl)-1H-imidazol-5-yl]-N-[4-(difluoromethoxy)benzyl]methanamine | 544.24 | 1.37 |

TABLE II-continued

| CMP # | STRUCTURE | Ca²⁺ Mob. | IUPAC Name | MASS | RT (min.) |
|---|---|---|---|---|---|
| 739 | 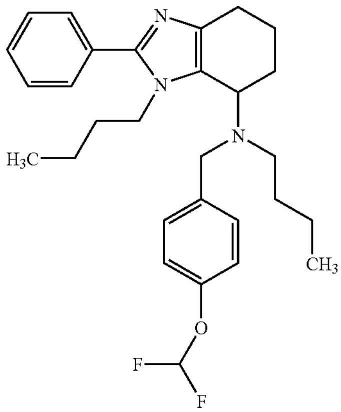 | * | N,1-dibutyl-N-[4-(difluoromethoxy)benzyl]-2-phenyl-4,5,6,7-tetrahydro-1H-benzimidazol-7-amine | 482.33 | 1.21 |
| 740 | 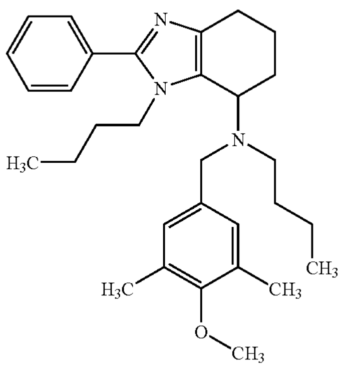 | * | N,1-dibutyl-N-(4-methoxy-3,5-dimethylbenzyl)-2-phenyl-4,5,6,7-tetrahydro-1H-benzimidazol-7-amine | 474.37 | 1.26 |
| 741 | 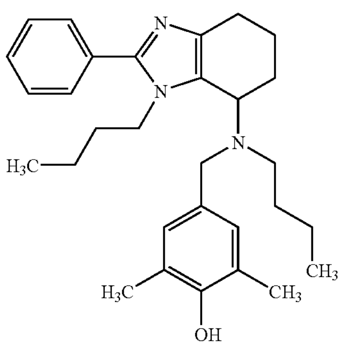 | * | 4-{[butyl(1-butyl-2-phenyl-4,5,6,7-tetrahydro-1H-benzimidazol-7-yl)amino]methyl}-2,6-dimethylphenol | 460.34 | 1.21 |
| 742 | 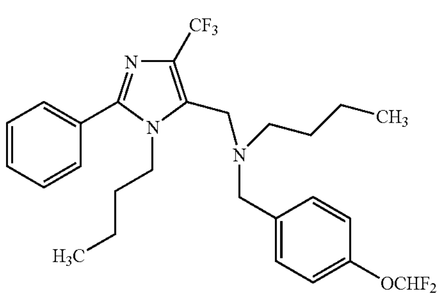 | * | N-{[1-butyl-2-phenyl-4-(trifluoromethyl)-1H-imidazol-5-yl]methyl}-N-[4-(difluoromethoxy)benzyl]butan-1-amine | 510.27 | 1.28 |

TABLE II-continued

| CMP # | STRUCTURE | Ca²⁺ Mob. | IUPAC Name | MASS | RT (min.) |
|---|---|---|---|---|---|
| 743 | 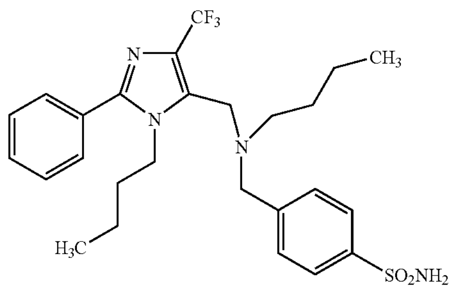 | * | 4-[(butyl{[1-butyl-2-phenyl-4-(trifluoromethyl)-1H-imidazol-5-yl]methyl}amino)methyl]benzene-sulfonamide | 523.27 | 1.23 |
| 744 | 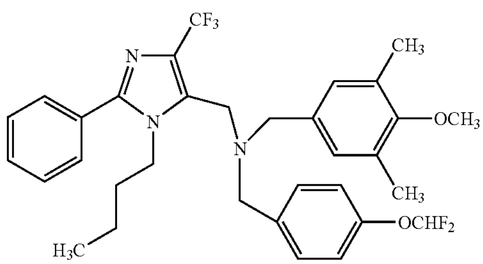 | * | 1-[1-butyl-2-phenyl-4-(trifluoromethyl)-1H-imidazol-5-yl]-N-[4-(difluoromethoxy)benzyl]-N-(4-methoxy-3,5-dimethylbenzyl)methanamine | 603.39 | 1.39 |
| 745 | 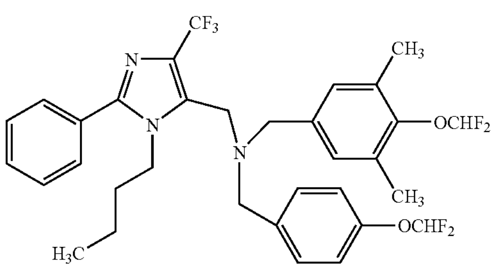 | * | 1-[1-butyl-2-phenyl-4-(trifluoromethyl)-1H-imidazol-5-yl]-N-[4-(difluoromethoxy)benzyl]-N-[4-(difluoromethoxy)-3,5-dimethylbenzyl]methanamine | 639.38 | 1.37 |
| 746 | 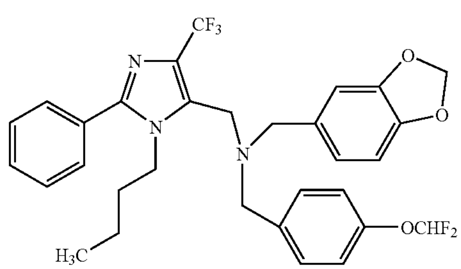 | * | 1-(1,3-benzodioxol-5-yl)-N-{[1-butyl-2-phenyl-4-(trifluoromethyl)-1H-imidazol-5-yl]methyl}-N-[4-(difluoromethoxy)benzyl]methanamine | 588.30 | 1.34 |
| 747 | 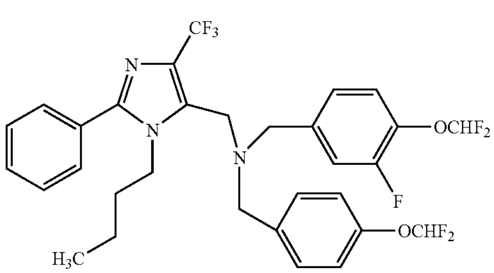 | * | 1-[1-butyl-2-phenyl-4-(trifluoromethyl)-1H-imidazol-5-yl]-N-[4-(difluoromethoxy)benzyl]-N-[4-(difluoromethoxy)-3-fluorobenzyl]methanamine | 628.29 | 1.32 |

TABLE II-continued

| CMP # | STRUCTURE | Ca²⁺ Mob. | IUPAC Name | MASS | RT (min.) |
|---|---|---|---|---|---|
| 748 | 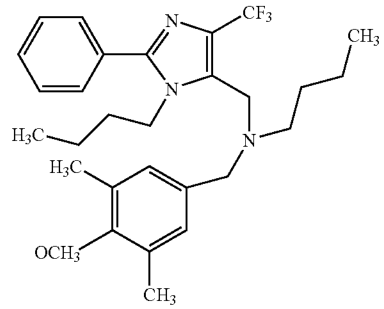 | * | N-{[1-butyl-2-phenyl-4-(trifluoromethyl)-1H-imidazol-5-yl]methyl}-N-(4-methoxy-3,5-dimethylbenzyl)butan-1-amine | 502.37 | 1.27 |
| 749 | 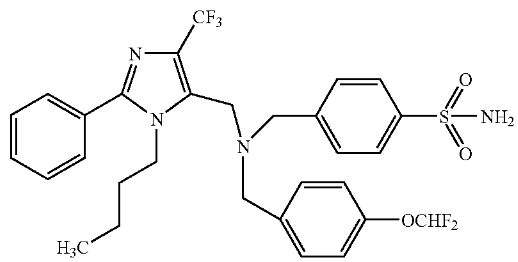 | * | 4-({{[1-butyl-2-phenyl-4-(trifluoromethyl)-1H-imidazol-5-yl]methyl}[4-(difluoromethoxy)benzyl]amino}methyl)benzenesulfonamide | 623.26 | 1.24 |
| 750 | 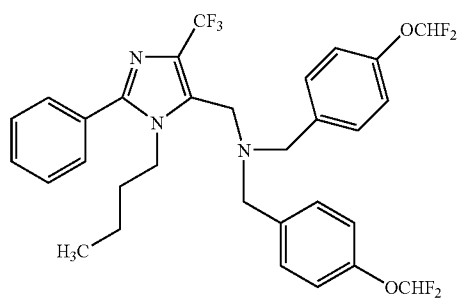 | * | 1-[1-butyl-2-phenyl-4-(trifluoromethyl)-1H-imidazol-5-yl]-N,N-bis[4-(difluoromethoxy)benzyl]methanamine | 610.26 | 1.33 |
| 751 | 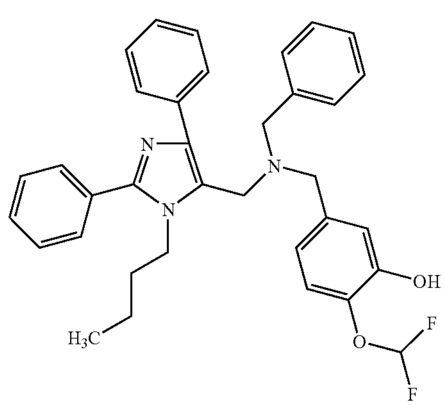 | * | 5-({benzyl[(1-butyl-2,4-diphenyl-1H-imidazol-5-yl)methyl]amino}methyl)-2-(difluoromethoxy)phenol | 568.28 | 1.21 |

TABLE II-continued

| CMP # | STRUCTURE | Ca²⁺ Mob. | IUPAC Name | MASS | RT (min.) |
|---|---|---|---|---|---|
| 752 | 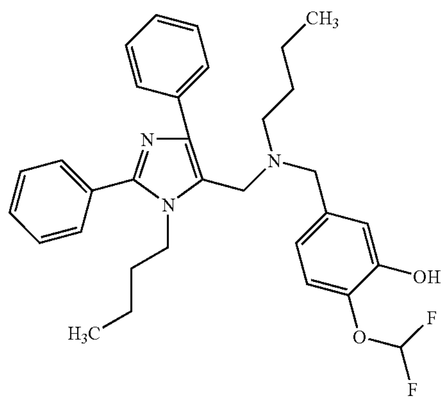 | * | 5-({butyl[(1-butyl-2,4-diphenyl-1H-imidazol-5-yl)methyl]amino}methyl)-2-(difluoromethoxy)phenol | 534.30 | 1.17 |
| 753 | 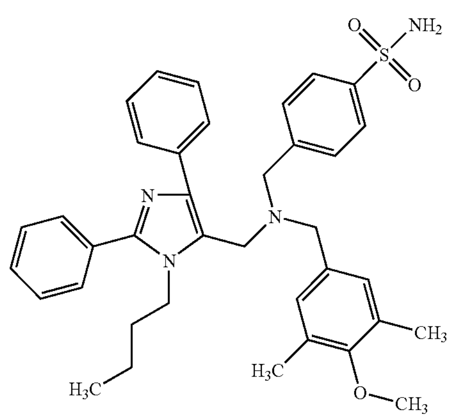 | * | 4-{[[(1-butyl-2,4-diphenyl-1H-imidazol-5-yl)methyl](4-methoxy-3,5-dimethylbenzyl)amino]methyl}benzenesulfonamide | 623.33 | 1.16 |
| 754 | 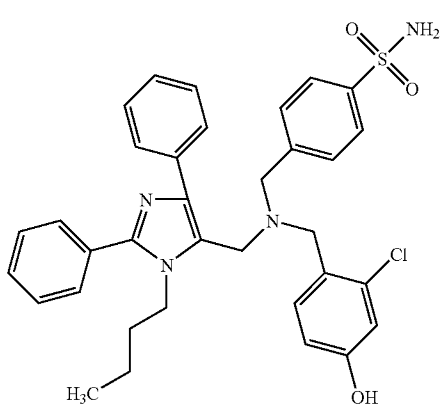 | * | 4-{[[(1-butyl-2,4-diphenyl-1H-imidazol-5-yl)methyl](2-chloro-4-hydroxybenzyl)amino]methyl}benzenesulfonamide | 615.25 | 1.12 |

TABLE II-continued

| CMP # | STRUCTURE | Ca²⁺ Mob. | IUPAC Name | MASS | RT (min.) |
|---|---|---|---|---|---|
| 755 | 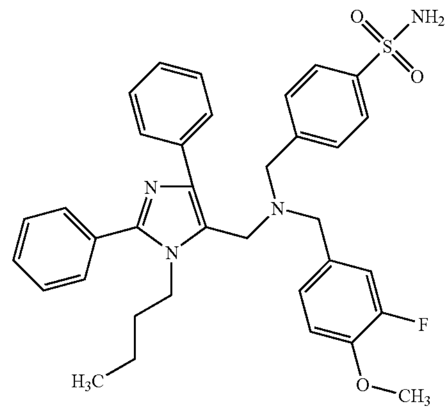 | * | 4-{[[(1-butyl-2,4-diphenyl-1H-imidazol-5-yl)methyl](3-fluoro-4-methoxybenzyl)amino]methyl}benzenesulfonamide | 613.29 | 1.12 |
| 756 | 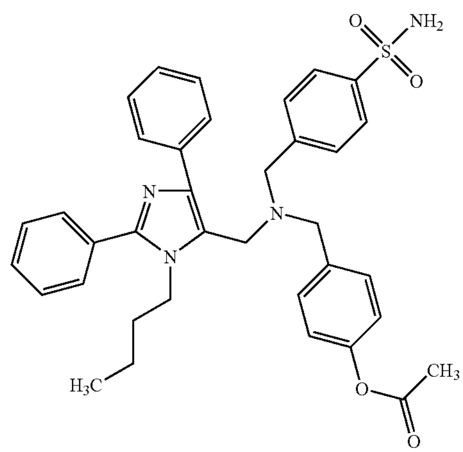 | * | 4-({[4-(aminosulfonyl)benzyl][(1-butyl-2,4-diphenyl-1H-imidazol-5-yl)methyl]amino}methyl)phenyl acetate | 623.29 | 1.11 |
| 757 | 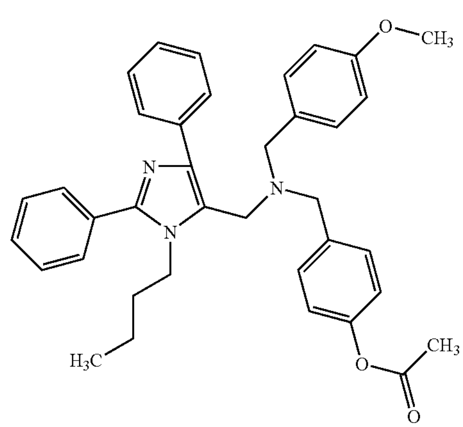 | * | 4-{[[(1-butyl-2,4-diphenyl-1H-imidazol-5-yl)methyl](4-methoxybenzyl)amino]methyl}phenyl acetate | 574.31 | 1.2 |

TABLE II-continued

| CMP # | STRUCTURE | Ca²⁺ Mob. | IUPAC Name | MASS | RT (min.) |
|---|---|---|---|---|---|
| 758 | 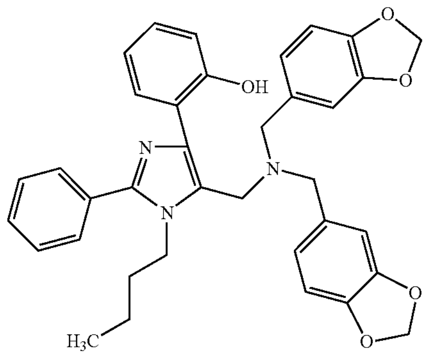 | * | 2-(5-{[bis(1,3-benzodioxol-5-ylmethyl)amino]methyl}-1-butyl-2-phenyl-1H-imidazol-4-yl)phenol | 590.28 | 1.21 |
| 759 | 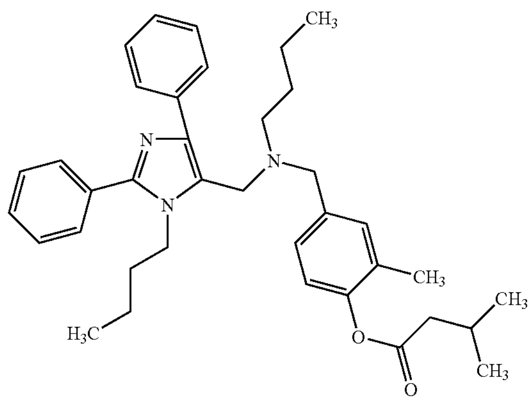 | * | 4-({butyl[(1-butyl-2,4-diphenyl-1H-imidazol-5-yl)methyl]amino}methyl)-2-methylphenyl 3-methylbutanoate | 567.40 | 1.26 |
| 760 | 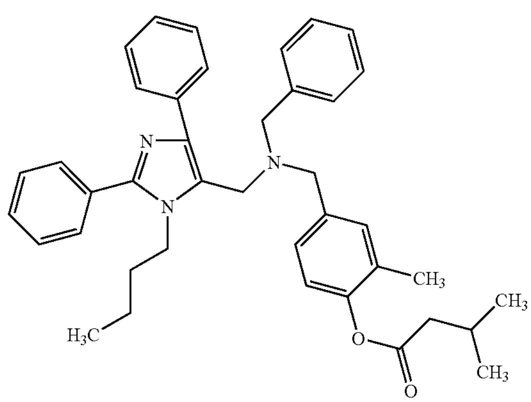 | * | 4-({benzyl[(1-butyl-2,4-diphenyl-1H-imidazol-5-yl)methyl]amino}methyl)-2-methylphenyl 3-methylbutanoate | 600.36 | 1.28 |
| 761 | 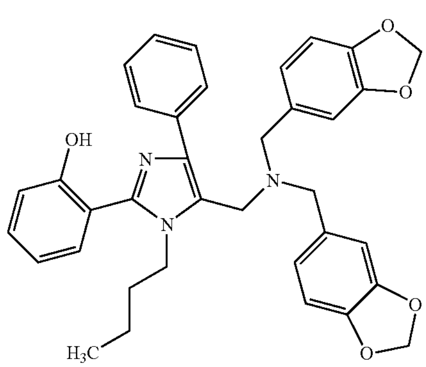 | * | 2-(5-{[bis(1,3-benzodioxol-5-ylmethyl)amino]methyl}-1-butyl-4-phenyl-1H-imidazol-2-yl)phenol | 590.28 | 1.22 |

TABLE II-continued

| CMP # | STRUCTURE | Ca²⁺ Mob. | IUPAC Name | MASS | RT (min.) |
|---|---|---|---|---|---|
| 762 | 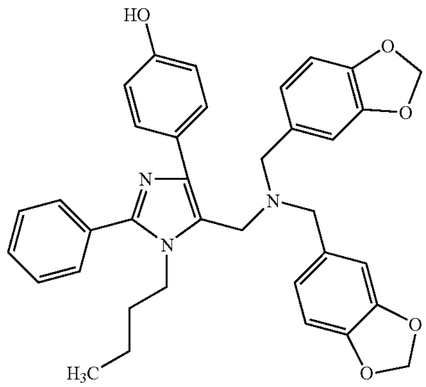 | * | 4-(5-{[bis(1,3-benzodioxol-5-ylmethyl)amino]methyl}-1-butyl-2-phenyl-1H-imidazol-4-yl)phenol | 590.27 | 1.2 |
| 763 | 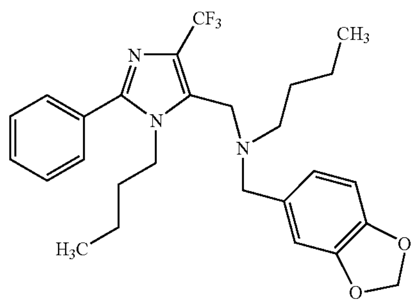 | * | N-(1,3-benzodioxol-5-ylmethyl)-N-{[1-butyl-2-phenyl-4-(trifluoromethyl)-1H-imidazol-5-yl]methyl}butan-1-amine | 488.25 | 1.25 |
| 764 | 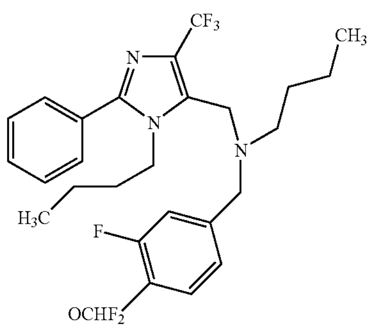 | * | N-{[1-butyl-2-phenyl-4-(trifluoromethyl)-1H-imidazol-5-yl]methyl}-N-[4-(difluoromethoxy)-3-fluorobenzyl]butan-1-amine | 528.24 | 1.34 |
| 765 | 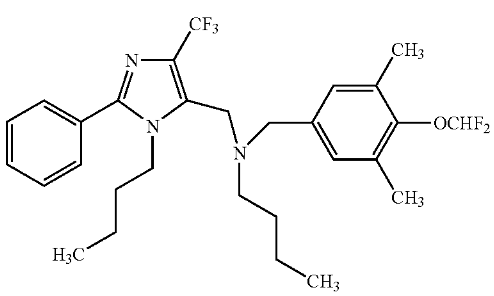 | * | N-{[1-butyl-2-phenyl-4-(trifluoromethyl)-1H-imidazol-5-yl]methyl}-N-[4-(difluoromethoxy)-3,5-dimethylbenzyl]butan-1-amine | 538.28 | 1.32 |

TABLE II-continued

| CMP # | STRUCTURE | Ca²⁺ Mob. | IUPAC Name | MASS | RT (min.) |
|---|---|---|---|---|---|
| 766 | 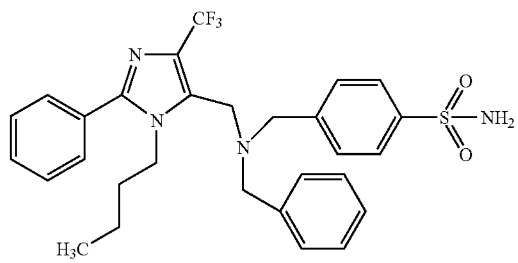 | * | 4-[(benzyl{[1-butyl-2-phenyl-4-(trifluoromethyl)-1H-imidazol-5-yl]methyl}amino)methyl]benzene-sulfonamide | 557.22 | 1.26 |
| 767 | 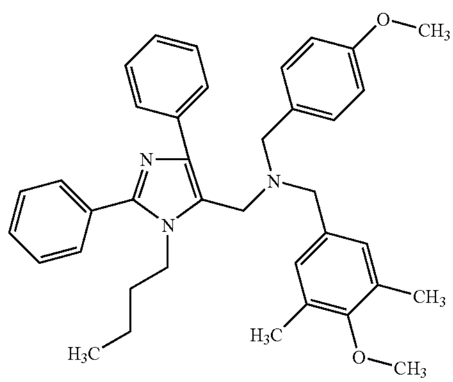 | * | 1-(1-butyl-2,4-diphenyl-1H-imidazol-5-yl)-N-(4-methoxybenzyl)-N-(4-methoxy-3,5-dimethylbenzyl)methanamine | 575.42 | 1.25 |
| 768 | 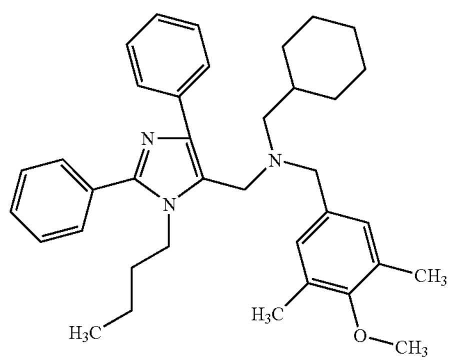 | * | 1-(1-butyl-2,4-diphenyl-1H-imidazol-5-yl)-N-(cyclohexylmethyl)-N-(4-methoxy-3,5-dimethylbenzyl)methanamine | 551.45 | 1.3 |
| 769 | 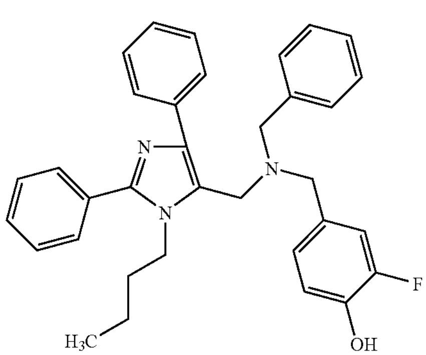 | * | 4-({benzyl[(1-butyl-2,4-diphenyl-1H-imidazol-5-yl)methyl]amino}methyl)-2-fluorophenol | 520.32 | 1.19 |

TABLE II-continued

| CMP # | STRUCTURE | Ca²⁺ Mob. | IUPAC Name | MASS | RT (min.) |
|---|---|---|---|---|---|
| 770 | 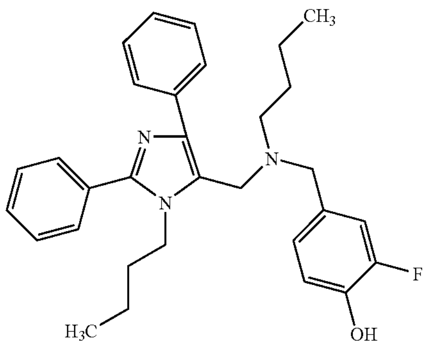 | * | 4-({butyl[(1-butyl-2,4-diphenyl-1H-imidazol-5-yl)methyl]amino}methyl)-2-fluorophenol | 486.34 | 1.15 |
| 771 | 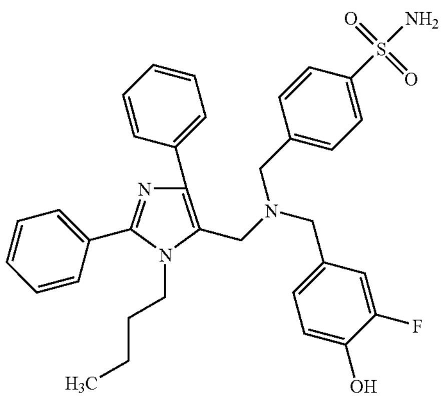 | * | 4-{[[(1-butyl-2,4-diphenyl-1H-imidazol-5-yl)methyl](3-fluoro-4-hydroxybenzyl)amino]methyl}benzenesulfonamide | 599.33 | 1.08 |
| 772 | 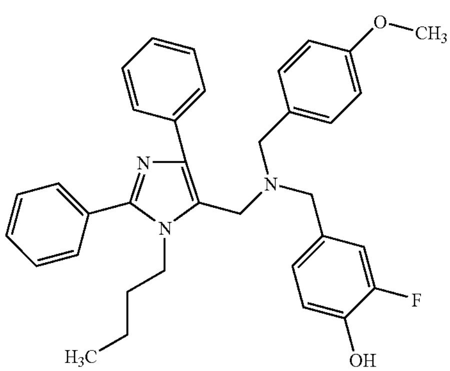 | * | 4-{[[(1-butyl-2,4-diphenyl-1H-imidazol-5-yl)methyl](4-methoxybenzyl)amino]methyl}-2-fluorophenol | 550.34 | 1.18 |
| 773 | 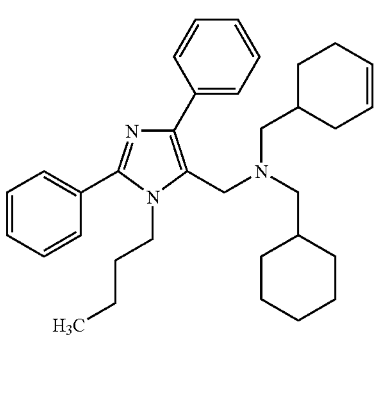 | * | 1-(1-butyl-2,4-diphenyl-1H-imidazol-5-yl)-N-(cyclohex-3-en-1-ylmethyl)-N-(cyclohexylmethyl)methanamine | 496.39 | 1.32 |

TABLE II-continued

| CMP # | STRUCTURE | Ca²⁺ Mob. | IUPAC Name | MASS | RT (min.) |
|---|---|---|---|---|---|
| 774 | 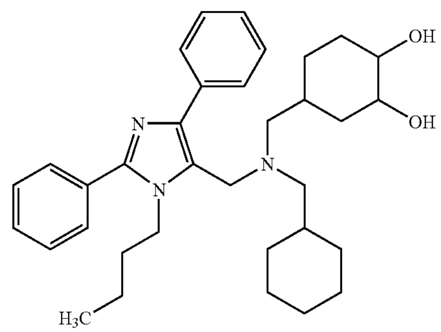 | * | 4-{[[(1-butyl-2,4-diphenyl-1H-imidazol-5-yl)methyl](cyclohexylmethyl)amino]methyl}cyclohexane-1,2-diol | 530.41 | 1.2 |
| 775 | 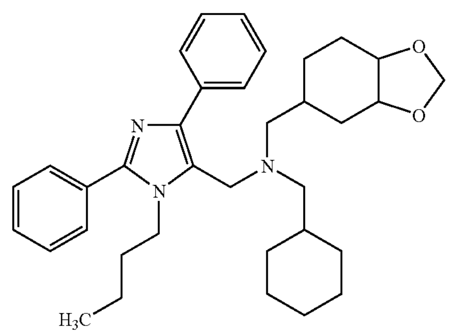 | * | 1-(1-butyl-2,4-diphenyl-1H-imidazol-5-yl)-N-(cyclohexylmethyl)-N-(hexahydro-1,3-benzodioxol-5-ylmethyl)methanamine | 542.42 | 1.26 |
| 776 | 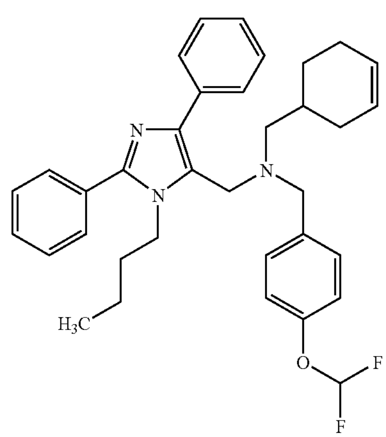 | * | 1-(1-butyl-2,4-diphenyl-1H-imidazol-5-yl)-N-(cyclohex-3-en-1-ylmethyl)-N-[4-(difluoromethoxy)benzyl]methanamine | 556.34 | 1.25 |
| 777 | 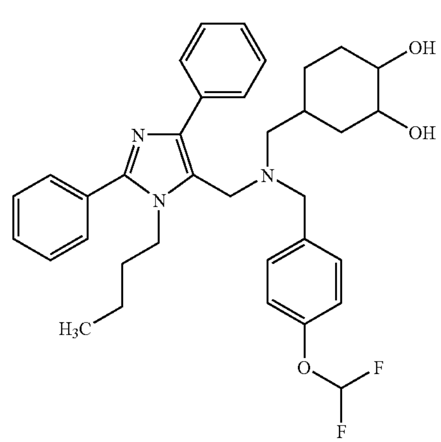 | * | 4-({[(1-butyl-2,4-diphenyl-1H-imidazol-5-yl)methyl][4-(difluoromethoxy)benzyl]amino}methyl)cyclohexane-1,2-diol | 590.36 | 1.15 |

TABLE II-continued

| CMP # | STRUCTURE | Ca²⁺ Mob. | IUPAC Name | MASS | RT (min.) |
|---|---|---|---|---|---|
| 778 | 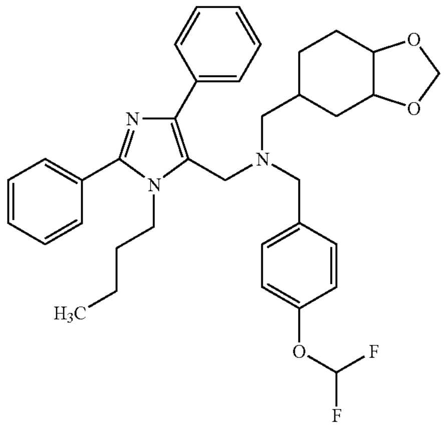 | * | 1-(1-butyl-2,4-diphenyl-1H-imidazol-5-yl)-N-[4-(difluoromethoxy)benzyl]-N-(hexahydro-1,3-benzodioxol-5-ylmethyl)methanamine | 602.35 | 1.19 |
| 779 | 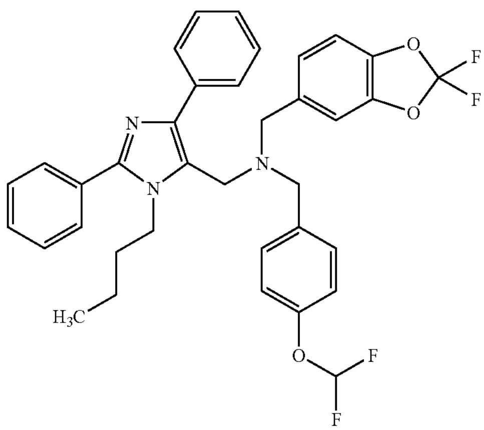 | * | 1-(1-butyl-2,4-diphenyl-1H-imidazol-5-yl)-N-[(2,2-difluoro-1,3-benzodioxol-5-yl)methyl]-N-[4-(difluoromethoxy)benzyl]methanamine | 632.31 | 1.24 |
| 780 | 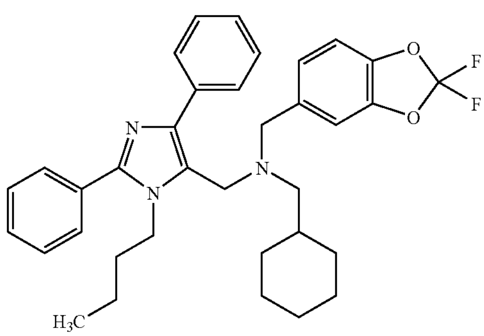 | * | 1-(1-butyl-2,4-diphenyl-1H-imidazol-5-yl)-N-(cyclohexylmethyl)-N-[(2,2-difluoro-1,3-benzodioxol-5-yl)methyl]methanamine | 573.38 | 1.29 |
| 781 | 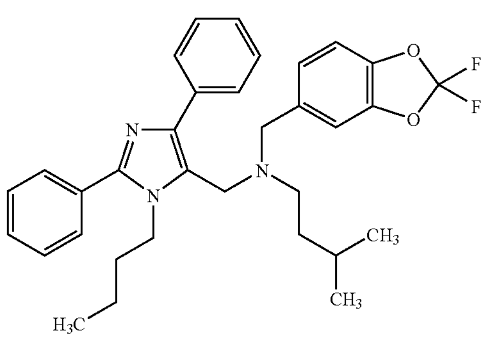 | | N-[(1-butyl-2,4-diphenyl-1H-imidazol-5-yl)methyl]-N-[(2,2-difluoro-1,3-benzodioxol-5-yl)methyl]-3-methylbutan-1-amine | 546.33 | 1.26 |

TABLE II-continued

| CMP # | STRUCTURE | Ca²⁺ Mob. | IUPAC Name | MASS | RT (min.) |
|---|---|---|---|---|---|
| 782 | 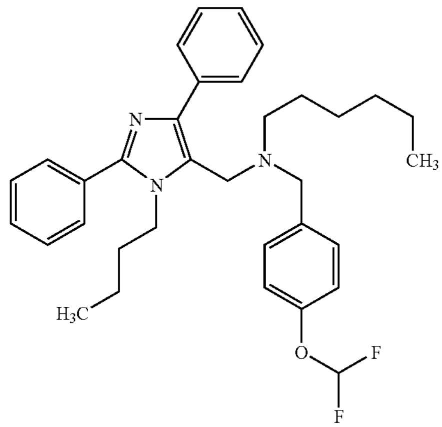 | * | N-[(1-butyl-2,4-diphenyl-1H-imidazol-5-yl)methyl]-N-[4-(difluoromethoxy)benzyl]hexan-1-amine | 547.40 | 1.25 |
| 783 | 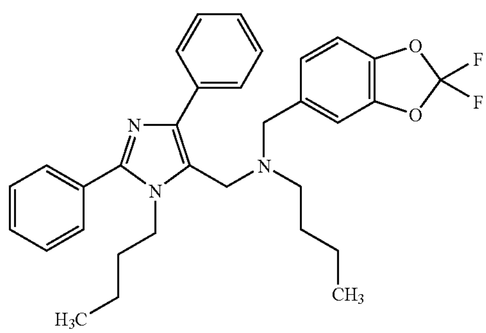 | * | N-[(1-butyl-2,4-diphenyl-1H-imidazol-5-yl)methyl]-N-[(2,2-difluoro-1,3-benzodioxol-5-yl)methyl]butan-1-amine | 532.32 | 1.25 |
| 784 | 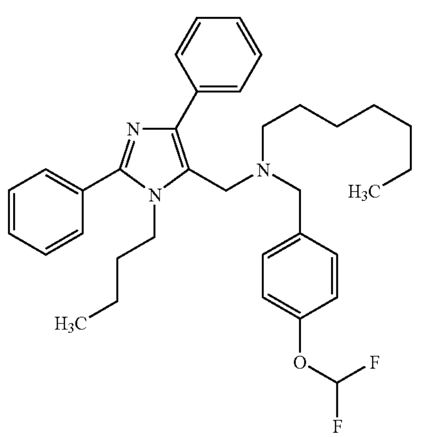 | * | N-[(1-butyl-2,4-diphenyl-1H-imidazol-5-yl)methyl]-N-[4-(difluoromethoxy)benzyl]heptan-1-amine | 560.39 | 1.26 |

TABLE II-continued

| CMP # | STRUCTURE | Ca²⁺ Mob. | IUPAC Name | MASS | RT (min.) |
|---|---|---|---|---|---|
| 785 | 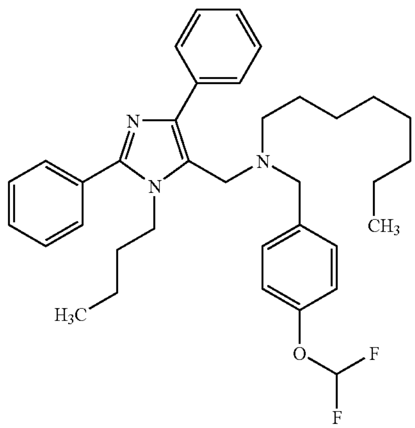 | * | N-[(1-butyl-2,4-diphenyl-1H-imidazol-5-yl)methyl]-N-[4-(difluoromethoxy)benzyl]octan-1-amine | 574.41 | 1.28 |
| 786 | 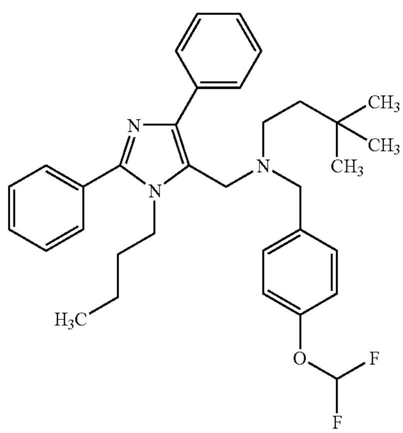 | * | N-[(1-butyl-2,4-diphenyl-1H-imidazol-5-yl)methyl]-N-[4-(difluoromethoxy)benzyl]-3,3-dimethylbutan-1-amine | 546.38 | 1.23 |
| 787 | 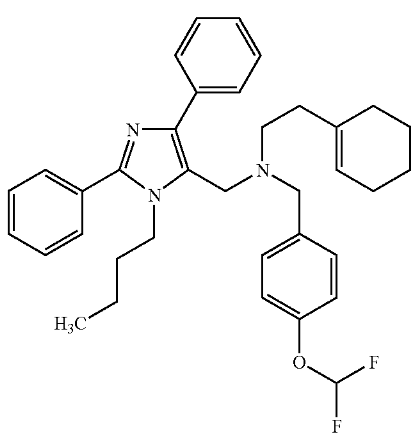 | * | N-[(1-butyl-2,4-diphenyl-1H-imidazol-5-yl)methyl]-2-cyclohex-1-en-1-yl-N-[4-(difluoromethoxy)benzyl]ethanamine | 570.38 | 1.26 |

TABLE II-continued

| CMP # | STRUCTURE | Ca²⁺ Mob. | IUPAC Name | MASS | RT (min.) |
|---|---|---|---|---|---|
| 788 | 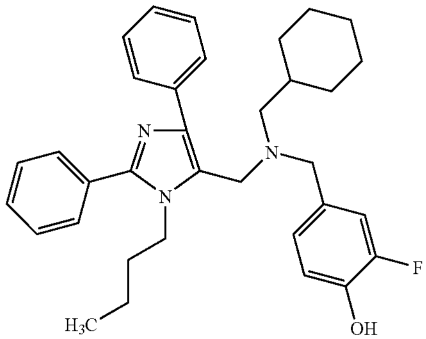 | * | 4-{[[(1-butyl-2,4-diphenyl-1H-imidazol-5-yl)methyl](cyclohexylmethyl)amino]methyl}-2-fluorophenol | 526.37 | 1.24 |
| 789 | 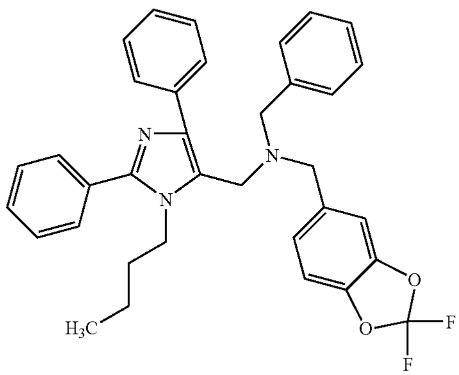 | * | N-benzyl-1-(1-butyl-2,4-diphenyl-1H-imidazol-5-yl)-N-[(2,2-difluoro-1,3-benzodioxol-5-yl)methyl]methanamine | 566.32 | 1.24 |
| 790 | 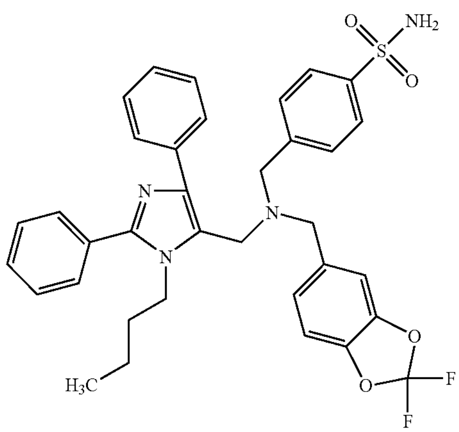 | * | 4-({[[(1-butyl-2,4-diphenyl-1H-imidazol-5-yl)methyl][(2,2-difluoro-1,3-benzodioxol-5-yl)methyl]amino}methyl)benzenesulfonamide | 645.31 | 1.16 |
| 791 | 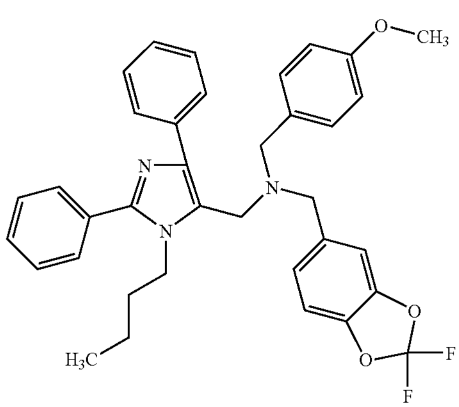 | * | 1-(1-butyl-2,4-diphenyl-1H-imidazol-5-yl)-N-[(2,2-difluoro-1,3-benzodioxol-5-yl)methyl]-N-(4-methoxybenzyl)methanamine | 596.33 | 1.25 |

TABLE II-continued

| CMP # | STRUCTURE | Ca²⁺ Mob. | IUPAC Name | MASS | RT (min.) |
|---|---|---|---|---|---|
| 792 | 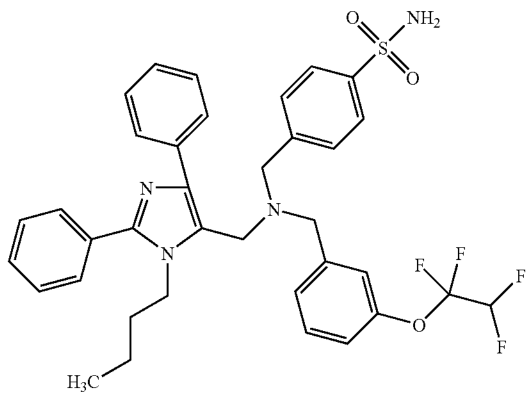 | * | 4-({[(1-butyl-2,4-diphenyl-1H-imidazol-5-yl)methyl][3-(1,1,2,2-tetrafluoroethoxy)benzyl]amino}methyl)benzenesulfonamide | 681.33 | 1.14 |
| 793 | 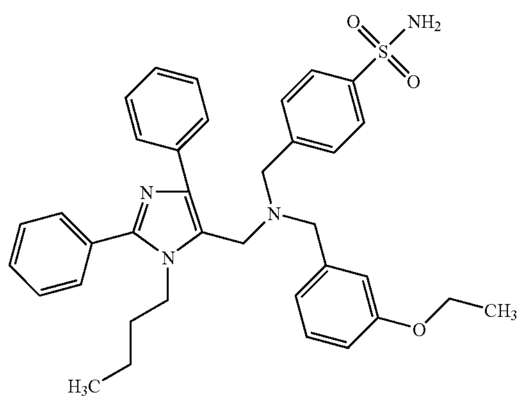 | * | 4-{[[(1-butyl-2,4-diphenyl-1H-imidazol-5-yl)methyl](3-ethoxybenzyl)amino]methyl}benzenesulfonamide | 609.36 | 1.16 |
| 794 | 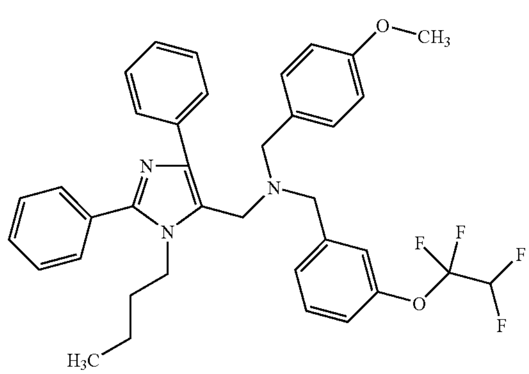 | * | 1-(1-butyl-2,4-diphenyl-1H-imidazol-5-yl)-N-(4-methoxybenzyl)-N-[3-(1,1,2,2-tetrafluoroethoxy)benzyl]methanamine | 632.35 | 1.23 |
| 795 | 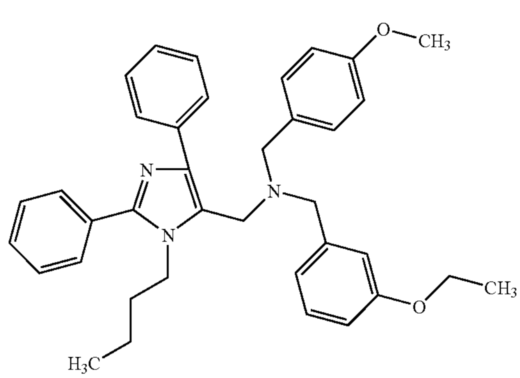 | * | 1-(1-butyl-2,4-diphenyl-1H-imidazol-5-yl)-N-(3-ethoxybenzyl)-N-(4-methoxybenzyl)methanamine | 560.37 | 1.25 |

TABLE II-continued

| CMP # | STRUCTURE | Ca²⁺ Mob. | IUPAC Name | MASS | RT (min.) |
|---|---|---|---|---|---|
| 796 | 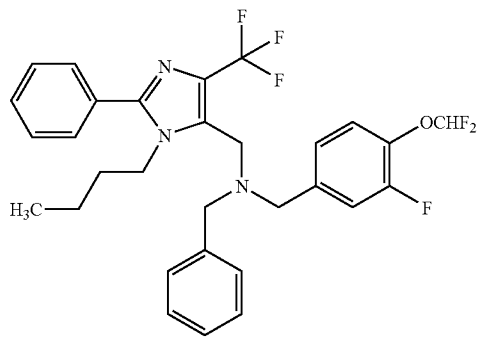 | * | N-benzyl-1-[1-butyl-2-phenyl-4-(trifluoromethyl)-1H-imidazol-5-yl]-N-[4-(difluoromethoxy)-3-fluorobenzyl]methanamine | 562.27 | 1.36 |
| 797 | 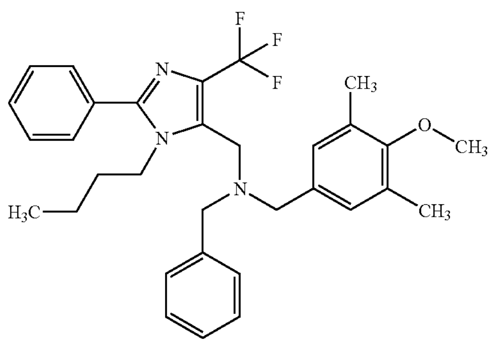 | * | N-benzyl-1-[1-butyl-2-phenyl-4-(trifluoromethyl)-1H-imidazol-5-yl]-N-(4-methoxy-3,5-dimethylbenzyl)methanamine | 536.32 | 1.43 |
| 798 | 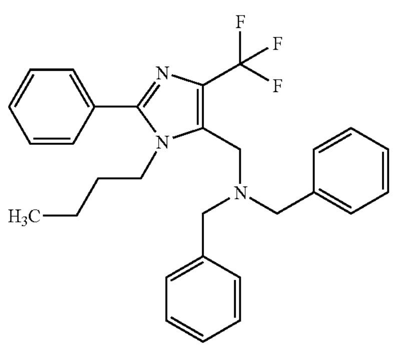 | * | N,N-dibenzyl-1-[1-butyl-2-phenyl-4-(trifluoromethyl)-1H-imidazol-5-yl]methanamine | 478.28 | 1.4 |
| 799 | 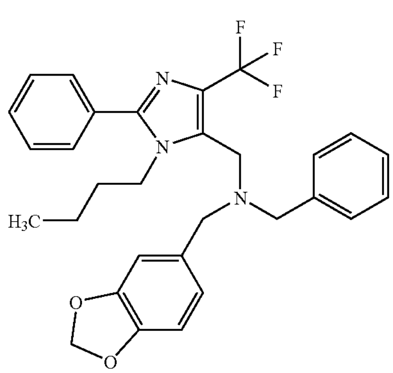 | * | 1-(1,3-benzodioxol-5-yl)-N-benzyl-N-{[1-butyl-2-phenyl-4-(trifluoromethyl)-1H-imidazol-5-yl]methyl}methanamine | 522.28 | 1.39 |

TABLE II-continued

| CMP # | STRUCTURE | Ca²⁺ Mob. | IUPAC Name | MASS | RT (min.) |
|---|---|---|---|---|---|
| 800 | 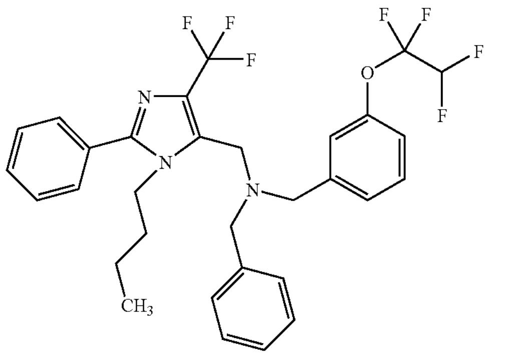 | * | N-benzyl-1-[1-butyl-2-phenyl-4-(trifluoromethyl)-1H-imidazol-5-yl]-N-[3-(1,1,2,2-tetrafluoroethoxy)benzyl]methanamine | 594.28 | 1.37 |
| 801 | 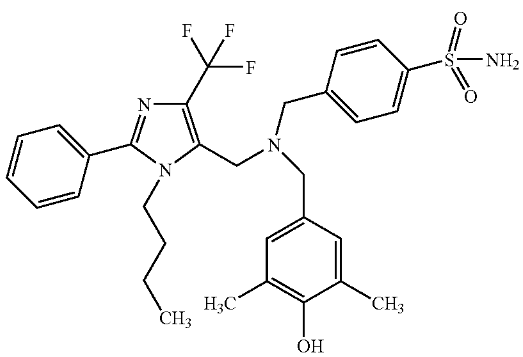 | * | 4-{[{[1-butyl-2-phenyl-4-(trifluoromethyl)-1H-imidazol-5-yl]methyl}(4-hydroxy-3,5-dimethylbenzyl)amino]methyl}benzenesulfonamide | 601.29 | 1.23 |
| 802 | 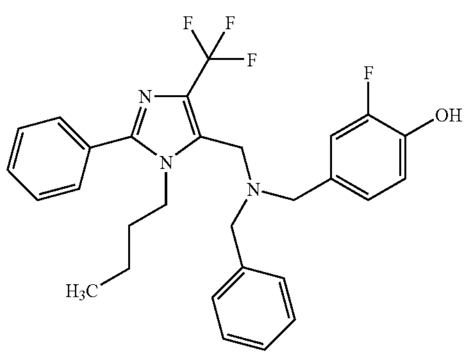 | * | 4-[(benzyl{[1-butyl-2-phenyl-4-(trifluoromethyl)-1H-imidazol-5-yl]methyl}amino)methyl]-2-fluorophenol | 512.28 | 1.32 |
| 803 | 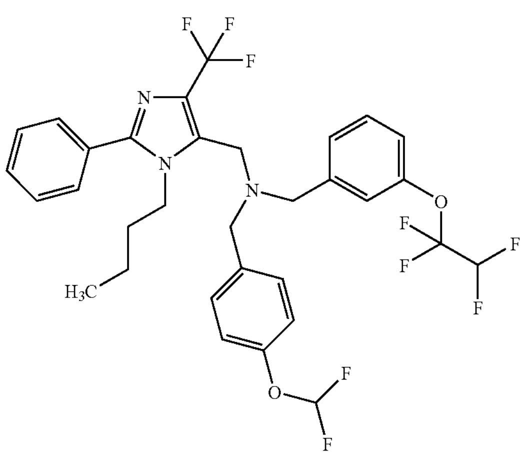 | * | 1-[1-butyl-2-phenyl-4-(trifluoromethyl)-1H-imidazol-5-yl]-N-[4-(difluoromethoxy)benzyl]-N-[3-(1,1,2,2-tetrafluoroethoxy)benzyl]methanamine | 660.28 | 1.34 |

TABLE II-continued

| CMP # | STRUCTURE | Ca²⁺ Mob. | IUPAC Name | MASS | RT (min.) |
|---|---|---|---|---|---|
| 804 | 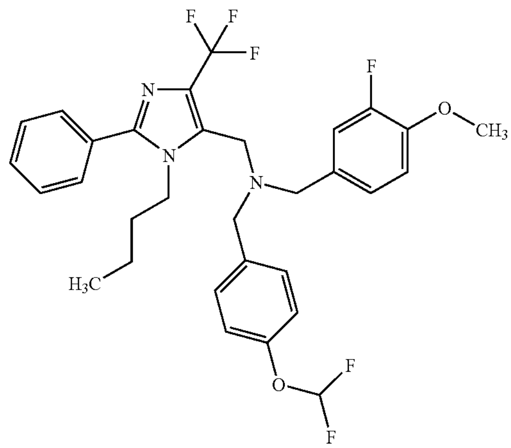 | * | 1-[1-butyl-2-phenyl-4-(trifluoromethyl)-1H-imidazol-5-yl]-N-[4-(difluoromethoxy)benzyl]-N-(3-fluoro-4-methoxybenzyl)methanamine | 592.29 | 1.34 |
| 805 | 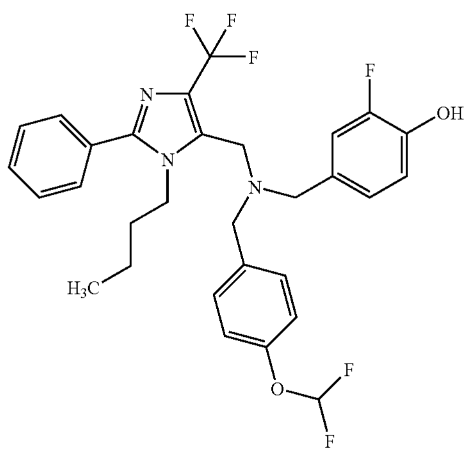 | * | 4-({{[1-butyl-2-phenyl-4-(trifluoromethyl)-1H-imidazol-5-yl]methyl}[4-(difluoromethoxy)benzyl]amino}methyl)-2-fluorophenol | 578.29 | 1.29 |
| 806 | 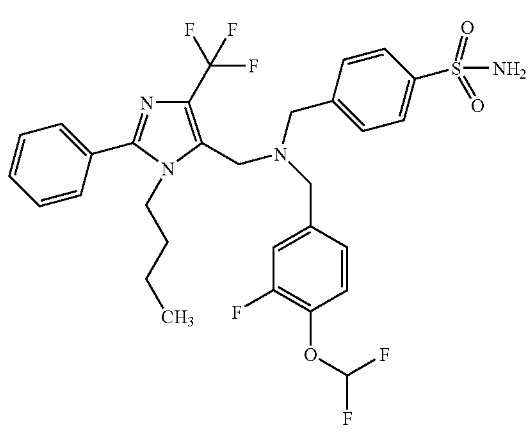 | * | 4-({{[1-butyl-2-phenyl-4-(trifluoromethyl)-1H-imidazol-5-yl]methyl}[4-(difluoromethoxy)-3-fluorobenzyl]amino}methyl)benzenesulfonamide | 641.24 | 1.23 |

TABLE II-continued

| CMP # | STRUCTURE | Ca²⁺ Mob. | IUPAC Name | MASS | RT (min.) |
|---|---|---|---|---|---|
| 807 | 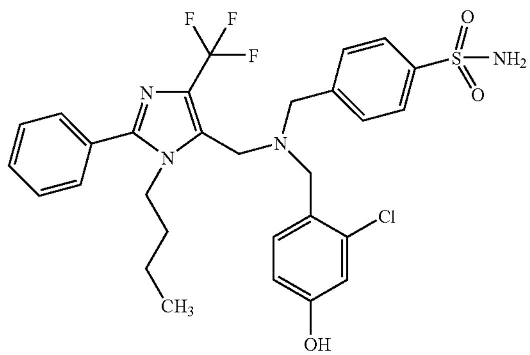 | * | 4-{[{[1-butyl-2-phenyl-4-(trifluoromethyl)-1H-imidazol-5-yl]methyl}(2-chloro-4-hydroxybenzyl)amino]methyl}benzenesulfonamide | 607.22 | 1.22 |
| 808 | 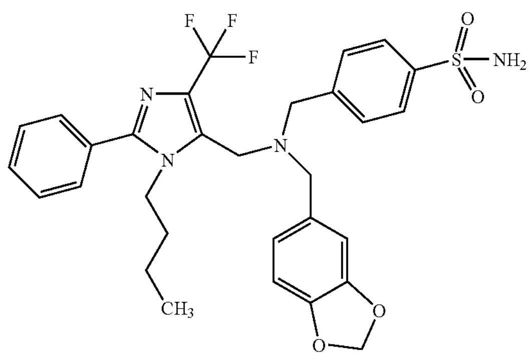 | * | 4-[((1,3-benzodioxol-5-ylmethyl){[1-butyl-2-phenyl-4-(trifluoromethyl)-1H-imidazol-5-yl]methyl}amino)methyl]benzenesulfonamide | 601.25 | 1.24 |
| 809 | 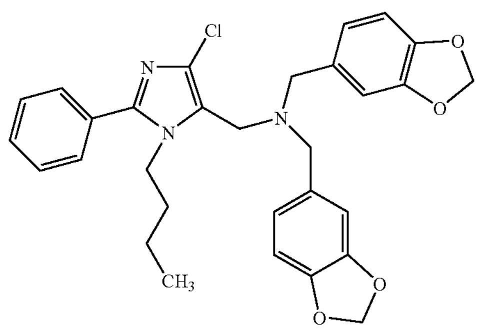 | * | 1-(1,3-benzodioxol-5-yl)-N-(1,3-benzodioxol-5-ylmethyl)-N-[(1-butyl-4-chloro-2-phenyl-1H-imidazol-5-yl)methyl]methanamine | 532.23 | 1.31 |
| 810 | 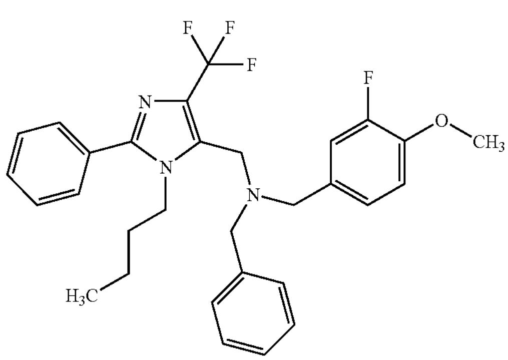 | * | N-benzyl-1-[1-butyl-2-phenyl-4-(trifluoromethyl)-1H-imidazol-5-yl]-N-(3-fluoro-4-methoxybenzyl)methanamine | 526.29 | 1.37 |

TABLE II-continued

| CMP # | STRUCTURE | Ca²⁺ Mob. | IUPAC Name | MASS | RT (min.) |
|---|---|---|---|---|---|
| 811 | 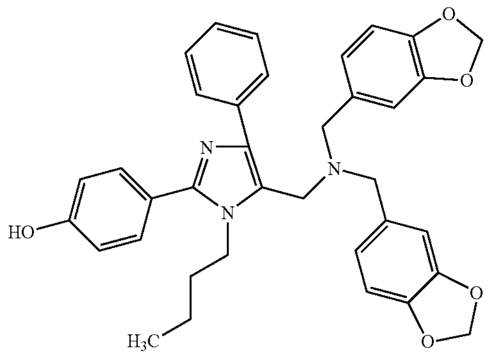 | * | 4-(5-{[bis(1,3-benzodioxol-5-ylmethyl)amino]methyl{-1-butyl-4-phenyl-1H-imidazol-2-yl)phenol | 590.32 | 1.2 |
| 812 | 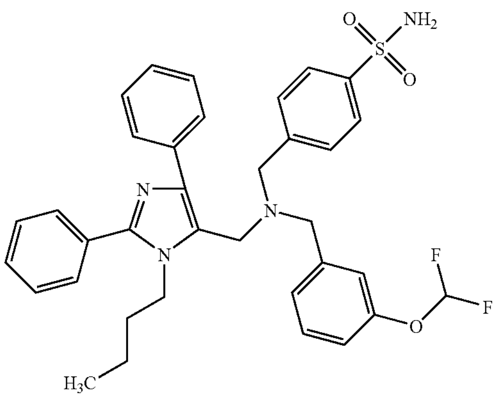 | * | 4-({[(1-butyl-2,4-diphenyl-1H-imidazol-5-yl)methyl][3-(difluoromethoxy)benzyl]amino}methyl)benzenesulfonamide | 631.32 | 1.13 |
| 813 | 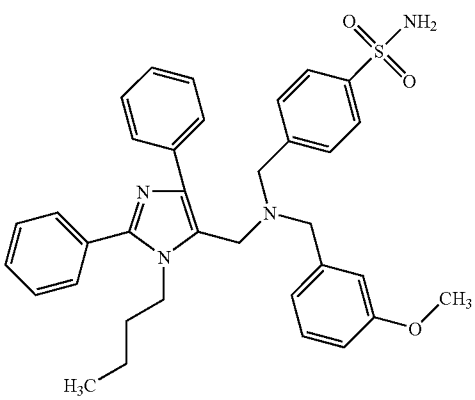 | * | 4-{[[(1-butyl-2,4-diphenyl-1H-imidazol-5-yl)methyl](3-methoxybenzyl)amino]methyl}benzenesulfonamide | 595.33 | 1.13 |
| 814 | 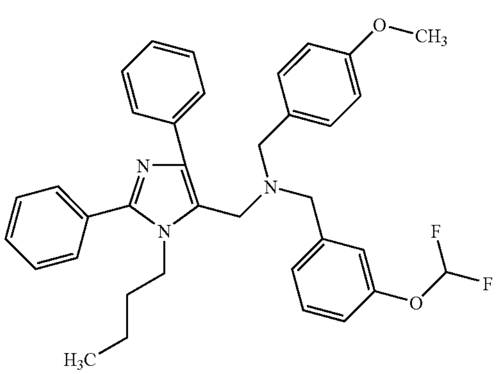 | * | 1-(1-butyl-2,4-diphenyl-1H-imidazol-5-yl)-N-[3-(difluoromethoxy)benzyl]-N-(4-methoxybenzyl)methanamine | 582.34 | 1.22 |

TABLE II-continued

| CMP # | STRUCTURE | Ca²⁺ Mob. | IUPAC Name | MASS | RT (min.) |
|---|---|---|---|---|---|
| 815 | 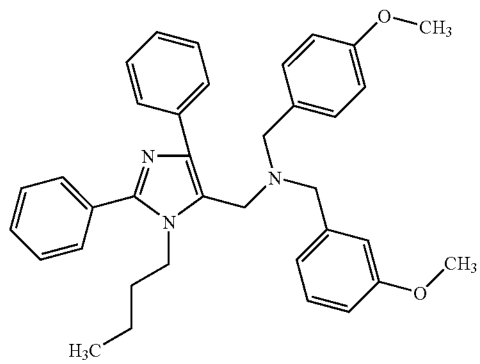 | * | 1-(1-butyl-2,4-diphenyl-1H-imidazol-5-yl)-N-(3-methoxybenzyl)-N-(4-methoxybenzyl)methanamine | 546.35 | 1.22 |
| 816 | 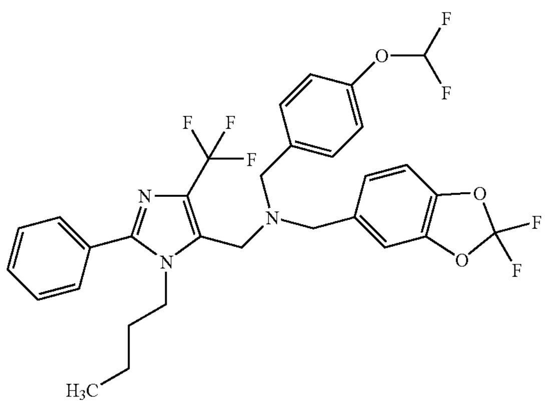 | * | 1-[1-butyl-2-phenyl-4-(trifluoromethyl)-1H-imidazol-5-yl]-N-[(2,2-difluoro-1,3-benzodioxol-5-yl)methyl]-N-[4-(difluoromethoxy)benzyl]methanamine | 624.25 | 1.36 |
| 817 | 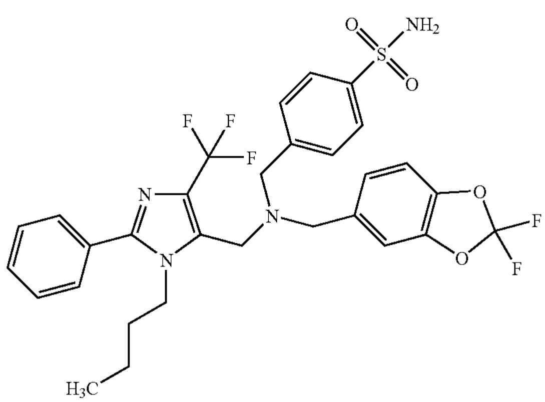 | * | 4-({{[1-butyl-2-phenyl-4-(trifluoromethyl)-1H-imidazol-5-yl]methyl}[(2,2-difluoro-1-3-benzodioxol-5-yl)methyl]amino}methyl)benzene-sulfonamide | 637.24 | 1.27 |
| 818 | 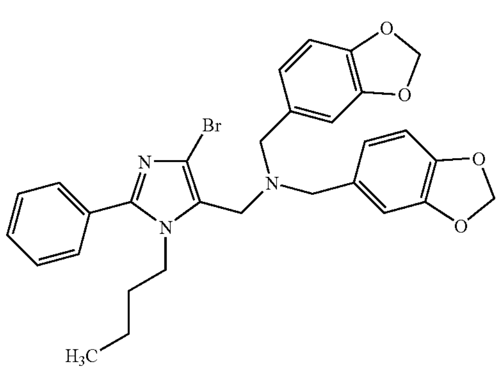 | * | 1-(1,3-benzodioxol-5-yl)-N-(1,3-benzodioxol-5-ylmethyl)-N-[(4-bromo-1-butyl-2-phenyl-1H-imidazol-5-yl)methyl]methanamine | 576.21 | 1.31 |

TABLE II-continued

| CMP # | STRUCTURE | Ca²⁺ Mob. | IUPAC Name | MASS | RT (min.) |
|---|---|---|---|---|---|
| 819 | 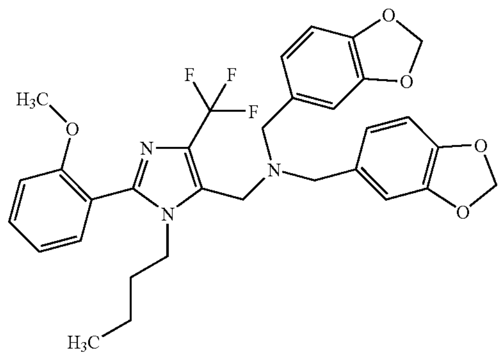 | * | 1-(1,3-benzodioxol-5-yl)-N-(1-3-benzodioxol-5-ylmethyl)-N-{[1-butyl-2-(2-methoxyphenyl)-4-(trifluoromethyl)-1H-imidazol-5-yl]methyl}methanamine | 596.27 | 1.35 |
| 820 | 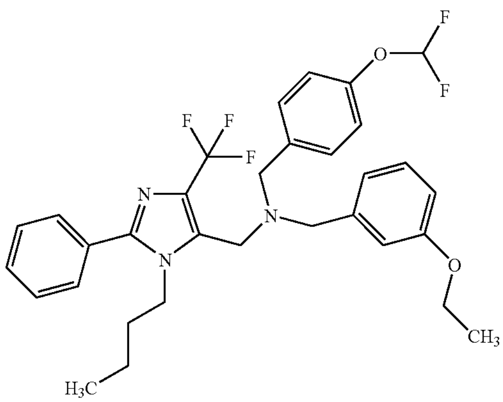 | * | 1-[1-butyl-2-phenyl-4-(trifluoromethyl)-1H-imidazol-5-yl]-N-[4-(difluoromethoxy)benzyl]-N-(3-ethoxybenzyl)methanamine | 588.30 | 1.38 |
| 821 | 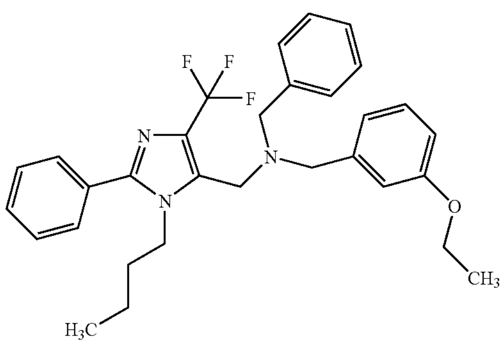 | * | N-benzyl-1-[1-butyl-2-phenyl-4-(trifluoromethyl)-1H-imidazol-5-yl]-N-(3-ethoxybenzyl)methanamine | 522.30 | 1.41 |
| 822 | Chiral | * | 4-(({(1,3-benzodioxol-5-ylmethyl)[(1R)-1-(1-butyl-2,4-diphenyl-1H-imidazol-5-yl)ethyl]amino}methyl)benzene-sulfonamide | 623.30 | 1.14 |

TABLE II-continued

| CMP # | STRUCTURE | Ca²⁺ Mob. | IUPAC Name | MASS | RT (min.) |
|---|---|---|---|---|---|
| 823 | Chiral | * | 4-({(1,3-benzodioxol-5-ylmethyl)[(1S)-1-(1-butyl-2,4-diphenyl-1H-imidazol-5-yl)ethyl]amino}methyl)benzenesulfonamide | 623.30 | 1.13 |
| 824 | Chiral | * | 4-{[[(1R)-1-(1-butyl-2,4-diphenyl-1H-imidazol-5-yl)ethyl](cyclohexylmethyl)amino]methyl}benzenesulfonamide | 303.21 | 1.1 |
| 825 | Chiral | * | 4-({(1,3-benzodioxol-5-ylmethyl)[(1S)-1-(1-butyl-2,4-diphenyl-1H-imidazol-5-yl)pentyl]amino}methyl)benzene-sulfonamide | 665.37 | 1.19 |
| 826 | 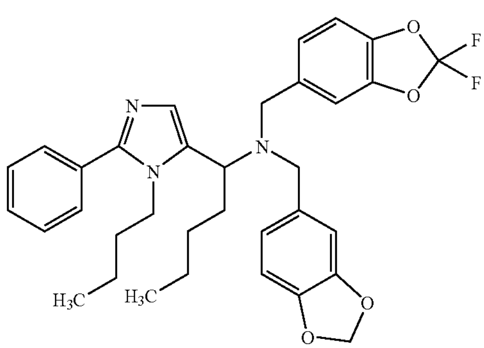 | * | N-(1,3-benzodioxol-5-ylmethyl)-1-(1-butyl-2-phenyl-1H-imidazol-5-yl)-N-[(2,2-difluoro-1,3-benzodioxol-5-yl)methyl]pentan-1-amine | | |

TABLE II-continued

| CMP # | STRUCTURE | Ca²⁺ Mob. | IUPAC Name | MASS | RT (min.) |
|---|---|---|---|---|---|
| 827 | 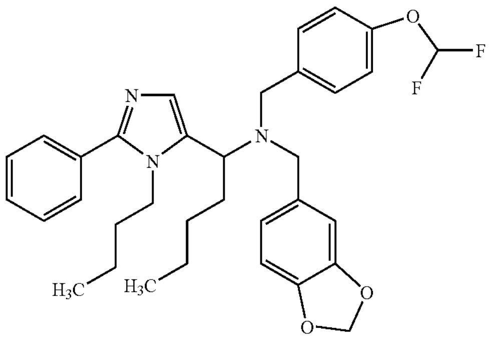 | * | N-(1,3-benzodioxol-5-ylmethyl)-1-(1-butyl-2-phenyl-1H-imidazol-5-yl)-N-[4-(difluoromethoxy)benzyl]pentan-1-amine | 576.32 | 1.22 |
| 828 | 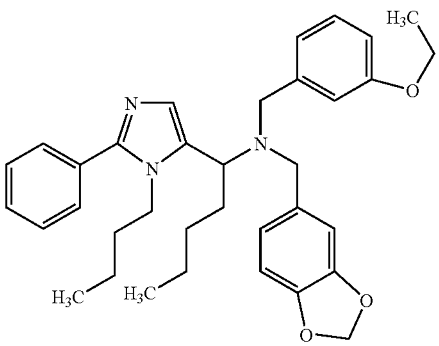 | * | N-(1,3-benzodioxol-5-ylmethyl)-1-(1-butyl-2-phenyl-1H-imidazol-5-yl)-N-(3-ethoxybenzyl)pentan-1-amine | 554.34 | 1.25 |
| 829 | 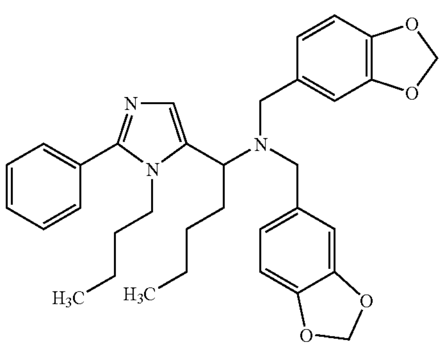 | * | N,N-bis(1,3-benzodioxol-5-ylmethyl)-1-(1-butyl-2-phenyl-1H-imidazol-5-yl)pentan-1-amine | 554.31 | 1.23 |
| 830 | 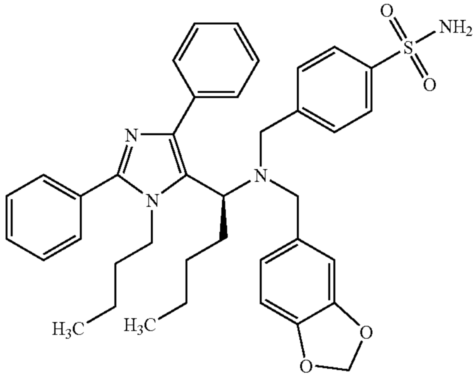 | * | 4-({(1,3-benzodioxol-5-ylmethyl)[(1R)-1-(1-butyl-2,4-diphenyl-1H-imidazol-5-yl)pentyl]amino}methyl)benzene-sulfonamide | 665.34 | 1.18 |

TABLE II-continued

| CMP # | STRUCTURE | Ca²⁺ Mob. | IUPAC Name | MASS | RT (min.) |
|---|---|---|---|---|---|
| 831 | 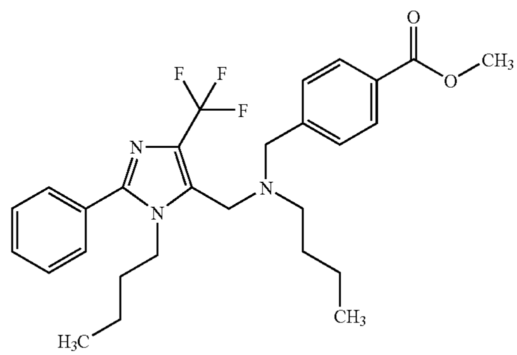 | * | methyl 4-[(butyl{[1-butyl-2-phenyl-4-(trifluoromethyl)-1H-imidazol-5-yl]methyl}amino)methyl]benzoate | 502.29 | 1.35 |
| 832 | 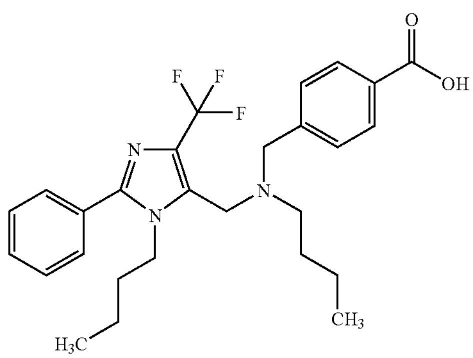 | * | 4-[(butyl{[1-butyl-2-phenyl-4-(trifluoromethyl)-1H-imidazol-5-yl]methyl}amino)methyl]benzoic acid | 488.27 | 1.28 |
| 833 | 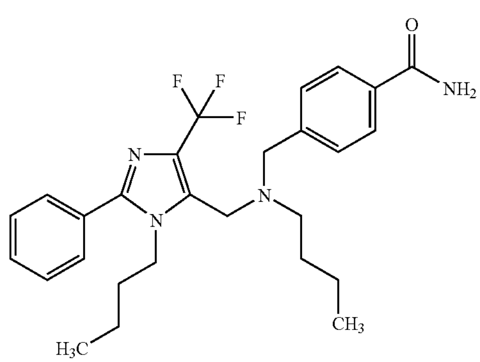 | * | 4-[(butyl{[1-butyl-2-phenyl-4-(trifluoromethyl)-1H-imidazol-5-yl]methyl}amino)methyl]benzamide | 487.32 | 1.25 |
| 834 | 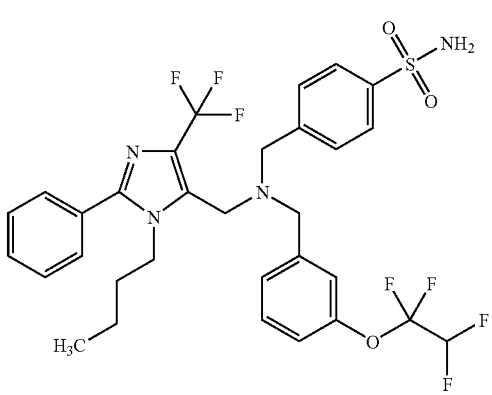 | * | 4-({{[1-butyl-2-phenyl-4-(trifluoromethyl)-1H-imidazol-5-yl]methyl}[3-(1,1,2,2-tetrafluoroethoxy)benzyl]amino}methyl)benzenesulfonamide | 673.27 | 1.24 |

| CMP # | STRUCTURE | Ca²⁺ Mob. | IUPAC Name | MASS | RT (min.) |
|---|---|---|---|---|---|
| 835 | 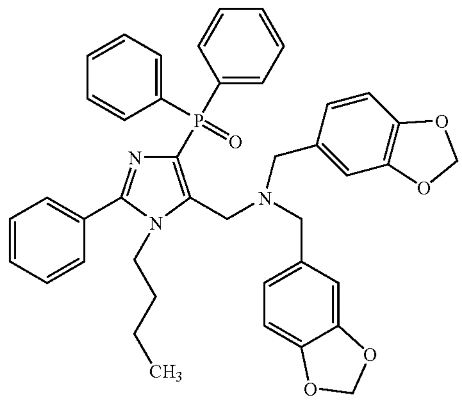 | | 1-(1,3-benzodioxol-5-yl)-N-(1,3-benzodioxol-5-ylmethyl)-N-{[1-butyl-4-(diphenylphosphoryl)-2-phenyl-1H-imidazol-5-yl]methyl}methanamine | 698.34 | 1.22 |
| 836 | 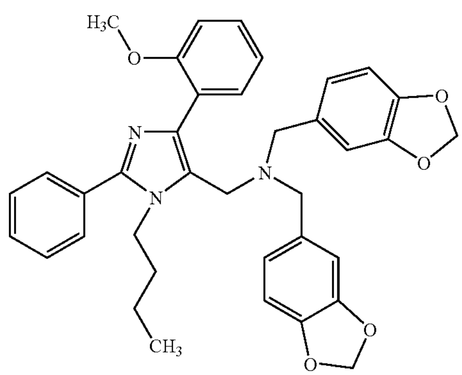 | * | 1-(1,3-benzodioxol-5-yl)-N-(1,3-benzodioxol-5-ylmethyl)-N-{[1-butyl-4-(2-methoxyphenyl)-2-phenyl-1H-imidazol-5-yl]methyl}methanamine | 604.34 | 1.22 |
| 837 | 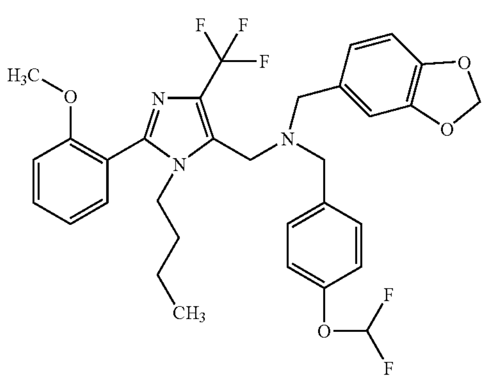 | * | 1-(1,3-benzodioxol-5-yl)-N-{[1-butyl-2-(2-methoxyphenyl)-4-(trifluoromethyl)-1H-imidazol-5-yl]methyl}-N-[4-(difluoromethoxy)benzyl]methanamine | 619.32 | 1.35 |
| 838 | 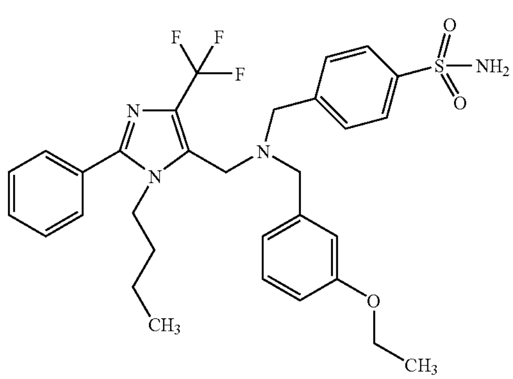 | * | 4-{[{[1-butyl-2-phenyl-4-(trifluoromethyl)-1H-imidazol-5-yl]methyl}(3-ethoxybenzyl)amino]methyl}benzenesulfonamide | 601.25 | 1.27 |

TABLE II-continued

| CMP # | STRUCTURE | Ca²⁺ Mob. | IUPAC Name | MASS | RT (min.) |
|---|---|---|---|---|---|
| 839 | 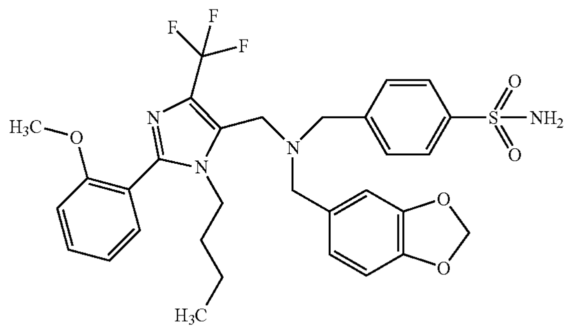 | * | 4-[((1,3-benzodioxol-5-ylmethyl){[1-butyl-2-(2-methoxyphenyl)-4-(trifluoromethyl)-1H-imidazol-5-yl]methyl}amino)methyl]benzene-sulfonamide | 631.22 | 1.24 |
| 840 | 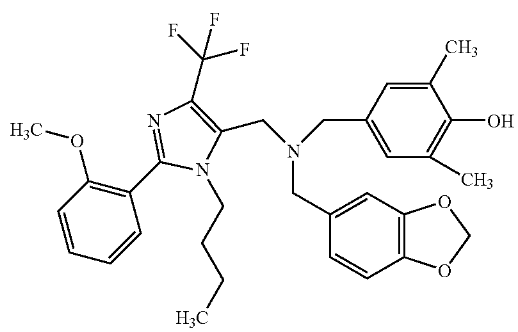 | * | 4-[((1,3-benzodioxol-5-ylmethyl){[1-butyl-2-(2-methoxyphenyl)-4-(trifluoromethyl)-1H-imidazol-5-yl]methyl}amino)methyl]-2,6-dimethylphenol | 596.29 | 1.3 |
| 841 | 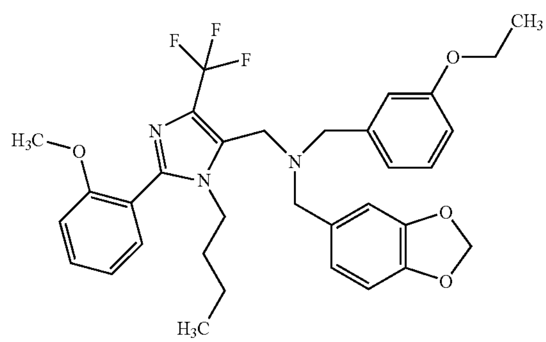 | * | 1-(1,3-benzodioxol-5-yl)-N-{[1-butyl-2-(2-methoxyphenyl)-4-(trifluoromethyl)-1H-imidazol-5-yl]methyl}-N-(3-ethoxybenzyl)methanamine | | |
| 842 | 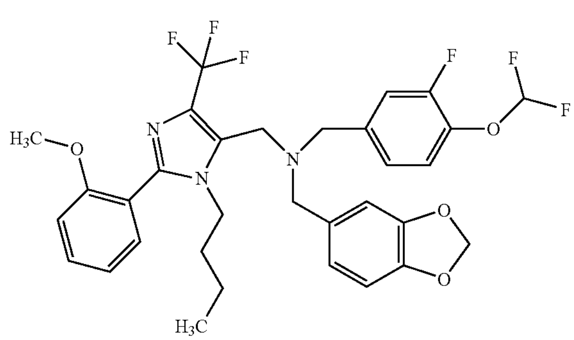 | * | 1-(1,3-benzodioxol-5-yl)-N-{[1-butyl-2-(2-methoxyphenyl)-4-(trifluoromethyl)-1H-imidazol-5-yl]methyl}-N-[4-(difluoromethoxy)-3-fluorobenzyl]methanamine | 637.26 | 1.34 |

TABLE II-continued

| CMP # | STRUCTURE | Ca²⁺ Mob. | IUPAC Name | MASS | RT (min.) |
|---|---|---|---|---|---|
| 843 | 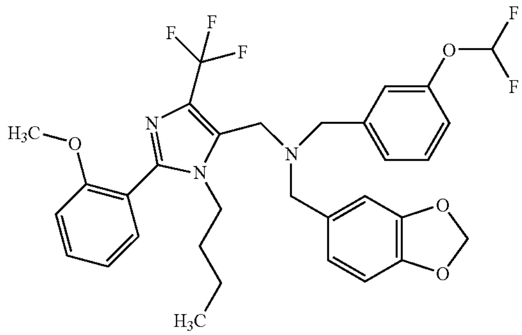 | * | 1-(1,3-benzodioxol-5-yl)-N-{[1-butyl-2-(2-methoxyphenyl)-4-(trifluoromethyl)-1H-imidazol-5-yl]methyl}-N-[3-(difluoromethoxy)benzyl]methanamine | 619.27 | 1.34 |
| 844 | 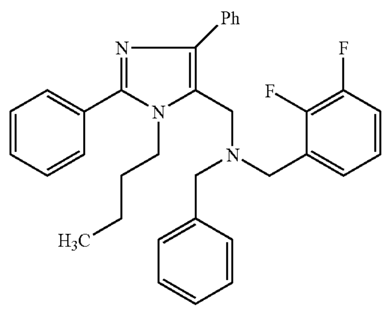 | * | N-benzyl-1-(1-butyl-2,4-diphenyl-1H-imidazol-5-yl)-N-(2,3-difluorobenzyl)methanamine | 522.31 | 1.23 |
| 845 | 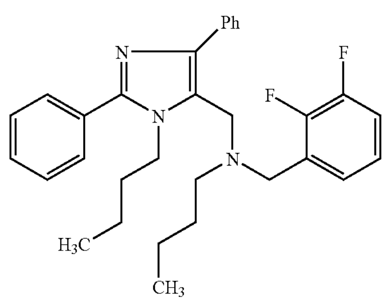 | * | N-[(1-butyl-2,4-diphenyl-1H-imidazol-5-yl)methyl]-N-(2,3-difluorobenzyl)butan-1-amine | 488.32 | 1.25 |
| 846 | 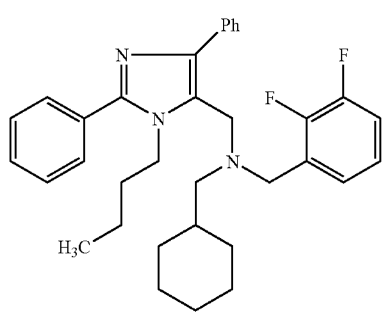 | * | 1-(1-butyl-2,4-diphenyl-1H-imidazol-5-yl)-N-(cyclohexylmethyl)-N-(2,3-difluorobenzyl)methanamine | 529.39 | 1.28 |

TABLE II-continued

| CMP # | STRUCTURE | Ca²⁺ Mob. | IUPAC Name | MASS | RT (min.) |
|---|---|---|---|---|---|
| 847 | 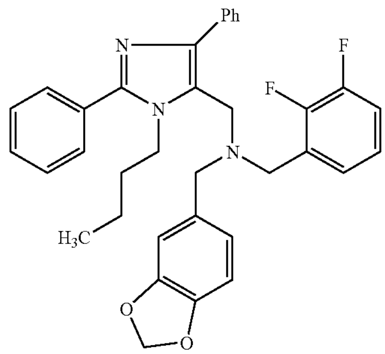 | * | 1-(1,3-benzodioxol-5-yl)-N-[(1-butyl-2,4-diphenyl-1H-imidazol-5-yl)methyl]-N-(2,3-difluorobenzyl)methanamine | 567.34 | 1.21 |
| 848 | 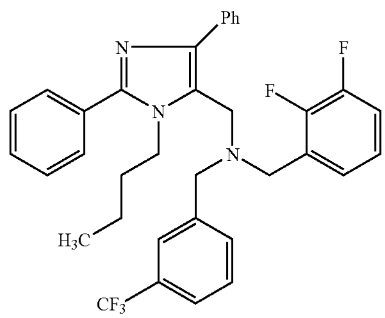 | * | 1-(1-butyl-2,4-diphenyl-1H-imidazol-5-yl)-N-(2,3-difluorobenzyl)-N-[3-(trifluoromethyl)benzyl]methanamine | 591.34 | 1.23 |
| 849 | 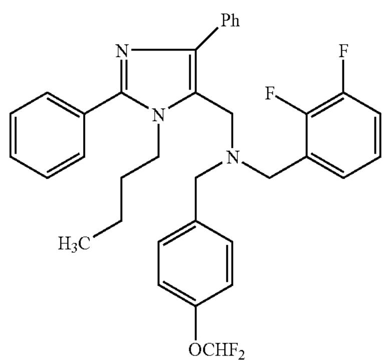 | * | 1-(1-butyl-2,4-diphenyl-1H-imidazol-5-yl)-N-(2,3-difluorobenzyl)-N-[4-(difluoromethoxy)benzyl]methanamine | 588.31 | 1.24 |
| 850 | 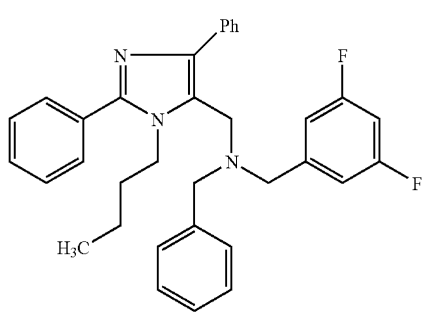 | * | N-benzyl-1-(1-butyl-2,4-diphenyl-1H-imidazol-5-yl)-N-(3,5-difluorobenzyl)methanamine | 522.32 | 1.24 |

TABLE II-continued

| CMP # | STRUCTURE | Ca²⁺ Mob. | IUPAC Name | MASS | RT (min.) |
|---|---|---|---|---|---|
| 851 | 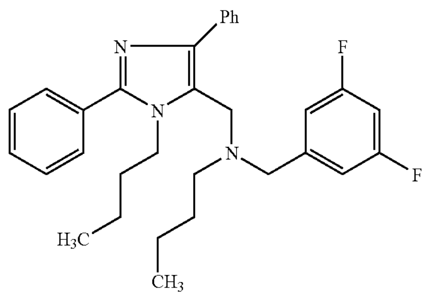 | * | N-[(1-butyl-2,4-diphenyl-1H-imidazol-5-yl)methyl]-N-(3,5-difluorobenzyl)butan-1-amine | 489.35 | 1.23 |
| 852 | 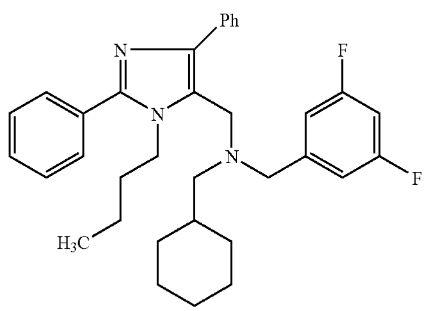 | * | 1-(1-butyl-2,4-diphenyl-1H-imidazol-5-yl)-N-(cyclohexylmethyl)-N-(3,5-difluorobenzyl)methanamine | 528.37 | 1.29 |
| 853 | 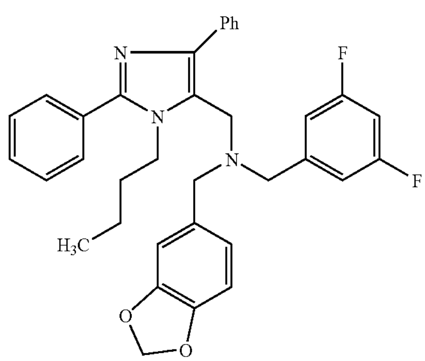 | * | 1-(1,3-benzodioxol-5-yl)-N-[(1-butyl-2,4-diphenyl-1H-imidazol-5-yl)methyl]-N-(3,5-difluorobenzyl)methanamine | 567.34 | 1.22 |
| 854 | 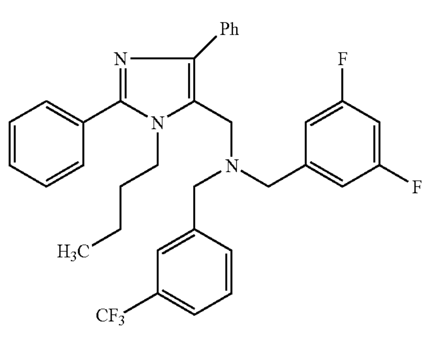 | * | 1-(1-butyl-2,4-diphenyl-1H-imidazol-5-yl)-N-(3,5-difluorobenzyl)-N-[3-(trifluoromethyl)benzyl]methanamine | 590.30 | 1.24 |

TABLE II-continued

| CMP # | STRUCTURE | Ca²⁺ Mob. | IUPAC Name | MASS | RT (min.) |
|---|---|---|---|---|---|
| 855 | 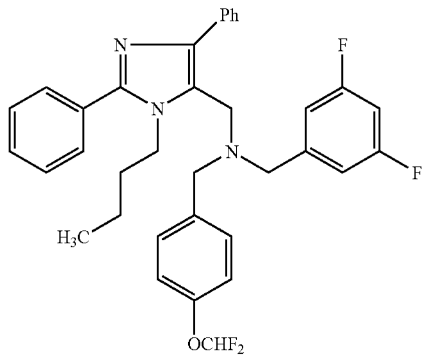 | * | 1-(1-butyl-2,4-diphenyl-1H-imidazol-5-yl)-N-(3,5-difluorobenzyl)-N-[4-(difluoromethoxy)benzyl]methanamine | 588.31 | 1.22 |
| 856 | 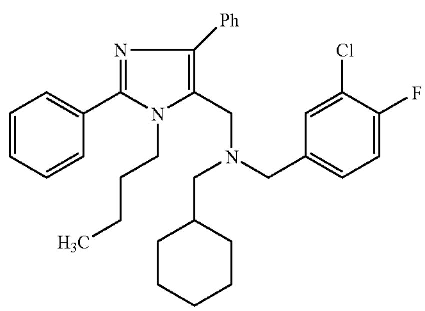 | * | 1-(1-butyl-2,4-diphenyl-1H-imidazol-5-yl)-N-(3-chloro-4-fluorobenzyl)-N-(cyclohexylmethyl)methanamine | 544.35 | 1.29 |
| 857 | 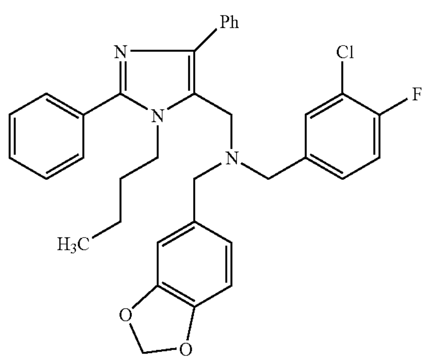 | * | 1-(1,3-benzodioxol-5-yl)-N-[(1-butyl-2,4-diphenyl-1H-imidazol-5-yl)methyl]-N-(3-chloro-4-fluorobenzyl)methanamine | 582.29 | 1.23 |
| 858 | 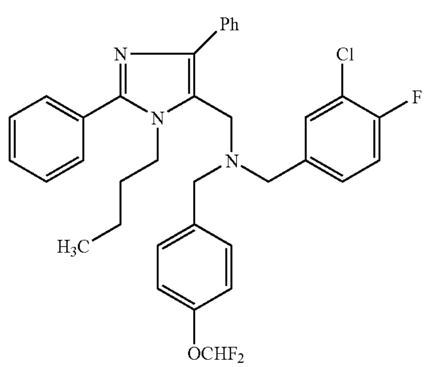 | * | 1-(1-butyl-2,4-diphenyl-1H-imidazol-5-yl)-N-(3-chloro-4-fluorobenzyl)-N-[4-(difluoromethoxy)benzyl]methanamine | 604.29 | 1.23 |

TABLE II-continued

| CMP # | STRUCTURE | Ca²⁺ Mob. | IUPAC Name | MASS | RT (min.) |
|---|---|---|---|---|---|
| 859 | 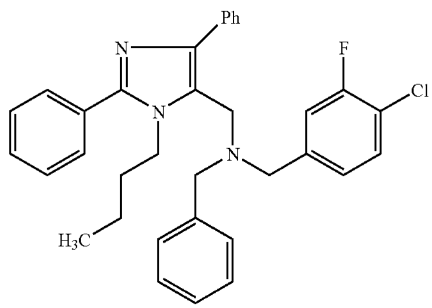 | * | N-benzyl-1-(1-butyl-2,4-diphenyl-1H-imidazol-5-yl)-N-(4-chloro-3-fluorobenzyl)methanamine | 538.29 | 1.25 |
| 860 | 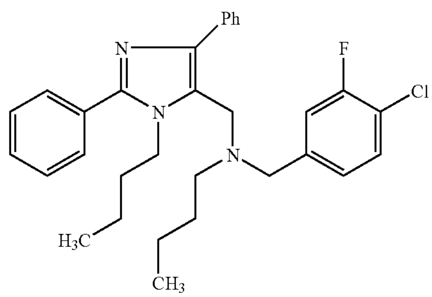 | * | N-[(1-butyl-2,4-diphenyl-1H-imidazol-5-yl)methyl]-N-(4-chloro-3-fluorobenzyl)butan-1-amine | 504.30 | 1.24 |
| 861 | 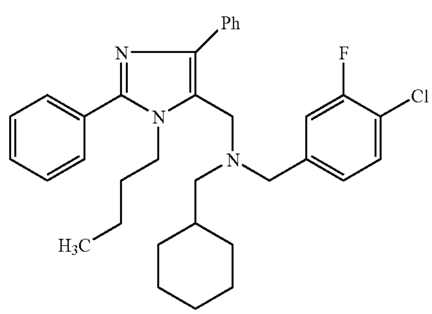 | * | 1-(1-butyl-2,4-diphenyl-1H-imidazol-5-yl)-N-(4-chloro-3-fluorobenzyl)-N-(cyclohexylmethyl)methanamine | 544.35 | 1.29 |
| 862 | 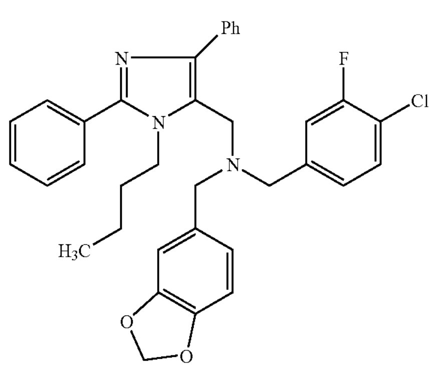 | * | 1-(1,3-benzodioxol-5-yl)-N-[(1-butyl-2,4-diphenyl-1H-imidazol-5-yl)methyl]-N-(4-chloro-3-fluorobenzyl)methanamine | 582.29 | 1.24 |

TABLE II-continued

| CMP # | STRUCTURE | Ca²⁺ Mob. | IUPAC Name | MASS | RT (min.) |
|---|---|---|---|---|---|
| 863 | 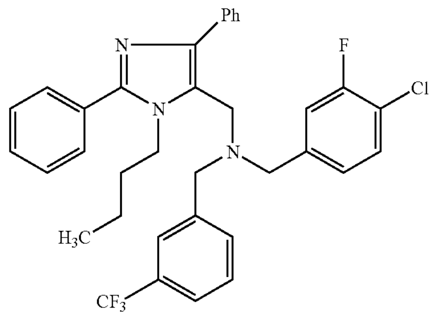 | * | 1-(1-butyl-2,4-diphenyl-1H-imidazol-5-yl)-N-(4-chloro-3-fluorobenzyl)-N-[3-(trifluoromethyl)benzyl]methanamine | 606.28 | 1.25 |
| 864 | 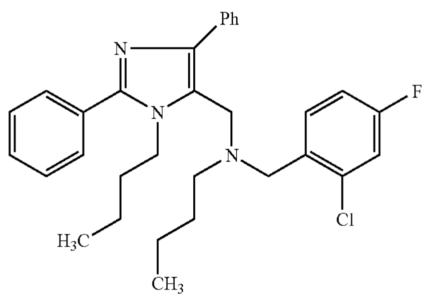 | * | N-[(1-butyl-2,4-diphenyl-1H-imidazol-5-yl)methyl]-N-(2-chloro-4-fluorobenzyl)butan-1-amine | 504.30 | 1.25 |
| 865 | 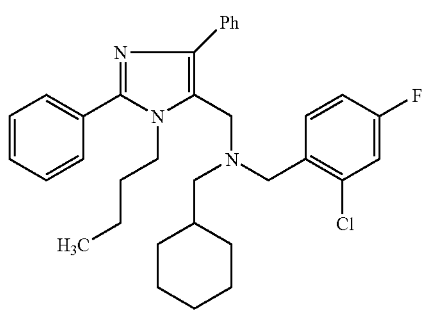 | * | 1-(1-butyl-2,4-diphenyl-1H-imidazol-5-yl)-N-(2-chloro-4-fluorobenzyl)-N-(cyclohexylmethyl)methanamine | 544.35 | 1.3 |
| 866 | 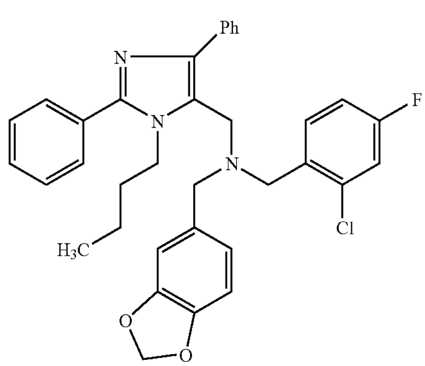 | * | 1-(1,3-benzodioxol-5-yl)-N-[(1-butyl-2,4-diphenyl-1H-imidazol-5-yl)methyl]-N-(2-chloro-4-fluorobenzyl)methanamine | 582.29 | 1.24 |

TABLE II-continued

| CMP # | STRUCTURE | Ca²⁺ Mob. | IUPAC Name | MASS | RT (min.) |
|---|---|---|---|---|---|
| 867 | 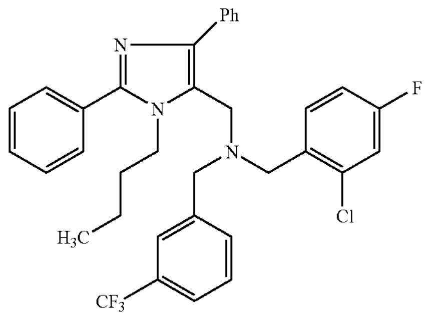 | * | 1-(1-butyl-2,4-diphenyl-1H-imidazol-5-yl)-N-(2-chloro-4-fluorobenzyl)-N-[3-(trifluoromethyl)benzyl]methanamine | 606.28 | 1.25 |
| 868 | 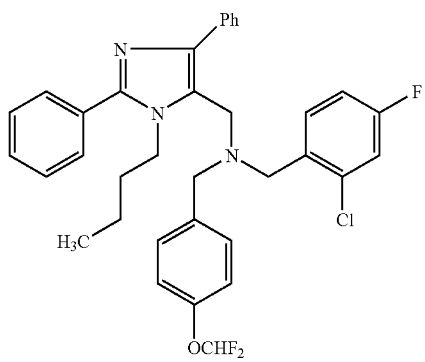 | * | 1-(1-butyl-2,4-diphenyl-1H-imidazol-5-yl)-N-(2-chloro-4-fluorobenzyl)-N-[4-(difluoromethoxy)benzyl]methanamine | 604.28 | 1.24 |
| 869 | 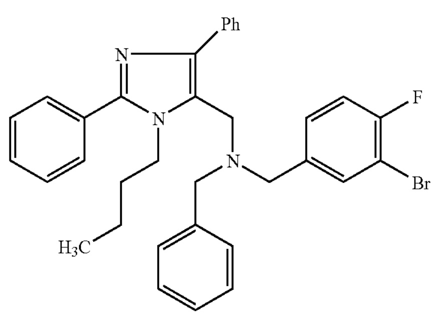 | * | N-benzyl-1-(3-bromo-4-fluorophenyl)-N-[(1-butyl-2,4-diphenyl-1H-imidazol-5-yl)methyl]methanamine | 582.26 | 1.24 |
| 870 | 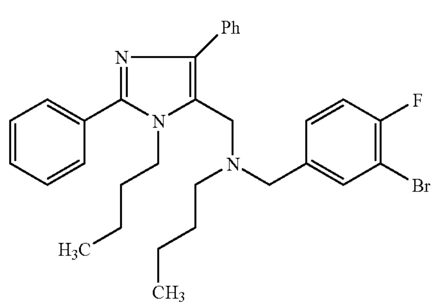 | * | N-(3-bromo-4-fluorobenzyl)-N-[(1-butyl-2,4-diphenyl-1H-imidazol-5-yl)methyl]butan-1-amine | 548.26 | 1.25 |

TABLE II-continued

| CMP # | STRUCTURE | Ca²⁺ Mob. | IUPAC Name | MASS | RT (min.) |
|---|---|---|---|---|---|
| 871 | 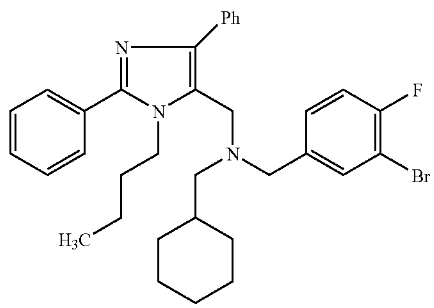 | * | 1-(3-bromo-4-fluorophenyl)-N-[(1-butyl-2,4-diphenyl-1H-imidazol-5-yl)methyl]-N-(cyclohexylmethyl)methanamine | 588.30 | 1.3 |
| 872 | 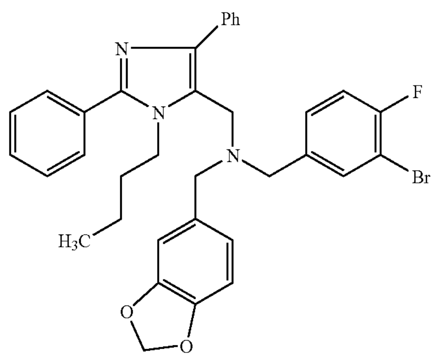 | * | 1-(1,3-benzodioxol-5-yl)-N-(3-bromo-4-fluorobenzyl)-N-[(1-butyl-2,4-diphenyl-1H-imidazol-5-yl)methyl]methanamine | 626.25 | 1.23 |
| 873 | 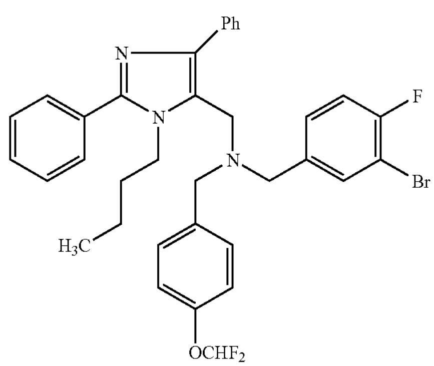 | * | 1-(3-bromo-4-fluorophenyl)-N-[(1-butyl-2,4-diphenyl-1H-imidazol-5-yl)methyl]-N-[4-(difluoromethoxy)benzyl]methanamine | 648.25 | 1.23 |
| 874 | 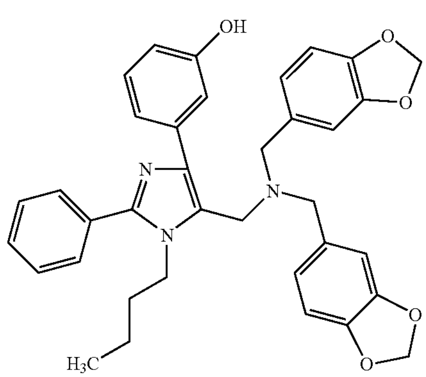 | * | 3-(5-{[bis(1,3-benzodioxol-5-ylmethyl)amino]methyl}-1-butyl-2-phenyl-1H-imidazol-4-yl)phenol | 590.27 | 1.2 |

TABLE II-continued

| CMP # | STRUCTURE | Ca²⁺ Mob. | IUPAC Name | MASS | RT (min.) |
|---|---|---|---|---|---|
| 875 | 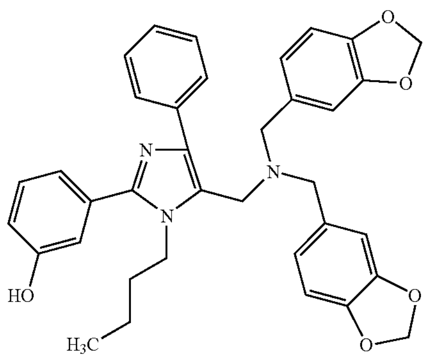 | * | 3-(5-{[bis(1,3-benzodioxol-5-ylmethyl)amino]methyl}-1-butyl-4-phenyl-1H-imidazol-2-yl)phenol | 590.27 | 1.21 |
| 876 | 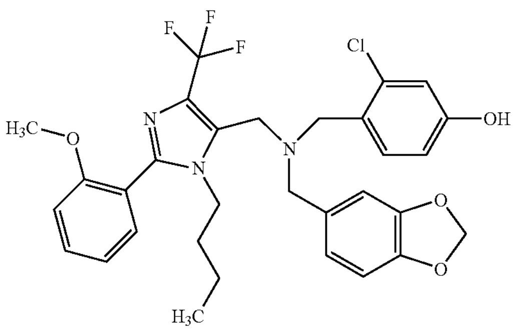 | * | 4-[((1,3-benzodioxol-5-ylmethyl){[1-butyl-2-(2-methoxyphenyl)-4-(trifluoromethyl)-1H-imidazol-5-yl]methyl}amino)methyl]-3-chlorophenol | 602.20 | 1.32 |
| 877 | 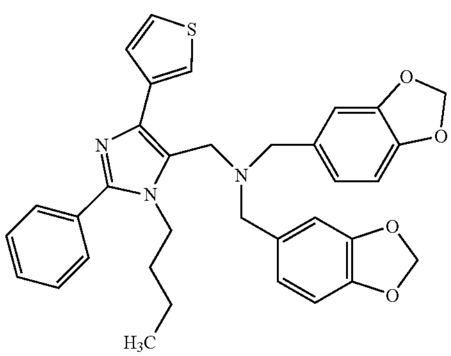 | * | 1-(1,3-benzodioxol-5-yl)-N-(1,3-benzodioxol-5-ylmethyl)-N-[(1-butyl-2-phenyl-4-thien-3-yl-1H-imidazol-5-yl)methyl]methanamine | 580.22 | 1.2 |
| 878 | 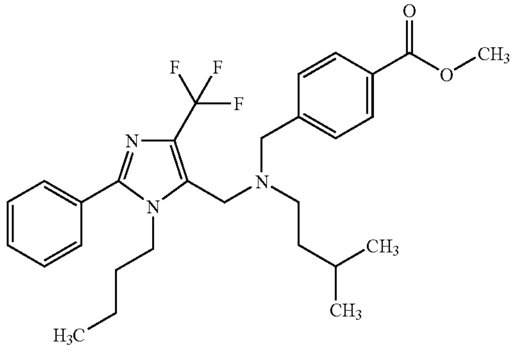 | * | methyl 4-{[{[1-butyl-2-phenyl-4-(trifluoromethyl)-1H-imidazol-5-yl]methyl}(isopentyl)amino]methyl}benzoate | 516.28 | 1.36 |

TABLE II-continued

| CMP # | STRUCTURE | Ca²⁺ Mob. | IUPAC Name | MASS | RT (min.) |
|---|---|---|---|---|---|
| 879 | 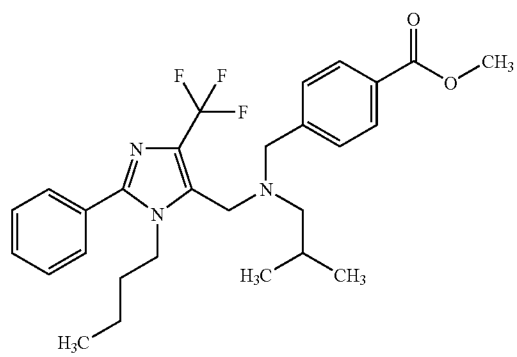 | * | methyl 4-{[{[1-butyl-2-phenyl-4-(trifluoromethyl)-1H-imidazol-5-yl]methyl}(isobutyl)amino]methyl}benzoate | 502.26 | 1.37 |
| 880 | 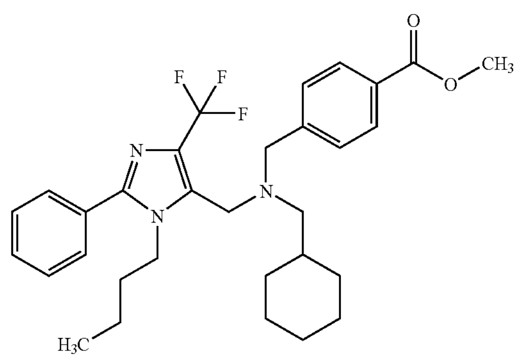 | | methyl 4-{[{[1-butyl-2-phenyl-4-(trifluoromethyl)-1H-imidazol-5-yl]methyl}(cyclohexylmethyl)amino]methyl}benzoate | 542.30 | 1.45 |
| 881 | 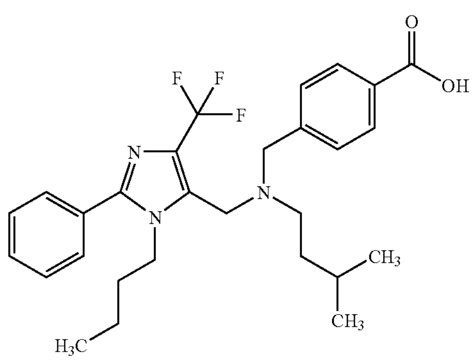 | * | 4-{[{[1-butyl-2-phenyl-4-(trifluoromethyl)-1H-imidazol-5-yl]methyl}(isopentyl)amino]methyl}benzoic acid | 502.26 | 1.3 |
| 882 | 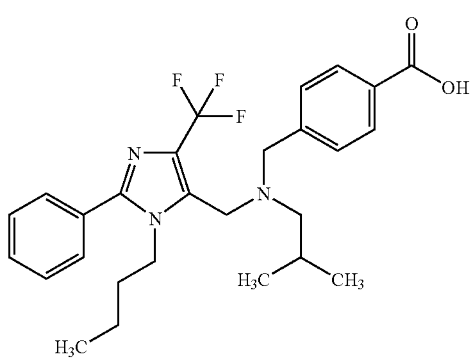 | * | 4-{[{[1-butyl-2-phenyl-4-(trifluoromethyl)-1H-imidazol-5-yl]methyl}(isobutyl)amino]methyl}benzoic acid | 488.25 | 1.32 |

TABLE II-continued

| CMP # | STRUCTURE | Ca²⁺ Mob. | IUPAC Name | MASS | RT (min.) |
|---|---|---|---|---|---|
| 883 | 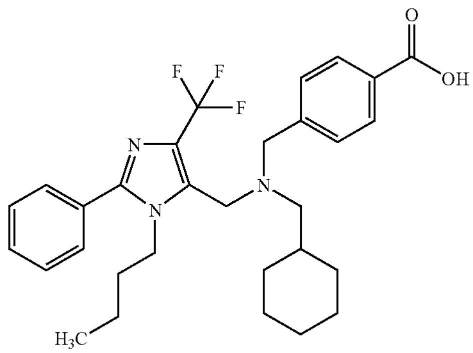 | * | 4-{[{[1-butyl-2-phenyl-4-(trifluoromethyl)-1H-imidazol-5-yl]methyl}(cyclohexylmethyl)amino]methyl}benzoic acid | 528.28 | 1.39 |
| 884 | 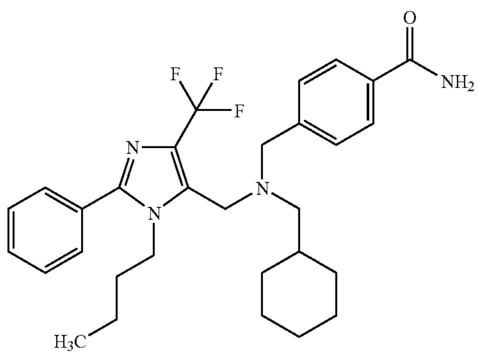 | * | 4-{[{[1-butyl-2-phenyl-4-(trifluoromethyl)-1H-imidazol-5-yl]methyl}(cyclohexylmethyl)amino]methyl}benzamide | 527.30 | 1.34 |
| 885 | 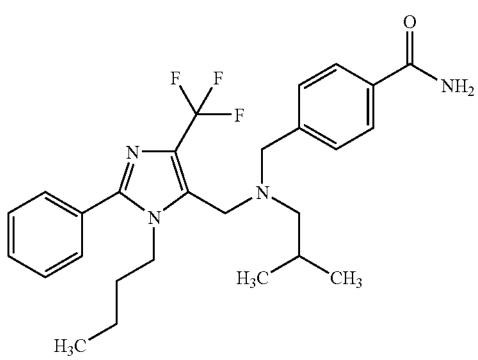 | * | 4-{[{[1-butyl-2-phenyl-4-(trifluoromethyl)-1H-imidazol-5-yl]methyl}(isobutyl)amino]methyl}benzamide | 487.27 | 1.28 |
| 886 | 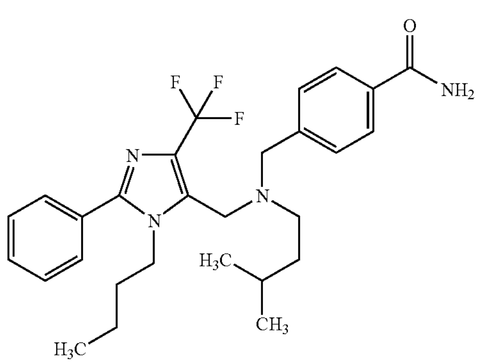 | * | 4-{[{[1-butyl-2-phenyl-4-(trifluoromethyl)-1H-imidazol-5-yl]methyl}(isopentyl)amino]methyl}benzamide | 501.29 | 1.25 |

TABLE II-continued

| CMP # | STRUCTURE | Ca²⁺ Mob. | IUPAC Name | MASS | RT (min.) |
|---|---|---|---|---|---|
| 887 | 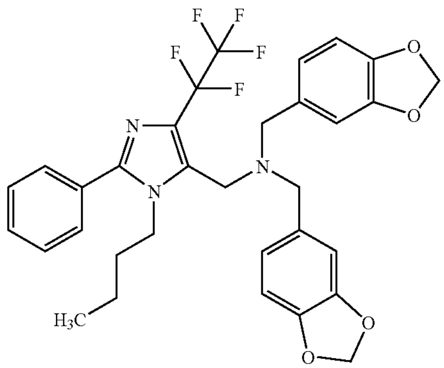 | * | 1-(1,3-benzodioxol-5-yl)-N-(1,3-benzodioxol-5-ylmethyl)-N-{[1-butyl-4-(pentafluoroethyl)-2-phenyl-1H-imidazol-5-yl]methyl}methanamine | 616.34 | 1.4 |
| 888 | 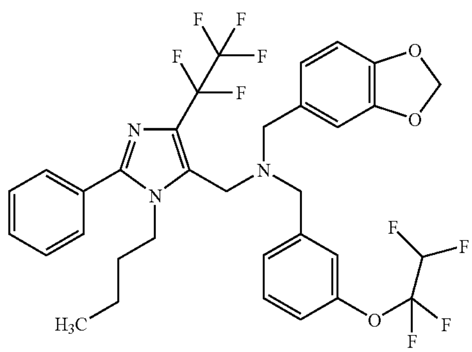 | * | 1-(1,3-benzodioxol-5-yl)-N-{[1-butyl-4-(pentafluoroethyl)-2-phenyl-1H-imidazol-5-yl]methyl}-N-[3-(1,1,2,2-tetrafluoroethoxy)benzyl]methanamine | 688.36 | 1.38 |
| 889 | 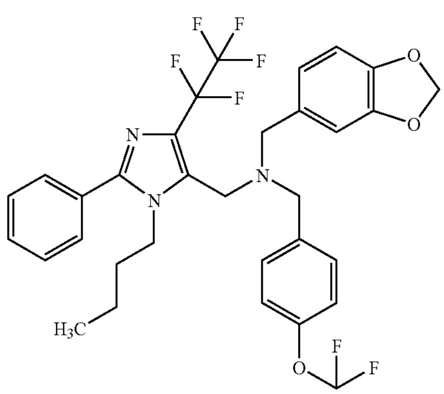 | * | 1-(1,3-benzodioxol-5-yl)-N-{[1-butyl-4-(pentafluoroethyl)-2-phenyl-1H-imidazol-5-yl]methyl}-N-[4-(difluoromethoxy)benzyl]methanamine | 638.35 | 1.37 |
| 890 | 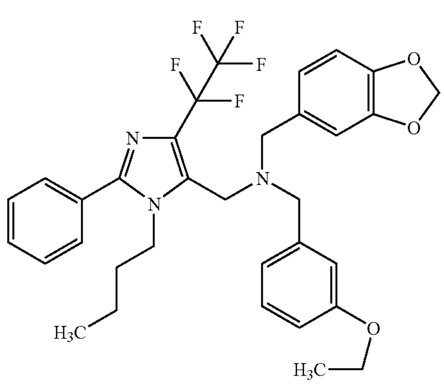 | * | 1-(1,3-benzodioxol-5-yl)-N-{[1-butyl-4-(pentafluoroethyl)-2-phenyl-1H-imidazol-5-yl]methyl}-N-(3-ethoxybenzyl)methanamine | 616.38 | 1.44 |

TABLE II-continued

| CMP # | STRUCTURE | Ca²⁺ Mob. | IUPAC Name | MASS | RT (min.) |
|---|---|---|---|---|---|
| 891 | 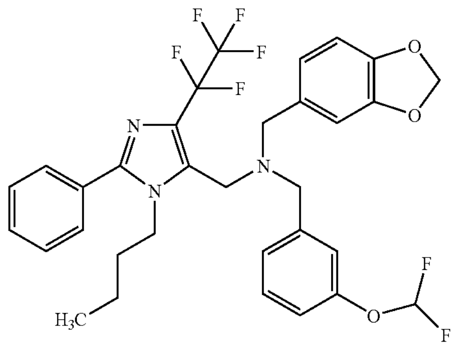 | * | 1-(1,3-benzodioxol-5-yl)-N-{[1-butyl-4-(pentafluoroethyl)-2-phenyl-1H-imidazol-5-yl]methyl}-N-[3-(difluoromethoxy)benzyl]methanamine | 638.34 | 1.37 |
| 892 | 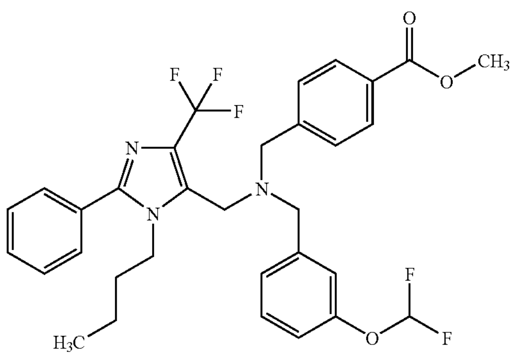 | * | methyl 4-({{[1-butyl-2-phenyl-4-(trifluoromethyl)-1H-imidazol-5-yl]methyl}[3-(difluoromethoxy)benzyl]amino}methyl)benzoate | 602.35 | 1.33 |
| 893 | 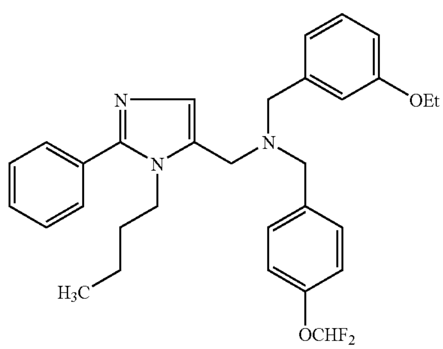 | * | 1-(1-butyl-2-phenyl-1H-imidazol-5-yl)-N-[4-(difluoromethoxy)benzyl]-N-(3-ethoxybenzyl)methanamine | 520.26 | 1.21 |
| 894 | 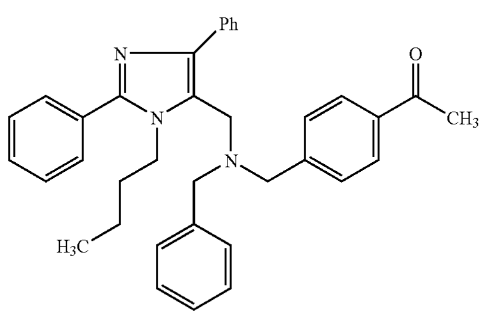 | * | 1-[4-({benzyl[(1-butyl-2,4-diphenyl-1H-imidazol-5-yl)methyl]amino}methyl)phenyl]ethanone | 528.29 | 1.19 |

TABLE II-continued

| CMP # | STRUCTURE | Ca²⁺ Mob. | IUPAC Name | MASS | RT (min.) |
|---|---|---|---|---|---|
| 895 | 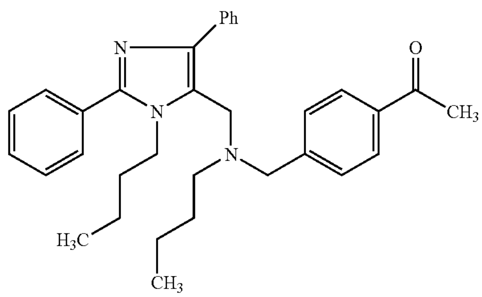 | * | 1-[4-({butyl[(1-butyl-2,4-diphenyl-1H-imidazol-5-yl)methyl]amino}methyl)phenyl]ethanone | 494.31 | 1.18 |
| 896 | 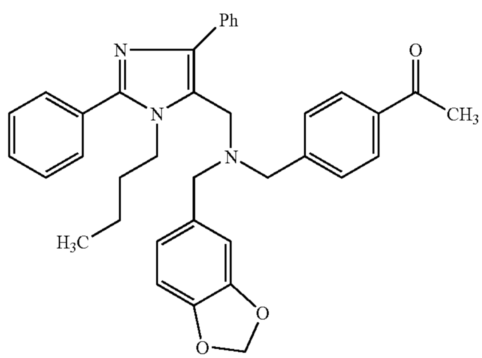 | * | 1-[4-({(1,3-benzodioxol-5-ylmethyl)[(1-butyl-2,4-diphenyl-1H-imidazol-5-yl)methyl]amino}methyl)phenyl]ethanone | 572.29 | 1.18 |
| 897 | 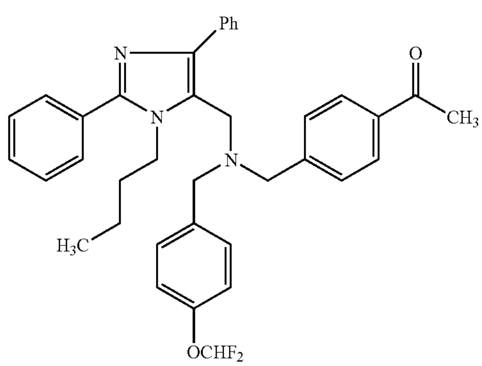 | * | 1-[4-({[(1-butyl-2,4-diphenyl-1H-imidazol-5-yl)methyl][4-(difluoromethoxy)benzyl]amino}methyl)phenyl]ethanone | 594.29 | 1.18 |
| 898 | 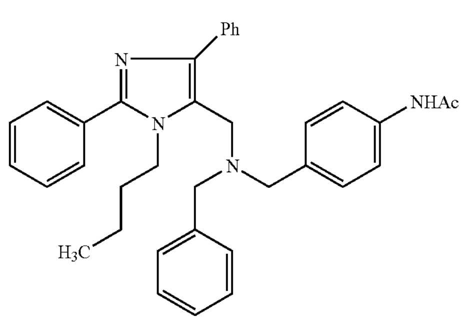 | * | N-[4-({benzyl[(1-butyl-2,4-diphenyl-1H-imidazol-5-yl)methyl]amino}methyl)phenyl]acetamide | 543.31 | 1.17 |

TABLE II-continued

| CMP # | STRUCTURE | Ca²⁺ Mob. | IUPAC Name | MASS | RT (min.) |
|---|---|---|---|---|---|
| 899 | 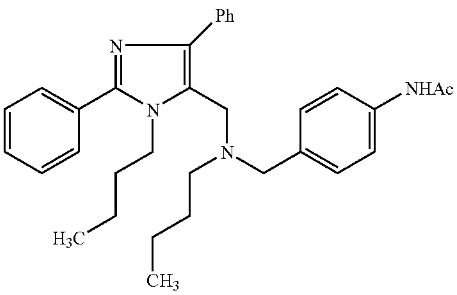 | * | N-[4-({butyl[(1-butyl-2,4-diphenyl-1H-imidazol-5-yl)methyl]amino}methyl)phenyl]acetamide | 509.33 | 1.13 |
| 900 | 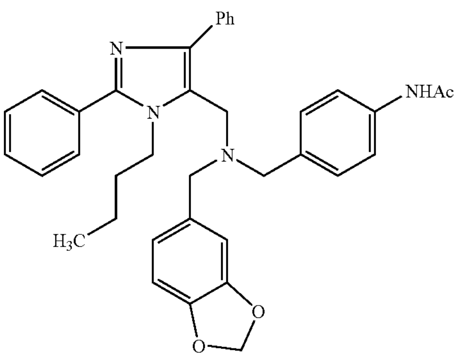 | * | N-[4-({(1,3-benzodioxol-5-ylmethyl)[(1-butyl-2,4-diphenyl-1H-imidazol-5-yl)methyl]amino}methyl)phenyl]acetamide | 587.31 | 1.17 |
| 901 | 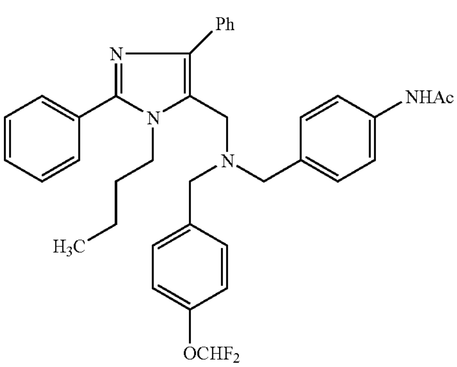 | * | N-[4-({[(1-butyl-2,4-diphenyl-1H-imidazol-5-yl)methyl][4-(difluoromethoxy)benzyl]amino}methyl)phenyl]acetamide | 609.31 | 1.18 |
| 902 | 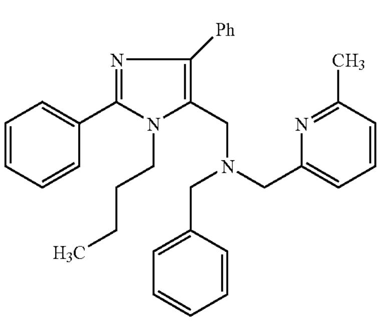 | * | N-benzyl-1-(1-butyl-2,4-diphenyl-1H-imidazol-5-yl)-N-[(6-methylpyridin-2-yl)methyl]methanamine | 501.30 | 1.1 |

TABLE II-continued

| CMP # | STRUCTURE | Ca²⁺ Mob. | IUPAC Name | MASS | RT (min.) |
|---|---|---|---|---|---|
| 903 | 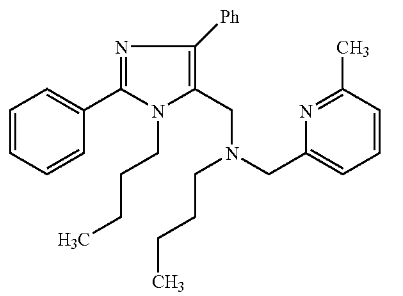 | * | N-[(1-butyl-2,4-diphenyl-1H-imidazol-5-yl)methyl]-N-[(6-methylpyridin-2-yl)methyl]butan-1-amine | 467.31 | 1.09 |
| 904 | 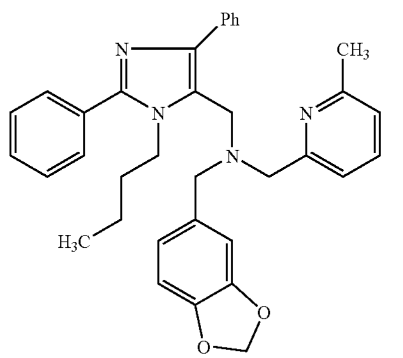 | * | 1-(1,3-benzodioxol-5-yl)-N-[(1-butyl-2,4-diphenyl-1H-imidazol-5-yl)methyl]-N-[(6-methylpyridin-2-yl)methyl]methanamine | 545.30 | 1.09 |
| 905 | 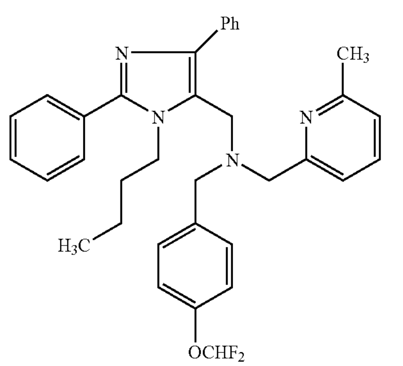 | * | 1-(1-butyl-2,4-diphenyl-1H-imidazol-5-yl)-N-[4-(difluoromethoxy)benzyl]-N-[(6-methylpyridin-2-yl)methyl]methanamine | 567.37 | 1.1 |
| 906 | 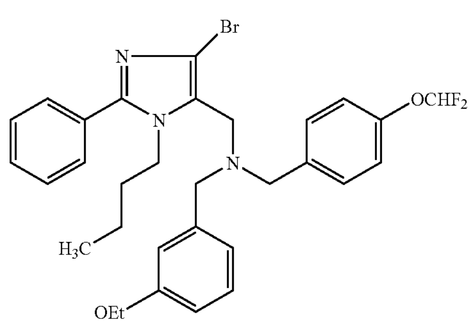 | * | N-[(4-bromo-1-butyl-2-phenyl-1H-imidazol-5-yl)methyl]-N-[4-(difluoromethoxy)benzyl]-N-(3-ethoxybenzyl)amine | 598.27 | 1.36 |

TABLE II-continued

| CMP # | STRUCTURE | Ca²⁺ Mob. | IUPAC Name | MASS | RT (min.) |
|---|---|---|---|---|---|
| 907 | 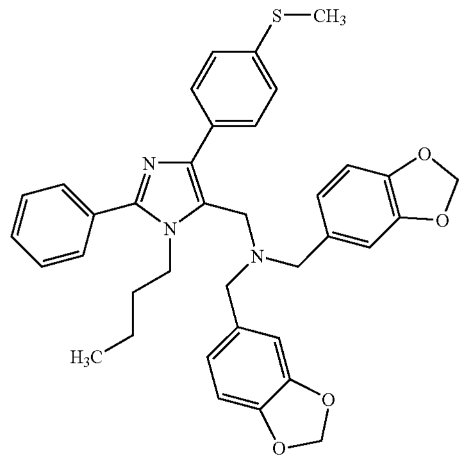 | * | 1-(1,3-benzodioxol-5-yl)-N-(1,3-benzodioxol-5-ylmethyl)-N-({1-butyl-4-[4-(methylthio)phenyl]-2-phenyl-1H-imidazol-5-yl}methyl)methanamine | 620.32 | 1.24 |
| 908 | 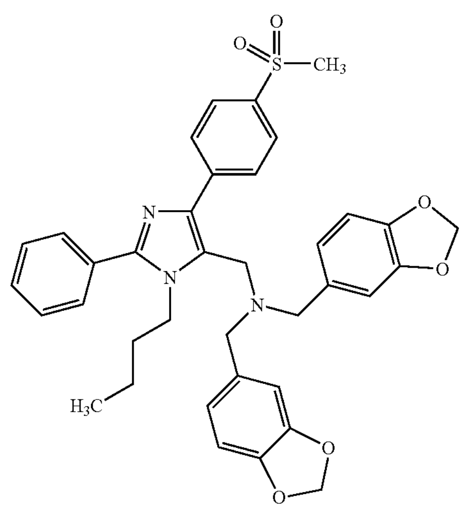 | * | 1-(1,3-benzodioxol-5-yl)-N-(1,3-benzodioxol-5-ylmethyl)-N-({1-butyl-4-[4-(methylsulfonyl)phenyl]-2-phenyl-1H-imidazol-5-yl}methyl)methanamine | 652.32 | 1.19 |
| 909 | 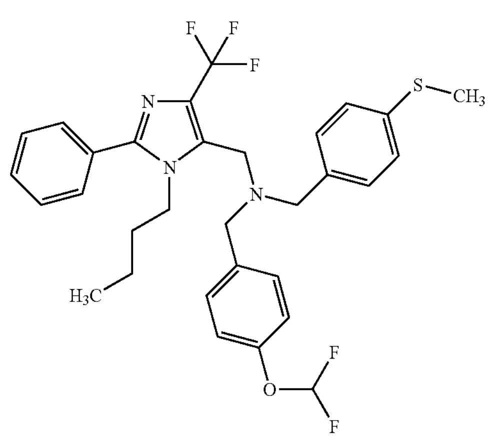 | * | 1-[1-butyl-2-phenyl-4-(trifluoromethyl)-1H-imidazol-5-yl]-N-[4-(difluoromethoxy)benzyl]-N-[4-(methylthio)benzyl]methanamine | 590.27 | 1.38 |

TABLE II-continued

| CMP # | STRUCTURE | Ca²⁺ Mob. | IUPAC Name | MASS | RT (min.) |
|---|---|---|---|---|---|
| 910 | 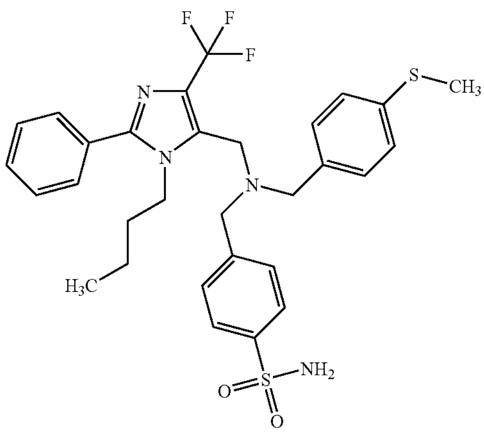 | * | 4-({{[1-butyl-2-phenyl-4-(trifluoromethyl)-1H-imidazol-5-yl]methyl}[4-(methylthio)benzyl]amino}methyl)benzenesulfonamide | 603.27 | 1.27 |
| 911 | 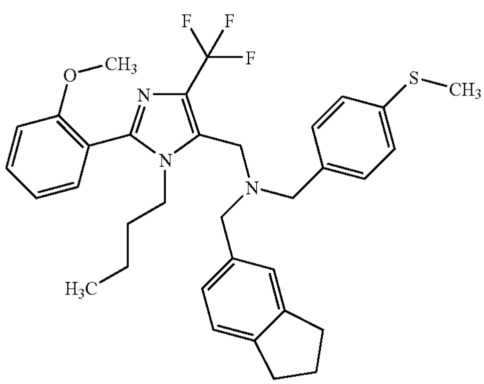 | * | 1-(1,3-benzodioxol-5-yl)-N-{[1-butyl-2-(2-methoxyphenyl)-4-(trifluoromethyl)-1H-imidazol-5-yl]methyl}-N-[4-(methylthio)benzyl]methanamine | 598.28 | 1.4 |
| 912 | 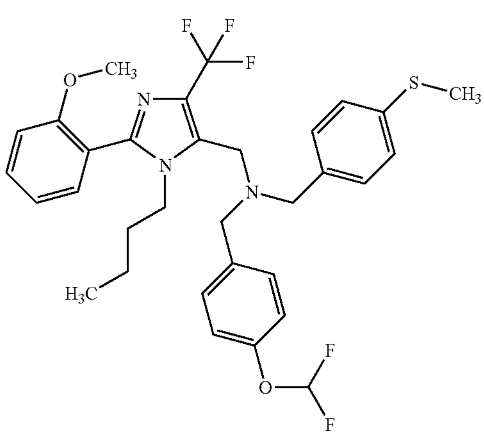 | | 1-[1-butyl-2-(2-methoxyphenyl)-4-(trifluoromethyl)-1H-imidazol-5-yl]-N-[4-(difluoromethoxy)benzyl]-N-[4-(methylthio)benzyl]methanamine | 621.33 | 1.37 |

TABLE II-continued

| CMP # | STRUCTURE | Ca²⁺ Mob. | IUPAC Name | MASS | RT (min.) |
|---|---|---|---|---|---|
| 913 | 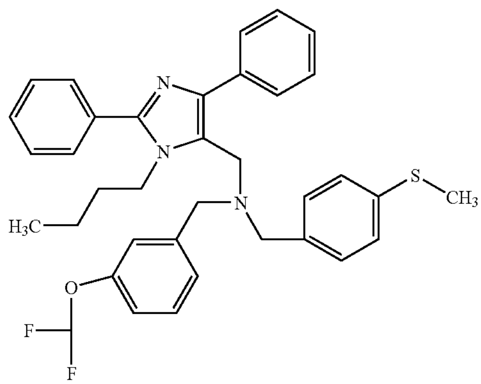 | * | 1-(1-butyl-2,4-diphenyl-1H-imidazol-5-yl)-N-[3-(difluoromethoxy)benzyl]-N-[4-(methylthio)benzyl]methanamine | 599.35 | 1.23 |
| 914 | 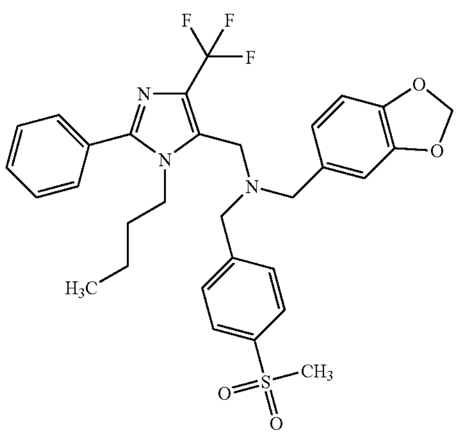 | | 1-(1,3-benzodioxol-5-yl)-N-{[1-butyl-2-phenyl-4-(trifluoromethyl)-1H-imidazol-5-yl]methyl}-N-[4-(methylsulfonyl)benzyl]methanamine | 600.27 | 1.26 |
| 915 | 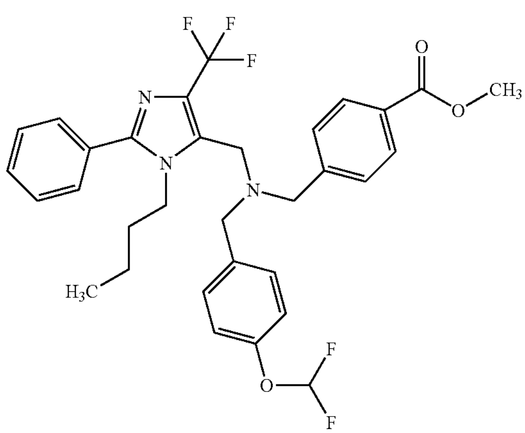 | * | methyl 4-({{[1-butyl-2-phenyl-4-(trifluoromethyl)-1H-imidazol-5-yl]methyl}[4-(difluoromethoxy)benzyl]amino}methyl)benzoate | 603.32 | 1.34 |

TABLE II-continued

| CMP # | STRUCTURE | Ca²⁺ Mob. | IUPAC Name | MASS | RT (min.) |
|---|---|---|---|---|---|
| 916 | 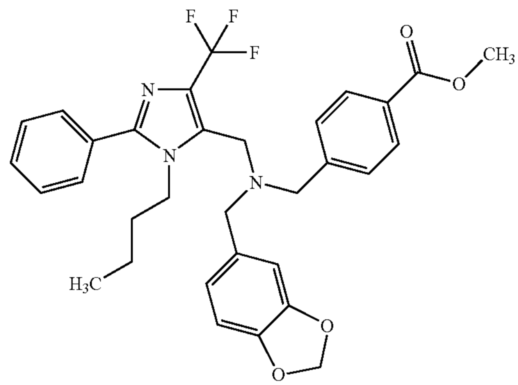 | * | methyl 4-[(((1,3-benzodioxol-5-ylmethyl){[1-butyl-2-phenyl-4-(trifluoromethyl)-1H-imidazol-5-yl]methyl}amino)methyl]benzoate | 581.32 | 1.36 |
| 917 | 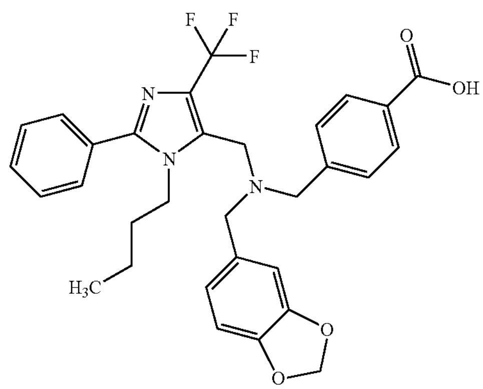 | * | 4-[(((1,3-benzodioxol-5-ylmethyl){[1-butyl-2-phenyl-4-(trifluoromethyl)-1H-imidazol-5-yl]methyl}amino)methyl]benzoic acid | 566.29 | 1.31 |
| 918 | 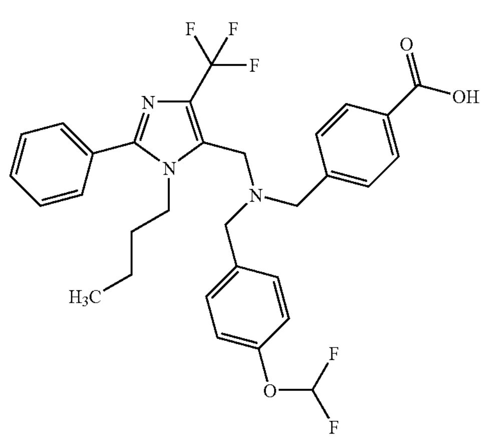 | * | 4-({{[1-butyl-2-phenyl-4-(trifluoromethyl)-1H-imidazol-5-yl]methyl}[4-(difluoromethoxy)benzyl]amino}methyl)benzoic acid | 588.28 | 1.29 |

TABLE II-continued

| CMP # | STRUCTURE | Ca²⁺ Mob. | IUPAC Name | MASS | RT (min.) |
|---|---|---|---|---|---|
| 919 | 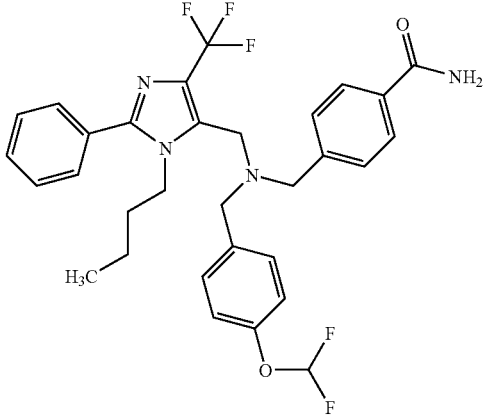 | * | 4-({{[1-butyl-2-phenyl-4-(trifluoromethyl)-1H-imidazol-5-yl]methyl}[4-(difluoromethoxy)benzyl]amino}methyl)benzamide | 587.29 | 1.26 |
| 920 | 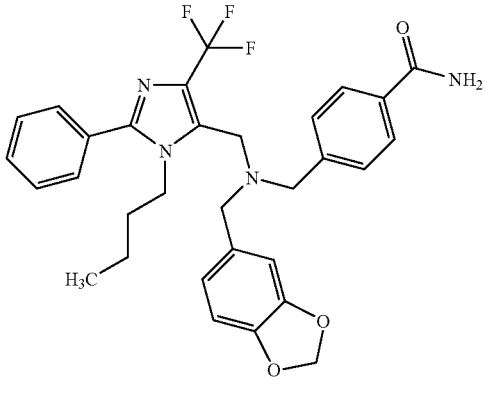 | * | 4-[((1,3-benzodioxol-5-ylmethyl){[1-butyl-2-phenyl-4-(trifluoromethyl)-1H-imidazol-5-yl]methyl}amino)methyl]benzamide | 565.29 | 1.27 |
| 921 | 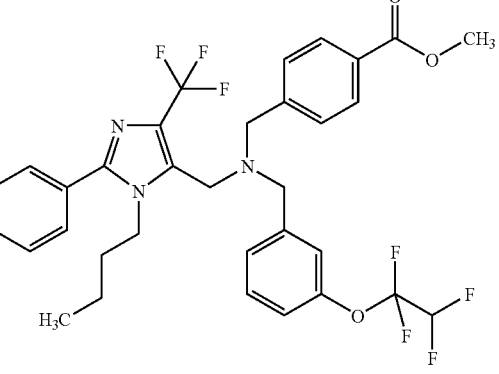 | * | methyl 4-({{[1-butyl-2-phenyl-4-(trifluoromethyl)-1H-imidazol-5-yl]methyl}[3-(1,1,2,2-tetrafluoroethoxy)benzyl]amino}methyl)benzoate | 652.37 | 1.33 |
| 922 | 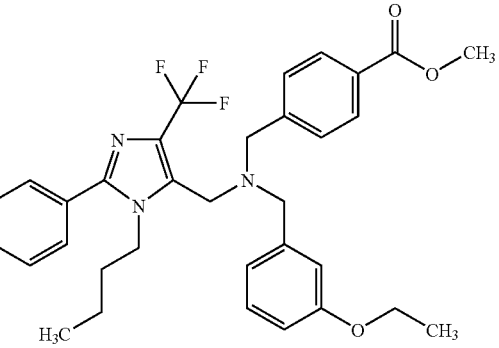 | * | methyl 4-{[{[1-butyl-2-phenyl-4-(trifluoromethyl)-1H-imidazol-5-yl]methyl}(3-ethoxybenzyl)amino]methyl}benzoate | 580.39 | 1.39 |

TABLE II-continued

| CMP # | STRUCTURE | Ca²⁺ Mob. | IUPAC Name | MASS | RT (min.) |
|---|---|---|---|---|---|
| 923 | 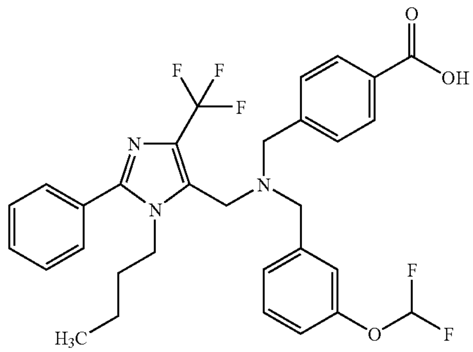 | * | 4-({{[1-butyl-2-phenyl-4-(trifluoromethyl)-1H-imidazol-5-yl]methyl}[3-(difluoromethoxy)benzyl]amino}methyl)benzoic acid | 588.35 | 1.28 |
| 924 | 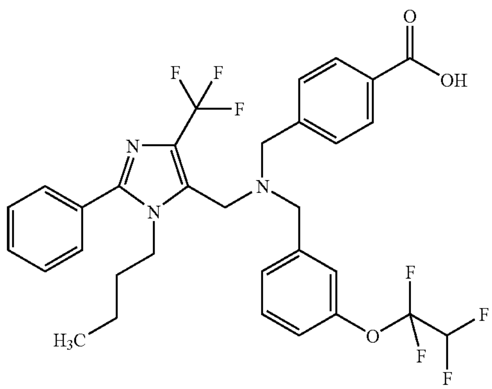 | * | 4-({{[1-butyl-2-phenyl-4-(trifluoromethyl)-1H-imidazol-5-yl]methyl}[3-(1,1,2,2-tetrafluoroethoxy)benzyl]amino}methyl)benzoic acid | 638.36 | 1.3 |
| 925 | 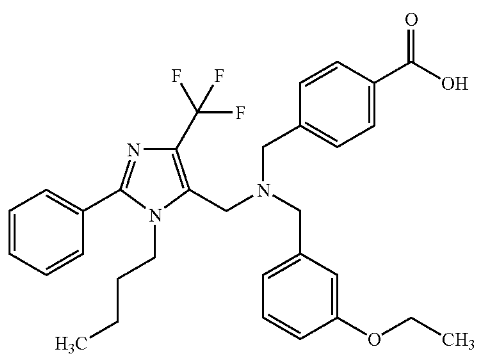 | * | 4-{[{[1-butyl-2-phenyl-4-(trifluoromethyl)-1H-imidazol-5-yl]methyl}(3-ethoxybenzyl)amino]methyl}benzoic acid | 566.38 | 1.34 |
| 926 | 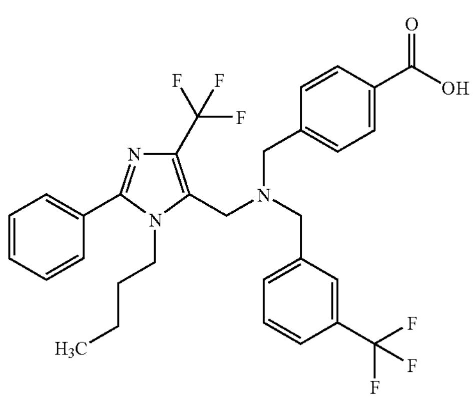 | * | 4-({{[1-butyl-2-phenyl-4-(trifluoromethyl)-1H-imidazol-5-yl]methyl}[3-(trifluoromethyl)benzyl]amino}methyl)benzoic acid | 590.35 | 1.32 |

TABLE II-continued

| CMP # | STRUCTURE | Ca²⁺ Mob. | IUPAC Name | MASS | RT (min.) |
|---|---|---|---|---|---|
| 927 | 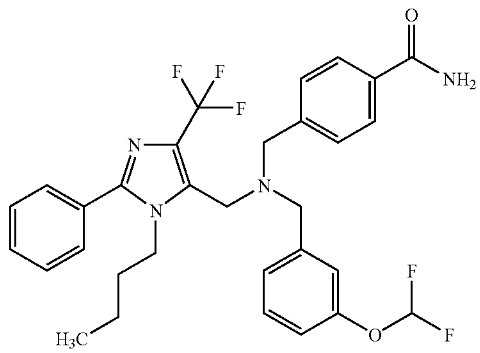 | * | 4-({{[1-butyl-2-phenyl-4-(trifluoromethyl)-1H-imidazol-5-yl]methyl}[3-(difluoromethoxy)benzyl]amino}methyl)benzamide | 587.37 | 1.26 |
| 928 | 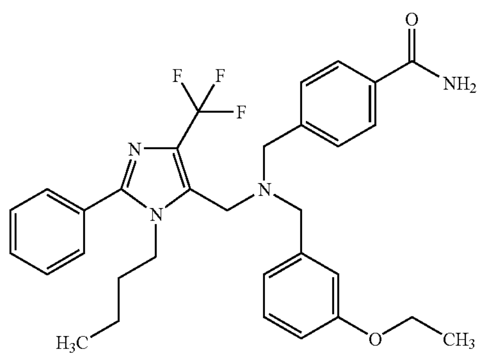 | * | 4-{[{[1-butyl-2-phenyl-4-(trifluoromethyl)-1H-imidazol-5-yl]methyl}(3-ethoxybenzyl)amino]methyl}benzamide | 565.39 | 1.3 |
| 929 | 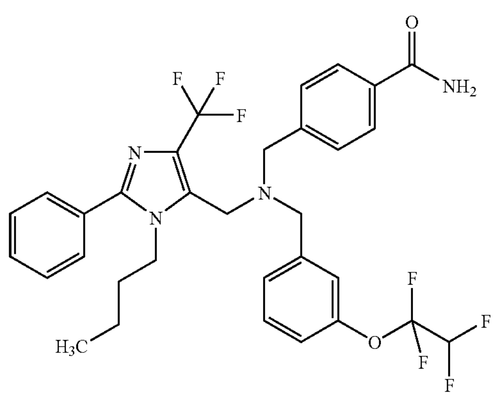 | * | 4-({{[1-butyl-2-phenyl-4-(trifluoromethyl)-1H-imidazol-5-yl]methyl}[3-(1,1,2,2-tetrafluoroethoxy)benzyl]amino}methyl)benzamide | 637.38 | 1.27 |
| 930 | 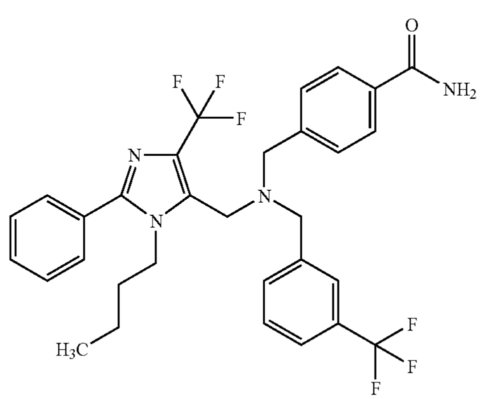 | * | 4-({{[1-butyl-2-phenyl-4-(trifluoromethyl)-1H-imidazol-5-yl]methyl}[3-(trifluoromethyl)benzyl]amino}methyl)benzamide | 589.36 | 1.29 |

TABLE II-continued

| CMP # | STRUCTURE | Ca²⁺ Mob. | IUPAC Name | MASS | RT (min.) |
|---|---|---|---|---|---|
| 931 | 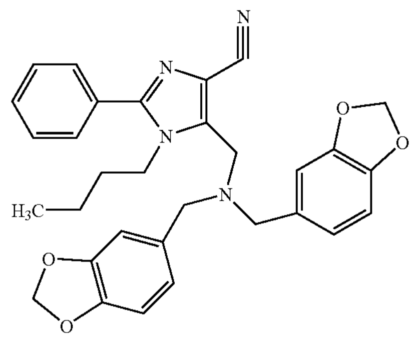 | * | 5-{[bis(1,3-benzodioxol-5-ylmethyl)amino]methyl}-1-butyl-2-phenyl-1H-imidazole-4-carbonitrile | 523.33 | 1.3 |
| 932 | 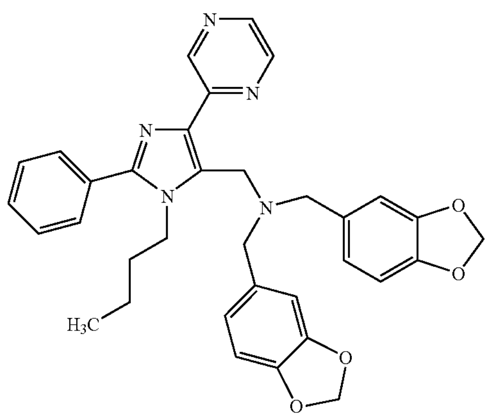 | * | 1-(1,3-benzodioxol-5-yl)-N-(1,3-benzodioxol-5-ylmethyl)-N-[(1-butyl-2-phenyl-4-pyrazin-2-yl-1H-imidazol-5-yl)methyl]methanamine | 576.27 | 1.15 |
| 933 | 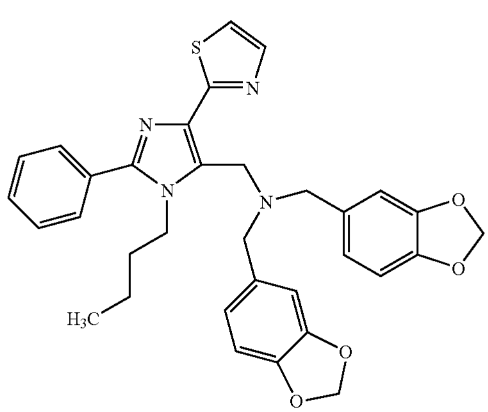 | * | 1-(1,3-benzodioxol-5-yl)-N-(1,3-benzodioxol-5-ylmethyl)-N-{[1-butyl-2-phenyl-4-(1,3-thiazol-2-yl)-1H-imidazol-5-yl]methyl}methanamine | 581.23 | 1.15 |

TABLE II-continued
| CMP # | STRUCTURE | Ca²⁺ Mob. | IUPAC Name | MASS | RT (min.) |
|---|---|---|---|---|---|
| 934 | 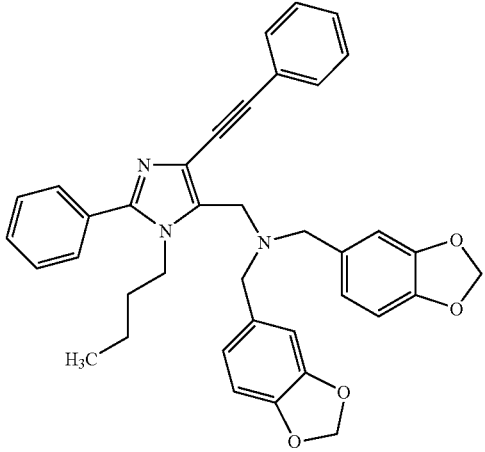 | * | 1-(1,3-benzodioxol-5-yl)-N-(1,3-benzodioxol-5-ylmethyl)-N-{[1-butyl-2-phenyl-4-(phenylethynyl)-1H-imidazol-5-yl]methyl}methanamine | 598.28 | 1.28 |
| 935 | 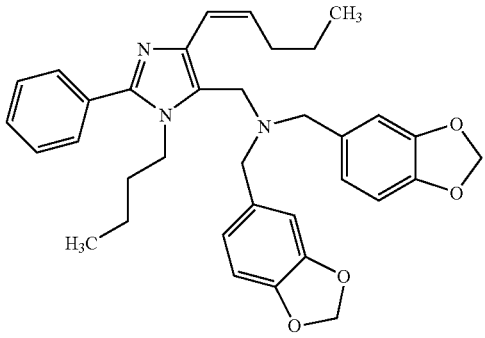 | * | 1-(1,3-benzodioxol-5-yl)-N-(1,3-benzodioxol-5-ylmethyl)-N-({1-butyl-4-[(1E)-pent-1-enyl]-2-phenyl-1H-imidazol-5-yl}methyl)methanamine | 566.31 | 1.23 |
| 936 | 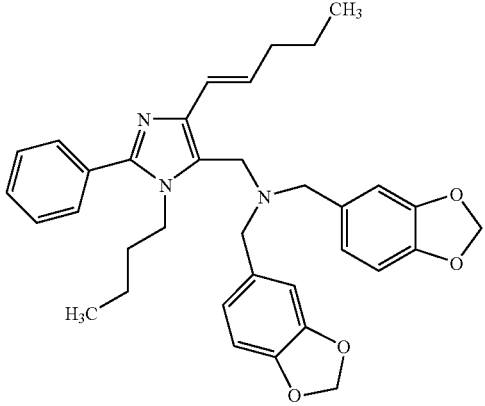 | * | | 566.31 | 1.24 |
| 937 | 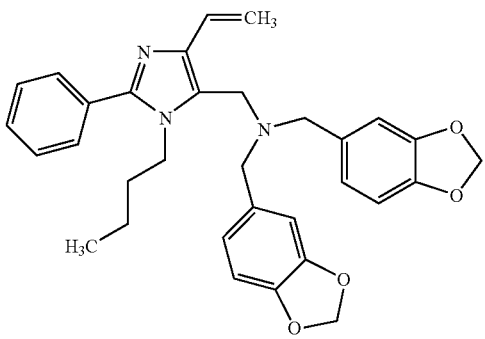 | * | 1-(1,3-benzodioxol-5-yl)-N-(1,3-benzodioxol-5-ylmethyl)-N-[(1-butyl-2-phenyl-4-vinyl-1H-imidazol-5-yl)methyl]methanamine | 524.25 | 1.19 |

TABLE II-continued

| CMP # | STRUCTURE | Ca²⁺ Mob. | IUPAC Name | MASS | RT (min.) |
|---|---|---|---|---|---|
| 938 | 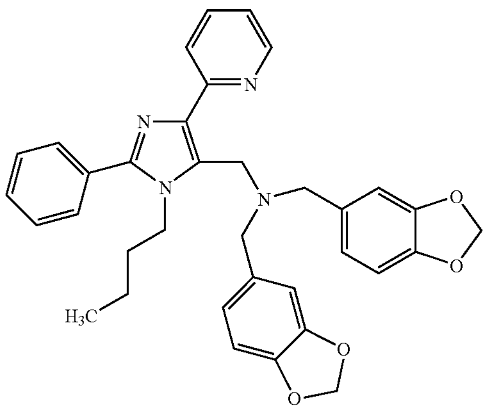 | * | 1-(1,3-benzodioxol-5-yl)-N-(1,3-benzodioxol-5-ylmethyl)-N-[(1-butyl-2-phenyl-4-pyridin-2-yl-1H-imidazol-5-yl)methyl]methanamine | 575.28 | 1.15 |
| 939 | 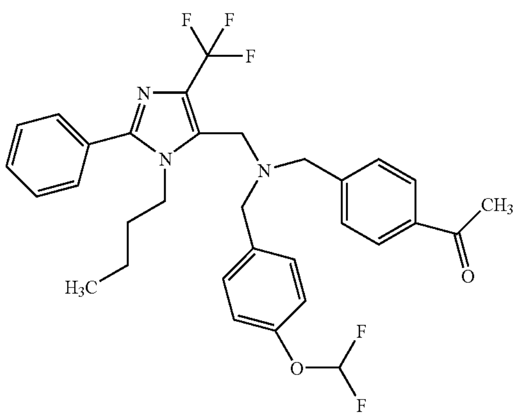 | * | 1-[4-({{[1-butyl-2-phenyl-4-(trifluoromethyl)-1H-imidazol-5-yl]methyl}[4-(difluoromethoxy)benzyl]amino}methyl)phenyl]ethanone | 587.27 | 1.3 |
| 940 | 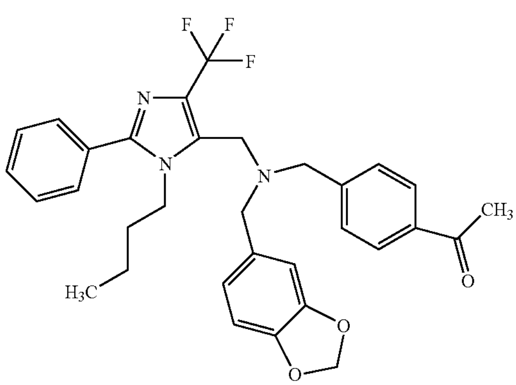 | * | 1-{4-[((1,3-benzodioxol-5-ylmethyl){[1-butyl-2-phenyl-4-(trifluoromethyl)-1H-imidazol-5-yl]methyl}amino)methyl]phenyl}ethanone | 564.24 | 1.32 |

TABLE II-continued

| CMP # | STRUCTURE | Ca²⁺ Mob. | IUPAC Name | MASS | RT (min.) |
|---|---|---|---|---|---|
| 941 | 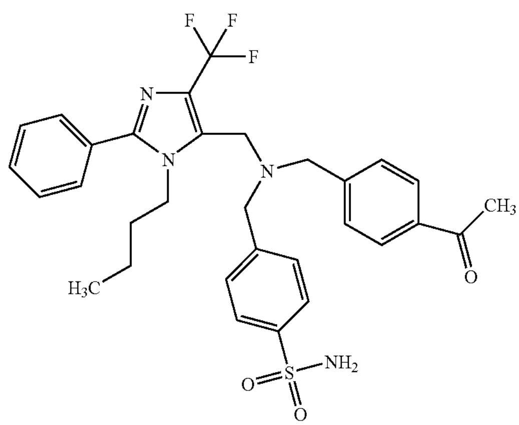 | * | 4-[((4-acetylbenzyl){[1-butyl-2-phenyl-4-(trifluoromethyl)-1H-imidazol-5-yl]methyl}amino)methyl]benzenesulfonamide | 599.23 | 1.2 |
| 942 | 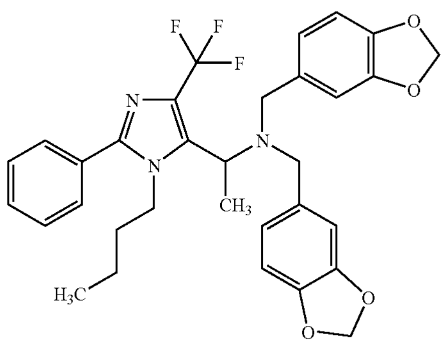 | * | N,N-bis(1,3-benzodioxol-5-ylmethyl)-1-[1-butyl-2-phenyl-4-(trifluoromethyl)-1H-imidazol-5-yl]ethanamine | 580.27 | 1.37 |
| 943 | 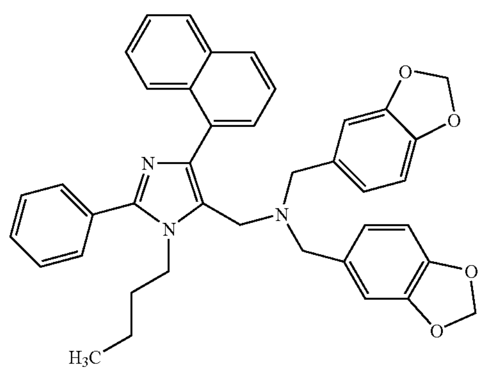 | * | 1-(1,3-benzodioxol-5-yl)-N-(1,3-benzodioxol-5-ylmethyl)-N-{[1-butyl-4-(1-naphthyl)-2-phenyl-1H-imidazol-5-yl]methyl}methanamine | 624.31 | 1.24 |
| 944 | 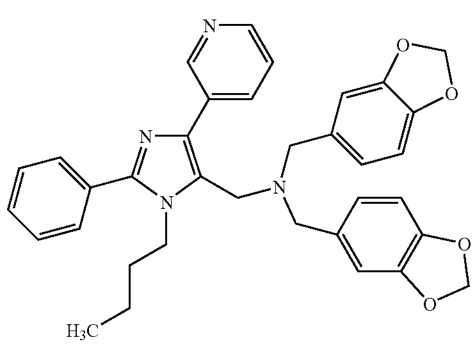 | * | 1-(1,3-benzodioxol-5-yl)-N-(1,3-benzodioxol-5-ylmethyl)-N-[(1-butyl-2-phenyl-4-pyridin-3-yl-1H-imidazol-5-yl)methyl]methanamine | 575.29 | 1.21 |

TABLE II-continued

| CMP # | STRUCTURE | Ca²⁺ Mob. | IUPAC Name | MASS | RT (min.) |
|---|---|---|---|---|---|
| 945 | 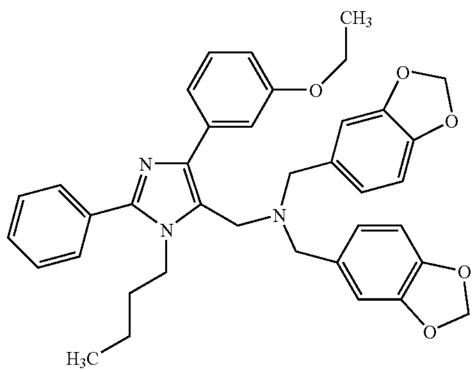 | * | 1-(1,3-benzodioxol-5-yl)-N-(1,3-benzodioxol-5-ylmethyl)-N-{[1-butyl-4-(3-ethoxyphenyl)-2-phenyl-1H-imidazol-5-yl]methyl}methanamine | 618.30 | 1.24 |
| 946 | 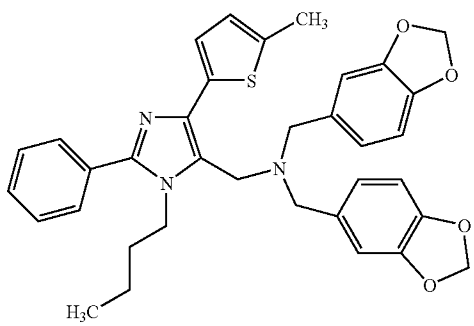 | * | 1-(1,3-benzodioxol-5-yl)-N-(1,3-benzodioxol-5-ylmethyl)-N-{[1-butyl-4-(5-methylthien-2-yl)-2-phenyl-1H-imidazol-5-yl]methyl}methanamine | 595.29 | 1.24 |
| 947 | 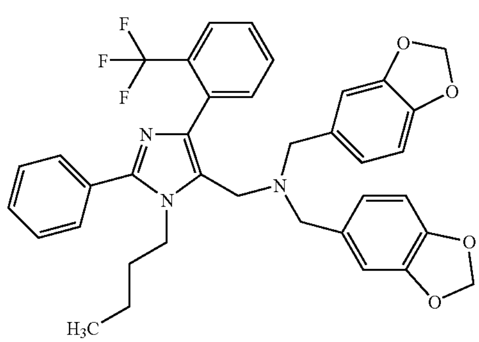 | * | 1-(1,3-benzodioxol-5-yl)-N-(1,3-benzodioxol-5-ylmethyl)-N-({1-butyl-2-phenyl-4-[2-(trifluoromethyl)phenyl]-1H-imidazol-5-yl}methyl)methanamine | 643.32 | 1.25 |
| 948 | 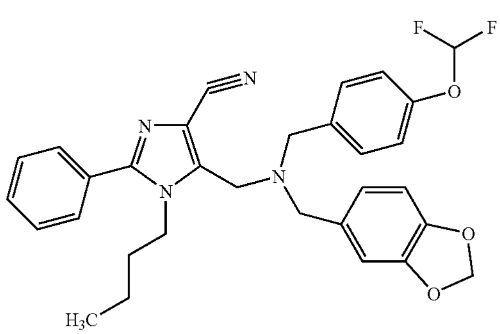 | * | 5-({(1,3-benzodioxol-5-ylmethyl)[4-(difluoromethoxy)benzyl]amino}methyl)-1-butyl-2-phenyl-1H-imidazole-4-carbonitrile | 545.25 | 1.3 |

TABLE II-continued

| CMP # | STRUCTURE | Ca²⁺ Mob. | IUPAC Name | MASS | RT (min.) |
|---|---|---|---|---|---|
| 949 | 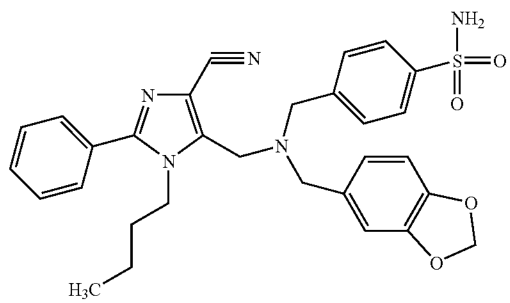 | * | 4-({(1,3-benzodioxol-5-ylmethyl)[(1-butyl-4-cyano-2-phenyl-1H-imidazol-5-yl)methyl]amino}methyl)benzene-sulfonamide | 558.25 | 1.22 |
| 950 | 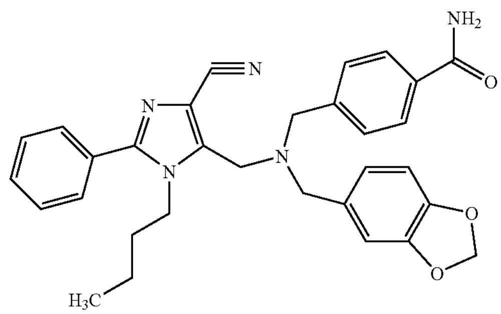 | * | 4-({(1,3-benzodioxol-5-ylmethyl)[(1-butyl-4-cyano-2-phenyl-1H-imidazol-5-yl)methyl]amino}methyl)benzamide | 522.27 | 1.22 |
| 951 | 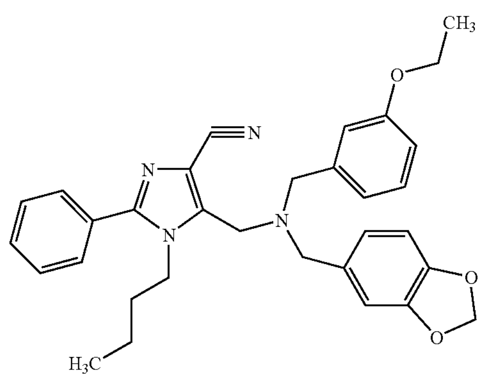 | * | 5-{[(1,3-benzodioxol-5-ylmethyl)(3-ethoxybenzyl)amino]methyl}-1-butyl-2-phenyl-1H-imidazole-4-carbonitrile | 523.29 | 1.34 |
| 952 | 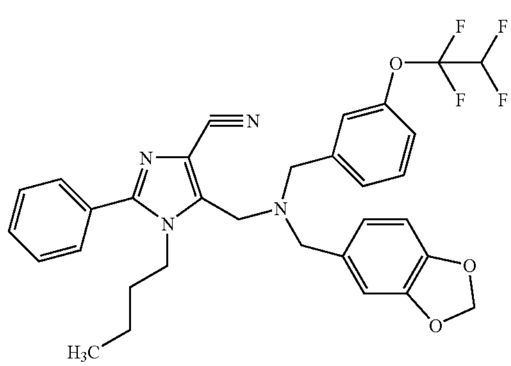 | * | 5-({(1,3-benzodioxol-5-ylmethyl)[3-(1,1,2,2-tetrafluoroethoxy)benzyl]amino}methyl)-1-butyl-2-phenyl-1H-imidazole-4-carbonitrile | 596.29 | 1.3 |

TABLE II-continued

| CMP # | STRUCTURE | Ca²⁺ Mob. | IUPAC Name | MASS | RT (min.) |
|---|---|---|---|---|---|
| 953 | 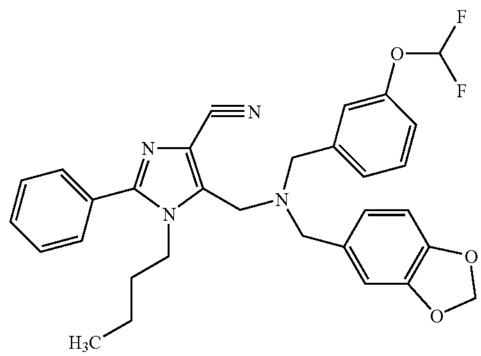 | * | 5-({(1,3-benzodioxol-5-ylmethyl)[3-(difluoromethoxy)benzyl]amino}methyl)-1-butyl-2-phenyl-1H-imidazole-4-carbonitrile | 546.28 | 1.29 |
| 954 | 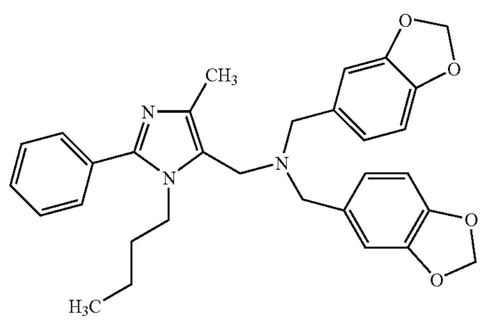 | * | 1-(1,3-benzodioxol-5-yl)-N-(1,3-benzodioxol-5-ylmethyl)-N-[(1-butyl-4-methyl-2-phenyl-1H-imidazol-5-yl)methyl]methanamine | 512.27 | 1.19 |
| 955 | 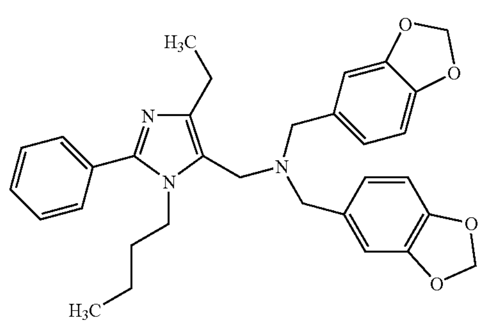 | * | 1-(1,3-benzodioxol-5-yl)-N-(1,3-benzodioxol-5-ylmethyl)-N-[(1-butyl-4-ethyl-2-phenyl-1H-imidazol-5-yl)methyl]methanamine | 526.30 | 1.2 |
| 956 | 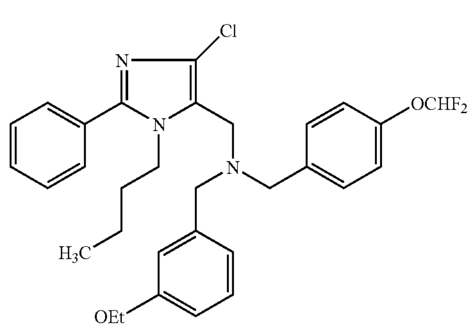 | * | N-[1-butyl-4-chloro-2-phenyl-1H-imidazol-5-yl)methyl]-N-[4-(difluoromethoxy)benzyl]-N-(3-ethoxybenzyl)amine | 554.28 | 1.36 |

TABLE II-continued
| CMP # | STRUCTURE | Ca²⁺ Mob. | IUPAC Name | MASS | RT (min.) |
|---|---|---|---|---|---|
| 957 | 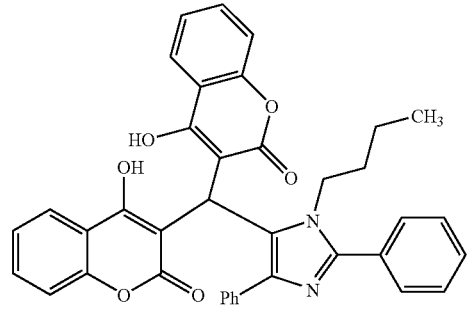 | | | 611.25 | 1.22 |
| 958 | 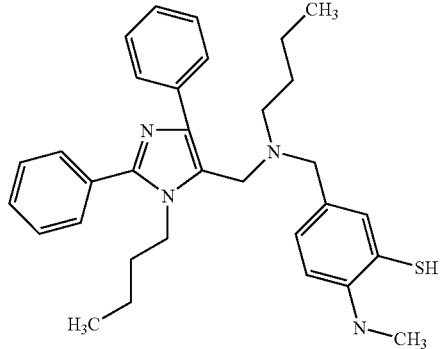 | * | 5-({butyl[(1-butyl-2,4-diphenyl-1H-imidazol-5-yl)methyl]amino}methyl)-2-(methylamino)benzenethiol | 512.33 | 1.23 |
| 959 | 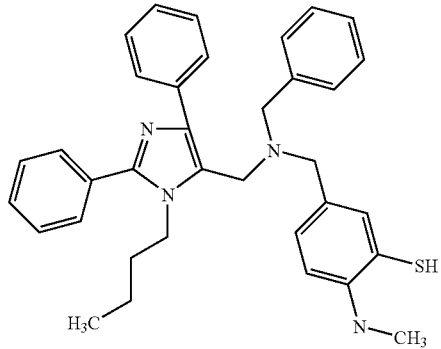 | * | 5-({benzyl[(1-butyl-2,4-diphenyl-1H-imidazol-5-yl)methyl]amino}methyl)-2-(methylamino)benzenethiol | 546.33 | 1.26 |
| 960 | 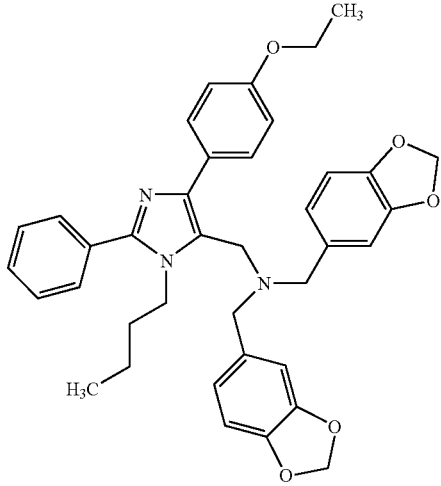 | * | 1-(1,3-benzodioxol-5-yl)-N-(1,3-benzodioxol-5-ylmethyl)-N-{[1-butyl-4-(4-ethoxyphenyl)-2-phenyl-1H-imidazol-5-yl]methyl}methanamine | 618.35 | 1.23 |

| CMP # | STRUCTURE | Ca²⁺ Mob. | IUPAC Name | MASS | RT (min.) |
|---|---|---|---|---|---|
| 961 | 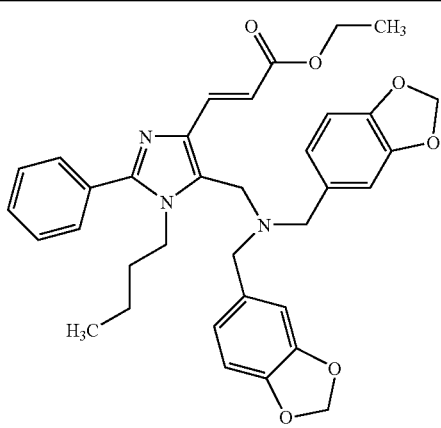 | * | ethyl (2E)-3-(5-{[bis(1,3-benzodioxol-5-ylmethyl)amino]methyl}-1-butyl-2-phenyl-1H-imidazol-4-yl)prop-2-enoate | 596.31 | 1.23 |
| 962 | 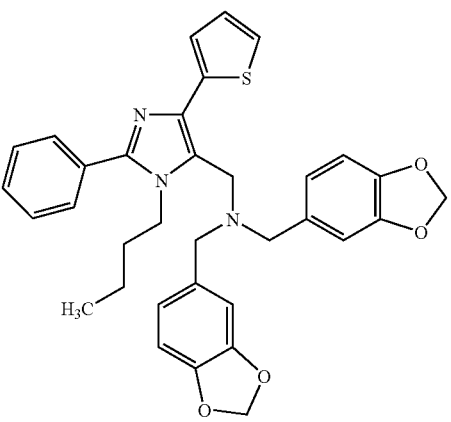 | * | 1-(1,3-benzodioxol-5-yl)-N-(1,3-benzodioxol-5-ylmethyl)-N-[(1-butyl-2-phenyl-4-thien-2-yl-1H-imidazol-5-yl)methyl]methanamine | 580.28 | 1.22 |
| 963 | 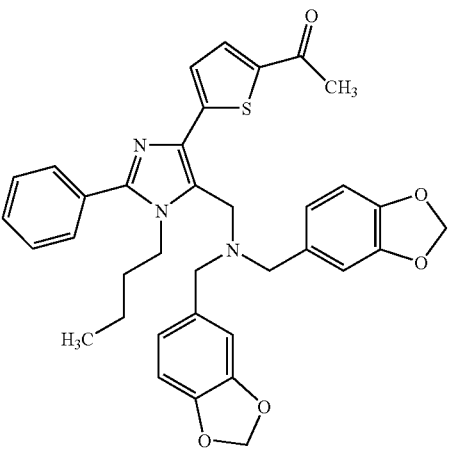 | * | 1-[5-(5-{[bis(1,3-benzodioxol-5-ylmethyl)amino]methyl}-1-butyl-2-phenyl-1H-imidazol-4-yl)thien-2-yl]ethanone | 622.28 | 1.25 |

TABLE II-continued

| CMP # | STRUCTURE | Ca²⁺ Mob. | IUPAC Name | MASS | RT (min.) |
|---|---|---|---|---|---|
| 964 | 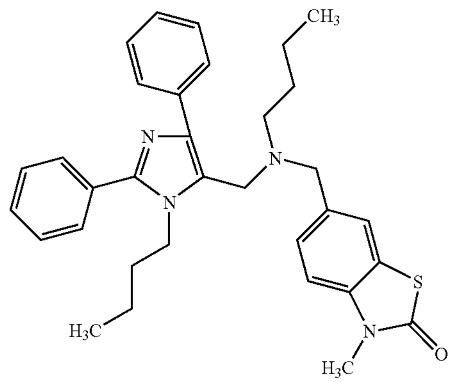 | * | 6-({butyl[(1-butyl-2,4-diphenyl-1H-imidazol-5-yl)methyl]amino}methyl)-3-methyl-1,3-benzothiazol-2(3H)-one | 539.33 | 1.18 |
| 965 | 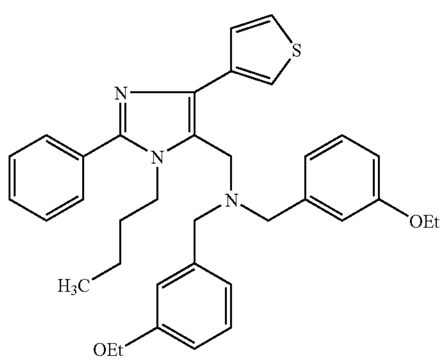 | * | 1-(1-butyl-2-phenyl-4-thien-3-yl-1H-imidazol-5-yl)-N,N-bis(3-ethoxybenzyl)methanamine | | |
| 966 | 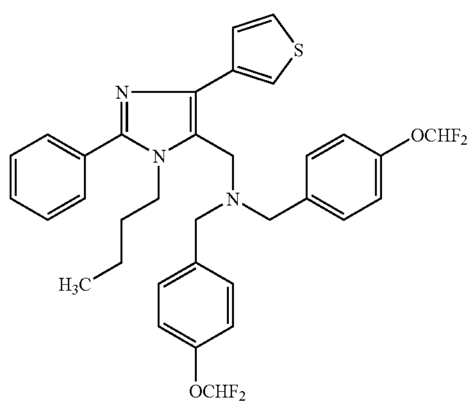 | * | 1-(1-butyl-2-phenyl-4-thien-3-yl-1H-imidazol-5-yl)-N,N-bis[4-(difluoromethoxy)benzyl]methanamine | 624.24 | 1.2 |
| 967 | 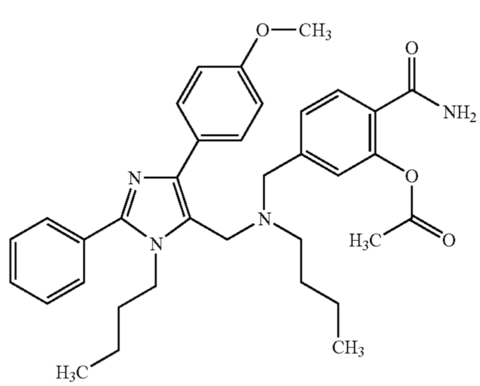 | * | 2-(aminocarbonyl)-5-[(butyl{[1-butyl-4-(4-methoxyphenyl)-2-phenyl-1H-imidazol-5-yl]methyl}amino)methyl]phenyl acetate | 583.35 | 1.18 |

TABLE II-continued

| CMP # | STRUCTURE | Ca²⁺ Mob. | IUPAC Name | MASS | RT (min.) |
|---|---|---|---|---|---|
| 968 | 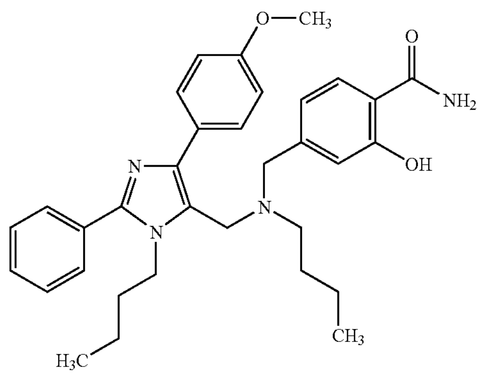 | * | 4-[(butyl{[1-butyl-4-(4-methoxyphenyl)-2-phenyl-1H-imidazol-5-yl]methyl}amino)methyl]-2-hydroxybenzamide | 541.33 | 1.16 |
| 969 | 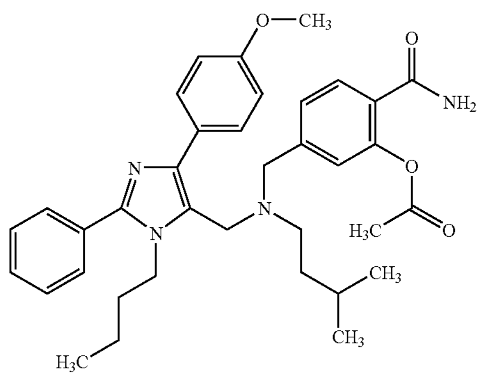 | * | 2-(aminocarbonyl)-5-{[{[1-butyl-4-(4-methoxyphenyl)-2-phenyl-1H-imidazol-5-yl]methyl}(isopentyl)amino]methyl} phenyl acetate | 597.36 | 1.21 |
| 970 | 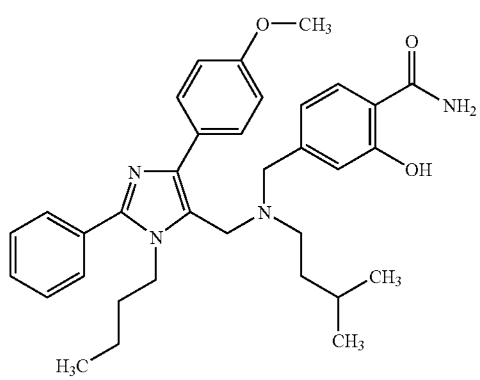 | * | 4-{[{[1-butyl-4-(4-methoxyphenyl)-2-phenyl-1H-imidazol-5-yl]methyl}(isopentyl)amino]methyl}-2-hydroxybenzamide | 555.35 | 1.18 |
| 971 | 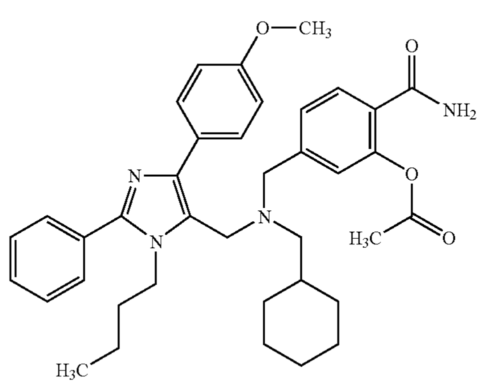 | * | 2-(aminocarbonyl)-5-{[{[1-butyl-4-(4-methoxyphenyl)-2-phenyl-1H-imidazol-5-yl]methyl}(cyclohexylmethyl)amino]methyl}phenyl acetate | 623.38 | 1.24 |

TABLE II-continued

| CMP # | STRUCTURE | Ca²⁺ Mob. | IUPAC Name | MASS | RT (min.) |
|---|---|---|---|---|---|
| 972 | 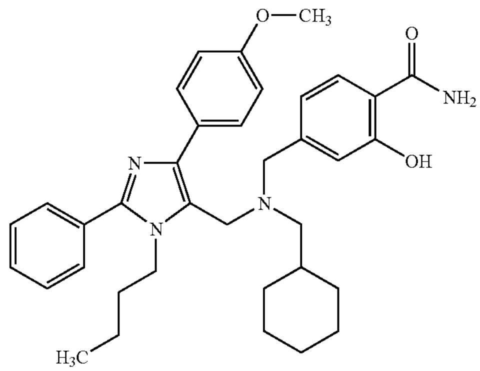 | * | 4-{[{[1-butyl-4-(4-methoxyphenyl)-2-phenyl-1H-imidazol-5-yl]methyl}(cyclohexylmethyl)amino]methyl}-2-hydroxybenzamide | 581.37 | 1.23 |
| 973 | 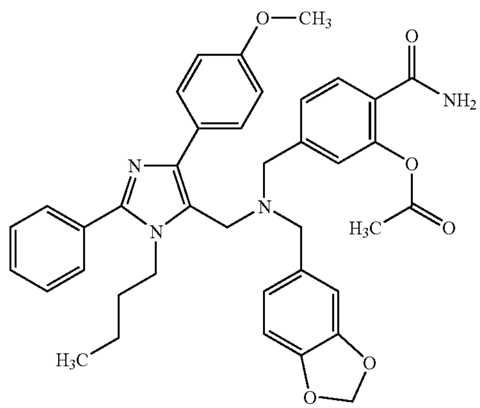 | * | 2-(aminocarbonyl)-5-[((1,3-benzodioxol-5-ylmethyl){[1-butyl-4-(4-methoxyphenyl)-2-phenyl-1H-imidazol-5-yl]methyl}amino)methyl]phenyl acetate | 661.33 | 1.18 |
| 974 | 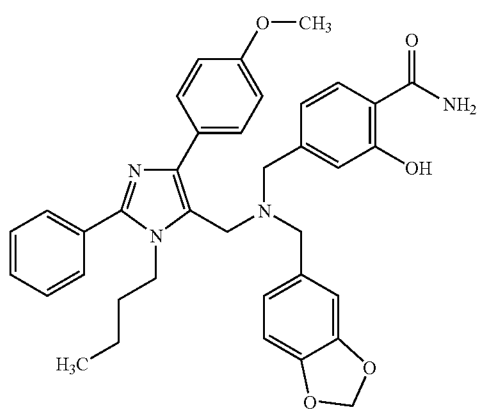 | * | 4-[((1,3-benzodioxol-5-ylmethyl){[1-butyl-4-(4-methoxyphenyl)-2-phenyl-1H-imidazol-5-yl]methyl}amino)methyl]-2-hydroxybenzamide | 619.32 | 1.17 |
| 975 | 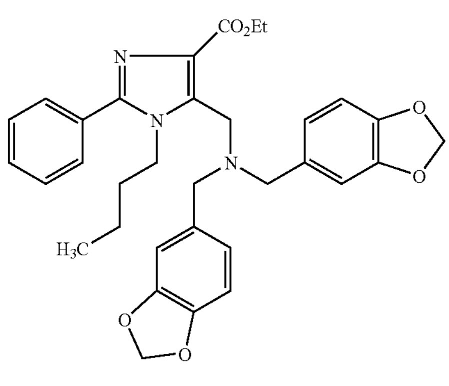 | * | ethyl 5-{[bis(1,3-benzodioxol-5-ylmethyl)amino]methyl}-1-butyl-2-phenyl-1H-imidazole-4-carboxylate | 570.27 | 1.23 |

TABLE II-continued

| CMP # | STRUCTURE | Ca²⁺ Mob. | IUPAC Name | MASS | RT (min.) |
|---|---|---|---|---|---|
| 976 | 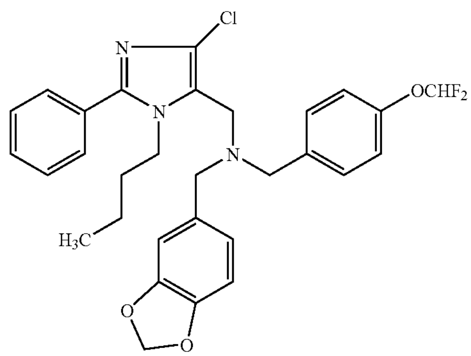 | * | 1-(1,3-benzodioxol-5-yl)-N-[(1-butyl-4-chloro-2-phenyl-1H-imidazol-5-yl)methyl]-N-[4-(difluoromethoxy)benzyl]methanamine | 554.22 | 1.32 |
| 977 | 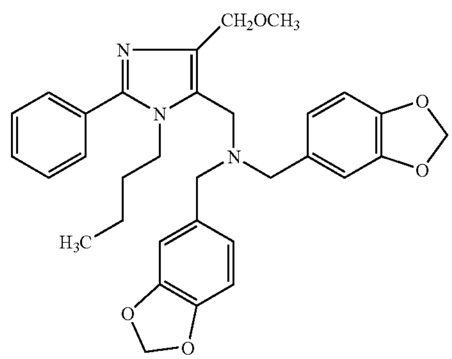 | * | 1-(1,3-benzodioxol-5-yl)-N-(1,3-benzodioxol-5-ylmethyl)-N-{[1-butyl-4-(methoxymethyl)-2-phenyl-1H-imidazol-5-yl]methyl}methanamine | 542.28 | 1.18 |
| 978 | 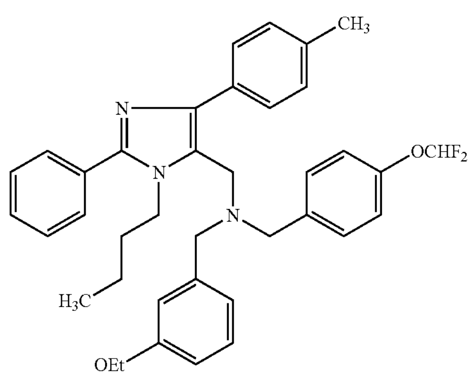 | * | N-{[1-butyl-4-(4-methylphenyl)-2-phenyl-1H-imidazol-5-yl]methyl}-N-[4-(difluoromethoxy)benzyl]-N-(3-ethoxybenzyl)amine | 610.33 | 1.24 |
| 979 | 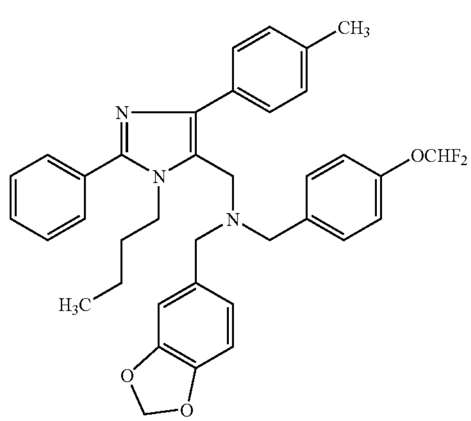 | * | 1-(1,3-benzodioxol-5-yl)-N-{[1-butyl-4-(4-methylphenyl)-2-phenyl-1H-imidazol-5-yl]methyl}-N-[4-(difluoromethoxy)benzyl]methanamine | 610.30 | 1.22 |

TABLE II-continued

| CMP # | STRUCTURE | Ca²⁺ Mob. | IUPAC Name | MASS | RT (min.) |
|---|---|---|---|---|---|
| 980 | 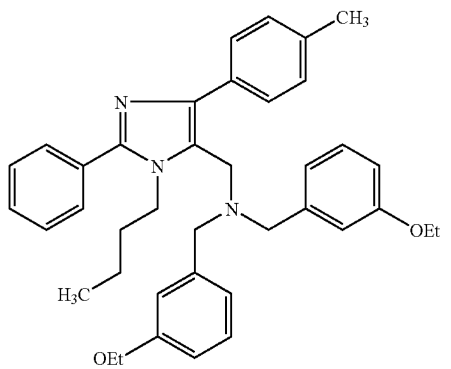 | * | N-{[1-butyl-4-(4-methylphenyl)-2-phenyl-1H-imidazol-5-yl]methyl}-N,N-bis(3-ethoxybenzyl)amine | 588.36 | 1.28 |
| 981 | 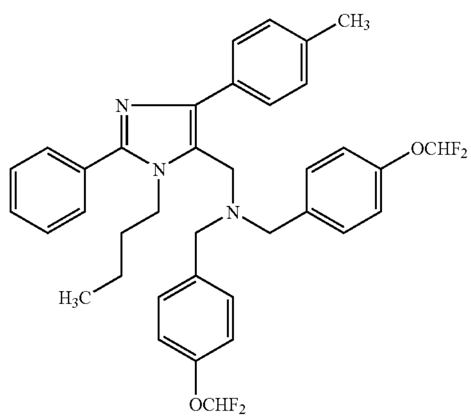 | * | N-{[1-butyl-4-(4-methylphenyl)-2-phenyl-1H-imidazol-5-yl]methyl}-N,N-bis[4-(difluoromethoxy)benzyl]amine | 632.30 | 1.21 |
| 982 | 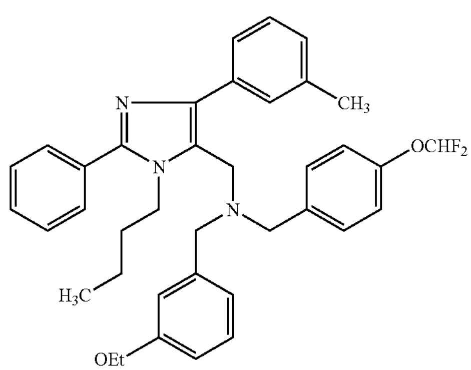 | * | N-{[1-butyl-4-(3-methylphenyl)-2-phenyl-1H-imidazol-5-yl]methyl}-N-[4-(difluoromethoxy)benzyl]-N-(3-ethoxybenzyl)amine | 611.36 | 1.24 |
| 983 | 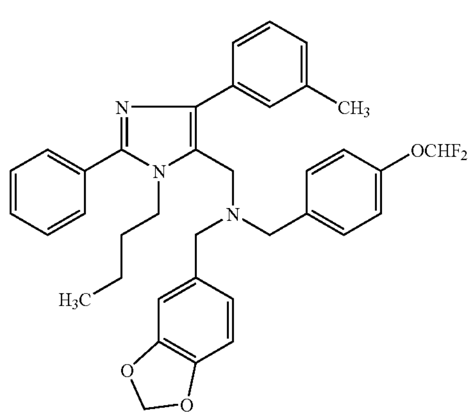 | * | 1-(1,3-benzodioxol-5-yl)-N-{[1-butyl-4-(3-methylphenyl)-2-phenyl-1H-imidazol-5-yl]methyl}-N-[4-(difluoromethoxy)benzyl]methanamine | 610.30 | 1.22 |

TABLE II-continued

| CMP # | STRUCTURE | Ca²⁺ Mob. | IUPAC Name | MASS | RT (min.) |
|---|---|---|---|---|---|
| 984 | 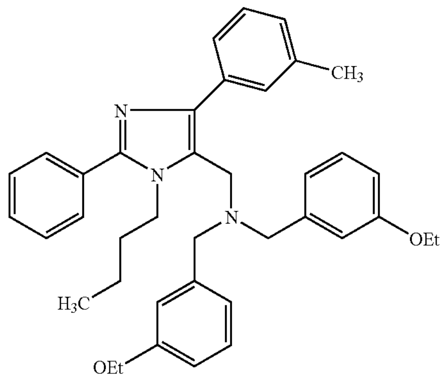 | * | N-{[1-butyl-4-(3-methylphenyl)-2-phenyl-1H-imidazol-5-yl]methyl}-N,N-bis(3-ethoxybenzyl)amine | 588.36 | 1.27 |
| 985 | 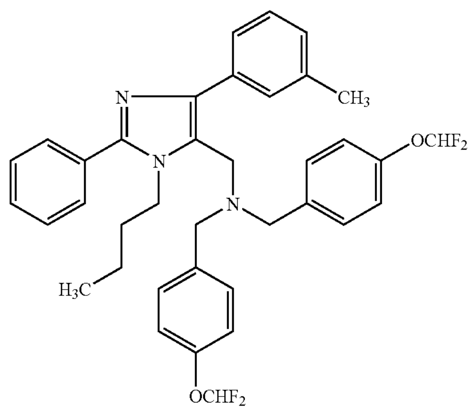 | * | N-{[1-butyl-4-(3-methylphenyl)-2-phenyl-1H-imidazol-5-yl]methyl}-N,N-bis[4-(difluoromethoxy)benzyl]amine | 632.29 | 1.22 |
| 986 | 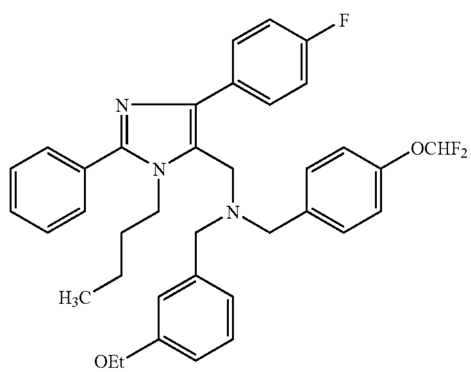 | * | N-{[1-butyl-4-(4-fluorophenyl)-2-phenyl-1H-imidazol-5-yl]methyl}-N-[4-(difluoromethoxy)benzyl]-N-(3-ethoxybenzyl)amine | 614.30 | 1.23 |
| 987 | 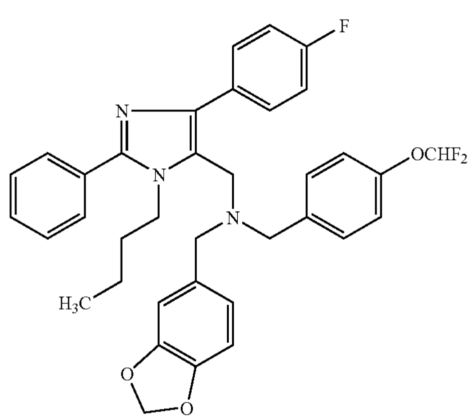 | * | 1-(1,3-benzodioxol-5-yl)-N-{[1-butyl-4-(4-fluorophenyl)-2-phenyl-1H-imidazol-5-yl]methyl}-N-[4-(difluoromethoxy)benzyl]methanamine | 614.28 | 1.21 |

TABLE II-continued

| CMP # | STRUCTURE | Ca²⁺ Mob. | IUPAC Name | MASS | RT (min.) |
|---|---|---|---|---|---|
| 988 | 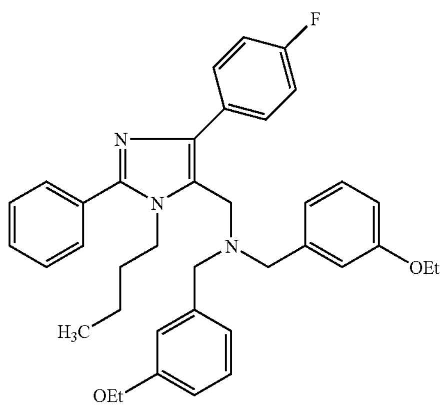 | * | N-{[1-butyl-4-(4-fluorophenyl)-2-phenyl-1H-imidazol-5-yl]methyl}-N,N-bis(3-ethoxybenzyl)amine | 592.34 | 1.26 |
| 989 | 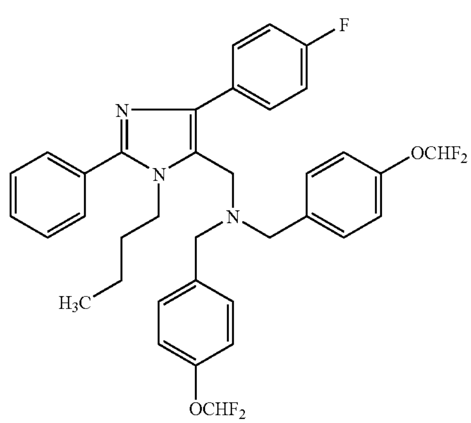 | * | N-{[1-butyl-4-(4-fluorophenyl)-2-phenyl-1H-imidazol-5-yl]methyl}-N,N-bis[4-(difluoromethoxy)benzyl]amine | 636.28 | 1.2 |
| 990 | 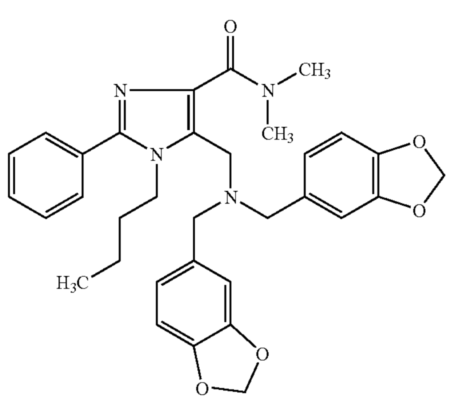 | * | 5-{[bis(1,3-benzodioxol-5-ylmethyl)amino]methyl}-1-butyl-N,N-dimethyl-2-phenyl-1H-N,N-dimethyl-2-phenyl-1H-imidazole-4-carboxamide | 583.38 | 1.23 |

TABLE II-continued
| CMP # | STRUCTURE | Ca²⁺ Mob. | IUPAC Name | MASS | RT (min.) |
|---|---|---|---|---|---|
| 991 | 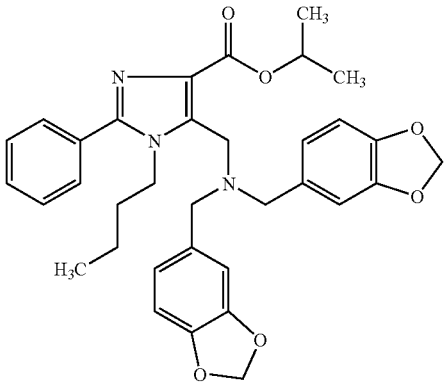 | * | isopropyl 5-{[bis(1,3-benzodioxol-5-ylmethyl)amino]methyl}-1-butyl-2-phenyl-1H-imidazole-4-carboxylate | 523.37 | 1.31 |
| 992 | 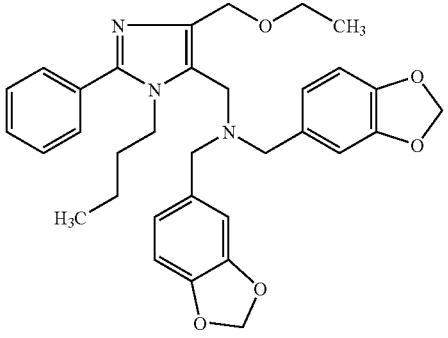 | * | 1-(1,3-benzodioxol-5-yl)-N-(1,3-benzodioxol-5-ylmethyl)-N-{[1-butyl-4-(ethoxymethyl)-2-phenyl-1H-imidazol-5-yl]methyl}methanamine | 585.42 | 1.22 |
| 993 | 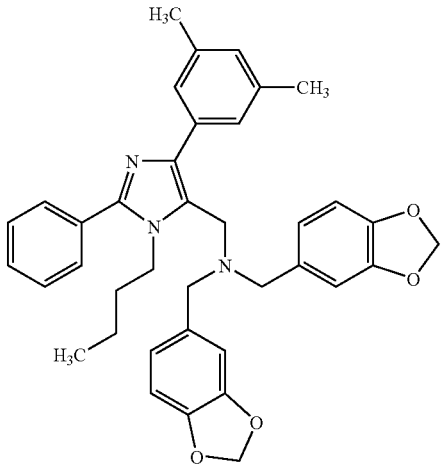 | * | 1-(1,3-benzodioxol-5-yl)-N-(1,3-benzodioxol-5-ylmethyl)-N-{[1-butyl-4-(3,5-dimethylphenyl)-2-phenyl-1H-imidazol-5-yl]methyl}methanamine | 585.42 | 1.24 |

TABLE II-continued

| CMP # | STRUCTURE | Ca²⁺ Mob. | IUPAC Name | MASS | RT (min.) |
|---|---|---|---|---|---|
| 994 | 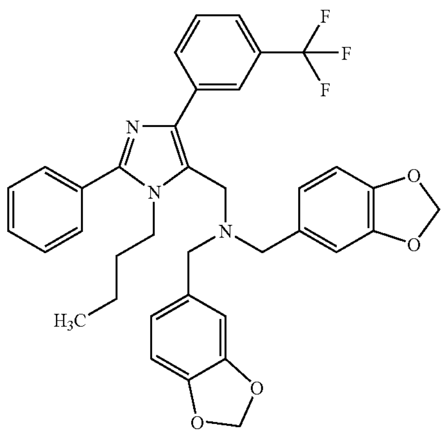 | * | 1-(1,3-benzodioxol-5-yl)-N-(1,3-benzodiaxol-5-ylmethyl)-N-({1-butyl-2-phenyl-4-[3-(trifluoromethyl)phenyl]-1H-imidazol-5-yl}methyl)methanamine | 539.39 | 1.24 |
| 995 | 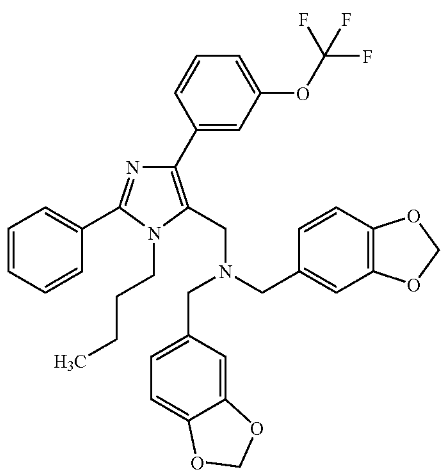 | * | 1-(1,3-benzodioxol-5-yl)-N-(1-3-benzodioxol-5-ylmethyl)-N-({1-butyl-2-phenyl-4-[3-(trifluoromethoxy)phenyl]-1H-imidazol-5-yl}methyl)methanamine | 605.41 | 1.23 |
| 996 | 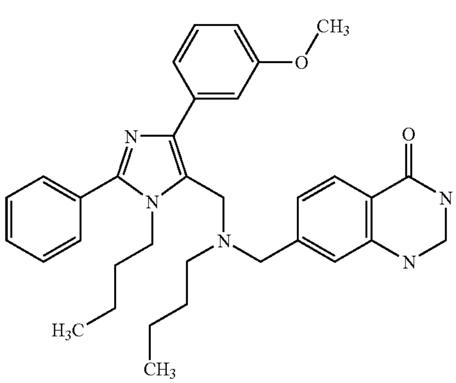 | * | 7-[(butyl{[1-butyl-4-(3-methoxyphenyl)-2-phenyl-1H-imidazol-5-yl]methyl}amino)methyl]-2,3-dihydroquinazolin-4(1H)-one | 583.38 | 1.23 |

TABLE II-continued

| CMP # | STRUCTURE | Ca²⁺ Mob. | IUPAC Name | MASS | RT (min.) |
|---|---|---|---|---|---|
| 997 | 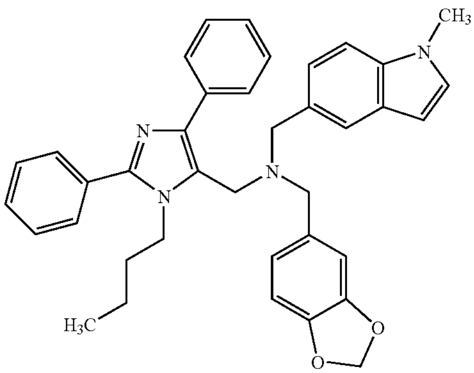 | * | 1-(1,3-benzodioxol-5-yl)-N-[(1-butyl-2,4-diphenyl-1H-imidazol-5-yl)methyl]-N-[(1-methyl-1H-indol-5-yl)methyl]methanamine | 523.37 | 1.31 |
| 998 | 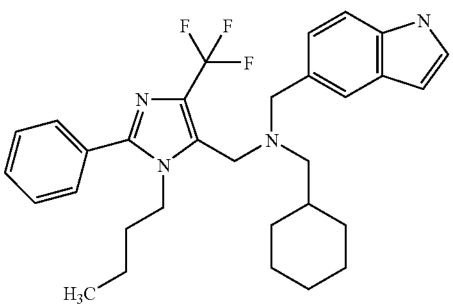 | * | 1-[1-butyl-2-phenyl-4-(trifluoromethyl)-1H-imidazol-5-yl]-N-(cyclohexylmethyl)-N-(1H-indol-5-ylmethyl)methanamine | 585.42 | 1.22 |
| 999 | 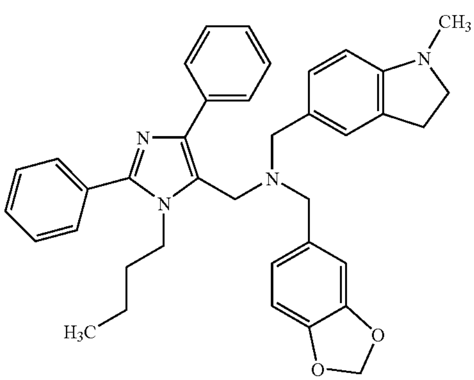 | * | 1-(1,3-benzodioxol-5-yl)-N-[(1-butyl-2,4-diphenyl-1H-imidazol-5-yl)methyl]-N-[(1-methyl-2,3-dihydro-1H-indol-5-yl)methyl]methanamine | 585.42 | 1.24 |
| 1000 | 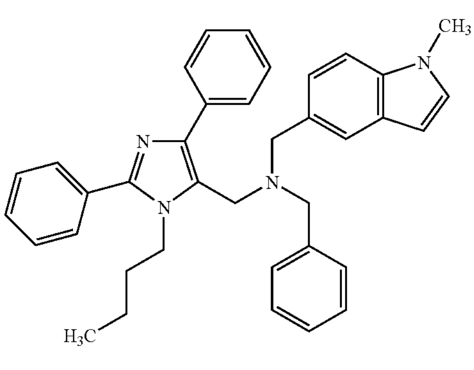 | * | N-benzyl-1-(1-butyl-2,4-diphenyl-1H-imidazol-5-yl)-N-[(1-methyl-1H-indol-5-yl)methyl]methanamine | 539.39 | 1.24 |

TABLE II-continued

| CMP # | STRUCTURE | Ca²⁺ Mob. | IUPAC Name | MASS | RT (min.) |
|---|---|---|---|---|---|
| 1001 | 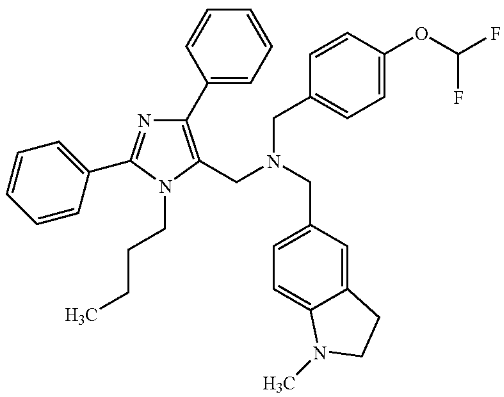 | * | 1-(1-butyl-2,4-diphenyl-1H-imidazol-5-yl)-N-[4-(difluoromethoxy)benzyl]-N-[(1-methyl-2,3-dihydro-1H-indol-5-yl)methyl]methanamine | 605.41 | 1.23 |
| 1002 | 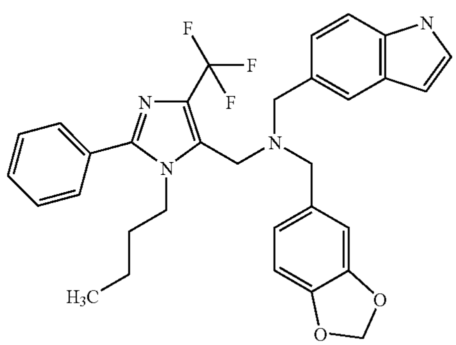 | * | 1-(1,3-benzodioxol-5-yl)-N-{[1-butyl-2-phenyl-4-(trifluoromethyl)-1H-imidazol-5-yl]methyl}-N-(1H-indol-5-ylmethyl)methanamine | 561.33 | 1.29 |
| 1003 | 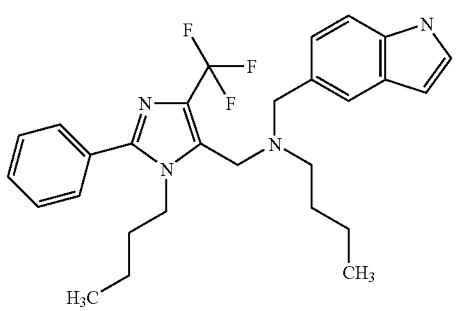 | * | N-{[1-butyl-2-phenyl-4-(trifluoromethyl)-1H-imidazol-5-yl]methyl}-N-(1H-indol-5-ylmethyl)butan-1-amine | 483.34 | 1.15 |
| 1004 | 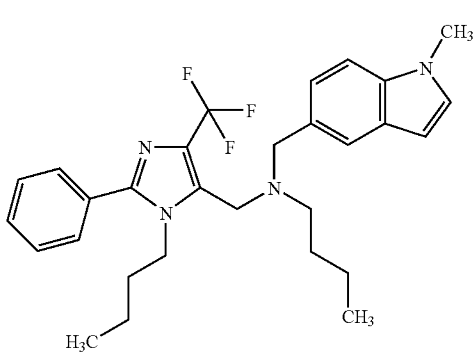 | * | N-{[1-butyl-2-phenyl-4-(trifluoromethyl)-1H-imidazol-5-yl]methyl}-N-[(1-methyl-1H-indol-5-yl)methyl]butan-1-amine | 497.35 | 1.18 |

TABLE II-continued

| CMP # | STRUCTURE | Ca²⁺ Mob. | IUPAC Name | MASS | RT (min.) |
|---|---|---|---|---|---|
| 1005 | 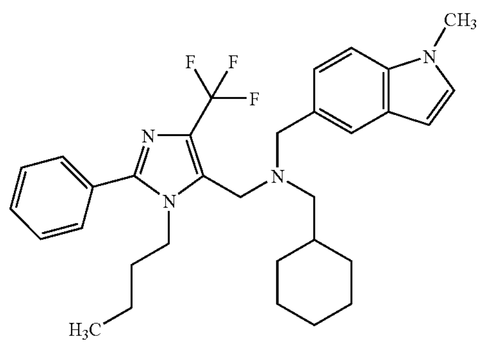 | * | 1-[1-butyl-2-phenyl-4-(trifluoromethyl)-1H-imidazol-5-yl]-N-(cyclohexylmethyl)-N-[(1-methyl-1H-indol-5-yl)methyl]methanamine | 537.39 | 1.37 |
| 1006 | 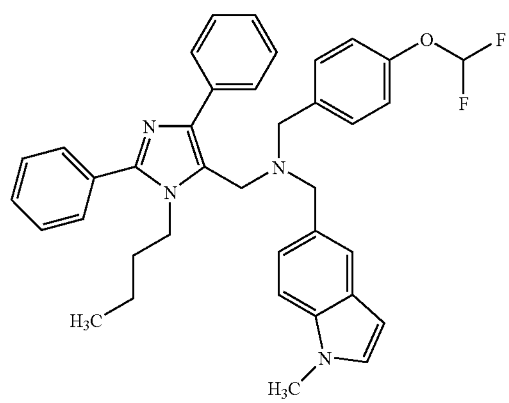 | * | 1-(1-butyl-2,4-diphenyl-1H-imidazol-5-yl)-N-[4-(difluoromethoxy)benzyl]-N-[(1-methyl-1H-indol-5-yl)methyl]methanamine | 605.39 | 1.23 |
| 1007 | 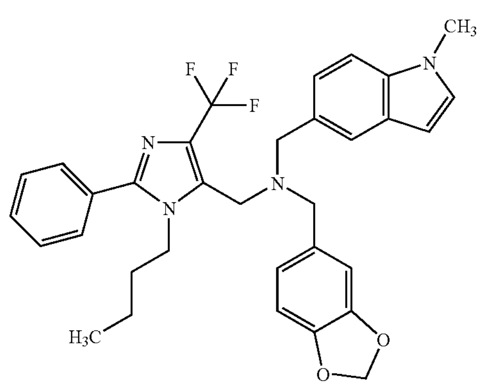 | * | 1-(1,3-benzodioxol-5-yl)-N-{[1-butyl-2-phenyl-4-(trifluoromethyl)-1H-imidazol-5-yl]methyl}-N-[(1-methyl-1H-indol-5-yl)methyl]methanamine | 575.33 | 1.34 |
| 1008 | 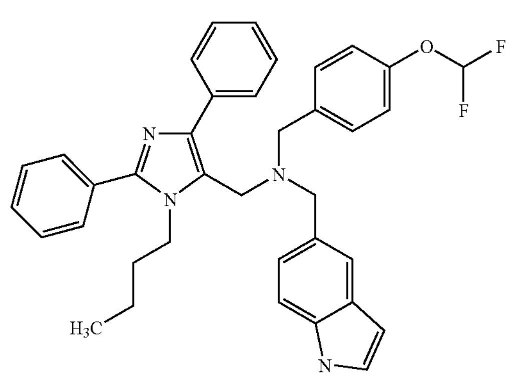 | * | 1-(1-butyl-2,4-diphenyl-1H-imidazol-5-yl)-N-[4-(difluoromethoxy)benzyl]-N-(1H-indol-5-ylmethyl)methanamine | 591.38 | 1.2 |

TABLE II-continued

| CMP # | STRUCTURE | Ca²⁺ Mob. | IUPAC Name | MASS | RT (min.) |
|---|---|---|---|---|---|
| 1009 | 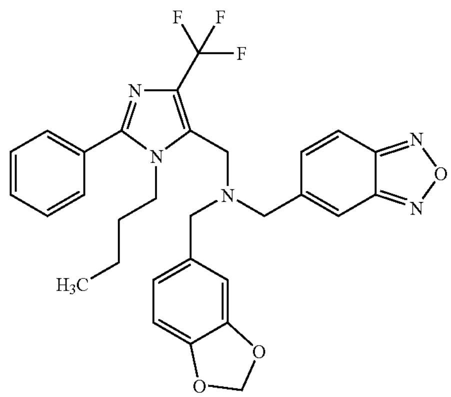 | * | 1-(1,3-benzodioxol-5-yl)-N-(2,1,3-benzoxadiazol-5-ylmethyl)-N-{[1-butyl-2-phenyl-4-(trifluoromethyl)-1H-imidazol-5-yl]methyl}methanamine | | |
| 1010 | 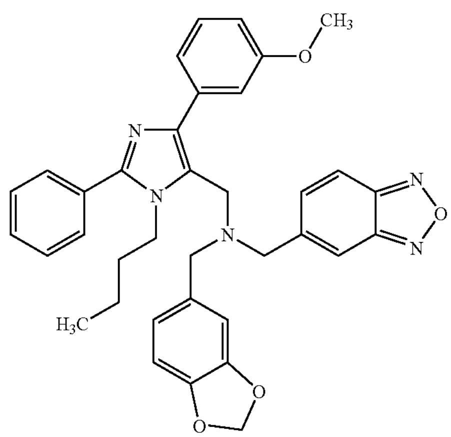 | * | 1-(1,3-benzodioxol-5-yl)-N-(2,1,3-benzoxadiazol-5-ylmethyl)-N-{[1-butyl-4-(3-methoxyphenyl)-2-phenyl-1H-imidazol-5-yl]methyl}methanamine | 602.36 | 1.2 |
| 1011 | 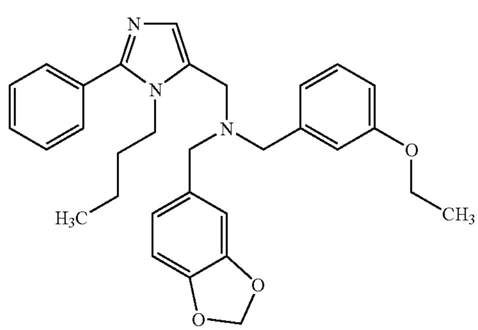 | * | 1-(1,3-benzodioxol-5-yl)-N-[(1-butyl-2-phenyl-1H-imidazol-5-yl)methyl]-N-(3-ethoxybenzyl)methanamine | 498.33 | 1.19 |
| 1012 | 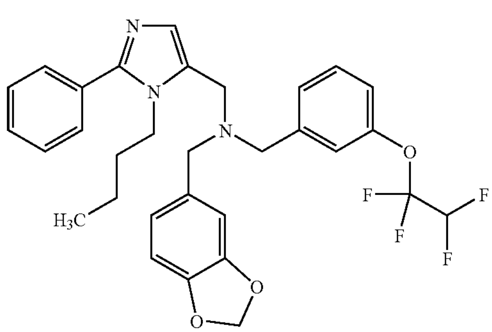 | * | 1-(1,3-benzodioxol-5-yl)-N-[(1-butyl-2-phenyl-1H-imidazol-5-yl)methyl]-N-[3-(1,1,2,2-tetrafluoroethoxy)benzyl]methanamine | 570.30 | 1.18 |

TABLE II-continued

| CMP # | STRUCTURE | Ca²⁺ Mob. | IUPAC Name | MASS | RT (min.) |
|---|---|---|---|---|---|
| 1013 | 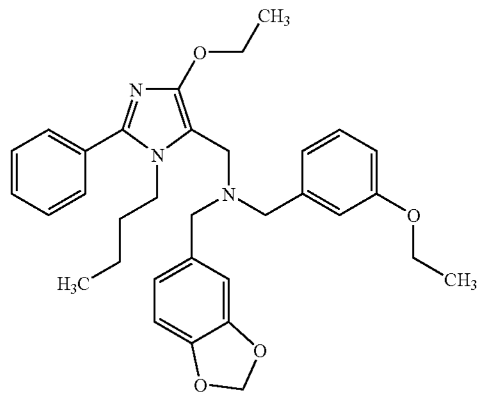 | * | 1-(1,3-benzodioxol-5-yl)-N-[(1-butyl-4-ethoxy-2-phenyl-1H-imidazol-5-yl)methyl]-N-(3-ethoxybenzyl)methanamine | 257.21 | 1.21 |
| 1014 | 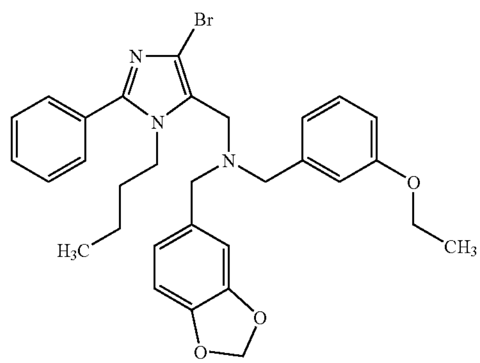 | * | 1-(1,3-benzodioxol-5-yl)-N-[(4-bromo-1-butyl-2-phenyl-1H-imidazol-5-yl)methyl]-N-(3-ethoxybenzyl)methanamine | 576.27 | 1.35 |
| 1015 | 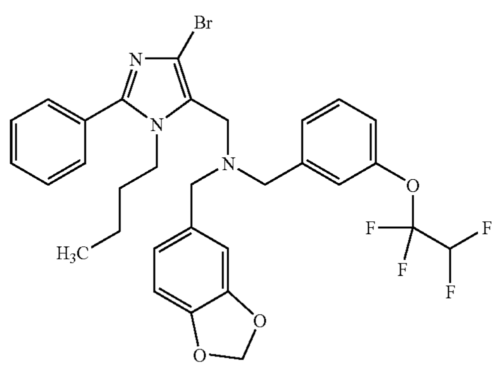 | * | 1-(1,3-benzodioxol-5-yl)-N-[(4-bromo-1-butyl-2-phenyl-1H-imidazol-5-yl)methyl]-N-[3-(1,1,2,2-tetrafluoroethoxy)benzyl]methanamine | 648.25 | 1.34 |
| 1016 | 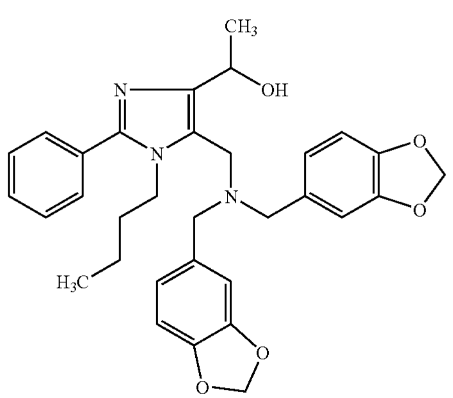 | * | 1-(5-{[bis(1,3-benzodioxol-5-ylmethyl)amino]methyl}-1-butyl-2-phenyl-1H-imidazol-4-yl)ethanol | | |

TABLE II-continued

| CMP # | STRUCTURE | Ca²⁺ Mob. | IUPAC Name | MASS | RT (min.) |
|---|---|---|---|---|---|
| 1017 | 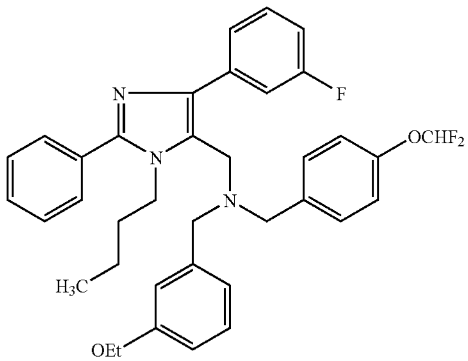 | * | N-{[1-butyl-4-(3-fluorophenyl)-2-phenyl-1H-imidazol-5-yl]methyl}-N-[4-(difluoromethoxy)benzyl]-N-(3-ethoxybenzyl)amine | | |
| 1018 | 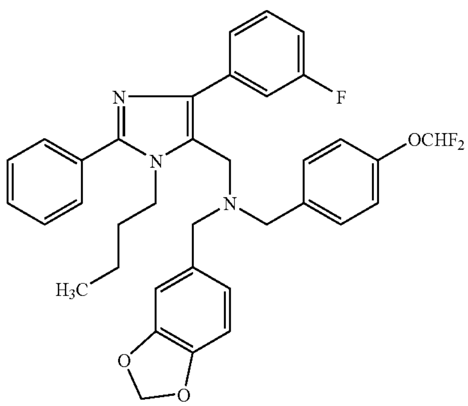 | * | 1-(1,3-benzodioxol-5-yl)-N-{[1-butyl-4-(3-fluorophenyl)-2-phenyl-1H-imidazol-5-yl]methyl}-N-[4-(difluoromethoxy)benzyl]methanamine | | |
| 1019 | 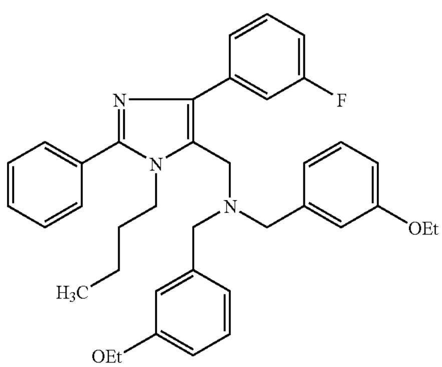 | * | N-{[1-butyl-4-(3-fluorophenyl)-2-phenyl-1H-imidazol-5-yl]methyl}-N,N-bis(3-ethoxybenzyl)amine | | |
| 1020 | 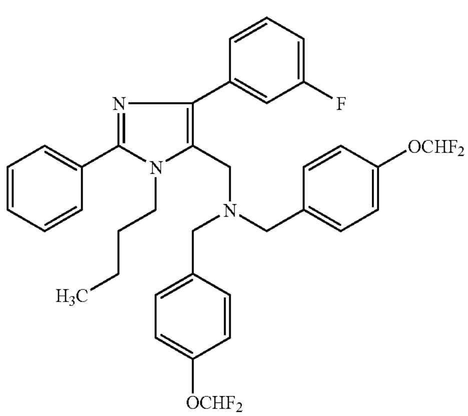 | * | N-{[1-butyl-4-(3-fluorophenyl)-2-phenyl-1H-imidazol-5-yl]methyl}-N,N-bis[4-(difluoromethoxy)benzyl]amine | | |

TABLE II-continued

| CMP # | STRUCTURE | Ca²⁺ Mob. | IUPAC Name | MASS | RT (min.) |
|---|---|---|---|---|---|
| 1021 | 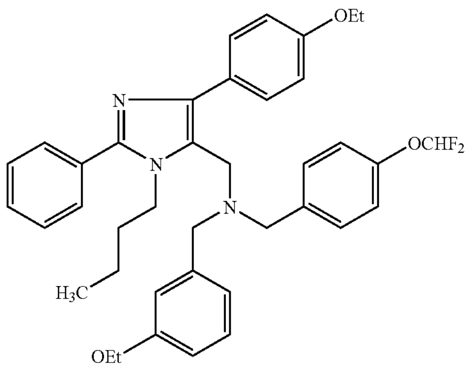 | * | N-{[1-butyl-4-(4-ethoxyphenyl)-2-phenyl-1H-imidazol-5-yl]methyl}-N-[4-(difluoromethoxy)benzyl]-N-(3-ethoxybenzyl)amine | | |
| 1022 | 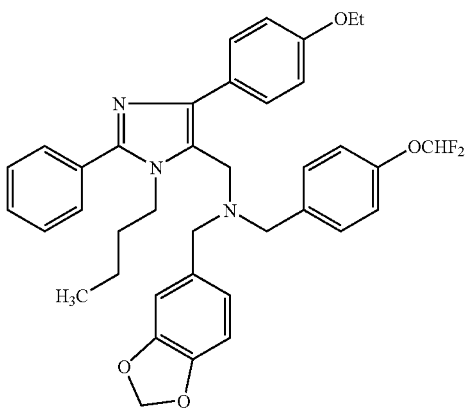 | * | 1-(1,3-benzodioxol-5-yl)-N-{[1-butyl-4-(4-ethoxyphenyl)-2-phenyl-1H-imidazol-5-yl]methyl}-N-[4-(difluoromethoxy)benzyl]methanamine | | |
| 1023 | 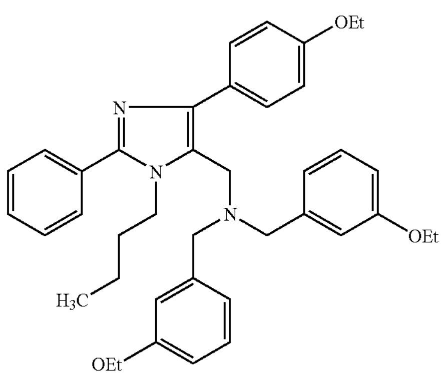 | * | N-{[1-butyl-4-(4-ethoxyphenyl)-2-phenyl-1H-imidazol-5-yl]methyl}-N,N-bis(3-ethoxybenzyl)amine | | |
| 1024 | 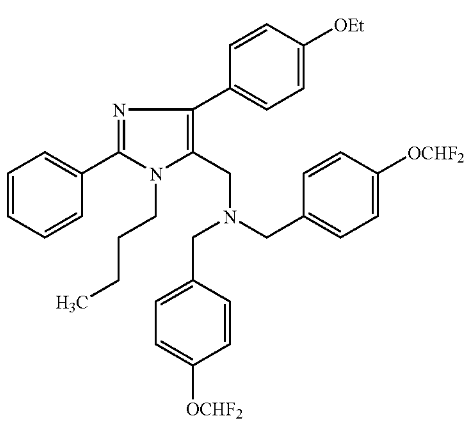 | * | N-{[1-butyl-4-(4-ethoxyphenyl)-2-phenyl-1H-imidazol-5-yl]methyl}-N,N-bis[4-(difluoromethoxy)benzyl]amine | | |

TABLE II-continued

| CMP # | STRUCTURE | Ca²⁺ Mob. | IUPAC Name | MASS | RT (min.) |
|---|---|---|---|---|---|
| 1025 | 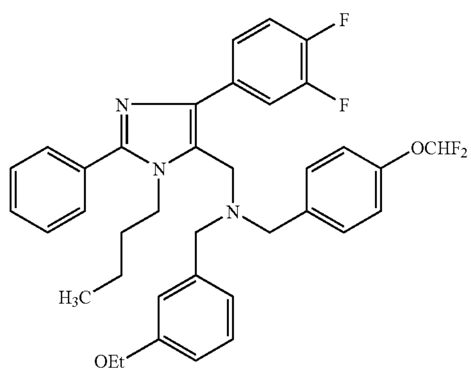 | * | 1-[1-butyl-4-(3,4-difluorophenyl)-2-phenyl-1H-imidazol-5-yl]-N-[4-(difluoromethoxy)benzyl]-N-(3-ethoxybenzyl)methanamine | | |
| 1026 | 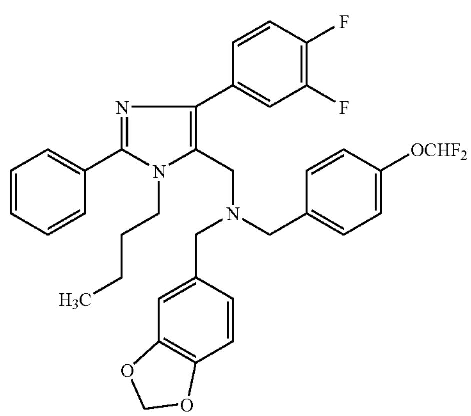 | * | 1-(1,3-benzodioxol-5-yl)-N-{[1-butyl-4-(3,4-difluorophenyl)-2-phenyl-1H-imidazol-5-yl]methyl}-N-[4-(difluoromethoxy)benzyl]methanamine | | |
| 1027 | 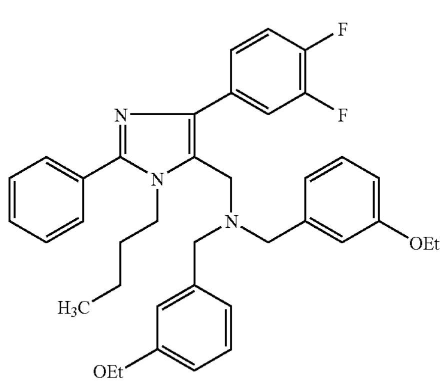 | * | 1-[1-butyl-4-(3,4-difluorophenyl)-2-phenyl-1H-imidazol-5-yl]-N,N-bis(3-ethoxybenzyl)methanamine | | |

TABLE II-continued

| CMP # | STRUCTURE | Ca²⁺ Mob. | IUPAC Name | MASS | RT (min.) |
|---|---|---|---|---|---|
| 1028 | 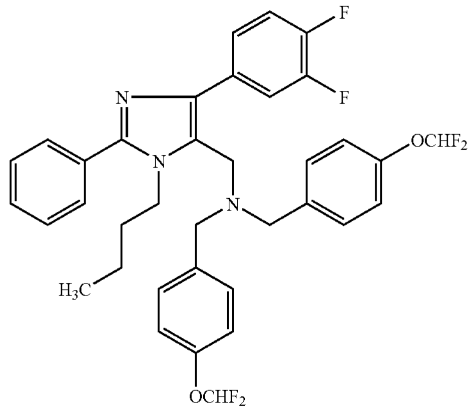 | * | 1-[1-butyl-4-(3,4-difluorophenyl)-2-phenyl-1H-imidazol-5-yl]-N,N-bis[4-(difluoromethoxy)benzyl]methanamine | | |
| 1029 | 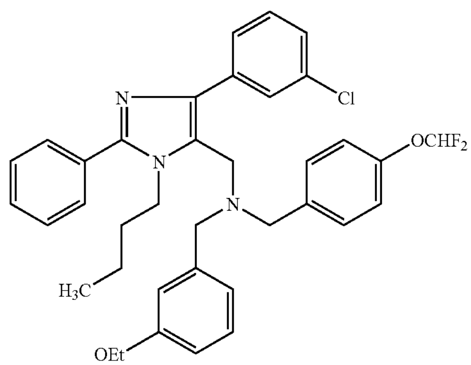 | * | N-{[1-butyl-4-(3-chlorophenyl)-2-phenyl-1H-imidazol-5-yl]methyl}-N-[4-(difluoromethoxy)benzyl]-N-(3-ethoxybenzyl)amine | | |
| 1030 | 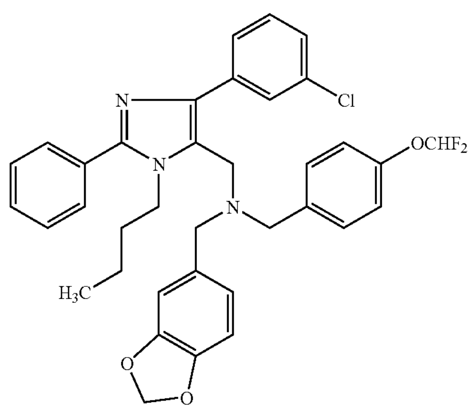 | * | 1-(1,3-benzodioxol-5-yl)-N-{[1-butyl-4-(3-chlorophenyl)-2-phenyl-1H-imidazol-5-yl]methyl}-N-[4-(difluoromethoxy)benzyl]methanamine | | |
| 1031 | 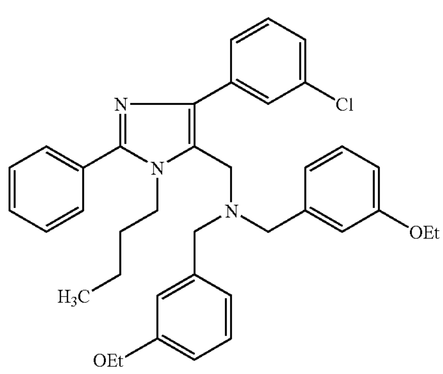 | * | N-{[1-butyl-4-(3-chlorophenyl)-2-phenyl-1H-imidazol-5-yl]methyl}-N,N-bis(3-ethoxybenzyl)amine | | |

TABLE II-continued

| CMP # | STRUCTURE | Ca²⁺ Mob. | IUPAC Name | MASS | RT (min.) |
|---|---|---|---|---|---|
| 1032 | 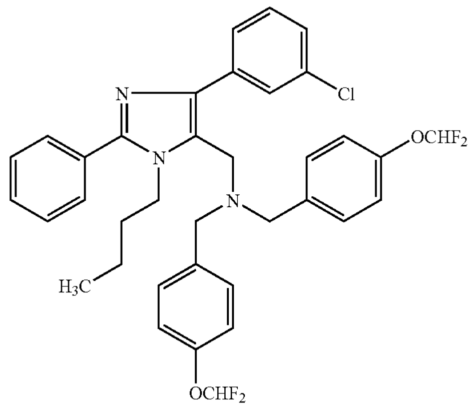 | * | N-{[1-butyl-4-(3-chlorophenyl)-2-phenyl-1H-imidazol-5-yl]methyl}-N,N-bis[4-(difluoromethoxy)benzyl]amine | | |
| 1033 | 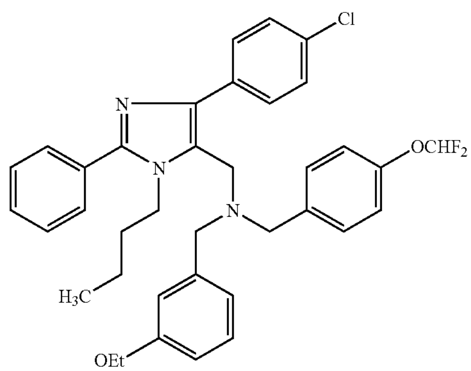 | * | N-{[1-butyl-4-(4-chlorophenyl)-2-phenyl-1H-imidazol-5-yl]methyl}-N-[4-(difluoromethoxy)benzyl]-N-(3-ethoxybenzyl)amine | | |
| 1034 | 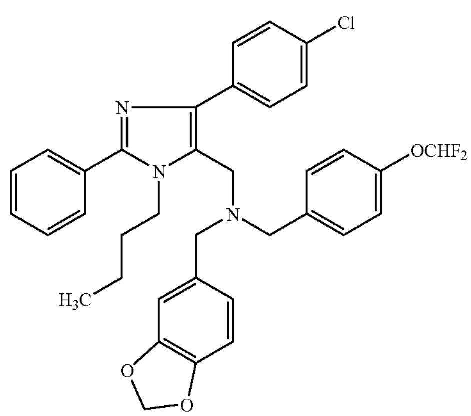 | * | 1-(1,3-benzodioxol-5-yl)-N-{[1-butyl-4-(4-chlorophenyl)-2-phenyl-1H-imidazol-5-yl]methyl}-N-[4-(difluoromethoxy)benzyl]methanamine | | |
| 1035 | 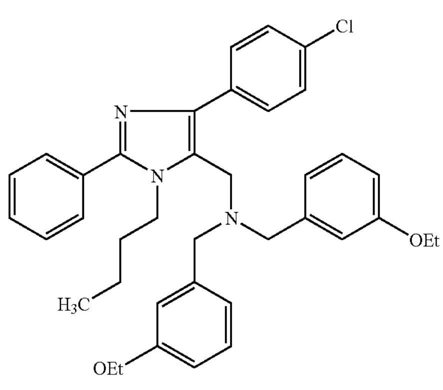 | * | N-{[1-butyl-4-(4-chlorophenyl)-2-phenyl-1H-imidazol-5-yl]methyl}-N,N-bis(3-ethoxybenzyl)amine | | |

TABLE II-continued

| CMP # | STRUCTURE | Ca²⁺ Mob. | IUPAC Name | MASS | RT (min.) |
|---|---|---|---|---|---|
| 1036 | 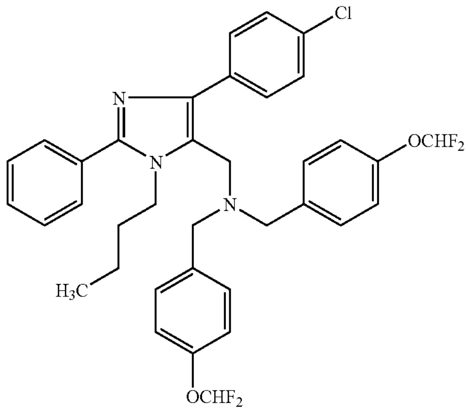 | * | N-{[1-butyl-4-(4-chlorophenyl)-2-phenyl-1H-imidazol-5-yl]methyl}-N,N-bis[4-(difluoromethoxy)benzyl]amine | | |
| 1037 | 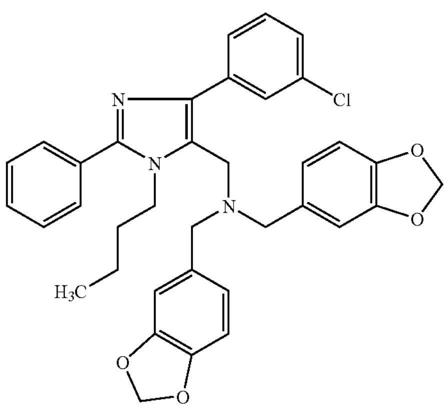 | * | 1-(1,3-benzodioxol-5-yl)-N-(1,3-benzodioxol-5-ylmethyl)-N-{[1-butyl-4-(3-chlorophenyl)-2-phenyl-1H-imidazol-5-yl]methyl}methanamine | | |
| 1038 | 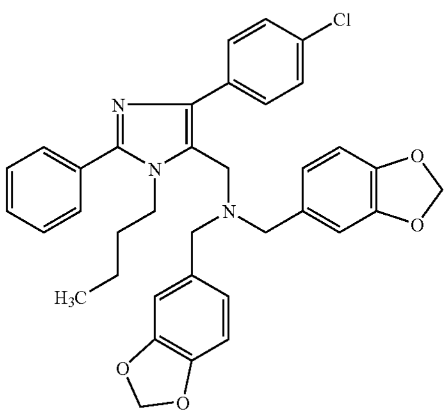 | * | 1-(1,3-benzodioxol-5-yl)-N-(1,3-benzodioxol-5-ylmethyl)-N-{[1-butyl-4-(4-chlorophenyl)-2-phenyl-1H-imidazol-5-yl]methyl}methanamine | | |

TABLE II-continued

| CMP # | STRUCTURE | Ca²⁺ Mob. | IUPAC Name | MASS | RT (min.) |
|---|---|---|---|---|---|
| 1039 | 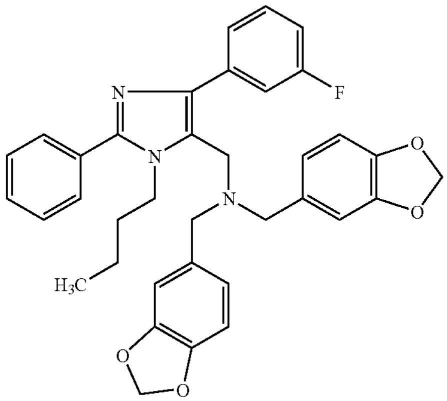 | * | 1-(1,3-benzodioxol-5-yl)-N-(1,3-benzodioxol-5-ylmethyl)-N-{[1-butyl-4-(3-fluorophenyl)-2-phenyl-1H-imidazol-5-yl]methyl}methanamine | | |
| 1040 | 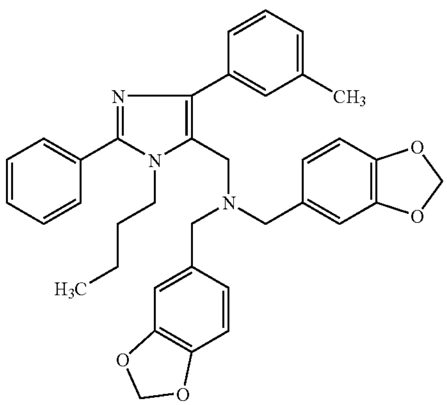 | * | 1-(1,3-benzodioxol-5-yl)-N-(1,3-benzodioxol-5-ylmethyl)-N-{[1-butyl-4-(3-methylphenyl)-2-phenyl-1H-imidazol-5-yl]methyl}methanamine | | |
| 1041 | 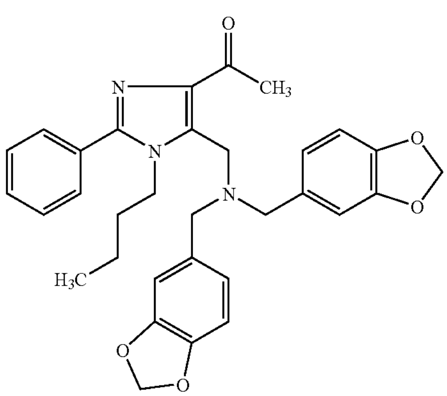 | * | 1-(5-{[bis(1,3-benzodioxol-5-ylmethyl)amino]methyl}-1-butyl-2-phenyl-1H-imidazol-4-yl)ethanone | | |
| 1042 | 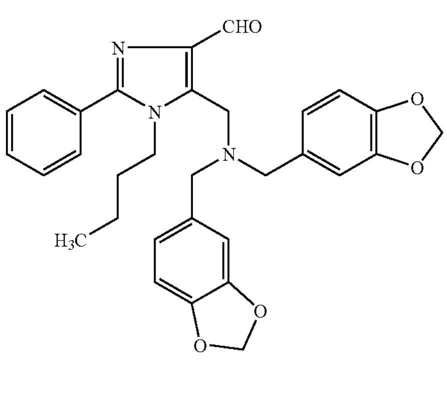 | * | 5-{[bis(1,3-benzodioxol-5-ylmethyl)amino]methyl}-1-butyl-2-phenyl-1H-imidazole-4-carbaldehyde | | |

TABLE II-continued

| CMP # | STRUCTURE | Ca²⁺ Mob. | IUPAC Name | MASS | RT (min.) |
|---|---|---|---|---|---|
| 1043 | 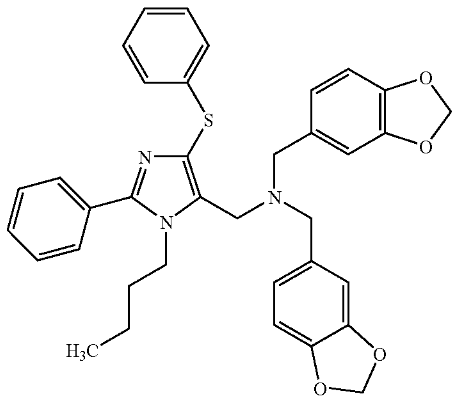 | * | 1-(1,3-benzodioxol-5-yl)-N-(1,3-benzodioxol-5-ylmethyl)-N-{[1-butyl-2-phenyl-4-(phenylthio)-1H-imidazol-5-yl]methyl}methanamine | | |
| 1044 | 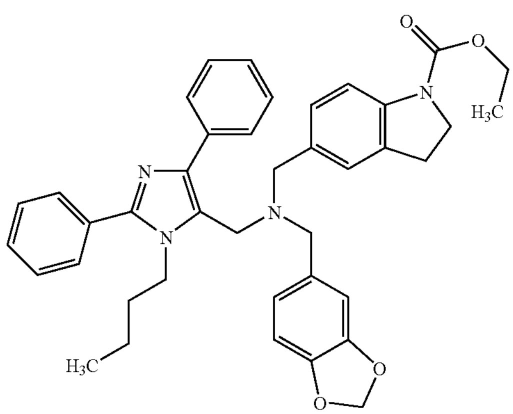 | * | ethyl 5-({(1,3-benzodioxol-5-ylmethyl)[(1-butyl-2,4-diphenyl-1H-imidazol-5-yl)methyl]amino}methyl)indoline-1-carboxylate | | |
| 1045 | 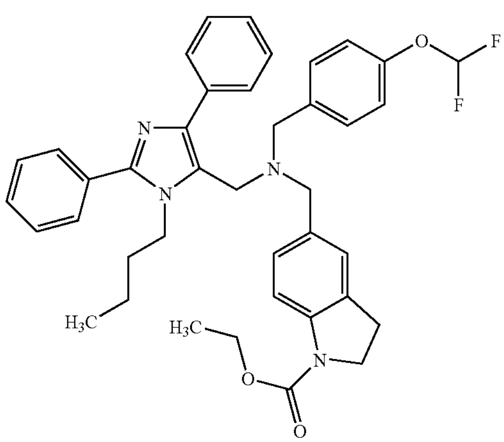 | * | ethyl 5-({[[(1-butyl-2,4-diphenyl-1H-imidazol-5-yl)methyl][4-(difluoromethoxy)benzyl]amino}methyl)indoline-1-carboxylate | | |
| 1046 | 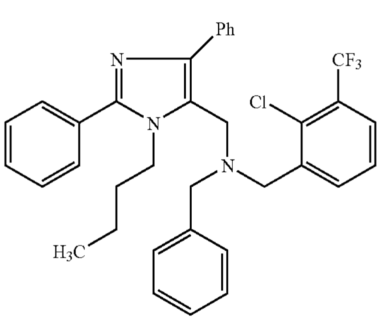 | | N-benzyl-1-(1-butyl-2,4-diphenyl-1H-imidazol-5-yl)-N-[2-chloro-3-(trifluoromethyl)benzyl]methanamine | | |

TABLE III

| CMP # | STRUCTURE | Ca2+ Mob. | IUPAC NAME | MASS |
|---|---|---|---|---|
| 1047 | 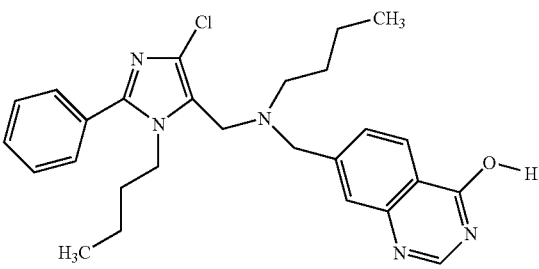 | * | 7-({butyl[(1-butyl-4-chloro-2-phenyl-1H-imidazol-5-yl)methyl]amino}methyl)quinazolin-4-ol | 478.037 |
| 1048 | 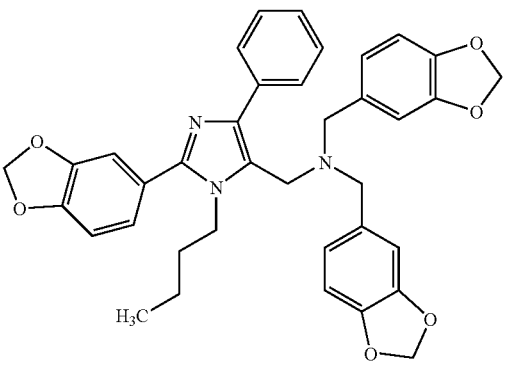 | * | 1-(1,3-benzodioxol-5-yl)-N-{[2-(1,3-benzodioxol-5-yl)-1-butyl-4-phenyl-1H-imidazol-5-yl]methyl}-N-(1,3-benzodioxol-5-ylmethyl)methanamine | 617.698 |
| 1049 | 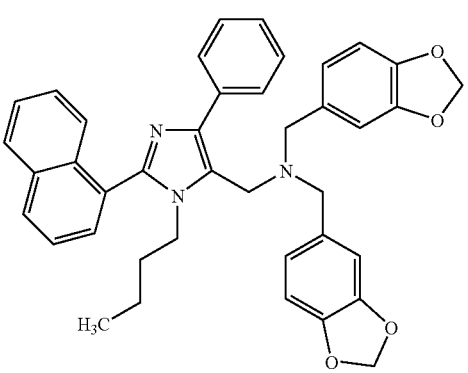 | * | 1-(1,3-benzodioxol-5-yl)-N-(1,3-benzodioxol-5-ylmethyl)-N-{[1-butyl-2-(1-naphthyl)-4-phenyl-1H-imidazol-5-yl]methyl}methanamine | 623.749 |
| 1050 | 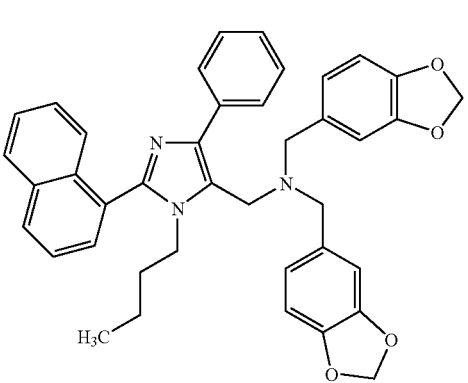 | * | 1-(1,3-benzodioxol-5-yl)-N-(1,3-benzodioxol-5-ylmethyl)-N-{[1-butyl-2-(2-naphthyl)-4-phenyl-1H-imidazol-5-yl]methyl}methanamine | 623.749 |

TABLE III-continued

| CMP # | STRUCTURE | Ca2+ Mob. | IUPAC NAME | MASS |
|---|---|---|---|---|
| 1051 | 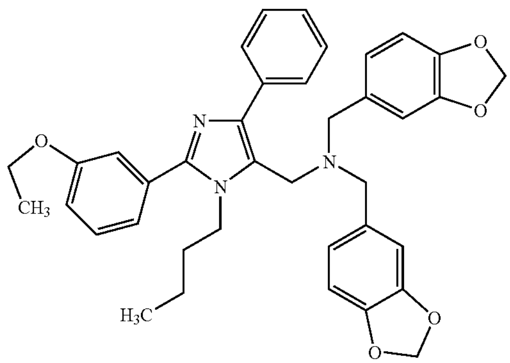 | * | 1-(1,3-benzodioxol-5-yl)-N-(1,3-benzodioxol-5-ylmethyl)-N-{[1-butyl-2-(3-ethoxyphenyl)-4-phenyl-1H-imidazol-5-yl]methyl}methanamine | 617.742 |
| 1052 | 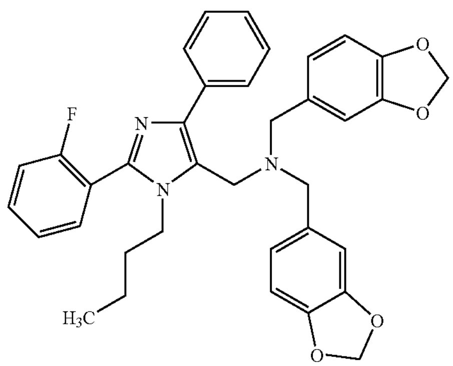 | * | 1-(1,3-benzodioxol-5-yl)-N-(1,3-benzodioxol-5-ylmethyl)-N-{[1-butyl-2-(2-fluorophenyl)-4-phenyl-1H-imidazol-5-yl]methyl}methanamine | 591.68 |
| 1053 | 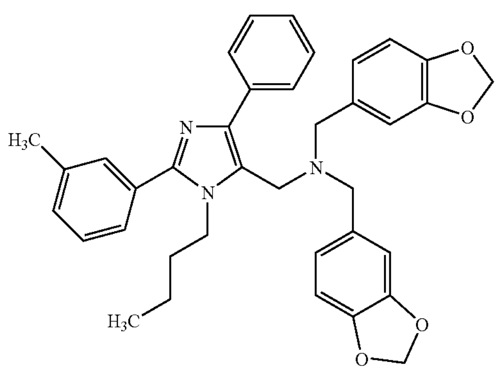 | * | 1-(1,3-benzodioxol-5-yl)-N-(1,3-benzodioxol-5-ylmethyl)-N-{[1-butyl-2-(3-methylphenyl)-4-phenyl-1H-imidazol-5-yl]methyl}methanamine | 587.716 |
| 1054 | 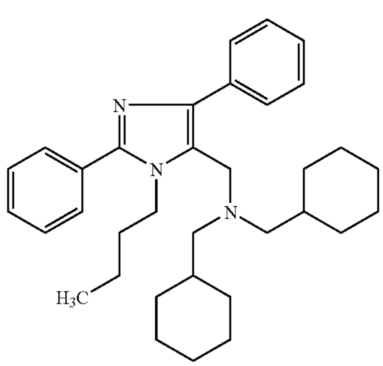 | * | 1-(1-butyl-2,4-diphenyl-1H-imidazol-5-yl)-N,N-bis(cyclohexylmethyl)methanamine | 497.766 |

TABLE III-continued

| CMP # | STRUCTURE | Ca2+ Mob. | IUPAC NAME | MASS |
|---|---|---|---|---|
| 1055 | 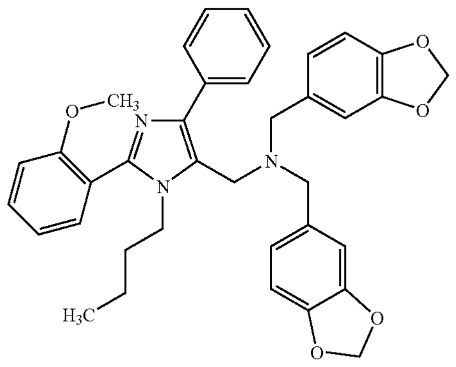 | * | 1-(1,3-benzodioxol-5-yl)-N-(1,3-benzodioxol-5-ylmethyl)-N-{[1-butyl-2-(2-methoxyphenyl)-4-phenyl-1H-imidazol-5-yl]methyl}methanamine | 603.715 |
| 1056 | 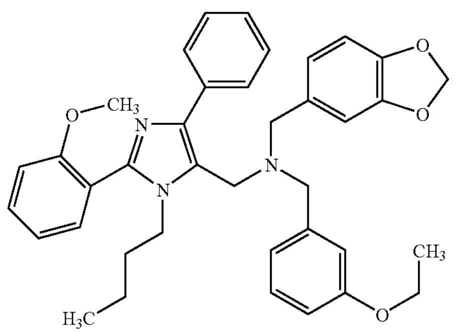 | * | 1-[1-butyl-2-(2-methoxyphenyl)-4-phenyl-1H-imidazol-5-yl]-N-(2,3-dihydro-1,4-benzodioxin-6-ylmethyl)-N-(3-ethoxybenzyl)methanamine | 617.786 |
| 1057 | 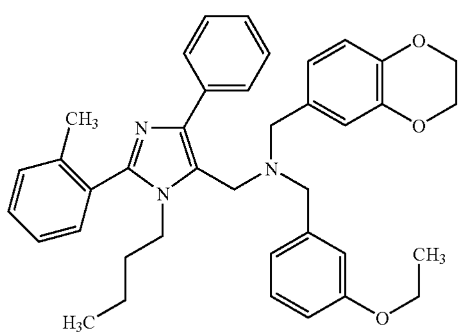 | * | N-{[-butyl-2-(2-methylphenyl)-4-phenyl-1H-imidazol-5-yl]methyl}-N-(2,3-dihydro-1,4-benzodioxin-6-ylmethyl)-N-(3-ethoxybenzyl)amine | 601.787 |
| 1058 | 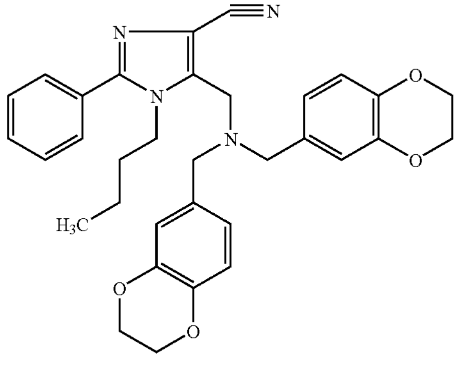 | * | 5-{[bis(2,3-dihydro-1,4-benzodioxin-6-ylmethyl)amino]methyl}-1-butyl-2-phenyl-1H-imidazole-4-carbonitrile | 550.656 |

TABLE III-continued

| CMP # | STRUCTURE | Ca2+ Mob. | IUPAC NAME | MASS |
|---|---|---|---|---|
| 1059 | 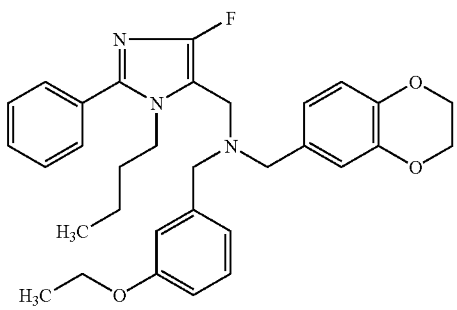 | * | N-[(1-butyl-4-fluoro-2-phenyl-1H-imidazol-5-yl)methyl]-N-(2,3-dihydro-1,4-benzodioxin-6-ylmethyl)-N-(3-ethoxybenzyl)amine | 529.652 |
| 1060 | 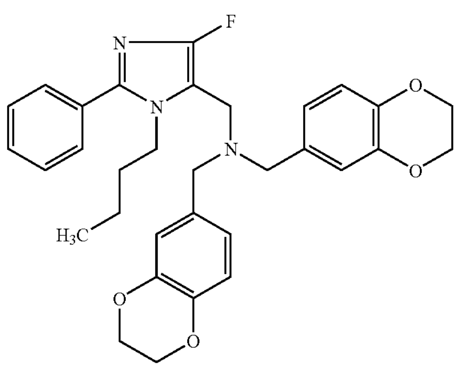 | * | N-[(1-butyl-4-fluoro-2-phenyl-1H-imidazol-5-yl)methyl]-N,N-bis(2,3-dihydro-1,4-benzodioxin-6-ylmethyl)amine | 543.636 |
| 1061 | 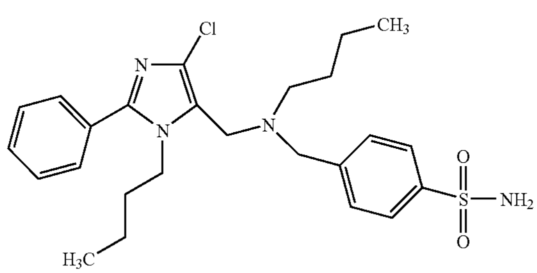 | * | 4-({butyl[(1-butyl-4-chloro-2-phenyl-1H-imidazol-5-yl)methyl]amino}methyl)benzenesulfonamide | 489.081 |
| 1062 | 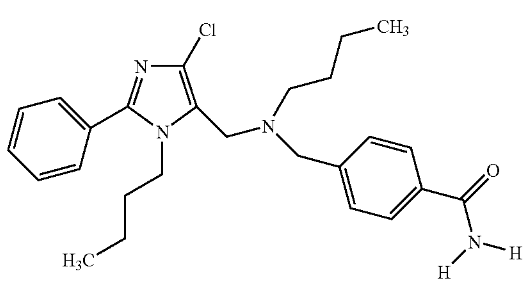 | * | 4-({butyl[(1-butyl-4-chloro-2-phenyl-1H-imidazol-5-yl)methyl]amino}methyl)benzamide | 453.027 |

TABLE III-continued

| CMP # | STRUCTURE | Ca2+ Mob. | IUPAC NAME | MASS |
|---|---|---|---|---|
| 1063 | 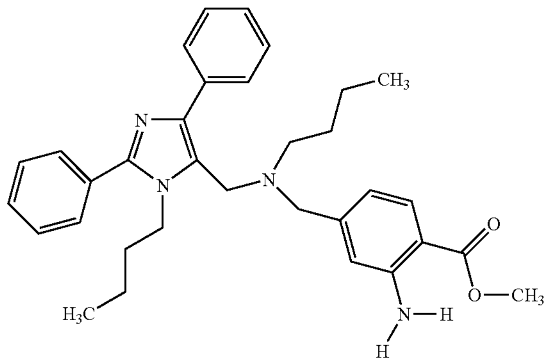 | * | methyl 2-amino-4-({butyl[(1-butyl-2,4-diphenyl-1H-imidazol-5-yl)methyl]amino}methyl)benzoate | 524.705 |
| 1064 | 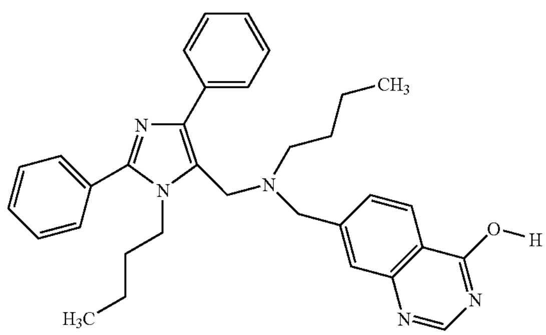 | * | 7-({butyl[(1-butyl-2,4-diphenyl-1H-imidazol-5-yl)methyl]amino}methyl)quinazolin-4-ol | 519.689 |
| 1065 | 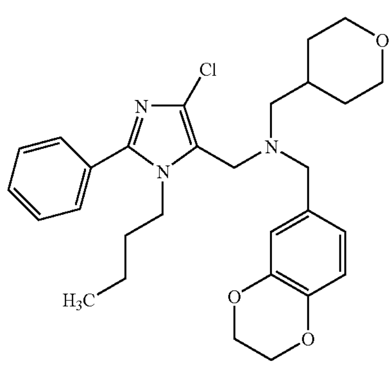 | * | N-[(1-butyl-4-chloro-2-phenyl-1H-imidazol-5-yl)methyl]-N-(2,3-dihydro-1,4-benzodioxin-6-ylmethyl)-N-(tetrahydro-2H-pyran-4-ylmethyl)amine | 510.074 |
| 1066 | 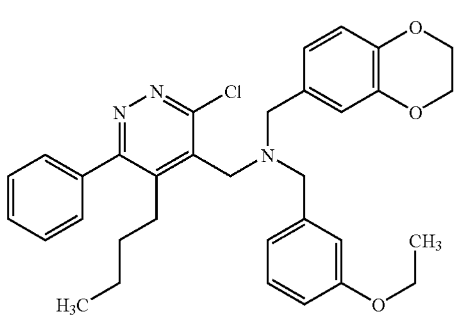 | * | 1-(5-butyl-3-chloro-6-phenylpyridazin-4-yl)-N-(2,3-dihydro-1,4-benzodioxin-6-ylmethyl)-N-(3-ethoxybenzyl)methanamine | 558.118 |

TABLE III-continued

| CMP # | STRUCTURE | Ca2+ Mob. | IUPAC NAME | MASS |
|---|---|---|---|---|
| 1067 | 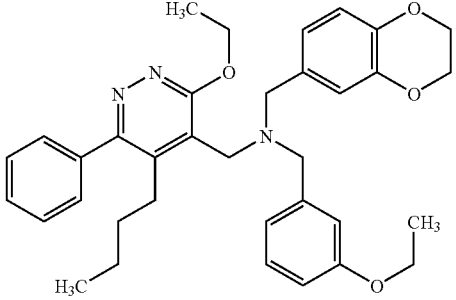 | * | 1-(5-butyl-3-ethoxy-6-phenylpyridazin-4-yl)-N-(2,3-dihydro-1,4-benzodioxin-6-ylmethyl)-N-(3-ethoxybenzyl)methanamine | 567.726 |
| 1068 | 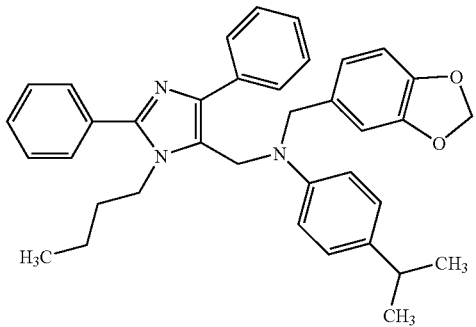 | * | N-(1,3-benzodioxol-5-ylmethyl)-N-[(1-butyl-2,4-diphenyl-1H-imidazol-5-yl)methyl]-4-isopropylaniline | 557.734 |
| 1069 | 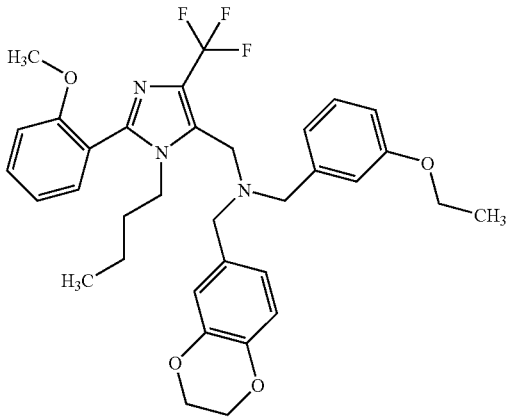 | * | 1-[1-butyl-2-(2-methoxyphenyl)-4-(trifluoromethyl)-1H-imidazol-5-yl]-N-(2,3-dihydro-1,4-benzodioxin-6-ylmethyl)-N-(3-ethoxybenzyl)methanamine | 609.685 |
| 1070 | 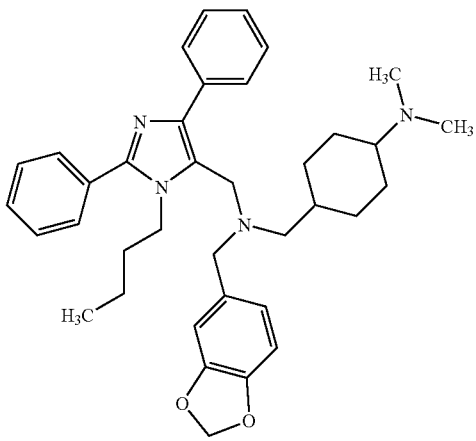 | * | 4-({(1,3-benzodioxol-5-ylmethyl)[(1-butyl-2,4-diphenyl-1H-imidazol-5-yl)methyl]amino}methyl)-N,N-dimethylcyclohexanamine | 578.796 |

TABLE III-continued

| CMP # | STRUCTURE | Ca2+ Mob. | IUPAC NAME | MASS |
|---|---|---|---|---|
| 1071 | 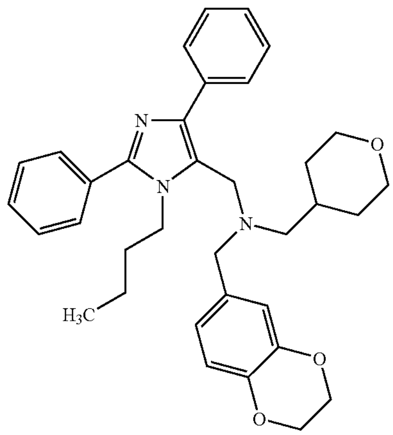 | * | 1-(1-butyl-2,4-diphenyl-1H-imidazol-5-yl)-N-(2,3-dihydro-1,4-benzodioxin-6-ylmethyl)-N-(tetrahydro-2H-pyran-4-ylmethyl)methanamine | 551.727 |
| 1072 | 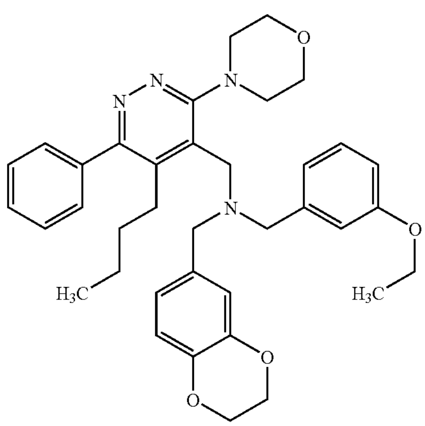 | * | 1-(5-butyl-3-morpholin-4-yl-6-phenylpyridazin-4-yl)-N-(2,3-dihydro-1,4-benzodioxin-6-ylmethyl)-N-(3-ethoxybenzyl)methanamine | 608.779 |
| 1073 | 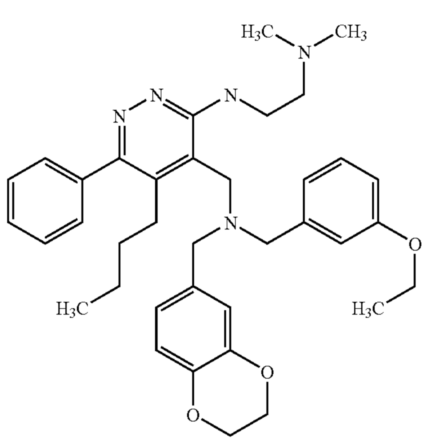 | * | N~1~-(5-butyl-4-{[(2,3-dihydro-1,4-benzodioxin-6-ylmethyl)(3-ethoxybenzyl)amino]methyl}-6-phenylpyridazin-3-yl)-N~2~,N~2~-dimethylethane-1,2-diamine | 609.81 |

TABLE III-continued

| CMP # | STRUCTURE | Ca2+ Mob. | IUPAC NAME | MASS |
|---|---|---|---|---|
| 1074 | 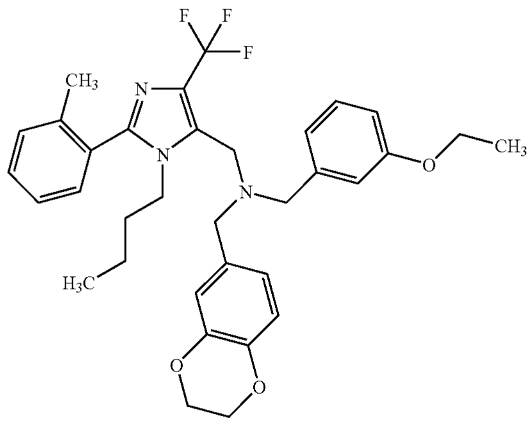 | * | N-{[1-butyl-2-(2-methylphenyl)-4-(trifluoromethyl)-1H-imidazol-5-yl]methyl}-N-(2,3-dihydro-1,4-benzodioxin-6-ylmethyl)-N-(3-ethoxybenzyl)amine | 593.686 |
| 1075 | 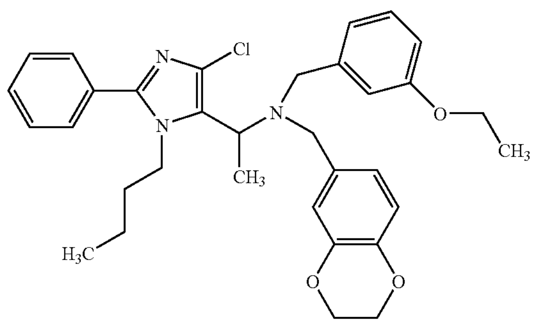 | * | N-[1-(1-butyl-4-chloro-2-phenyl-1H-imidazol-5-yl)ethyl]-N-(2,3-dihydro-1,4-benzodioxin-6-ylmethyl)-N-(3-ethoxybenzyl)amine | 560.134 |
| 1076 | 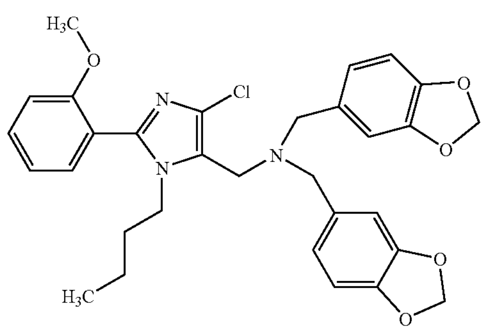 | * | 1-(1,3-benzodioxol-5-yl)-N-(1,3-benzodioxol-5-ylmethyl)-N-{[1-butyl-4-chloro-2-(2-methoxyphenyl)-1H-imidazol-5-yl]methyl}methanamine | 562.063 |
| 1077 | 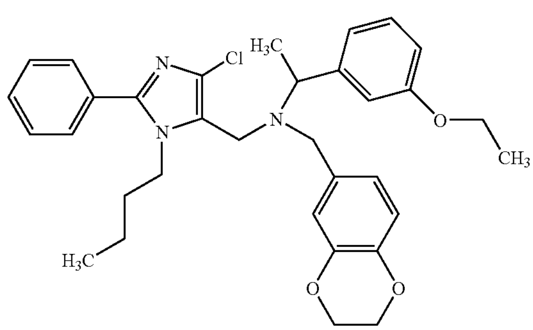 | * | N-[(1-butyl-4-chloro-2-phenyl-1H-imidazol-5-yl)methyl]-N-(2,3-dihydro-1,4-benzodioxin-6-ylmethyl)-1-(3-ethoxyphenyl)ethanamine | 560.134 |

TABLE III-continued

| CMP # | STRUCTURE | Ca2+ Mob. | IUPAC NAME | MASS |
|---|---|---|---|---|
| 1078 | 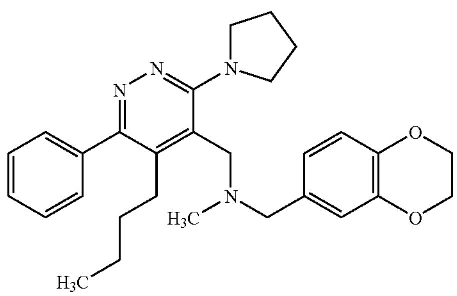 | * | 1-(5-butyl-6-phenyl-3-pyrrolidin-1-ylpyridazin-4-yl)-N-(2,3-dihydro-1,4-benzodioxin-6-ylmethyl)-N-methylmethanamine | 472.629 |
| 1079 | 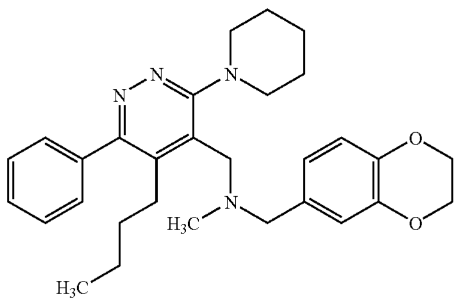 | * | 1-(5-butyl-6-phenyl-3-piperidin-1-ylpyridazin-4-yl)-N-(2,3-dihydro-1,4-benzodioxin-6-ylmethyl)-N-methylmethanamine | 486.656 |
| 1080 | 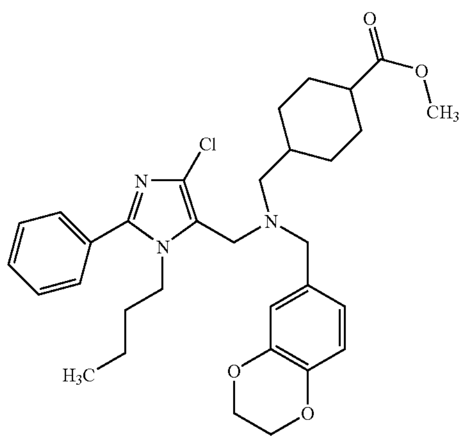 | * | methyl 4-{[[(1-butyl-4-chloro-2-phenyl-1H-imidazol-5-yl)methyl](2,3-dihydro-1,4-benzodioxin-6-ylmethyl)amino]methyl}cyclohexanecarboxylate | 566.138 |
| 1081 | 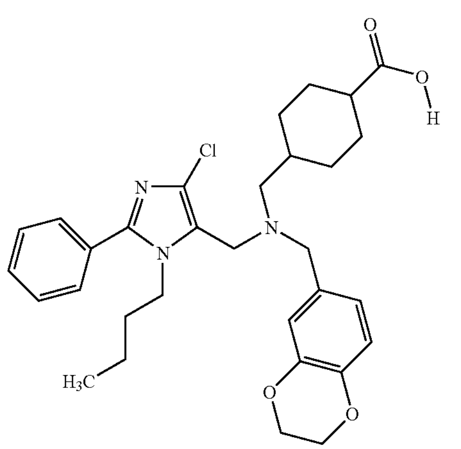 | * | 4-{[[(1-butyl-4-chloro-2-phenyl-1H-imidazol-5-yl)methyl](2,3-dihydro-1,4-benzodioxin-6-ylmethyl)amino]methyl}cyclohexanecarboxylic acid | 552.111 |

TABLE III-continued

| CMP # | STRUCTURE | Ca2+ Mob. | IUPAC NAME | MASS |
|---|---|---|---|---|
| 1082 | 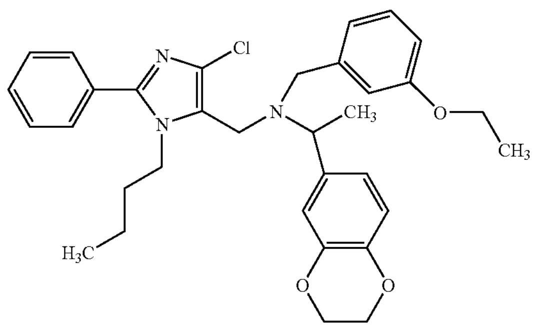 | * | N-[(1-butyl-4-chloro-2-phenyl-1H-imidazol-5-yl)methyl]-1-(2,3-dihydro-1,4-benzadioxin-6-yl)-N-(3-ethoxybenzyl)ethanamine | 560.134 |
| 1083 | 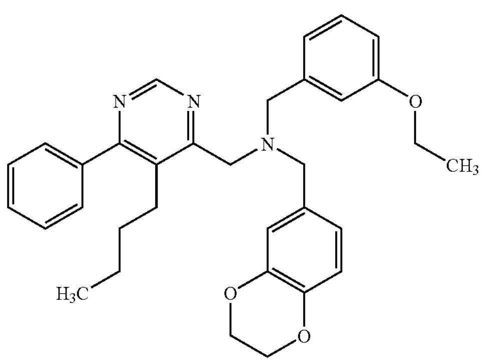 | * | N-[(5-butyl-6-phenylpyrimidin-4-yl)methyl]-N-(2,3-dihydro-1,4-benzodioxin-6-ylmethyl)-N-(3-ethoxybenzyl)amine | 523.673 |
| 1084 | 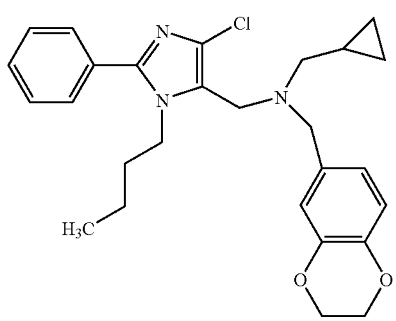 | * | N-[(1-butyl-4-chloro-2-phenyl-1H-imidazol-5-yl)methyl]-N-(cyclopropylmethyl)-N-(2,3-dihydro-1,4-benzadioxin-6-ylmethyl)amine | 466.022 |
| 1085 | 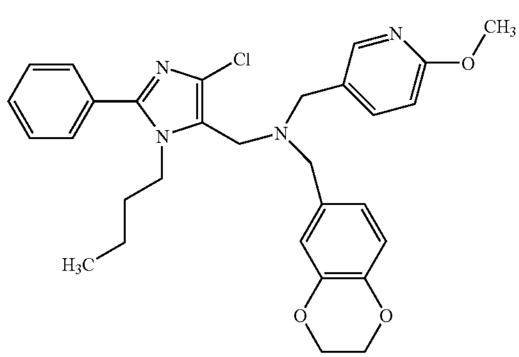 | * | N-[(1-butyl-4-chloro-2-phenyl-1H-imidazol-5-yl)methyl]-N-(2,3-dihydro-1,4-benzodioxin-ylmethyl)-N-[(6-methoxypyridin-3-yl)methyl]amine | 533.069 |

TABLE III-continued

| CMP # | STRUCTURE | Ca2+ Mob. | IUPAC NAME | MASS |
|---|---|---|---|---|
| 1086 | 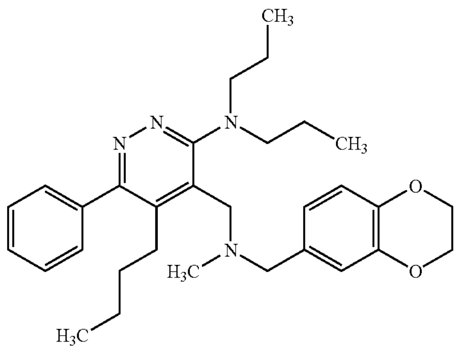 | * | 5-butyl-4-{[(2,3-dihydro-1,4-benzodioxin-6-ylmethyl)(methyl)amino]methyl}-6-phenyl-N,N-dipropylpyridazin-3-amine | 502.699 |
| 1087 | 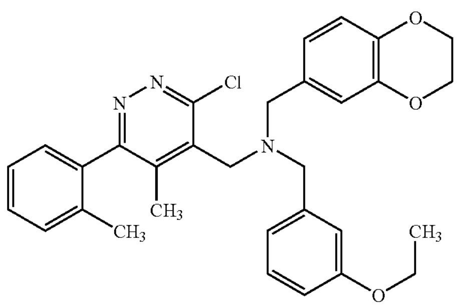 | * | 1-[3-chloro-5-methyl-6-(2-methylphenyl)pyridazin-4-yl]-N-(2,3-dihydro-1,4-benzodioxin-6-ylmethyl)-N-(3-ethoxybenzyl)methanamine | 530.065 |
| 1088 | 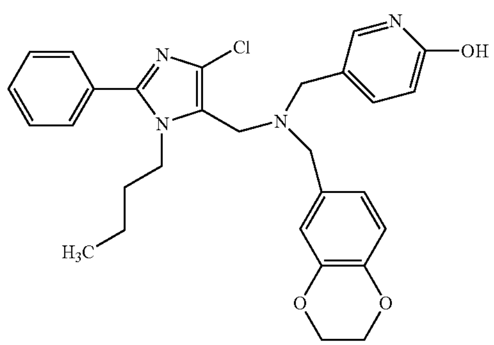 | * | 5-{[[(1-butyl-4-chloro-2-phenyl-1H-imidazol-5-yl)methyl](2,3-dihydro-1,4-benzodioxin-6-ylmethyl)amino]methyl}pyridin-2-ol | 519.042 |
| 1089 | 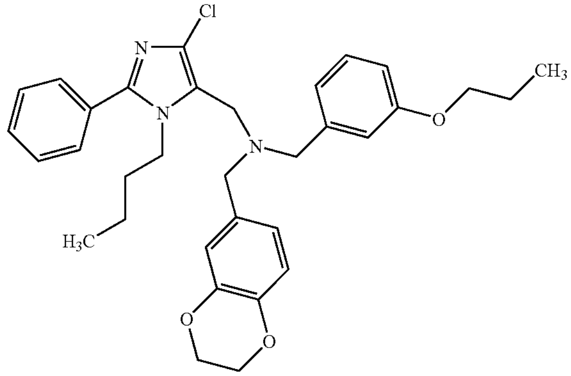 | * | N-[(1-butyl-4-chloro-2-phenyl-1H-imidazol-5-yl)methyl]-N-(2,3-dihydro-1,4-benzodioxin-6-ylmethyl)-N-(3-propoxybenzyl)amine | 560.134 |

TABLE III-continued

| CMP # | STRUCTURE | Ca2+ Mob. | IUPAC NAME | MASS |
|---|---|---|---|---|
| 1090 | 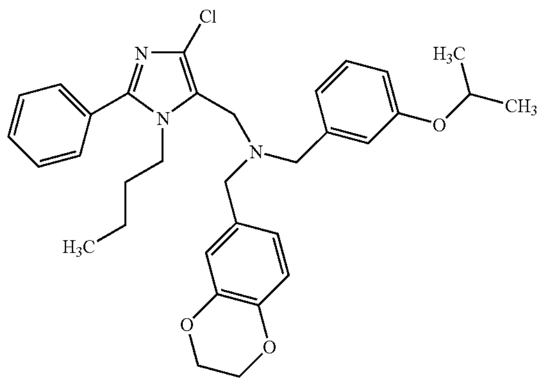 | * | N-[(1-butyl-4-chloro-2-phenyl-1H-imidazol-5-yl)methyl]-N-(2,3-dihydro-1,4-benzodioxin-6-ylmethyl)-N-(3-isopropoxybenzyl)amine | 560.134 |
| 1091 | 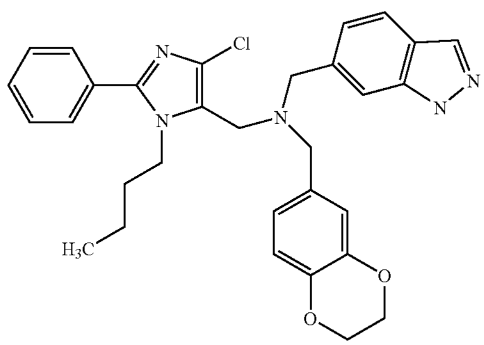 | * | N-[(1-butyl-4-chloro-2-phenyl-1H-imidazol-5-yl)methyl]-N-(2,3-dihydro-1,4-benzodioxin-6-ylmethyl)-N-(1H-indazol-6-ylmethyl)amine | 542.08 |
| 1092 | 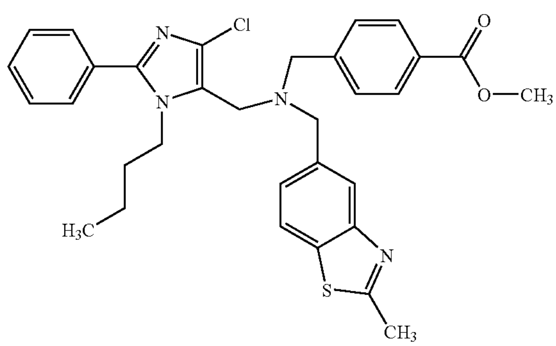 | * | methyl 4-({[(1-butyl-4-chloro-2-phenyl-1H-imidazol-5-yl)methyl][(2-methyl-1,3-benzothiazol-5-yl)methyl]amino}methyl)benzoate | 573.158 |
| 1093 | 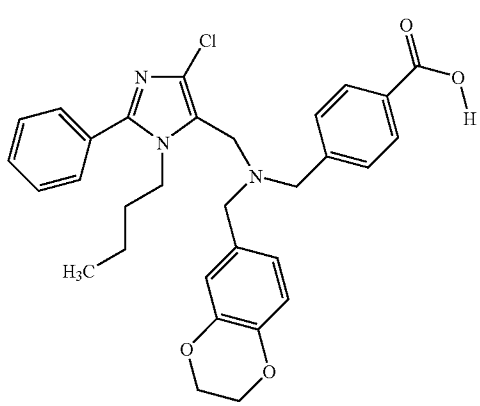 | * | 4-{[[(1-butyl-4-chloro-2-phenyl-1H-imidazol-5-yl)methyl](2,3-dihydro-1,4-benzodioxin-6-ylmethyl)amino]methyl}benzoic acid | 546.064 |

TABLE III-continued

| CMP # | STRUCTURE | Ca2+ Mob. | IUPAC NAME | MASS |
|---|---|---|---|---|
| 1094 | 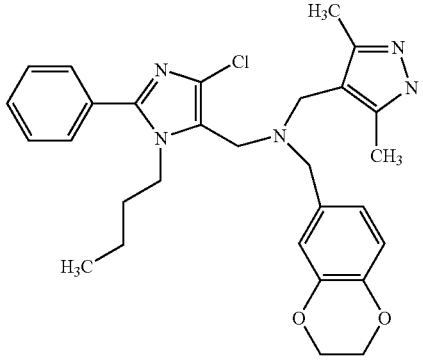 | * | N-[(1-butyl-4-chloro-2-phenyl-1H-imidazol-5-yl)methyl]-N-(2,3-dihydro-1,4-benzodioxin-6-ylmethyl)-N-[(3,5-dimethyl-1H-pyrazol-4-yl)methyl]amine | 520.074 |
| 1095 | 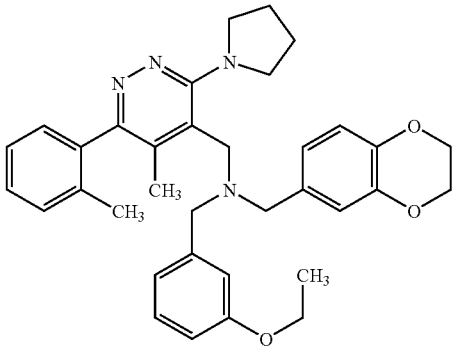 | * | 1-(2,3-dihydro-1,4-benzodioxin-6-yl)-N-(3-ethoxybenzyl)-N-{5-methyl-6-(2-methylphenyl)-3-pyrrolidin-1-ylpyridazin-4-yl]methyl}methanamine | 564.726 |
| 1096 | 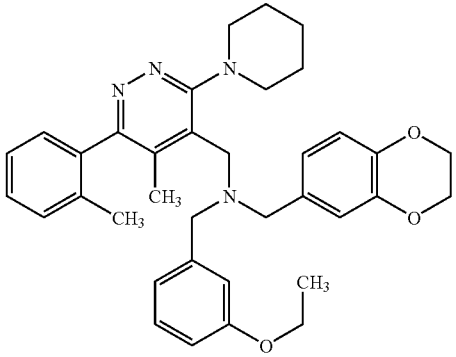 | * | 1-(2,3-dihydro-1,4-benzodioxin-6-yl)-N-(3-ethoxybenyl)-N-{[5-methyl-6-(2-methylphenyl)-3-piperidin-1-ylpyridazin-4-yl]methyl}methanamine | 578.753 |
| 1097 | 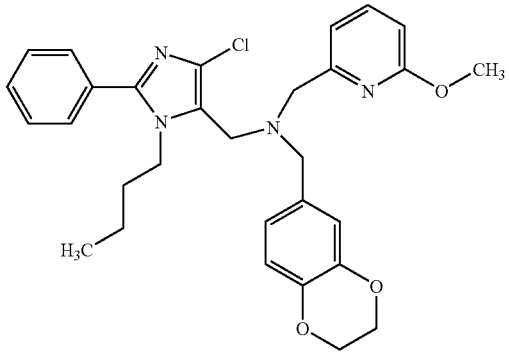 | * | N-[(1-butyl-4-chloro-2-phenyl-1H-imidazol-5-yl)methyl]-N-(2,3-dihydro-1,4-benzodioxin-6-ylmethyl)-N-[(6-methoxypyridin-2-yl)methyl]amine | 533.069 |

TABLE III-continued

| CMP # | STRUCTURE | Ca2+ Mob. | IUPAC NAME | MASS |
|---|---|---|---|---|
| 1098 | 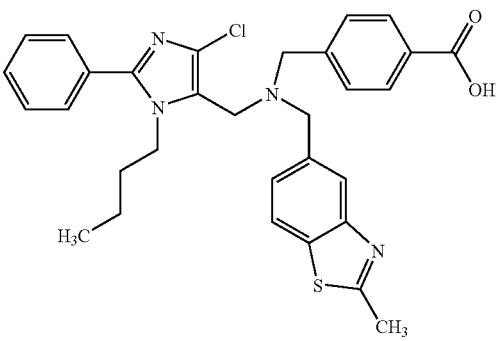 | * | 4-({[(1-butyl-4-chloro-2-phenyl-1H-imidazol-5-yl)methyl][(2-methyl-1,3-benzothiazol-5-yl)methyl]amino}methyl)benzoic acid | 559.131 |
| 1099 | 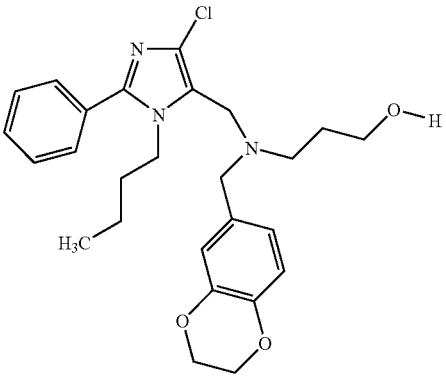 | * | 3-[[(1-butyl-4-chloro-2-phenyl-1H-imidazol-5-yl)methyl](2,3-dihydro-1,4-benzodioxin-6-ylmethyl)amino]propan-1-ol | 470.01 |
| 1100 | 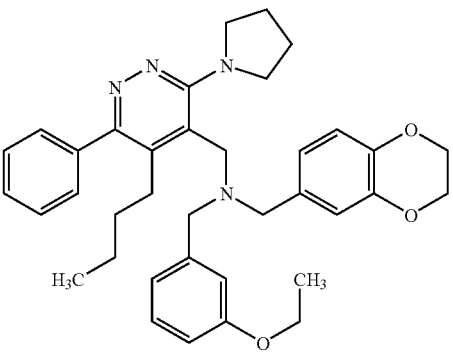 | * | 1-(5-butyl-6-phenyl-3-pyrrolidin-1-ylpyridazin-4-yl)-N-(2,3-dihydro-1,4-benzodioxin-6-ylmethyl)-N-(3-ethoxybenzyl)methanamine | 592.78 |
| 1101 | 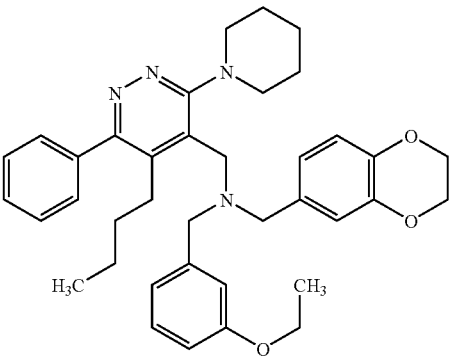 | * | 1-(5-butyl-6-phenyl-3-piperidin-1-ylpyridazin-4-yl)-N-(2,3-dihydro-1,4-benzodioxin-6-ylmethyl)-N-(3-ethoxybenzyl)methanamine | 606.806 |

TABLE III-continued

| CMP # | STRUCTURE | Ca2+ Mob. | IUPAC NAME | MASS |
|---|---|---|---|---|
| 1102 | 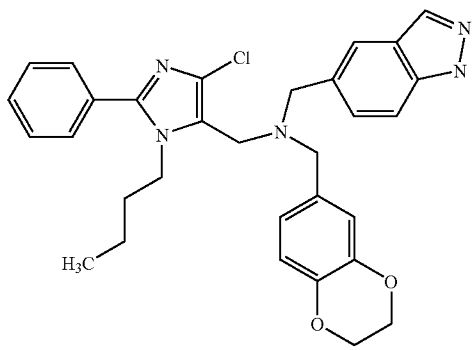 | * | N-[(1-butyl-4-chloro-2-phenyl-1H-imidazol-5-yl)methyl]-N-(2,3-dihydro-1,4-benzodioxin-6-ylmethyl)-N-(1H-indazol-5-ylmethyl)amine | 542.08 |
| 1103 | 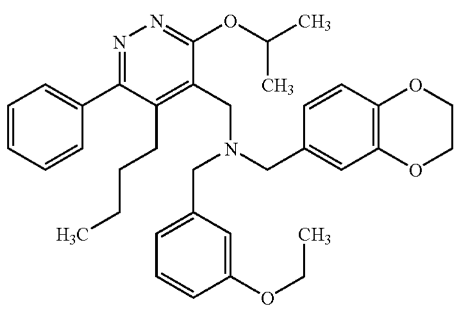 | * | 1-(5-butyl-3-isopropoxy-6-phenylpyridazin-4-yl)-N-(2,3-dihydro-1,4-benzodioxin-6-ylmethyl)-N-(3-ethoxybenzyl)methanamine | 581.753 |
| 1104 | 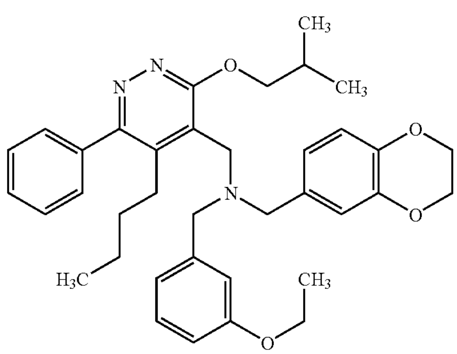 | * | 1-(5-butyl-3-isobutoxy-6-phenylpyridazin-4-yl)-N-(2,3-dihydro-1,4-benzodioxin-6-ylmethyl)-N-(3-ethoxybenzyl)methanamine | 595.779 |
| 1105 | 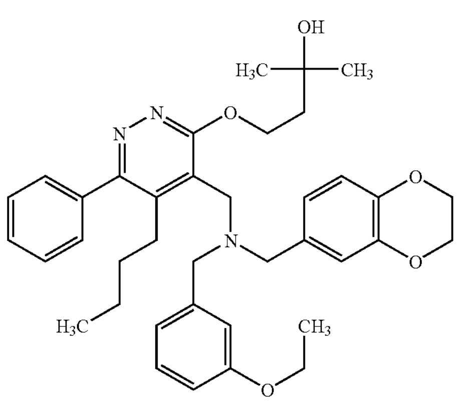 | * | 4-[(5-butyl-4-{[(2,3-dihydro-1,4-benzodioxin-6-ylmethyl)(3-ethoxybenzyl)amino]methyl}-6-phenylpyridazin-3-yl)oxy]-2-methylbutan-2-ol | 625.805 |

TABLE III-continued

| CMP # | STRUCTURE | Ca2+ Mob. | IUPAC NAME | MASS |
|---|---|---|---|---|
| 1106 | 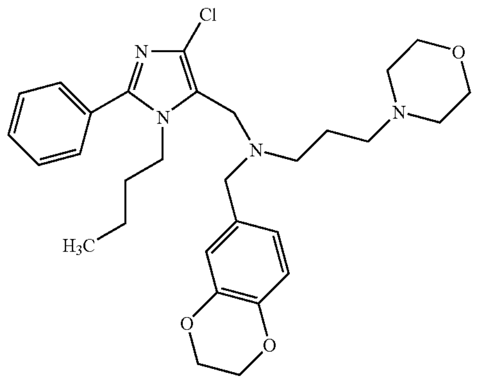 | * | N-[(1-butyl-4-chloro-2-phenyl-1H-imidazol-5-yl)methyl]-N-(2,3-dihydro-1,4-benzodioxin-6-ylmethyl)-3-morpholin-4-ylpropan-1-amine | 539.116 |
| 1107 | 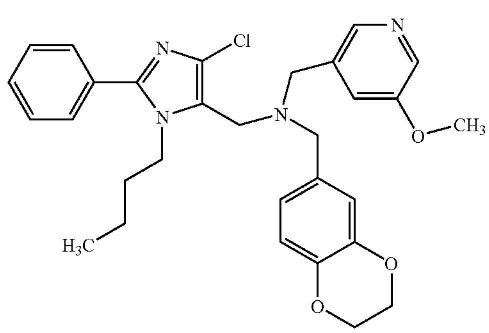 | * | N-[(1-butyl-4-chloro-2-phenyl-1H-imidazol-5-yl)methyl]-N-(2,3-dihydro-1,4-benzodioxin-6-ylmethyl)-N-[(5-methoxypyridin-3-yl)methyl]amine | 533.069 |
| 1108 | 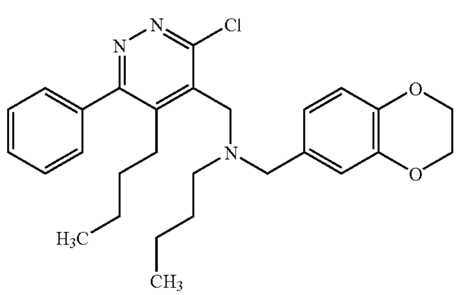 | * | N-[(5-butyl-3-chloro-6-phenylpyridazin-4-yl)methyl]-N-(2,3-dihydro-1,4-benzodioxin-6-ylmethyl)butan-1-amine | 480.049 |
| 1109 | 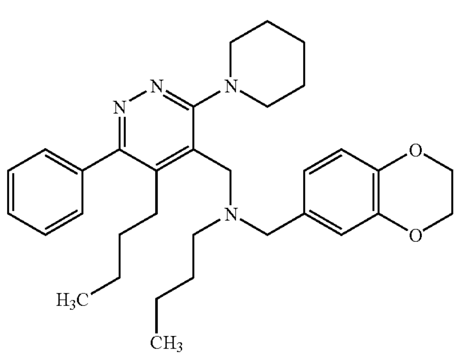 | * | N-[(5-butyl-6-phenyl-3-piperidin-1-ylpyridazin-4-yl)methyl]-N-(2,3-dihydro-1,4-benzodioxin-6-ylmethyl)butan-1-amine | 528.737 |

TABLE III-continued

| CMP # | STRUCTURE | Ca2+ Mob. | IUPAC NAME | MASS |
|---|---|---|---|---|
| 1110 | 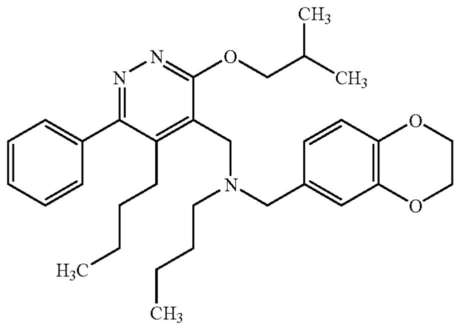 | * | N-[(5-butyl-3-isobutoxy-6-phenylpyridazin-4-yl)methyl]-N-(2,3-dihydro-1,4-benzodioxin-6-ylmethyl)butan-1-amine | 517.71 |
| 1111 | 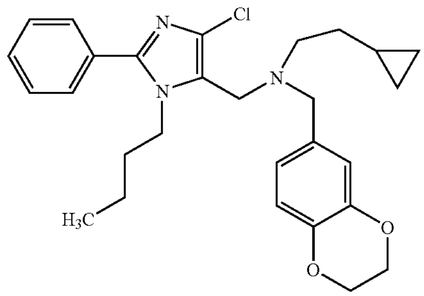 | * | N-[(1-butyl-4-chloro-2-phenyl-1H-imidazol-5-yl)methyl]-2-cyclopropyl-N-(2,3-dihydro-1,4-benzodioxin-6-ylmethyl)ethanamine | 480.049 |
| 1112 | 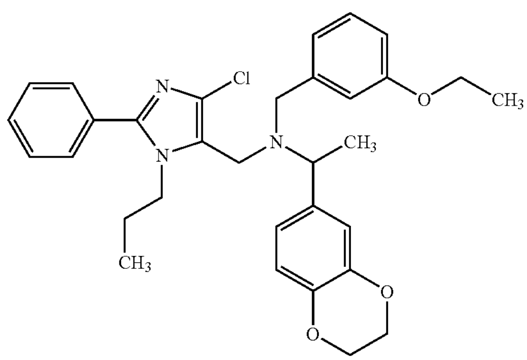 | * | N-[(4-chloro-2-phenyl-1-propyl-1H-imidazol-5-yl)methyl]-1-(2,3-dihydro-1,4-benzodioxin-6-yl)-N-(3-ethoxybenzyl)ethanamine | 546.107 |
| 1113 | 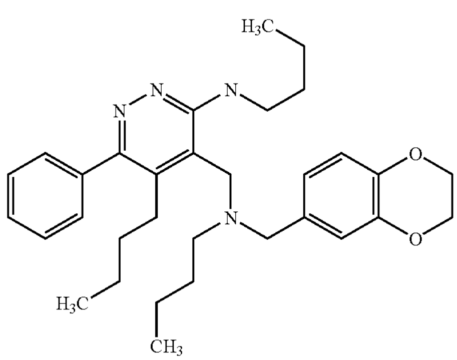 | * | N,5-dibutyl-4-{[butyl(2,3-dihydro-1,4-benzodioxin-6-ylmethyl)amino]methyl-6-phenylpyridazin-3-amine | 516.726 |

TABLE III-continued

| CMP # | STRUCTURE | Ca2+ Mob. | IUPAC NAME | MASS |
|---|---|---|---|---|
| 1114 | 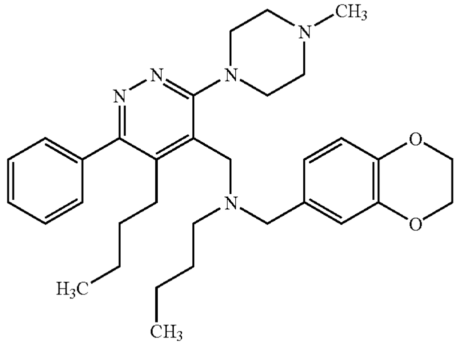 | * | N-{[5-butyl-3-(4-methylpiperazin-1-yl)-6-phenylpyridazin-4-yl]methyl}-N-(2,3-dihydro-1,4-benzodioxin-6-ylmethyl)butan-1-amine | 543.752 |
| 1115 | 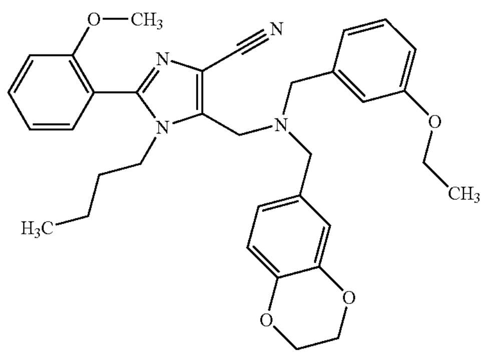 | * | 1-butyl-5-{[(2,3-dihydro-1,4-benzodioxin-6-ylmethyl)(3-ethoxybenzyl)amino]methyl}-2-(2-methoxyphenyl)-1H-imidazole-4-carbonitrile | 566.698 |
| 1116 | 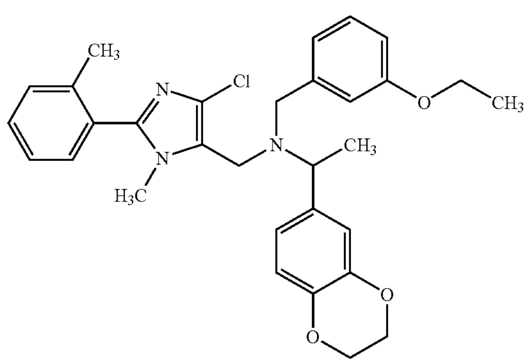 | * | N-{[4-chloro-1-methyl-2-(2-methylphenyl)-1H-imidazol-5-yl]methyl}-1-(2,3-dihydro-1,4-benzodioxin-6-yl)-N-(3-ethoxybenzyl)ethanamine | 532.081 |
| 1117 | 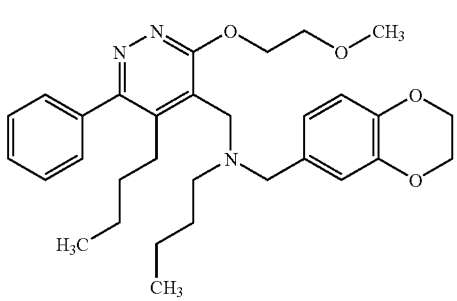 | * | N-{[5-butyl-3-(2-methoxyethoxy)-6-phenylpyridazin-4-yl]methyl}-N-(2,3-dihydro-1,4-benzodioxin-6-ylmethyl)butan-1-amine | 519.682 |

TABLE III-continued

| CMP # | STRUCTURE | Ca2+ Mob. | IUPAC NAME | MASS |
|---|---|---|---|---|
| 1118 | 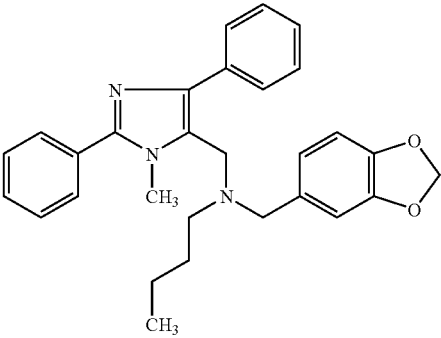 | * | N-(1,3-benzodioxol-5-ylmethyl)-N-[(1-methyl-2,4-diphenyl-1H-imidazol-5-yl)methyl]butan-1-amine | 453.583 |
| 1119 | 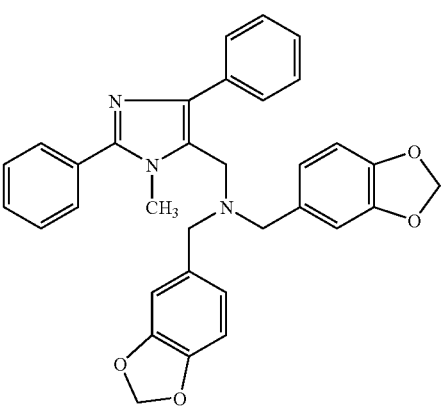 | * | 1-(1,3-benzodioxol-5-yl)-N-(1,3-benzodioxol-5-ylmethyl)-N-[(1-methyl-2,4-diphenyl-1H-imidazol-5-yl)methyl]methanamine | 531.609 |
| 1120 | 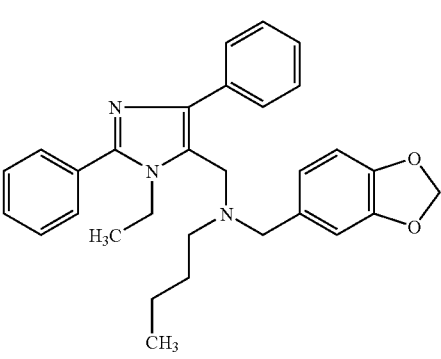 | * | N-(1,3-benzodioxol-5-ylmethyl)-N-[(1-ethyl-2,4-diphenyl-1H-imidazol-5-yl)methyl]butan-1-amine | 467.61 |
| 1121 | 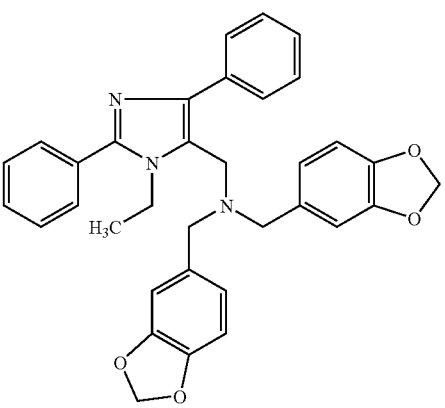 | * | 1-(1,3-benzodioxol-5-yl)-N-(1,3-benzodioxol-5-ylmethyl)-N-[(1-ethyl-2,4-diphenyl-1H-imadazol-5-yl)methyl]methanamine | 545.636 |

TABLE III-continued

| CMP # | STRUCTURE | Ca2+ Mob. | IUPAC NAME | MASS |
|---|---|---|---|---|
| 1122 | 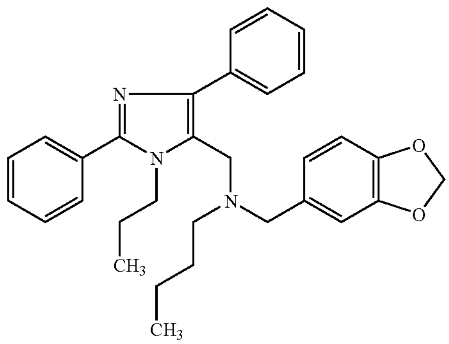 | * | N-(1,3-benzodioxol-5-ylmethyl)-N-[(2,4-diphenyl-1-propyl-1H-imidazol-5-yl)methyl]butan-1-amine | 481.637 |
| 1123 | 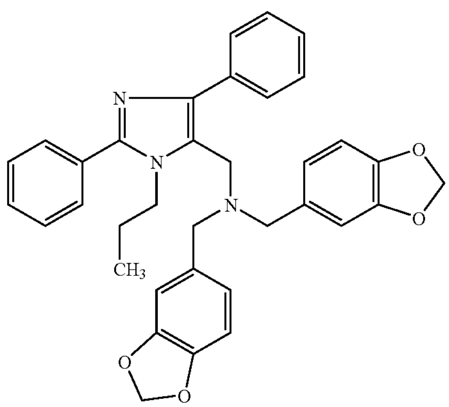 | * | 1-(1,3-benzodioxol-5-yl)-N-(1,3-benzodioxol-5-ylmethyl)-N-[(2,4-diphenyl-1-propyl-1H-imidazol-5-yl)methyl]methanamine | 559.663 |
| 1124 | 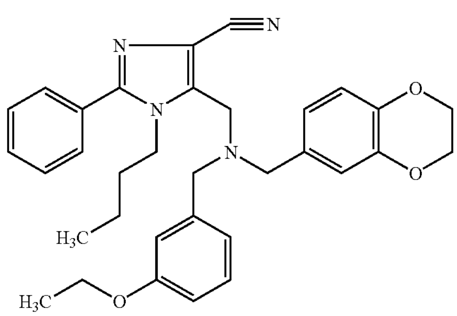 | * | 1-butyl-5-{[(2,3-dihydro-1,4-benzodioxin-6-ylmethyl)(3-ethoxybenzyl)amino]methyl}-2-phenyl-1H-imidazole-4-carbonitrile | 536.672 |
| 1125 | 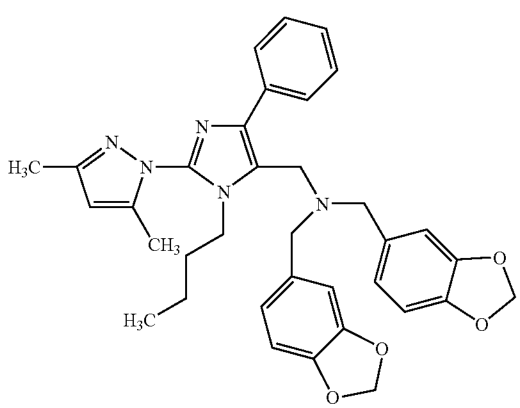 | * | 1-(1,3-benzodioxol-5-yl)-N-(1,3-benzodioxol-5-ylmethyl)-N-{[1-butyl-2-(3,5-dimethyl-1H-pyrazol-1-yl)-4-phenyl-1H-imidazol-5-yl]methyl}methanamine | 591.708 |

TABLE III-continued

| CMP # | STRUCTURE | Ca2+ Mob. | IUPAC NAME | MASS |
|---|---|---|---|---|
| 1126 | 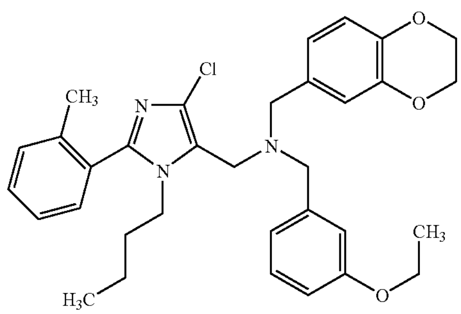 | * | 1-[1-butyl-4-chloro-2-(2-methylphenyl)-1H-imidazol-5-yl]-N-(2,3-dihydro-1,4-benzodioxin-6-ylmethyl)-N-(3-ethoxybenzyl)methanamine | 560.134 |
| 1127 | 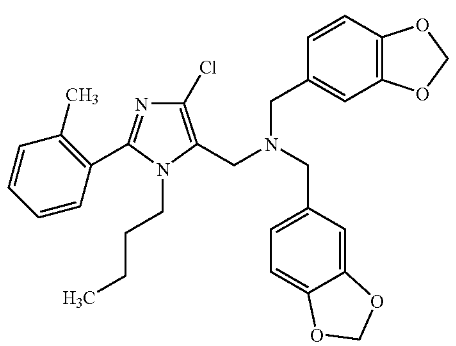 | * | 1-(1,3-benzodioxol-5-yl)-N-(1,3-benzodioxol-5-ylmethyl)-N-{[1-butyl-4-chloro-2-(2-methylphenyl)-1H-imidazol-5-yl]methyl}methanamine | 546.064 |
| 1128 | 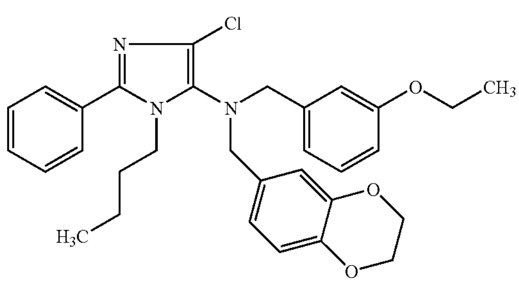 | * | 1-butyl-4-chloro-N-(2,3-dihydro-1,4-benzodioxin-6-ylmethyl)-N-(3-ethoxybenzyl)-2-phenyl-1H-imidazol-5-amine | 532.081 |
| 1129 | 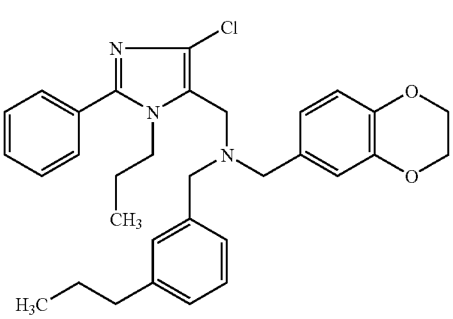 | * | 1-(4-chloro-2-phenyl-1-propyl-1H-imidazol-5-yl)-N-(2,3-dihydro-1,4-benzodioxin-6-ylmethyl)-N-(3-ethoxybenzyl)methanamine | 532.081 |

TABLE III-continued

| CMP # | STRUCTURE | Ca2+ Mob. | IUPAC NAME | MASS |
|---|---|---|---|---|
| 1130 | 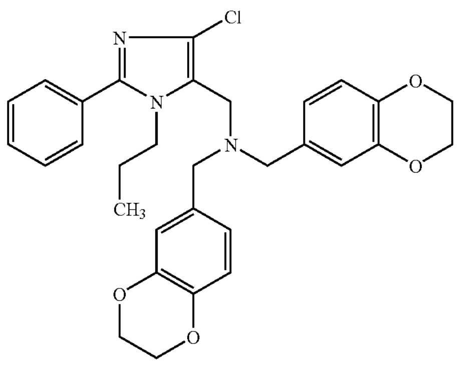 | * | 1-(4-chloro-2-phenyl-1-propyl-1H-imidazol-5-yl)-N,N-bis(2,3-dihydro-1,4-benzodioxin-6-ylmethyl)methanamine | 546.064 |
| 1131 | 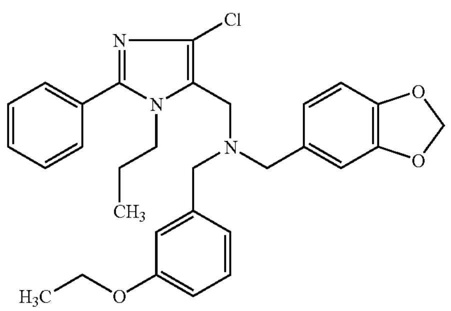 | * | 1-(1,3-benzodioxol-5-yl)-N-[(4-chloro-2-phenyl-1-propyl-1H-imidazol-5-yl)methyl]-N-(3-ethoxybenzyl)methanamine | 518.054 |
| 1132 | 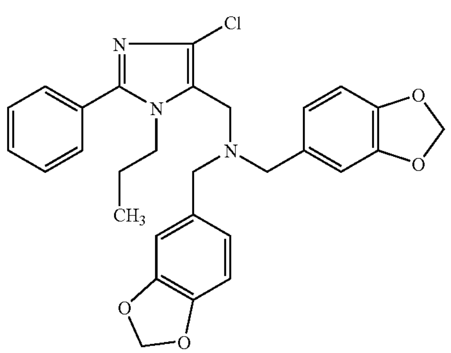 | * | 1-(1,3-benzodioxol-5-yl)-N-(1,3-benzodaoxol-5-ylmethyl)-N-[(4-chloro-2-phenyl-1-propyl-1H-imidazol-5-yl)methyl]methanamine | 518.01 |
| 1133 | 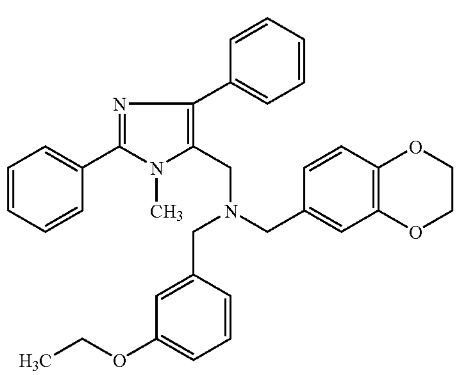 | * | 1-(2,3-dihydro-1,4-benzodioxin-6-yl)-N-(3-ethoxybenzyl)-N-[(1-methyl-2,4-diphenyl-1H-imidazol-5-yl)methyl]methanamine | 545.68 |

TABLE III-continued

| CMP # | STRUCTURE | Ca2+ Mob. | IUPAC NAME | MASS |
|---|---|---|---|---|
| 1134 | 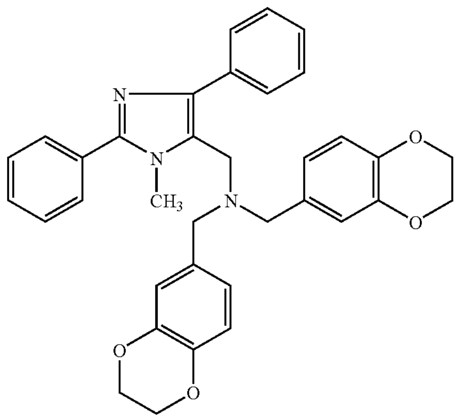 | * | 1-(2,3-dihydro-1,4-benzadioxin-6-yl)-N-(2,3-dihydro-1,4-benzodioxin-6-ylmethyl)-N-[(1-methyl-2,4-diphenyl-1H-imidazol-5-yl)methyl]methanamine | 559.663 |
| 1135 | 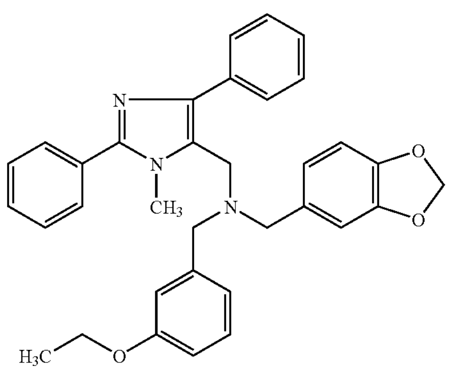 | * | 1-(1,3-benzodioxol-5-yl)-N-(3-ethoxybenzyl)-N-[(1-methyl-2,4-diphenyl-1H-imidazol-5-yl)methyl]methanamine | 531.653 |
| 1136 | 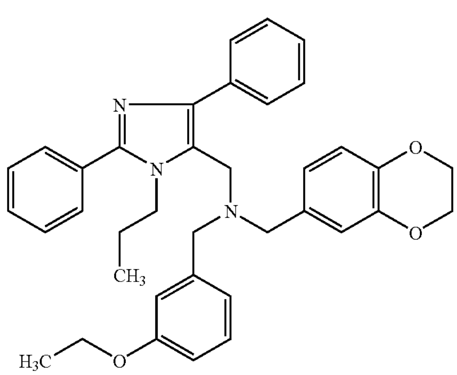 | * | 1-(2,3-dihydro-1,4-benzodioxin-6-yl)-N-[(2,4-diphenyl-1-propyl-1H-imidazol-5-yl)methyl]-N-(3-ethoxybenzyl)methanamine | 573.733 |

TABLE III-continued

| CMP # | STRUCTURE | Ca2+ Mob. | IUPAC NAME | MASS |
|---|---|---|---|---|
| 1137 | 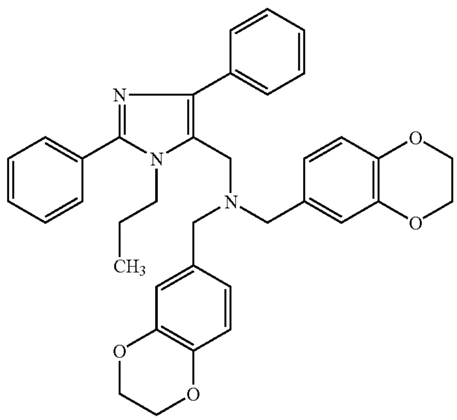 | * | 1-(2,3-dihydro-1,4-benzodioxin-6-yl)-N-(2,3-dihydro-1,4-benzodioxin-6-ylmethyl)-N-[(2,4-diphenyl-1-propyl-1H-imidazol-5-yl)methyl]methanamine | 587.716 |
| 1138 | 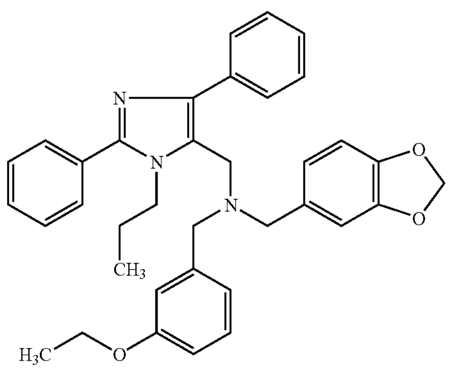 | * | 1-(1,3-benzodioxol-5-yl)-N-[(2,4-diphenyl-1-propyl-1H-imidazol-5-yl)methyl]-N-(3-ethoxybenzyl)methanamine | 559.706 |
| 1139 | 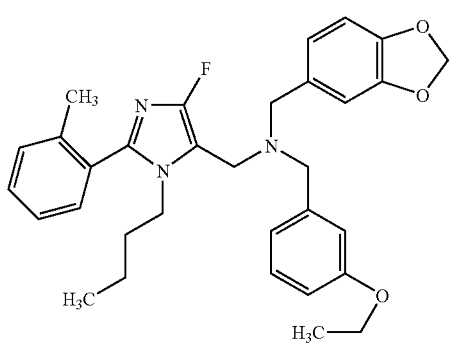 | * | 1-(1,3-benzodioxol-5-yl)-N-{[1-butyl-4-fluoro-2-(2-methylphenyl)-1H-imidazol-5-yl]methyl}-N-(3-ethoxybenzyl)methanamine | 529.652 |
| 1140 | 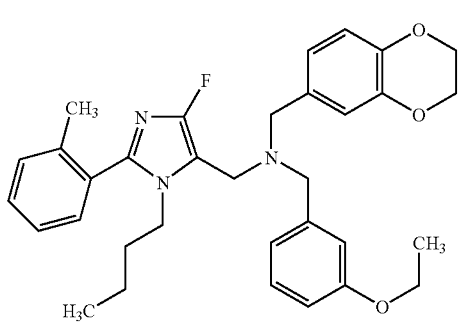 | * | 1-[1-butyl-4-fluoro-2-(2-methylphenyl)-1H-imidazol-5-yl]-N-(2,3-dihydro-1,4-benzodioxin-6-ylmethyl)-N-(3-ethoxybenzyl)methanamine | 543.679 |

TABLE III-continued

| CMP # | STRUCTURE | Ca2+ Mob. | IUPAC NAME | MASS |
|---|---|---|---|---|
| 1141 | 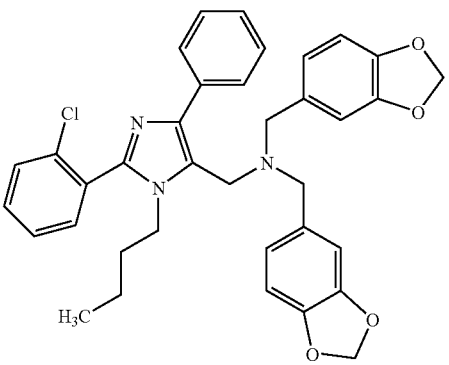 | * | 1-(1,3-benzodioxol-5-yl)-N-(1,3-benzodioxol-5-ylmethyl)-N-{[1-butyl-2-(2-chlorophenyl)-4-phenyl-1H-imidazol-5-yl]methyl}methanamine | 608.135 |
| 1142 | 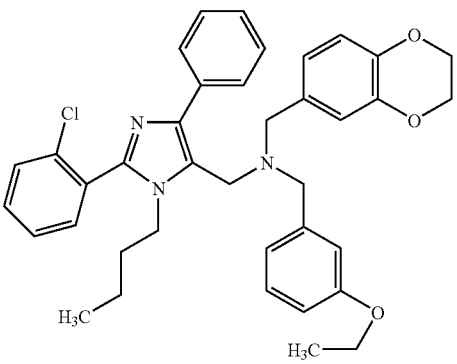 | * | N-{[1-butyl-2-(2-chlorophenyl)-4-phenyl-1H-imidazol-5-yl]methyl}-N-(2,3-dihydro-1,4-benzodioxin-6-ylmethyl)-N-(3-ethoxybenzyl)amine | 622.205 |
| 1143 | 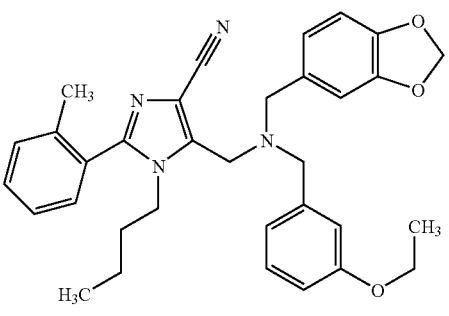 | * | 5-{[(1,3-benzodioxol-5-ylmethyl)(3-ethoxybenzyl)amino]methyl}-1-butyl-2-(2-methylphenyl)-1H-imidazole-4-carbonitrile | 536.672 |
| 1144 | 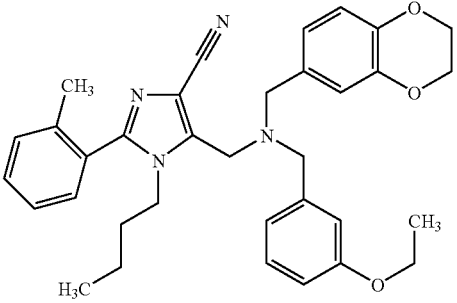 | * | 1-butyl-5-{[(2,3-dihydro-1,4-benzadioxin-6-ylmethyl)(3-ethoxybenzyl)amino]methyl}-2-(2-methylphenyl)-1H-imidazole-4-carbonitrile | 550.699 |

TABLE III-continued

| CMP # | STRUCTURE | Ca2+ Mob. | IUPAC NAME | MASS |
|---|---|---|---|---|
| 1145 | 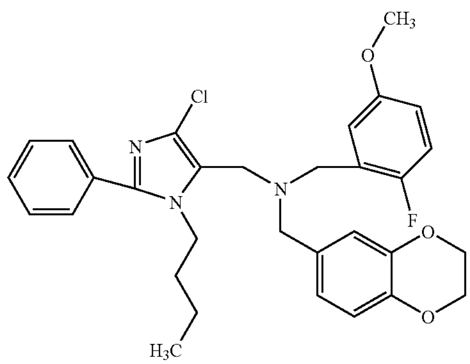 | * | N-[(1-butyl-4-chloro-2-phenyl-1H-imidazol-5-yl)methyl]-N-(2,3-dihydro-1,4-benzodioxin-6-ylmethyl)-N-(2-fluoro-5-methoxybenzyl)amine | 550.071 |
| 1146 | 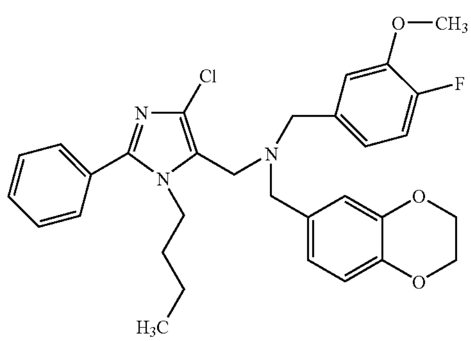 | * | N-[(1-butyl-4-chloro-2-phenyl-1H-imidazol-5-yl)methyl]-N-(2,3-dihydro-1,4-benzodioxin-6-ylmethyl)-N-(4-fluoro-3-methoxybenzyl)amine | 550.071 |
| 1147 | 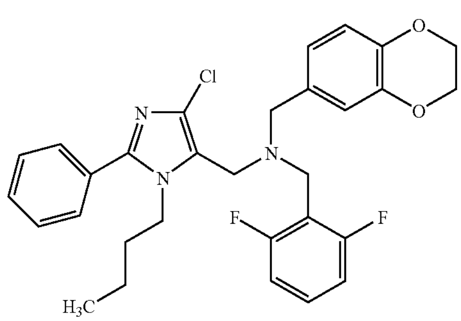 | * | N-[(1-butyl-4-chloro-2-phenyl-1H-imidazol-5-yl)methyl]-N-(2,6-difluorobenzyl)-N-(2,3-dihydro-1,4-benzodioxin-6-ylmethyl)amine | 538.035 |
| 1148 | 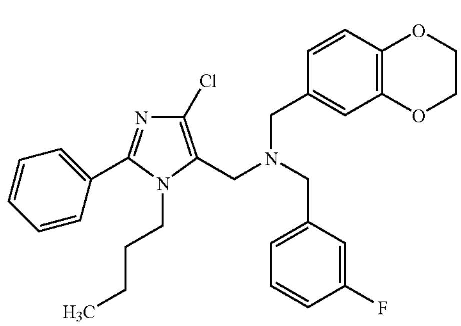 | * | N-[(1-butyl-4-chloro-2-phenyl-1H-imidazol-5-yl)methyl]-N-(2,3-dihydro-1,4-benzodioxin-6-ylmethyl)-N-(3-fluorobenzyl)amine | 520.045 |

TABLE III-continued

| CMP # | STRUCTURE | Ca2+ Mob. | IUPAC NAME | MASS |
|---|---|---|---|---|
| 1149 | 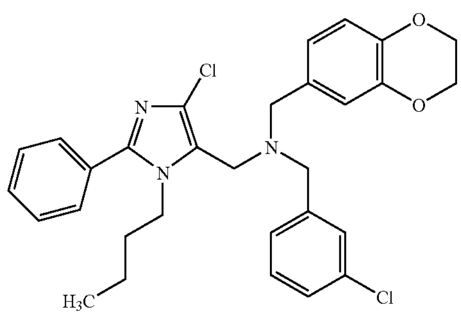 | * | N-[(1-butyl-4-chloro-2-phenyl-1H-imidazol-5-yl)methyl]-N-(3-chlorobenzyl)-N-(2,3-dihydro-1,4-benzodioxin-6-ylmethyl)amine | 536.5 |
| 1150 | 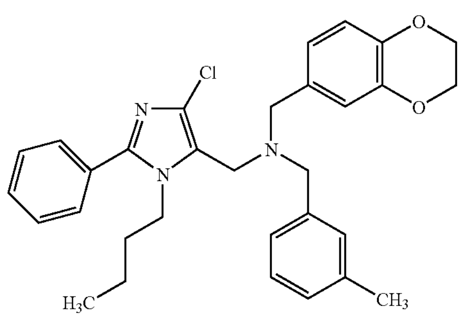 | * | N-[(1-butyl-4-chloro-2-phenyl-1H-imidazol-5-yl)methyl]-N-(2,3-dihydro-1,4-benzodioxin-6-ylmethyl)-N-(3-methylbenzyl)amine | 516.082 |
| 1151 | 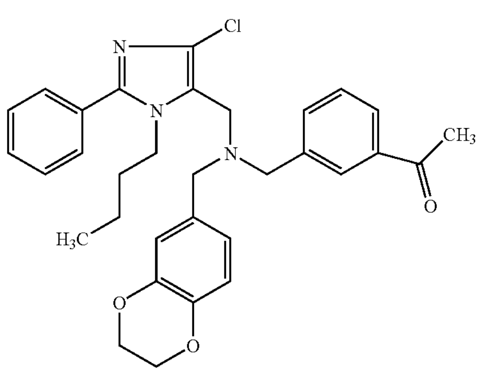 | * | 1-(3-{[[(1-butyl-4-chloro-2-phenyl-1H-imidazol-5-yl)methyl](2,3-dihydro-1,4-benzodioxin-6-ylmethyl)amino]methyl}phenyl)ethanone | 544.092 |
| 1152 | 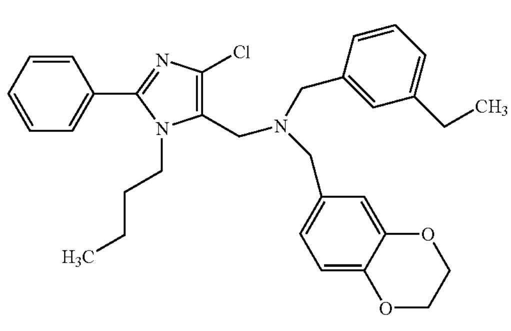 | * | N-[(1-butyl-4-chloro-2-phenyl-1H-imidazol-5-yl)methyl]-N-(2,3-dihydro-1,4-benzodioxin-6-ylmethyl)-N-(3-methoxybenzyl)amine | 532.081 |

TABLE III-continued

| CMP # | STRUCTURE | Ca2+ Mob. | IUPAC NAME | MASS |
|---|---|---|---|---|
| 1153 | 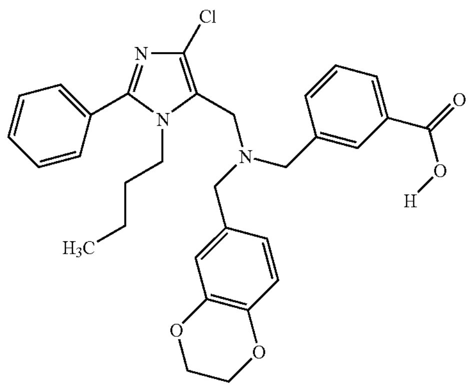 | * | 3-{[[(1-butyl-4-chloro-2-phenyl-1H-imidazol-5-yl)methyl](2,3-dihydro-1,4-benzodioxin-6-ylmethyl)amino]methyl}benzoic acid | 546.064 |
| 1154 | 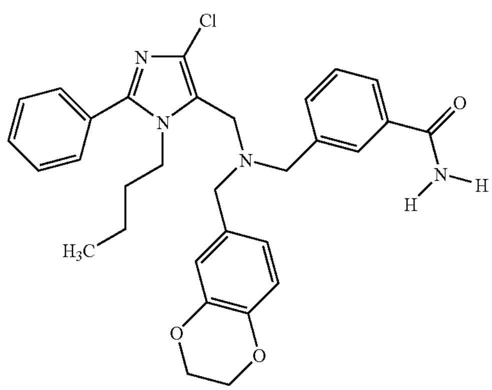 | * | 3-{[[(1-butyl-4-chloro-2-phenyl-1H-imidazol-5-yl)methyl](2,3-dihydro-1,4-benzodioxin-6-ylmethyl)amino]methyl}benzamide | 545.08 |
| 1155 | 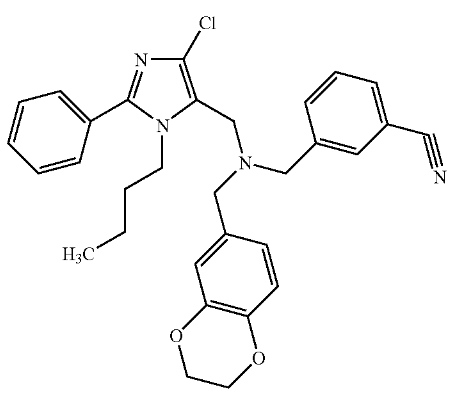 | * | 3-{[[(1-butyl-4-chloro-2-phenyl-1H-imidazol-5-yl)methyl](2,3-dihydro-1,4-benzodioxin-6-ylmethyl)amino]methyl}benzonitrile | 527.065 |
| 1156 | 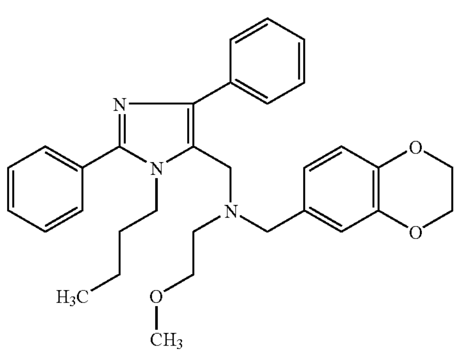 | * | N-[(1-butyl-2,4-diphenyl-1H-imidazol-5-yl)methyl]-N-(2,3-dihydro-1,4-benzodioxin-6-ylmethyl)-2-methoxyethanamine | 511.662 |

TABLE III-continued

| CMP # | STRUCTURE | Ca2+ Mob. | IUPAC NAME | MASS |
|---|---|---|---|---|
| 1157 | 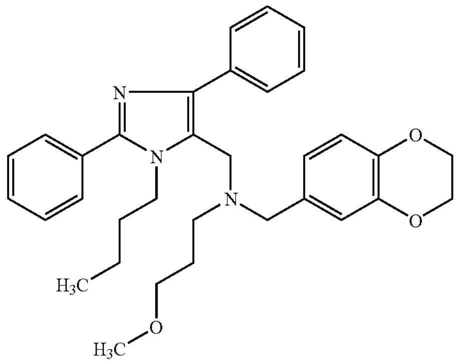 | * | N-[(1-butyl-2,4-diphenyl-1H-imidazol-5-yl)methyl]-N-(2,3-dihydro-1,4-benzodioxin-6-ylmethyl)-3-methoxypropan-1-amine | 525.689 |
| 1158 | 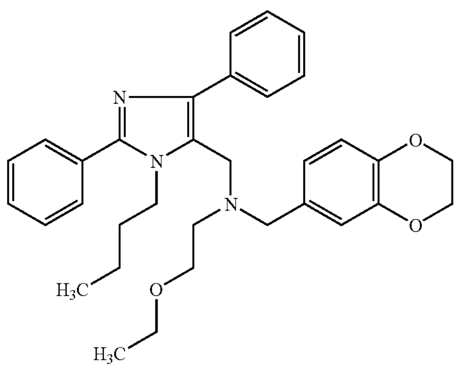 | * | N-[(1-butyl-2,4-diphenyl-1H-imidazol-5-yl)methyl]-N-(2,3-dihydro-1,4-benzodioxin-6-ylmethyl)-2-ethoxyethanamine | 525.689 |
| 1159 | 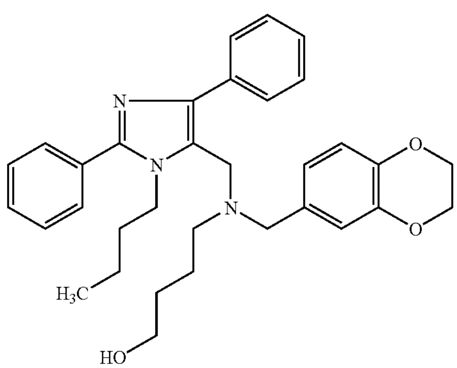 | * | 4-[[(1-butyl-2,4-diphenyl-1H-imidazol-5-yl)methyl](2,3-dihydro-1,4-benzodioxin-6-ylmethyl)amino]butan-1-ol | 525.689 |
| 1160 | 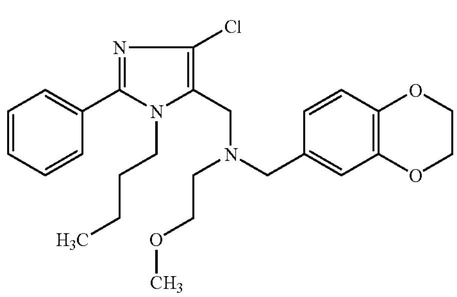 | * | N-[(1-butyl-4-chloro-2-phenyl-1H-imidazol-5-yl)methyl]-N-(2,3-dihydro-1,4-benzodioxin-6-ylmethyl)-2-methoxyethanamine | 470.01 |

TABLE III-continued

| CMP # | STRUCTURE | Ca2+ Mob. | IUPAC NAME | MASS |
|---|---|---|---|---|
| 1161 | 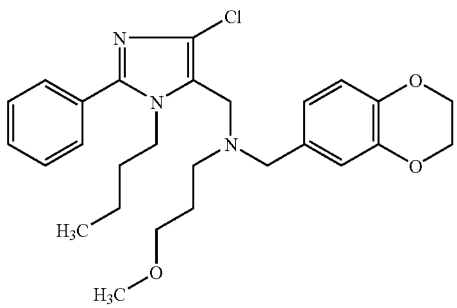 | * | N-[(1-butyl-4-chloro-2-phenyl-1H-imidazol-5-yl)methyl]-N-(2,3-dihydro-1,4-benzodioxin-6-ylmethyl)-3-methoxypropan-1-amine | 484.037 |
| 1162 | 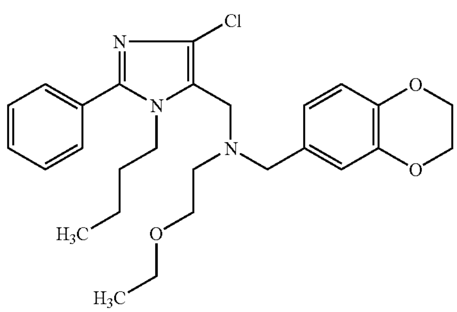 | * | N-[(1-butyl-4-chloro-2-phenyl-1H-imidazol-5-yl)methyl]-N-(2,3-dihydro-1,4-benzodioxin-6-ylmethyl)-2-ethoxyethanamine | 484.037 |
| 1163 | 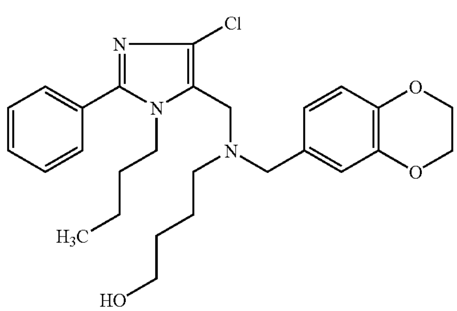 | * | 4-[[(1-butyl-4-chloro-2-phenyl-1H-imidazol-5-yl)methyl](2,3-dihydro-1,4-benzodioxin-6-ylmethyl)amino]butan-1-ol | 484.037 |
| 1164 | 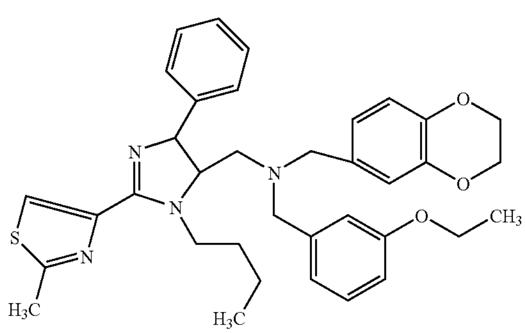 | * | 1-[1-butyl-2-(2-methyl-1,3-thiazol-4-yl)-4-phenyl-1H-imidazol-5-yl]-N-(2,3-dihydro-1,4-benzodioxin-6-ylmethyl)-N-(3-ethoxybenzyl)methanamine | 608.803 |

TABLE III-continued

| CMP # | STRUCTURE | Ca2+ Mob. | IUPAC NAME | MASS |
|---|---|---|---|---|
| 1165 | 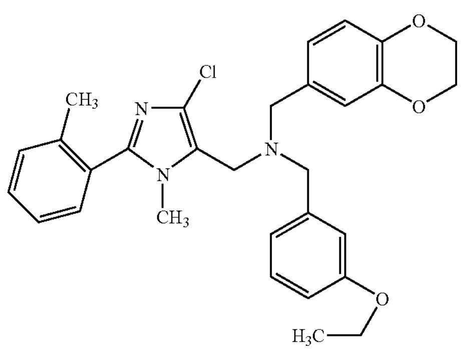 | * | 1-[4-chloro-1-methyl-2-(2-methylphenyl)-1H-imidazol-5-yl]-N-(2,3-dihydro-1,4-benzodioxin-6-ylmethyl)-N-(3-ethoxybenzyl)methanamine | 518.054 |
| 1166 | 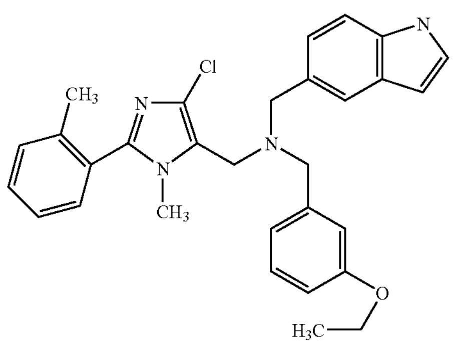 | * | 1-[4-chloro-1-methyl-2-(2-methylphenyl)-1H-imidazol-5-yl]-N-(3-ethoxybenzyl)-N-(1H-indol-5-ylmethyl)methanamine | 499.055 |
| 1167 | 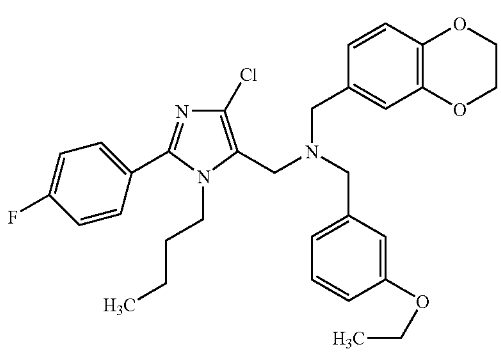 | * | 1-[1-butyl-4-chloro-2-(4-fluorophenyl)-1H-imidazol-5-yl]-N-(2,3-dihydro-1,4-benzodioxin-6-ylmethyl)-N-(3-ethoxybenzyl)methanamine | 564.097 |
| 1168 | 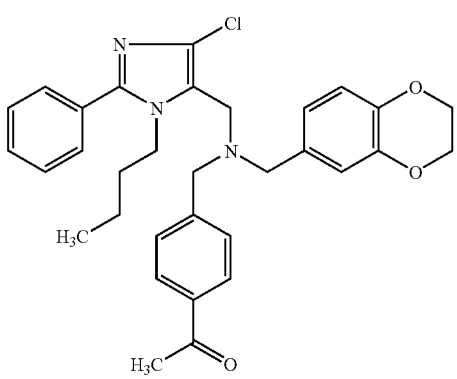 | * | 1-(4-{[[(1-butyl-4-chloro-2-phenyl-1H-imidazol-5-yl)methyl](2,3-dihydro-1,4-benzodioxin-6-ylmethyl)amino]methyl}phenyl)ethanone | 544.092 |

TABLE III-continued

| CMP # | STRUCTURE | Ca2+ Mob. | IUPAC NAME | MASS |
|---|---|---|---|---|
| 1169 | 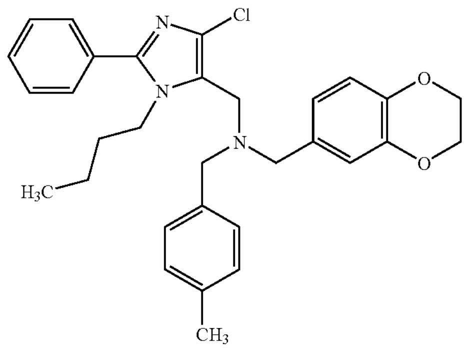 | * | N-[(1-butyl-4-chloro-2-phenyl-1H-imidazol-5-yl)methyl]-N-(2,3-dihydro-1,4-benzodioxin-6-ylmethyl)-N-(4-methylbenzyl)amine | 516.082 |
| 1170 | 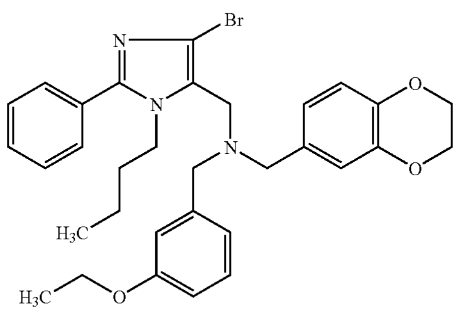 | * | N-[(4-bromo-1-butyl-2-phenyl-1H-imidazol-5-yl)methyl]-N-(2,3-dihydro-1,4-benzodioxin-6-ylmethyl)-N-(3-ethoxybenzyl)amine | 590.558 |
| 1171 | 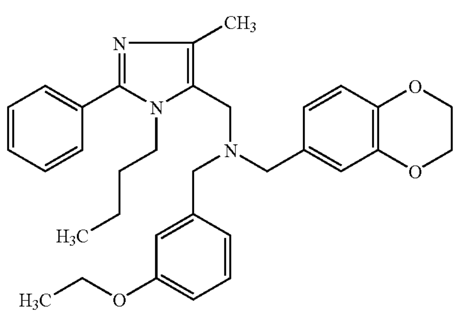 | * | N-[(1-butyl-4-methyl-2-phenyl-1H-imidazol-5-yl)methyl]-N-(2,3-dihydro-1,4-benzodioxin-6-ylmethyl)-N-(3-ethoxybenzyl)amine | 525.689 |
| 1172 | 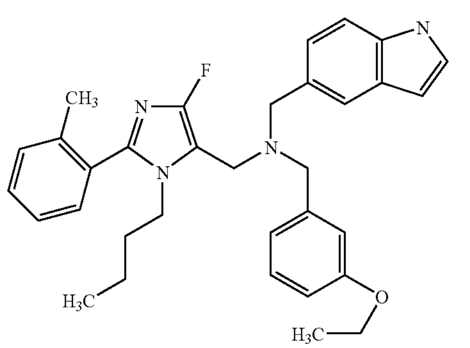 | * | 1-[1-butyl-4-fluoro-2-(2-methylphenyl)-1H-imidazol-5-yl]-N-(3-ethoxybenzyl)-N-(1H-indol-5-ylmethyl)methanamine | 524.68 |

TABLE III-continued

| CMP # | STRUCTURE | Ca2+ Mob. | IUPAC NAME | MASS |
|---|---|---|---|---|
| 1173 | 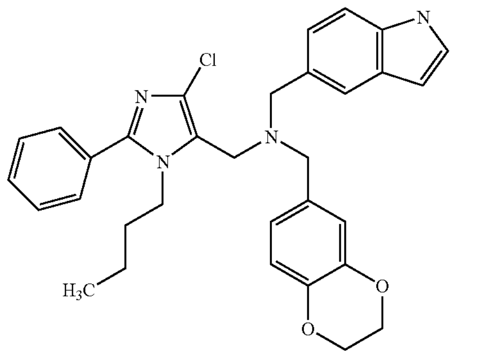 | * | N-[(1-butyl-4-chloro-2-phenyl-1H-imidazol-5-yl)methyl]-N-(2,3-dihydro-1,4-benzodioxin-6-ylmethyl)-N-(1H-indol-5-ylmethyl)amine | 541.092 |
| 1174 | 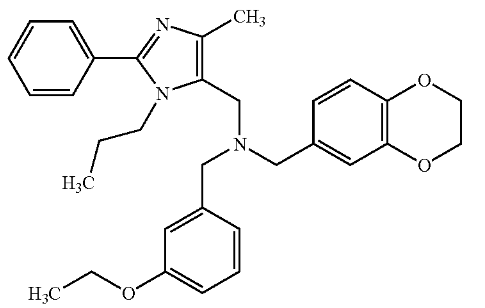 | * | 1-(2,3-dihydro-1,4-benzodioxin-6-yl)-N-(3-ethoxybenzyl)-N-[(4-methyl-2-phenyl-1-propyl-1H-imidazol-5-yl)methyl]methanamine | 511.662 |
| 1175 | 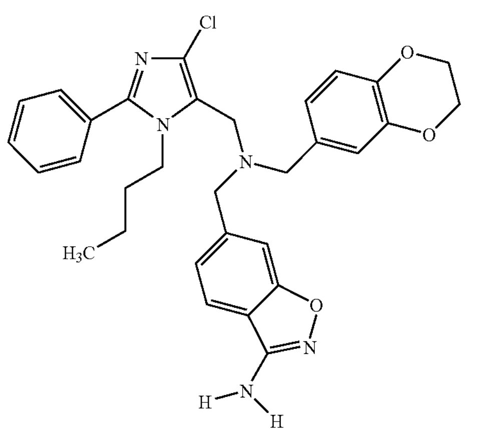 | * | 6-{[[(1-butyl-4-chloro-2-phenyl-1H-imidazol-5-yl)methyl](2,3-dihydro-1,4-benzodioxin-6-ylmethyl)amino]methyl}-1,2-benzisoxazol-3-amine | 558.079 |
| 1176 | 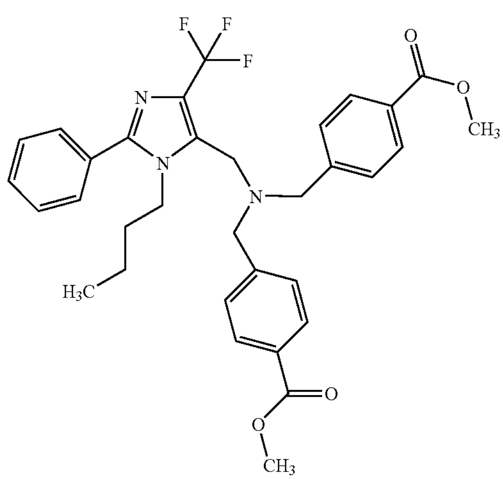 | * | | 593.643 |

TABLE III-continued

| CMP # | STRUCTURE | Ca2+ Mob. | IUPAC NAME | MASS |
|---|---|---|---|---|
| 1177 | 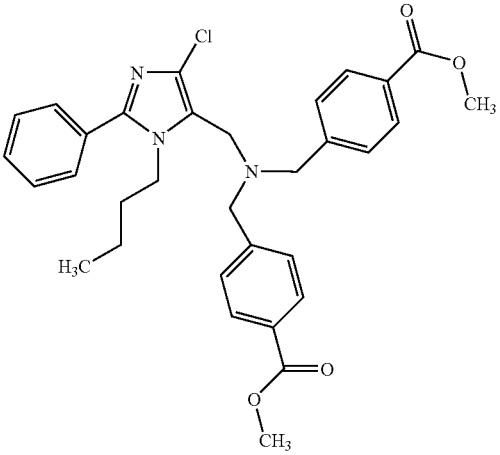 | * | | 560.091 |
| 1178 | 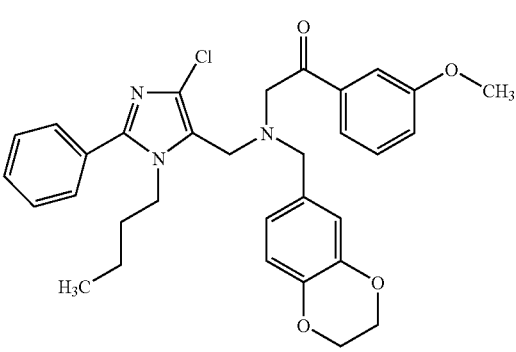 | * | 2-[[(1-butyl-4-chloro-2-phenyl-1H-imidazol-5-yl)methyl](2,3-dihydro-1,4-benzodioxin-6-ylmethyl)amino]-1-(3-methoxyphenyl)ethanone | 560.091 |
| 1179 | 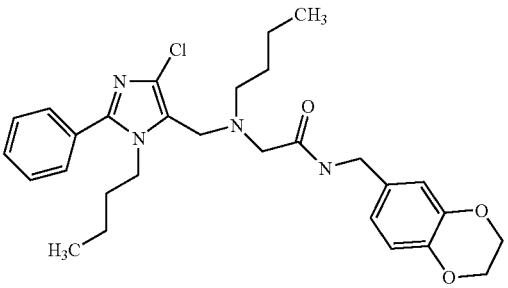 | * | N~2~-butyl-N~2~-{(1-butyl-4-chloro-2-phenyl-1H-imidazol-5-yl)methyl]-N~1~-(2,3-dihydro-1,4-benzodioxin-6-ylmethyl)glycinamide | 525.089 |
| 1180 | 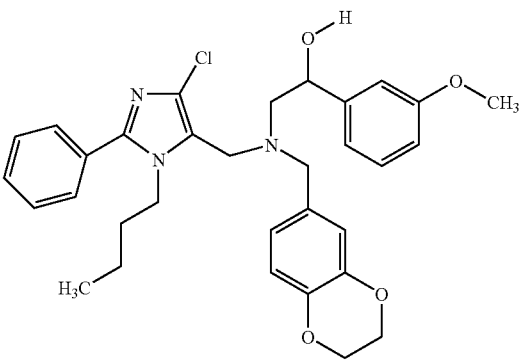 | * | 2-[[(1-butyl-4-chloro-2-phenyl-1H-imidazol-5-yl)methyl](2,3-dihydro-1,4-benzadioxin-6-ylmethyl)amino]-1-(3-methoxyphenyl)ethanol | 562.106 |

TABLE III-continued

| CMP # | STRUCTURE | Ca2+ Mob. | IUPAC NAME | MASS |
|---|---|---|---|---|
| 1181 | 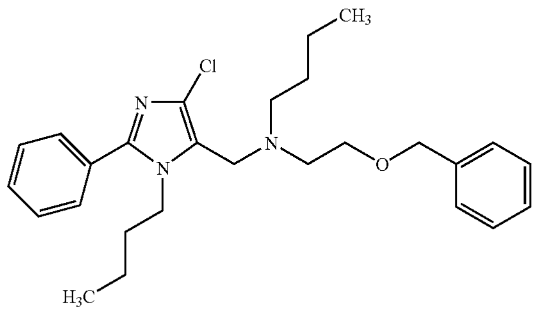 | * | N-[2-(benzyloxy)ethyl]-N-[(1-butyl-4-chloro-2-phenyl-1H-imidazol-5-yl)methyl]butan-1-amine | 454.054 |
| 1182 | 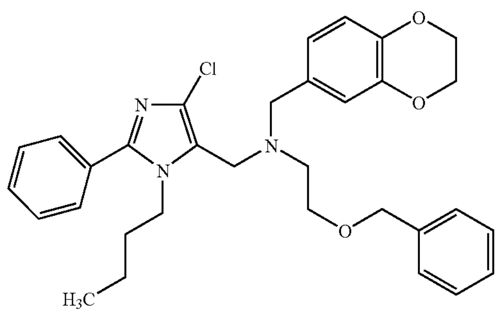 | * | N-[2-(benzyloxy)ethyl]-N-[(1-butyl-4-chloro-2-phenyl-1H-imidazol-5-yl)methyl]-N-(2,3-dihydro-1,4-benzodioxin-6-ylmethyl)amine | 546.107 |
| 1183 | 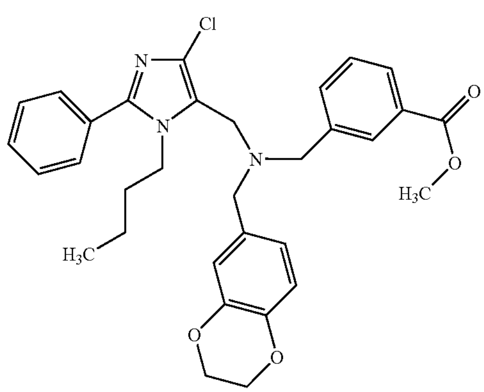 | * | methyl 3-{[[(1-butyl-4-chloro-2-phenyl-1H-imidazol-5-yl)methyl](2,3-dihydro-1,4-benzodioxin-6-ylmethyl)amino]methyl}benzoate | 560.091 |
| 1184 | 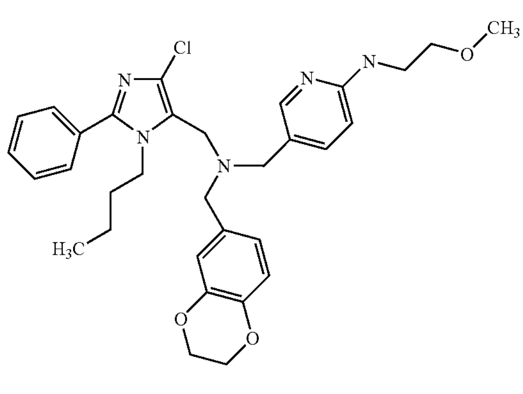 | * | 5-{[[(1-butyl-4-chloro-2-phenyl-1H-imidazol-5-yl)methyl](2,3-dihydro-1,4-benzodioxin-6-ylmethyl)amino]methyl}-N-(2-methoxyethyl)pyridin-2-amine | 576.137 |

TABLE III-continued

| CMP # | STRUCTURE | Ca2+ Mob. | IUPAC NAME | MASS |
|---|---|---|---|---|
| 1185 | 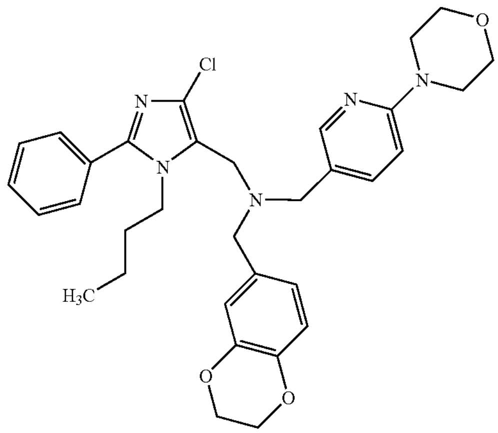 | * | N-[(1-butyl-4-chloro-2-phenyl-1H-imidazol-5-yl)methyl]-N-(2,3-dihydro-1,4-benzodioxin-6-ylmethyl)-N-[(6-morpholin-4-ylpyridin-3-yl)methyl]amine | 588.148 |
| 1186 | 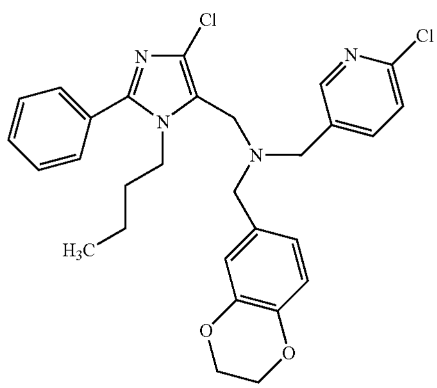 | * | N-[(1-butyl-4-chloro-2-phenyl-1H-imidazol-5-yl)methyl]-N-[(6-chloropyridin-3-yl)methyl]-N-(2,3-dihydro-1,4-benzodioxin-6-ylmethyl)amine | 537.488 |
| 1187 | 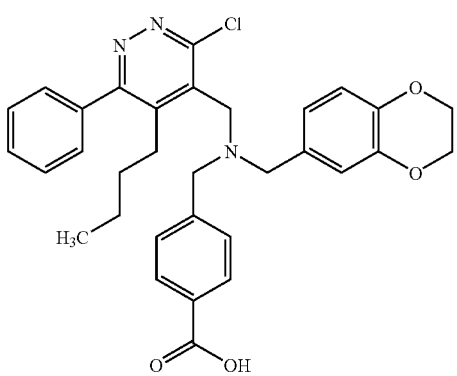 | * | 4-{[[(5-butyl-3-chloro-6-phenylpyridazin-4-yl)methyl](2,3-dihydro-1,4-benzodioxin-6-ylmethyl)amino]methyl}benzoic acid | 558.075 |
| 1188 | 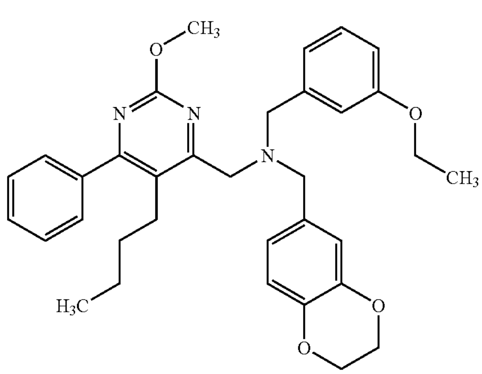 | * | 1-(5-butyl-2-methoxy-6-phenylpyrimidin-4-yl)-N-(2,3-dihydro-1,4-benzodioxin-6-ylmethyl)-N-(3-ethoxybenzyl)methanamine | 553.699 |

TABLE III-continued

| CMP # | STRUCTURE | Ca2+ Mob. | IUPAC NAME | MASS |
|---|---|---|---|---|
| 1189 | 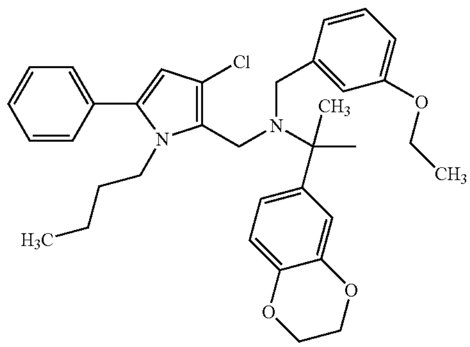 | * | N-[(1-butyl-4-chloro-2-phenyl-1H-imidazol-5-yl)methyl]-2-(2,3-dihydro-1,4-benzodioxin-6-yl)-N-(3-ethoxybenzyl)propan-2-amine | 574.161 |
| 1190 | 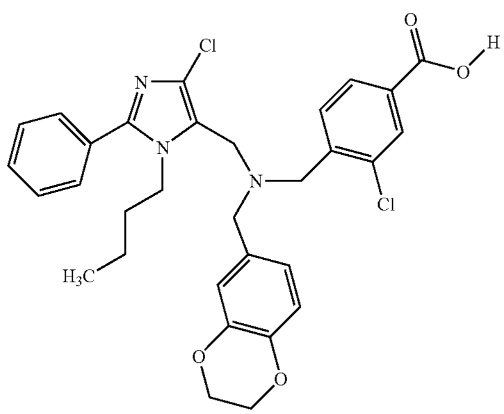 | * | 4-{[[(1-butyl-4-chloro-2-phenyl-1H-imidazol-5-yl)methyl](2,3-dihydro-1,4-benzodioxin-6-ylmethyl)amino]methyl}-3-chlorobenzoic acid | 580.509 |
| 1191 | 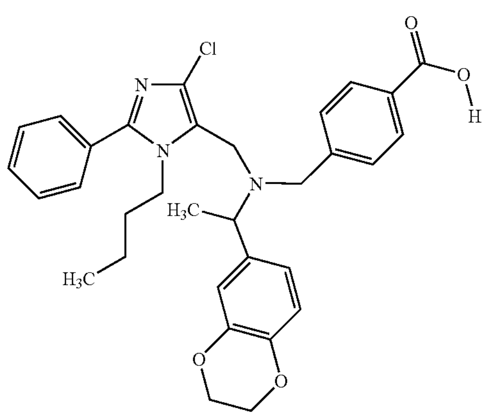 | * | 4-({[[(1-butyl-4-chloro-2-phenyl-1H-imidazol-5-yl)methyl][1-(2,3-dihydro-1,4-benzodioxin-6-yl)ethyl]amino}methyl)benzoic acid | 560.091 |
| 1192 | 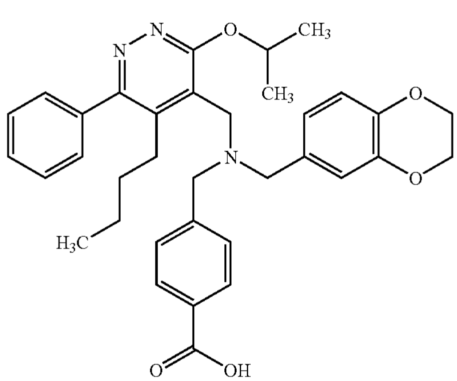 | * | 4-{[[(5-butyl-3-isopropoxy-6-phenylpyridazin-4-yl)methyl](2,3-dihydro-1,4-benzodioxin-6-ylmethyl)amino]methyl}benzoic acid | 581.709 |

TABLE III-continued

| CMP # | STRUCTURE | Ca2+ Mob. | IUPAC NAME | MASS |
|---|---|---|---|---|
| 1193 | 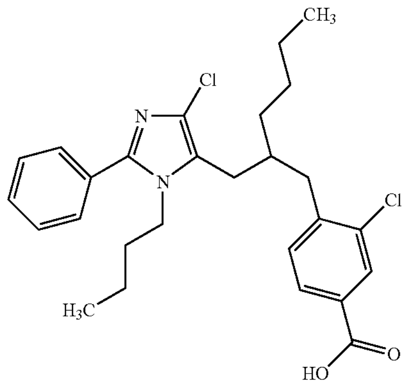 | * | 4-({butyl[(1-butyl-4-chloro-2-phenyl-1H-imidazol-5-yl)methyl]amino}methyl)-3-chlorobenzoic acid | 488.456 |
| 1194 | 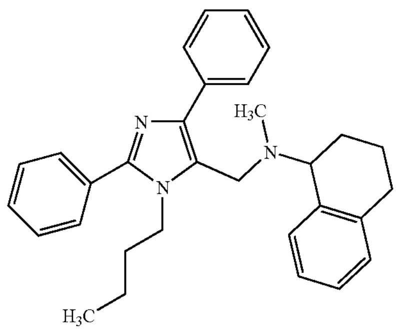 | * | N-[(1-butyl-2,4-diphenyl-1H-imidazol-5-yl)methyl]-N-methyl-1,2,3,4-tetrahydronaphthalen-1-amine | 449.638 |
| 1195 | 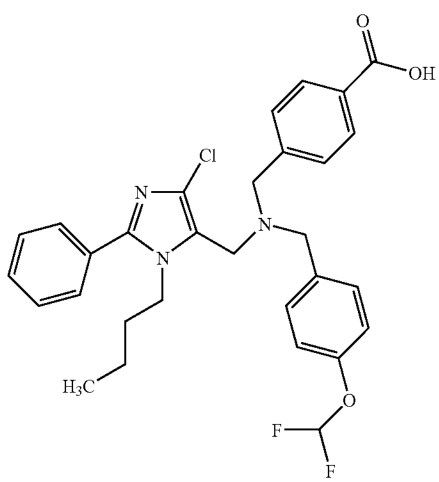 | * | 4-({[(1-butyl-4-chloro-2-phenyl-1H-imidazol-5-yl)methyl][4-(difluoromethoxy)benzyl]amino}methyl)benzoic acid | 554.034 |
| 1196 | 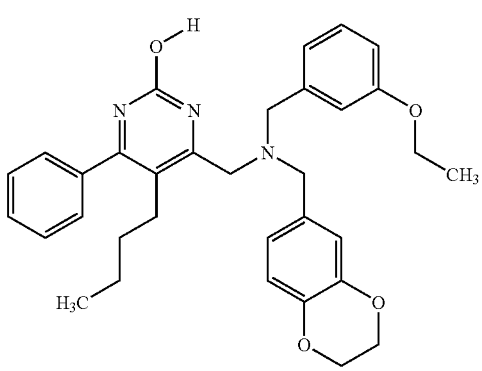 | * | 5-butyl-4-{[(2,3-dihydro-1,4-benzodioxin-6-ylmethyl)(3-ethoxybenzyl)amino]methyl}-6-phenylpyrimidin-2-ol | 539.672 |

TABLE III-continued

| CMP # | STRUCTURE | Ca2+ Mob. | IUPAC NAME | MASS |
|---|---|---|---|---|
| 1197 | 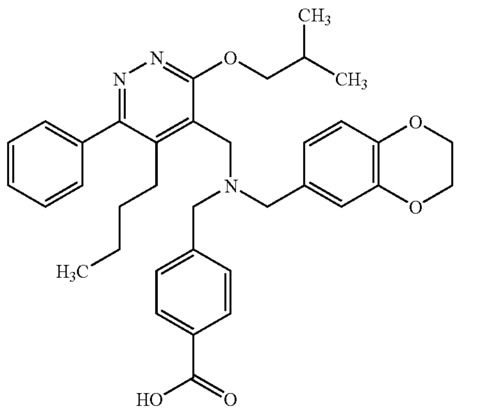 | * | 4-{[[(5-butyl-3-isobutoxy-6-phenypyridazin-4-yl)methyl](2,3-dihydro-1,4-benzodioxin-6-ylmethyl)amino]methyl}benzoic acid | 595.736 |
| 1198 | 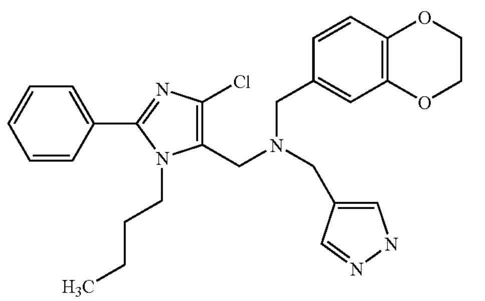 | * | N-[(1-butyl-4-chloro-2-phenyl-1H-imidazol-5-yl)methyl]-N-(2,3-dihydro-1,4-benzodioxin-6-ylmethyl)-N-(1H-pyrazol-4-ylmethyl)amine | 492.02 |
| 1199 | 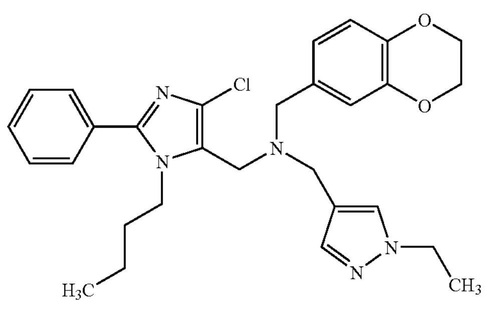 | * | N-[(1-butyl-4-chloro-2-phenyl-1H-imidazol-5-yl)methyl]-N-(2,3-dihydro-1,4-benzodioxin-6-ylmethyl)-N-[(1-ethyl-1H-pyrazol-4-yl)methyl]amine | 520.074 |
| 1200 | 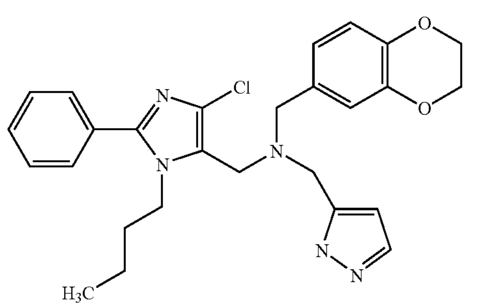 | * | N-[(1-butyl-4-chloro-2-phenyl-1H-imidazol-5-yl)methyl]-N-(2,3-dihydro-1,4-benzodioxin-6-ylmethyl)-N-(1H-pyrazol-5-ylmethyl)amine | 492.02 |

TABLE III-continued

| CMP # | STRUCTURE | Ca2+ Mob. | IUPAC NAME | MASS |
|---|---|---|---|---|
| 1201 | 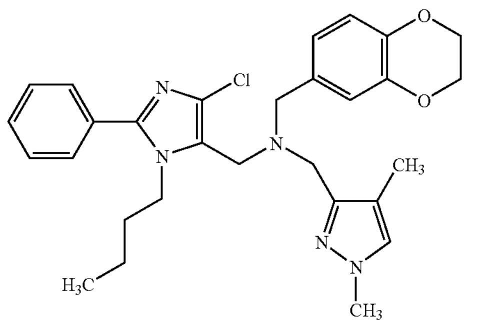 | * | N-[(1-butyl-4-chloro-2-phenyl-1H-imidazol-5-yl)methyl]-N-(2,3-dihydro-1,4-benzodioxin-6-ylmethyl)-N-[(1,4-dimethyl-1H-pyrazol-3-yl)methyl]amine | 520.074 |
| 1202 | 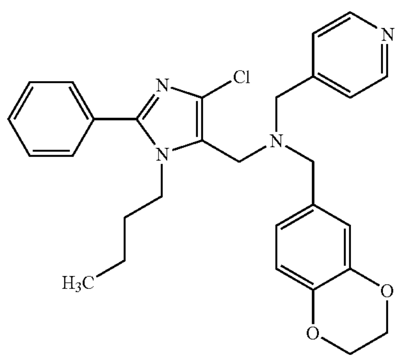 | * | N-[(1-butyl-4-chloro-2-phenyl-1H-imadazol-5-yl)methyl]-N-(2,3-dihydro-1,4-benzodioxin-6-ylmethyl)-N-(pyridin-4-ylmethyl)amine | 503.043 |
| 1203 | 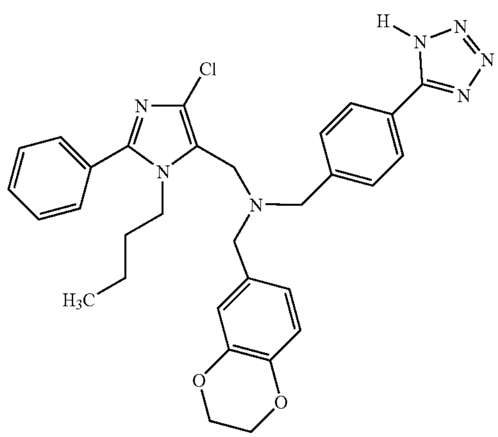 | * | N-[(1-butyl-4-chloro-2-phenyl-1H-imidazol-5-yl)methyl]-N-(2,3-dihydro-1,4-benzodioxin-6-ylmethyl)-N-[4-(1H-tetraazol-5-yl)benzyl]amine | 570.094 |
| 1204 | 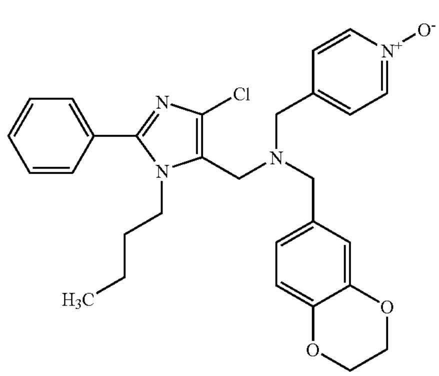 | * | N-[(1-butyl-4-chloro-2-phenyl-1H-imidazol-5-yl)methyl]-N-(2,3-dihydro-1,4-benzodioxin-6-ylmethyl)-N-[(1-oxidopyridin-4-yl)methyl]amine | 519.042 |

TABLE III-continued

| CMP # | STRUCTURE | Ca2+ Mob. | IUPAC NAME | MASS |
|---|---|---|---|---|
| 1205 | 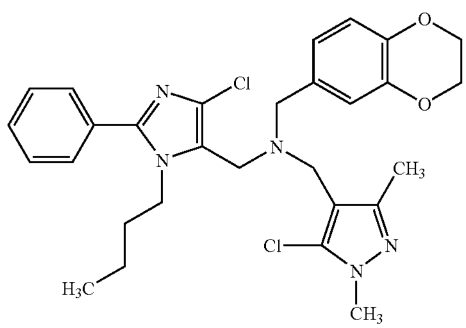 | * | N-[(1-butyl-4-chloro-2-phenyl-1H-imidazol-5-yl)methyl]-N-[(5-chloro-1,3-dimethyl-1H-pyrazol-4-yl)methyl]-N-(2,3-dihydro-1,4-benzodioxin-6-ylmethyl)amine | 554.519 |
| 1206 | 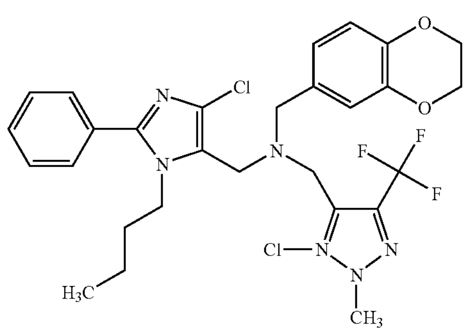 | * | N-[(1-butyl-4-chloro-2-phenyl-1H-imidazol-5-yl)methyl]-N-{[5-chloro-1-methyl-3-(trifluoromethyl)-1H-pyrazol-4-yl]methyl}-N-(2,3-dihydro-1,4-benzodioxin-6-ylmethyl)amine | 608.489 |
| 1207 | 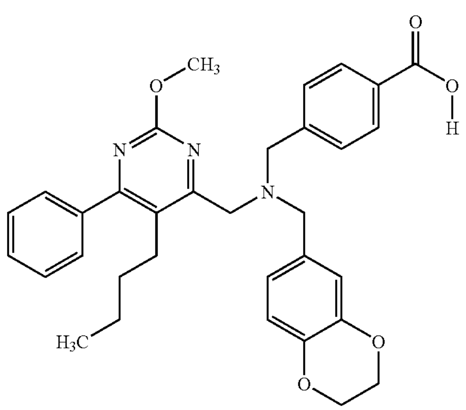 | * | 4-{[[(5-butyl-2-methoxy-6-phenylpyrimidin-4-yl)methyl](2,3-dihydro-1,4-benzodioxin-6-ylmethyl)amino]methyl}benzoic acid | 553.656 |
| 1208 | 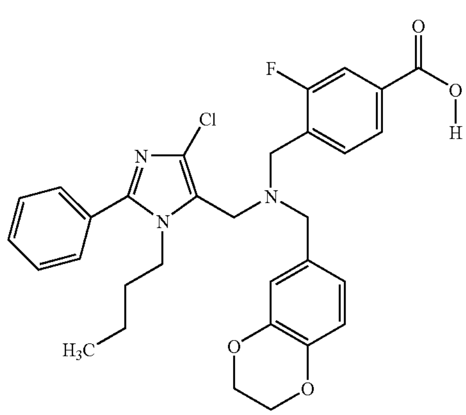 | * | 4-{[[(1-butyl-4-chloro-2-phenyl-1H-imidazol-5-yl)methyl](2,3-dihydro-1,4-benzodioxin-6-ylmethyl)amino]methyl}-3-fluorobenzoic acid | 564.054 |

TABLE III-continued

| CMP # | STRUCTURE | Ca2+ Mob. | IUPAC NAME | MASS |
|---|---|---|---|---|
| 1209 | 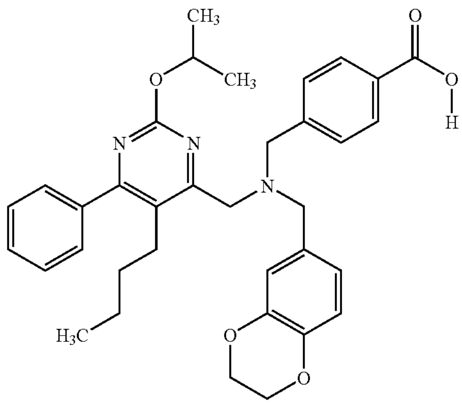 | * | 4-{[[(5-butyl-2-isopropoxy-6-phenylpyrimidin-4-yl)methyl](2,3-dihydro-1,4-benzodioxin-6-ylmethyl)amino]methyl}benzoic acid | 581.709 |
| 1210 | 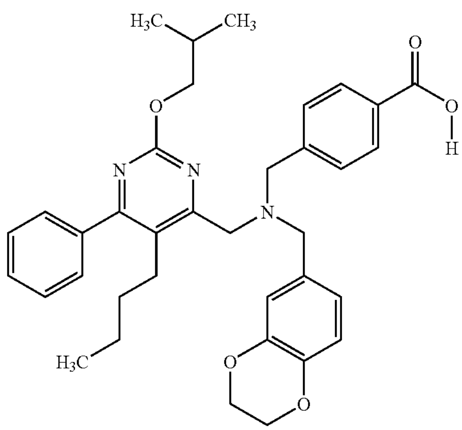 | * | 4-{[[(5-butyl-2-isobutoxy-6-phenylpyrimidin-4-yl)methyl](2,3-dihydro-1,4-benzodioxin-6-ylmethyl)amino]methyl}benzoic acid | 595.736 |
| 1211 | 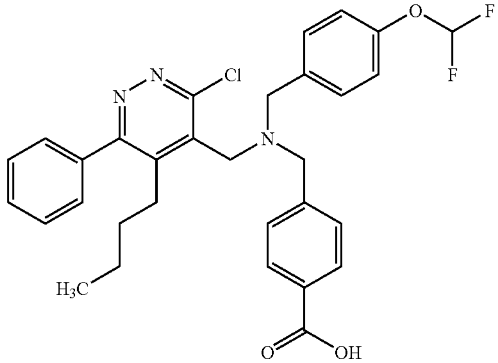 | * | 4-({[(5-butyl-3-chloro-6-phenylpyridazin-4-yl)methyl][4-(difluoromethoxy)benzyl]amino}methyl)benzoic acid | 566.045 |

TABLE III-continued
| CMP # | STRUCTURE | Ca2+ Mob. | IUPAC NAME | MASS |
|---|---|---|---|---|
| 1212 | 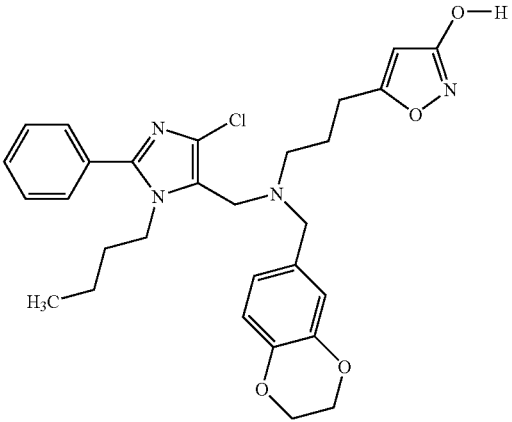 | * | 5-{3-[[(1-butyl-4-chloro-2-phenyl-1H-imidazol-5-yl)methyl](2,3-dihydro-1,4-benzodioxin-6-ylmethyl)amino]propyl}isoxazol-3-ol | 537.057 |
| 1213 | 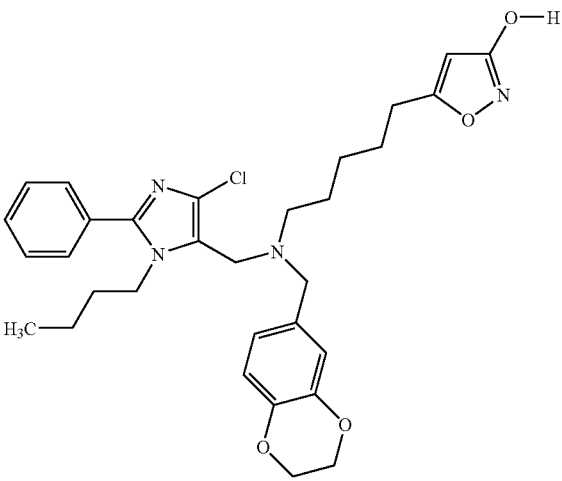 | * | 5-{5-[[(1-butyl-4-chloro-2-phenyl-1H-imidazol-5-yl)methyl](2,3-dihydro-1,4-benzodioxin-6-ylmethyl)amino]pentyl}isoxazol-3-ol | 565.11 |
| 1214 | 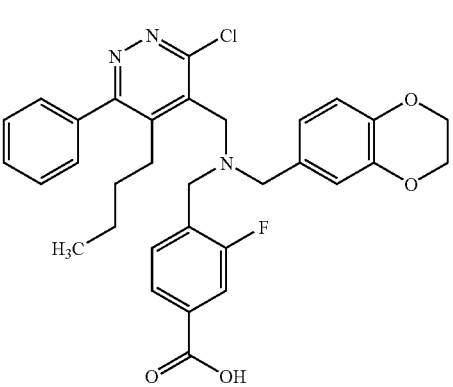 | * | 4-{[[(5-butyl-3-chloro-6-phenylpyridazin-4-yl)methyl](2,3-dihydro-1,4-benzodioxin-6-ylmethyl)amino]methyl}-3-fluorobenzoic acid | 576.065 |

TABLE III-continued

| CMP # | STRUCTURE | Ca2+ Mob. | IUPAC NAME | MASS |
|---|---|---|---|---|
| 1215 | 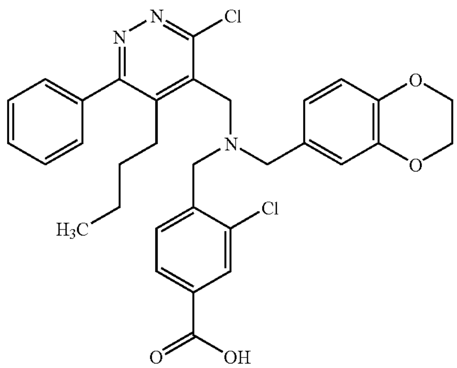 | * | 4-{[[(5-butyl-3-chloro-6-phenylpyridazin-4-yl)methyl](2,3-dihydro-1,4-benzodioxin-6-ylmethyl)amino]methyl}-3-chlorobenzoic acid | 592.52 |
| 1216 | 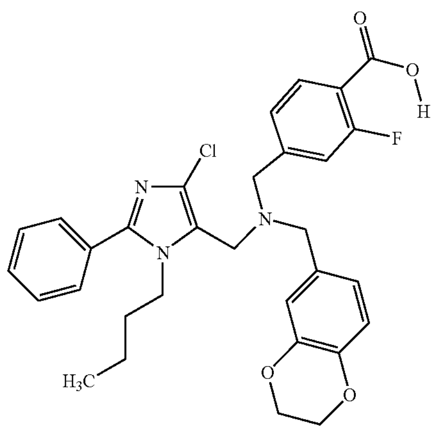 | * | 4-{[[(1-butyl-4-Chloro-2-phenyl-1H-imidazol-5-yl)methyl](2,3-dihydro-1,4-benzodioxin-6-ylmethyl)amino]methyl}-2-fluorobenzoic acid | 564.054 |
| 1217 | 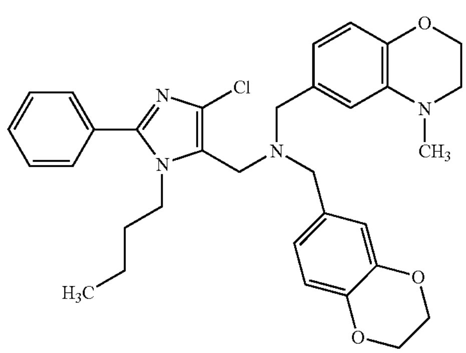 | * | N-[(1-butyl-4-chloro-2-phenyl-1H-imidazol-5-yl)methyl]-N-(2,3-dihydro-1,4-benzodioxin-6-ylmethyl)-N-[(4-methyl-3,4-dihydro-2H-1,4-benzoxazin-6-yl)methyl]amine | 573.133 |
| 1218 | 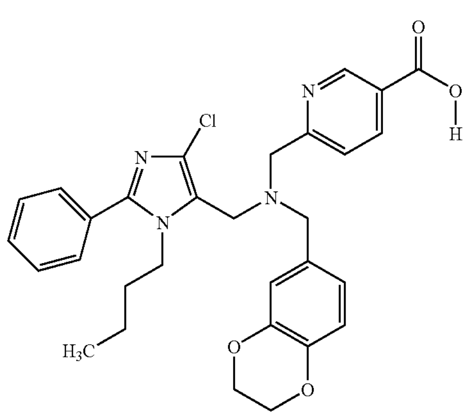 | * | 6-{[[(1-butyl-4-chloro-2-phenyl-1H-imidazol-5-yl)methyl](2,3-dihydro-1,4-benzodioxin-6-ylmethyl)amino]methyl}nicotinic acid | 547.052 |

TABLE III-continued

| CMP # | STRUCTURE | Ca2+ Mob. | IUPAC NAME | MASS |
|---|---|---|---|---|
| 1219 | 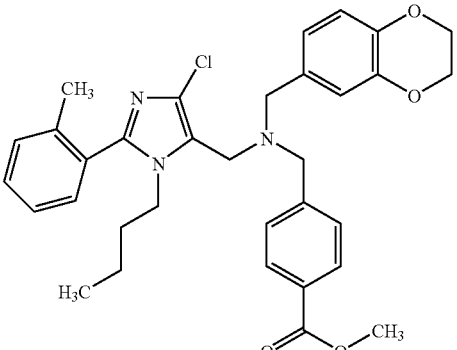 | * | methyl 4-{[{[1-butyl-4-chloro-2-(2-methylphenyl)-1H-imidazol-5-yl]methyl}(2,3-dihydro-1,4-benzodioxin-6-ylmethyl)amino]methyl}benzoate | 574.117 |
| 1220 | 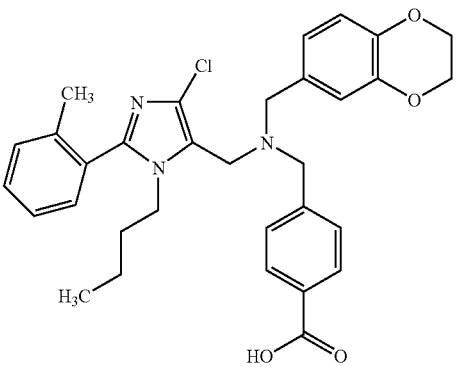 | * | 4-{[{[1-butyl-4-chloro-2-(2-methylphenyl)-1H-imidazol-5-yl]methyl}(2,3-dihydro-1,4-benzodioxin-6-ylmethyl)amino]methyl}benzoic acid | 560.091 |
| 1221 | 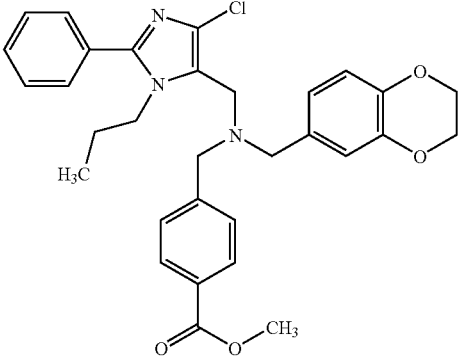 | * | methyl 4-{[[(4-chloro-2-phenyl-1-propyl-1H-imidazol-5-yl)methyl](2,3-dihydro-1,4-benzodioxin-6-ylmethyl)amino]methyl}benzoate | 546.064 |
| 1222 | 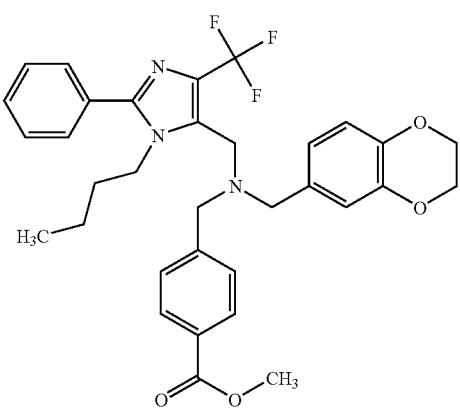 | * | methyl 4-{[{[1-butyl-2-phenyl-4-(trifluoromethyl)-1H-imidazol-5-yl]methyl}(2,3-dihydro-1,4-benzodioxin-6-ylmethyl)amino]methyl}benzoate | 593.643 |

TABLE III-continued

| CMP # | STRUCTURE | Ca2+ Mob. | IUPAC NAME | MASS |
|---|---|---|---|---|
| 1223 | 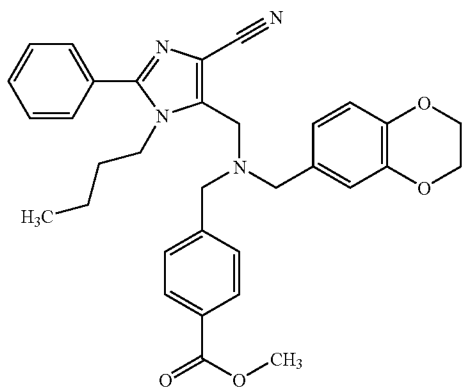 | * | methyl 4-{[[(1-butyl-4-cyano-2-phenyl-1H-imidazol-5-yl)methyl](2,3-dihydro-1,4-benzodioxin-6-ylmethyl)amino]methyl}benzoate | 550.656 |
| 1224 | 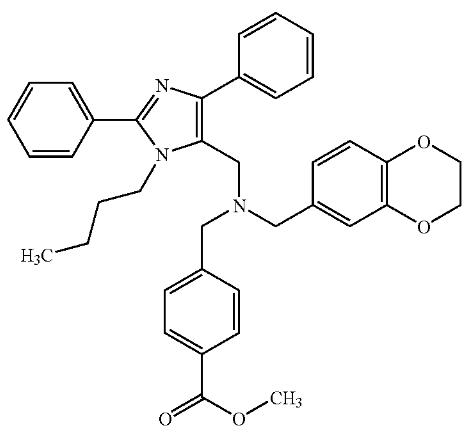 | * | methyl 4-{[[(1-butyl-2,4-diphenyl-1H-imidazol-5-yl)methyl](2,3-dihydro-1,4-benzodioxin-6-ylmethyl)amino]methyl}benzoate | 601.743 |
| 1225 | 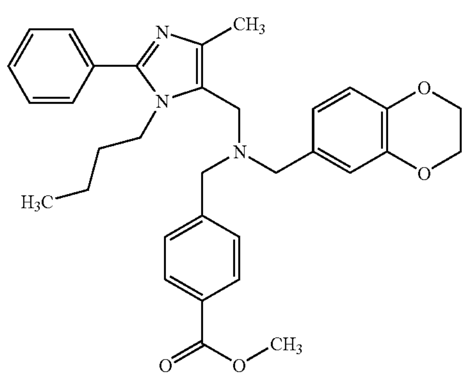 | * | methyl 4-{[[(1-butyl-4-methyl-2-phenyl-1H-imidazol-5-yl)methyl](2,3-dihydro-1,4-benzodioxin-6-ylmethyl)amino]methyl}benzoate | 539.672 |
| 1226 | 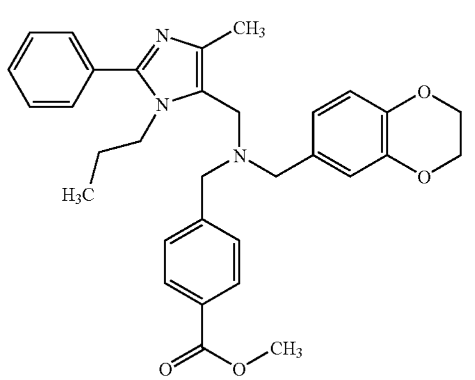 | * | methyl 4-({(2,3-dihydro-1,4-benzodioxin-6-ylmethyl)[(4-methyl-2-phenyl-1-propyl-1H-imidazol-5-yl)methyl]amino}methyl)benzoate | 525.646 |

TABLE III-continued

| CMP # | STRUCTURE | Ca2+ Mob. | IUPAC NAME | MASS |
|---|---|---|---|---|
| 1227 | 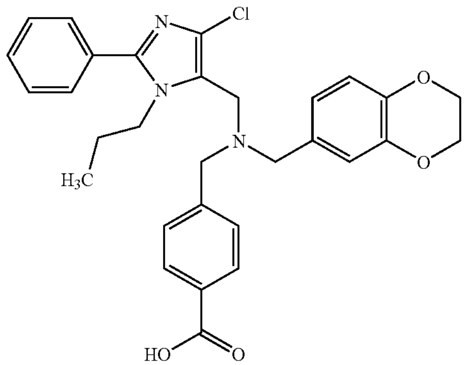 | * | 4-{[[(4-chloro-2-phenyl-1-propyl-1H-imadazol-5-yl)methyl](2,3-dihydro-1,4-benzodioxin-6-ylmethyl)amino]methyl}benzoic acid | 532.037 |
| 1228 | 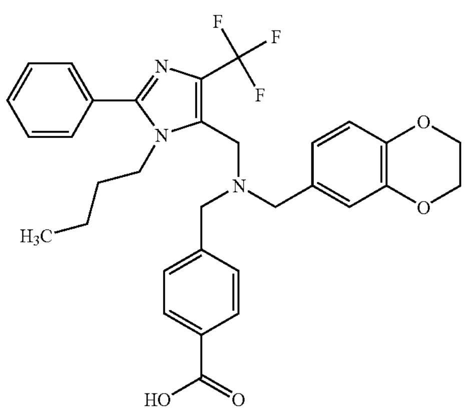 | * | 4-{[{[1-butyl-2-phenyl-4-(trifluoromethyl)-1H-imidazol-5-yl]methyl}(2,3-dihydro-1,4-benzodioxin-6-ylmethyl)amino]methyl}benzoic acid | 579.616 |
| 1229 | 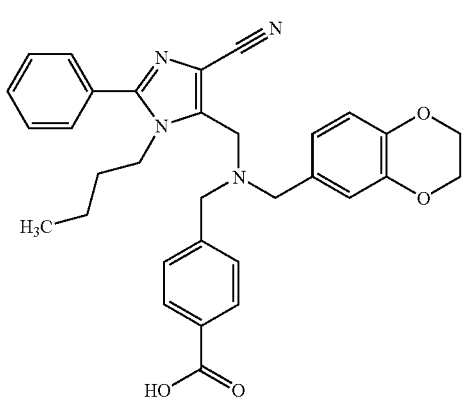 | * | 4-{[[(1-butyl-4-cyano-2-phenyl-1H-imidazol-5-yl)methyl](2,3-dihydro-1,4-benzodioxin-6-ylmethyl)amino]methyl}benzoic acid | 536.629 |

TABLE III-continued

| CMP # | STRUCTURE | Ca2+ Mob. | IUPAC NAME | MASS |
|---|---|---|---|---|
| 1230 | 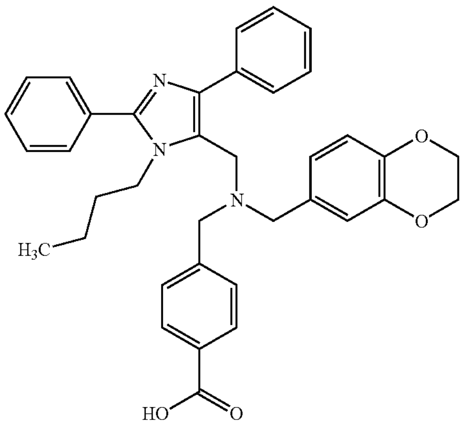 | * | 4-{[[(1-butyl-2,4-diphenyl-1H-imidazol-5-yl)methyl](2,3-dihydro-1,4-benzodioxin-6-ylmethyl)amino]methyl}benzoic acid | 587.716 |
| 1231 | 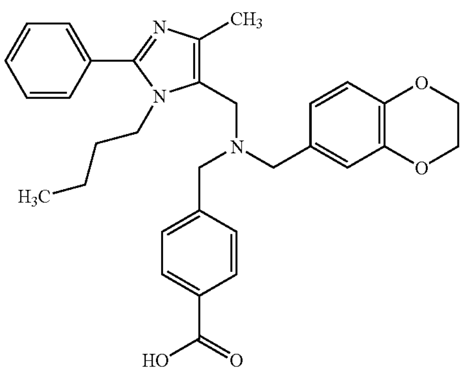 | * | 4-{[[(1-butyl-4-methyl-2-phenyl-1H-imidazol-5-yl)methyl](2,3-dihydro-1,4-benzodioxin-6-ylmethyl)amino]methyl}benzoic acid | 525.646 |
| 1232 | 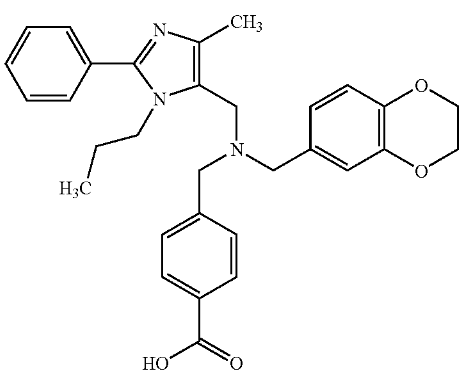 | * | 4-({(2,3-dihydro-1,4-benzodioxin-6-ylmethyl)[(4-methyl-2-phenyl-1-propyl-1H-imidazol-5-yl)methyl]amino}methyl)benzoic acid | 511.619 |
| 1233 | 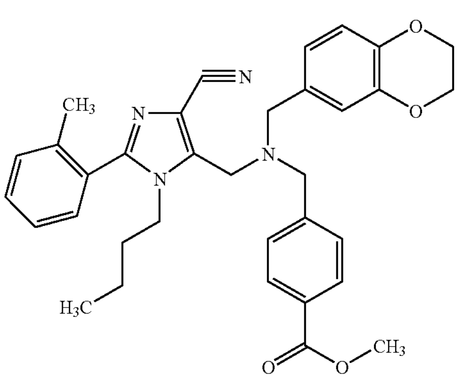 | * | methyl 4-{[{[1-butyl-4-cyano-2-(2-methylphenyl)-1H-imidazol-5-yl]methyl}(2,3-dihydro-1,4-benzodioxin-6-ylmethyl)amino]methyl}benzoate | 564.682 |

TABLE III-continued

| CMP # | STRUCTURE | Ca2+ Mob. | IUPAC NAME | MASS |
|---|---|---|---|---|
| 1234 | 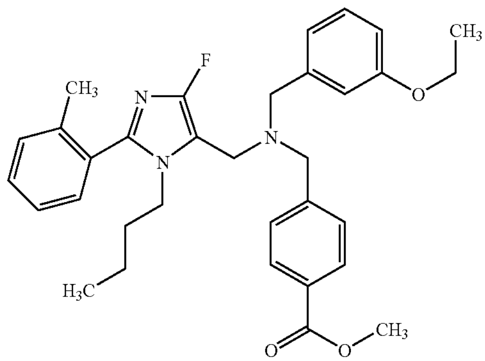 | * | methyl 4-{[{[1-butyl-4-fluoro-2-(2-methylphenyl)-1H-imidazol-5-yl]methyl}(3-ethoxybenzyl)amino]methyl}benzoate | 543.679 |
| 1235 | 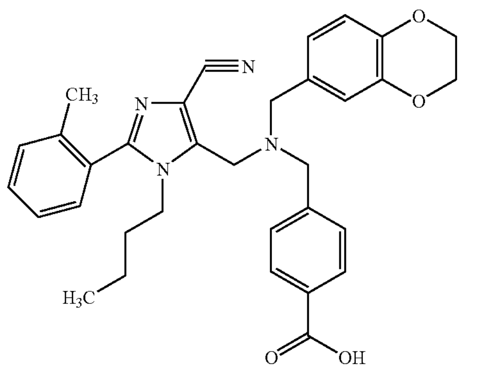 | * | 4-{[{[1-butyl-4-cyano-2-(2-methylphenyl)-1H-imidazol-5-yl]methyl}(2,3-dihydro-1,4-benzodioxin-6-ylmethyl)amino]methyl}benzoic acid | 550.656 |
| 1236 | 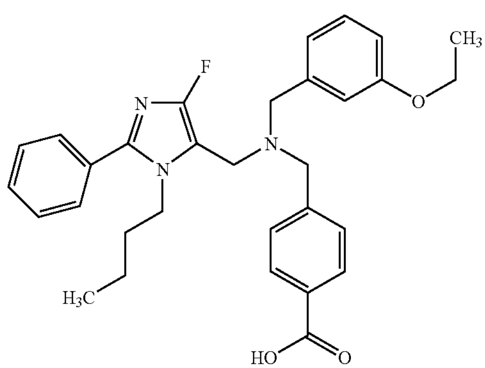 | * | 4-{[{[1-butyl-4-fluoro-2-(2-methylphenyl)-1H-imidazol-5-yl]methyl}(3-ethoxybenzyl)amino]methyl}benzoic acid | 529.652 |
| 1237 | 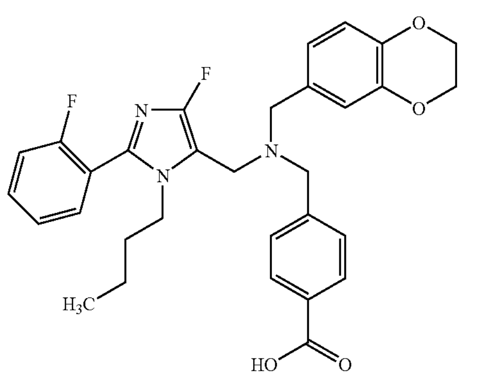 | * | 4-{({[1-butyl-4-fluoro-2-(2-methylphenyl)-1H-imidazol-5-yl]methyl}(2,3-dihydro-1,4-benzodioxin-6-ylmethyl)amino]methyl}benzoic acid | 543.636 |

TABLE III-continued

| CMP # | STRUCTURE | Ca2+ Mob. | IUPAC NAME | MASS |
|---|---|---|---|---|
| 1238 | 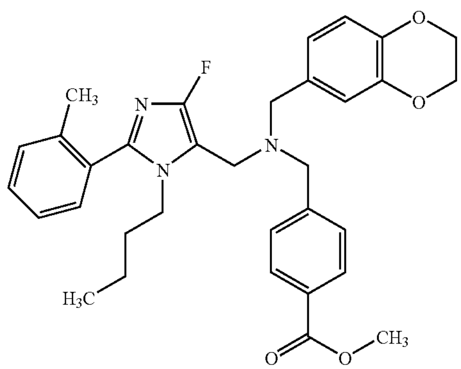 | * | methyl 4-{[{[1-butyl-4-fluoro-2-(2-methylphenyl)-1H-imidazol-5-yl]methyl}(2,3-dihydro-1,4-benzodioxin-6-ylmethyl)amino]methyl}benzoate | 557.662 |
| 1239 | 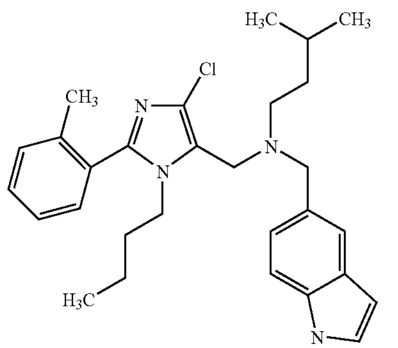 | * | N-{[1-butyl-4-chloro-2-(2-methylphenyl)-1H-imidazol-5-yl]methyl}-N-(1H-indol-5-ylmethyl)-3-methylbutan-1-amine | 477.092 |
| 1240 | 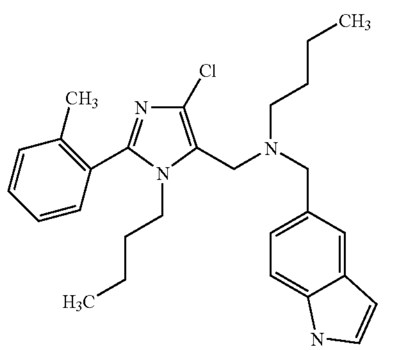 | * | N-{[1-butyl-4-chloro-2-(2-methylphenyl)-1H-imidazol-5-yl]methyl)-N-(1H-indol-5-ylmethyl)butan-1-amine | 463.065 |
| 1241 | 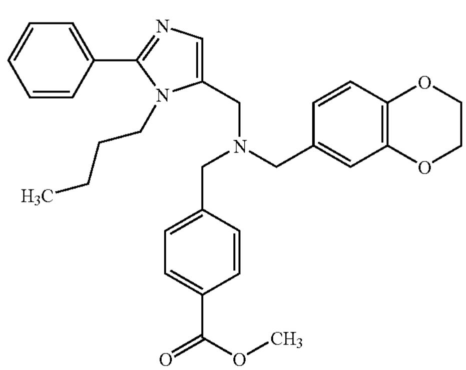 | * | methyl 4-{[[(1-butyl-2-phenyl-1H-imidazol-5-yl)methyl](2,3-dihydro-1,4-benzodioxin-6-ylmethyl)amino]methyl}benzoate | 525.646 |

TABLE III-continued

| CMP # | STRUCTURE | Ca2+ Mob. | IUPAC NAME | MASS |
|---|---|---|---|---|
| 1242 | 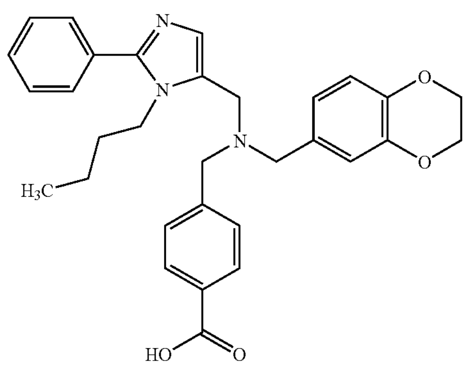 | * | 4-{[[(1-butyl-2-phenyl-1H-imidazol-5-yl)methyl](2,3-dihydro-1,4-benzodioxin-6-ylmethyl)amino]methyl}benzoic acid | 511.619 |
| 1243 | 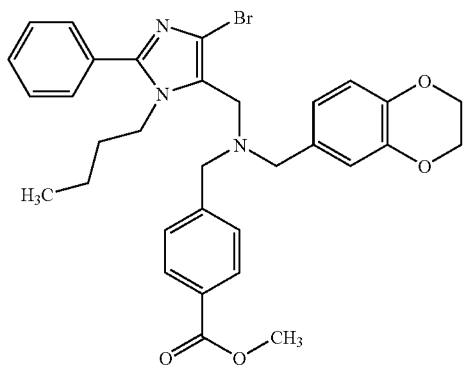 | * | methyl 4-{[[(4-bromo-1-butyl-2-phenyl-1H-imidazol-5-yl)methyl](2,3-dihydro-1,4-benzodioxin-6-ylmethyl)amino]methyl}benzoate | 604.542 |
| 1244 | 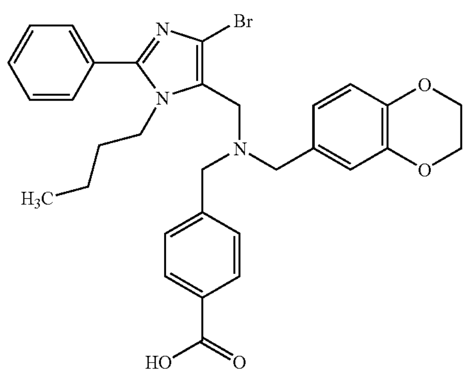 | * | 4-{[[(4-bromo-1-butyl-2-phenyl-1H-imidazol-5-yl)methyl](2,3-dihydro-1,4-benzodioxin-6-ylmethyl)amino]methyl}benzoic acid | 590.515 |
| 1245 | 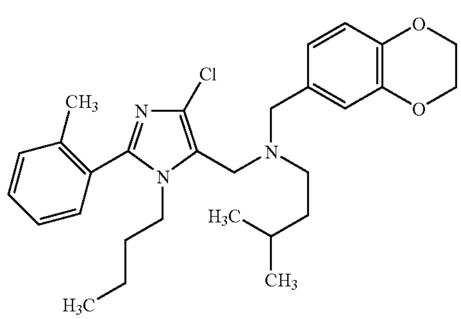 | * | N-{[1-butyl-4-chloro-2-(2-methylphenyl)-1H-imidazol-5-yl]methyl}-N-(2,3-dihydro-1,4-benzodioxin-6-ylmethyl)-3-methylbutan-1-amine | 496.091 |

TABLE III-continued

| CMP # | STRUCTURE | Ca2+ Mob. | IUPAC NAME | MASS |
|---|---|---|---|---|
| 1246 | 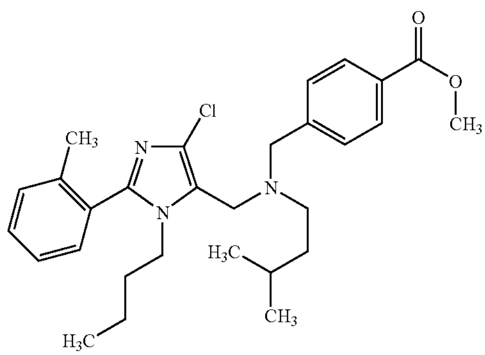 | * | methyl 4-{[{[1-butyl-4-chloro-2-(2-methylphenyl)-1H-imidazol-5-yl]methyl}(isopentyl)amino]methyl}benzoate | 496.091 |
| 1247 | 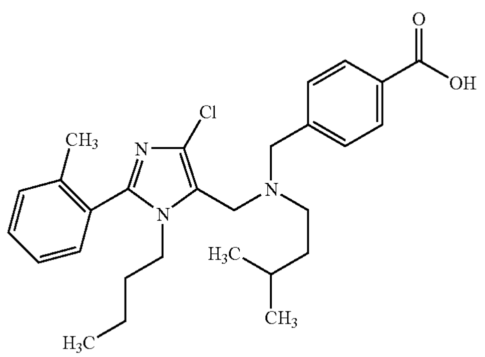 | * | 4-{[{[1-butyl-4-chloro-2-(2-methylphenyl)-1H-imidazol-5-yl]methyl}(isopentyl)amino]methyl}benzoic acid | 482.064 |
| 1248 | 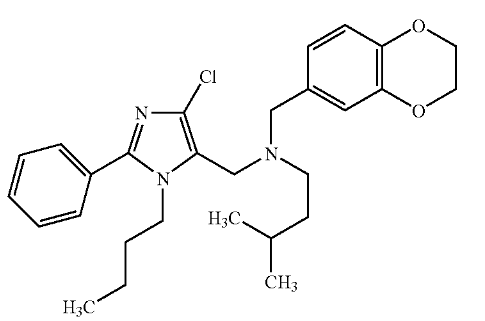 | * | N-[(1-butyl-4-chloro-2-phenyl-1H-imidazol-5-yl)methyl]-N-(2,3-dihydro-1,4-benzodioxin-6-ylmethyl)-3-methylbutan-1-amine | 482.064 |
| 1249 | 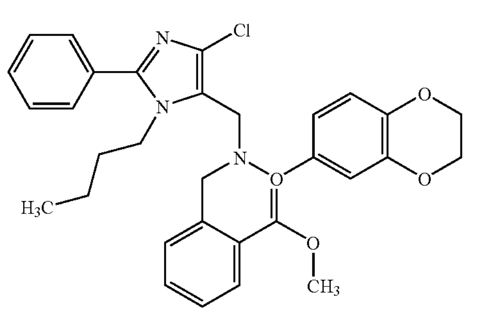 | * | methyl 2-{[[(1-butyl-4-chloro-2-phenyl-1H-imidazol-5-yl)methyl](2,3-dihydro-1,4-benzodioxin-6-ylmethyl)amino]methyl}benzoate | 560.091 |

TABLE III-continued

| CMP # | STRUCTURE | Ca2+ Mob. | IUPAC NAME | MASS |
|---|---|---|---|---|
| 1250 | 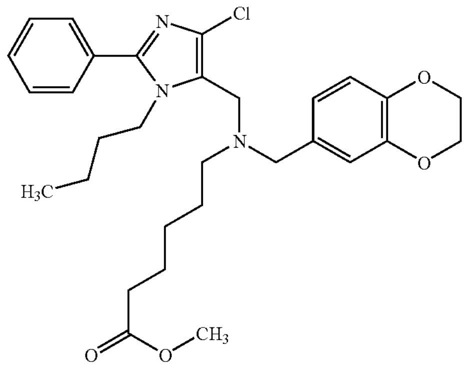 | * | methyl 6-{[[(1-butyl-4-chloro-2-phenyl-1H-imidazol-5-yl)methyl](2,3-dihydro-1,4-benzodioxin-6-ylmethyl)amino]hexanoate | 540.1 |
| 1251 | 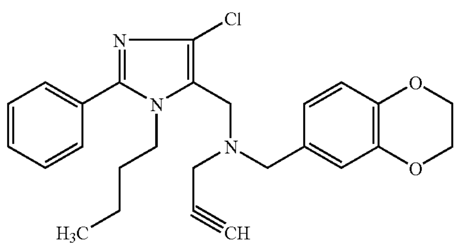 | * | N-[(1-butyl-4-chloro-2-phenyl-1H-imidazol-5-yl)methyl]-N-(2,3-dihydro-1,4-benzodioxin-6-ylmethyl)prop-2-yn-1-amine | 449.979 |
| 1252 | 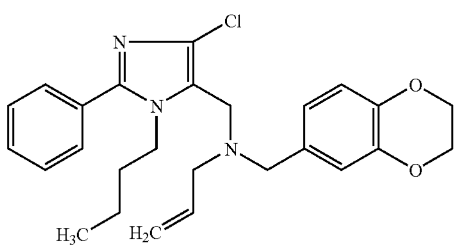 | * | N-[(1-butyl-4-chloro-2-phenyl-1H-imidazol-5-yl)methyl]-N-(2,3-dihydro-1,4-benzodioxin-6-ylmethyl)prop-2-en-1-amine | 451.995 |
| 1253 | 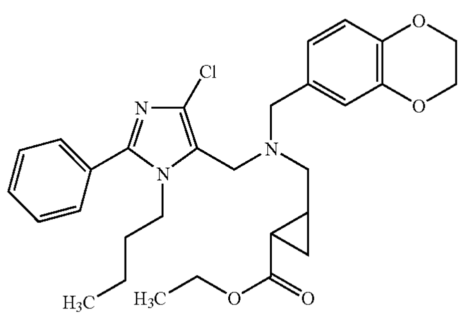 | * | ethyl 2-{[[(1-butyl-4-chloro-2-phenyl-1H-imidazol-5-yl)methyl](2,3-dihydro-1,4-benzodioxmn-6-ylmethyl)amino]methyl} cyclopropane carboxylate | 538.084 |
| 1254 | 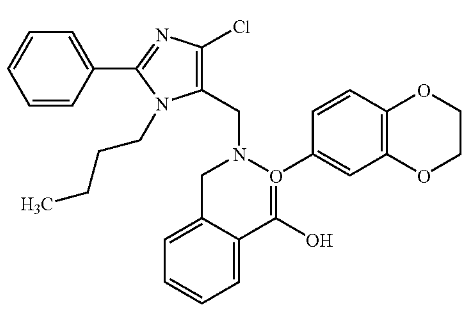 | * | 2-{[[(1-butyl-4-chloro-2-phenyl-1H-imidazol-5-yl)methyl](2,3-dihydro-1,4-benzodioxin-6-ylmethyl)amino]methyl}benzoic acid | 546.064 |

TABLE III-continued

| CMP # | STRUCTURE | Ca2+ Mob. | IUPAC NAME | MASS |
|---|---|---|---|---|
| 1255 | 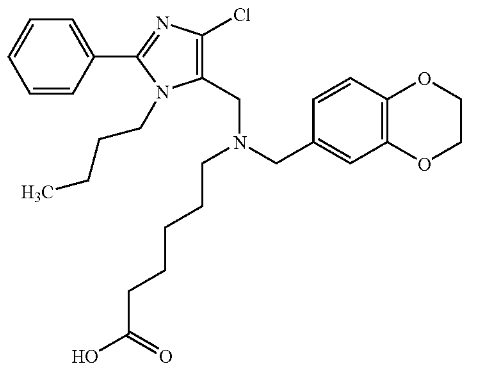 | * | 6-[[(1-butyl-4-chloro-2-phenyl-1H-imidazol-5-yl)methyl](2,3-dihydro-1,4-benzodioxin-6-ylmethyl)amino]hexanoic acid | 526.073 |
| 1256 | 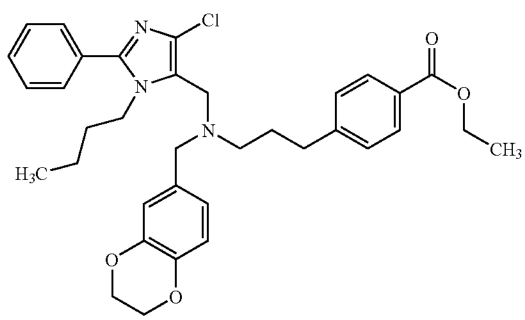 | * | ethyl 4-{3-[[(1-butyl-4-chloro-2-phenyl-1H-imidazol-5-yl)methyl](2,3-dihydro-1,4-benzodioxin-6-ylmethyl)amino]propyl}benzoate | 602.171 |
| 1257 | 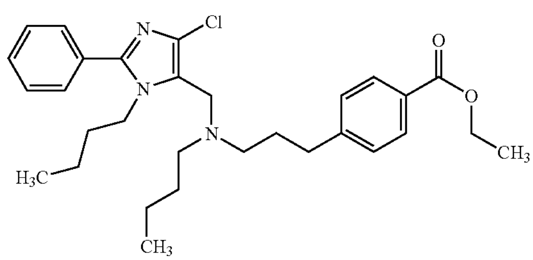 | * | ethyl 4-(3-{butyl[(4-chloro-2-phenyl-1-propyl-1H-imidazol-5-yl)methyl]amino}propyl)benzoate | 496.091 |
| 1258 | 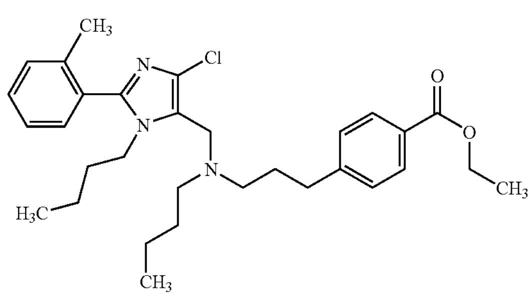 | * | ethyl 4-[3-(butyl{[1-butyl-4-chloro-2-(2-methylphenyl)-1H-imidazol-5-yl]methyl}amino)propyl]benzoate | 524.145 |

TABLE III-continued

| CMP # | STRUCTURE | Ca2+ Mob. | IUPAC NAME | MASS |
|---|---|---|---|---|
| 1259 | 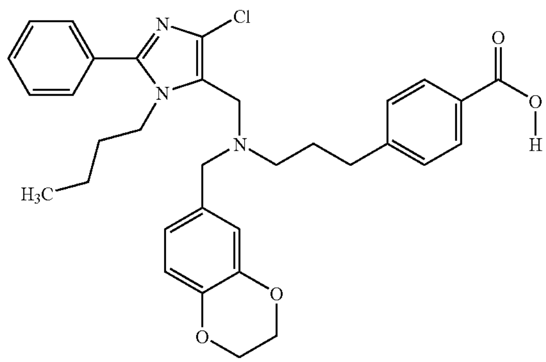 | * | 4-{3-[[(1-butyl-4-chloro-2-phenyl-1H-imidazol-5-yl)methyl](2,3-dihydro-1,4-benzodioxin-6-ylmethyl)amino]propyl}benzoic acid | 574.117 |
| 1260 | 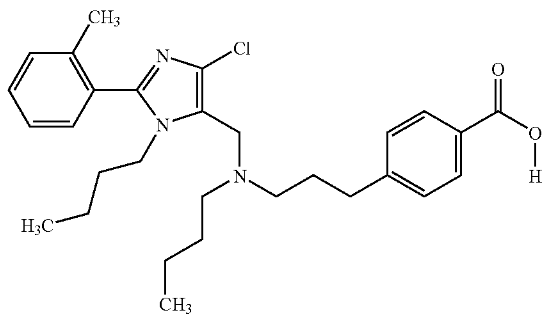 | * | 4-[3-(butyl{[1-butyl-4-chloro-2-(2-methylphenyl)-1H-imidazol-5-yl]methyl}amino)propyl]benzoic acid | 496.091 |
| 1261 | 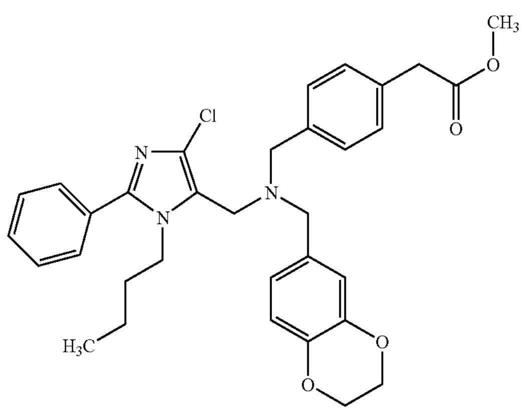 | * | methyl (4-{[[(1-butyl-4-chloro-2-phenyl-1H-imidazol-5-yl)methyl](2,3-dihydro-1,4-benzodioxin-6-ylmethyl)amino]methyl}phenyl)acetate | 574.117 |
| 1262 | 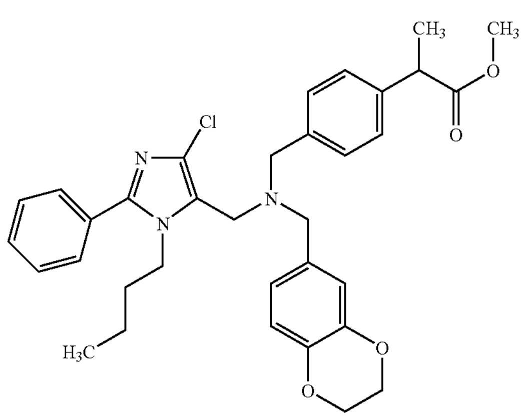 | * | methyl 2-(4-{[[(1-butyl-4-chloro-2-phenyl-1H-imidazol-5-yl)methyl](2,3-dihydro-1,4-benzodioxin-6-ylmethyl)amino]methyl}phenyl)propanoate | 588.144 |

TABLE III-continued

| CMP # | STRUCTURE | Ca2+ Mob. | IUPAC NAME | MASS |
|---|---|---|---|---|
| 1263 | 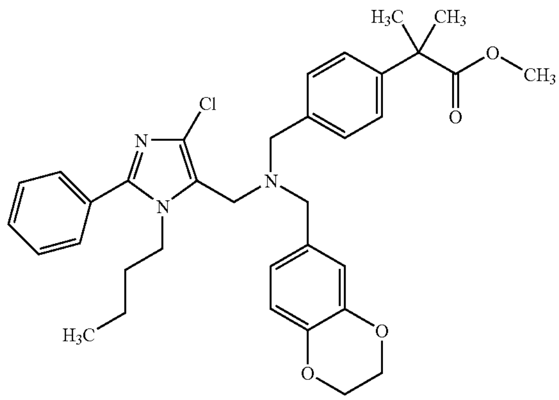 | * | methyl 2-(4-{[[(1-butyl-4-chloro-2-phenyl-1H-imidazol-5-yl)methyl](2,3-dihydro-1,4-benzodioxin-6-ylmethyl)amino]methyl}phenyl)-2-methylpropanoate | 602.171 |
| 1264 | 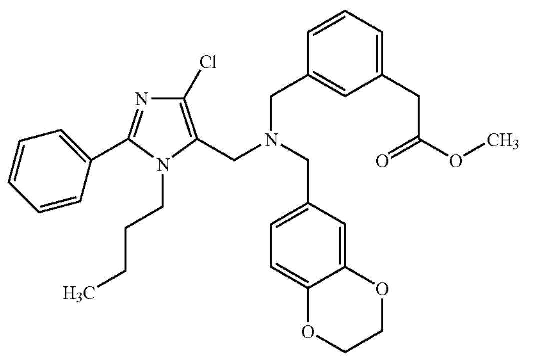 | * | methyl (3-{[[(1-butyl-4-chloro-2-phenyl-1H-imidazol-5-yl)methyl](2,3-dihydro-1,4-benzodioxin-6-ylmethyl)amino]methyl}phenyl)acetate | 574.117 |
| 1265 | 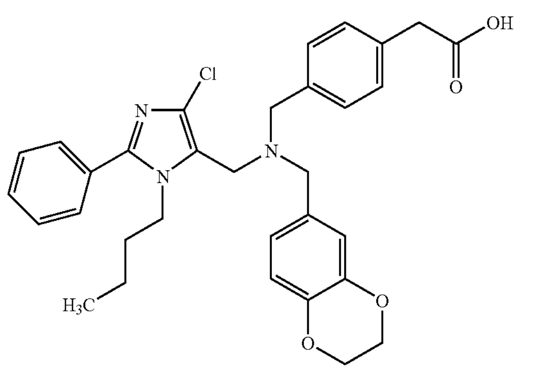 | * | (4-{[[-butyl-4-chloro-2-phenyl-1H-imidazol-5-yl)methyl](2,3-dihydro-1,4-benzodioxin-6-ylmethyl)amino]methyl}phenyl)acetic acid | 560.091 |
| 1266 | 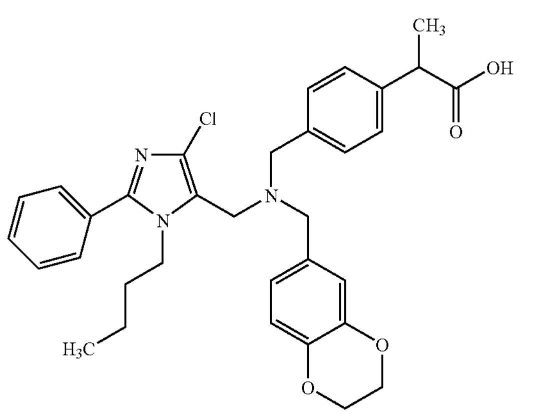 | * | 2-(4-{[[(1-butyl-4-chloro-2-phenyl-1H-imidazol-5-yl)methyl](2,3-dihydro-1,4-benzodioxin-6-ylmethyl)amino]methyl}phenyl)propanoic acid | 574.117 |

TABLE III-continued
| CMP # | STRUCTURE | Ca2+ Mob. | IUPAC NAME | MASS |
|---|---|---|---|---|
| 1267 | 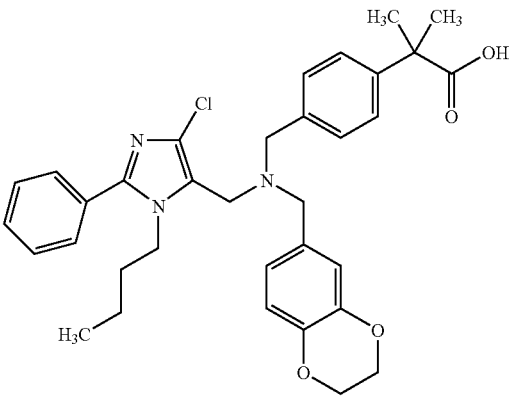 | * | 2-(4-{[[(1-butyl-4-chloro-2-phenyl-1H-imidazol-5-yl)methyl](2,3-dihydro-1,4-benzodioxin-6-ylmethyl)amino]methyl}phenyl)-2-methylpropanoic acid | 588.144 |
| 1268 | 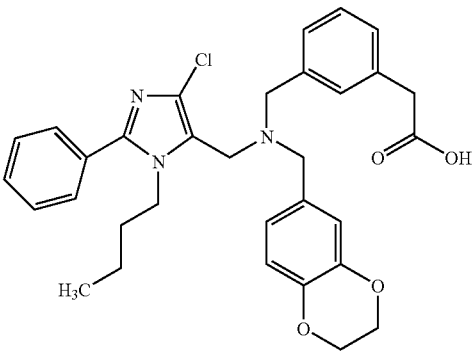 | * | (3-{[[(1-butyl-4-chloro-2-phenyl-1H-imidazol-5-yl)methyl](2,3-dihydro-1,4-benzodioxin-6-ylmethyl)amino]methyl}phenyl)acetic acid | 560.091 |
| 1269 | 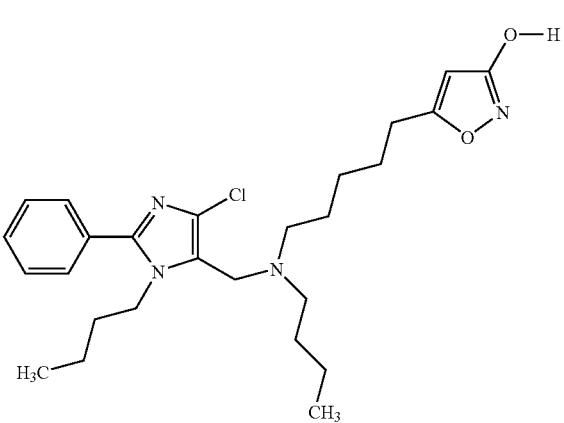 | * | 5-(5-{butyl[(1-butyl-4-chloro-2-phenyl-1H-imidazol-5-yl)methyl]amino}pentyl)isoxazol-3-ol | 473.057 |

TABLE IV

| Cmp.# | MOLSTRUCTURE | IUPAC Name | LCMS (min.) | MW | LCMS Mass |
|---|---|---|---|---|---|
| 1270 | | methyl 4-{[{[1-butyl-4-chloro-2-(2-methylphenyl)-1H-imidazol-5-yl]methyl}(neopentyl)amino]methyl}-2-methoxybenzoate | 1.36 | 526.12 | 525.28 |
| 1271 | | 4-{[{[1-butyl-4-chloro-2-(2-methylphenyl)-1H-imidazol-5-yl]methyl}(neopentyl)amino]methyl}-2-methoxybenzoic acid | 1.32 | 512.09 | 511.26 |
| 1272 | | 4-{[{[1-butyl-4-chloro-2-(2-methylphenyl)-1H-imidazol-5-yl]methyl}(neopentyl)amino]methyl}-2-methoxybenzamide | 1.31 | 511.11 | 510.28 |
| 1273 | | 4-{[{[1-butyl-4-chloro-2-(2-methylphenyl)-1H-imidazol-5-yl]methyl}(neopentyl)amino]methyl}-2-hydroxybenzamide | 1.31 | 497.08 | 496.26 |

TABLE IV-continued

| Cmp.# | MOLSTRUCTURE | IUPAC Name | LCMS (min.) | MW | LCMS Mass |
|---|---|---|---|---|---|
| 1274 | | 4-{[{[1-butyl-4-(4-methoxyphenyl)-2-phenyl-1H-imidazol-5-yl]methyl}(neopentyl)amino]methyl})-2-hydroxybenzamide | 1.19 | 554.73 | 554.33 |
| 1275 | | 4-[(benzyl{[1-butyl-4-(4-methoxyphenyl)-2-phenyl-1H-imidazol-5-yl]methyl}amino)methyl]-2-hydroxybenzamide | 1.18 | 574.72 | 574.29 |
| 1276 | | methyl (4-{[[(1-butyl-4-chloro-2-phenyl-1H-imidazol-5-yl)methyl](2,3-dihydro-1,4-benzodioxin-6-ylmethyl)amino]methyl]phenyl)acetate | 1.29 | 574.12 | 573.24 |

TABLE IV-continued

| Cmp.# | MOLSTRUCTURE | IUPAC Name | LCMS (min.) | MW | LCMS Mass |
|---|---|---|---|---|---|
| 1277 | | methyl 2-(4-{[[(1-butyl-4-chloro-2-phenyl-1H-imidazol-5-yl)methyl](2,3-dihydro-1,4-benzodioxin-6-ylmethyl)amino]methyl)phenyl)propanoate | 1.31 | 588.14 | 587.26 |
| 1278 | | methyl 2-(4-{[[(1-butyl-4-chloro-2-phenyl-1H-imidazol-5-yl)methyl](2,3-dihydro-1,4-benzodioxin-6-ylmethyl)amino]methyl}phenyl)-2-methylpropanoate | 1.33 | 602.17 | 601.27 |
| 1279 | | methyl (3-{[[(1-butyl-4-chloro-2-phenyl-1H-imidazol-5-yl)methyl](2,3-dihydro-1,4-benzodioxin-6-ylmethyl)amino]methyl}phenyl)acetate | 1.29 | 574.12 | 573.24 |
| 1280 | | (4-{[[(1-butyl-4-chloro-2-phenyl-1H-imidazol-5-yl)methyl](2,3-dihydro-1,4-benzodioxin-6-ylmethyl)amino]methyl}phenyl) acetic acid | 1.24 | 560.09 | 559.22 |

TABLE IV-continued

| Cmp.# | MOLSTRUCTURE | IUPAC Name | LCMS (min.) | MW | LCMS Mass |
|---|---|---|---|---|---|
| 1281 | | 2-(4-{[[(1-butyl-4-chloro-2-phenyl-1H-imidazol-5-yl)methyl](2,3-dihydro-1,4-benzodioxin-6-ylmethyl)amino]methyl} phenyl)propanoic acid | 1.26 | 574.12 | 573.24 |
| 1282 | | 2-(4-{[[(1-butyl-4-chloro-2-phenyl-1H-imidazol-5-yl)methy](2,3-dihydro-1,4-benzodioxin-6-ylmethyl)amino]methyl} phenyl)-2-methylpropanoic acid | 1.28 | 588.14 | 587.26 |
| 1283 | | (3-{[[(1-butyl-4-chloro-2-phenyl-1H-imidazol-5-yl)methyl](2,3-dihydro-1,4-benzodioxin-6-ylmethyl)amino]methyl} phenyl) acetic acid | 1.25 | 560.09 | 559.22 |
| 1284 | | N-{[1-butyl-4-chloro-2-(2-methylphenyl)-1H-imidazol-5-yl]methyl}-N-(2,3-dihydro-1,4-benzodioxin-6-ylmethyl)butan-1-amine | 1.16 | 482.06 | 481.25 |

TABLE IV-continued

| Cmp.# | MOLSTRUCTURE | IUPAC Name | LCMS (min.) | MW | LCMS Mass |
|---|---|---|---|---|---|
| 1285 | | 4-[(butyl{[1-butyl-4-chloro-2-(2-methyl phenyl)-1H-imidazol-5-yl]methyl} amino)methyl]benzene sulfonamide | 1.17 | 503.11 | 502.22 |
| 1286 | | 4-{[{[1-butyl-4-chloro-2-(2-methyl phenyl)-1H-imidazol-5-yl] methyl}(isopentyl)amino] methyl}benzene sulfonamide | 1.2 | 517.13 | 516.23 |
| 1287 | | 4-{[[(1-butyl-4-chloro-2-phenyl-1H-imidazol-5-yl) methyl](2,3-dihydro-1,4-benzodioxin-6-ylmethyl)amino]methyl} benzenesulfonamide | 1.24 | 581.13 | 580.19 |
| 1288 | | N-{1-butyl-4-chloro-2-(2-methylphenyl)-1H-imidazol-5-yl]methyl}-N-[(3-chloro-1H-indol-5-yl)methyl]-3-methylbutan-1-amine | 1.18 | 511.54 | 510.23 |

TABLE IV-continued

| Cmp.# | MOLSTRUCTURE | IUPAC Name | LCMS (min.) | MW | LCMS Mass |
|---|---|---|---|---|---|
| 1289 | | 5-{[{[1-butyl-4-chloro-2-(2-methylphenyl)-1H-imidazol-5-yl]methyl}(isopentyl)amino]methyl}-1H-indole-3-carbonitrile | 1.15 | 502.10 | 501.27 |
| 1290 | | 4-{[{[1-butyl-4-chloro-2-(2-methylphenyl)-1H-imidazol-5-yl]methyl}(2,3-dihydro-1,4-benzodioxin-6-ylmethyl)amino]methyl}benzenesulfonamide | 1.24 | 595.16 | 594.21 |
| 1291 | | N-{[1-butyl-4-chloro-2-(2-methylphenyl)-1H-imidazol-5-yl]methyl}-N-(quinoxalin-6-ylmethyl)butan-1-amine | 1.25 | 476.07 | 475.25 |
| 1292 | | methyl [[(1-butyl-4-chloro-2-phenyl-1H-imidazol-5-yl)methyl](2,3-dihydro-1,4-benzodioxin-6-ylmethyl)amino](phenyl)acetate | 1.33 | 560.09 | 559.22 |

TABLE IV-continued

| Cmp.# | MOLSTRUCTURE | IUPAC Name | LCMS (min.) | MW | LCMS Mass |
|---|---|---|---|---|---|
| 1293 | | N-[(1-butyl-2-phenyl-4-vinyl-1H-imidazol-5-yl)methyl]-N-(2,3-dihydro-1,4-benzodioxin-6-ylmethyl)-N-(3-ethoxybenzyl) amine | 1.2 | 537.70 | 537.30 |
| 1294 | | methyl 4-{[[(1-butyl-2-phenyl-4-vinyl-1H-imidazol-5-yl)methyl](2,3-dihydro-1,4-benzodioxin-6-ylmethyl)amino]methyl}benzoate | 1.2 | 551.68 | 551.28 |
| 1295 | | N-[(1-butyl-4-ethyl-2-phenyl-1H-imidazol-5-yl)methyl]-N-(2,3-dihydro-1,4-benzodioxin-6-ylethyl)-N-(3-ethoxybenzyl) amine | 1.22 | 539.72 | 539.31 |
| 1296 | | methyl 4-{[[(1-butyl-4-ethyl-2-phenyl-1H-imidazol-5-yl)methyl](2,3-dihydro-1,4-benzodioxin-6-ylmethyl)amino]methyl}benzoate | 1.18 | 553.70 | 553.29 |

TABLE IV-continued

| Cmp.# | MOLSTRUCTURE | IUPAC Name | LCMS (min.) | MW | LCMS Mass |
|---|---|---|---|---|---|
| 1297 | | (1S)-N-(1,3-benzodioxol-5-ylmethyl)-1-(1-butyl-2,4-diphenyl-1H-imidazol-5-yl)-N-methylpentan-1-amine | 1.18 | 509.69 | 509.30 |
| 1298 | Chiral | (1S)-N-(1,3-benzodioxol-5-ylmethyl)-1-(1-butyl-2,4-diphenyl-1H-imidazol-5-yl)-N-methylpentan-1-amine | 1.18 | 509.69 | 509.30 |
| 1299 | | N-[(1-butyl-4-chloro-2-phenyl-1H-imidazol-5-yl)methyl]-N-(2,3-dihydro-1,4-benzodioxin-6-ylmethyl)-N-(quinoxalin-6-ylmethyl)amine | 1.29 | 554.09 | 553.22 |
| 1300 | | 4-{[[(1-butyl-2-phenyl-4-vinyl-1H-imidazol-5-yl)methyl](2,3-dihydro-1,4-benzodioxin-6-ylmethyl)amino]methyl}benzoic acid | | 537.66 | |

TABLE IV-continued

| Cmp.# | MOLSTRUCTURE | IUPAC Name | LCMS (min.) | MW | LCMS Mass |
|---|---|---|---|---|---|
| 1301 | | N-{1-[1-butyl-4-chloro-2-(2-methylphenyl)-1H-imidazol-5-yl]ethyl}-N-(2,3-dihydro-1,4-benzodioxin-6-ylmethyl)butan-1-amine | 1.16 | 496.09 | 495.27 |
| 1302 | | N-{1-[1-butyl-4-chloro-2-(2-methylphenyl)-1H-imidazol-5-yl]ethyl}-N-(2,3-dihydro-1,4-benzodioxin-6-ylmethyl)-3-methylbutan-1-amine | 1.18 | 510.12 | 509.28 |
| 1303 | | N-{1-[1-butyl-4-chloro-2-(2-methylphenyl)-1H-imidazol-5-yl]ethyl}-N-(1H-indol-5-ylmethyl)butan-1-amine | 1.13 | 477.09 | 476.27 |
| 1304 | | N-{[1-butyl-4-chloro-2-(2-methylphenyl)-1H-imidazol-5-yl]methyl}-3-methyl-N-[(2-methyl-1H-indol-5-yl)methyl]butan-1-amine | 1.15 | 491.12 | 490.29 |

TABLE IV-continued

| Cmp.# | MOLSTRUCTURE | IUPAC Name | LCMS (min.) | MW | LCMS Mass |
|---|---|---|---|---|---|
| 1305 | | 1-(1-butyl-2-phenyl-1H-imidazol-5-yl)-N-(cyclohexylmethyl)-N-methylpentan-1-amine | 1.11 | 395.63 | 395.33 |
| 1306 | | 4-{[[(1-butyl-4-ethyl-2-phenyl-1H-imidazol-5-yl)methyl](2,3-dihydro-1,4-benzodioxin-6-ylmethyl)amino]methyl}benzoicacid | 1.16 | 539.67 | 539.28 |
| 1307 | | N-{[4-chloro-1-(ethoxymethyl)-2-phenyl-1H-imidazol-5-yl]methyl}-N-(2,3-dihydro-1,4-benzodioxin-6-ylmethyl)-N-(3-ethoxybenzyl) amine | | | 548.08 |
| 1308 | | N-{[1-butyl-4-chloro-2-(2-methylphenyl)-1H-imidazol-5-yl]methyl-N-methyl-1,2,3,4-tetrahydronaphthalen-1-amine | | | 422.01 |

TABLE IV-continued

| Cmp.# | MOLSTRUCTURE | IUPAC Name | LCMS (min.) | MW | LCMS Mass |
|---|---|---|---|---|---|
| 1309 | | 1-(1-butyl-2,4-diphenyl-1H-imidazol-5-yl)-N-(cyclohexylmethyl)-N-(1,2,3,4-tetrahydroquinolin-6-ylmethyl) methanamine | 1.2 | 546.80 | 546.37 |
| 1310 | | 1-[1-butyl-2-phenyl-4-(trifluoromethyl)-1H-imidazol-5-yl]-N-(cyclohexylmethyl)-N-(1,2,3,4-tetrahydroquinolin-6-ylmethyl)methanamine | 1.28 | 538.70 | 538.33 |
| 1311 | | N-{[4-bromo-1-butyl-2-(2,6-diethylphenyl)-1H-imidazol-5-yl]methyl}-N-methyl-1,2,3,4-tetrahydronaphthalen-1-amine | 1.27 | 508.54 | 507.22 |
| 1312 | | methyl 4-{[{[1-butyl-4-(4-methylphenyl)-2-phenyl-1H-imidazol-5-yl] methyl} (2,3-dihydro-1,4-benzodioxin-6-ylmethyl)amino]methyl}benzoate | 1.22 | 615.77 | 615.31 |

TABLE IV-continued

| Cmp.# | MOLSTRUCTURE | IUPAC Name | LCMS (min.) | MW | LCMS Mass |
|---|---|---|---|---|---|
| 1313 | | methyl 4-{[{[1-butyl-4-(3-fluorophenyl)-2-phenyl-1H-imidazol-5-yl]methyl} 2,3-dihydro-1,4-benzodioxin-6-ylmethyl)amino]methyl}benzoate | 1.2 | 619.73 | 619.28 |
| 1314 | | 4-{[{[1-butyl-4-(4-methylphenyl)-2-phenyl-1H-imidazol-5-yl]methyl}(2,3-dihydro-1,4-benzodioxin-6-ylmethyl)amino]methyl} benzoic acid | 1.19 | 601.74 | 601.29 |
| 1315 | | 4-{[{[1-butyl-4-(3-fluorophenyl)-2-phenyl-1H-imidazol-5-yl]methyl}(2,3-dihydro-1,4-benzodioxin-6-ylmethyl)amino]methyl} benzoic acid | 1.18 | 605.71 | 605.27 |
| 1316 | | N-{[1-butyl-4-chloro-2-(2-methylphenyl)-1H-imidazol-5-yl]methyl}-N-(3-methoxybenzyl)butan-1-amine | 1.2 | 454.05 | 453.25 |

TABLE IV-continued

| Cmp.# | MOLSTRUCTURE | IUPAC Name | LCMS (min.) | MW | LCMS Mass |
|---|---|---|---|---|---|
| 1317 | | N-{[1-butyl-4-chloro-2-(2-methylphenyl)-1H-imidazol-5-yl]methyl}-N-(3-ethoxybenzyl)butan-1-amine | 1.22 | 468.08 | 467.27 |
| 1318 | | N-{[1-butyl-4-chloro-2-(2-methylphenyl)-1H-imidazol-5-yl]methyl}-N-(1H-indol-5-ylmethyl)-3,3-dimethylbutan-1-amine | 1.14 | 491.12 | 490.29 |
| 1319 | | 6-[(butyl{[1-butyl-4-chloro-2-(2-methylphenyl)-1H-imidazol-5-yl]methyl}amino)methyl]-3,4-dihydroquinolin-2(1H)-one | 1.11 | 493.09 | 492.27 |
| 1320 | | N-{[1-butyl-4-chloro-2-(2-methylphenyl)-1H-imidazol-5-yl]methyl}-N-(1,2,3,4-tetrahydroquinolin-6-ylmethyl)butan-1-amine | 1.13 | 479.11 | 478.29 |
| 1321 | | N-{[1-butyl-4-chloro-2-(2,6-diethylphenyl)-1H-imidazol-5-yl]methyl}-N-methyl-1,2,3,4-tetrahydronaphthalen-1-amine | 1.24 | 464.09 | 463.28 |

TABLE IV-continued

| Cmp.# | MOLSTRUCTURE | IUPAC Name | LCMS (min.) | MW | LCMS Mass |
|---|---|---|---|---|---|
| 1322 | | (1S)-N-{[1-butyl-4-chloro-2-(2,6-diethylphenyl)-1H-imidazol-5-yl]methyl}-N-methyl-1,2,3,4-tetrahydronaphthalen-1-amine | 1.24 | 464.09 | 463.28 |
| 1323 | | 6-{[{[1-butyl-4-chloro-2-(2-methylphenyl)-1H-imidazol-5-yl]methyl}(isopentyl)amino]methyl}-3,4-dihydroquinolin-2(1H)-one | 1.14 | 507.12 | 506.28 |
| 1324 | | N-{[1-butyl-4-chloro-2-(2-methylphenyl)-1H-imidazol-5-yl]methyl}-N-(2,3-dihydro-1-benzofuran-5-ylmethyl)-3-methylbutan-1-amine | 1.16 | 480.09 | 479.27 |
| 1325 | | N-{[1-butyl-4-chloro-2-(2-methylphenyl)-1H-imidazol-5-yl]methyl}-N-(4-methoxybenzyl)-3-methylbutan-1-amine | 1.17 | 468.08 | 467.27 |
| 1326 | | N-{[1-butyl-4-chloro-2-(2-methylphenyl)-1H-imidazol-5-yl]methyl}-N-(3-methoxybenzyl)-3-methylbutan-1-amine | 1.21 | 468.08 | 467.27 |

TABLE IV-continued

| Cmp.# | MOLSTRUCTURE | IUPAC Name | LCMS (min.) | MW | LCMS Mass |
|---|---|---|---|---|---|
| 1327 | | N-{[1-butyl-4-chloro-2-(2-methylphenyl)-1H-imidazol-5-yl]methyl}-N-(4-ethoxybenzyl)-3-methylbutan-1-amine | 1.19 | 482.11 | 481.29 |
| 1328 | | N-{[1-butyl-4-chloro-2-(2-methylphenyl)-1H-imidazol-5-yl]methyl}-N-(3-ethoxybenzyl)-3-methylbutan-1-amine | 1.23 | 482.11 | 481.29 |
| 1329 | | ethyl N-{[1-butyl-4-chloro-2-(2-methylphenyl)-1H-imidazol-5-yl]methyl}-N-(2,3-dihydro-1,4-benzodioxin-6-ylmethyl)-beta-alaninate | 1.25 | 526.07 | 525.24 |
| 1330 | | 4-[{[1-butyl-4-chloro-2-(2-methylphenyl)-1H-imidazol-5-yl]methyl}(2,3-dihydro-1,4-benzodioxin-6-ylmethyl)amino]-2-methylbutan-2-ol | 1.11 | 512.09 | 511.26 |
| 1331 | | ethyl N-{[1-butyl-4-chloro-2-(2-methylphenyl)-1H-imidazol-5-yl]methyl}-N-(1H-indol-5-ylmethyl)-beta-alaninate | 1.15 | 507.07 | 506.24 |

TABLE IV-continued

| Cmp.# | MOLSTRUCTURE | IUPAC Name | LCMS (min.) | MW | LCMS Mass |
|---|---|---|---|---|---|
| 1332 | | 4-[{[1-butyl-4-chloro-2-(2-methylphenyl)-1H-imidazol-5-yl]methyl}(1H-indol-5-ylmethyl)amino]-2-methylbutan-2-ol | 1.1 | 493.09 | 492.27 |
| 1333 | | N-{[1-butyl-4-chloro-2-(2-methylphenyl)-1H-imidazol-5-yl]methyl}-N-[(3-chloro-1H-indol-5-yl)methyl]-3,3-dimethylbutan-1-amine | 1.19 | 525.56 | 524.25 |
| 1334 | | N-{[1-butyl-2-(2,6-diethylphenyl)-4-(4-methylphenyl)-1H-imidazol-5-yl]methyl}-N-methyl-1,2,3,4-tetrahydronaphthalen-1-amine | 1.26 | 519.77 | 519.36 |
| 1335 | | N-{[1-butyl-2-(2,6-diethylphenyl)-1H-imidazol-5-yl]methyl}-N-methyl-1,2,3,4-tetrahydronaphthalen-1-amine | 1.18 | 429.65 | 429.31 |
| 1336 | | N-{[1-butyl-2-(2,6-diethylphenyl)-4-methyl-1H-imidazol-5-yl]methyl}-N-methyl-1,2,3,4-tetrahydronaphthalen-1-amine | 1.2 | 443.68 | 443.33 |

TABLE IV-continued

| Cmp.# | MOLSTRUCTURE | IUPAC Name | LCMS (min.) | MW | LCMS Mass |
|---|---|---|---|---|---|
| 1337 | | methyl 4-{[{[1-butyl-4-(4-fluorophenyl)-2-phenyl-1H-imidazol-5-yl]methyl}(2,3-dihydro-1,4-benzodioxin-6-ylmethyl)amino]methyl} benzoate | 1.2 | 619.73 | 619.28 |
| 1338 | | methyl 4-{[{[1-butyl-4-(3-methylphenyl)-2-phenyl-1H-imidazol-5-yl]methyl}(2,3-dihydro-1,4-benzodioxin-6-ylmethyl)amino]methyl} benzoate | 1.21 | 615.77 | 615.31 |
| 1339 | | methyl 4-{[{[1-butyl-4-(3-methoxyphenyl)-2-phenyl-1H-imidazol-5-yl]methyl}(2,3-dihydro-1,4-benzodioxin-6-ylmethyl)amino]methyl} benzoate | 1.21 | 631.77 | 631.30 |
| 1340 | | methyl 4-{[{[1-butyl-4-(4-methoxyphenyl)-2-phenyl-1H-imidazol-5-yl]methyl}(2,3-dihydro-1,4-benzodioxin-6-ylmethyl)amino]methyl}benzoate | 1.2 | 631.77 | 631.30 |

TABLE IV-continued

| Cmp.# | MOLSTRUCTURE | IUPAC Name | LCMS (min.) | MW | LCMS Mass |
|---|---|---|---|---|---|
| 1341 | | methyl 4-{[{[1-butyl-4-(4-chlorophenyl)-2-phenyl-1H-imidazol-5-yl]methyl}(2,3-dihydro-1,4-benzodioxin-6-ylmethyl)amino]methyl}benzoate | 1.22 | 636.19 | 635.26 |
| 1342 | | 4-{{[1-butyl-4-chloro-2-(2-methylphenyl)-1H-imidazol-5-yl]methyl}[(3-chloro-1H-indol-5-yl)methyl]amino}-2-methylbutan-2-ol | 1.13 | 527.54 | 526.23 |
| 1343 | | N-{[butyl-4-chloro-2-(2-methylphenyl)-1H-imidazol-5-yl]methyl}-N-(1H-indol-5-ylmethyl)-2,2-dimethylpropan-1-amine | | 477.09 | |
| 1344 | | N-{[1-butyl-4-chloro-2-(2-methylphenyl)-1H-imidazol-5-yl]methyl}-N-[(3-chloro-1H-indol-5-yl)methyl]-2,2-dimethylpropan-1-amine | 1.37 | 511.54 | 510.23 |

TABLE IV-continued

| Cmp.# | MOLSTRUCTURE | IUPAC Name | LCMS (min.) | MW | LCMS Mass |
|---|---|---|---|---|---|
| 1345 | 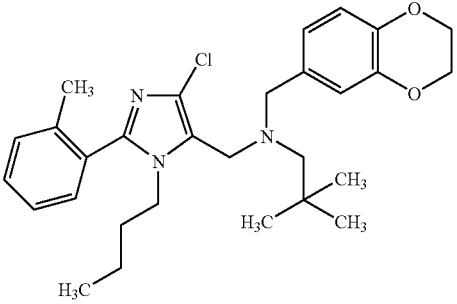 | N-{[1-butyl-4-chloro-2-(2-methylphenyl)-1H-imidazol-5-yl]methyl}-N-(2,3-dihydro-1,4-benzodioxin-6-ylmethyl)-2,2-dimethylpropan-1-amine | | 496.09 | |
| 1346 | 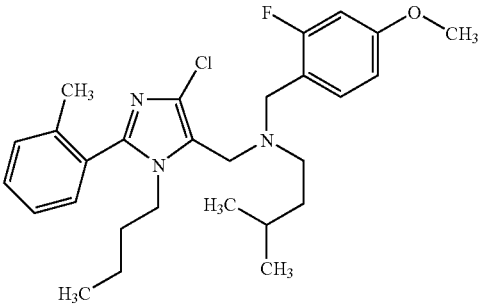 | N-{[1-butyl-4-chloro-2-(2-methylphenyl)-1H-imidazol-5-yl]methyl}-N-(2-fluoro-4-methoxybenzyl)-3-methylbutan-1-amine | | 486.07 | |
| 1347 | 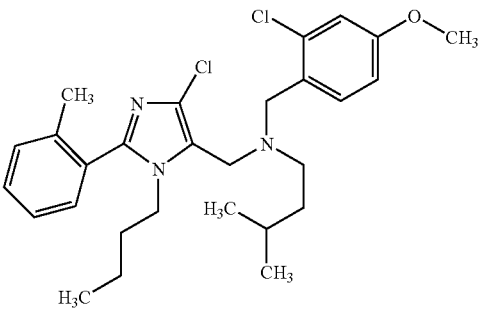 | N-{[1-butyl-4-chloro-2-(2-methylphenyl)-1H-imidazol-5-yl]methyl}-N-(2-chloro-4-methoxybenzyl)-3-methylbutan-1-amine | | 502.53 | |
| 1348 | 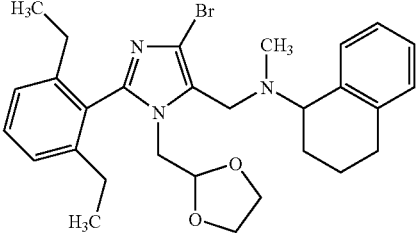 | N-{[4-bromo-2-(2,6-diethylphenyl)-1-(1,3-dioxolan-2-ylmethyl)-1H-imidazol-5-yl]methyl}-N-methyl-1,2,3,4-tetrahydronaphthalen-1-amine | | 538.53 | |
| 1349 | 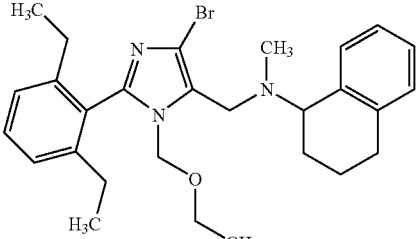 | N-{[4-bromo-2-(2,6-diethylphenyl)-1-(ethoxymethyl)-1H-imidazol-5-yl]methyl}-N-methyl-1,2,3,4-tetrahydronaphthalen-1-amine | | 510.52 | |

TABLE IV-continued

| Cmp.# | MOLSTRUCTURE | IUPAC Name | LCMS (min.) | MW | LCMS Mass |
|---|---|---|---|---|---|
| 1350 | | 4-{[{[1-butyl-4-(4-fluorophenyl)-2-phenyl-1H-imidazol-5-yl]methyl}(2,3-dihydro-1,4-benzodioxin-6-ylmethyl)amino]methyl}benzoic acid | | 605.71 | |
| 1351 | | 4-{[{[1-butyl-4-(3-methylphenyl)-2-phenyl-1H-imidazol-5-yl]methyl}(2,3-dihydro-1,4-benzodioxin-6-ylmethyl)amino]methyl}benzoic acid | | 601.74 | |
| 1352 | | 4-{[{[1-butyl-4-(3-methoxyphenyl)-2-phenyl-1H-imidazol-5-yl]methyl}(2,3-dihydro-1,4-benzodioxin-6-ylmethyl)amino]methyl}benzoic acid | | 617.74 | |
| 1353 | | 4-{[{[1-butyl-4-(4-chlorophenyl)-2-phenyl-1H-imidazol-5-yl]methyl}(2,3-dihydro-1,4-benzodioxin-6-ylmethyl)amino]methyl}benzoic acid | | 622.16 | |

TABLE IV-continued

| Cmp.# | MOLSTRUCTURE | IUPAC Name | LCMS (min.) | MW | LCMS Mass |
|---|---|---|---|---|---|
| 1354 | | 4-{[{[1-butyl-4-(4-methoxyphenyl)-2-phenyl-1H-imidazol-5-yl]methyl}(2,3-dihydro-1,4-benzodioxin-6-ylmethyl)amino]methyl}benzoic acid | | 617.74 | |
| 1355 | | N-{[4-bromo-2-(2,6-diethylphenyl)-1-(2-morpholin-4-ylethyl)-1H-imidazol-5-yl]methyl}-N-methyl-1,2,3,4-tetrahydronaphthalen-1-amine | 1.16 | 565.60 | 564.25 |
| 1356 | | N-{[4-chloro-1-(2-morpholin-4-ylethyl)-2-phenyl-1H-imidazol-5-yl]methyl}-N-(2,3-dihydro-1,4-benzodioxin-6-ylmethyl)-N-(3-ethoxybenzyl) amine | 1.2 | 603.16 | 602.27 |
| 1357 | | 1-[4-chloro-2-phenyl-1-(2-piperidin-1-ylethyl)-1H-imidazol-5-yl]-N-(2,3-dihydro-1,4-benzodioxin-6-ylmethyl)-N-(3-ethoxybenzyl) methanamine | 1.19 | 601.19 | 600.29 |

TABLE IV-continued

| Cmp.# | MOLSTRUCTURE | IUPAC Name | LCMS (min.) | MW | LCMS Mass |
|---|---|---|---|---|---|
| 1358 | | methyl 4-[(butyl{[1-butyl-2-(2-methylphenyl)-4-(4-methylphenyl)-1H-imidazol-5-yl]methyl}amino)methyl]benzoate | 1.23 | 537.74 | 537.34 |
| 1359 | | methyl 4-{[{[1-butyl-2-(2-methylphenyl)-4-(4-methylphenyl)-1H-imidazol-5-yl]methyl}(isobutyl)amino]methyl}benzoate | 1.24 | 537.74 | 537.34 |
| 1360 | | methyl 4-{[{[1-butyl-2-(2-methylphenyl)-4-(4-methylphenyl)-1H-imidazol-5-yl]methyl}(2-ethylbutyl)amino]methyl}benzoate | 1.27 | 565.80 | 565.37 |

TABLE IV-continued

| Cmp.# | MOLSTRUCTURE | IUPAC Name | LCMS (min.) | MW | LCMS Mass |
|---|---|---|---|---|---|
| 1361 | | methyl 4-{[{[1-butyl-2-(2-methylphenyl)-4-(4-methylphenyl)-1H-imidazol-5-yl]methyl}(isopentyl)amino]methyl}benzoate | 1.25 | 551.77 | 551.35 |
| 1362 | | methyl 4-{[{[1-butyl-2-(2-methylphenyl)-4-(4-methylphenyl)-1H-imidazol-5-yl]methyl}(cyclohexylmethyl)amino]methyl}benzoate | 1.28 | 577.81 | 577.37 |
| 1363 | | methyl 4-[(benzyl{[1-butyl-2-(2-methylphenyl)-4-(4-methylphenyl)-1H-imidazol-5-yl]methyl}amino)methyl]benzoate | 1.25 | 571.76 | 571.32 |

TABLE IV-continued

| Cmp.# | MOLSTRUCTURE | IUPAC Name | LCMS (min.) | MW | LCMS Mass |
|---|---|---|---|---|---|
| 1364 | | methyl 4-{[{[1-butyl-2-(2-methylphenyl)-4-(4-methylphenyl)-1H-imidazol-5-yl]methyl}(2,3-dihydro-1,4-benzodioxin-6-ylmethyl)amino]methyl}benzoate | 1.23 | 629.80 | 629.33 |
| 1365 | | methyl 4-{[{[1-butyl-2-(2-methylphenyl)-4-phenyl-1H-imidazol-5-yl]methyl}(isopentyl)amino]methyl}benzoate | 1.24 | 537.74 | 537.34 |
| 1366 | | methyl 4-{[{(1-butyl-2-(2-methylphenyl)-4-phenyl-1H-imidazol-5-yl]methyl}(2,3-dihydro-1,4-benzodioxin-6-ylmethyl)amino]methyl}benzoate | 1.22 | 615.77 | 615.31 |

TABLE IV-continued

| Cmp.# | MOLSTRUCTURE | IUPAC Name | LCMS (min.) | LCMS MW | LCMS Mass |
|---|---|---|---|---|---|
| 1367 | | methyl 4-[(benzyl{[1-butyl-2-(2-methylphenyl)-4-phenyl-1H-imidazol-5-yl]methyl}amino)methyl]benzoate | 1.22 | 557.73 | 557.30 |
| 1368 | | 4-[(butyl{[1-butyl-2-(2-methylphenyl)-4-(4-methylphenyl)-1H-imidazol-5-yl]methyl}amino)methyl]benzoic acid | 1.21 | 523.72 | 523.32 |
| 1369 | | 4-{[{[1-butyl-2-(2-methylphenyl)-4-(4-methylphenyl)-1H-imidazol-5-yl]methyl}(isobutyl)amino]methyl) benzoic acid | 1.21 | 523.72 | 523.32 |

TABLE IV-continued

| Cmp.# | MOLSTRUCTURE | IUPAC Name | LCMS (min.) | LCMS MW | LCMS Mass |
|---|---|---|---|---|---|
| 1370 | | 4-{[{[1-butyl-2-(2-methylphenyl)-4-(4-methylphenyl)-1H-imidazol-5-yl]methyl}(2-ethylbutyl)amino]metyl}benzoic acid | 1.24 | 551.77 | 551.35 |
| 1371 | | 4-{[{[1-butyl-2-(2-methylphenyl)-4-(4-methylphenyl)-1H-imidazol-5-yl]methyl}(isopentyl)amino]methyl}benzoic acid | 1.22 | 537.74 | 537.34 |
| 1372 | | 4-{[{[1-butyl-2-(2-methylphenyl)-4-(4-methylphenyl)-1H-imidazol-5-yl]methyl}(cyclohexylmethyl)amino]methyl}benzoic acid | 1.25 | 563.78 | 563.35 |

TABLE IV-continued

| Cmp.# | MOLSTRUCTURE | IUPAC Name | LCMS (min.) | MW | LCMS Mass |
|---|---|---|---|---|---|
| 1373 | | 4-[(benzyl{[1-butyl-2-(2-methylphenyl)-4-(4-methylphenyl)-1H-imidazol-5-yl]methyl}amino)methyl]benzoic acid | 1.21 | 557.73 | 557.30 |
| 1374 | | N-{[4-chloro-2-(2,6-dimethylphenyl)-1-methyl-1H-imidazol-5-yl]methyl}-N-methyl-1,2,3,4-tetrahydronaphthalen-1-amine | 1.09 | 393.96 | 393.20 |
| 1375 | | 4-{[{[1-butyl-2-(2-methylphenyl)-4-(4-methylphenyl)-1H-imidazol-5-yl]methyl}(2,3-dihydro-1,4-benzodioxin-6-ylmethyl)amino]methyl}benzoic acid | 1.2 | 615.77 | 615.31 |
| 1376 | | 4-{[{[1-butyl-2-(2-methylphenyl)-4-phenyl-1H-imidazol-5-yl]methyl}(isopentyl)amino]methyl}benzoic acid | | 523.72 | |

TABLE IV-continued

| Cmp.# | MOLSTRUCTURE | IUPAC Name | LCMS (min.) | MW | LCMS Mass |
|---|---|---|---|---|---|
| 1377 | | 4-{[{[1-butyl-2-(2-methylphenyl)-4-phenyl-1H-imidazol-5-yl]methyl}(2,3-dihydro-1,4-benzodioxin-6-ylmethyl)amino]methyl} benzoic acid | | 601.74 | |
| 1378 | | 4-[(benzyl{[1-butyl-2-(2-methylphenyl)-4-phenyl-1H-imidazol-5-yl]methyl}amino) methyl]benzoic acid | | 543.71 | |
| 1379 | | 4-[(butyl{[1-butyl-2-(2-methylphenyl)-4-phenyl-1H-imidazol-5-yl]methyl}amino)methyl] benzoic acid | 1.19 | 509.69 | 509.30 |

TABLE IV-continued

| Cmp.# | MOLSTRUCTURE | IUPAC Name | LCMS (min.) | MW | LCMS Mass |
|---|---|---|---|---|---|
| 1380 | | methyl 4-{[{[1-butyl-2-(2-methylphenyl)-4-(4-methylphenyl)-1H-imidazol-5-yl]methyl}(propyl)amino]methyl}benzoate | | 523.72 | |
| 1381 | | methyl 4-{[{[1-butyl-2-(2-methylphenyl)-4-(4-methylphenyl)-1H-imidazol-5-yl]methyl}(neopentyl)amino]methyl}benzoate | | 551.77 | |
| 1382 | | methyl 4-{[{[1-butyl-2-(2-methylphenyl)-4-(4-methylphenyl)-1H-imidazol-5-yl]methyl}(3,3-dimethylbutyl)amino]methyl}benzoate | | 565.80 | |

TABLE IV-continued

| Cmp.# | MOLSTRUCTURE | IUPAC Name | LCMS (min.) | MW | LCMS Mass |
|---|---|---|---|---|---|
| 1383 | | methyl 4-{[{[1-butyl-2-(2-methylphenyl)-4-(4-methylphenyl)-1H-imidazol-5-yl]methyl}(pentyl)amino]methyl}benzoate | | 551.77 | |
| 1384 | | methyl 4-{[{[1-butyl-2-(2-methylphenyl)-4-(4-methylphenyl)-1H-imidazol-5-yl]methyl}(hexyl)amino]methyl}benzoate | | 565.80 | |
| 1385 | | methyl 4-{[{[1-butyl-2-(2-methylphenyl)-4-(4-methylphenyl)-1H-imidazol-5-yl]methyl}(3-methylbut-2-enyl)amino]methyl}benzoate | | 549.76 | |

TABLE IV-continued

| Cmp.# | MOLSTRUCTURE | IUPAC Name | LCMS (min.) | MW | LCMS Mass |
|---|---|---|---|---|---|
| 1386 | | methyl 4-[((bicyclo[2.2.1]hept-5-en-2-ylmethyl){[1-butyl-2-(2-methylphenyl)-4-(4-methylphenyl)-1H-imidazol-5-yl]methyl}amino)methyl]benzoate | | 587.80 | |
| 1387 | | methyl 4-{[{[1-butyl-2-(2-methylphenyl)-4-(4-methylphenyl)-1H-imidazol-5-yl]methyl}(tetrahydrofuran-3-ylmethyl)amino]methyl}benzoate | | 565.75 | |
| 1388 | | methyl 4-{[{[1-butyl-2-(2-methylphenyl)-4-(4-methylphenyl)-1H-imidazol-5-yl]methyl}(thien-3-ylmethyl)amino]methyl}benzoate | | 577.79 | |

TABLE IV-continued

| Cmp.# | MOLSTRUCTURE | IUPAC Name | LCMS (min.) | MW | LCMS Mass |
|---|---|---|---|---|---|
| 1389 | | 4-{[{[1-butyl-2-(2-methylphenyl)-4-(4-methylphenyl)-1H-imidazol-5-yl]methyl}(propyl)amino]methyl}benzoic acid | 1.19 | 509.69 | 509.30 |
| 1390 | | 4-{[{[1-butyl-2-(2-methylphenyl)-4-(4-methylphenyl)-1H-imidazol-5-yl]methyl}(neopentyl)amino]methyl}benzoic acid | 1.23 | 537.74 | 537.34 |
| 1391 | | 4-{[{[1-butyl-2-(2-methylphenyl)-4-(4-methylphenyl)-1H-imidazol-5-yl]methyl}(3,3-dimethylbutyl)amino]methyl}benzoic acid | 1.23 | 551.77 | 551.35 |

TABLE IV-continued

| Cmp.# | MOLSTRUCTURE | IUPAC Name | LCMS (min.) | MW | LCMS Mass |
|---|---|---|---|---|---|
| 1392 | | 4-{[{[1-butyl-2-(2-methylphenyl)-4-(4-methylphenyl)-1H-imidazol-5-yl]methyl}(pentyl)amino]methyl}benzoic acid | 1.23 | 537.74 | 537.34 |
| 1393 | | 4-{[{[1-butyl-2-(2-methylphenyl)-4-(4-methylphenyl)-1H-imidazol-5-yl]methyl}(hexyl)amino]methyl}benzoic acid | 1.24 | 551.77 | 551.35 |
| 1394 | | 4-{[{[1-butyl-2-(2-methylphenyl)-4-(4-methylphenyl)-1H-imidazol-5-yl]methyl}(3-methylbut-2-enyl)amino]methyl]benzoic acid | 1.22 | 535.73 | 535.32 |

TABLE IV-continued

| Cmp.# | MOLSTRUCTURE | IUPAC Name | LCMS (min.) | MW | LCMS Mass |
|---|---|---|---|---|---|
| 1395 | | 4-[((bicyclo[2.2.1]hept-5-en-2-ylmethyl){[1-butyl-2-(2-methylphenyl)-4-(4-methylphenyl)-1H-imidazol-5-yl]methyl}amino)methyl]benzoic acid | 1.24 | 573.78 | 573.34 |
| 1396 | | 4-{[{[1-butyl-2-(2-methylphenyl)-4-(4-methylphenyl)-1H-imidazol-5-yl]methyl}(thien-3-ylmethyl)amino]methyl}benzoic acid | 1.19 | 563.76 | 563.26 |
| 1397 | | methyl 4-{[{[1-butyl-2-(2-methylphenyl)-4-(4-methylphenyl)-1H-imidazol-5-yl]methyl}(1H-indol-5-ylmethyl)amino]methyl}benzoate | 1.27 | 610.80 | 610.33 |

TABLE IV-continued

| Cmp.# | MOLSTRUCTURE | IUPAC Name | LCMS (min.) | MW | LCMS Mass |
|---|---|---|---|---|---|
| 1398 | 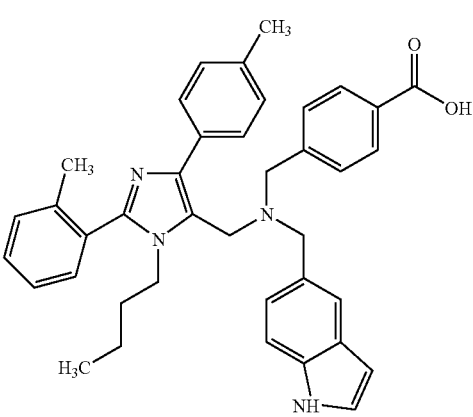 | 4-{[{[1-butyl-2-(2-methylphenyl)-4-(4-methylphenyl)-1H-imidazol-5-yl]methyl}(1H-indol-5-ylmethyl)amino]methyl}benzoic acid | 1.24 | 596.77 | 596.32 |
| 1399 | 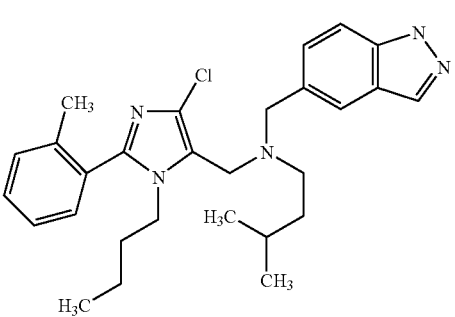 | N-{[1-butyl-4-chloro-2-(2-methylphenyl)-1H-imidazol-5-yl]methyl}-N-(1H-indazol-5-ylmethyl)-3-methylbutan-1-amine | 1.18 | 478.08 | 477.27 |
| 1400 | 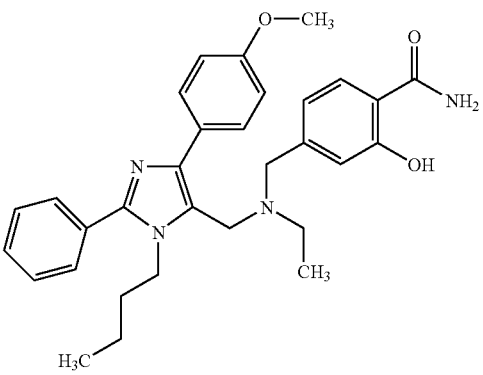 | 4-{[{[1-butyl-4-(4-methoxyphenyl)-2-phenyl-1H-imidazol-5-yl]methyl}(ethyl)amino]methyl}-2-hydroxybenzamide | 1.16 | 512.65 | 512.28 |
| 1401 | 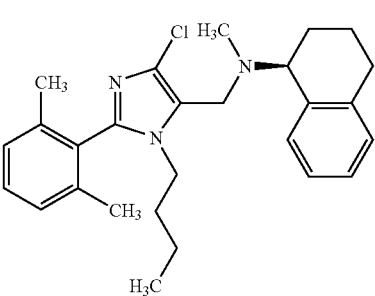 | (1S)-N-{[1-butyl-4-chloro-2-(2,6-dimethylphenyl)-1H-imidazol-5-yl]methyl}-N-methyl-1,2,3,4-tetrahydronaphthalen-1-amine | 1.24 | 436.04 | 435.24 |

TABLE IV-continued

| Cmp.# | MOLSTRUCTURE | IUPAC Name | LCMS (min.) | MW | LCMS Mass |
|---|---|---|---|---|---|
| 1402 | | N-{[1-butyl-4-chloro-2-(2-methylphenyl)-1H-imidazol-5-yl]methyl}-N-(1H-indazol-5-ylmethyl)-2,2-dimethylpropan-1-amine | 1.31 | 478.08 | 477.27 |
| 1403 | | 1-[1-butyl-4-chloro-2-(2-methylphenyl)-1H-imidazol-5-yl]-N-(1H-indazol-5-ylmethyl)-N-(3-methoxybenzyl)methanamine | 1.33 | 528.10 | 527.25 |
| 1404 | | 1-[1-butyl-4-chloro-2-(2-methylphenyl)-1H-imidazol-5-yl]-N-(1H-indazol-5-ylmethyl)-N-(4-methoxybenzyl)methanamine | 1.29 | 528.10 | 527.25 |
| 1405 | | 4-{[{[1-butyl-4-chloro-2-(2-methylphenyl)-1H-imidazol-5-yl]methyl}(4-methoxybenzyl)amino]methyl}-2-hydroxybenzamide | 1.28 | 547.10 | 546.24 |

TABLE IV-continued

| Cmp.# | MOLSTRUCTURE | IUPAC Name | LCMS (min.) | MW | LCMS Mass |
|---|---|---|---|---|---|
| 1406 | | 4-{[{[1-butyl-4-chloro-2-(2-methylphenyl)-1H-imidazol-5-yl]methyl}(3-methoxybenzyl)amino]methyl}-2-hydroxybenzamide | 1.26 | 547.10 | 546.24 |
| 1407 | | 4-{[{(1-butyl-4-(4-methoxyphenyl)-2-phenyl-1H-imidazol-5-yl]methyl}(2-methoxyethyl)amino]methyl}-2-hydroxybenzamide | 1.11 | 542.68 | 542.29 |
| 1408 | | 4-{[{[1-butyl-4-(4-methoxyphenyl)-2-pyridin-3-yl-1H-imidazol-5-yl]methyl}(cyclohexylmethyl)amino]methyl}-2-hydroxybenzamide | 1.21 | 581.76 | 581.34 |
| 1409 | | 7-{[{[1-butyl-4-(4-methoxyphenyl)-2-phenyl-1H-imidazol-5-yl]methyl}(neopentyl)amino]methyl}-2H-1,3-benzoxazine-2,4(3H)-dione | 1.23 | 580.73 | 580.30 |

TABLE IV-continued

| Cmp.# | MOLSTRUCTURE | IUPAC Name | LCMS (min.) | MW | LCMS Mass |
|---|---|---|---|---|---|
| 1410 | | 1-(1-butyl-2,4-diphenyl-1H-imidazol-5-yl)-N-(cyclohexylmethyl)-N-(1H-indazol-5-ylmethyl) methanamine | 1.26 | 531.74 | 531.34 |
| 1411 | | N-[(1-butyl-2,4-diphenyl-1H-imidazol-5-yl)methyl]-N-(1H-indazol-5-ylmethyl)-2,2-dimethylpropan-1-amine | 1.23 | 505.71 | 505.32 |
| 1412 | | 1-[1-butyl-4-(4-methoxyphenyl)-2-phenyl-1H-imidazol-5-yl]-N-(cyclohexylmethyl)-N-(1H-indazol-5-ylmethyl) methanamine | 1.27 | 561.77 | 561.35 |
| 1413 | | methyl 4-[((cyclohexylmethyl){[1-[2-(dimethylamino)ethyl]-4-(4-methoxyphenyl)-2-phenyl-1H-imidazol-5-yl]methyl} amino)methyl]-2-methoxybenzoate | 1.19 | 624.82 | 624.37 |

TABLE IV-continued

| Cmp.# | MOLSTRUCTURE | IUPAC Name | LCMS (min.) | MW | LCMS Mass |
|---|---|---|---|---|---|
| 1414 | | N-{[4-chloro-2-(2,6-diethylphenyl)-1-(2-methoxyethyl)-1H-imidazol-5-yl]methyl}-N-propylpropan-1-amine | 1.11 | 406.01 | 405.25 |
| 1415 | | 4-[((cyclahexylmethyl){1-[2-(dimethylamino)ethyl]-4-(4-methoxyphenyl)-2-phenyl-1H-imidazol-5-yl]methyl}amino)methyl]-2-hydroxybenzamide | 1.18 | 595.78 | 595.35 |
| 1416 | | 1-butyl-5-{[(1H-indazol-5-ylmethyl)(neopentyl)amino]methyl}-2-(2-methylphenyl)-1H-imidazole-4-carbonitrile | 1.32 | 468.65 | 468.30 |
| 1417 | | 1-butyl-5-{[(cyclohexylmethyl)(1H-indazol-5-ylmethyl)amino]methyl}-2-(2-methylphenyl)-1H-mmidazole-4-carbonitrile | 1.35 | 494.68 | 494.32 |

TABLE IV-continued

| Cmp.# | MOLSTRUCTURE | IUPAC Name | LCMS (min.) | MW | LCMS Mass |
|---|---|---|---|---|---|
| 1418 | | N-{[4-chloro-2-(2,6-diethylphenyl)-1-(2-methoxyethyl)-1H-imidazol-5-yl]methyl}-N-(4-methoxybenzyl)-2,2-dimethylpropan-1-amine | 1.32 | 512.13 | 511.30 |
| 1419 | | 4-{[{[1-butyl-4-cyano-2-(2-methylphenyl)-1H-imidazol-5-yl]methyl}cyclohexylmethyl)amino]methyl}-2-hydroxybenzamide | 1.33 | 513.68 | 513.31 |
| 1420 | | N-{[4-chloro-2-(2,6-diethylphenyl)-1-(2-methoxyethyl)-1H-imidazol-5-yl]methyl}-N-(3-ethoxybenzyl)-2,2-dimethylpropan-1-amine | 1.42 | 526.16 | 525.31 |
| 1421 | | N-{[4-chloro-2-(2,6-diethylphenyl)-1-(2-methoxyethyl)-1H-imidazol-5-yl]methyl}-N-(cyclohexylmethyl)-2,2-dimethylpropan-1-amine | 1.37 | 488.16 | 487.33 |

TABLE IV-continued

| Cmp.# | IUPAC Name | LCMS (min.) | MW | LCMS Mass |
|---|---|---|---|---|
| 1422 | N-{[4-chloro-2-(2,6-diethylphenyl)-1-(2-methoxyethyl)-1H-imidazol-5-yl]methyl}-N-(cyclohexylmethyl)-2-methylpropan-2-amine | 1.16 | 474.13 | 473.32 |
| 1423 | 4-{[{[1-butyl-4-(4-methoxyphenyl)-2-pyridin-4-yl-1H-imidazol-5-yl]methyl}(cyclohexylmethyl)amino]methyl}-2-hydroxybenzamide | 1.25 | 581.76 | 581.34 |
| 1424 | N-{[1-butyl-4-chloro-2-(2,6-dimethylphenyl)-1H-imidazol-5-yl]methyl}-N-(4-methoxybenzyl)-2,2-dimethylpropan-1-amine | 1.48 | 482.11 | 481.29 |
| 1425 | N-{[1-butyl-4-chloro-2-(2,6-dimethylphenyl)-1H-imidazol-5-yl]methyl}-N-(3-ethoxybenzyl)-2,2-dimethylpropan-1-amine | 1.54 | 496.14 | 495.30 |
| 1426 | N-{[1-butyl-4-chloro-2-(2,6-dimethylphenyl)-1H-imidazol-5-yl]methyl}-N-(cyclohexylmethyl)-2,2-dimethylpropan-1-amine | 1.57 | 458.13 | 457.32 |

TABLE IV-continued

| Cmp.# | MOLSTRUCTURE | IUPAC Name | LCMS (min.) | MW | LCMS Mass |
|---|---|---|---|---|---|
| 1427 | | N-{[1-butyl-4-chloro-2-(2,6-dimethylphenyl)-1H-imidazol-5-yl]methyl}-N-(cyclohexylmethyl)-2-methylpropan-2-amine | 1.19 | 444.10 | 443.31 |
| 1428 | | N-(2,3-dihydro-1,4-benzodioxin-6-ylmethyl)-N-{[1-(2-methoxyethyl)-4-(4-methoxyphenyl)-2-phenyl-1H-imidazol-5-yl]methyl}-2,2-dimethylpropan-1-amine | 1.25 | 555.72 | 555.31 |
| 1429 | | N-(2,3-dihydro-1,4-benzodioxin-6-ylmethyl)-N-{[1-(2-methoxyethyl)-4-(4-methoxyphenyl)-2-phenyl-1H-imidazol-5-yl]methyl}-2-methylpropan-1-amine | | 541.69 | |
| 1430 | | 1-cyclopropyl-N-(2,3-dihydro-1,4-benzodioxin-6-ylmethyl)-N-{[1-(2-methoxyethyl)-4-(4-methoxyphenyl)-2-phenyl-1H-imidazol-5-yl]methyl}methanamine | | 539.67 | |

TABLE IV-continued

| Cmp.# | MOLSTRUCTURE | IUPAC Name | LCMS (min.) | MW | LCMS Mass |
|---|---|---|---|---|---|
| 1431 | | N-benzyl-N-{[4-chloro-2-(2,6-diethylphenyl)-1-(2-methoxyethyl)-1H-imidazol-5-yl]methyl}-2,2-dimethylpropan-1-amine | | 482.11 | |
| 1432 | | N-{[1-butyl-4-chloro-2-(2,6-dimethylphenyl)-1H-imidazol-5-yl]methyl}-N-isopentylheptan-4-amine | | 460.15 | |
| 1433 | | N-{[1-butyl-4-chloro-2-(2,6-dimethylphenyl)-1H-imidazol-5-yl]methyl}-1-[4-(difluoromethoxy)phenyl]-N,4-dimethylpentan-1-amine | | 532.12 | |
| 1434 | | ethyl (4-chloro-5-{[(4-methoxybenzyl)(neopentyl)amino]methyl)-2-phenyl-1H-imidazol-1-yl)acetate | | 484.04 | |

TABLE IV-continued

| Cmp.# | IUPAC Name | LCMS (min.) | MW | LCMS Mass |
|---|---|---|---|---|
| 1435 | ethyl (4-chloro-5-{[(2,3-dihydro-1,4-benzodioxin-6-ylmethyl)(neopentyl)amino]methyl}-2-phenyl-1H-imidazol-1-yl)acetate | | 512.05 | |
| 1436 | N-{[4-chloro-2-(2,6-diethylphenyl)-1-(2-methoxyethyl)-1H-imidazol-5-yl]methyl}-N-(1H-indazol-5-ylmethyl)-2-methoxy-ethanamine | | 510.078 | |
| 1437 | N-{[1-butyl-4-chloro-2-(2,6-dimethylphenyl)-1H-imidazol-5-yl]methyl}-N-(1H-indazol-5-ylmethyl)-2-methoxy-ethanamine | | 480.053 | |
| 1438 | N-{[4-bromo-2-(2,6-diethylphenyl)-1-ethyl-1H-imidazol-5-yl]methyl}-N-(4-methoxybenzyl)-2,2-dimethylpropan-1-amine | | 526.559 | |

TABLE IV-continued

| Cmp.# | MOLSTRUCTURE | IUPAC Name | LCMS (min.) | MW | LCMS Mass |
|---|---|---|---|---|---|
| 1439 | | N-{[4-bromo-2-(2,6-diethylphenyl)-1-ethyl-1H-imidazol-5-yl]methyl}-N-(2,3-dihydro-1,4-benzodioxin-6-ylmethyl)-2,2-dimethylpropan-1-amine | | 554.569 | |
| 1440 | | 2-hydroxy-4-{[{[1-(2-methoxyethyl)-4-(4-methoxyphenyl)-2-phenyl-1H-imidazol-5-yl]methyl}(neopentyl)amino]methyl)benzamide | | 556.703 | |

Example 44

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably 3H), sulfur (preferably $^{35}$S), or iodine (preferably $^{125}$I. Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 45

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Examples.

Example 46

Assay for C5a Receptor Mediated Chemotaxis

This assay is a standard assay of C5a receptor mediated chemotaxis.

Human promonocytic U937 cells or purified human or non-human neutrophils are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 ug/ml calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3 \times 10^6$ cells/mL. Aliquots of this cell suspension are transferred to clean test tubes, which contain vehicle (1% DMSO) or varying concentrations of a compound of interest, and incubated at room temperature for at least 30 minutes. The chemotaxis assay is performed in CHEMO TX 101-8, 96 well plates (Neuro Probe, Inc. Gaithersburg, Md.). The bottom wells of the plate are filled with medium containing 0–10 nM of C5a, preferably derived from the same species of mammal as are the neutrophils or other cells (e.g., human C5a for the human U937 cells). The top wells of the plate are filled with cell suspensions (compound or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $IC_{50}$ value.

As a control to ensure that cells retain chemotactic ability in the presence of the compound of interest, the bottom wells of the plate may be filled with varying concentrations chemo-attractants that do not mediate chemotaxis via the C5a receptor (e.g., zymosan-activated serum (ZAS), N-formylmethionyl-leucyl-phenylalanine (FMLP) or leukotriene B4 (LTB4)), rather than C5a, under which conditions the compounds provided herein preferably do not inhibit chemotaxis.

Preferred compounds exhibit $IC_{50}$ values of less than 1 μM in the above assay for C5a receptor mediated chemotaxis.

Example 47

Expression of a C5a Receptor

A human C5a receptor cDNA is obtained by PCR using 1) a forward primer adding a Kozak ribosome binding site and 2) a reverse primer that added no additional sequence, and 3) an aliquot of a Stratagene Human Fetal Brain cDNA library as template. The sequence of the resulting PCR product is as described by Gerard and Gerard, (1991) *Nature* 349:614–17. The PCR product is subcloned into the cloning vector pCR-Script AMP (STRATAGENE, La Jolla, Calif.) at the Srf I site. It is then excised using the restriction enzymes EcoRI and NotI and subcloned in the appropriate orientation for expression into the baculoviral expression vector pBac-PAK 9 (CLONTECH, Palo Alto, Calif.) that has been digested with EcoRI and NotI.

Example 48

Baculoviral Preparations for C5a Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Lenexa, Kans.) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing $2 \times 10^6$ Sf9 cells in 5 m/s of insect medium. After five days of incubation at 27° C., supernatant medium is harvested from each of the T25 infections for use as passage 1 inoculum.

Two of seven recombinant baculoviral clones are then chosen for a second round of amplification, using 1 ml of passage 1 stock to infect $1 \times 10^8$ cells in 100 ml of insect medium divided into 2 T175 flasks. Forty-eight hours post infection, passage 2 medium from each 100 ml prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post, infection the supernatant medium is harvested to yield passage 3 baculoviral stock.

The remaining cell pellet is assayed for affinity binding using the "Binding Assays" essentially as described by DeMartino et al. (1994) *J. Biol. Chem.* 269:14446–50 at page 14447, adapted as follows. Radioligand is 0.005–0.500 nM $[^{125}I]$C5a (human recombinant; New England Nuclear Corp., Boston, Mass.); the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/ml aprotinin; filtration is carried out using GF/C WHATMAN filters (presoaked in 1.0% polyethyeneimine for 2 hours prior to use); and the filters are washed twice with 5 mLs cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression. A multiplicity of infection of 0.1 and a 72-hour incubation were the best infection parameters found for hC5a receptor expression in up to 1-liter Sf9 cell infection cultures.

Example 49

Baculoviral Infections

Log-phase Sf9 cells (INVITROGEN Corp., Carlsbad Calif.) are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $G\alpha_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V6B003), all of which may be obtained from BIOSIGNAL Inc. (Montreal, Canada).

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 50

Purified Recombinant Insect Cell Membranes

Sf9 cell pellets are resuspended in homogenization buffer (10 mM HEPES, 250 mM sucrose, 0.5 ug/ml leupeptin, 2 ug/ml Aprotinin, 200 uM PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.)

and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100–150 mg of total membrane protein.

Example 51

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, 0.1% BSA, pH 7.4, 0.1 mM bacitracin, 100 KUI/ml aprotinin).

For saturation binding analysis, membranes (5–50 μg) are added to polypropylene tubes containing 0.005–0.500 nM [$^{125}$I]C5a (human (recombinant), New England Nuclear Corp., Boston, Mass.). Nonspecific binding is determined in the presence of 300 nM hC5a (Sigma Chemical Co., St. Louis, Mo.) and accounts for less than 10% of total binding. For evaluation of guanine nucleotide effects on receptor affinity, GTPγS is added to duplicate tubes at the final concentration of 50 μM.

For competition analysis, membranes (5–50 μg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounts for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mLs cold binding buffer without BSA, bacitracin, or aprotinin. Remaining bound radioactivity is quantified by gamma counting. K, and Hill coefficient ("nH") are determined by fitting the Hill equation to the measured values with the aid of SIGMAPLOT software (SPSS Inc., Chicago, Ill.).

Example 52

Agonist-induced GTP Binding

Agonist-stimulated GTP-gamma $^{35}$S binding ("GTP binding") activity can be used to identify agonist and antagonist compounds and to differentiate neutral antagonist compounds from those that possess inverse agonist activity. This activity can also be; used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described in Example 49.

Agonist-stimulated GTP binding on purified membranes (prepared as described in Example 50) is assessed using hC5a (Sigma Chemical Co., St. Louis, Mo.) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM MgCl2, 2 mM EGTA, 0.1% BSA, 0.1 mM bacitracin, 100 KIU/mL aprotinin, 5 μM GDP) and added to reaction tubes at a concentration of 30 μg protein/reaction tube. After adding increasing doses of the agonist hC5a at concentrations ranging from $10^{-12}$ M to $10^{-6}$ M, reactions are initiated by the addition of 100 μM GTP-gamma $^{35}$S. In competition experiments, non-radiolabeled test compounds are added to separate assays at concentrations ranging from $10^{-10}$ M to $10^{-5}$M along with 10 nM hC5a to yield a final volume of 0.25 ML.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a certain preferred compounds will reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound that elevates GTP binding activity above baseline in the absence of added hC5a in this GTP binding assay is characterized as having partial agonist activity. Preferred antagonist compounds do not elevate GTP binding activity under such conditions more than 10%, 5% or 2% above baseline.

Following a 60-minute incubation at room temperature, the reactions are terminated by vacuum filtration over GF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTP-gamma $^{35}$S is determined by measuring the bound radioactivity, preferably by liquid scintillation spectrometry of the washed filters. Non-specific binding is determined using 10 mM GTP-gamma $^{35}$S and typically represents less than 5 percent of total binding. Data is expressed as percent above basal (baseline). The results of these GTP binding experiments may be conveniently analyzed using SIGMAPLOT software.

Example 53

Calcium Mobilization Assays

A. Response to C5a

U937 cells are grown in differentiation media (1 mM dibutyrl cAMP in RPMI 1640 medium containing 10% fetal bovine serum) for 48 hrs at 37° C. then reseeded onto 96-well plates suitable for use in a FLIPR™ Plate Reader (Molecular Devices Corp., Sunnyvale Calif.). Cells are grown an additional 24 hours (to 70–90% confluence) before the assay. The cells are then washed once with Krebs Ringer solution. FLUO-3 calcium sensitive dye (Molecular Probes, Inc. Eugene, Oreg.) is added to 10 μg/mL and incubated with the cells at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01–30.0 nM, using the FLIPR™ device (Molecular Devices). Differentiated U937 cells typically exhibit signals of 5,000–50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 µM. This stimulation typically triggers a signal of 1,000 to 12,000 arbitrary fluorescence light units. Certain preferred compounds produce less than a 10%, less than a 5%, or less than a 2% alteration of this calcium mobilization signal when this control assay is carried out in the presence of the compound, as compared to the signal when the assay is performed in the absence of the compound.

C. Assays for the Identification of Receptor Modulatory Agents: Antagonists and Agonists The calcium mobilization assay described above may be readily adapted for identifying test compounds that have agonist or antagonist activity at the human C5a receptor.

For example, in order to identify antagonist compounds, differentiated U937 cells are washed and incubated with Fluo-3 dye as described above. One hour prior to measuring the fluorescence signal, a subset of the cells is incubated with 1 µM of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 54.

Assays to Evaluate Agonist Activity of Small Molecule C5a Receptor Antagonists

Preferred compounds provided herein are C5a receptor antagonists that do not possess significant (e.g., greater than 5%) agonist activity in any of the C5a mediated functional assays discussed herein. Specifically, this undesired agonist activity can be evaluated, for example, in the GTP binding assay of Example 52, by measuring small molecule mediated GTP binding in the absence of the natural agonist, C5a. Similarly, in a calcium mobilization assay (e.g., that of Example 53), a small molecule compound can be directly assayed for the ability of the compound to stimulate calcium levels in the absence of the natural agonist, C5a. The preferred extent of C5a agonist activity exhibited by compounds provided herein is less than 10%, more preferably less than 5% and most preferably less than 2% of the response elicited by the natural agonist, C5a.

The foregoing description is illustrative thereof, and it will be understood that variations and modifications can be effected without departing from the scope or spirit of the invention as set forth in the following claims.

What is claimed is:

1. A compound of Formula I:

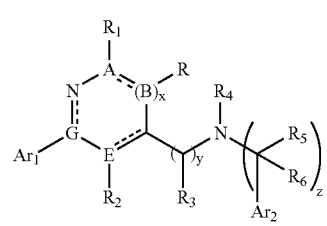

Formula I or a pharmaceutically acceptable salt thereof, wherein the ring system represented by

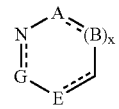

is a 5 membered heteroaryl ring system, in which x is 0, A and E are independently carbon or nitrogen, and G is carbon;

$R_1$ represents:
i) hydrogen, hydroxy, halogen, amino, cyano, nitro, —CHO, —CONH$_2$, $C_1$–$C_6$haloalkyl, or $C_1$–$C_6$haloalkoxy,
ii) $C_1$–$C_6$alkyl, $C_1$–$C_6$alkenyl, $C_1$–$C_6$alkynyl, $C_1$–$C_6$alkanoyl, $C_1$–$C_6$alkoxy, $C_3$–$C_7$cycloalkyl, ($C_3$–$C_7$cycloalkyl)$C_1$–$C_4$alkyl, mono- or di-$C_1$–$C_6$alkylamino, mono- or di-$C_1$–$C_6$alkylamino$C_1$–$C_6$alkyl, mono- or di-$C_1$–$C_6$alkylcarboxamide, $C_1$–$C_6$alkoxycarbonyl, —SO$_n$($C_1$–$C_6$alkyl), —NHSO$_n$$C_1$–$C_6$alkyl, —SO$_n$N($C_1$–$C_6$alkyl) ($C_1$–$C_6$alkyl), phenyl-SO$_n$—, each of which is optionally substituted, or
iii) naphthyl, phenyl, phenyl$C_1$–$C_4$carbhydryl, 5- or 6-membered heteroaryl, or 5- or 6-membered heteroaryl$C_1$–$C_4$carbhydryl, each of which is optionally substituted;

$R_2$, when E is Nitrogen, is chosen from $C_1$–$C_7$alkyl, $C_2$–$C_7$alkenyl, $C_2$–$C_7$alkynyl, $C_3$–$C_7$cycloalkyl ($C_1$–$C_4$alkyl), benzyl, and $C_1$–$C_6$haloalkyl, each of which is optionally substituted;

$R_2$, when E is Carbon, is chosen from
(i) hydrogen, halogen, hydroxy; $C_1$–$C_6$haloalkyl, and $C_1$–$C_6$haloalkoxy, and
(ii) $C_1$–$C_7$ alkyl, $C_2$–$C_7$ alkenyl, $C_2$–$C_7$ alkynyl, $C_1$–$C_7$ alkoxy, $C_1$–$C_7$alkylamino, $C_3$–$C_7$cycloalkyl ($C_1$–$C_4$alkyl), and benzyl; each of which is optionally substituted;

$R_3$ is hydrogen, $C_1$–$C_6$alkyl, $C_2$–$C_6$ alkenyl, $C_1$–$C_6$hydroxyalkyl, $C_1$–$C_6$haloalkyl, $C_3$–$C_7$cycloalkyl, ($C_3$–$C_7$cycloalkyl)$C_1$–$C_4$alkyl, or phenyl($C_1$–$C_4$alkyl);

$R_4$ is $C_1$–$C_6$alkyl, $C_2$–$C_6$ alkenyl, $C_2$–$C_6$ alkynyl, $C_3$–$C_7$ cycloalkyl, $C_3$–$C_7$ cycloalkenyl, ($C_3$–$C_7$cycloalkyl)$C_1$–$C_4$alkyl, ($C_3$–$C_7$cycloalkenyl)$C_1$–$C_4$alkyl, or hexahydro-1,3-benzodioxolylmethyl, each of which is optionally substituted; or $R_4$ is (i) optionally substituted aryl$C_0$–$C_4$alkyl having from 1 ring or 2 fused or pendant rings, (ii) an arylC$_1$–C$_4$alkyl group, wherein the aryl portion is fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy, (iii) optionally substituted heterocycloalkyl (C$_0$–C$_4$alkyl), (iv) optionally substituted heteroarylC$_0$–C$_2$alkyl, having 1 ring or 2 fused or pendant rings, from 5 to 7 members in each ring, and in at least one ring 1 to 3 heteroatoms selected from N, O, and S, or (v) optionally substituted saturated or partially unsaturated heterocyclic(C$_0$–C$_4$alkyl) wherein the heterocyclic portion has from 4 to 7 ring members, 1 or 2 of which ring members are N, S or O, with remaining ring members being carbon;

R$_5$ and R$_6$ are independently chosen from hydrogen and C$_1$–C$_6$alkyl, and z is 1;

Ar$_1$ represents
(i) optionally substituted aryl,
(ii) optionally substituted phenyl fused to a 5- to 7-membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, alkyl, alkoxy, haloalkyl, and haloalkoxy, or
(iii) optionally substituted heteroaryl, having 1 ring or 2 fused or pendant rings, from 5 to 7 members in each ring, and in at least one ring 1 to 3 heteroatoms selected from N, O, and S;

Ar$_2$ is a salicylamide group of the formula:

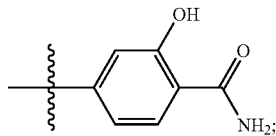

n is independently chosen from 0, 1, or 2; and y is 1.

2. A compound or salt according to claim 1 wherein R$_1$ is chosen from:
i) hydrogen, hydroxy, halogen, amino, cyano, nitro, —CHO, —CONH$_2$, C$_1$–C$_6$haloalkyl, C$_1$–C$_6$haloalkoxy,
ii) C$_1$–C$_6$alkyl, C$_1$–C$_6$alkenyl, C$_1$–C$_6$alkynyl, C$_1$–C$_6$alkanoyl, C$_1$–C$_6$alkoxy, C$_3$–C$_7$cycloalkyl, (C$_3$–C$_7$cycloalkyl)C$_1$–C$_4$alkyl, mono- and di-C$_1$–C$_6$alkylamino, mono- and di-C$_1$–C$_6$alkylaminoC$_1$–C$_6$alkyl, mono- and di-C$_1$–C$_6$alkylcarboxamide, C$_1$–C$_6$alkoxycarbonyl, —NHSO$_n$C$_1$–C$_6$alkyl, —SO$_n$(C$_1$–C$_6$alkyl), —(C$_1$–C$_6$alkyl)SO$_n$(C$_1$–C$_6$alkyl), —SO$_n$N(C$_1$–C$_6$alkyl) (C$_1$–C$_6$alkyl), and phenyl-SO$_n$—, each of which is substituted with from 0 to 3 substituents independently chosen from hydrogen, hydroxy, halogen, amino, cyano, oxo, C$_1$–C$_4$alkyl, C$_1$–C$_4$alkoxy, and C$_1$–C$_2$alkoxycarbonyl, and
iii) naphthyl, phenyl, phenylC$_1$–C$_4$carbhydryl, pyridyl, thiazolyl, pyrimidinyl, thienyl, pyridylC$_1$–C$_4$carbhydryl, thiazolylC$_1$–C$_4$carbhydryl, pyrimidinylC$_1$–C$_4$carbhydryl, and thienylC$_1$–C$_4$carbhydryl, each of which is substituted with from 0 to 3 substitutents independently chosen from hydroxy, halogen, amino, cyano, nitro, —COOH, —CONH$_2$, —SO$_2$NH$_2$, C$_1$–C$_6$haloalkyl, C$_1$–C$_6$haloalkoxy, C$_1$–C$_6$alkyl, C$_1$–C$_6$alkoxy, 1,3-dioxol-5-yl, C$_1$–C$_6$alkanoyl, C$_1$–C$_6$alkylsulfonyl, C$_1$–C$_6$alkylsulfinyl, C$_1$–C$_6$alkylthio, C$_2$–C$_6$alkanone; C$_1$–C$_6$alkanoyl; C$_2$–C$_6$alkyl ether; C$_1$–C$_6$ alkanoyloxy; C$_1$–C$_6$alkoxycarbonyl, and C$_1$–C$_6$alkylcarboxamide;

R$_2$, when E is Nitrogen, is chosen from C$_1$–C$_7$alkyl, substituted with from 0 to 3 substitutents independently chosen from hydroxy, halogen, amino, cyano, oxo, C$_1$–C$_4$alkyl, C$_1$–C$_4$alkoxy, C$_2$–C$_7$ alkenyl, C$_2$–C$_7$ alkynyl, C$_3$–C$_7$cycloalkyl(C$_1$–C$_4$alkyl), benzyl, C$_1$–C$_6$haloalkyl, and C$_1$–C$_6$haloalkoxy;

R$_2$, when E is Carbon, is chosen from (i) hydrogen; halogen, and hydroxy; and (ii) C$_1$–C$_7$alkyl substituted with from 0 to 3 substitutents independently chosen from hydroxy, halogen, amino, cyano, oxo, C$_1$–C$_4$alkyl, C$_1$–C$_4$alkoxy, C$_2$–C$_7$alkenyl, C$_2$–C$_7$alkynyl, C$_1$–C$_7$alkoxy; C$_1$–C$_7$alkylamino; C$_3$–C$_7$cycloalkyl(C$_1$–C$_4$alkyl), benzyl, C$_1$–C$_6$haloalkyl, and C$_1$–C$_6$haloalkoxy;

R$_4$ represents C$_1$–C$_6$alkyl, C$_2$–C$_6$ alkenyl, C$_2$–C$_6$ alkynyl, C$_3$–C$_7$ cycloalkyl, C$_3$–C$_7$ cycloalkenyl, (C$_3$–C$_7$cycloalkyl)C$_1$–C$_4$alkyl, (C$_3$–C$_7$cycloalkenyl) C$_1$–C$_4$alkyl, or hexahydro-1,3-benzodioxolylmethyl, each of which is substituted with from 0 to 3 substitutents independently chosen from hydrogen, hydroxy, halogen, amino, cyano, C$_1$–C$_2$alkyl, C$_1$–C$_2$alkoxy, and C$_1$–C$_2$alkoxycarbonyl; or R$_4$ represents:
(i) arylC$_0$–C$_4$alkyl having 1 ring or 2 fused or pendant rings,
(ii) benzyl fused to a 5 to 7 membered saturated or partially unsaturated ring that (a) has 0, 1 or 2 ring atoms independently chosen from N, O and S, with remaining ring atoms being carbon, and (b) is substituted with from 0 to 3 substituents independently chosen from halogen, C$_1$–C$_4$alkyl, C$_1$–C$_4$alkoxy, C$_1$–C$_2$haloalkyl, and C$_1$–C$_2$haloalkoxy,
(iii) heterocycloalkyl(C$_0$–C$_4$alkyl), or
(iv) heteroarylC$_0$–C$_2$alkyl, having 1 ring to 2 fused or pendant rings, from 5 to 7 members in each ring, and in at least one ring 1 to 3 heteroatoms selected from N, O, and S, wherein each of (i), (ii) (iii) and (iv) are substituted with from 0 to 4 substituents independently chosen from hydroxy, halogen, amino, cyano, nitro, —COOH, —CONH$_2$, —SO$_2$NH$_2$, oxo, C$_1$–C$_6$haloalkyl, C$_1$–C$_6$haloalkoxy, C$_1$–C$_6$alkyl, C$_1$–C$_6$alkoxy, mono- and di-(C$_1$–C$_6$)alkylamino, C$_1$–C$_6$alkanoyl, C$_1$–C$_6$sulfonate, C$_1$–C$_6$alkylsulfonyl, C$_1$–C$_6$alkylsulfinyl, C$_1$–C$_6$alkylthio, C$_2$–C$_6$alkanone, C$_2$–C$_6$alkyl ether; C$_1$–C$_6$alkanoyloxy; C$_1$–C$_6$alkoxycarbonyl, and C$_1$–C$_6$alkylcarboxamide; and Ar$_1$ represents phenyl, quinolinyl, isoquinolinyl, phthalizinayl, benzimidazolyl, indanyl, tetralinyl, chromanyl, naphthyl, pyridyl, pyrimidinyl, pyridizinyl, pyrazinyl, pyrazolyl, imidazolyl, thiazolyl, isothiazolyl, pyrrolyl, oxazolyl, furanyl, or thienyl, each of which is substituted with from 0 to 3 substituents independently chosen from hydroxy, halogen, amino, C$_1$–C$_6$alkylamino, C$_1$–C$_6$alkylaminoC$_1$–C$_6$alkyl, cyano, nitro, $C_1$–$C_6$haloalkyl, $C_1$–$C_6$ haloalkoxy, $C_1$–$C_6$alkyl, and $C_1$–$C_6$ alkoxy.

3. A compound or salt according to claim 2 wherein A is carbon; and E is nitrogen.

4. A compound or salt according to claim 2 wherein E is carbon; and A is nitrogen.

5. A compound or salt according to claim 2 wherein and A and E are nitrogen.

6. A compound or salt according to claim 2 wherein $R_5$ is hydrogen; and $R_6$ is hydrogen, methyl, or ethyl.

7. A compound or salt according to claim 2 wherein
$R_5$ is hydrogen, $R_6$ is hydrogen, methyl, or ethyl; and
$Ar_1$ is phenyl, pyrazolyl, or thienyl, each of which is substituted with 0 to 2 substituents independently chosen from halogen, hydroxy, $C_1$–$C_2$alkyl, $C_1$–$C_2$alkoxy, $C_1$–$C_2$haloalkyl, and $C_1$–$C_2$haloalkoxy.

8. A compound or salt according to claim 2 wherein $R_5$ and $R_6$ are hydrogen, and $Ar_1$ is unsubstituted phenyl or unsubstituted thienyl.

9. A compound or salt according to claim 2 wherein $R_1$ is phenyl substituted with from 0 to 4 substituents independently chosen from hydroxy, halogen, amino, cyano, nitro, —COOH, —CONH$_2$, —SO$_2$NH$_2$, $C_1$–$C_6$ haloalkyl, $C_1$–$C_6$haloalkoxy, $C_1$–$C_6$alkyl, $C_1$–$C_6$alkoxy, 1,3-dioxol-5-yl, $C_1$–$C_6$alkanoyl, $C_1$–$C_6$alkylsulfonyl, $C_1$–$C_6$alkylsulfinyl, $C_1$–$C_6$alkylthio, $C_2$–$C_6$alkanone; $C_1$–$C_6$alkanoyl; $C_2$–$C_6$alkyl ether; $C_1$–$C_6$alkanoyloxy, $C_1$–$C_6$alkoxycarbonyl, and $C_1$–$C_6$alkylcarboxamide.

10. A compound or salt according to claim 2 wherein $R_1$ is phenyl substituted with from 0 to 2 substituents independently chosen from hydroxy, halogen, amino, cyano, nitro, —COOH, —CONH$_2$, —SO$_2$NH$_2$, $C_1$–$C_2$ haloalkyl, $C_1$–$C_2$ haloalkoxy, $C_1$–$C_2$alkyl, and $C_1$–$C_2$alkoxy.

11. A compound or salt according to claim 2 wherein $R_1$ is unsubstituted phenyl.

12. A compound or salt according to claim 2 wherein $R_1$ is thienyl or pyridyl, each of which is substituted with from 0 to 2 substituents independently chosen from hydroxy, halogen, amino, cyano, nitro, —COOH, —CONH$_2$, —SO$_2$NH$_2$, $C_1$–$C_2$ haloalkyl, $C_1$–$C_2$ haloalkoxy, $C_1$–$C_2$alkyl, and $C_1$–$C_2$alkoxy.

13. A compound or salt according to claim 2 wherein $R_1$ is hydrogen.

14. A compound or salt according to claim 2 wherein $R_1$ is halogen, $C_1$–$C_4$alkyl, $C_1$–$C_4$alkoxy, cyano, trifluoromethyl, pentafluoroethyl, $C_1$–$C_2$alkylamino$C_1$–$C_2$alkyl, hydroxymethyl, or hydroxyethyl.

15. A compound or salt according to claim 2 wherein $R_2$ is propyl, butyl, pentyl, 3-methylbutyl, or methoxyethyl.

16. A compound or salt according to claim 2 wherein $R_3$ is hydrogen.

17. A compound or salt according to claim 2 wherein $R_3$ is $C_1$–$C_5$ alkyl.

18. A compound or salt according to claim 2 wherein $R_4$ represents $C_1$–$C_6$alkyl, $C_2$–$C_6$ alkenyl, $C_2$–$C_6$ alkynyl, $C_3$–$C_7$ cycloalkyl, $C_3$–$C_7$ cycloalkenyl, ($C_3$–$C_7$cycloalkyl)$C_1$–$C_4$alkyl, ($C_3$–$C_7$cycloalkenyl)$C_1$–$C_4$alkyl, or hexahydro-1,3-benzodioxolylmethyl, each of which is substituted with from 0 to 3 substituents independently chosen from hydroxy, halogen, amino, cyano, $C_1$–$C_2$alkyl, $C_1$–$C_2$alkoxy, and $C_1$–$C_2$alkoxycarbonyl.

19. A compound or salt according to claim 2 wherein $R_4$ represents cyclopentyl, cyclohexyl, cyclohexenyl, cyclohexylmethyl, cyclohexenylmethyl, cyclhexenyl, or hexahydro-1,3-benzodioxolylmethyl.

20. A compound or salt according to claim 2 wherein $R_4$ represents cyclohexylmethyl.

21. A compound or salt according to claim 2 wherein $R_4$ represents
(i) aryl or aryl($C_1$–$C_2$)alkyl having 1 ring or 2 fused or pendant rings,
(ii) benzyl fused to a 5- to 7-membered saturated or partially unsaturated ring that (a) has 0, 1, or 2 ring atoms independently chosen from N, O and S, with remaining ring atoms being carbon, and (b) is substituted with from 0 to 3 substituents independently chosen from halogen, $C_1$–$C_4$alkyl, $C_1$–$C_4$alkoxy, $C_1$–$C_2$haloalkyl, and $C_1$–$C_2$haloalkoxy;
(iii) saturated or partially unsaturated heterocyclic ($C_0$–$C_4$alkyl) having 1 ring or 2 fused or pendant rings, from 5 to 7 members in each ring, and in at least one ring 1 to 3 heteroatoms selected from N, O, and S; or
(iv) heteroaryl or heteroaryl($C_0$–$C_2$alkyl), having 1 ring or 2 fused or pendant rings, from 5 to 7 members in each ring, and in at least one ring 1 to 3 heteroatoms selected from N, O, and S, wherein each of (i), (ii), (iii), and (iv) are substituted with from 0 to 4 substituents independently chosen from hydroxy, halogen, amino, cyano, nitro, —COOH, —CONH$_2$, —SO$_2$NH$_2$, oxo, $C_1$–$C_6$ haloalkyl, $C_1$–$C_6$haloalkoxy, $C_1$–$C_6$alkyl, $C_1$–$C_6$alkoxy, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_1$–$C_6$alkanone, $C_2$–$C_6$alkyl ether, $C_1$–$C_6$ alkanoyloxy, $C_1$–$C_6$alkoxycarbonyl, and $C_1$–$C_6$alkylcarboxamide.

22. A compound or salt according to claim 2 wherein $R_4$ represents benzyl substituted with from 0 to 4 substituents independently chosen from hydroxy, halogen, amino, cyano, nitro, —COOH, —CONH$_2$, —SO$_2$NH$_2$, $C_1$–$C_6$ haloalkyl, $C_1$–$C_6$ haloalkoxy, mono- and di-($C_1$–$C_6$)alkylamino, $C_1$–$C_6$ alkyl, $C_1$–$C_6$alkoxy, $C_1$–$C_6$alkanoyl, $C_1$–$C_6$alkylsulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkyl ether, $C_1$–$C_6$ alkanoyloxy, $C_1$–$C_6$alkoxycarbonyl, and $C_1$–$C_6$alkylcarboxamide.

23. A compound or salt according to claim 2 wherein $R_4$ represents benzyl substituted with from 0 to 3 substituents independently chosen from hydroxy, halogen, amino, cyano, nitro, —COOH, —CONH$_2$, —SO$_2$NH$_2$, —SH, $C_1$–$C_2$haloalkyl, $C_1$–$C_2$ haloalkoxy, mono- and di-($C_1$–$C_2$) alkylamino, $C_1$–$C_4$alkoxy, $C_1$–$C_2$alkanoyl, $C_1$–$C_2$alkylsulfonate, $C_1$–$C_2$alkylsulfonyl, $C_1$–$C_2$alkylsulfinyl, $C_1$–$C_2$alkylthio, $C_2$–$C_3$alkanone, $C_2$–$C_6$alkylether, $C_1$–$C_4$ alkanoyloxy, $C_1$–$C_4$alkoxycarbonyl, and $C_1$–$C_2$alkylcarboxamide.

24. A compound or salt according to claim 2 wherein $R_4$ represents benzyl substituted with from 0 to 3 substituents independently chosen from hydroxy, halogen, amino, cyano, nitro, —COOH, —CONH$_2$, —SO$_2$NH$_2$, pentafluoroethyl, tetrafluoromethyl, trifluoromethyl, difluoromethyl, pentafluoroethoxy, tetrafluoroethoxy, trifluoromethoxy, difluoromethoxy, $C_1$–$C_2$ alkyl, $C_1$–$C_4$alkoxy, $C_1$–$C_2$alkanoyl, $C_1$–$C_2$alkylsulfonate, $C_1$–$C_2$alkylsulfonyl, $C_1$–$C_2$alkylsulfinyl, $C_1$–$C_2$alkylthio, $C_2$–$C_3$alkanone; $C_1$–$C_4$ alkanoyloxy, ethoxycarbonyl, methoxycarbonyl, and —NH$_2$(C=O)CH$_3$.

25. A compound or salt according to claim 2 wherein $R_4$ represents pyridylmethyl, pyrimidylmethyl, thienylmethyl, napthylmethyl, indolylmethyl, benzoxadialolylmethyl, benzoxazolylmethyl, quinazolinylmethyl, benzothiazolylmethyl, or benzimidazolylmethyl, each of which is optionally substituted with from 0 to 2 substituents independently chosen from hydroxy, halogen, amino, cyano, $C_1$–$C_2$ alkyl, $C_1$–$C_2$alkoxy, $C_1$–$C_2$haloalkyl, $C_1$–$C_2$haloalkoxy, and mono- and di-($C_1$–$C_2$)alkylamino.

26. A compound or salt according to claim 2 wherein $R_4$ represents benzyl fused to a 5- to 7-membered saturated or partially unsaturated ring that (a) has 0, 1, or 2 ring atoms independently chosen from N, O and S, with remaining ring atoms being carbon, and (b) is substituted with from 0 to 3 substituents independently chosen from hydroxy, halogen, amino, cyano, nitro, —COOH, —CONH$_2$, —SO$_2$NH$_2$, oxo, $C_1$–$C_6$ haloalkyl, $C_1$–$C_6$ haloalkoxy, $C_1$–$C_6$alkyl, $C_1$–$C_6$alkoxy, mono- and di-($C_1$–$C_6$)alkylamino, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkyl ether; $C_1$–$C_6$ alkanoyloxy; $C_1$–$C_6$alkoxycarbonyl, and $C_1$–$C_6$alkylcarboxamide.

27. A compound or salt according to claim 2 wherein $R_4$ represents 1,3-benzodioxol-5-ylmethyl, 2,3-dihydro-1-benzofuran-6-ylmethyl, 2,3-dihydro-1-benzofuran-5-ylmethyl, 2,3-dihydro-1,4-benzodioxin-6-ylmethyl, chroman-6-ylmethyl, chroman-7-ylmethyl, 1,3-benzothiazolylmethyl, 2,3-dihydroindol-5-ylmethyl, each of which is substituted from 0 to 2 substituents independently selected from hydroxy, halogen, amino, cyano, oxo, $C_1$–$C_2$haloalkyl, $C_1$–$C_2$haloalkoxy, $C_1$–$C_2$alkyl, $C_1$–$C_2$alkoxy, mono- and di-($C_1$–$C_2$)alkylamino.

28. A compound or salt according to claim 2 wherein $R_4$ is a saturated or partially unsaturated heterocyclic ($C_0$–$C_4$alkyl) group having from 4 to 7 ring members, 1 or 2 of which ring members are N, S or O, with remaining ring members being carbon, substituted with from 0 to 4 substituents independently chosen from hydroxy, halogen, amino, cyano, nitro, —COOH, —CONH$_2$, —SO$_2$NH$_2$, oxo, $C_1$–$C_6$ haloalkyl, $C_1$–$C_6$haloalkoxy, $C_1$–$C_6$alkyl, $C_1$–$C_6$alkoxy, mono- and di-($C_1$–$C_6$)alkylamino, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_2$–$C_6$alkanone, $C_2$–$C_6$alkylether, $C_1$–$C_6$alkanoyloxy, $C_1$–$C_6$alkoxycarbonyl, and $C_1$–$C_6$alkylcarboxamide.

29. A compound or salt according to claim 2 wherein $R_4$ is morpholinyl($C_0$–$C_4$alkyl), azetidinyl($C_0$–$C_4$alkyl), piperazinyl($C_0$–$C_4$alkyl), piperidinyl($C_0$–$C_4$alkyl), pyrrolidinyl($C_0$–$C_4$alkyl), tetrahydropyranyl($C_0$–$C_4$alkyl), or tetrahydropyridinyl($C_0$–$C_4$alkyl), each of which is substituted by from 0 to 2 substituents independently selected from hydroxy, halogen, amino, cyano, oxo, $C_1$–$C_2$ alkyl, $C_1$–$C_2$alkoxy, $C_1$–$C_2$haloalkyl, $C_1$–$C_2$haloalkoxy, mono- and di-($C_1$–$C_2$)alkylamino.

30. A compound according to claim 2 wherein $R_4$ is a heteroaryl or heteroaryl($C_1$–$C_2$alkyl) group, having 1 ring or 2 fused or pendant rings, from 5 to 7 members in each ring, and in at least one ring 1 to 3 heteroatoms selected from N, O, and S, substituted with from 0 to 4 substituents independently chosen from hydroxy, halogen, amino, cyano, nitro, —COOH, —CONH$_2$, —SO$_2$NH$_2$, oxo, $C_1$–$C_6$ alkyl, $C_1$–$C_6$alkoxy, $C_1$–$C_6$haloalkyl, $C_1$–$C_6$haloalkoxy, $C_1$–$C_6$alkanoyl, $C_1$–$C_6$sulfonate, $C_1$–$C_6$alkylsulfonyl, $C_1$–$C_6$alkylsulfinyl, $C_1$–$C_6$alkylthio, $C_1$–$C_6$alkanone, $C_2$–$C_6$alkyl ether, $C_1$–$C_6$ alkanoyloxy, $C_1$–$C_6$alkoxycarbonyl, and $C_1$–$C_6$alkylcarboxamide.

31. A compound according to claim 2 wherein $R_4$ is pyridylmethyl, pyrimidinylmethyl, thienylmethyl, naphthylmethyl, indolylmethyl, benzoxadiazolylmethyl, benzoxazolylmethyl, quinazolinylmethyl, or benzimidazolylmethyl, each of which is substituted with from 0 to 2 substituents independently chosen from hydroxy, halogen, amino, cyano, $C_1$–$C_2$haloalkyl, $C_1$–$C_2$haloalkoxy, $C_1$–$C_2$ alkyl, and $C_1$–$C_2$alkoxy.

32. A pharmaceutical composition comprising at least one compound or salt according to claim 1, or a prodrug or hydrate thereof, in combination with a physiologically acceptable carrier or excipient.

33. A compound or salt according to claim 1, wherein the compound exhibits an IC$_{50}$ of 500 nM or less in a standard in vitro C5a receptor-mediated chemotaxis or calcium mobilization assay.

34. A method for treating a patient suffering from rheumatoid arthritis, psoriasis, reperfusion injury, or bronchial asthma comprising administering to the patient a C5a receptor modulatory amount of a compound according to claim 1.

35. A method for treating a patient suffering from myocardial infarction, atherosclerosis, ischemic heart disease, or ischemia-reperfusion injury comprising administering to the patient a C5a receptor modulatory amount of a compound according to claim 1.

36. A pharmaceutical composition according to claim 32, wherein the pharmaceutical composition is formulated as an injectible fluid, an aerosol, a cream, a gel, a pill, a capsule, a syrup, or a transdermal patch.

* * * * *